US012440496B2

(12) United States Patent
Hong et al.

(10) Patent No.: US 12,440,496 B2
(45) Date of Patent: Oct. 14, 2025

(54) NATRIURETIC PEPTIDE RECEPTOR A AGONISTS USEFUL FOR THE TREATMENT OF CARDIOMETABOLIC DISEASES, KIDNEY DISEASE AND DIABETES

(71) Applicants: Merck Sharp & Dohme LLC, Rahway, NJ (US); Changhong Shi, Scotch Plains, NJ (US)

(72) Inventors: Qingmei Hong, Scotch Plains, NJ (US); Jason E. Imbriglio, Bridgewater, NJ (US); Angela D. Kerekes, Plainfield, NJ (US); Tanweer Khan, Bridgewater, NJ (US); Claire Lankin, Highbridge, NJ (US); Derun Li, West Roxbury, MA (US); Rui Liang, East Brunswick, NJ (US); Pengcheng Patrick Shao, Fanwood, NJ (US); Zhicai Wu, Montvale, NJ (US); Yusheng Xiong, Plainsboro, NJ (US); Feng Ye, Scotch Plains, NJ (US); Hyewon Youm, Berkeley Heights, NJ (US); Yang Yu, Edison, NJ (US); Anthappan Tony Kurissery, Bangalore (IN); Venukrishnan Komanduri, Manchester (GB)

(73) Assignee: Merck Sharp & Dohme LLC, Rahway, NJ (US)

( * ) Notice: Subject to any disclaimer, the term of this patent is extended or adjusted under 35 U.S.C. 154(b) by 660 days.

(21) Appl. No.: 17/611,540

(22) PCT Filed: May 18, 2020

(86) PCT No.: PCT/US2020/033354

§ 371 (c)(1),
(2) Date: Nov. 15, 2021

(87) PCT Pub. No.: WO2020/236688

PCT Pub. Date: Nov. 26, 2020

(65) Prior Publication Data

US 2022/0273669 A1 Sep. 1, 2022

Related U.S. Application Data

(60) Provisional application No. 62/851,539, filed on May 22, 2019.

(51) Int. Cl.

| | |
|---|---|
| ***C07D 495/04*** | (2006.01) |
| ***A61K 31/438*** | (2006.01) |
| ***A61K 31/444*** | (2006.01) |
| ***A61K 31/4545*** | (2006.01) |
| ***A61K 31/54*** | (2006.01) |
| ***C07D 513/04*** | (2006.01) |
| ***C07D 519/00*** | (2006.01) |

(52) U.S. Cl.

CPC ............ *A61K 31/54* (2013.01); *A61K 31/438* (2013.01); *A61K 31/444* (2013.01); *A61K 31/4545* (2013.01); *C07D 495/04* (2013.01); *C07D 513/04* (2013.01); *C07D 519/00* (2013.01)

(58) Field of Classification Search

CPC .. C07D 495/04; C07D 513/04; C07D 519/00; A61K 31/54

See application file for complete search history.

(56) References Cited

U.S. PATENT DOCUMENTS

2006/0247320 A1 11/2006 Tagat et al.
2016/0152635 A1 6/2016 Olsen et al.

FOREIGN PATENT DOCUMENTS

WO 2006098961 A2 9/2006
WO 2018175534 A1 9/2018
WO 2020236690 A1 11/2020

OTHER PUBLICATIONS

PubChem-CID-20966414, Create Date: Dec. 5, 2007 (Dec. 5, 2007), p. 2, Fig (8 pages).

*Primary Examiner* — Kamal A Saeed
*Assistant Examiner* — Karen Cheng
(74) *Attorney, Agent, or Firm* — Patricia A. Shatynski; John C. Todaro

(57) ABSTRACT

The present invention relates to Compounds of Formula I:

I

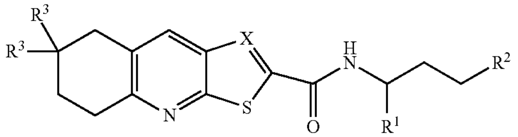

and pharmaceutically acceptable salts or prodrug thereof. The present invention also relates to compositions comprising at least one compound of Formula I, and methods of using the compounds of Formula I for treatment of cardiometabolic diseases including high blood pressure, heart failure, kidney disease, and diabetes in a subject.

15 Claims, No Drawings

NATRIURETIC PEPTIDE RECEPTOR A AGONISTS USEFUL FOR THE TREATMENT OF CARDIOMETABOLIC DISEASES, KIDNEY DISEASE AND DIABETES

CROSS-REFERENCE TO RELATED APPLICATIONS

This application is a U.S. National Stage application of International Patent Application No. PCT/US20/033354, filed May 18, 2020, which claims priority to U.S. Provisional Patent Application No. 62/851,539, filed May 22, 2019.

FIELD OF THE INVENTION

The present invention relates to compounds useful for activating Natriuretic Peptide Receptor A (NPRA) and for treating or prevention of cardiometabolic diseases including high blood pressure, heart failure, kidney disease, and diabetes.

BACKGROUND OF THE INVENTION

Natriuretic Peptide Receptor A (NPRA) is a receptor widely distributed in the human myocardium. (Molecular Biology of the Natriuretic Peptide System Implications for Physiology and Hypertension David G. Gardner, Songcang Chen, Denis J. Glenn, Chris L. Grigsby Hypertension. 2007; 49:419-426). The peptide hormone Atrial natriuretic peptide (ANP) and B-type natriuretic peptide (BNP), secreted from heart, and their homolog urodilatin (URO), secreted from vasculature and kidney, all activate NPRA to stimulate the production of cyclic guanosine monophosphate ("cGMP"). (Potter L R, Abbey-Hosch S, Dickey D M. Natriuretic peptides, their receptors, and cyclic guanosine monophosphate-dependent signaling functions. Endocr Rev. 2006; 27:47-72).

The biologic effects of these natriuretic peptides range from acute vassal dilation, diuresis and natriuresis to long lasting effect of anti-proliferation, tissue remodeling, and energy metabolism. Recombinant ANP (Carperitide) and BNP (Nesiritide) have been used as treatment for congestive heart failure. But the very short half-lives of these peptide hormones (2 to 20 min), and complex processing and clearance of ANP and BNP in local tissues are part of the difficulties in studying the impact of sustained activation of NPRA over long period in clinical settings. (The Pharmacokinetics of Alpha-Human Atrial Natriuretic Polypeptide in Healthy Subjects; Nakao K, Sugawara A, Morii N, Sakamoto M, Yamada T, Itoh H et al (1986). Eur J Clin Pharmacol 31:101-103). Small molecules that activate NPRA over long periods of time can mimic the beneficial effects of the natriuretic peptides.

Thus, there is a need for small molecule NPRA agonists that are useful in treating cardiometabolic diseases including high blood pressure, heart failure, kidney disease, and diabetes.

SUMMARY OF THE INVENTION

In one aspect, the present invention provides compounds of Formula I or pharmaceutically acceptable salts thereof:

I

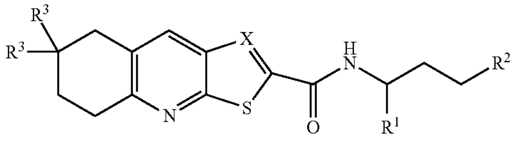

wherein

X is N or CH;

$R^1$ is selected from phenyl, pyridyl, thiazolyl, imidazolyl, pyrazinyl, and oxadiazolyl, wherein $R^1$ is substituted by 0, 1, 2, or 3, $R^5$;

$R^2$ is independently selected from:

arylC$_{0-10}$ alkyl, $C_{3-12}$ cycloalkylC$_{0-10}$ alkyl, heteroarylC$_{0-10}$ alkyl, heterocyclylC$_{0-10}$ alkyl, $C_{1-10}$alkylaminoC$_{0-10}$ alkyl, heteroaryl 1C$_{0-10}$alkylaminoC$_{0-10}$ alkyl, heterocyclylC$_{0-10}$alkylaminoC$_{0-10}$ alkyl, $C_{1-10}$ heteroalkyl aminoC$_{0-10}$ alkyl, $C_{3-12}$ cycloalkyl $C_{0-10}$ alkylaminoC$_{0-10}$ alkyl, aryl $C_{0-10}$ alkylaminoC$_{0-10}$ alkyl, amino, and ($C_{1-10}$ alkyl)$_{1-2}$ amino;

wherein $R^2$ is each substituted with 0, 1, 2, 3, or 4 $R^4$ substituents;

each $R^3$ is independently selected from hydrogen, halogen, $C_{1-6}$alkyl, and $C_{3-12}$ cycloalkyl $C_{0-10}$ alkyl, and heterocyclylC$_{0-10}$ alkyl, wherein $R^3$ is substituted by 0, 1, 2 or 3 groups independently selected from $C_{1-6}$ alkyl, $C_{1-6}$ haloalkyl, and halogen;

each $R^4$ is independently selected from:

halogen, $C_{1-10}$ alkyl, $C_{1-10}$ heteroalkyl, aryl $C_{0-10}$ alkyl, $C_{3-12}$ cycloalkyl $C_{0-10}$ alkyl, heteroaryl $C_{0-10}$ alkyl, heterocyclylC$_{0-10}$ alkyl, amino $C_{0-10}$ alkyl, (($C_{1-10}$)alkyl)$_{1-2}$amino, —$CO_2$ ($C_{1-10}$ alkyl), ($C_{0-10}$ alkyl) $CO_2H$, Oxo (=O), hydroxy, ($C_{1-10}$ alkyl)OH, $C_{1-10}$ alkoxy, cyano, and $C_{1-6}$haloalkyl;

wherein $R^4$ is each substituted with 0, 1, 2, 3, or 4 $R^8$ substituents and each $R^8$ is independently selected from: $C_{1-10}$ alkyl, —$CO_2$ ($C_{1-10}$ alkyl), —($C_{0-10}$ alkyl) $CO_2H$, $C_{1-10}$ alkoxy, halogen, $C_{1-6}$haloalkyl, cyano, oxo, hydroxy, and amino;

$R^5$ is independently selected from:

halogen, $C_{1-10}$ alkyl, aryl $C_{0-10}$ alkyl, $C_{3-12}$ cycloalkylC$_{0-10}$ alkyl, heteroaryl $C_{0-10}$ alkyl, heterocyclyl $C_{0-10}$ alkyl, $C_{1-10}$ alkylcarbonylC$_{0-10}$ alkyl, $C_{1-10}$ heteroalkylcarbonylC$_{0-10}$ alkyl, arylcarbonylC$_{0-10}$ alkyl, $(C_{3-12})$cycloalkyl carbonyl$C_{0-10}$ alkyl,
heteroarylcarbonyl$C_{0-10}$ alkyl,
heterocyclylcarbonyl$C_{0-10}$ alkyl,
$((C_{0-10})$alkyl$)_{1-2}$aminocarbonyl,
$C_{1-10}$ alkoxy,
aryl $C_{0-10}$ alkyloxy,
$C_{3-12}$ cycloalkyloxy,
heteroaryl $C_{0-10}$ alkyloxy,
heterocyclyl $C_{0-10}$ alkyloxy,
$(C_{0-10})$alkylaminocarbonyl,
$(C_{1-10})$heteroalkylaminocarbonyl,
aryl$(C_{0-10})$alkylaminocarbonyl,
$(C_{3-12})$cycloalkyl$(C_{0-10})$alkylaminocarbonyl,
heteroaryl$(C_{0-10})$alkylaminocarbonyl,
heterocyclyl$(C_{0-10})$alkylaminocarbonyl,
$C_{0-10}$ alkylcarbonylamino$C_{0-10}$ alkyl,
$C_{1-10}$ heteroalkylcarbonylamino$C_{0-10}$ alkyl,
$C_{3-12}$ cycloalkyl $C_{0-10}$ alkylcarbonylamino$C_{0-10}$ alkyl,
aryl $C_{0-10}$ alkylcarbonylamino$C_{0-10}$ alkyl,
heteroaryl $C_{0-10}$ alkylcarbonylamino$C_{0-10}$ alkyl,
heterocyclyl $C_{0-10}$ alkylcarbonylamino,
—$SO_2N(C_{1-6}$ alkyl$)_{0-2}$,
$C_{0-6}$ alkyl$S(O)_{1-2}$amino,
—$SO_2CF_3$,
—$SO_2CF_2H$,
amino,
$(C_{0-10}$ alkyl$)_{1-2}$ amino,
hydroxy,
$(C_{1-10}$ alkyl)OH,
cyano,
$C_{1-6}$haloalkyl,
—$CO_2$ $(C_{1-10}$ alkyl),
$(C_{0-10}$ alkyl) $CO_2H$,
Oxo (=O);
$C_{1-10}$ alkyl$S(O)_{1-2}$,
$C_{1-10}$ heteroalkyl $S(O)_{1-2}$,
$(C_{3-12})$cycloalkyl$S(O)_{1-2}$,
heterocyclyl $S(O)_{1-2}$,
heteroaryl$S(O)_{1-2}$, and
aryl$S(O)_{1-2}$;

wherein $R^5$ is each substituted with 0, 1, 2, 3, or 4 $R^6$;

each $R^6$ is independently selected from:
halogen,
$C_{1-10}$ alkyl,
$C_{1-6}$ haloalkyl,
$C_{1-10}$ heteroalkyl,
aryl $C_{0-10}$ alkyl,
$C_{3-12}$ cycloalkyl $C_{0-10}$ alkyl,
heteroaryl $C_{0-10}$ alkyl,
heterocyclyl $C_{0-10}$ alkyl,
amino $C_{0-10}$ alkyl,
$((C_{1-10})$alkyl$)_{1-2}$amino,
—$CO_2$ $(C_{1-10}$ alkyl),
$(C_{0-10}$ alkyl) $CO_2H$,
Oxo (=O),
hydroxy,
$(C_{1-10}$ alkyl)OH,
$C_{1-10}$ alkoxy,
cyano, and
aminocarbonyl; and wherein $R^6$ is each substituted with 0, 1, 2, or 3, $R^7$ substituents and each $R^7$ is independently selected from: $C_{1-4}$ alkyl, hydroxy, —$CO_2$ $(C_{1-6}$ alkyl), —$(C_{0-6}$ alkyl) $CO_2H$, $C_{1-6}$ alkoxy, halogen, $C_{1-6}$haloalkyl, cyano, and amino.

The Compounds of Formula I and pharmaceutically acceptable salts or prodrugs thereof may be useful, for example, for activating NPRA and for treating or preventing cardiometabolic diseases including high blood pressure, heart failure, kidney disease, and diabetes.

Accordingly, the present invention provides methods for treating or preventing cardiometabolic diseases including high blood pressure, heart failure, kidney disease, and diabetes, in a subject, comprising administering to the subject an effective amount of at least one compound of Formula I.

The present invention also includes pharmaceutical compositions containing a compound of the present invention and methods of preparing such pharmaceutical compositions.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I are agonists of Natriuretic Peptide Receptor A (NPRA) and are useful for treating or prevention of cardiometabolic diseases including high blood pressure, heart failure, kidney disease, and diabetes.

In a first embodiment of the invention, X is N and the other groups are as provided in the general formula above.

In a second embodiment of the invention, X is CH and the other groups are as provided in the general formula above.

In a third embodiment of the invention, $R^1$ is phenyl or pyridyl, wherein $R^1$ is substituted by 0, 1, 2 or 3 $R^5$, and the other groups are as provided in the general formula above, or as in the first through second embodiments.

In a fourth embodiment of the invention, $R^5$ is independently selected from: halogen, $C_{1-10}$ alkyl, aryl $C_{0-10}$ alkyl, $C_{3-12}$ cycloalkyl$C_{0-10}$ alkyl, heteroaryl $C_{0-10}$ alkyl, heterocyclyl $C_{0-10}$ alkyl, $C_{1-10}$ alkylcarbonyl$C_{0-10}$ alkyl, $C_{1-10}$ heteroalkylcarbonyl$C_{0-10}$ alkyl, arylcarbonyl$C_{0-10}$ alkyl, $(C_{3-12})$cycloalkyl carbonyl$C_{0-10}$ alkyl, heteroarylcarbonyl$C_{0-10}$ alkyl, heterocyclylcarbonyl$C_{0-10}$ alkyl, $((C_{0-10})$alkyl$)_{1-2}$aminocarbonyl, $C_{1-10}$ alkoxy, aryl $C_{0-10}$ alkyloxy, $C_{3-12}$ cycloalkyloxy, heteroaryl $C_{0-10}$ alkyloxy, heterocyclyl $C_{0-10}$ alkyloxy, $(C_{0-10})$alkylaminocarbonyl, $(C_{1-10})$heteroalkylaminocarbonyl, aryl$(C_{0-10})$alkylaminocarbonyl, $(C_{3-12})$cycloalkyl$(C_{0-10})$alkylaminocarbonyl, heteroaryl$(C_{0-10})$alkylaminocarbonyl, heterocyclyl$(C_{0-10})$alkylaminocarbonyl, $C_{0-10}$ alkylcarbonylamino$C_{0-10}$ alkyl, heterocyclyl $C_{0-10}$ alkylcarbonylamino, —$SO_2N(C_{1-6}$ alkyl$)_{0-2}$, $C_{0-6}$ alkyl$S(O)_{1-2}$amino, amino, $(C_{0-10}$ alkyl$)_{11-2}$ amino, hydroxy, —$(C_{1-10}$ alkyl)OH, cyano, $C_{1-6}$haloalkyl, —$(C_{0-10}$ alkyl) $CO_2H$, Oxo (=O), $C_{1-10}$ alkyl$S(O)_{1-2}$, wherein $R^5$ is each substituted with 0, 1, 2, 3, or 4 $R^6$; and the other groups are provided in the general formula above, or as in the first through third embodiments.

In a fifth embodiment of the invention, $R^5$ is independently selected from: halogen, aryl $C_{0-10}$ alkyl, heteroaryl $C_{0-10}$ alkyl, heterocyclyl $C_{0-10}$ alkyl, heterocyclylcarbonyl$C_{0-10}$ alkyl, $((C_{0-10})$alkyl$)_{1-2}$aminocarbonyl, $C_{1-10}$ alkoxy, aryl $C_{0-10}$ alkyloxy, heteroaryl $C_{0-10}$ alkyloxy, $(C_{0-10})$alkylaminocarbonyl, heterocyclyl$(C_{0-10})$alkylaminocarbonyl, $C_{0-10}$ alkylcarbonylamino$C_{0-10}$ alkyl, heterocyclyl $C_{0-10}$ alkylcarbonylamino, —$SO_2N(C_{1-6}$ alkyl$)_{0-2}$, $C_{0-6}$ alkyl$S(O)_{1-2}$amino, amino, and $(C_{0-10}$ alkyl$)_{1-2}$ amino, wherein $R^5$ is each substituted with 0, 1, 2, 3, or 4 $R^6$, and the other groups are provided in the general formula above, or as in the first through third embodiments.

In a sixth embodiment of the invention, $R^5$ is independently selected from: pyridyl, pyrimidinyl, furyl, pyrazolyl, thiophenyl, methylsulfonylamino, pyrrolidinylcarbamoyl, imidazolyl, triazoylyl, oxazolidinyl, azetidinylcarbamoyl, (pyrrolidinylmethyl) carbamoyl, diazaspiro[3.3]heptane-carbonyl, ethylcarbamoyl, azetidinylcarbonyl, aminocarbonyl, morpholinylcarbonyl, piperazinylcarbonyl, methylcarbamoyl, 1-oxa-3,8-diazaspiro[4.5]decanyl, imidazolidinyl, pyrrolidinylcarbonylamino, ethylcarbonylamino, thiophenyl, phenyl, 1-oxa-4,7-diazaspiro[4.4]nonane-carbonyl, 2,8-diazaspiro[3.5]nonane-carbonyl, piperidylcarbamoyl, octahydropyrrolo[2,3-b]pyrrole-carbonyl, (morpholinoethyl) carbamoyl, morpholinocarbonyl, octahydropyrrolo[3,4-b][1,4]oxazine-carbonyl, pyridazinyl, 1,2-dihydropyridazinyl, 1,2,4-thiadiazolyl, 1,2,4-triazolyl, isoxazolyl, tetrazolyl, 1,2,3,4-tetrahydropyrimidinyl, 1,2,4-thiadiazolyl, pyrrolidinyl, pyrazolyloxy, ethoxy, phenoxy, 1,2-dihydropyridinyl, —$NHS(O)_2H$, 1,3,4-oxathiazinanyl, halogen, and pyridazinyl, wherein $R^5$ is each substituted with 0, 1, 2, 3, or 4 $R^6$, and the other groups are provided in the general formula above, or as in the first through third embodiments.

In a seventh embodiment of the invention, each $R^6$ is selected from hydroxy, oxo, methyl, carboxy, fluoro, chloro, amino, hydroxyethyl, pyrrolidinylmethyl, 2,2,2-trifluoroethyl, benzyl, cyclopropyl, ethoxy, morpholinyl, cyano, trifluoromethyl, methylcarboxy, aminocarbonyl (carbamoyl), dimethylamino, dimethylsulfamoyl, ethylsulfonyl, and methoxy, wherein $R^6$ is each substituted with 0, 1, or 2, $R^7$ substituents, and the other groups are provided in the general formula above, or as in the first through sixth embodiments.

In a eighth embodiment of the invention, each $R^7$ is independently selected from: $C_{1-6}$ alkoxy, or halogen, and the other groups are provided in the general formula above, or as in the first through seventh embodiments.

In an ninth embodiment of the invention, $R^2$ is independently selected from: heteroaryl$C_{0-10}$ alkyl, heterocyclyl$C_{0-10}$ alkyl, $C_{1-10}$alkylamino$C_{0-10}$ alkyl, heteroaryl$C_{0-10}$alkylamino$C_{0-10}$ alkyl, heterocyclyl$C_{0-10}$alkylamino$C_{0-10}$ alkyl, $C_{3-12}$ cycloalkyl $C_{0-10}$ alkylamino$C_{0-10}$ alkyl, amino, and $(C_{1-10}$ alkyl$)_{1-2}$ amino; wherein $R^2$ is each substituted with 0, 1, 2, 3, or 4 $R^4$ substituents, and the other groups are provided in the general formula above, or as in the first through eighth embodiments.

In a tenth embodiment of the invention, $R^2$ is independently selected from: piperidinyl, dimethylamino, tetrahydropyranylamino, 5-azaspiro[2.5]octanyl, cyclobutylamino, 2,7-diazaspiro[4.5]decanyl, azetidinyl, oxetanylamino, cyclohexylamino, cyclopentylamino, azabicyclo[3.1.0]hexanyl, pyrrolidinyl, diethylamino, tetrazolyl, 1-oxa-3-azaspiro[4.5]decanyl, methylamino, ethylamino, 2-oxa-5-azabicyclo[2.2.1]heptanyl, piperidylamino, pyrrolidinylamino, piperazinyl, (tetrahydrofuranyl)amino, morpholinyl, N-methylethylamino, octahydro-2H-pyrano[3,2-c]pyridine, oxazepanyl, 1,2,3,6-tetrahydropyridyl, cyclopropylamino, isobutylamino, (pyrazolylmethyl)amino, and diazepanyl; wherein $R^2$ is each substituted with 0, 1, 2, 3, or 4 $R^4$ substituents, and the other groups are provided in the general formula above, or as in the first through eighth embodiments.

In a eleventh embodiment of the invention, each $R^4$ is independently selected from: halogen, $C_{1-10}$ alkyl, aryl $C_{0-10}$ alkyl, $C_{3-12}$ cycloalkyl $C_{0-10}$ alkyl, heteroaryl $C_{0-10}$ alkyl, amino $C_{0-10}$ alkyl, $((C_{1-10})$alkyl$)_{1-2}$amino, —$CO_2$ ($C_{1-10}$ alkyl), —($C_{0-10}$ alkyl) $CO_2H$, Oxo, hydroxy, —($C_{1-10}$ alkyl) OH, $C_{1-10}$ alkoxy, cyano, and $C_{1-6}$haloalkyl; wherein $R^4$ is each substituted with 0, 1, 2, 3, or 4 $R^8$ substituents, and the other groups are provided in the general formula above, or as in the first through tenth embodiments.

In an twelfth embodiment of the invention, $R^4$ is independently selected from: hydroxy, halogen, hydroxymethyl, methyl, imidazolyl, pyridyl, oxo, dimethylamino, 1,2,4-triazolyl, tetrazolyl, carboxy, aminomethyl, difluoromethyl, cyano, carboxymethyl, hydroxyethyl, phenyl, methoxycarbonylmethyl, methylcarboxy, aminomethyl, and trifluoromethyl, wherein $R^4$ is each substituted with 0, 1, 2, 3, or 4 $R^8$, and the other groups are provided in the general formula above, or as in the first through tenth embodiments.

In a thirteenth embodiment of the invention, each $R^8$ is independently selected from: methyl, ethyl, propyl, methoxy, ethoxy, amino or carboxy, and the other groups are provided in the general formula above, or as in the first through twelfth embodiments.

In a fourteenth embodiment of the invention, each $R^8$ is independently selected from: methoxy or carboxy, and the other groups are provided in the general formula above, or as in the first through twelfth embodiments.

In a fifteenth embodiment of the invention, each $R^3$ is independently selected from hydrogen, halogen, $C_{1-6}$alkyl, and $C_{3-12}$ cycloalkyl $C_{0-10}$ alkyl, wherein $R^3$ is substituted by 0, 1, 2 or 3 groups independently selected from $C_{1-6}$ alkyl, $C_{1-6}$ haloalkyl, and halogen, and the other groups are provided in the general formula above, or as in the first through fourteenth embodiments.

In a sixteenth embodiment of the invention, each $R^3$ is independently selected from hydrogen, fluoro, isopropyl, tert-butyl, and cyclopropyl, wherein $R^3$ is substituted by 0, 1, 2 or 3 groups independently selected from $C_{1-6}$ alkyl, $C_{1-6}$ haloalkyl, and halogen, and the other groups are provided in the general formula above, or as in the first through fourteenth embodiments. Non-limiting examples of the Compounds of Formula I include compounds 1-15 as set forth in the Examples below:

ammonium;5-[4-[(1R)-3-(1-piperidyl)-1-[[(6S)-6-tert-butyl-5,6,7,8-tetrahydrothieno[2,3-b]quinoline-2-carbonyl]amino]propyl]phenyl]yridine-2-olate;

(6S)-6-tert-butyl-N-[(1R)-1-[4-(2-oxo-1H-pyrimidin-5-yl)phenyl]-3-(1-piperidyl)propyl]-5,6,7,8-tetrahydrothieno[2,3-b]quinoline-2-carboxamide;

(6S)-6-tert-butyl-N-[(1R)-1-[4-(3-furyl)phenyl]-3-(1-piperidyl)propyl]-5,6,7,8-tetrahydrothieno[2,3-b]quinoline-2-carboxamide;

(6S)-6-tert-butyl-N-[(1R)-1-[4-(3-furyl)phenyl]-3-(1-piperidyl)propyl]-5,6,7,8-tetrahydrothieno[2,3-b]quinoline-2-carboxamide;

(6S)-6-tert-butyl-N-[(1R)-1-[4-(2-methylpyrazol-3-yl)phenyl]-3-(1-piperidyl)propyl]-5,6,7,8-tetrahydrothieno[2,3-b]quinoline-2-carboxamide;

(6S)-6-tert-butyl-N-[(1R)-3-(1-piperidyl)-1-[4-(1H-pyrazol-4-yl)phenyl]propyl]-5,6,7,8-tetrahydrothieno[2,3-b]quinoline-2-carboxamide;

ammonium;4-[4-[(1R)-3-(1-piperidyl)-1-[[(6S)-6-tert-butyl-5,6,7,8-tetrahydrothieno[2,3-b]quinoline-2-carbonyl]amino]propyl]phenyl]thiophene-2-carboxylate;

(6S)-6-tert-butyl-N-[(1R)-3-(1-piperidyl)-1-(4-pyrimidin-5-ylphenyl)propyl]-5,6,7,8-tetrahydrothieno[2,3-b]quinoline-2-carboxamide;

ammonium; methylsulfonyl-[3-[(1R)-3-(4-hydroxy-1-piperidyl)-1-[[(6S)-6-tert-butyl-5,6,7,8-tetrahydrothieno[2,3-b]quinoline-2-carbonyl]amino]propyl]phenyl]azanide;

ammonium methylsulfonyl-[3-[(1R)-3-(dimethylamino)-1-[[(6S)-6-tert-butyl-5,6,7,8-tetrahydrothieno[2,3-b]quinoline-2-carbonyl]amino]propyl]phenyl]azanide;

ammonium methylsulfonyl-[3-[(1R)-1-[[(6S)-6-tert-butyl-5,6,7,8-tetrahydrothieno[2,3-b]quinoline-2-carbonyl]amino]-3-(tetrahydropyran-4-ylamino) propyl]phenyl]azanide;

ammonium; methylsulfonyl-[3-[(1R)-3-(1-piperidyl)-1-[[(6S)-6-tert-butyl-5,6,7,8-tetrahydrothieno[2,3-b]quinoline-2-carbonyl]amino]propyl]phenyl]azanide;

ammonium methylsulfonyl-[3-[(1R)-3-(3-hydroxy-1-piperidyl)-1-[[(6S)-6-tert-butyl-5,6,7,8-tetrahydrothieno[2,3-b]quinoline-2-carbonyl]amino]propyl]phenyl]azanide;

ammonium methylsulfonyl-[3-[(1R)-3-(5-azaspiro[2.5]octan-5-yl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(4-fluoro-1-piperidyl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-[[1-(hydroxymethyl)cyclobutyl]amino]-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(3-hydroxy-3-methyl-azetidin-1-yl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(4-imidazol-1-yl-1-piperidyl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-[3-(3-pyridyl)-1-piperidyl]-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(1-oxo-2,9-diazaspiro[4.5]decan-9-yl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(azetidin-1-yl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(oxetan-3-ylamino)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-[3-(2-pyridyl) azetidin-1-yl]-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-[4-(2-pyridyl)-1-piperidyl]-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-1-[[(6S)-6-tert-butyl-5,6,7,8-tetrahydrothieno[2,3-b]quinoline-2-carbonyl]amino]-3-[[(1S,2R)-3,3-difluoro-2-hydroxy-cyclohexyl]amino]propyl]phenyl]azanide;

dimethyl-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

[(1S,2R,3S,4S)-2,3-dihydroxy-4-(hydroxymethyl)cyclopentyl]-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-[6-(hydroxymethyl)-3-azoniabicyclo[3.1.0]hexan-3-yl]-1-[4-(6-oxo-1H-pyridin-3-yl)phenyl]propyl]-5,6,7,8-tetrahydrothieno[2,3-b]quinoline-2-carboxamide;formate;

dimethyl-[1-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]-4-piperidyl]ammonium; formate;

(6S)-6-tert-butyl-N-[(1R)-1-[4-(6-oxo-1H-pyridin-3-yl)phenyl]-3-[4-(1,2,4-triazol-4-yl)piperidin-1-ium-1-yl]propyl]-5,6,7,8-tetrahydrothieno[2,3-b]quinoline-2-carboxamide;formate;

(6S)-6-tert-butyl-N-[(1R)-3-[2-(hydroxymethyl)piperidin-1-ium-1-yl]-1-[4-(6-oxo-1H-pyridin-3-yl)phenyl]propyl]-5,6,7,8-tetrahydrothieno[2,3-b]quinoline-2-carboxamide;formate;

(6S)-6-tert-butyl-N-[(1R)-1-[4-(6-oxo-1H-pyridin-3-yl)phenyl]-3-[(2R,3S)-3-hydroxy-2-(hydroxymethyl)piperidin-1-ium-1-yl]propyl]-5,6,7,8-tetrahydrothieno[2,3-b]quinoline-2-carboxamide;formate;

(6S)-6-tert-butyl-N-[(1R)-1-[4-(6-oxo-1H-pyridin-3-yl)phenyl]-3-piperidin-1-ium-1-yl-propyl]-5,6,7,8-tetrahydrothieno[2,3-b]quinoline-2-carboxamide;formate;

(6S)-6-tert-butyl-N-[(1R)-1-[4-(6-oxo-1H-pyridin-3-yl)phenyl]-3-pyrrolidin-1-ium-1-yl-propyl]-5,6,7,8-tetrahydrothieno[2,3-b]quinoline-2-carboxamide;formate;

(6S)-6-tert-butyl-N-[(1R)-3-[bis(2-hydroxyethyl)amino]-1-[4-(6-oxo-1H-pyridin-3-yl)phenyl]propyl]-5,6,7,8-tetrahydrothieno[2,3-b]quinoline-2-carboxamide;

(6S)-6-tert-butyl-N-[(1R)-1-[4-(6-oxo-1H-pyridin-3-yl)phenyl]-3-[4-(tetrazol-2-yl)piperidin-1-ium-1-yl]propyl]-5,6,7,8-tetrahydrothieno[2,3-b]quinoline-2-carboxamide;formate;

[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]-tetrahydropyran-4-yl-ammonium;formate;

[(3R,4S)-3,4-dihydroxycyclopentyl]-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-1-[4-(6-oxo-1H-pyridin-3-yl)phenyl]-3-[(2S)-2-(hydroxymethyl)pyrrolidin-1-ium-1-yl]propyl]-5,6,7,8-tetrahydrothieno[2,3-b]quinoline-2-carboxamide;formate;

[(3R,4S)-3,4-dihydroxycyclopentyl]-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-(2-oxo-1-oxa-3-aza-8-azoniaspiro[4.5]decan-8-yl)-1-[4-(6-oxo-1H-pyridin-3-yl)phenyl]propyl]-5,6,7,8-tetrahydrothieno[2,3-b]quinoline-2-carboxamide;formate;

(6S)-6-tert-butyl-N-[(1R)-3-(3-hydroxypyrrolidin-1-ium-1-yl)-1-[4-(6-oxo-1H-pyridin-3-yl)phenyl]propyl]-5,6,7,8-tetrahydrothieno[2,3-b]quinoline-2-carboxamide;formate;

(6S)-6-tert-butyl-N-[(1R)-3-(methylamino)-1-[4-(6-oxo-1H-pyridin-3-yl)phenyl]propyl]-5,6,7,8-tetrahydrothieno[2,3-b]quinoline-2-carboxamide;

(6S)-6-tert-butyl-N-[(1R)-1-[4-(6-oxo-1H-pyridin-3-yl)phenyl]-3-[(2S)-2-(methoxymethyl)pyrrolidin-1-yl]propyl]-5,6,7,8-tetrahydrothieno[2,3-b]quinoline-2-carboxamide;

1-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]piperidin-1-ium-4-carboxylic acid; formate;

(6S)-6-tert-butyl-N-[(1R)-3-(4-hydroxy-4-methyl-piperidin-1-ium-1-yl)-1-[4-(6-oxo-1H-pyridin-3-yl)phenyl]propyl]-5,6,7,8-tetrahydrothieno[2,3-b]quinoline-2-carboxamide;formate;

[3-methyl-1-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]azetidin-3-yl]methylammonium;formate;

(6S)-6-tert-butyl-N-[(1R)-3-(5-azoniaspiro[2.5]octan-5-yl)-1-[4-(6-oxo-1H-pyridin-3-yl)phenyl]propyl]-5,6,7,8-tetrahydrothieno[2,3-b]quinoline-2-carboxamide;formate;

(6S)-6-tert-butyl-N-[(1R)-3-(3-hydroxyazetidin-1-ium-1-yl)-1-[4-(6-oxo-1H-pyridin-3-yl)phenyl]propyl]-5,6,7,8-tetrahydrothieno[2,3-b]quinoline-2-carboxamide;formate;

2-hydroxyethyl-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

cyclopentyl-methyl-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-1-[4-(6-oxo-1H-pyridin-3-yl)phenyl]-3-[(3R,4R)-3,4-dihydroxypyrrolidin-1-ium-1-yl]propyl]-5,6,7,8-tetrahydrothieno[2,3-b]quinoline-2-carboxamide;formate;

cyclopentyl-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-(2-oxa-5-azoniabicyclo[2.2.1]heptan-5-yl)-1-[4-(6-oxo-1H-pyridin-3-yl)phenyl]propyl]-5,6,7,8-tetrahydrothieno[2,3-b]quinoline-2-carboxamide;formate;

(2-oxo-4-piperidyl)-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-(3-hydroxypiperidin-1-ium-1-yl)-1-[4-(6-oxo-1H-pyridin-3-yl)phenyl]propyl]-5,6,7,8-tetrahydrothieno[2,3-b]quinoline-2-carboxamide;formate;

1-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]piperidin-1-ium-3-carboxylic acid; formate;

(5-oxopyrrolidin-3-yl)-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-1-[4-(6-oxo-1H-pyridin-3-yl)phenyl]-3-[3-(2H-tetrazol-5-yl)pyrrolidin-1-ium-1-yl]propyl]-5,6,7,8-tetrahydrothieno[2,3-b]quinoline-2-carboxamide;formate;

(6S)-6-tert-butyl-N-[(1R)-3-(4-fluoropiperidin-1-ium-1-yl)-1-[4-(6-oxo-1H-pyridin-3-yl)phenyl]propyl]-5,6,7,8-tetrahydrothieno[2,3-b]quinoline-2-carboxamide;formate;

(6S)-6-tert-butyl-N-[(1R)-3-[4-(difluoromethyl)piperidin-1-ium-1-yl]-1-[4-(6-oxo-1H-pyridin-3-yl)phenyl]propyl]-5,6,7,8-tetrahydrothieno[2,3-b]quinoline-2-carboxamide; formate;

(6S)-6-tert-butyl-N-[(1R)-1-[4-(6-oxo-1H-pyridin-3-yl)phenyl]-3-[(3S,4R)-3,4-dihydroxypyrrolidin-1-ium-1-yl]propyl]-5,6,7,8-tetrahydrothieno[2,3-b]quinoline-2-carboxamide;formate;

[(1R,2S,3R,4R)-2,3-dihydroxy-4-(hydroxymethyl)cyclopentyl]-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-(4-methoxypiperidin-1-ium-1-yl)-1-[4-(6-oxo-1H-pyridin-3-yl)phenyl]propyl]-5,6,7,8-tetrahydrothieno[2,3-b]quinoline-2-carboxamide;formate;

(1-methylazetidin-3-yl)-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-(3-hydroxy-3-methyl-azetidin-1-ium-1-yl)-1-[4-(6-oxo-1H-pyridin-3-yl)phenyl]propyl]-5,6,7,8-tetrahydrothieno[2,3-b]quinoline-2-carboxamide;formate;

(6S)-6-tert-butyl-N-[(1R)-3-[4-(2-methoxyethyl)piperazin-1-yl]-1-[4-(6-oxo-1H-pyridin-3-yl)phenyl]propyl]-5,6,7,8-tetrahydrothieno[2,3-b]quinoline-2-carboxamide;

(2-oxopyrrolidin-3-yl)-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-(4-cyanopiperidin-1-ium-1-yl)-1-[4-(6-oxo-1H-pyridin-3-yl)phenyl]propyl]-5,6,7,8-tetrahydrothieno[2,3-b]quinoline-2-carboxamide;formate;

[(3S,4R)-4-hydroxytetrahydrofuran-3-yl]-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-1-[4-(6-oxo-1H-pyridin-3-yl)phenyl]-3-[(3S,4S)-3-(dimethylamino)-4-hydroxy-pyrrolidin-1-ium-1-yl]propyl]-5,6,7,8-tetrahydrothieno[2,3-b]quinoline-2-carboxamide;formate;

(6S)-6-tert-butyl-N-[(1R)-1-[4-(6-oxo-1H-pyridin-3-yl)phenyl]-3-[(2S,4R)-4-hydroxy-2-(hydroxymethyl)pyrrolidin-1-ium-1-yl]propyl]-5,6,7,8-tetrahydrothieno[2,3-b]quinoline-2-carboxamide;formate;

(6S)-6-tert-butyl-N-[(1R)-3-morpholino-1-[4-[[(3S,4S)-4-hydroxypyrrolidin-3-yl]carbamoyl]phenyl]propyl]-5,6,7,8-tetrahydrothieno[2,3-b]quinoline-2-carboxamide;

(7S)-7-tert-butyl-N-[(1R)-3-(4-hydroxy-1-piperidyl)-1-[4-(6-oxo-1H-pyridin-3-yl)phenyl]propyl]-5,6,7,8-tetrahydrothiazolo[5,4-b]quinoline-2-carboxamide;

(7S)-7-tert-butyl-N-[(1R)-3-[3-(hydroxymethyl)pyrrolidin-1-yl]-1-[4-(6-oxo-1H-pyridin-3-yl)phenyl]propyl]-5,6,7,8-tetrahydrothiazolo[5,4-b]quinoline-2-carboxamide;

(7S)-7-tert-butyl-N-[(1R)-1-[4-(6-oxo-1H-pyridin-3-yl)phenyl]-3-(tetrahydropyran-4-ylamino) propyl]-5,6,7,8-tetrahydrothiazolo[5,4-b]quinoline-2-carboxamide;

(7S)-7-tert-butyl-N-[(1R)-3-(dimethylamino)-1-[4-(6-oxo-1H-pyridin-3-yl)phenyl]propyl]-5,6,7,8-tetrahydrothiazolo[5,4-b]quinoline-2-carboxamide;

(7S)-7-tert-butyl-N-[(1R)-3-(3,3-dimethylazetidin-1-yl)-1-[4-(6-oxo-1H-pyridin-3-yl)phenyl]propyl]-5,6,7,8-tetrahydrothiazolo[5,4-b]quinoline-2-carboxamide;

(7S)-7-tert-butyl-N-[(1R)-3-(3-hydroxypyrrolidin-1-yl)-1-[4-(6-oxo-1H-pyridin-3-yl)phenyl]propyl]-5,6,7,8-tetrahydrothiazolo[5,4-b]quinoline-2-carboxamide;

(7S)-7-tert-butyl-N-[(1R)-3-(4-hydroxypiperidin-1-ium-1-yl)-1-[4-(6-oxo-1H-pyridin-3-yl)phenyl]propyl]-5,6,7,8-tetrahydrothiazolo[5,4-b]quinoline-2-carboxamide;formate;

(7S)-7-tert-butyl-N-[(1R)-3-(4-hydroxypiperidin-1-ium-1-yl)-1-[4-(1H-pyrazol-4-yl)phenyl]propyl]-5,6,7,8-tetrahydrothiazolo[5,4-b]quinoline-2-carboxamide;formate;

(7S)-7-tert-butyl-N-[(1R)-3-(4-hydroxypiperidin-1-ium-1-yl)-1-[4-(2-methylpyrazol-3-yl)phenyl]propyl]-5,6,7,8-tetrahydrothiazolo[5,4-b]quinoline-2-carboxamide;formate;

(7S)-7-tert-butyl-N-[(1R)-1-[4-(5-fluoro-6-hydroxy-3-pyridyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxypiperidin-1-ium-1-yl)-1-(4-imidazol-1-ylphenyl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-[4-(1,2,4-triazol-1-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxy-1-piperidyl)-1-[4-(2-oxooxazolidin-3-yl)phenyl]propyl]-5,6,7,8-tetrahydrothiazolo[5,4-b]quinoline-2-carboxamide;

(7S)-7-tert-butyl-N-[(1R)-3-(dimethylamino)-1-[3-[(1-methylazetidin-3-yl) carbamoyl]phenyl]propyl]-5,6,7,8-tetrahydrothiazolo[5,4-b]quinoline-2-carboxamide;

(7S)-7-tert-butyl-N-[(1R)-3-(dimethylamino)-1-[3-[[(3S)-1-methylpyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-3-(dimethylamino)-1-[3-[(1-methylpyrrolidin-3-yl)methylcarbamoyl]phenyl]propyl]-5,6,7,8-tetrahydrothiazolo[5,4-b]quinoline-2-carboxamide;

(7S)-7-tert-butyl-N-[(1R)-3-(dimethylamino)-1-[3-[(3S)-pyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-3-(dimethylamino)-1-[3-[[(3R,4R)-4-hydroxypyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-1-[3-(2,6-diazaspiro[3.3]heptane-2-carbonyl)phenyl]-3-(dimethylamino) propyl]-5,6,7,8-tetrahydrothiazolo[5,4-b]quinoline-2-carboxamide;

(7S)-7-tert-butyl-N-[(1R)-1-[3-(2-aminoethylcarbamoyl) phenyl]-3-(dimethylamino) propyl]-5,6,7,8-tetrahydrothiazolo[5,4-b]quinoline-2-carboxamide;

(7S)-7-tert-butyl-N-[(1R)-3-(dimethylamino)-1-[3-(3-hydroxy-3-methyl-azetidine-1-carbonyl)phenyl]propyl]-5,6,7,8-tetrahydrothiazolo[5,4-b]quinoline-2-carboxamide;

(7S)-7-tert-butyl-N-[(1R)-1-[3-(3-aminoazetidine-1-carbonyl)phenyl]-3-(dimethylamino) propyl]-5,6,7,8-tetrahydrothiazolo[5,4-b]quinoline-2-carboxamide;

(7S)-7-tert-butyl-N-[(1R)-3-(dimethylamino)-1-[3-(2-hydroxyethylcarbamoyl)phenyl]propyl]-5,6,7,8-tetrahydrothiazolo[5,4-b]quinoline-2-carboxamide;

(7S)-7-tert-butyl-N-[(1R)-3-(dimethylamino)-1-[3-(morpholine-4-carbonyl)phenyl]propyl]-5,6,7,8-tetrahydrothiazolo[5,4-b]quinoline-2-carboxamide;

(7S)-7-tert-butyl-N-[(1R)-3-(dimethylamino)-1-[3-(piperazine-1-carbonyl)phenyl]propyl]-5,6,7,8-tetrahydrothiazolo[5,4-b]quinoline-2-carboxamide;

(7S)-7-tert-butyl-N-[(1R)-3-(dimethylamino)-1-[3-(methylcarbamoyl)phenyl]propyl]-5,6,7,8-tetrahydrothiazolo[5,4-b]quinoline-2-carboxamide;

(7S)-7-tert-butyl-N-[(1R)-1-(3-carbamoylphenyl)-3-(dimethylamino) propyl]-5,6,7,8-tetrahydrothiazolo[5,4-b]quinoline-2-carboxamide;

(7S)-7-tert-butyl-N-[(1R)-3-(dimethylamino)-1-[3-[[1-(2,2,2-trifluoroethyl)pyrrolidin-3-yl]carbamoyl]phenyl]propyl]-5,6,7,8-tetrahydrothiazolo[5,4-b]quinoline-2-carboxamide;

2-[1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]-4-piperidyl]acetic acid;2,2,2-trifluoroacetate;

(7S)-7-tert-butyl-N-[(1R)-3-[4-(2-hydroxyethyl)-1-piperidyl]-1-[3-[(1-methylazetidin-1-ium-3-yl) carbamoyl]phenyl]propyl]-5,6,7,8-tetrahydrothiazolo[5,4-b]quinoline-2-carboxamide;2,2,2-trifluoroacetate;

(7S)-7-tert-butyl-N-[(1R)-1-[3-[(1-methylazetidin-1-ium-3-yl) carbamoyl]phenyl]-3-[4-(1H-tetrazol-5-yl)-1-piperidyl]propyl]-5,6,7,8-tetrahydrothiazolo[5,4-b]quinoline-2-carboxamide;2,2,2-trifluoroacetate;

(7S)-7-tert-butyl-N-[(1R)-3-[4-(hydroxymethyl)-1-piperidyl]-1-[3-[(1-methylazetidin-1-ium-3-yl) carbamoyl]phenyl]propyl]-5,6,7,8-tetrahydrothiazolo[5,4-b]quinoline-2-carboxamide;2,2,2-trifluoroacetate;

4-[1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]-4-piperidyl]benzoic acid;2,2,2-trifluoroacetate;

2-[(2S)-1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]pyrrolidin-2-yl]acetic acid;2,2,2-trifluoroacetate;

3-[1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]-4-piperidyl]benzoic acid;2,2,2-trifluoroacetate;

3-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]-3-azabicyclo[3.1.0]hexane-6-carboxylic acid;2,2,2-trifluoroacetate;

(7S)-7-tert-butyl-N-[(1R)-3-(4-methoxy-1-piperidyl)-1-[3-[(1-methylazetidin-1-ium-3-yl) carbamoyl]phenyl]propyl]-5,6,7,8-tetrahydrothiazolo[5,4-b]quinoline-2-carboxamide;2,2,2-trifluoroacetate;

methyl 2-[1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]-4-piperidyl]acetate;2,2,2-trifluoroacetate;

3-[methyl-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]amino]propanoic acid;2,2,2-trifluoroacetate;

(3R)-1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]pyrrolidine-3-carboxylic acid;2,2,2-trifluoroacetate;

(3S)-1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]pyrrolidine-3-carboxylic acid;2,2,2-trifluoroacetate;

methyl 1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]piperidine-4-carboxylate;2,2,2-trifluoroacetate;

carboxymethyl-[(3R)-3-[3-[(1-methylazetidin-3-yl) carbamoyl]phenyl]-3-[[(7S)-7-tert-butyl-5,6,7,8-tetrahydrothiazolo[5,4-b]quinoline-2-carbonyl]amino]propyl]ammonium;2,2,2-trifluoroacetate;

(7S)-7-tert-butyl-N-[(1R)-3-(4-hydroxy-1-piperidyl)-1-[3-(2-oxo-1-oxa-3-aza-8-azoniaspiro[4.5]decan-3-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-[3-(2-oxoimidazolidin-1-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxy-1-piperidyl)-1-[3-(pyrrolidin-1-ium-3-carbonylamino)phenyl]propyl]-5,6,7,8-tetrahydrothiazolo[5,4-b]quinoline-2-carboxamide;2,2,2 trifluoroacetate;

[3-oxo-3-[3-[(1R)-3-(4-hydroxy-1-piperidyl)-1-[[(7S)-7-tert-butyl-5,6,7,8-tetrahydrothiazolo[5,4-b]quinoline-2-carbonyl]amino]propyl]anilino]propyl]ammonium;2,2,2-trifluoroacetate;

(7S)-7-tert-butyl-N-[(1R)-3-(4-hydroxypiperidin-1-ium-1-yl)-1-[3-(2-oxooxazolidin-3-yl)phenyl]propyl]-5,6,7,8-tetrahydrothiazolo[5,4-b]quinoline-2-carboxamide;2,2,2-trifluoroacetate;

1-[(3R)-3-[3-[(1-methylpyrrolidin-3-yl) carbamoyl]phenyl]-3-[[(7S)-7-tert-butyl-5,6,7,8-tetrahydrothiazolo[5,4-b]quinoline-2-carbonyl]amino]propyl]piperidine-4-carboxylic acid;

1-[(3R)-3-[3-(azetidin-1-ium-3-ylcarbamoyl)phenyl]-3-[[(7S)-7-tert-butyl-5,6,7,8-tetrahydrothiazolo[5,4-b]quinoline-2-carbonyl]amino]propyl]piperidine-4-carboxylic acid;2,2,2-trifluoroacetate;

1-[(3R)-3-[3-[(1-benzylazetidin-3-yl) carbamoyl]phenyl]-3-[[(7S)-7-tert-butyl-5,6,7,8-tetrahydrothiazolo[5,4-b]quinoline-2-carbonyl]amino]propyl]piperidin-1-ium-4-carboxylic acid;2,2,2-trifluoroacetate;

1-[(3R)-3-[3-[(1-cyclopropylpyrrolidin-3-yl) carbamoyl]phenyl]-3-[[(7S)-7-tert-butyl-5,6,7,8-tetrahydrothiazolo[5,4-b]quinoline-2-carbonyl]amino]propyl]piperidin-1-ium-4-carboxylic acid;2,2,2-trifluoroacetate;

1-[(3R)-3-[3-[(3-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]piperidine-4-carboxylic acid;2,2,2-trifluoroacetate;

4-[4-[(1R)-3-(4-hydroxy-1-piperidyl)-1-[[(7S)-7-tert-butyl-5,6,7,8-tetrahydrothiazolo[5,4-b]quinoline-2-carbonyl]amino]propyl]phenyl]thiophene-2-carboxylic acid;

(7S)-7-tert-butyl-N-[(1R)-3-(4-hydroxypiperidin-1-ium-1-yl)-1-[4-(2-oxo-1H-pyrimidin-5-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-1-[4-[6-(2-fluoroethoxy)-3-pyridyl]phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-1-[4-(4-hydroxyphenyl)phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxy-1-piperidyl)-1-[3-[[(3R)-pyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-1-[3-(2,8-diazaspiro[3.5]nonane-2-carbonyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[3-(pyrrolidin-1-ylmethyl) azetidine-1-carbonyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(4-piperidylcarbamoyl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[[(3R)-1-methylpyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[[(3R,4R)-4-hydroxypyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-1-[3-(azetidin-3-ylcarbamoyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[[(3S,4S)-4-hydroxypyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[[(3S)-1-methylpyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-1-[3-[(2,2-dimethylpyrrolidin-3-yl) carbamoyl]phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methyl-3-piperidyl) carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methyl-4-piperidyl) carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methylpyrrolidin-3-yl)methylcarbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(3-piperidylcarbamoyl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(5-methyl-6-oxo-7-oxa-2,5-diazaspiro[3.4]octane-2-carbonyl)phenyl]propyl]-5,6,7,8-tetrahydrothiazolo[5,4-b]quinoline-2-carboxamide;

(7S)-7-tert-butyl-N-[(1R)-1-[3-(3-hydroxy-3-methyl-azetidine-1-carbonyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-1-[3-(2,3,3a,5,6,6a-hexahydro-1H-pyrrolo[3,2-b]pyrrole-4-carbonyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-1-[3-(3-aminoazetidine-1-carbonyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-1-[3-[3-(dimethylamino) azetidine-1-carbonyl]phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methyl-5-oxo-pyrrolidin-3-yl) carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(2-morpholinoethylcarbamoyl)phenyl]propyl]-5,6,7,8-tetrahydrothiazolo[5,4-b]quinoline-2-carboxamide;

(7S)-7-tert-butyl-N-[(1R)-1-[3-(2-hydroxyethylcarbamoyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(pyrrolidin-3-ylmethylcarbamoyl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[3-hydroxy-3-(trifluoromethyl) azetidine-1-carbonyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(2-oxopyrrolidin-3-yl) carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(5-oxopyrrolidin-3-yl) carbamoyl]phenyl]propyl]-5,6,7,8-tetrahydrothiazolo[5,4-b]quinoline-2-carboxamide;

(7S)-7-tert-butyl-N-[(1R)-1-[3-(3-hydroxyazetidine-1-carbonyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(3-morpholinoazetidine-1-carbonyl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methyl-6-oxo-3-piperidyl) carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methyl-5-oxo-pyrrolidin-3-yl)methylcarbamoyl]phenyl]propyl]-5,6,7,8-tetrahydrothiazolo[5,4-b]quinoline-2-carboxamide;

methyl 4-[3-[(1R)-3-(4-hydroxy-1-piperidyl)-1-[[(7S)-7-tert-butyl-5,6,7,8-tetrahydrothiazolo[5,4-b]quinoline-2-carbonyl]amino]propyl]benzoyl]morpholine-2-carboxylate;

(7S)-7-tert-butyl-N-[(1R)-3-(4-hydroxy-1-piperidyl)-1-[3-[(4aR,7aS)-3,4a,5,6,7,7a-hexahydro-2H-pyrrolo[3,4-b][1,4]oxazine-4-carbonyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-(4-pyridazin-4-ylphenyl)propyl]-5,6,7,8-tetrahydrothiazolo[5,4-b]quinoline-2-carboxamide;

(7S)-7-tert-butyl-N-[(1R)-3-(4-hydroxypiperidin-1-ium-1-yl)-1-[4-(1-oxidopyridazin-1-ium-4-yl)phenyl]propyl]-5,6,7,8-tetrahydrothiazolo[5,4-b]quinoline-2-carboxamide; 2,2,2-trifluoroacetate;

(7S)-7-tert-butyl-N-[(1R)-3-(4-hydroxypiperidin-1-ium-1-yl)-1-[4-(6-hydroxy-3-pyridyl)phenyl]propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-[4-(6-hydroxypyridazin-3-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-1-[4-(3-cyano-1H-pyrazol-4-yl) phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-[4-[3-(trifluoromethyl)-1H-pyrazol-4-yl]phenyl] propyl]-5,6,7,8-tetrahydrothiazolo[5,4-b]quinoline-2-carboxamide;2,2,2-trifluoroacetate;

(7S)-7-tert-butyl-N-[(1R)-1-[4-(2-amino-4-pyridyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(1,2,4-thiadiazol-5-yl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(4-methyl-1,2,4-triazol-3-yl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(3-methyl-1H-pyrazol-4-yl)phenyl]propyl]-5,6,7,8-tetrahydrothiazolo[5,4-b]quinoline-2-carboxamide;

(7S)-7-tert-butyl-N-[(1R)-1-[4-(5-cyano-6-hydroxy-3-pyridyl)phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-1-[4-(3,5-dimethyl-1H-pyrazol-4-yl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(5-methyl-1H-imidazol-4-yl)phenyl]propyl]-5,6,7,8-tetrahydrothiazolo[5,4-b]quinoline-2-carboxamide;

(7S)-7-tert-butyl-N-[(1R)-1-[4-(3-amino-4-pyridyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxypiperidin-1-ium-1-yl)-1-(4-isoxazol-4-ylphenyl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-[4-(1-methyltetrazol-5-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-1-[4-(5-cyano-1H-imidazol-4-yl) phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(3-methylimidazol-4-yl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-(4-isothiazol-4-ylphenyl)propyl]-5,6,7,8-tetrahydrothiazolo[5,4-b]quinoline-2-carboxamide;

(7S)-7-tert-butyl-N-[(1R)-1-[4-(3-fluoro-5-hydroxy-2-pyridyl)phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-1-[4-(2,4-dioxo-1H-pyrimidin-6-yl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(1,2,5-thiadiazol-3-yl)phenyl]propyl]-5,6,7,8-tetrahydrothiazolo[5,4-b]quinoline-2-carboxamide;

(7S)-7-tert-butyl-N-[(1R)-1-[4-(3,5-difluoro-4-hydroxyphenyl)phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-(4-thiazol-5-ylphenyl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxy-1-piperidyl)-1-[6-(2-oxooxazolidin-3-yl)-3-pyridyl]propyl]-5,6,7,8-tetrahydrothiazolo[5,4-b]quinoline-2-carboxamide;

ammonium;3,5-dimethyl-1-[5-[(1R)-3-(4-hydroxy-1-piperidyl)-1-[[(7S)-7-tert-butyl-5,6,7,8-tetrahydrothiazolo[5,4-b]quinoline-2-carbonyl]amino]propyl]-2-pyridyl]pyrazol-4-olate;

(7S)-7-tert-butyl-N-[(1R)-1-[6-(3-hydroxy-2-oxo-pyrrolidin-1-yl)-3-pyridyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[6-(4-hydroxy-1-piperidyl)-3-pyridyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[6-(3-hydroxypyrrolidin-1-yl)-3-pyridyl]propyl]-5,6,7,8-tetrahydrothiazolo[5,4-b]quinoline-2-carboxamide;

(7S)-7-tert-butyl-N-[(1R)-1-[6-[(3,5-dimethyl-1H-pyrazol-4-yl)oxy]-3-pyridyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-1-[6-(2-hydroxyethoxy)-3-pyridyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-1-[6-(2-amino-2-oxo-ethoxy)-3-pyridyl]-3-(4-hydroxy-1-piperidyl)propyl]-5,6,7,8-tetrahydrothiazolo[5,4-b]quinoline-2-carboxamide;

ammonium; 4-[[5-[(1R)-3-(4-hydroxy-1-piperidyl)-1-[[(7S)-7-tert-butyl-5,6,7,8-tetrahydrothiazolo[5,4-b]quinoline-2-carbonyl]amino]propyl]-2-pyridyl]oxy]phenolate;

(7S)-7-tert-butyl-N-[(1R)-3-(4-hydroxy-1-piperidyl)-1-[6-(6-oxo-1H-pyridin-3-yl)-3-pyridyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[6-(1H-pyrazol-4-yl)-3-pyridyl]propyl]-5,6,7,8-tetrahydrothiazolo[5,4-b]quinoline-2-carboxamide;

4-[5-[(1R)-3-(4-hydroxypiperidin-1-ium-1-yl)-1-[[(7S)-7-tert-butyl-5,6,7,8-tetrahydrothiazolo[5,4-b]quinoline-2-carbonyl]amino]propyl]-2-pyridyl]thiophene-2-carboxylic acid;2,2,2-trifluoroacetate;

[1-[(3R)-3-[4-(5-fluoro-6-hydroxy-3-pyridyl)phenyl]-3-[[(7S)-7-tert-butyl-5,6,7,8-tetrahydrothiazolo[5,4-b]quinoline-2-carbonyl]amino]propyl]-4-piperidyl]ammonium;formate;

[4-hydroxy-1-[(3R)-3-[4-(5-fluoro-6-hydroxy-3-pyridyl)phenyl]-3-[[(7S)-7-tert-butyl-5,6,7,8-tetrahydrothiazolo[5,4-b]quinoline-2-carbonyl]amino]propyl]-4-piperidyl]methylammonium;formate;

(7S)-7-tert-butyl-N-[(1R)-3-[4-[(dimethylamino)methyl]-4-hydroxy-piperidin-1-ium-1-yl]-1-[4-(5-fluoro-6-hydroxy-3-pyridyl)phenyl]propyl]-5,6,7,8-tetrahydrothiazolo[5,4-b]quinoline-2-carboxamide;formate;

(3R,4S)-3-fluoro-1-[(3R)-3-[4-(5-fluoro-6-hydroxy-3-pyridyl)phenyl]-3-[[(7S)-7-tert-butyl-5,6,7,8-tetrahydrothiazolo[5,4-b]quinoline-2-carbonyl]amino]propyl]piperidin-1-ium-4-carboxylic acid;formate;

diethyl-[(3R)-3-[4-(5-fluoro-6-hydroxy-3-pyridyl)phenyl]-3-[[(7S)-7-tert-butyl-5,6,7,8-tetrahydrothiazolo[5,4-b]quinoline-2-carbonyl]amino]propyl]ammonium;formate;

(3R,4R)-3-fluoro-1-[(3R)-3-[4-(5-fluoro-6-hydroxy-3-pyridyl)phenyl]-3-[[(7S)-7-tert-butyl-5,6,7,8-tetrahydrothiazolo[5,4-b]quinoline-2-carbonyl]amino]propyl]piperidin-1-ium-4-carboxylic acid;formate;

(7S)-7-tert-butyl-N-[(1R)-3-(3,4,4a,5,6,7,8,8a-octahydro-2H-pyrano[3,2-c]pyridin-6-ium-6-yl)-1-[4-(5-fluoro-6-hydroxy-3-pyridyl)phenyl]propyl]-5,6,7,8-tetrahydrothiazolo[5,4-b]quinoline-2-carboxamide;formate;

(7S)-7-tert-butyl-N-[(1R)-1-[6-(dimethylsulfamoylamino)-3-pyridyl]-3-(1,4-oxazepan-4-ium-4-yl)propyl]-5,6,7,8-tetrahydrothiazolo[5,4-b]quinoline-2-carboxamide;2,2,2-trifluoroacetate;

2-hydroxyethyl-methyl-[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]ammonium;2,2,2-trifluoroacetate;

[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]-bis(trideuteriomethyl) ammonium;2,2,2-trifluoroacetate;

(7S)-7-tert-butyl-N-[(1R)-1-[6-(dimethylsulfamoylamino)-3-pyridyl]-3-(1,2,3,6-tetrahydropyridin-1-ium-1-yl)propyl]-5,6,7,8-tetrahydrothiazolo[5,4-b]quinoline-2-carboxamide;2,2,2-trifluoroacetate;

(1-hydroxycyclopropyl)methyl-methyl-[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]ammonium;2,2,2-trifluoroacetate;

2-methoxyethyl-methyl-[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]ammonium;2,2,2-trifluoroacetate;

(7S)-7-tert-butyl-N-[(1R)-1-[6-(dimethylsulfamoylamino)-3-pyridyl]-3-[(3R)-3-hydroxypyrrolidin-1-ium-1-yl]propyl]-5,6,7,8-tetrahydrothiazolo[5,4-b]quinoline-2-carboxamide;2,2,2-trifluoroacetate;

isobutyl-methyl-[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]ammonium;2,2,2-trifluoroacetate;

(7S)-7-tert-butyl-N-[(1R)-1-[6-(dimethylsulfamoylamino)-3-pyridyl]-3-[(2S)-2-(hydroxymethyl) azetidin-1-ium-1-yl]propyl]-5,6,7,8-tetrahydrothiazolo[5,4-b]quinoline-2-carboxamide;2,2,2-trifluoroacetate;

methyl-(1H-pyrazol-5-ylmethyl)-[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]ammonium;2,2,2-trifluoroacetate;

(7S)-7-tert-butyl-N-[(1R)-1-[6-(dimethylsulfamoylamino)-3-pyridyl]-3-(5-oxo-1,4-diazepan-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-1-[3-(dimethylsulfamoylamino)phenyl]-3-(4-hydroxypiperidin-1-ium-1-yl)propyl]-5,6,7,8-tetrahydrothiazolo[5,4-b]quinoline-2-carboxamide;formate;

(S)-N-((R)-1-(6-(3,3-dioxido-1,3,4-oxathiazinan-4-yl)pyridin-3-yl)-3-(4-hydroxypiperidin-1-yl)propyl)-7-fluoro-7-isopropyl-5,6,7,8-tetrahydrothiazolo[5,4-b]quinoline-2-carboxamide;

(S)-N-((R)-1-(6-(2,4-dioxoimidazolidin-1-yl)pyridin-3-yl)-3-(4-hydroxypiperidin-1-yl)propyl)-7-(1-methylcyclopropyl)-5,6,7,8-tetrahydrothiazolo[5,4-b]quinoline-2-carboxamide;

(S)-N-((R)-1-(6-(2,4-dioxoimidazolidin-1-yl)pyridin-3-yl)-3-(4-hydroxypiperidin-1-yl)propyl)-7-fluoro-7-isopropyl-5,6,7,8-tetrahydrothiazolo[5,4-b]quinoline-2-carboxamide;

(S)-7-(tert-butyl)-N-((R)-1-(6-(2,4-dioxoimidazolidin-1-yl)pyridin-3-yl)-3-(4-hydroxypiperidin-1-yl)propyl)-5,6,7,8-tetrahydrothiazolo[5,4-b]quinoline-2-carboxamide;

(S)-N-((R)-1-(6-(2,4-dioxoimidazolidin-1-yl)pyridin-3-yl)-3-(4-hydroxypiperidin-1-yl)propyl)-7-(1-(trifluoromethyl)cyclopropyl)-5,6,7,8-tetrahydrothiazolo[5,4-b]quinoline-2-carboxamide;

(S)-N-((R)-3-amino-1-phenylpropyl)-6-(tert-butyl)-5,6,7,8-tetrahydrothieno[2,3-b]quinoline-2-carboxamide;

1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylic acid;

sodium 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylate;

(S)-N-((R)-3-amino-1-(3-(((S)-pyrrolidin-3-yl) carbamoyl)phenyl)propyl)-6-(tert-butyl)-5,6,7,8-tetrahydrothieno[2,3-b]quinoline-2-carboxamide;

(S)-7-(tert-butyl)-N-((R)-1-(4-((N,N-dimethylsulfamoyl)amino)-3-fluorophenyl)-3-(4-hydroxypiperidin-1-yl)propyl)-5,6,7,8-tetrahydrothiazolo[5,4-b]quinoline-2-carboxamide;

(S)-7-(tert-butyl)-N-((R)-1-(6-(ethylsulfonyl)pyridin-3-yl)-3-(4-hydroxypiperidin-1-yl)propyl)-5,6,7,8-tetrahydrothiazolo[5,4-b]quinoline-2-carboxamide;

(S)-7-(tert-butyl)-N-((R)-1-(4-(4-fluoro-5-hydroxypyridin-2-yl)phenyl)-3-(4-hydroxypiperidin-1-yl)propyl)-5,6,7,8-tetrahydrothiazolo[5,4-b]quinoline-2-carboxamide;

1-((R)-3-((S)-7-(tert-butyl)-5,6,7,8-tetrahydrothiazolo[5,4-b]quinoline-2-carboxamido)-3-(6-(2,4-dioxoimidazolidin-1-yl)pyridin-3-yl)propyl)piperidine-4-carboxylic acid;

(S)-7-(tert-butyl)-N-((R)-3-(4-hydroxypiperidin-1-yl)-1-(4-(2-oxooxazolidin-3-yl)phenyl)propyl)-5,6,7,8-tetrahydrothiazolo[5,4-b]quinoline-2-carboxamide;

(S)-N-((R)-3-(4-hydroxypiperidin-1-yl)-1-(4-(2-oxooxazolidin-3-yl)phenyl)propyl)-7-(1-methylcyclopropyl)-5,6,7,8-tetrahydrothiazolo[5,4-b]quinoline-2-carboxamide;

(S)-N-((R)-3-(4-hydroxypiperidin-1-yl)-1-(4-(2-oxooxazolidin-3-yl)phenyl)propyl)-7-(1-(trifluoromethyl)cyclopropyl)-5,6,7,8-tetrahydrothiazolo[5,4-b]quinoline-2-carboxamide;

7-fluoro-N-((R)-3-(4-hydroxypiperidin-1-yl)-1-(4-(2-oxooxazolidin-3-yl)phenyl)propyl)-7-isopropyl-5,6,7,8-tetrahydrothiazolo[5,4-b]quinoline-2-carboxamide;

(S)-N-((R)-1-(4-(5-fluoro-6-oxo-1,6-dihydropyridin-3-yl)phenyl)-3-(4-hydroxypiperidin-1-yl)propyl)-7-(1-methylcyclopropyl)-5,6,7,8-tetrahydrothiazolo[5,4-b]quinoline-2-carboxamide;

(S)-N-((R)-1-(4-(5-fluoro-6-oxo-1,6-dihydropyridin-3-yl)phenyl)-3-(4-hydroxypiperidin-1-yl)propyl)-7-(1-(trifluoromethyl)cyclopropyl)-5,6,7,8-tetrahydrothiazolo[5,4-b]quinoline-2-carboxamide;

(S)-7-(tert-butyl)-N-((R)-1-(4-(5-fluoro-6-oxo-1,6-dihydropyridin-3-yl)phenyl)-3-(4-hydroxypiperidin-1-yl)propyl)-5,6,7,8-tetrahydrothiazolo[5,4-b]quinoline-2-carboxamide;

(6S)-6-tert-butyl-N-{(1R)-1-[4-(5-chloro-6-hydroxypyridin-3-yl)phenyl]-3-piperidin-1-ylpropyl}-5,6,7,8-tetrahydrothieno[2,3-b]quinoline-2-carboxamide;

(S)-6-(tert-butyl)-N-((R)-1-(4-(5-fluoro-6-hydroxypyridin-3-yl)phenyl)-3-(piperidin-1-yl)propyl)-5,6,7,8-tetrahydrothieno[2,3-b]quinoline-2-carboxamide;

(6S)-6-tert-butyl-N-{(1R)-1-[4-(6-hydroxy-5-methylpyridin-3-yl)phenyl]-3-piperidin-1-ylpropyl}-5,6,7,8-tetrahydrothieno[2,3-b]quinoline-2-carboxamide;

(6S)-6-tert-butyl-N-{(1R)-1-[4-(6-hydroxy-2-methylpyridin-3-yl)phenyl]-3-piperidin-1-ylpropyl}-5,6,7,8-tetrahydrothieno[2,3-b]quinoline-2-carboxamide;

(6S)-N-{(1R)-1-[4-(5-amino-6-hydroxypyridin-3-yl)phenyl]-3-piperidin-1-ylpropyl}-6-tert-butyl-5,6,7,8-tetrahydrothieno[2,3-b]quinoline-2-carboxamide;

(6S)-6-tert-butyl-N-(1-phenyl-3-piperidin-1-ylpropyl)-5,6,7,8-tetrahydrothieno[2,3-b]quinoline-2-carboxamide;

(6S)-6-tert-butyl-N-(3-morpholin-4-yl-1-phenylpropyl)-5,6,7,8-tetrahydrothieno[2,3-b]quinoline-2-carboxamide;

(6S)-6-tert-butyl-N-[3-(diethylamino)-1-phenylpropyl]-5,6,7,8-tetrahydrothieno[2,3-b]quinoline-2-carboxamide;

(6S)-6-tert-butyl-N-(1-phenyl-3-piperazin-1-ylpropyl)-5,6,7,8-tetrahydrothieno[2,3-b]quinoline-2-carboxamide;

(6S)-6-tert-butyl-N-{(1R)-1-phenyl-3-[(2,2,2-trifluoroethyl)amino]propyl}-5,6,7,8-tetrahydrothieno[2,3-b]quinoline-2-carboxamide;

(6S)-6-tert-butyl-N-{(1R)-3-[(2-fluoroethyl)amino]-1-phenylpropyl}-5,6,7,8-tetrahydrothieno[2,3-b]quinoline-2-carboxamide;

(6S)-6-tert-butyl-N-[(1R)-1-phenyl-3-(tetrahydro-2H-pyran-4-ylamino) propyl]-5,6,7,8-tetrahydrothieno[2,3-b]quinoline-2-carboxamide;

(6S)-6-tert-butyl-N-{(1R)-3-[(4-hydroxycyclohexyl) amino]-1-phenylpropyl}-5,6,7,8-tetrahydrothieno[2,3-b]quinoline-2-carboxamide;

(6S)-6-tert-butyl-N-[(1R)-3-(4-hydroxypiperidin-1-yl)-1-phenylpropyl]-5,6,7,8-tetrahydrothieno[2,3-b]quinoline-2-carboxamide;

(6S)-6-tert-butyl-N-[(1R)-3-(3-hydroxypiperidin-1-yl)-1-phenylpropyl]-5,6,7,8-tetrahydrothieno[2,3-b]quinoline-2-carboxamide;

(6S)-6-tert-butyl-N-[(1R)-3-(4-fluoropiperidin-1-yl)-1-phenylpropyl]-5,6,7,8-tetrahydrothieno[2,3-b]quinoline-2-carboxamide;

(6S)-6-tert-butyl-N-[(1R)-1-phenyl-3-pyrrolidin-1-ylpropyl]-5,6,7,8-tetrahydrothieno[2,3-b]quinoline-2-carboxamide;

(6S)-6-tert-butyl-N-{(1R)-3-[3-(hydroxymethyl) azetidin-1-yl]-1-phenylpropyl}-5,6,7,8-tetrahydrothieno[2,3-b]quinoline-2-carboxamide;

(6S)-6-tert-butyl-N-{(1R)-3-[4-(hydroxymethyl)piperidin-1-yl]-1-phenylpropyl}-5,6,7,8-tetrahydrothieno[2,3-b]quinoline-2-carboxamide;

(6S)-6-tert-butyl-N-[(1R)-3-(3-hydroxyazetidin-1-yl)-1-phenylpropyl]-5,6,7,8-tetrahydrothieno[2,3-b]quinoline-2-carboxamide;

(6S)-6-tert-butyl-N-{(1R)-3-[(2S)-2-(hydroxymethyl)pyrrolidin-1-yl]-1-phenylpropyl}-5,6,7,8-tetrahydrothieno[2,3-b]quinoline-2-carboxamide;

1-[(3R)-3-({[(6S)-6-tert-butyl-5,6,7,8-tetrahydrothieno[2,3-b]quinolin-2-yl]carbonyl}amino)-3-phenylpropyl]piperidine-4-carboxylic acid;

(6S)-6-tert-butyl-N-{(1R)-3-[3-(hydroxymethyl)pyrrolidin-1-yl]-1-phenylpropyl}-5,6,7,8-tetrahydrothieno[2,3-b]quinoline-2-carboxamide;

(6S)-6-tert-butyl-N-{(1R)-3-[(trans-3-hydroxycyclobutyl)amino]-1-phenylpropyl}-5,6,7,8-tetrahydrothieno[2,3-b]quinoline-2-carboxamide;

(6S)-6-tert-butyl-N-[(1R)-3-(3-hydroxypyrrolidin-1-yl)-1-phenylpropyl]-5,6,7,8-tetrahydrothieno[2,3-b]quinoline-2-carboxamide;

(6S)-6-tert-butyl-N-{(1R)-3-[(2R)-2-(hydroxymethyl)pyrrolidin-1-yl]-1-phenylpropyl}-5,6,7,8-tetrahydrothieno[2,3-b]quinoline-2-carboxamide;

(S)-7-(tert-butyl)-N-((R)-3-(4-hydroxypiperidin-1-yl)-1-(6-(pyridazin-4-yl)pyridin-3-yl)propyl)-5,6,7,8-tetrahydrothiazolo[5,4-b]quinoline-2-carboxamide;

(S)-N-((R)-3-(4-hydroxypiperidin-1-yl)-1-(6-(pyridazin-4-yl)pyridin-3-yl)propyl)-7-(1-methylcyclopropyl)-5,6,7,8-tetrahydrothiazolo[5,4-b]quinoline-2-carboxamide;

(S)-7-fluoro-N-((R)-3-(4-hydroxypiperidin-1-yl)-1-(6-(pyridazin-4-yl)pyridin-3-yl)propyl)-7-isopropyl-5,6,7,8-tetrahydrothiazolo[5,4-b]quinoline-2-carboxamide;

(S)-7-(tert-butyl)-N-((R)-1-(5-fluoro-6-(pyridazin-4-yl)pyridin-3-yl)-3-(4-hydroxypiperidin-1-yl)propyl)-5,6,7,8-tetrahydrothiazolo[5,4-b]quinoline-2-carboxamide;

(S)-N-((R)-1-(4-(1H-pyrazol-4-yl)phenyl)-3-(4-hydroxypiperidin-1-yl)propyl)-7-(1-methylcyclopropyl)-5,6,7,8-tetrahydrothiazolo[5,4-b]quinoline-2-carboxamide;

(S)-N-((R)-1-(4-(1H-pyrazol-4-yl)phenyl)-3-(4-hydroxypiperidin-1-yl)propyl)-7-(1-(trifluoromethyl)cyclopropyl)-5,6,7,8-tetrahydrothiazolo[5,4-b]quinoline-2-carboxamide;

methyl 1-((R)-3-((S)-7-fluoro-7-isopropyl-5,6,7,8-tetrahydrothiazolo[5,4-b]quinoline-2-carboxamido)-3-(6-(pyridazin-4-yl)pyridin-3-yl)propyl)piperidine-4-carboxylate;

1-((R)-3-((S)-7-fluoro-7-isopropyl-5,6,7,8-tetrahydrothiazolo[5,4-b]quinoline-2-carboxamido)-3-(6-(pyridazin-4-yl)pyridin-3-yl)propyl)piperidine-4-carboxylic acid;

(R)-N-((R)-3-(4-(2H-tetrazol-5-yl)piperidin-1-yl)-1-(4-(5-fluoro-6-hydroxypyridin-3-yl)phenyl)propyl)-7-(tert-butyl)-5,6,7,8-tetrahydrothiazolo[5,4-b]quinoline-2-carboxamide;

(7S)-7-(tert-butyl)-N-(1-(pyridin-4-yl)-3-(pyrrolidin-1-yl)propyl)-5,6,7,8-tetrahydrothiazolo[5,4-b]quinoline-2-carboxamide; and(S)-7-(tert-butyl)-N-((R)-1-(6-(3,3-dioxido-1,3,4-oxathiazinan-4-yl)pyridin-3-yl)-3-(4-hydroxypiperidin-1-yl)propyl)-5,6,7,8-tetrahydrothiazolo[5,4-b]quinoline-2-carboxamide;

The present invention encompasses for each of the various embodiments of the compounds of the invention described herein, including those of Formula I and the various embodiments thereof and the compounds of the examples, all forms of the compounds such as, for example, any solvates, hydrates, stereoisomers, and tautomers of said compounds and of any pharmaceutically acceptable salts thereof. Additionally, in the examples described herein, the compounds of the invention may be depicted in the salt form. In such cases, it is to be understood that the compounds of the invention include the free acid or free base forms of such salts, and any pharmaceutically acceptable salt of said free acid or free base forms.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the term "salt(s)" as used herein. It is understood that certain compounds of the invention may . . . exist in zwitterionic form, having both anionic and cationic centers within the same compound and a net neutral charge. Such zwitterions are included within the invention.

Other embodiments of the present invention include the following:

(a) A pharmaceutical composition comprising a compound of formula I and a pharmaceutically acceptable carrier.

(b) The pharmaceutical composition of (a), further comprising a second therapeutic agent.

(c) A pharmaceutical combination that is (i) a compound of formula I and (ii) a second therapeutic agent wherein the compound of formula I and the second therapeutic agent are each employed in an amount that renders the combination effective for treatment or prophylaxis of cardiometabolic diseases, kidney disease, or diabetes.

(d) A use of a compound of formula I in the preparation of a medicament for modulating NPRA activity in a subject in need thereof.

(e) A use of a compound of formula I in the preparation of a medicament for treatment or prophylaxis of cardiometabolic diseases, kidney disease, or diabetes in a subject in need thereof.

(f) A use of a compound of formula I in the preparation of a medicament for treatment of cardiometabolic diseases, kidney disease, or diabetes in a subject in need thereof.

(g) A method of treating impairments associated with cardiometabolic diseases, kidney disease, or diabetes, and/or reducing the likelihood or severity of symptoms of cardiometabolic diseases, kidney disease, or diabetes, in a subject in need thereof, which comprises administering to the subject an effective amount of a compound of formula I.

(h) The method of (f), wherein the compound of formula I is administered in combination with an effective amount of at least one second therapeutic agent.

(i) A method of modulating NPRA activity in a subject in need thereof, which comprises administering to the subject the pharmaceutical composition of (a), (b), or (c) or the combination of (d) or (f).

(j) A method of treating impairments associated with cardiometabolic diseases, kidney disease, or diabetes and/or reducing the likelihood or severity of symptoms of impairments associated with cardiometabolic diseases, kidney disease, or diabetes in a subject in need thereof, which comprises administering to the subject the pharmaceutical composition of (a) or (b), or the combination of (c).

(k) A compound of (a) or (b) for use in the treatment of cardiometobolic diseases, kidney disease or diabetes.

(i) A compound of (a) or (b) for use in therapy.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (k) above are understood to include all embodiments of the compounds and/or salts, including such embodiments as result from combinations of embodiments.

Additional embodiments of the invention include the pharmaceutical compositions, combinations, uses and methods set forth in (a) through (j) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt as appropriate.

The present invention also includes a compound of the present invention for use (i) in, (ii) as a medicament for, or (iii) in the preparation of a medicament for: (a) preventing or treating cardiometabolic diseases, kidney disease, or diabetes or (c) use in medicine. In these uses, the compounds of the present invention can optionally be employed in combination with one or more second therapeutic agents.

Additional embodiments of the invention include the pharmaceutical compositions, combinations and methods set forth in (a)-(j) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (j) above are understood to include all embodiments of the compounds, including such embodiments as result from combinations of embodiments.

The present invention also relates to processes for the preparation of the compounds of Formula I which are described in the following and by which the compounds of the invention are obtainable.

Exemplifying the invention is the use of the compounds disclosed in the Examples and herein.

The compounds of Formula I according to the invention effect an increase of the cGMP concentration via the activation of NPRA, and they are therefore useful agents for the therapy and prophylaxis of disorders which are associated with a low or decreased cGMP level or which are caused thereby, or for whose therapy or prophylaxis an increase of the present cGMP level is desired. The activation of NPRA by the compounds of the Formula I can be examined, for example, in the activity assay described below.

Disorders and pathological conditions which are associated with a low cGMP level or in which an increase of the cGMP level is desired and for whose therapy and prophylaxis it is possible to use compounds of the Formula I are, for example, cardiovascular diseases, such as endothelial dysfunction, diastolic dysfunction, atherosclerosis, hypertension, heart failure, pulmonary hypertension, stable and unstable angina pectoris, thromboses, restenosis, myocardial infarction, strokes, cardiac insufficiency or pulmonary hypertonia, or, for example, erectile dysfunction, asthma bronchial, chronic kidney insufficiency and diabetes.

Compounds of the Formula I can additionally be used in the therapy of cirrhosis of the liver and also for improving a restricted memory performance or ability to learn.

The invention also relates to the use of compounds of the invention for the preparation of a medicament for the treatment and/or prophylaxis of the above-mentioned diseases.

The compounds of the Formula I and their physiologically acceptable salts can be administered to animals, preferably to mammals, and in particular to humans, as pharmaceuticals by themselves, in mixtures with one another or in the form of pharmaceutical preparations. A subject of the present invention therefore also are the compounds of the Formula I and their physiologically acceptable salts for use as pharmaceuticals, their use for activating NPRA, for normalizing a disturbed cGMP balance and in particular their use in the therapy and prophylaxis of the abovementioned syndromes as well as their use for preparing medicaments for these purposes.

Furthermore, a subject of the present invention are pharmaceutical preparations (or pharmaceutical compositions) which comprise as active component an effective dose of at least one compound of the Formula I and/or a physiologically acceptable salt thereof and a customary pharmaceutically acceptable carrier, i.e., one or more pharmaceutically acceptable carrier substances and/or additives.

Thus, a subject of the invention are, for example, said compound and its physiologically acceptable salts for use as a pharmaceutical, pharmaceutical preparations which comprise as active component an effective dose of said compound and/or a physiologically acceptable salt thereof and a customary pharmaceutically acceptable carrier, and the uses of said compound and/or a physiologically acceptable salt thereof in the therapy or prophylaxis of the abovementioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the Formula I and their physiologically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Compositions containing a compound of Formula I described herein will provide immediate release of the drug after administration as that term is understood in the art, but the compositions can be formulated to modify the release rate to achieve controlled, extended or delayed release and the like (collectively referred to herein as controlled release). Controlled release dosage forms can be prepared by methods known to those skilled in the art, for example, by granule or tablet enteric coatings or by admixture of a controlled release matrix component in the composition. For example, a fixed-dose combination composition containing a compound of Formula I admixed with one or more additional pharmaceutically active agents (therapeutic agents) may have an immediate release or controlled release tablet dissolution profile.

The compounds of the Formula I activate Natriuretic Peptide Receptor A (NPRA). Due to this property, apart from use as pharmaceutically active compounds in human medicine and veterinary medicine, they can also be employed as a scientific tool or as aid for biochemical investigations in which such an effect on cGMP is intended, and also for diagnostic purposes, for example in the in vitro diagnosis of cell samples or tissue samples. The compounds of the Formula I and salts thereof can furthermore be employed, as already mentioned above, as intermediates for the preparation of other pharmaceutically active compounds.

The above-mentioned compounds of Formula I are also of use in combination with other pharmacologically active compounds. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents).

When administered to a subject, the Compounds of Formula I may be administered as a component of a composition that comprises a pharmaceutically acceptable carrier or vehicle. The present invention provides pharmaceutical compositions comprising an effective amount of at least one Compound of Formula I and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Compounds of Formula I are administered orally.

In another embodiment, the one or more Compounds of Formula I are administered intravenously.

In one embodiment, a pharmaceutical preparation comprising at least one Compound of Formula I is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Compound(s) of Formula I by weight or volume. In various embodiments, the present compositions can contain, in one embodiment, from about 1% to about 70% or from about 5% to about 60% of the Compound(s) of Formula I by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Compounds of Formula I may be administered at varying frequencies. In one embodiment, a unit dosage of a Compound of Formula I may be administered once daily. In another embodiment, a unit dosage of a Compound of Formula I may be administered twice weekly. In another embodiment, a unit dosage of a Compound of Formula I may be administered once weekly. In still another embodiment, a unit dosage of a Compound of Formula I may be administered once biweekly. In another embodiment, a unit dosage of a Compound of Formula I may be administered once monthly. In yet another embodiment, a unit dosage of a Compound of Formula I may be administered once bimonthly. In another embodiment, a unit dosage of a Compound of Formula I may be administered once every 3 months. In a further embodiment, a unit dosage of a Compound of Formula I may be administered once every 6 months. In another embodiment, a unit dosage of a Compound of Formula I may be administered once yearly.

The amount and frequency of administration of the Compounds of Formula I will be regulated according to the judgment of the attending clinician considering such factors as age, condition and size of the subject as well as severity of the symptoms being treated. The compositions of the invention can further comprise one or more additional therapeutic agents (active agents), selected from those listed above herein.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference The compounds of Formula I are of use in combination with other pharmacologically active compounds comprising angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan, valsartan, candesartan, olmesartan, telmesartan) neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2 (S),4 (S),5 (S),7 (S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409.

(b) biguanides, such as metformin and phenformin;

(c) protein tyrosine phosphatase-1B (PTP-1B) inhibitors;

(d) dipeptidyl peptidase-IV (DPP-4) inhibitors, such as sitagliptin, saxagliptin, vildagliptin, and alogliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-COA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPAR agonists, such as fenofibric acid derivatives (gemfibrozil, clofibrate, fenofibrate and bezafibrate), (v) cholesterol absorption inhibitors, such as ezetimibe, (vi) acyl CoA: cholesterol acyltransferase (ACAT) inhibitors, such as avasimibe, (vii) CETP inhibitors, such as torcetrapib, and (viii) phenolic antioxidants, such as probucol;

(i) PPARα/γ dual agonists, such as muraglitazar, tesaglitazar, farglitazar, and JT-501;

(j) PPARδ agonists, such as those disclosed in WO97/28149;

(k) anti-obesity compounds, such as fenfluramine, dexfenfluramine, phentiramine, subitramine, orlistat, neuropeptide Y Y5 inhibitors, MC4R agonists, cannabinoid receptor 1 (CB-1) antagonists/inverse agonists (e.g., rimonabant and taranabant), and β3 adrenergic receptor agonists;

(l) ileal bile acid transporter inhibitors;

(m) agents intended for use in inflammatory conditions, such as aspirin, non-steroidal anti-inflammatory drugs, glucocorticoids, azulfidine, and cyclooxygenase-2 (Cox-2) selective inhibitors;

(n) glucagon receptor antagonists;

(o) GLP-1;

(p) GIP-1;

(q) GLP-1 analogs and derivatives, such as exendins, (e.g., exenatide and liruglatide), and (r) 11β-hydroxysteroid dehydrogenase-1 (HSD-1) inhibitors.

Other examples of additional pharmacologically active agents that may be administered in combination with a compound of Formula I include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP)

such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2 (S),4 (S),5 (S),7 (S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-COA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-COA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-COA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-COA reductase inhibitor, niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

In one aspect, the present invention provides a kit comprising a therapeutically effective amount of at least one Compound of Formula I, or a pharmaceutically acceptable salt or prodrug of said compound and a pharmaceutically acceptable carrier, vehicle or diluent.

In another aspect the present invention provides a kit comprising an amount of at least one Compound of Formula I, or a pharmaceutically acceptable salt or prodrug of said compound and an amount of at least one additional therapeutic agent listed above, wherein the amounts of the two or more active ingredients result in a desired therapeutic effect. In one embodiment, the one or more Compounds of Formula I and the one or more additional therapeutic agents are provided in the same container. In one embodiment, the one or more Compounds of Formula I and the one or more additional therapeutic agents are provided in separate containers.

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, the term "administration" and variants thereof (e.g., "administering" a compound) in reference to a compound of the invention means providing the compound to the individual in need of treatment. When a compound of the invention is provided in combination with one or more other active agents (e.g., angiotensin converting enzyme inhibitors), "administration" and its variants are each understood to include concurrent and sequential administration of the compound or salt and other agents.

A "subject" (alternatively referred to herein as "patient") is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to modulate NPRA activity and thereby elicit the response being sought (i.e., a "therapeutically effective amount"). When the active compound (i.e., active ingredient) is administered as the salt, references to the amount of active ingredient are to the free acid or free base form of the compound.

The terms "treating" or "treatment" as used herein with respect to cardiometabolic diseases including high blood pressure, heart failure, kidney disease, and diabetes, includes inhibiting the severity of the cardiometabolic diseases including high blood pressure, heart failure, kidney disease, and diabetes, i.e., arresting or reducing the development of the diseases or its clinical symptoms; or relieving the diseases, i.e., causing regression of the severity of the diseases or their clinical symptoms.

The terms "preventing," or "prophylaxis," as used herein with respect to the cardiometabolic diseases including high blood pressure, heart failure, kidney disease, and diabetes, refers to reducing the likelihood or severity of the diseases.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

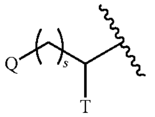
, wherein s is an integer equal to zero, 1 or 2, the structure is

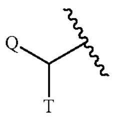

when s is zero.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "carbonyl" means a functional group composed of a carbon atom double-bonded to an oxygen atom, C═O.

The term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on. Bicyclic cycloalkyl ring systems include fused ring systems, where two rings share two atoms, and spiro ring systems, where two rings share one atom.

The term "heteroalkyl" refers to an alkyl group where 1, 2, or 3 of the carbon atoms is substituted by a heteroatom independently chosen from N, O, or S.

The term "alkoxy" refers to an alkyl (carbon and hydrogen chain) group singularly bonded to oxygen (R—O). Non-limiting examples of alkoxy are methoxy ($CH_3$ O—), ethoxy ($CH_3$ $CH_2$ O—) and butoxy ($CH_3$ $CH_2$ $CH_2$ O—).

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In on embodiment of the present invention, aryl is phenyl.

The term "halogen" includes fluorine, chlorine, bromine, and iodine.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$ haloalkyl, for example, includes —$CF_3$, —$CF_2CF_3$, —$CHFCH_3$, and the like.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

The term "heteroaryl", as used herein, represents a stable monocyclic, bicyclic or tricyclic ring system containing 5-14 carbon atoms and containing at least one ring heteroatom selected from N, S (including SO and $SO_2$) and O, wherein at least one of the heteroatom containing rings is aromatic. In the case of a heteroaryl ring system where one or more of the rings are saturated and contain one or more N atoms, the N can be in the form of quarternary amine. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzothiazolyl, benzo[d]isothiazole, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrrolyl, pyrazolopyrimidinyl, pyridazinyl, pyridyl, pyrimidyl, pyrimidinyl, pyrrolyl, quinazolinyl, quinolyl, quinoxalinyl, tetrazolyl, tetrazolopyridyl, thiadiazolyl, 5H-pyrrolo[3,4-b]pyridine, thiazolyl, thienyl, triazolyl, triazinyl, benzothiazolyl, benzothienyl, quinolinyl, quinazolinyl, and isoquinolinyl, and oxazolyl. If the heteroaryl contains nitrogen atoms, it is understood that the corresponding N-oxides thereof are also encompassed by this definition.

The term "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. In a bicyclic ring system, the second ring may be a heteroaryl, heterocycle or a saturated, partially unsaturated or aromatic carbocycle, and the point (s) of attachment to the rest of the molecule may be on either ring. "Heterocyclyl" therefore include dihydro and tetrahydro analogs of heteroaryls (for example, a bicyclic having an aromatic ring and non-aromatic ring, such as, dihydrobenzoimidazolyl, dihydroquinolinyl). Attachment of a heterocyclyl substituent can occur via a carbon atom or via a heteroatom.

"Heterocyclyl" therefore includes, but is not limited to the following: azaspirononanyl, azabicyclo[3.1.0]hexanyl, azaspirooctanyl, azetidinyl, dioxanyl, diazapanyl, diazaspiroheptanyl, diazaspirodecanyl, diazaspirononanyl, dihydropyridazinyl, dihydropyridinyl, dihydrobenzoxazolyl, morpholinyl, octahydropyrrolopyrrolyl, octahydropyranopyridinyl, octahydropyrrolooxazinyl, oxazolidinyl, oxaazaspitodecanyl, oxaazobicyclo[2.2.1]heptanyl, oxadiazaspirodecanyl, oxadiazaspirononanyl, oxaspirooctanyl, oxazolidinonyl, oxazepanyl, oxathiazinanyl, oxetanyl, piperazinyl, piperidyl, piperidinyl, pyrrolidinyl, morpholinyl, thiomorpholinyl, tetrahydrofurnayl, tetrahydropyrimidinyl, tetrahydropyridyl, tetrahydropyranyl, dihydropiperidinyl, dihydroquinolinyl, dihydroindolyl, tetrahydrothiophenyl, dihydrobenzofuranyl, dihydrobenzoimidazolyl, tetra-hydroquinoline, methylenedioxybenzene, dihydrobenzodioxinyl, and the like. If the heterocycle contains a nitrogen, it is understood that the corresponding N-oxides thereof are also encompassed by this definition.

"Oxo" means an oxygen atom connected to another atom by a double bound and is repressed by "=O" herein.

The term "sulfamoyl" is a suffix to denote radicals derived from sulfamide such as $—SO_2NH_2$, $—SO_2NHR$ and $—SO_2N(RR^1)$.

By "pharmaceutically acceptable" is meant that the ingredients of the pharmaceutical composition must be compatible with each other and not deleterious to the recipient thereof.

Where any amine is present in the compound, the N atom may be optionally in the form of a quaternary amine having one or more appropriate additional substitutions, as further described herein.

When any variable (e.g., n, $R^a$, $R^b$, etc.) occurs more than one time in any constituent or in Formula I, its definition on each occurrence is independent of its definition at every other occurrence. Also, combinations of substuents and/or variables are permissible only if such combinations result in stable compounds.

When any ring atom is specified as being optionally substituted with, or in a specified form, for example, S substituted with oxo groups, or N in the form of a N-oxide, this does not preclude the substitution of any ring atom with the other listed optional substuents when not substituted with oxo groups or in the form of a N-oxide.

"Celite®" (Fluka) diatomite is diatomaceous earth, and can be referred to as "celite".

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

By "stable compound" or "stable structure" is meant a compound that is sufficiently robust to survive isolation to a useful degree of purity from a reaction mixture, and formulation into an efficacious therapeutic agent (active agent). The compounds of the present invention are limited to stable compounds embraced by Formula I.

The term "compound" refers to the compound and, in certain embodiments, to the extent they are stable, any hydrate or solvate thereof. A hydrate is the compound complexed with water, and a solvate is the compound complexed with an organic solvent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

Under standard nomenclature used throughout this disclosure, the terminal portion of the designated side chain is described last, preceded by the adjacent functionality toward the point of attachment. For example, a $C_{1-5}$ alkylcarbonylamino $C_{1-6}$ alkyl substituent is equivalent to

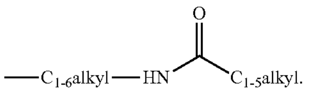

Structural representations of compounds having substituents terminating with a methyl group may display the terminal methyl group either using the characters "$CH_3$", e.g. "$—CH_3$" or using a straight line representing the presence of the methyl group, e.g. "—", i.e., “” and “”

have equivalent meanings.

For variable definitions containing terms having repeated terms, e.g., (CRiRj)r, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then (CRiRj)2 can be

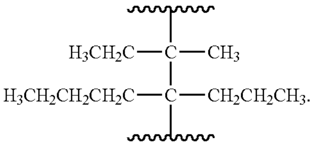

Unless expressly stated to the contrary, all ranges cited herein are inclusive. For example, a heteroaromatic ring described as containing from “1 to 4 heteroatoms” means the ring can contain, 1, 2, 3 or r heteroatoms. It is also to be understood that any range cited herein includes within its scope all of the sub-ranges within that range. Thus, for example, a heterocyclic ring described as containing from “1 to 4 heteroatoms” is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatims, 3 heteroatoms, and 4 heteroatoms. Similarly, $C_1$-$C_6$ when used with a chain, for example an alkyl chains means that the chain can contain 1, 2, 3, 4, 5, or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

In choosing compounds of the present invention, one of ordinary skill in the art will recognize that the various substuents, i.e. $R^1$, $R^A$, etc., are to be chosen in conformity with well-known principles of chemical structure connectivity and stability.

As used herein, the term “composition” is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term “prodrug” means a compound (e.g., a drug precursor) that is transformed in vivo to provide a compound of Formula I or a pharmaceutically acceptable salt of the compound. The transformation may occur by various mechanisms (e.g., by metabolic or chemical processes), such as, for example, through hydrolysis in blood. For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$-$C_2$)alkylamino ($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino ($C_2$-$C_3$)alkyl, and the like.

Similarly, if a compound of Formula I contains an alcohol functional group, a prodrug can be formed by the replacement of one or more of the hydrogen atoms of the alcohol groups with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$) alkanoyl, a-amino ($C_1$-$C_4$)alkyl, α-amino ($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a compound of Formula I incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$) alkyl, ($C_3$-$C_7$)cycloalkyl, benzyl, a natural α aminoacyl, —C(OH)C(O)OY$^1$ wherein Y1 is H, ($C_1$-$C_6$)alkyl or benzyl, —C(OY$^2$)Y$^3$ wherein Y$^2$ is ($C_1$-$C_4$)alkyl and Y$^3$ is ($C_1$-$C_6$) alkyl; carboxy ($C_1$-$C_6$)alkyl; amino ($C_1$-$C_4$)alkyl or mono-N- or di-N,N-($C_1$-$C_6$)alkylaminoalkyl; —C(Y$^4$)Y$^5$ wherein Y$^4$ is H or methyl and Y$^5$ is mono-N— or di-N,N-($C_1$-$C_6$) alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3)amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$) acyl glycerol.

One or more compounds of the invention may exist in unsolvated as well as solvated forms with pharmaceutically acceptable solvents such as water, ethanol, and the like, and it is intended that the invention embrace both solvated and unsolvated forms. “Solvate” means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.,* 93 (3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.,* 5 (1), article 12 (2004); and A. L. Bingham et al, *Chem. Commun.,* 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The compound of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-V C H; S. Berge et al, *Journal of Pharmaceutical Sciences* (1977) 66 (1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the compound of Formula I may be atropisomers (e.g., substituted biaryls) and are considered as part of this invention. Enantiomers can also be directly separated using chiral chromatographic techniques.

It is also possible that the compound of Formula I may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound of Formula I incorporates a double bond or a fused ring, both the cis- and trans-forms, as well as mixtures, are embraced within the scope of the invention.

When a substituent on a chiral carbon atom is depicted without specific stereochemistry (by using a straight line bond to a chiral center), it is to be understood that both the alpha and beta configurations of said substituent group are to be considered part of the present invention. For example, the compound of the present invention, which is drawn as follows:

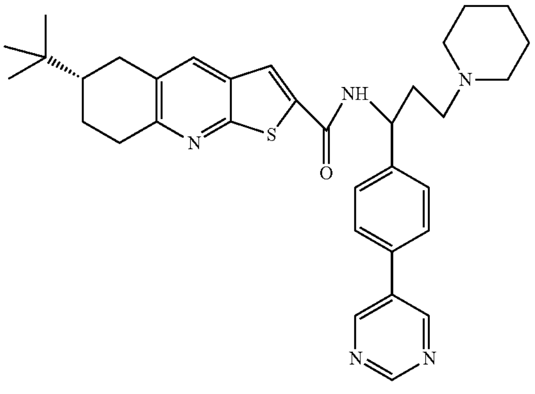

, is understood to encompass both stereoisomers at the indicated chiral center, the structures of which are as follows:

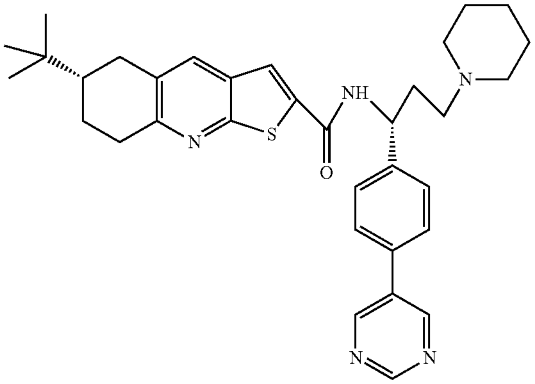

and

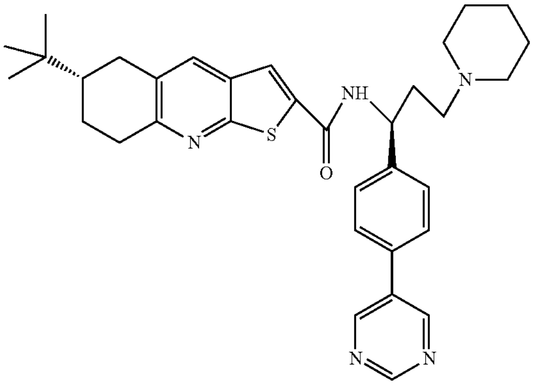

.

In the Examples section below, compounds of the present invention that have been purified as individual stereoisomers are sometimes depicted in non-stereospecific form but identified using one or more of the terms: "diastereomer 1," "diastereomer 2," "isomer 1," "isomer 2," "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula I can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula I has one or more of its hydrogen atoms replaced with deuterium.

In another embodiment, the Compounds of Formula I are in substantially purified form.

Biological Activity Determination

NPRA Functional Cell Assay

Materials

Assay Buffer components HEPES and Opti-MEM® I Reduced-Serum with Glutamine (no phenol red) were from Gibco/Invitrogen (Thermo Fisher Scientific, Waltham, MA USA). 3-Isobutyl-1-methylxanthine (IBMX) and 4-(3-Butoxy-4-methoxybenzyl) imidazolidin-2-one (RO20) were obtained from Sigma-Aldrich (St. Louis, MO, USA). DPBS (Dulbecco's phosphate-buffered saline) without Ca2+ and Mg2+ was purchased from GE Healthcare Bio-Sciences (Pittsburgh, PA, USA). 384 well white Optiplates were from Perkin Elmer (Atlantic Highlands, NJ, USA). Human ANP (Atrial Natriuretic Peptide) (1-28) was purchased from Sigma-Aldrich (Catalog #A1663) and rat ANP (1-28) from Bachem (Torrance, CA, USA) (Catalog #H2100). Human-BNP (Human-Brain Natriuretic Peptide) (1-32 AA) was purchased from American Peptide Company (Sunnyvale, CA, USA) (product No. 14-1-90). cGMP kits were purchased from Cisbio. The assay ready frozen (ARF) Human/rat/dog NPRA HEK JumpIn Stable frozen cells (low passage number 5-11) were prepared in-house.

Methods

Test compounds were titrated in DMSO in a 10-point dose response in a separate step followed by a 100-fold dilution into the reaction. Positive response for each assay was determined using 10 nM rat-ANP peptide (rat cells) or 50 nM h-ANP peptide (human and dog cells).

Cells were thawed, washed with DPBS and resuspended in assay buffer (Opti-MEM+Glutamine, phenol red free media, 10 mM HEPES, 100 uM IBMX and 100 uM RO20) that was warmed to 37° C. Cells were then transferred to microplates via a Microplate Combi dispenser at a density of 1500, 400 and 1200 cells/well for human, rat and dog cells respectively, followed by acoustic transfer (Echo) of compound.

Compounds and cells were incubated at 37° C. with 5% $CO_2$ for 1 hour, after which the cells were lysed and cGMP was captured using a CisBio cGMP HTRF assay kit. The TRF signal was measured with an Envision plate reader (emission set to 615 and 665 nm) after 1 hour incubation at ambient temperature. The TRF signal was converted to [cGMP] through the use of a cGMP calibration curve on each microplate. $EC_{50}$'s were generated from the resulting dose response curves by use of a 4 parameter logistic algorithm.

Methods of Synthesis

The compounds of the present invention can be prepared according to the following general schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following schemes.

In some cases, the order of carrying out the foregoing reaction schemes may be varied to facilitate the reaction or to avoid unwanted reaction products. Additionally, various protecting group strategies familiar to one skilled in the art of organic synthesis may be employed to facilitate the reaction or to avoid unwanted reaction products.

In some cases, the final product may be further modified, for example, by manipulation of substituents. These manipulations may include, but are not limited to, reduction, oxidation, alkylation, acylation, and hydrolysis reactions which are commonly known to those skilled in the art.

The following examples are provided so that the invention might be more fully understood. These examples are illustrative only and should not be construed as limiting the invention in any way. Wherein a racemic mixture is produced, the enantiomers may be separated using SFC reverse or normal phase chiral resolution conditions either after isolation of the final product or at a suitable Intermediate, followed by processing of the single isomers individually. It is understood that alternative methodologies may also be employed in the synthesis of these key intermediates and examples. Asymmetric methodologies (e.g. chiral catalysis, auxiliaries) may be used where possible and appropriate. The exact choice of reagents, solvents, temperatures, and other reaction conditions, depends upon the nature of the intended product.

Unless otherwise indicated, when ratios of compounds (such as for examples solvents) are given, the ratio is on a volume to volume basis. For example, a 1:1 mixture of THF/H2O means a mixture of 1 parts by volume THF to 1 parts by volume of H2O. Additionally, unless otherwise specifically indicated, all reagents are commercially available, known in the literature, or readily synthesized by one skilled in the art. Straightforward protecting group strategies were applied in some routes.

The following abbreviations are used throughout the text:

| | |
|---|---|
| Ac | acetyl |
| aq | aqueous |
| Ar | aryl |
| Boc | tert-butoxycarbonyl |
| $Boc_2O$ | di-tert-butyl dicarbonate |
| BrettPhos precatalyst | [(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate |
| Bu | butyl |
| Celite ® | diatomaceous earth |

-continued

| | |
|---|---|
| DAST | (diethylamino)sulfur trifluoride |
| DCE | 1,2-dichloroethane |
| DCM | dichloromethane |
| DEA | diethylamine |
| Dess-Martin periodinane, Dess Martin Agent | 1,1,1-Tris(acetyloxy)-1,1-dihydro-1,2-benziodoxol-3-(1H)-one |
| DIAD | diisopropyl azodicarboxylate |
| DIEA, DIPEA | N,N-diisopropylethylamine |
| di-t-Bu | di-tert-butyl |
| DMAP | 4-(dimethylamino)pyridine |
| DMF | N,N-dimethylformamide |
| DMP | 1,1,1-Tris(acetyloxy)-1,1-dihydro-1,2-benziodoxol-3-(1H)-one |
| DMSO | dimethylsulfoxide |
| EA/PE | Ethyl acetate/petroleum ether |
| EDC | N-(3-dimethylaminopropyl)-N'-ethylcarbodiimide hydrochloride |
| $Et_3N$ | triethylamine |
| EtOAc | Ethyl acetate |
| Eq, equiv. | equivalents |
| ESI | electrospray ionization |
| Et | ethyl |
| h | hours |
| HATU | O-(7-azabenzotriazol-1-yl)-N,N,N'N'-tetramethyluronium hexafluorophosphate |
| HTRF | Homogeneous Time Resolved Fluorescence |
| HOAc | Acetic acid |
| HOAt | 1-hydroxy-7-azabenzotriazole |
| HOBt | 1-hydroxybenzotriazole |
| HPLC | high performance liquid chromatography |
| i-Pr | isopropyl |
| KOAc | Potassium acetate |
| LCMS | liquid chromatography-mass spectrometry |
| M | molar |
| Me | methyl |
| min | minutes |
| MsCl | methanesulfonylchloride |
| MW | molecular weight |
| n-BuLi | n-butyllithium |
| NMR | nuclear magnetic resonance |
| OPMP | |
| $PPh_3$ | triphenylphosphine |
| $Pd(OAc)_2$ | Palladium(II) acetate |
| Pd/C | palladium on carbon |
| $Pd2(dba)_3$ | Tris(dibenzylideneacetone)diapalladium(0) |
| $PdCl_2$(dtbpf) | [1,1'-Bis(di-tert-butylphosphino)ferrocene]dichloropalladium(II) |
| $Pd(dppf)Cl_2$ | [1,1'-Bis(diphenylphosphino)ferrocene]dichloro-palladium(II) |
| Ph | phenyl |
| psi | pounds per square inch |
| RB | Round bottomed |
| Rt. RT | ambient temperature |
| SFC | supercritical fluid chromatography |
| SM | starting material |
| t-Bu | tert-butyl |
| TBME | Methyl tert-butyl ether |
| TBTU | 2-(1H-benzotriazole-1-yl)-1,1,3,3-tetramethyl-aminium tetrafluoroborate |
| TEA | triethylamine |
| TEMPO | 2,2,6,6-Tetramethyl-1-piperidinyloxy |
| TFA | trifluoroacetic acid |
| Tf | trifluoromethanesulfonyl |
| THF | tetrahydrofuran |
| TMSCl | Trimethylsilyl chloride |
| TRF | Time Resolved Fluorescence |
| Ts-OH | p-Toluenesulfonic acid |
| V/V | volume to volume |
| Xantphos | (9,9-dimethyl-9H-xanthene-4,5-diyl)bis(diphenylphosphane) |

General Procedures

Starting materials and intermediates are purchased or are made using known procedures, or as otherwise illustrated. The general route applied to the synthesis of compounds of Formula I is described in the Schemes that follows. In some cases the order of carrying out the reaction steps in the schemes may be varied to facilitate the reaction or to avoid unwanted reaction products.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC/MS).

Biological Activity Testing

NPRA Functional Cell Assay

Materials:

Assay Buffer components HEPES and Opti-MEM® I Reduced-Serum with Glutamine (no phenol red) were from Gibco/Invitrogen. 3-Isobutyl-1-methylxanthine (IBMX) and 4-(3-Butoxy-4-methoxybenzyl) imidazolidin-2-one (RO20) were obtained from Sigma. DPBS (Dulbecco's phosphate-buffered saline) without Ca2+ and Mg2+ was purchased from GE Healthcare Bio-Sciences (Pittsburgh, PA, USA). 384 well white Optiplates were from Perkin Elmer (Atlantic Highlands, NJ, USA). Human ANP (1-28) was purchased from Sigma (A1663) and rat ANP (1-28) from Bachem (H2100). Human-BNP (1-32 AA) was purchased from American Peptide Company (Sunnyvale, CA, USA) (product No. 14-1-90). cGMP kits were purchased from Cisbio (Bedford, MA, USA). The assay ready frozen (ARF) Human/rat/dog NPRA HEK JumpIn Stable frozen cells (low passage number 5-11) were prepared in-house.

Methods:

Test compounds were titrated in DMSO in a 10-point dose response in a separate step followed by a 100-fold dilution into the reaction. Positive response for each assay was determined using 10 nM rat-ANP peptide (rat cells) or 50 nM h-ANP peptide (human and dog cells).

Cells were thawed, washed with DPBS and resuspended in assay buffer (Opti-MEM+Glutamine, phenol red free media, 10 mM HEPES, 100 uM IBMX and 100 uM RO20) that was warmed to 37° C. Cells were then transferred to microplates via a Microplate Combi dispenser at a density of 1500, 400 and 1200 cells/well for human, rat and dog cells respectively, followed by acoustic transfer (Echo) of compound.

Compounds and cells were incubated at 37° C. with 5% $CO_2$ for 1 hour, after which the cells were lysed and cGMP was captured using a CisBio cGMP HTRF assay kit. The TRF signal was measured with an Envision® plate reader (Perkin Elmer) (emission set to 615 and 665 nm) after 1 hour incubation at ambient temperature. The TRF signal was converted to [cGMP] through the use of a cGMP calibration curve on each microplate. $EC_{50}$'s were generated from the resulting dose response curves by use of a 4 parameter logistic algorithm.

hNPRA $EC_{50}$ (nM) were determined for the compounds of Example 1 through Example 273 and are reported in the Experimental section of this application.

Intermediates

The following experimental procedures detail the preparation of intermediates used in n the synthesis of examples of the instant invention. The exemplified procedures are for illustrative purposes only, and are not intended to limit the scope of the instant invention in any way.

Scheme A: Synthesis of Intermediate I-1

Intermediate I-1 was made by modifying the procedure disclosed in international patent application publication WO 2006098961 (Tagat, J. R. et al.) to that shown in Scheme A.

Scheme A

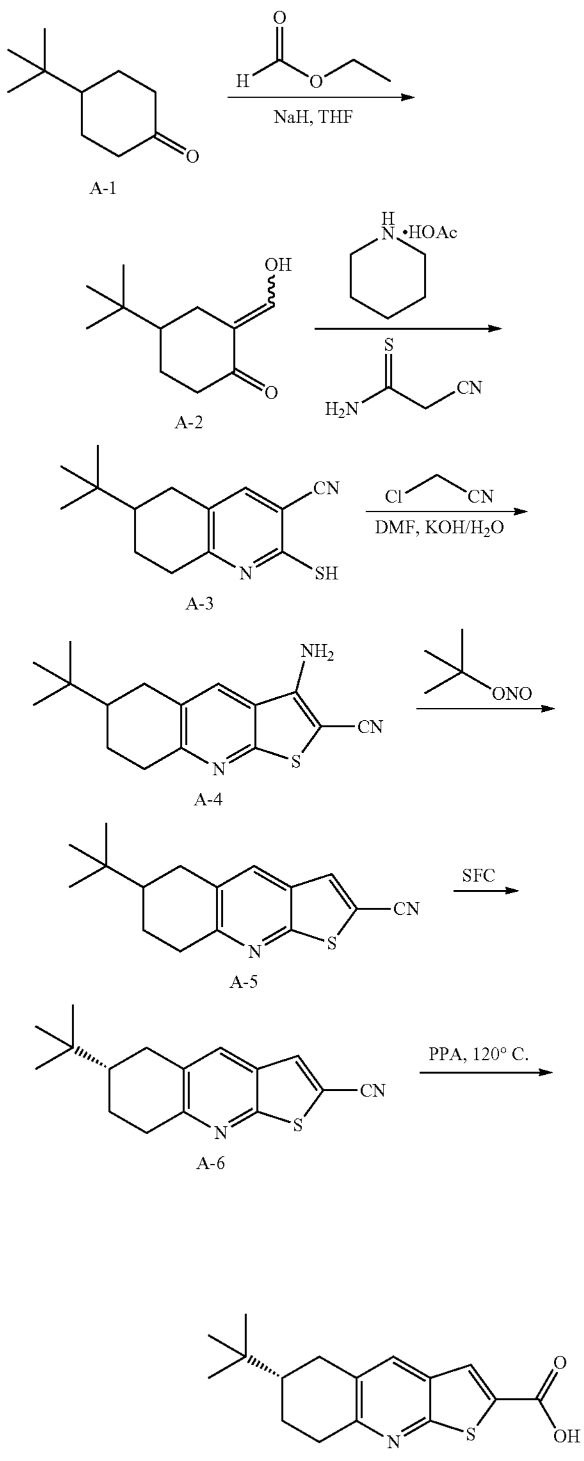

I-1

Step 1 4-(tert-butyl)-2-(hydroxymethylene)cyclohexan-1-one (A-2)

A-2

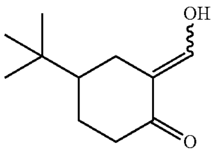

Into a 20,000-mL 3-necked round-bottom flask was placed tetrahydrofuran (6,000 mL), then added sodium hydride (60%, 78 g, 1.95 mol) in several batches. This was followed by the addition of 4-tert-butylcyclohexan-1-one (A-1) (200 g, 1.30 mol) and ethyl formate (144 g, 1.94 mol) at 0° C. This was followed by the addition of ethanol (42 g, 911.66 mmol) dropwise with stirring at −5 to 0° C. The resulting solution was stirred for 3.5 hours at 0° C. in an ice/salt bath. The reaction was then quenched by the addition of 3,000 mL of water/ice. The pH value of the solution was adjusted to 3 with 4M aqueous HCl (hydrochloric acid). The resulting solution was extracted with 3×2,000 mL of ethyl acetate. The organic layers were combined, dried over anhydrous sodium sulfate and concentrated under vacuum. This resulted in compound A-2. LC-MS: 183 (M+1).

Step 2 6-(tert-butyl)-2-mercapto-5,6,7,8-tetrahydroquinoline-3-carbonitrile (A-3)

A-3

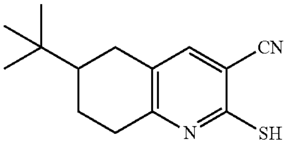

Into a 10,000-mL 3-necked round-bottom flask, purged and maintained with an inert atmosphere of nitrogen, was placed a solution of piperidine (330.4 g, 3.88 mol) in water (640 mL). This was followed by the addition of acetic acid (233.6 g, 3.89 mol) dropwise with stirring. One hour later, to this was added water (2800 mL), (2Z)-4-tert-butyl-2-(hydroxymethylidene)cyclohexan-1-one (A-2) (236 g, 1.29 mol) and 2-cyanoethanethioamide (134.5 g, 1.34 mol). The resulting solution was stirred for one hour at 100° C. HOAc (850 mL) was added next. The resulting solution was stirred overnight at RT. The reaction progress was monitored by LCMS. The solid was collected by filtration and then re-crystallized from EA/PE (1:1) to give product A-3. LC-MS: 247 (M+H).

Step 3 3-amino-6-(tert-butyl)-5,6,7,8-tetrahydrothieno[2,3-b]quinoline-2-carbonitrile (A-4)

A-4

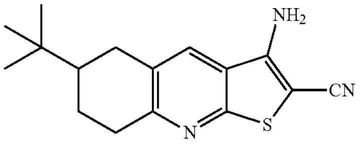

Into a 5,000-mL 4-necked round-bottom flask purged and maintained with an inert atmosphere of nitrogen was placed 6-tert-butyl-2-sulfanyl-5,6,7,8-tetrahydroquinoline-3-carbonitrile (A-3) (230 g, 933.55 mmol), 2-chloroacetonitrile (78.2 g, 1.04 mol) and N,N-dimethylformamide (2530 mL). This was followed by the addition of a solution of potassium hydroxide (92 g) in water (368 mL) dropwise with stirring at 0° C. The resulting solution was stirred for 3 hours at 0° C. in an ice/salt bath. The reaction progress was monitored by LCMS. The reaction was then quenched by the addition of 2,000 mL of water/ice. The solid was collected by filtration, dried in an oven, and then applied onto a silica gel column and eluted with dichloromethane to give product A-4. MS: 286 (M+1).

Step 4 6-(tert-butyl)-5,6,7,8-tetrahydrothieno[2,3-b]quinoline-2-carbonitrile (A-5)

A-5

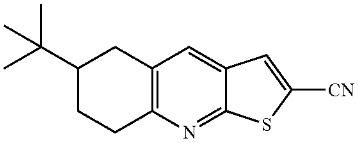

Into a 3,000-mL 3-necked round-bottom flask was placed tert-butyl nitrite (72.6 g, 710.85 mmol), and N,N-dimethylformamide (880 mL). To this was added a solution of 3-amino-6-tert-butyl-5H,6H,7H,8H-thieno[2,3-b]quinoline-2-carbonitrile (A-4) (110 g, 385.41 mmol) in N,N-dimethylformamide (1150 mL) dropwise with stirring at 65° C. The resulting solution was stirred for 4 hours at 65-70° C. in an oil bath. The reaction progress was monitored by LCMS. The reaction mixture was cooled to room temperature and diluted with 2,000 mL of EtOAc. The resulting mixture was washed with 2×500 mL of water and 2×500 mL of brine. The organic phase was dried over anhydrous sodium sulfate and concentrated under vacuum. The residue was purified by silica gel chromatography (EtOAc/petroleum ether) to give the compound A-5. MS: 271 (M+1).

Step 5 (S)-6-(tert-butyl)-5,6,7,8-tetrahydrothieno[2,3-b]quinoline-2-carbonitrile (A-6)

A-6

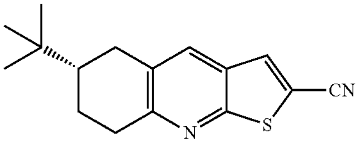

The racemate of 3-amino-6-tert-butyl-5H,6H, 7H,8H-thieno[2,3-b]quinoline-2-carbonitrile (58 g, 203.22 mmol) was purified with Prep-chiral SFC under the following conditions (SFC 350): Column, Chiralpak® AD-H (Daicel Corporation, Torrance, CA, USA); mobile phase, ethanol (0.2% DEA); Detector, 220 nm. The faster eluting peak is collected. This resulted in (6S)-3-amino-6-tert-butyl-5H,6H, 7H,8H-thieno[2,3-b]quinoline-2-carbonitrile. MS: 271 (M+1).

Step 6 (S)-6-(tert-butyl)-5,6,7,8-tetrahydrothieno[2,3-b]quinoline-2-carboxylic acid (I-1)

I-1

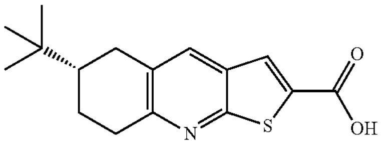

Into a 1,000-mL 3-necked round-bottom flask was placed (6S)-6-tert-butyl-5H,6H,7H,8H-thieno[2,3-b]quinoline-2-carbonitrile (A-6) (21 g, 77.66 mmol) and $H_3PO_4$ (315 mL). The resulting solution was stirred for 4 hours at 160° C. The reaction mixture was cooled to room temperature and then poured into 1000 mL of water/ice. The pH value of the solution was adjusted to 6-7 with aqueous sodium hydroxide solution (1 M). The solid was collected by filtration to give the title compound. MS: 290 (M+1).

Intermediate I-2

6-(1-methylcyclopropyl)-5,6,7,8-tetrahydrothieno[2,3-b]quinoline-2-carboxylic acid (I-2)

Following analogous methodology to that outlined for synthesizing intermediate I-1, using compound 4-(1-methylcyclopropyl)cyclohexan-1-one as starting material, (Stamford, Andrew; Miller, Michael W.; Demong, Duane Eugene; Greenlee, William J.; Kozlowski, Joseph A.; Lavey, Brian J.; Wong, Michael K. C.; Yu, Wensheng; Dai, Xing; Yang, De-Yi et al, WO 2010039789), intermediate I-2 was prepared.

I-2

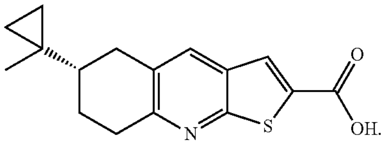

LC-MS: 288 (M + H)

Scheme B: Synthesis of intermediate I-3

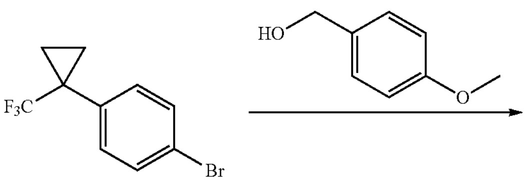

B-1

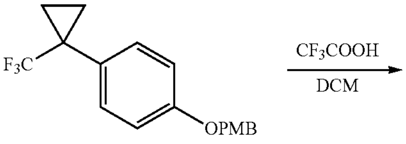

B-2

-continued

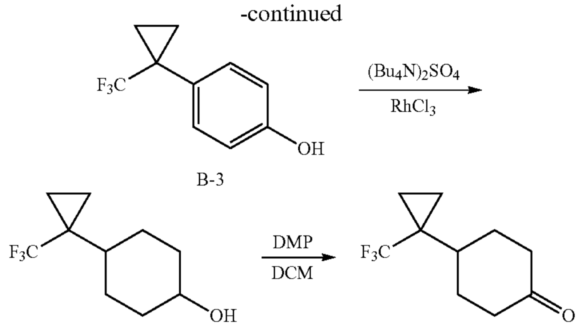

B-3

B-4

I-3

Step 1 1-methoxy-4-((4-(1-(trifluoromethyl)cyclopropyl)phenoxy) methyl)benzene (B-2)

B-2

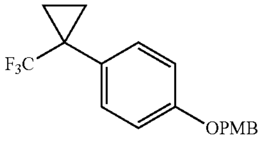

Into a 100-mL 3-necked round-bottom flask purged and maintained with an atmosphere of nitrogen was placed cesium carbonate (1.352 g, 4.14 mmol), copper iodide (72 mg, 0.38 mmol), (4-methoxyphenyl) methanol (782 mg, 5.66 mmol), 2,3,6,7-tetramethylpyrido[3,2-g]quinoline (178 mg, 0.75 mmol), a solution of 1-bromo-4-[1-(trifluoromethyl)cyclopropyl]benzene (B-1) (1 g, 3.77 mmol) in toluene (50 mL). The resulting solution was stirred at 110° C. for 24 h. The reaction was cooled to RT and diluted with 100 mL of EtOAc. The reaction was then quenched by the addition of saturated $NH_4Cl$ aqueous solution. The solid was filtered out. The separated organic phase was washed with brine, dried over anhydrous sodium sulfate and concentrated under reduced pressure. The residue was purified by silica gel chromatography (EtOAc/petroleum ether) to give the title compound B-2. MS: 346 (M+23).

Step 2 4-(1-(trifluoromethyl)cyclopropyl)phenol (B-3)

B-3

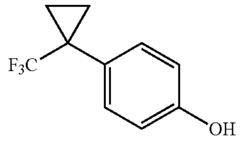

Into a 100-mL 3-necked round-bottom flask purged and maintained with an atmosphere of nitrogen was placed a solution of 1-[(4-methoxyphenyl) methoxy]-4-[1-(trifluoromethyl)cyclopropyl]benzene (B-2) (550 mg, 1.71 mmol) in dichloromethane (10 mL). This was followed by the addition of TFA (389 mg, 3.41 mmol) dropwise with stirring at 0° C. The resulting solution was stirred at 0° C. for 2 h. The resulting solution was diluted with 100 mL of DCM, then quenched by the addition of saturated $NaHCO_3$ aqueous solution. The organic layer was washed with 50 mL of brine, dried over anhydrous sodium sulfate and concentrated under vacuum. The residue was purified by silica gel chromatography (EtOAc/petroleum ether) to give the title compound. MS: 253 (M+51).

Step 3 4-(1-(trifluoromethyl)cyclopropyl)cyclohexan-1-ol (B-4)

B-4

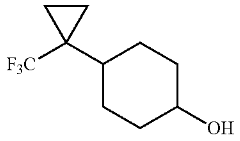

Into a 2,000-mL pressure tank reactor was placed a mixture of 4-[1-(trifluoromethyl)cyclopropyl]phenol (B-3) (22 g, 108.82 mmol) in hexane (650 mL), tetrabutylammonium sulphate (7.6 g, 13.04 mmol), phosphate buffer (650 mL), rhodium chloride (2.2 g, 10.51 mmol). The resulting solution was stirred for 20 h at RT under 60 psi $H_2$. The solid was filtered out. The filtrate was washed with 500 mL of brine. The organic layer was dried over anhydrous sodium sulfate and concentrated under reduced pressure. The residue was used in the next step without further purification. MS: 242 (M+34).

Step 3 4-(1-(trifluoromethyl)cyclopropyl)cyclohexan-1-one (I-3)

I-3

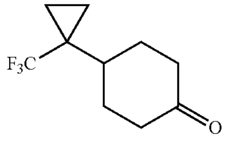

Into a 5,000-mL 4-necked round-bottom flask purged and maintained with an atmosphere of nitrogen was placed a solution of 4-[1-(trifluoromethyl)cyclopropyl]cyclohexan-1-ol (B-4) (56 g, 268.95 mmol) in dichloromethane (1,500 mL). This was followed by the addition of Dess-Martin agent (148 g, 349.06 mmol) in several batches at 0° C. The resulting solution was stirred and gradually warmed to RT for 3 h. The reaction was then quenched by the addition of aq. $NaHCO_3$ and $Na_2SO_3$ solution. The organic phase was separated. The water phase was extracted with 2×1,000 mL of dichloromethane. The organic layers were combined, dried over $Na_2SO_4$, filtered and concentrated under reduced pressure. The residue was purified by silica gel chromatography (EtOAc/petroleum ether) to give the title compound I-3. MS: 207 (M+1).

Intermediate I-4

(S)-6-(1-(trifluoromethyl)cyclopropyl)-5,6,7,8-tetrahydrothieno[2,3-b]quinoline-2-carboxylic acid (1-4)

I-4

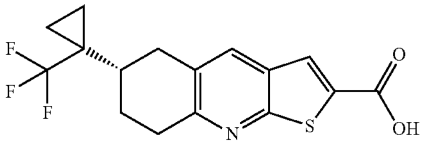

Following analogous methodology to that outlined for Intermediate I-1 above, by using intermediate I-3, the following intermediate I-4 was synthesized. MS: 342 (M+1).

Scheme C: Synthesis of Intermediate I-5

Intermediate I-5 was made by modifying the procedure disclosed in international patent application publication WO 2006098961 (Tagat, J. R. et al.) to that shown below.

Scheme C: Synthesis of intermediate I-5

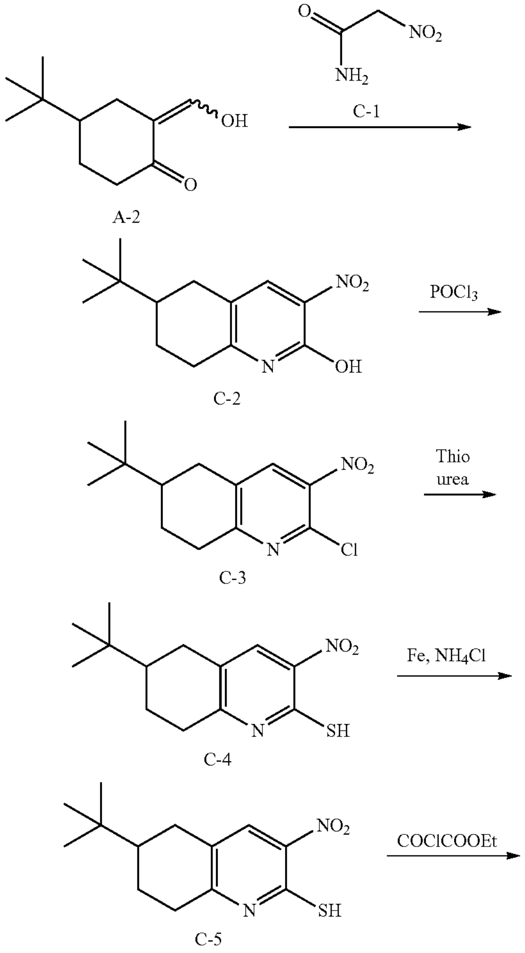

-continued

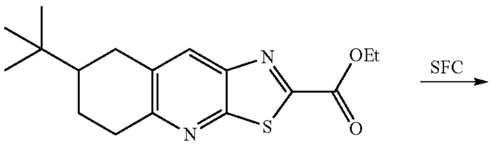

C-6

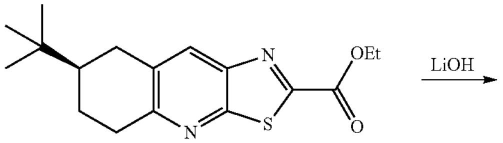

C-7A

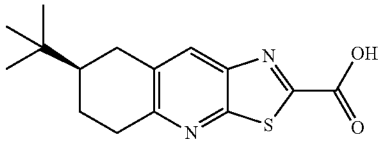

C-8

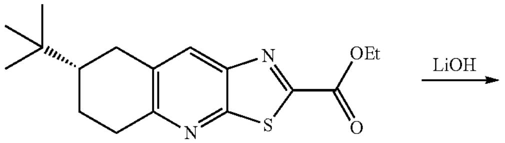

C-7B

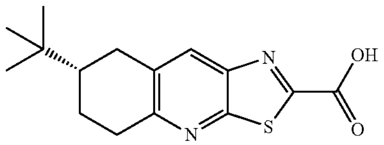

I-5

Step 1 6-(tert-butyl)-3-nitro-5,6,7,8-tetrahydroquinolin-2-ol (C-2)

C-2

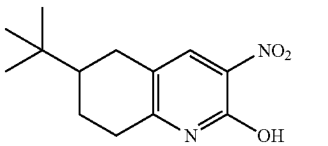

To a solution of compound 4-(tert-butyl)-2-(hydroxymethylene)cyclohexan-1-one (326 g, 1.789 mol) and NaOH (71.7 g, 1.79 mol) in $H_2O$ (6900 mL), was added aqueous piperidine acetate (274.6 ml) [prepared from $CH_3COOH$ (63 ml), and piperidine (108 ml), and $H_2O$ (6900 ml)]. The resulting solution was stirred at 100° C. for 5 min, then 2-nitroacetamide (251.5 g, 1.789 mol) was added slowly. The reaction mixture was stirred at reflux for 2 h, upon cooling to RT, the solid was collected by filtration and washed with EtOAc. The filter cake was dried to give the title compound. MS: 251 (M+1).

Step 2 6-(tert-butyl)-2-chloro-3-nitro-5,6,7,8-tetrahydroquinoline (C-3)

C-3

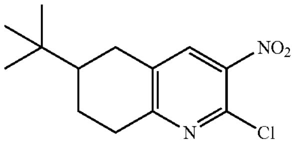

To a mixture of compound 6-(tert-butyl)-3-nitro-5,6,7,8-tetrahydroquinolin-2-ol (C-2) (200 g, 0.8 mol) in $POCl_3$ (2000 g, 13.1 mol), was added diisopropylethylamine (113.6 g, 0.88 mol). The reaction mixture was stirred at reflux for 2 h, upon cooling to RT, the reaction was concentrated to removed most of $POCl_3$ and the residue was poured into ice $H_2O$ and neutralized by 2N NaOH aqueous solution. The reaction was extracted with EtOAc. The organic layers were combined, dried over $Na_2SO_4$, filtered and concentrated under reduced pressure. The residue was purified by silica gel chromatography (EtOAc/petroleum ether) to give the title compound, C-3. MS: 251 (M+1).

Step 3 6-(tert-butyl)-3-nitro-5,6,7,8-tetrahydroquinoline-2-thiol (C-4)

C-4

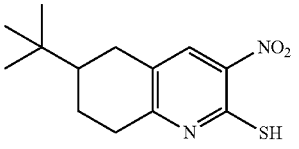

To a mixture of 6-(tert-butyl)-2-chloro-3-nitro-5,6,7,8-tetrahydroquinoline (C-3) (150 g, 558.16 mmol) and thiourea (535.34 g, 7.03 mol), was added ethanol (900 mL). The reaction was heated at reflux when $H_2O$ (600 mL) was added dropwise. The reaction was heated at reflux for 3 h, it was cooled to RT, and $H_2O$ was added. The mixture was filtered. The filter cake was dissolved in THF/$H_2O$ (1:1) and added tributyl phosphine (80 mL). The mixture was stirred at RT overnight, and then most of the THF was evaporated. The mixture was then treated with petroleum ether. The resulting mixture was filtered. The filter cake was dried to give the title compound, C-4. MS: 267 (M+1).

Step 4 3-amino-6-(tert-butyl)-5,6,7,8-tetrahydroquinoline-2-thiol (C-5)

C-5

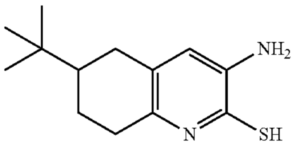

To a mixture of compound 6-(tert-butyl)-3-nitro-5,6,7,8-tetrahydroquinoline-2-thiol (C-4) (53 g, 0.2 mol) and iron (33.6 g, 0.6 mol) was added ethanol (530 mL), the mixture was heated at 75° C. $NH_4Cl$ (32.1 g, 0.6 mol) was then added into the reaction, and the reaction was refluxed at 85° C. for 1 h. The reaction mixture was cooled to RT and filtered through Celite®. The filtrate was concentrated under reduced pressure. The residue was purified by silica gel chromatography (EtOAc/petroleum ether) to give the title compound, C-5. MS: 237 (M+1).

Step 4 ethyl 7-(tert-butyl)-5,6,7,8-tetrahydrothiazolo [5,4-b]quinoline-2-carboxylate (C-6)

C-6

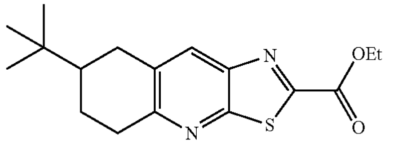

To a solution of 3-amino-6-(tert-butyl)-5,6,7,8-tetrahydroquinoline-2-thiol (C-5) (100 g, 423.05 mmol) and tributyl phosphine (30 mL) in toluene (2000 mL) was added COCl-COOEt (201.37 g, 1.48 mol) at RT, The reaction was stirred at RT for 1 h, and p-methylbenzene sulfonic acid (36.42 g, 211.52 mmol) was added. The reaction was refluxed for 1 h and then concentrated under reduced pressure. The resulting mixture was neutralized by saturated $NaHCO_3$ aqueous solution to PH 7~8. The mixture was extracted with EtOAc. The organic layers were combined, dried over $Na_2SO_4$, filtered and concentrated under reduced pressure. The residue was purified by silica gel chromatography (EtOAc/petroleum ether) to give racemic mixture of C-6. MS: 319 (M+1).

Step 5 ethyl (R)-7-(tert-butyl)-5,6,7,8-tetrahydrothiazolo[5,4-b]quinoline-2-carboxylate (C-7B)

C-7B

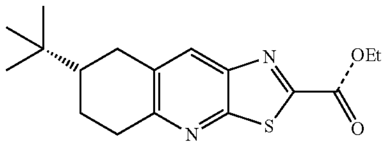

The racemate ethyl 7-(tert-butyl)-5,6,7,8-tetrahydrothiazolo[5,4-b]quinoline-2-carboxylate (C-6) was purified with Prep-chiral SFC under the following conditions: Instrument: Thar 200, Column: OD 250 mm*50 mm, 10 um; Mobile phase: A: Supercritical $CO_2$, B: EtOH, A: B=85:15 at 200 mL/min Detector, 220 nm. The faster eluting peak is collected. This afforded the title compound, 7B. MS: 319 (M+1).

Step 6: (S)-7-(tert-butyl)-5,6,7,8-tetrahydrothiazolo [5,4-b]quinoline-2-carboxylic acid (1-5)

I-5

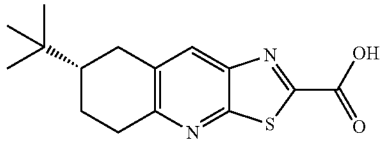

Into a 1,000-mL 3-necked round-bottom flask was placed a solution of ethyl (7S)-7-tert-butyl-5H,6H,7H,8H-[1,3]thiazolo[5,4-b]quinoline-2-carboxylate (C-7B) (30 g, 94.21 mmol) in tetrahydrofuran (150 mL). This was followed by the addition of a solution of $LiOH \cdot H_2O$ (12 g, 285.99 mmol) in water (300 mL) dropwise with stirring. The resulting solution was stirred at RT for 1 h. The reaction mixture was cooled to 0° C., then adjusted to pH 5 with aqueous HCl (1N). The solid was collected by filtration and dried in an oven under reduced pressure. This afforded compound I-5. MS: 291 [M+1].

Intermediate I-6

(S)-7-(1-methylcyclopropyl)-5,6,7,8-tetrahydrothiazolo[5,4-b]quinoline-2-carboxylic acid (I-6)

I-6

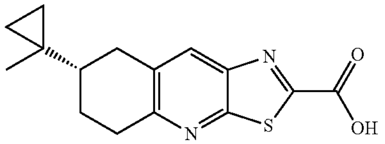

Following analogous methodology to that outlined for Intermediate I-5 above, using a known compound 4-(1-methylcyclopropyl)cyclohexan-1-one as starting material, (Stamford, Andrew; Miller, Michael W.; Demong, Duane Eugene; Greenlee, William J.; Kozlowski, Joseph A.; Lavey, Brian J.; Wong, Michael K. C.; Yu, Wensheng; Dai, Xing; Yang, De-Yi et al, WO 2010039789), intermediate I-6 was prepared. MS: 289 (M+1).

Intermediate I-7

(S)-7-(1-(trifluoromethyl)cyclopropyl)-5,6,7,8-tetrahydrothiazolo[5,4-b]quinoline-2-carboxylic acid (1-7)

I-7

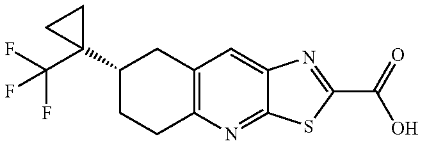

Following analogous methodology to that outlined for Intermediate I-5 above, using ketone intermediate 1-3, intermediate I-7 was prepared. MS: 343 (M+1).

Scheme D: Synthesis of intermediate I-8

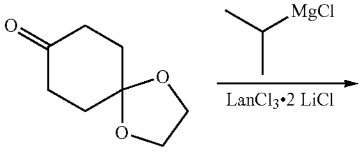

D-1

-continued

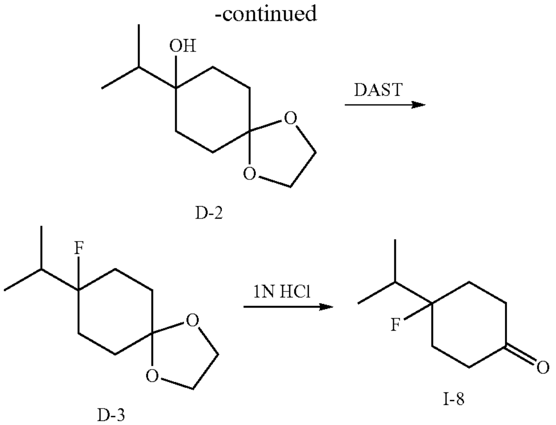

D-2

D-3

I-8

Step 1 8-isopropyl-1,4-dioxaspiro[4,5]decan-8-ol (D-2)

D-2

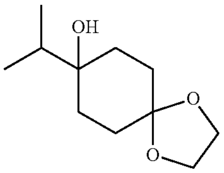

The lanthanum trichloride bis lithium chloride complex (0.6 M in THF, 117 mL, 70.4 mmol) was added to a solution of the 1,4-dioxaspiro[4,5]decan-8-one (10 g, 64.0 mmol) in THF (20 mL). The resulting mixture was stirred at RT under a nitrogen atmosphere for 1 h, then cooled in an ice-water bath. Isopropylmagnesium chloride (2.0 M in THF, 35.2 mL, 70.4 mmol) was added and the ice bath was removed. The reaction mixture was stirred at RT for 2 h. The reaction was quenched with sat. aq. ammonium chloride and most of the THF was removed under reduced pressure. The residue was extracted with EtOAc. The organic layer was dried over $Na_2SO_4$, filtered and concentrated under reduced pressure. The residue was purified by silica gel chromatography (EtOAc/petroleum ether) to give compound D-2. MS: 183 ($M-H_2O+1$).

Step 2 8-fluoro-8-isopropyl-1,4-dioxaspiro[4,5]decane (D-3)

D-3

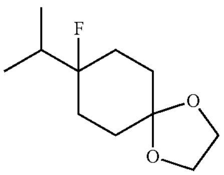

(8-isopropyl-1,4-dioxaspiro[4.5]decan-8-ol (4.63 g, 23.12 mmol) was dissolved in anhydrous toluene (50 mL) and cooled in an ice-water bath under a nitrogen atmosphere. DAST (7.45 g, 46.2 mmol) was added dropwise and the resulting reaction mixture was allowed to warm to RT and stirred overnight. The reaction was quenched saturated aqueous sodium bicarbonate, and extracted with EtOAc. The aqueous phase was further extracted with EtOAc (X2). The combined organic phases were dried over $Na_2SO_4$, filtered and concentrated under reduced pressure. The residue was purified by silica gel chromatography (EtOAc/petroleum ether) to give the title compound, D-3, which contains 8-isopropyl-1,4-dioxaspiro[4.5]dec-7-ene. The mixture was used in the next step without further purification. MS: 203 (M+1).

Step 3 4-fluoro-4-isopropylcyclohexan-1-one (I-8)

I-8

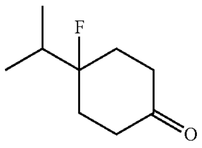

8-fluoro-8-isopropyl-1,4-dioxaspiro[4.5]decane (8 g, 39.6 mmol) in THF (15 mL) was treated with aqueous HCl (1N, 79 mL, 79 mmol) while cooled in an ice-water bath and the resulting reaction mixture was allowed to warm to RT and stirred overnight. The reaction was quenched with sat. aq. sodium bicarbonate in ice-water bath. The reaction was extracted with ether. The organic phase was dried over $Na_2SO_4$, filtered and concentrated under reduced pressure. The residue was purified by silica gel chromatography (EtOAc/petroleum ether) to give the title compound. MS: 158 (M+1).

Scheme E: Synthesis of intermediate I-9

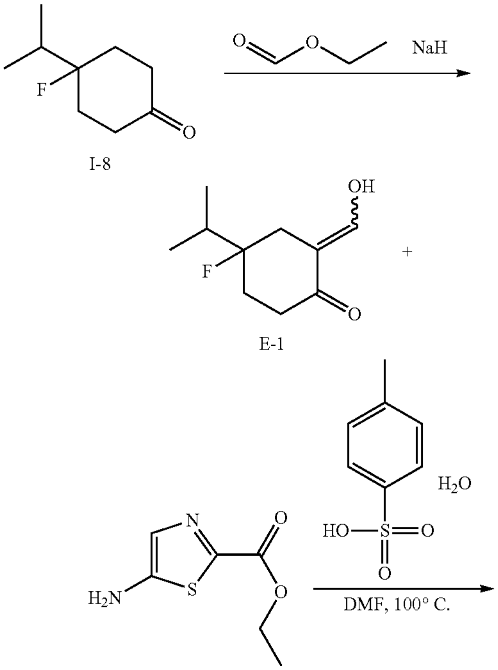

I-8

E-1

E-2

-continued

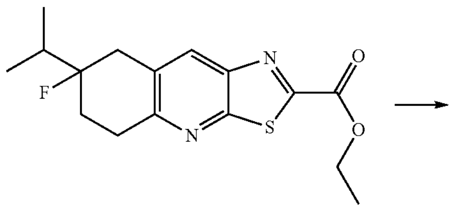

E-3

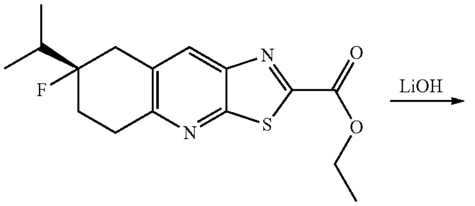

E-4

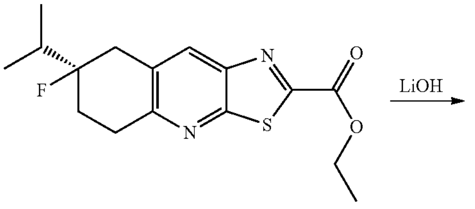

E-5

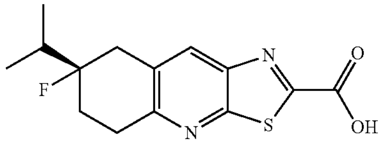

I-9

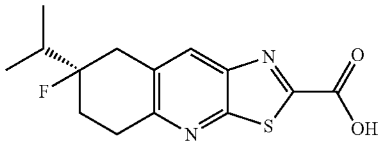

E-6

Step 1 4-fluoro-2-(hydroxymethylene)-4-isopropylcyclohexan-1-one (E-1)

E-1

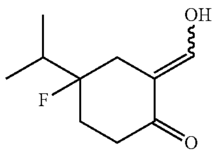

To a mixture of NaH (2654 mg, 66.4 mmol) in diethyl ether (100 mL) was added 4-fluoro-4-isopropylcyclohexanone (5 g, 31.6 mmol) and ethyl formate (5.40 mL, 66.4 mmol) at 0° C. The mixture was stirred at RT for 48 h, diluted with EtOAc (20 mL) and water (20 mL). The pH of the mixture was adjusted to 2 by using 1N aqueous HCl. The mixture was extracted with EtOAc. The organic layer was dried over $Na_2SO_4$, filtered and concentrated under reduced pressure to provide the title compound, E-1. The crude product was directly used in the next step without further purification. MS: 187 (M+1).

Step 2 ethyl 7-fluoro-7-isopropyl-5,6,7,8-tetrahydrothiazolo[5,4-b]quinoline-2-carboxylate (E-3)

E-3

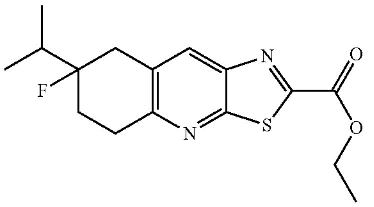

A mixture of Ts-OH (705 mg, 3.71 mmol), ethyl 5-aminothiazole-2-carboxylate (HCl salt, 2.58 g, 12.35 mmol), (4-fluoro-2-(hydroxymethylene)-4-isopropylcyclohexan-1-one (E-1) (2.3 g, 12.35 mmol) and DMF (80 mL) was stirred at 100° C. for 1 h, and the reaction was then cooled down to RT. The mixture was diluted with EtOAc (400 mL), quenched with solid $NaHCO_3$. The organic layer was washed with sat. $NaHCO_3$ (aq.), water and brine, dried over $Na_2SO_4$, filtered and concentrated under reduced pressure. The residue was purified by silica gel chromatography (EtOAc in hexane) to give the title compound, E-3. MS: 323 (M+1).

Step 3 ethyl(S)-7-fluoro-7-isopropyl-5,6,7,8-tetrahydrothiazolo[5,4-b]quinoline-2-carboxylate (E-4)

E-4

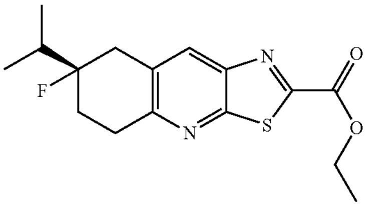

Ethyl 7-fluoro-7-isopropyl-5,6,7,8-tetrahydrothiazolo[5,4-b]quinoline-2-carboxylate (E-3) was resolved by Prep-SFC with the following conditions (SFC 350): Column, AD-H; mobile phase, ethanol (0.2% DEA); Detector, 220 nm. The faster eluting peak is collected to provide the title compound. MS: 323 (M+1).

Step 4 (S)-7-fluoro-7-isopropyl-5,6,7,8-tetrahydrothiazolo[5,4-b]quinoline-2-carboxylic acid (I-9)

I-9

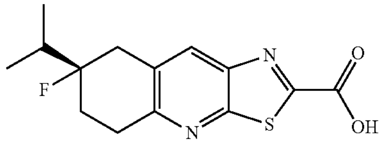

To a solution of ethyl(S)-7-fluoro-7-isopropyl-5,6,7,8-tetrahydrothiazolo[5,4-b]quinoline-2-carboxylate (E-4) (220 mg, 0.682 mmol) in THF (2 mL) and MeOH (1 mL) was added lithium hydroxide (1 M in $H_2O$, 0.96 mL, 0.96 mmol). The mixture was stirred at RT for 0.5 h. The reaction was quenched with 1N aqueous HCl (0.96 mL), The mixture then was lyophilized to give the title compound, I-9.

Scheme F: Synthesis of intermediate I-10

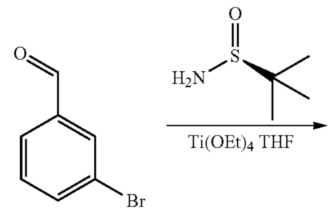

F-1

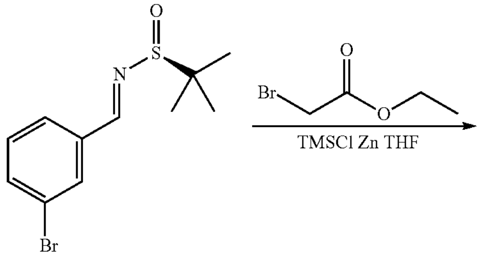

F-2

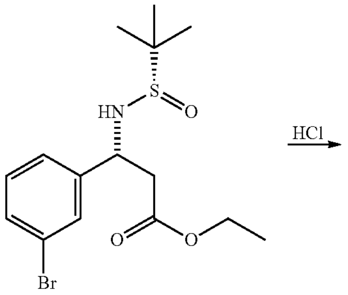

F-3

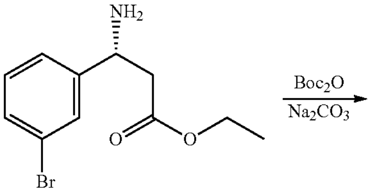

F-4

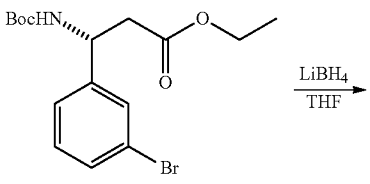

F-5

-continued

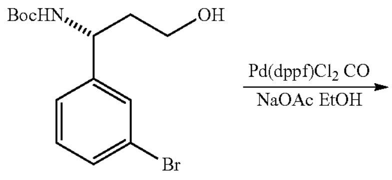

F-6

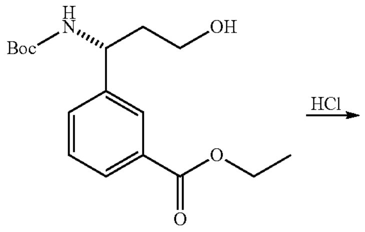

F-7

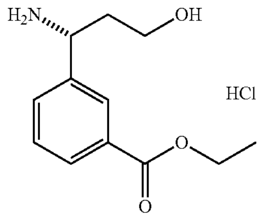

I-10

Step 1 (S,E)-N-(3-bromobenzylidene)-2-methylpropane-2-sulfinamide (F-2)

F-2

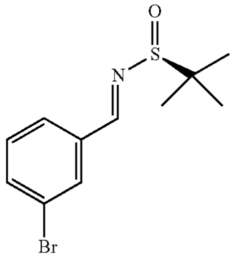

Into a 2-L 4-necked round-bottom flask, purged and maintained with an inert atmosphere of nitrogen, was placed 3-bromobenzaldehyde (70 g, 378.34 mmol), tetrahydrofuran (700 mL), and(S)-2-methylpropane-2-sulfinamide (50.4 g, 415.84 mmol). This was followed by the addition of $Ti(OEt)_4$ (129.4 g, 567.27 mmol) dropwise with stirring. The resulting solution was stirred at RT overnight. The reaction was then quenched by the addition of 700 mL of brine. The resulting solution was diluted with 500 mL of ethyl acetate. The solid was filtered out. The filtrate was extracted with of ethyl acetate. The organic layers were dried over $Na_2SO_4$, filtered and concentrated under reduced pressure to give the title compound, F-2, which was directly used in the next step without further purification. MS: 289 (M+1).

Step 2 ethyl (R)-3-(3-bromophenyl)-3-(((S)-tert-butylsulfinyl)amino) propanoate (F-3)

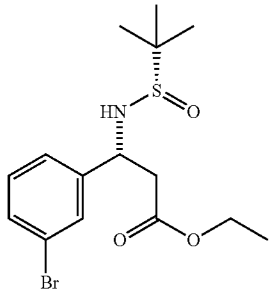

F-3

Into a 2-L 4-necked round-bottom flask, purged and maintained with an inert atmosphere of nitrogen, was placed Zn (81 g, 1.25 mol) and tetrahydrofuran (750 mL). This was followed by the addition of TMSCl (10 g, 92.59 mmol). The solution was stirred 10 minutes at 40° C. To this was added ethyl 2-bromoacetate (103.4 g, 619.16 mmol) dropwise with stirring. The solution was stirred at 40° C. for 50 minutes. The solution was cooled to −8° C. To the mixture was added a solution of(S)-N-[(1E)-(3-bromophenyl)methylidene]-2-methylpropane-2-sulfinamide (F-2) (100 g, 346.98 mmol) in tetrahydrofuran (250 mL) dropwise with stirring. The resulting solution was stirred at −8° C. overnight. The solid was filtered out. The filtrate was diluted with $H_2O$ and extracted with ethyl acetate. The organic layers were dried over $Na_2SO_4$, filtered and concentrated under reduced pressure to give the title compound (F-3), which was directly used in the next step without further purification. MS: 377 (M+1).

Step 3 ethyl (R)-3-amino-3-(3-bromophenyl)propanoate (F-4)

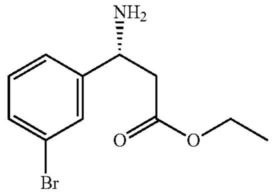

F-4

Into a 20-L 4-necked round-bottom flask, purged and maintained with an inert atmosphere of nitrogen, was placed ethyl (3R)-3-(3-bromophenyl)-3-[[(S)-2-methylpropane-2-sulfinyl]amino]propanoate (F-3) (1,100 g, 2.92 mol) and tetrahydrofuran (10 L). This was followed by the dropwise addition of HCl (3.4 L) with stirring. The resulting solution was stirred at RT for 30 minutes. The pH value of the solution was adjusted to 7 with sodium carbonate. The resulting solution was extracted with of ethyl acetate. The organic layers were dried over $Na_2SO_4$, filtered and concentrated under reduced pressure to give the title compound, F-4, which was directly used in the next step without further purification. MS: 273 (M+1).

Step 4 ethyl (R)-3-(3-bromophenyl)-3-((tert-butoxycarbonyl)amino) propanoate (F-5)

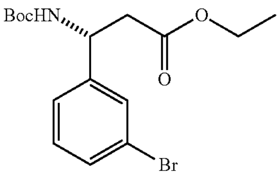

F-5

Into a 20-L 4-necked round-bottom flask purged and maintained with an inert atmosphere of nitrogen was placed ethyl (3R)-3-amino-3-(3-bromophenyl)propanoate (F-4) (750 g, 2.76 mol, 1.00 equiv), tetrahydrofuran (7.5 L), sodium carbonate (586 g, 5.53 mol, 2.00 equiv), and $Boc_2O$ (1195 g, 5.48 mol, 2.00 equiv). The resulting solution was stirred for 4 hours at room temperature. The solution was then diluted with $H_2O$ and extracted with ethyl acetate. The organic layers were combined, dried over anhydrous sodium sulfate and concentrated under vacuum to give the title compound, F-5, which was directly used in the next step without further purification. MS: 373 (M+1).

Step 5 tert-butyl (R)-(1-(3-bromophenyl)-3-hydroxypropyl) carbamate (F-6)

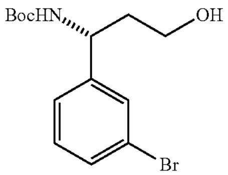

F-6

Into a 20-L 4-necked round-bottom flask purged and maintained with an inert atmosphere of nitrogen was placed ethyl (3R)-3-(3-bromophenyl)-3-[[(tert-butoxy)carbonyl]amino]propanoate (F-5) (1200 g, 3.22 mol, 1.00 equiv) and tetrahydrofuran (10 L). This was followed by the addition of $LiBH_4$ (149 g, 7.10 mol, 2.20 equiv), in portions at 0° C. The resulting solution was stirred overnight at room temperature. The reaction was then quenched by the addition of water/ice. The resulting solution was extracted with ethyl acetate. The organic layers were combined, dried and concentrated under vacuum to give the title compound, F-6, which was directly used in the next step without further purification. MS: 331 (M+1).

Step 6 ethyl (R)-3-(1-((tert-butoxycarbonyl)amino)-3-hydroxypropyl)benzoate (F-7)

F-7

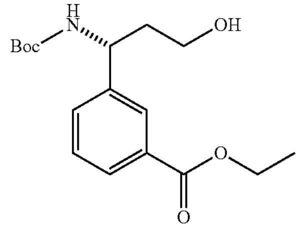

Into a 5-L 4-necked round-bottom flask, purged and maintained with an inert atmosphere of nitrogen, was placed tert-butyl N-[(1R)-1-(3-bromophenyl)-3-hydroxypropyl] carbamate (F-6) (150 g, 454.25 mmol, 1.00 equiv), ethanol (3 L), NaOAc (56.1 g, 684.15 mmol, 1.50 equiv), and $Pd(dppf)Cl_2$ (18.6 g, 25.42 mmol, 0.05 equiv). The flask was charged with CO and heated to reflux overnight in an oil bath. The reaction mixture was cooled to room temperature and concentrated under vacuum. The residue was diluted with $H_2O$ and extracted with ethyl acetate. The organic layers were combined, dried and concentrated under vacuum. The residue was purified by silica gel chromatography (EtOAc in petroleum ether) to give the title compound, F-7. MS: 324 (M+1).

Step 7 ethyl (R)-3-(1-amino-3-hydroxypropyl)benzoate (I-10)

I-10

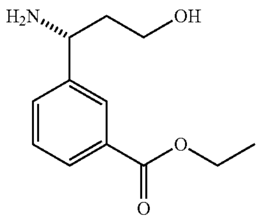

Into a 250-mL 3-necked round-bottom flask, purged and maintained with an inert atmosphere of nitrogen, was placed ethyl 3-[(1R)-1-[[(tert-butoxy)carbonyl]amino]-3-hydroxypropyl]benzoate (F-7) (10 g, 30.92 mmol, 1.00 equiv) and i-propanol (100 mL). This was followed by the addition of HCl (12M, 50 mL) dropwise with stirring at 0-10° C. The resulting solution was stirred for 3 hours at room temperature. The resulting mixture was concentrated under vacuum. This afforded the title compound, I-10. MS: 224 (M+1).

Scheme F: Synthesis of intermediate I-11

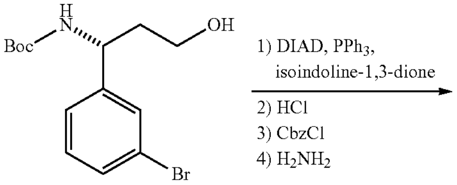

F-6

-continued

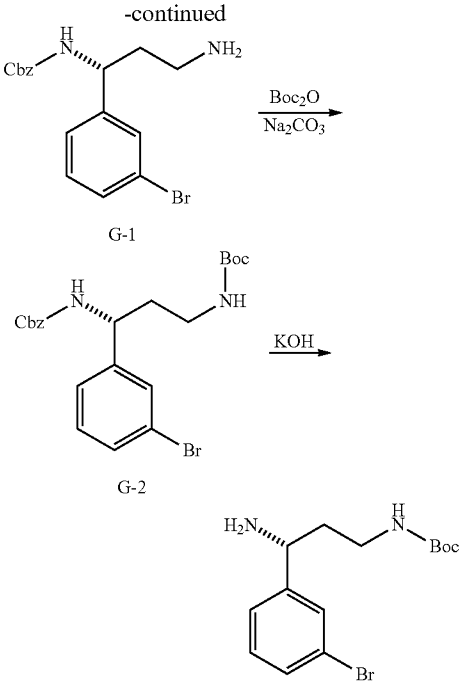

G-1

G-2

I-11

Step 1 benzyl (R)-(3-amino-1-(3-bromophenyl)propyl) carbamate (G-1)

G-1

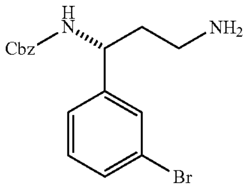

Into a 5,000-mL 3-necked round-bottom flask purged and maintained with an inert atmosphere of nitrogen was placed a solution of tert-butyl N-[(1R)-1-(3-bromophenyl)-3-hydroxypropyl]carbamate (F-6) (200 g, 605.66 mmol, 1.00 equiv) in THF (2 L), 2,3-dihydro-1H-isoindole-1,3-dione (93 g, 632.09 mmol, 1.10 equiv), $PPh_3$ (206 g, 785.39 mmol, 1.30 equiv). This was followed by the addition of DIAD (159 g, 786.31 mmol, 1.30 equiv) dropwise with stirring at 0-5° C. The resulting solution was stirred for 30 min at room temperature. This mixture was used for next step directly without workup.

Into a 5-L 3-necked round-bottom flask was placed tert-butyl N-[(1R)-1-(3-bromophenyl)-3-(1,3-dioxo-2,3-dihydro-1H-isoindol-2-yl)propyl]carbamate (G-1) (299 g, 650.94 mmol, 1.00 equiv), HCl (6M, 400 mL, 10.00 equiv). The resulting solution was stirred overnight at room temperature. The pH value of the solution was adjusted to 7 with sodium carbonate. Sodium carbonate (97 g, 915.18 mmol) was added to the solution. This was followed by the dropwise addition of benzyl chloroformate (115 g, 674.12 mmol) with stirring at 0-5° C. The resulting solution was stirred for 30 min at room temperature.

$NH_2NH_2 \cdot H_2O$ (500 mL) was then added to the solution. The resulting solution was heated to reflux for 5 hr. The reaction mixture was cooled to RT and extracted with 2×500 mL of ethyl acetate. The organic layers were combined, washed with 100 mL of brine, dried over anhydrous sodium sulfate and concentrated under vacuum to afford the title compound, G-1, which was directly used in the next step without further purification. MS: 363 (M+1).

Step 2 benzyl tert-butyl (1-(3-bromophenyl)propane-1,3-diyl) (R)-dicarbamate (G-2)

G-2

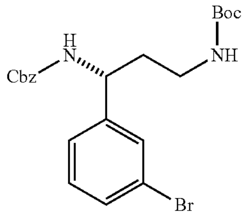

Into a 3 L 3-necked round-bottom flask was placed a solution of benzyl N-[(1R)-3-amino-1-(3-bromophenyl)propyl]carbamate (G-1) (176 g, 484.52 mmol, 1.00 equiv) in THF (2 L), sodium carbonate (77 g, 726.48 mmol, 1.50 equiv), $Boc_2O$ (116 g, 531.50 mmol, 1.10 equiv), water (1 L). The resulting solution was stirred for 20 min at RT. The resulting solution was extracted with 2×1 L of ethyl acetate. The organic layers were combined, washed with 1×500 mL of brine, dried over anhydrous sodium sulfate and concentrated under vacuum. The . . . residue was applied onto a silica gel column and eluted with ethyl acetate/petroleum ether to afford the title compound, G-2. MS: 463 (M+1).

Step 3 tert-butyl (R)-(3-amino-3-(3-bromophenyl) propyl) carbamate (I-11)

I-11

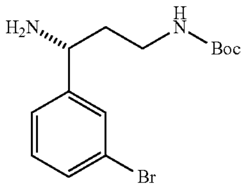

Into a 2-L 3-necked round-bottom flask was placed tert-butyl N-[(3R)-3-[[(benzyloxy)carbonyl]amino]-3-(3-bromophenyl)propyl]carbamate (G-2) (130 g, 280.56 mmol, 1.00 equiv), methanol (650 mL, 11.00 equiv, 42%), aq. potassium hydroxide (40%, 650 mL, 10.00 equiv). The resulting solution was stirred for 5 hr at 75° C. in an oil bath. The resulting mixture was cooled and concentrated under vacuum. The residual solution was diluted with 400 mL of ice water, then extracted with 2×500 mL of ethyl acetate. The organic layers were combined, washed with brine, dried over $Na_2SO_4$, and concentrated under vacuum. The residue was diluted with DCM (200 mL), followed by addition of a saturated solution of oxalic acid (40 g). The mixture was stirred at RT for 30 min, then diluted with TBME (600 mL). The precipitate was collected by filtration and washed with THF/TBME (1:3, 400 mL) to afford the title compound, I-11. MS: 329 (M+1).

Scheme H: Synthesis of intermediate I-12

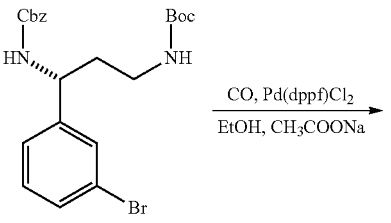

G-2

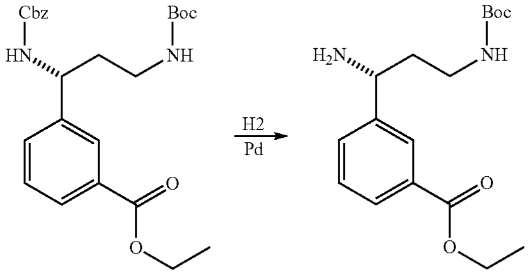

H-1

I-12

Step 1 ethyl (R)-3-(11,11-dimethyl-3,9-dioxo-1-phenyl-2,10-dioxa-4,8-diazadodecan-5-yl)benzoate (H-1)

H-1

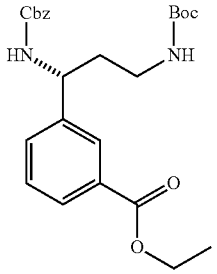

Into a 5-L 4-necked round-bottom flask purged and maintained with an inert atmosphere of nitrogen was placed tert-butyl N-[(3R)-3-[[(benzyloxy)carbonyl]amino]-3-(3-bromophenyl)propyl]carbamate (G-2, 100 g, 215.81 mmol, 1.00 equiv), ethanol (2 L), NaOAc (26.6 g, 324.39 mmol, 1.50 equiv), $Pd(dppf)Cl_2$ (8.83 g, 12.07 mmol, 0.05 equiv). The flask was charged with CO and heated to reflux overnight in an oil bath. The reaction mixture was cooled to room temperature and concentrated under vacuum. The residue was diluted with water, then extracted with ethyl acetate. The organic layer was dried and concentrated under vacuum to afford the title compound, H-1, which was used in the next step without further purification. MS: 479 (M+Na).

Step 2 ethyl (R)-3-(1-amino-3-((tert-butoxycarbonyl)amino) propyl)benzoate (I-12)

I-12

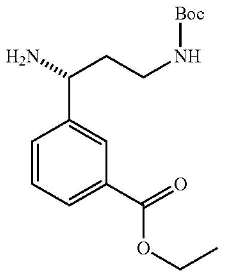

(R)-ethyl 3-(11,11-dimethyl-3,9-dioxo-1-phenyl-2,10-dioxa-4,8-diazadodecan-5-yl)benzoate (H-1) (1 g, 2.190 mmol) and Pd—C(0.233 g, 0.219 mmol) were put in a 100 mL RB flask. The RB flask was then degassed (×3) and purged with $N_2$ before adding methanol (21.90 mL). The reaction mixture was stirred under $H_2$ balloon pressure for 2 h at RT. The reaction mixture was filtered through Celite® and the filtrate was evaporated. The crude product was used in next step without further purification. MS: 323 (M+1).

Scheme J: Synthesis of intermediate I-13

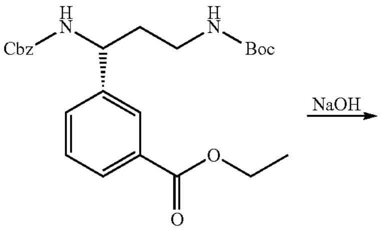

H-1

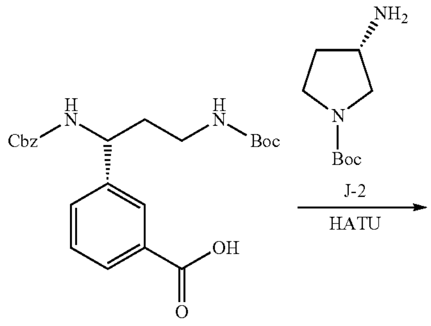

J-1

-continued

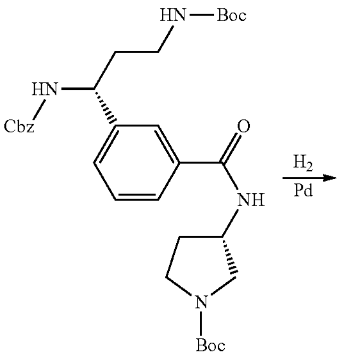

J-3

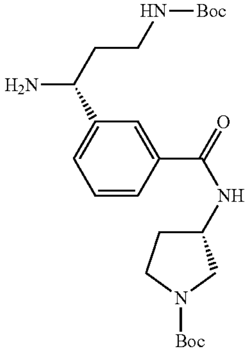

I-13

Step 1 (R)-3-(11,11-dimethyl-3,9-dioxo-1-phenyl-2,10-dioxa-4,8-diazadodecan-5-yl)benzoic acid (J-1)

J-1

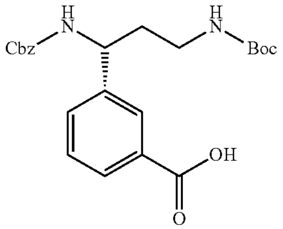

To a solution of (R)-ethyl 3-(11,11-dimethyl-3,9-dioxo-1-phenyl-2,10-dioxa-4,8-diazadodecan-5-yl)benzoate (H-1) (6.0 g, 13.14 mmol) in methanol (120 mL) was added 6 M aqueous NaOH solution (13.14 mL, 79 mmol). The mixture was stirred at RT overnight. Most of the MeOH was removed under reduced pressure. To the residue was added Teac (200 mL) and $H_2O$ (50 mL). The mixture was quenched with conc. HCl to pH 1 and extracted with EtOAc (200 mL×2). The organic layers were combined, washed with brine (20 mL), dried over $Na_2SO_4$, filtered and concentrated. The residue was purified by silica gel chromotograghpy (MeOH in DCM) to afford title compound, J-1. MS: 451 (M+Na).

Step 2 tert-butyl(S)-3-(3-((R)-11,11-dimethyl-3,9-dioxo-1-phenyl-2,10-dioxa-4,8-diazadodecan-5-yl) benzamido) pyrrolidine-1-carboxylate (J-3)

J-3

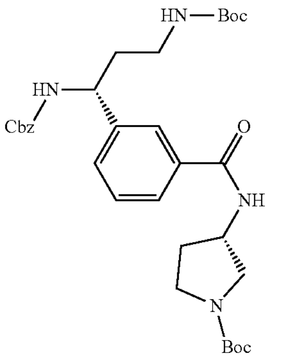

(R)-3-(11,11-dimethyl-3,9-dioxo-1-phenyl-2,10-dioxa-4,8-diazadodecan-5-yl)benzoic acid (J-1) (5.6 g, 13.07 mmol), (S)-tert-butyl 3-aminopyrrolidine-1-carboxylate (4.87 g, 26.1 mmol), HATU (8.94 g, 23.53 mmol) and DIPEA (6.83 mL, 39.2 mmol) were mixed together in DMF (100 mL) and stirred at RT for 2 h. Most of the DMF was removed under reduced pressure. The reaction mixture was diluted with EtOAc (500 mL). The organic layer was washed with saturated $NH_4Cl$ (50 mL×2), saturated $NaHCO_3$ (50 mL×2), brine, and dried over $Na_2SO_4$, filtered and concentrated under reduced pressure. The residue was purified by silica gel chromotograghpy (EtOAc/hexane) to afford the title compound, J-3. MS: 619 (M+23).

Step 3 tert-butyl(S)-3-(3-((R)-1-amino-3-((tert-butoxycarbonyl)amino) propyl)benzamido) pyrrolidine-1-carboxylate (1-13)

I-13

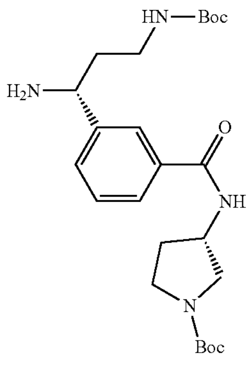

(S)-tert-butyl 3-(3-((R)-11,11-dimethyl-3,9-dioxo-1-phenyl-2,10-dioxa-4,8-diazadodecan-5-yl)benzamido) pyrrolidine-1-carboxylate (J-3, 1 g, 1.676 mmol) in MeOH (16 mL) under $N_2$ was added Pd on activated carbon (10% wt) (178 mg, 0.168 mmol). The mixture was flushed with $H_2$ three times and stirred at RT for 2 hr under 1 atmosphere $H_2$. The reaction mixture was filtered through a pad of Celite®, washed with MeOH (10 mL×3). The filtrate was concentrated under reduced pressure. The residue was purified by silica gel chromotograghpy (DCM: 2N $NH_3$/MeOH) to afford the title compound, I-13. MS: 463 (M+1).

Scheme K: Synthesis of intermediate I-14

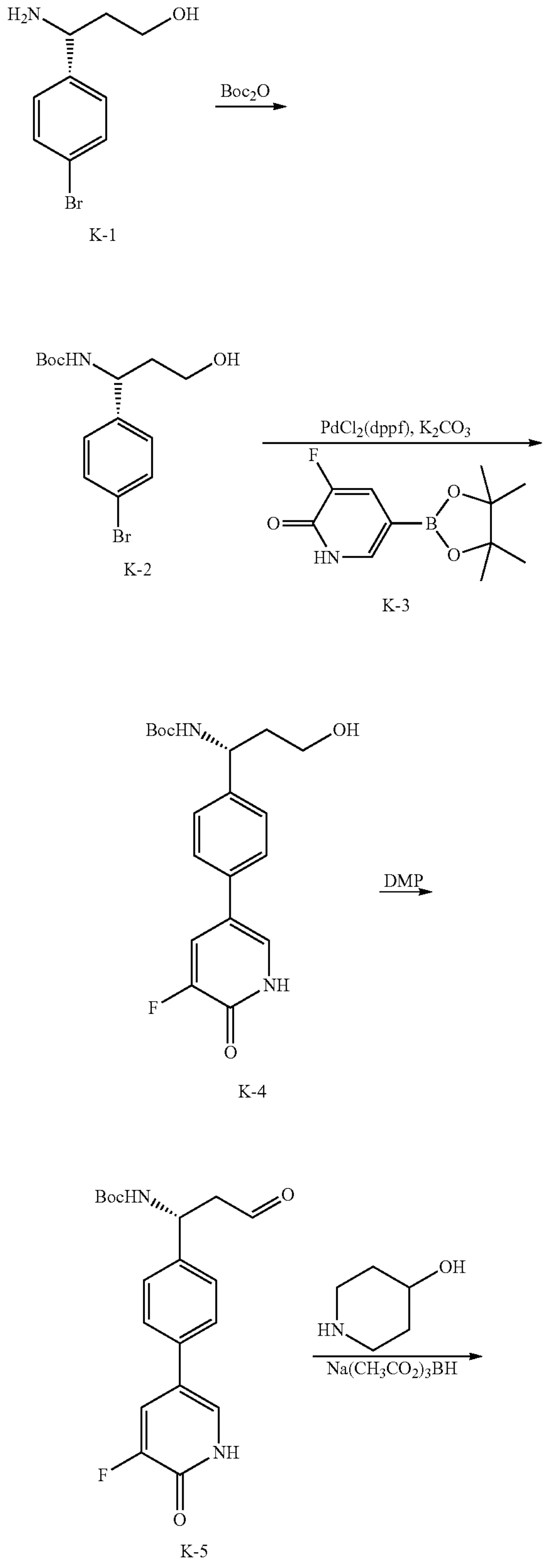

-continued

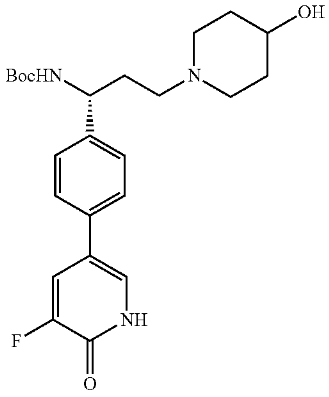

K-6

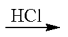

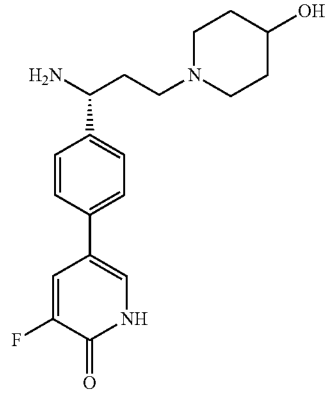

I-14

Step 1 (R)-tert-butyl (1-(4-bromophenyl)-3-hydroxypropyl) carbamate (K-2)

K-2

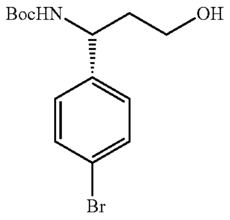

(R)-3-amino-3-(4-bromophenyl)propan-1-ol (2.48 g, 10.79 mmol) was put into a round bottom flask, dissolved in DCM (75 mL), and cooled to 0° C. $Et_3N$ (3.80 mL, 27.3 mmol) was added to the flask followed by di-tert-butyl decarbonate (3.57 g, 16.40 mmol). The reaction was warmed to RT overnight. To the reaction was added $NaHCO_3$ (aq.) and then diluted with DCM. The layers were separated, and the aqueous layer was extracted with DCM. The organic layers were combined, washed with brine, dried over $Na_2SO_4$, filtered and concentrated under reduced pressure. The residue was purified by silica gel chromatography (MeOH/DCM) to afford the title compound, K-2. MS: 332 (M+1).

Step 2 (R)-tert-butyl (1-(4-(5-fluoro-6-oxo-1,6-dihydropyridin-3-yl)phenyl)-3-hydroxypropyl) carbamate (K-4)

K-4

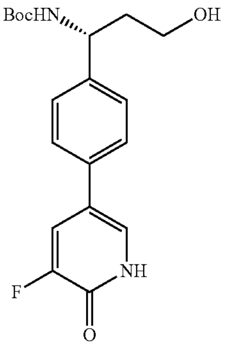

(R)-tert-butyl (1-(4-bromophenyl)-3-hydroxypropyl) carbamate (K-2) (172 mg, 0.521 mmol), 3-fluoro-5-(4,4,5,5-tetramethyl-1,3,2-dioxaborolan-2-yl)pyridin-2 (1H)-one (104.5 mg, 0.437 mmol), and $PdCl_2$(dtbpf) (28.7 mg, 0.44 mmol) were put into a round bottom flask under $N_2$. Dioxane (2 mL) was added to the reaction and then $N_2$ was bubbled through for approximately 1 min. 1M $K_2CO_3$ (aq., 1.05 mL, 1.050 mmol) was then added to the reaction and stirred at RT overnight. The reaction was diluted with EtOAc and $H_2O$, the layers were separated, and the aqueous layer was extracted with EtOAc. The organic layers were combined, dried over $Na_2SO_4$, filtered and concentrated under reduced pressure. The residue was purified by silica gel chromatography (MeOH/DCM) to afford the title compound, K-4. MS: 363 (M+1).

Step 3 (R)-tert-butyl (1-(4-(5-fluoro-6-oxo-1,6-dihydropyridin-3-yl)phenyl)-3-oxopropyl) carbamate (K-5)

K-5

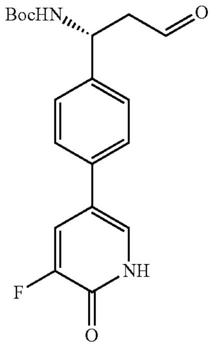

(R)-tert-butyl (1-(4-(5-fluoro-6-oxo-1,6-dihydropyridin-3-yl)phenyl)-3-hydroxypropyl) carbamate (K-4) (69.3 mg, 0.191 mmol) was dissolved in DCM (4 mL) and stirred at 0° C. Once cooled, Dess-Martin Periodinane (157.2 mg, 0.371 mmol) was added to the reaction. The reaction was allowed to warm to RT and was stirred for 3 h. The reaction was then diluted with DCM and saturated sodium thiosulfate aqueous solution and stirred for approximately 1 h. The layers were separated, and the organic was washed with saturated sodium thiosulfate aqueous solution and saturated $NaHCO_3$ aqueous solution. The layers were separated, and the organic layer was dried over $Na_2SO_4$, filtered and concentrated to afford the title compound, K-5. MS: 361 (M+1).

Step 4 (R)-tert-butyl (1-(4-(5-fluoro-6-oxo-1,6-dihydropyridin-3-yl)phenyl)-3-(piperidin-1-yl)propyl) carbamate (K-6)

K-6

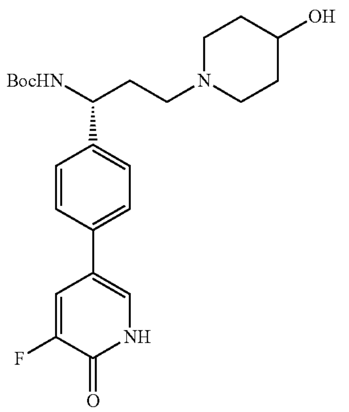

(R)-tert-butyl (1-(4-(5-fluoro-6-oxo-1,6-dihydropyridin-3-yl)phenyl)-3-oxopropyl) carbamate (K-5) (382.5 mg, 1.061 mmol) was dissolved in DCE (22 mL). To the mixture, piperidin-4-ol (197.1 mg, 1.949 mmol) was added and stirred at RT. After 5 min, sodium triacetoxyborohydride (686.8 mg, 3.24 mmol) was added to the reaction and stirred at RT overnight. The reaction was quenched with the addition of saturated $NaHCO_3$ aqueous solution and diluted with DCM. The layers were separated. The organic layers were dried over $Na_2SO_4$ and filtered. The filtrate was concentrated and purified by silica gel chromatography (MeOH to DCM) to afford the title compound, K-6. MS: 446 (M+1).

Step 5 (R)-5-(4-(1-amino-3-(4-hydroxypiperidin-1-yl)propyl)phenyl)-3-fluoropyridin-2 (1H)-one (I-14)

I-14

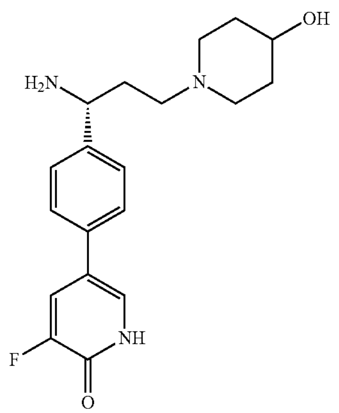

(R)-tert-butyl (1-(4-(5-fluoro-6-oxo-1,6-dihydropyridin-3-yl)phenyl)-3-(piperidin-1-yl)propyl) carbamate (K-6) (59.6 mg, 0.134 mmol) was dissolved in DCM (2 mL) and MeOH (1 mL). 4M HCl in dioxane (0.35 mL, 1.4 mmol) was then added to the flask and the reaction was stirred at RT for 3 h then heated at 70° C. for 1 h. Diethyl ether was added to the flask to crash out a solid. The solid was filtered to afford the title compound, I-14, which was used without further purification. MS: 346 (M+1).

Following analogous methodology to that outlined for intermediate I-14 above, intermediates I-15 and I-16 was prepared.

methyl (R)-1-(3-amino-3-(4-(5-fluoro-6-oxo-1,6-dihydropyridin-3 yl)phenyl)propyl)piperidine-4-carboxylate (I-15)

I-15

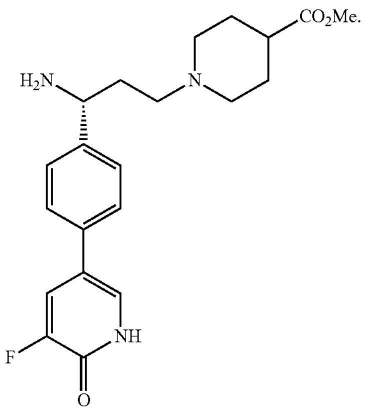

MS: 388 (M+1)

(R)-1-(3-(4-(1H-pyrazol-3-yl)phenyl)-3-aminopropyl)piperidin-4-ol (I-16)

I-16

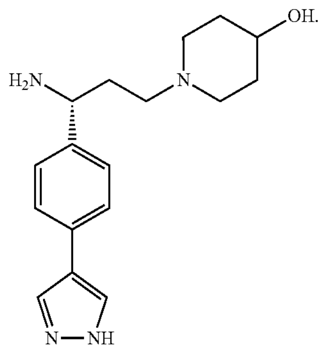

MS: 301 (M+1)

Scheme L: Synthesis of intermediate I-17

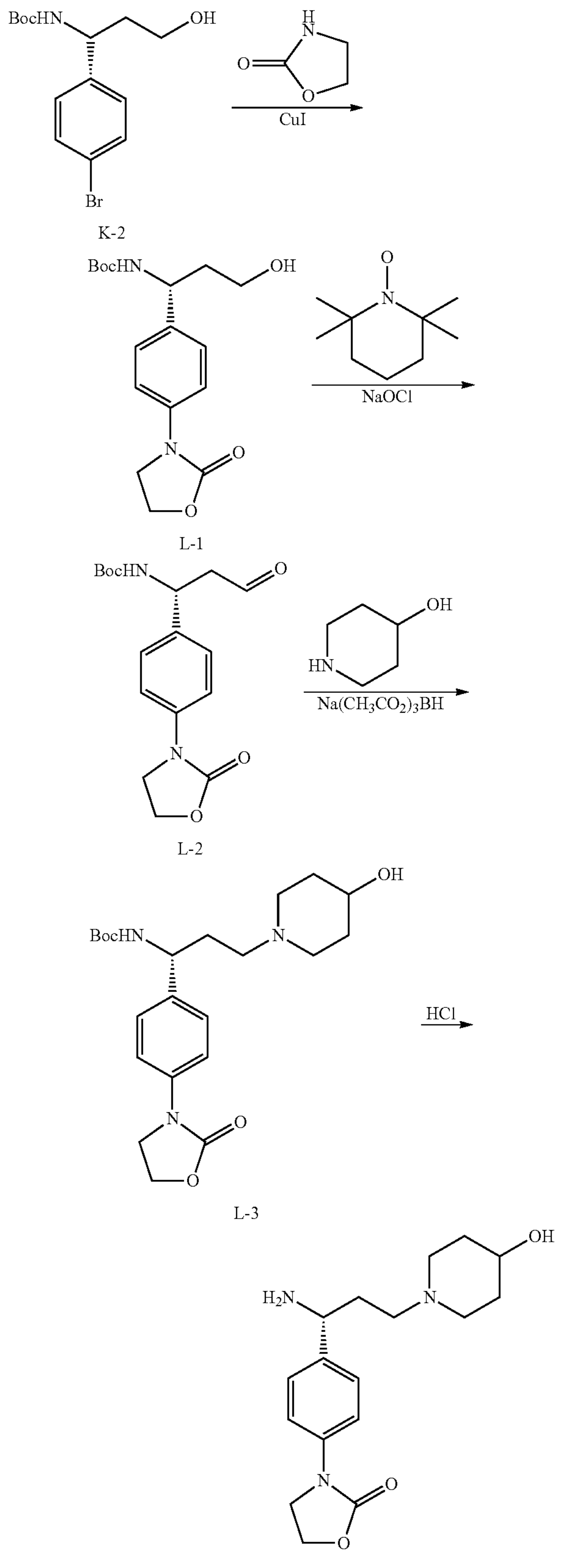

K-2

L-1

L-2

L-3

I-17

Step 1 tert-butyl (R)-(3-hydroxy-1-(4-(2-oxooxazolidin-3-yl)phenyl)propyl) carbamate (L-1)

L-1

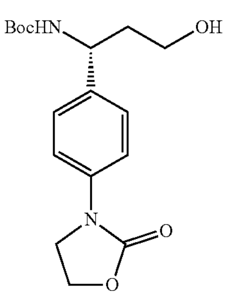

Tert-butyl (R)-(1-(4-bromophenyl)-3-hydroxypropyl) carbamate (5.76 g, 17.4 mmol), potassium carbonate (7.23 g, 52.3 mmol), and copper iodide (4.9 g, 26.2 mmol) were all put into a round bottom flask. Dioxane (174 mL) was added and the reaction was stirred at RT while $N_2$ was bubbled through for 5 min. Trans-N,N'-dimethylcyclohexane-1,2-diamine (8.3 mL, 52.6 mmol) was then added to the reaction and the reaction was stirred at 90° C. overnight. The reaction was cooled to RT and diluted with aqueous $NaHCO_3$ solution and EtOAc. The layers were separated and the organic layer was washed with brine. The organic phase was dried with anhydrous sodium sulfate, filtered, concentrated and purified by silica chromatography (0-10% MeOH/DCM) to provide the title compound. M: 337 (M+1).

Step 2 tert-butyl (R)-(3-oxo-1-(4-(2-oxooxazolidin-3-yl)phenyl)propyl) carbamate (L-2)

L-2

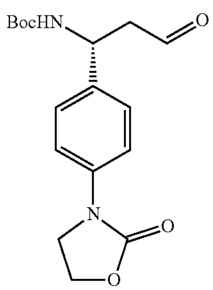

Tert-butyl (R)-(3-hydroxy-1-(4-(2-oxooxazolidin-3-yl)phenyl)propyl) carbamate (L-1) (5.92 g, 17.6 mmol) was dissolved in DCM (175 mL), TEMPO (0.287 g, 1.8 mmol) was added to the flask and the reaction was cooled to 0° C. Once cooled, bleach (6% aq., 50 mL) was added to the reaction. The reaction mixture was stirred for 3 h. The layers were separated. The organic layer was washed with 10% sodium thiosulfate (aq.). The organic phase was dried with anhydrous sodium sulfate and concentrated under reduced pressure to afford the title compound, L-2. MS: 335 (M+1).

Step 3 tert-butyl (R)-(3-(4-hydroxypiperidin-1-yl)-1-(4-(2-oxooxazolidin-3-yl)phenyl)propyl) carbamate (L-3)

L-3

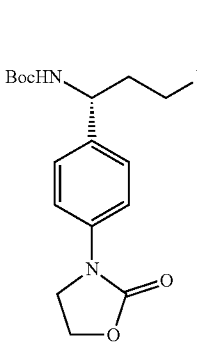

tert-butyl (R)-(3-oxo-1-(4-(2-oxooxazolidin-3-yl)phenyl) propyl) carbamate (L-2) (3.72 g, 11.1 mmol) was dissolved in DCE (200 mL) and piperidin-4-ol (1.81 g, 17.9 mmol) was added.

The mixture was stirred at RT for 5 min. Sodium triacetoxyborohydride (7.0 g, 33.1 mmol) was added to the reaction and the reaction mixture was stirred at RT over two days. The reaction was quenched with the addition of sat. $NaHCO_3$ (aq.) and diluted with DCM.

The layers were separated, and the organic layer was washed with brine. The organic layer was dried with anhydrous sodium sulfate, filtered, concentrated and purified by silica chromatography (0-30% MeOH/DCM) to provide the title compound, L-3. MS: 420 (M+1).

Step 4 (R)-3-(4-(1-amino-3-(4-hydroxypiperidin-1-yl)propyl)phenyl) oxazolidin-2-one (I-17)

I-17

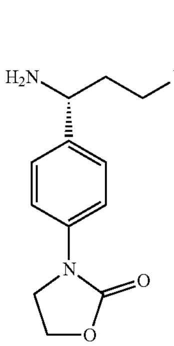

tert-butyl (R)-(3-(4-hydroxypiperidin-1-yl)-1-(4-(2-oxooxazolidin-3-yl)phenyl)propyl) carbamate (L-3) (1.09 g, 2.6 mmol) was dissolved in THF (12 mL) and MeOH (12 mL). 4M HCl in dioxane (12 mL) was then added to the flask and the reaction was stirred at 75° C. for 1 h. The reaction mixture was concentrated under reduced pressure. The residue was dissolved in small amount of MeOH, and then diethyl ether was added. A solid crashed out, and the mixture was filtered. The solid was collected to give title compound, I-17, which was used in the next step without further purification. MS: 320 (M+1).

Scheme M: Synthesis of intermediate I-18

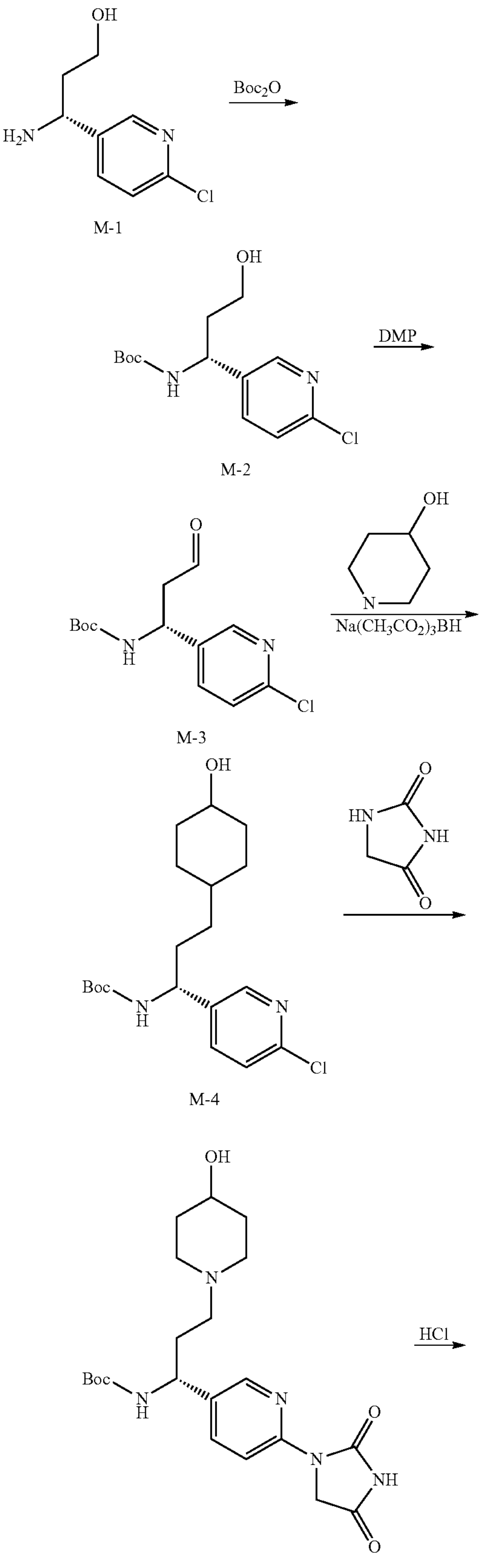

-continued

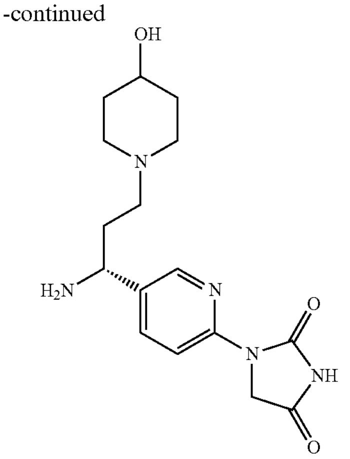

I-18

Step 1 tert-butyl (R)-(1-(6-chloropyridin-3-yl)-3-hydroxypropyl) carbamate (M-2)

M-2

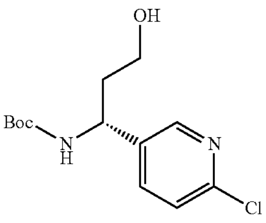

To a 250 ml round bottom flask (RBF0 was added $Boc_2O$ (5.00 mL, 21.52 mmol), (R)-3-amino-3-(6-chloropyridin-3-yl)propan-1-ol, HCl salt (4 g, 17.93 mmol), TEA (7.50 mL, 53.8 mmol), THF (30 ml) and MeOH (20 ml). The mixture was stirred at RT for 3 hours. The solvent was removed by reduced pressure and the residue was dissolved in EtOAc. The mixture was washed with water and brine. The organic layer was dried with anhydrous sodium sulfate, filtered, concentrated and purified by silica chromatography (0 to 100% EtOAc in Hexane) to provide the title compound, M-2. MS: 287 (M+1).

Step 2 tert-butyl (R)-(1-(6-chloropyridin-3-yl)-3-oxopropyl) carbamate (M-3)

M-3

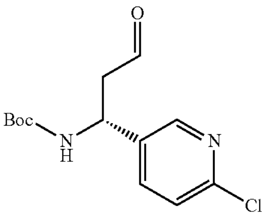

Dess-Martin Periodinane (3.37 g, 7.95 mmol) was added to a solution of (R)-tert-butyl (1-(6-chloropyridin-3-yl)-3-hydroxypropyl) carbamate (M-2) (1.9 g, 6.63 mmol) in DCM (100 mL). The mixture was stirred at RT for 1 h. Upon reaction completion, the reaction was diluted with DCM (100 mL), quenched with sat. $NaHCO_3$ (aq., 100 mL) and sat. $Na_2S_2O_3$ (aq., 20 mL). The mixture was stirred for 30 mins. Two layers were separated. The organic layer was washed with brine, dried with anhydrous sodium sulfate, filtered, concentrated under reduced pressure to provide the title compound (M-3), which was used in the next step without further purification. MS: 285 (M+1).

Step 3 tert-butyl (R)-(1-(6-chloropyridin-3-yl)-3-(4-hydroxypiperidin-1-yl)propyl) carbamate (M-4)

M-4

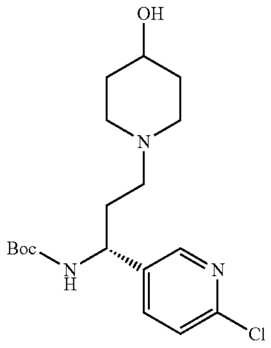

(R)-tert-butyl (1-(6-chloropyridin-3-yl)-3-oxopropyl) carbamate (M-3) (1.8 g, 6.32 mmol) and piperidin-4-ol (3.2 g, 31.6 mmol) was dissolved in 5% acetic acid in DCM (100 mL). The mixture was stirred at RT for 30 mins, and then sodium triacetoxy borohydride (4.01 g, 18.96 mmol) was added slowly. The reaction was stirred for 20 min at RT. Upon reaction completion, the reaction was quenched with sat. $NaHCO_3$ (aq.), saturated with NaCl, extracted with DCM (50 mL×5). The organic layer was dried with anhydrous sodium sulfate, filtered, concentrated and purified by silica chromatography (0 to 100% MeOH in DCM) to provide the title compound, M-4. MS: 370 (M+1).

Step 4 tert-butyl (R)-(1-(6-(2,4-dioxoimidazolidin-1-yl)pyridin-3-yl)-3-(4-hydroxypiperidin-1-yl)propyl) carbamate (M-5)

M-5

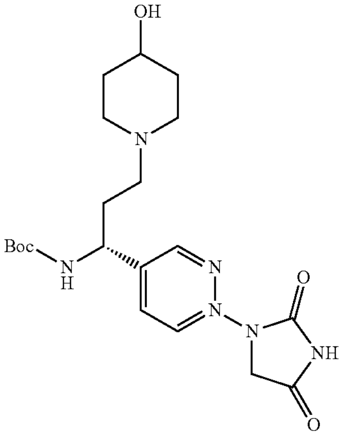

A mixture of (R)-tert-butyl (1-(6-chloropyridin-3-yl)-3-(4-hydroxypiperidin-1-yl)propyl) carbamate (M-4) (400 mg, 1.081 mmol), imidazolidine-2,4-dione (541 mg, 5.41 mmol), 4,5-Bis (diphenylphosphino)-9,9-dimethylxanthene (250 mg, 0.433 mmol), Pd(OAc) 2 (48.6 mg, 0.216 mmol) and cesium carbonate (1057 mg, 3.24 mmol) in dioxane (5 mL) was flushed with $N_2$ three times. The mixture was stirred at 100° C. in a sealed vial for 7 hr. Upon reaction completion, the mixture was diluted with DCM. The mixture was stirred for 3 min, filtered. The filtrate was concentrated and purified by silica chromatography (0 to 100% MeOH in DCM) to provide the title compound, M-5. MS: 434 (M+1).

Step 5 (R)-1-(5-(1-amino-3-(4-hydroxypiperidin-1-yl)propyl)pyridin-2-yl) imidazolidine-2,4-dione (I-18)

I-18

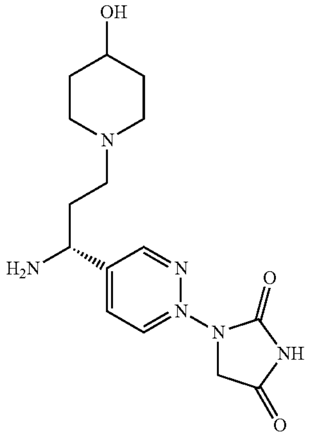

To a solution of (R)-tert-butyl (1-(6-(2,4-dioxoimidazolidin-1-yl)pyridin-3-yl)-3-(4-hydroxypiperidin-1-yl)propyl) carbamate (M-5) (400 mg, 0.923 mmol) in DCM (5 mL) and MeOH (5 mL) was added HCl (4 M in dioxane, 2.307 mL, 9.23 mmol). The mixture was stirred at RT for 5 h, and concentrated to give the title compound, I-18, as HCl salt, which was used in the next step without further purification. MS: 334 (M+1).

Following analogous methodology to that outlined for intermediate I-18 above, intermediate I-19 was prepared.

methyl (R)-1-(3-amino-3-(6-(2,4-dioxoimidazolidin-1-yl)pyridin-3-yl)propyl)piperidine-4-carboxylate (I-19)

I-19

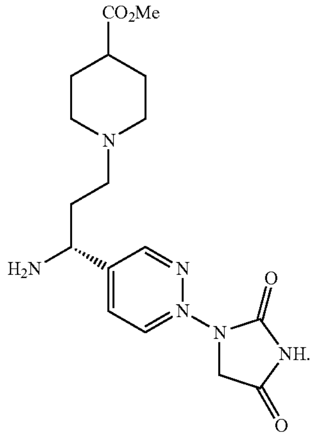

MS: 376 (M+1)

Scheme N: Synethsis of intermediate I-20

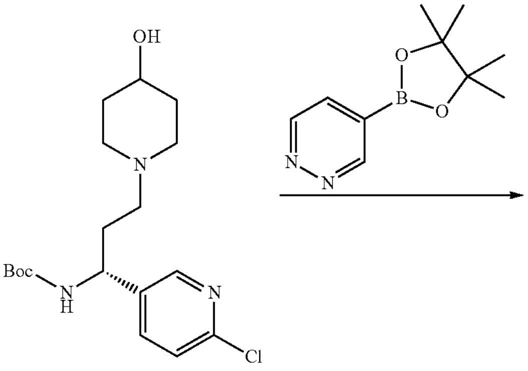

M-4

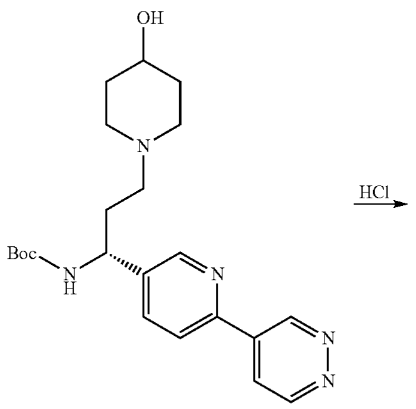

N-1

-continued

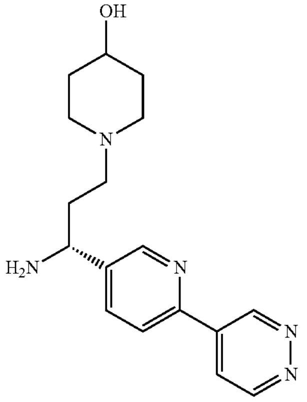

I-20

Step 1 tert-butyl (R)-(3-(4-hydroxypiperidin-1-yl)-1-(6-(pyridazin-4-yl)pyridin-3-yl)propyl) carbamate (N-1)

N-1

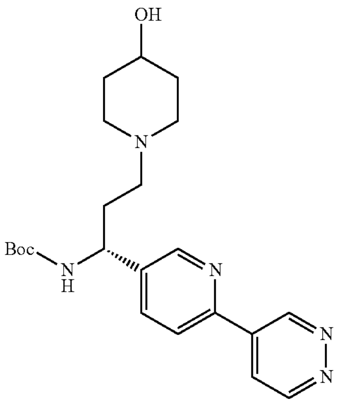

A mixture of (R)-tert-butyl (1-(6-chloropyridin-3-yl)-3-(4-hydroxypiperidin-1-yl)propyl) carbamate (M-4, 400 mg, 1.08 mmol), Pd(dppf)$Cl_2$ (188 mg, 0.162 mmol) and 4-(4,4,5,5-tetramethyl-1,3,2-dioxaborolan-2-yl)pyridazine (668 mg, 3.24 mmol) was flushed with $N_2$ three times. Then dioxane (10 mL) and $Na_2CO_3$ (2.5 N aq., 1.081 mL, 2.70 mmol), and water (1 mL) was added. The mixture was flushed with $N_2$ three times. Then the mixture was stirred at 100° C. for 4 h. After the reaction was cooled to RT, the reaction mixture was poured into DCM, dried over $Na_2SO_4$ and filtered. The filtrate was concentrated and purified by silica chromatography (0 to 100% MeOH in DCM) to provide the title compound, N-1. MS: 414 (M+1).

Step 2 (R)-1-(3-amino-3-(6-(pyridazin-4-yl)pyridin-3-yl)propyl)piperidin-4-ol (1-20)

I-20

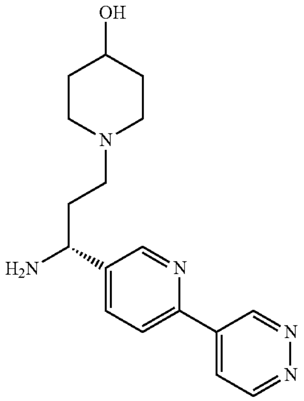

To a solution of (R)-tert-butyl (3-(4-hydroxypiperidin-1-yl)-1-(6-(pyridazin-4-yl)pyridin-3-yl)propyl) carbamate (N-2) (200 mg, 0.484 mmol) in DCM (5 ml) and MeOH (5 ml) was added HCl (4 M in dioxane, 1.209 ml, 4.84 mmol). The mixture was stirred at RT for 5 h and concentrated to give the title compound, I-20, as HCl salt, which was used without further purification. MS: 314 (M+1).

Following analogous methodology to that outlined for intermediate I-20 above, intermediate I-21 was prepared.

(R)-1-(3-amino-3-(5-fluoro-6-(pyridazin-4-yl)pyridin-3-yl)propyl)piperidin-4-ol (I-21)

I-21

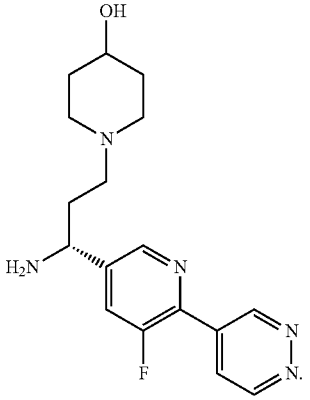

MS: 332 (M+1)

Scheme O: Synthesis of intermediate I-22

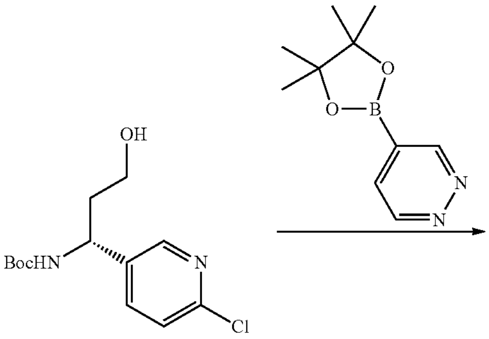

M-2

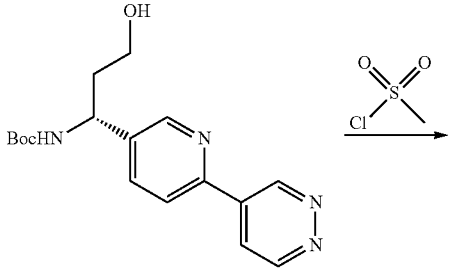

O-1

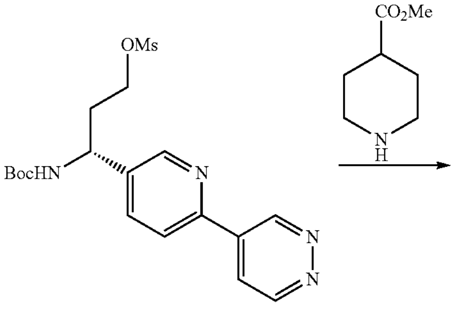

O-2

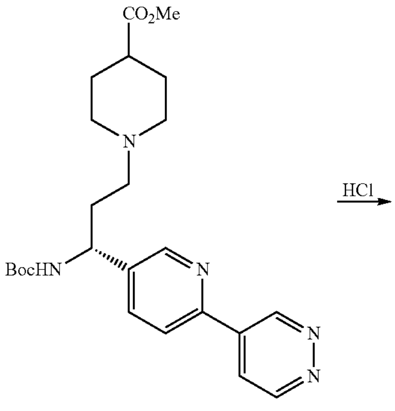

O-3

-continued

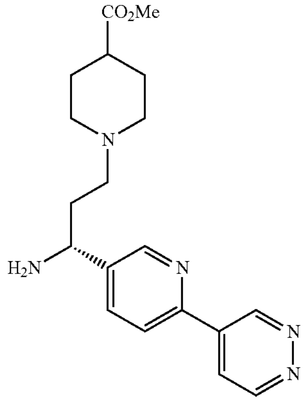

I-22

Step 1 tert-butyl (R)-(3-hydroxy-1-(6-(pyridazin-4-yl)pyridin-3-yl)propyl) carbamate (0-1)

O-1

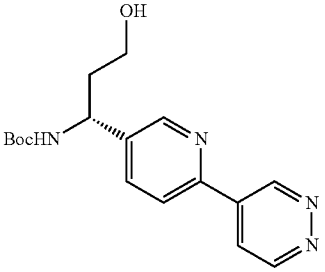

A mixture of (R)-tert-butyl (1-(6-chloropyridin-3-yl)-3-hydroxypropyl) carbamate (M-2) (2000 mg, 6.97 mmol), Pd(dppf)$Cl_2$ (806 mg, 0.697 mmol) and 4-(4,4,5,5-tetramethyl-1,3,2-dioxaborolan-2-yl)pyridazine (1796 mg, 8.72 mmol) was flushed with $N_2$ three times. Then dioxane (20 mL), $Na_2CO_3$ (2.5 N aq., 6.97 mL, 17.44 mmol), and water (2 mL) was added. The mixture was flushed with $N_2$ three times. Then the mixture was stirred at 100° C. for 2 h. After the reaction was cooled to RT, the reaction mixture was poured into DCM, dried over $Na_2SO_4$ and filtered. The filtrate was concentrated and purified by silica chromatography (0 to 100% acetone in hexane) to provide the title compound, O-1. MS: 331 (M+1).

Step 2 (R)-3-((tert-butoxycarbonyl)amino)-3-(6-(pyridazin-4-yl)pyridin-3-yl)propyl methane-sulfonate (O-2)

O-2

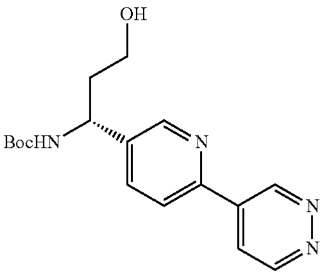

To a solution (R)-tert-butyl (3-hydroxy-1-(6-(pyridazin-4-yl)pyridin-3-yl)propyl) carbamate (0-1) (562 mg, 1.700 mmol) in DCM (30 ml) was added $Et_3N$ (0.592 mL, 4.25 mmol) and MsCl (0.185 mL, 2.380 mmol) at 0° C. The reaction mixture was then stirred at RT for 2 h. The mixture was diluted with DCM (200 mL), washed with sat. $NaHCO_3$ (aq., 50 mL) and brine (50 mL). The organic layer was dried over $Na_2SO_4$, filtered and concentrated under reduced pressure to afford the title compound, O-2, which was used in the next step without further purification. MS: 409 (M+1).

Step 3 methyl (R)-1-(3-((tert-butoxycarbonyl)amino)-3-(6-(pyridazin-4-yl)pyridin-3-yl)propyl)piperidine-4-carboxylate (0-3)

O-3

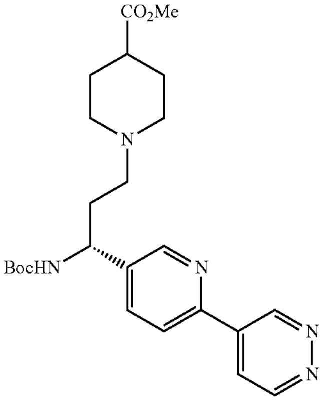

To the solution of (R)-3-((tert-butoxycarbonyl)amino)-3-(6-(pyridazin-4-yl)pyridin-3-yl)propyl methanesulfonate (0-2) (680 mg, 1.665 mmol) in $CH_3CN$ (30 mL) was added methyl piperidine-4-carboxylate (2384 mg, 16.65 mmol) and reaction was stirred at 90° C. for 90 min. The reaction mixture then was cooled to RT and evaporated. The residue was diluted with sat. $NaHCO_3$ solution (aq. 100 mL) and DCM (100 mL). The mixture was stirred for 10 min and extracted with DCM (100 mL). The combined organic layers were dried over $Na_2SO_4$ and filtered. The filtrate was concentrated and purified by silica chromatography (0 to 100% acetone in hexane) to provide the title compound, O-3. MS: 456 (M+1).

Step 4 methyl (R)-1-(3-amino-3-(6-(pyridazin-4-yl)pyridin-3-yl) propyl)piperidine-4-carboxylate (I-22)

I-22

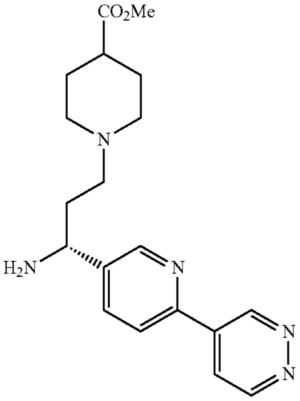

A solution of (R)-methyl 1-(3-((tert-butoxycarbonyl)amino)-3-(6-(pyridazin-4-yl)pyridin-3-yl)propyl)piperidine-4-carboxylate (0-3) (550 mg, 1.207 mmol) in MeOH (5 mL) and DCM (5 mL) was added HCl (4 M in dioxane, 3.02 mL, 12.07 mmol). The mixture was stirred at RT for 5 h and concentrated to give the title compound, I-22, as HCl salt, which was used without further purification. MS: 356 (M+1).

Scheme P: Synthesis of intermediate I-23

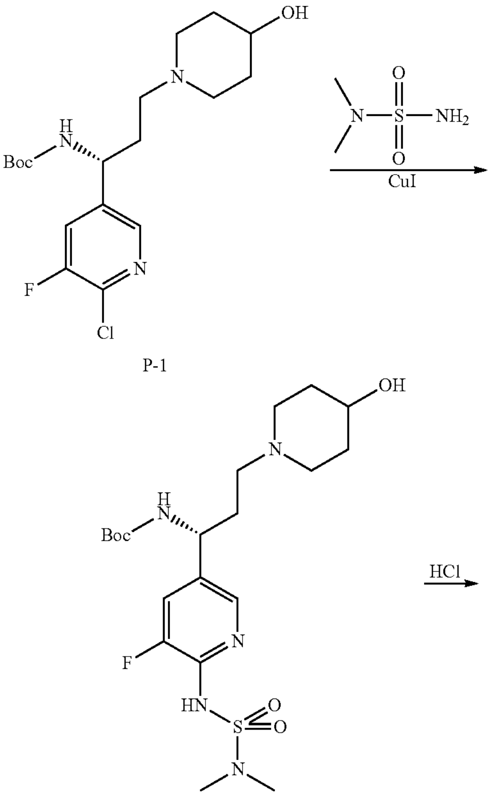

P-1

P-2

-continued

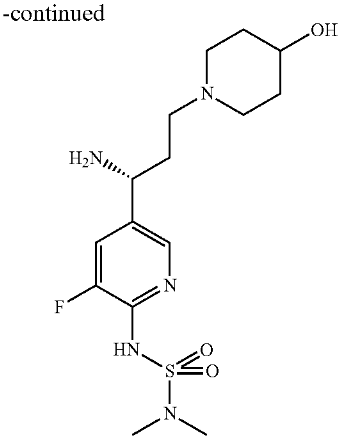

I-23

Step 1: Compound P-2

A mixture of trans-N,N'-dimethylcyclohexane-1,2-diamine (200 mg, 1.4 mmol), potassium phosphate (597 mg, 2.81 mmol), CuI (134 mg, 0.70 mmol), N,N-dimethylsulfamide (349 mg, 2.81 mmol), tert-butyl (R)-(1-(6-chloro-5-fluoropyridin-3-yl)-3-(4-hydroxypiperidin-1-yl)propyl) carbamate (P-1, prepared following analogous methodology to that outlined for compound M-4 above, 273 mg, 0.70 mmol) was added dioxane (7.0 mL). The reaction mixture was purged with $N_2$ for 5 min, and then stirred at 100° C. for 24 h. The reaction was cooled down to RT, filtered. The crude material was purified by mass-directed reverse phase chromatography (C-18, MeCN/water gradient with 0.1% TFA modifier) to afford the title compound, P-2. MS: 476 (M+1).

Step 2: tert-butyl (R)-(1-(6-((N,N-dimethylsulfamoyl)amino)-5-fluoropyridin-3-yl)-3-(4-hydroxypiperidin-1-yl)propyl) carbamate (I-23)

Following analogous methodology to that outlined for compound I-22, intermediate I-23 was prepared.

I-23

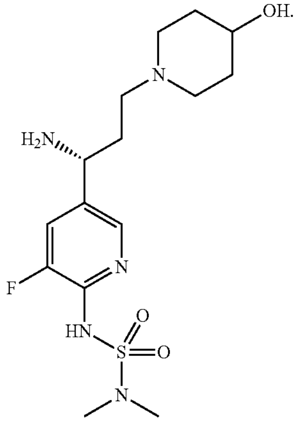

MS: 376 (M+1)

Scheme Q: Synthesis of intermediate I-24

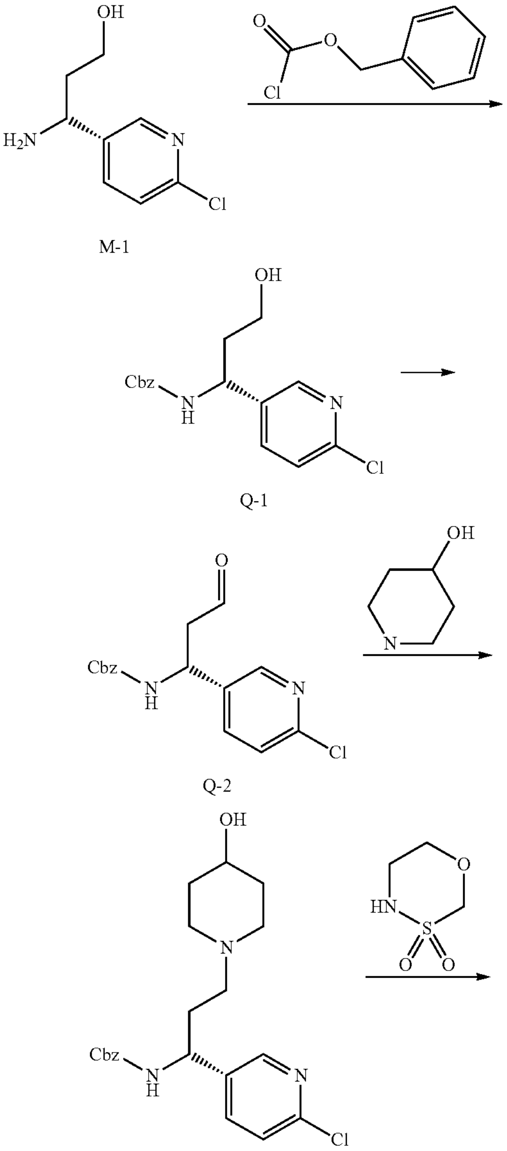

M-1

Q-1

Q-2

Q-3

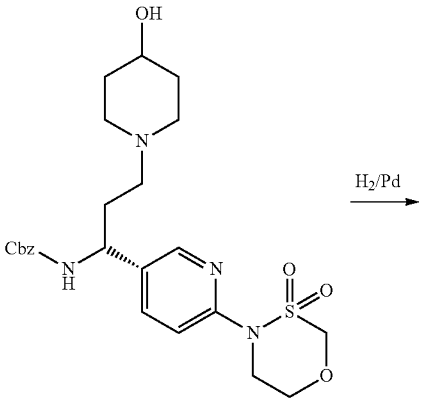

Q-4

-continued

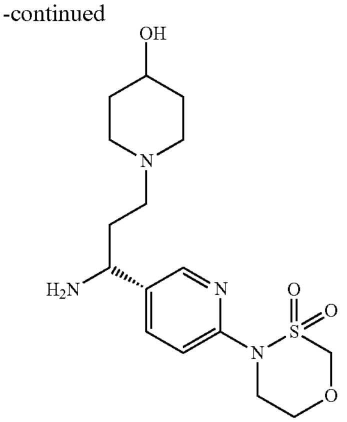

I-24

Step 1 benzyl (R)-(1-(6-chloropyridin-3-yl)-3-hydroxypropyl) carbamate (Q-1)

To a mixture of (R)-3-amino-3-(6-chloropyridin-3-yl)propan-1-ol (HCl salt, 2500 mg, 11.21 mmol) and $NaHCO_3$ (1977 mg, 23.53 mmol) was added water (56 mL). Then benzyl chloroformate (1.76 mL, 12.33 mmol) was added at 0° C. The reaction mixture was stirred at 0° C. for 1 h. The reaction was quenched with sat. $NaHCO_3$ (aq., 20 mL), saturated with solid NaCl, and extracted with ethyl acetate (100 mL×2). The combined organic layers were dried over $Na_2SO_4$ and filtered. The filtrate was concentrated and purified by silica chromatography (0 to 100% acetone in hexane) to provide the title compound. MS: 321 (M+1).

Step 2 benzyl (R)-(1-(6-chloropyridin-3-yl)-3-oxopropyl) carbamate (Q-2)

Q-2

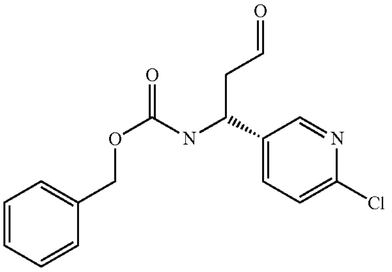

To a solution of (R)-benzyl (1-(6-chloropyridin-3-yl)-3-hydroxypropyl) carbamate (Q-1) (1.3 g, 4.05 mmol) in DCM (40.5 mL) was added Dess-Martin Periodinane (2.063 g, 4.86 mmol). The mixture was stirred at RT for 1 h. The mixture was diluted with DCM (100 mL), quenched with sat. $NaHCO_3$ (aq., 100 mL) and sat. $Na_2S_2O_3$ (aq., 20 mL). The mixture was stirred for 30 min. The reaction mixture was extracted with DCM (150 mL×2). The combined organic layers were dried over $Na_2SO_4$, filtered and concentrated under reduced pressure to afford the title compound, Q-2, which was used in the next step without further purification. MS: 319 (M+1).

Step 3 benzyl (R)-(1-(6-chloropyridin-3-yl)-3-(4-hydroxypiperidin-1-yl)propyl) carbamate (Q-3)

Q-3

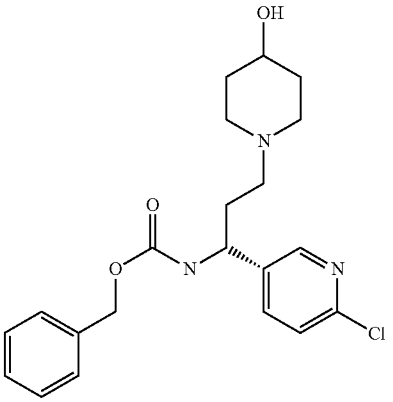

(R)-benzyl (1-(6-chloropyridin-3-yl)-3-oxopropyl) carbamate (Q-2) (1.275 g, 4 mmol) and piperidin-4-ol (2.02 g, 20.00 mmol) was dissolved in 5% acetic acid in DCM (40 mL). The mixture was stirred at RT for 30 min. Then the reaction mixture was cooled to 0° C., and to it was added sodium triacetoxyborohydride (2.54 g, 12.00 mmol) slowly. The reaction was stirred at RT for 20 min. The reaction was quenched with sat. $NaHCO_3$ (aq.). The mixture was saturated with NaCl and extracted with DCM (50 mlx3). The combined organic layers were dried over $Na_2SO_4$ and filtered. The filtrate was concentrated and purified by silica chromatography (0 to 100% MeOH in DCM) to provide the title compound, Q-3. MS: 404 (M+1).

Step 4 benzyl (R)-(1-(6-(3,3-dioxido-1,3,4-oxathiazinan-4-yl)pyridin-3-yl)-3-(4-hydroxypiperidin-1-yl)propyl) carbamate (Q-4)

Q-4

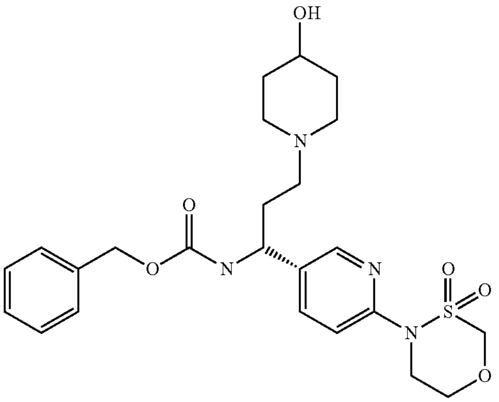

(R)-benzyl (1-(6-chloropyridin-3-yl)-3-(4-hydroxypiperidin-1-yl)propyl) carbamate (Q-3) (300 mg, 0.743 mmol), 1,3,4-oxathiazinane 3,3-dioxide (306 mg, 2.228 mmol), $Cs_2CO_3$. (1210 mg, 3.71 mmol), $Pd_2(dba)_3$ (102 mg, 0.111 mmol), and 4,5-bis(dipheylphosphino)-9,9-dimethylxanthene (129 mg, 0.223 mmol) were mixed together in dioxane (7428 μL). The reaction mixture was purged with $N_2$ for 5 min, then stirred at 100° C. for 2 h and cooled down to RT. The reaction mixture was diluted with DCM, stirred for 10 min and filtered. The filtrate was concentrated and purified by silica chromatography (0 to 40% MeOH in DCM) to provide the title compound, Q-4. MS: 505 (M+1).

Step 5 (R)-4-(5-(1-amino-3-(4-hydroxypiperidin-1-yl)propyl)pyridin-2-yl)-1,3,4-oxathiazinane 3,3-dioxide (I-24)

I-24

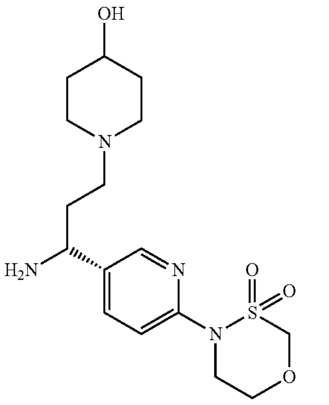

A dried round bottom flask was charged with (R)-benzyl (1-(6-(3,3-dioxido-1,3,4-oxathiazinan-4-yl)pyridin-3-yl)-3-(4-hydroxypiperidin-1-yl)propyl) carbamate (Q-4) (130 mg, 0.258 mmol) and Pd/C (5%, 54.8 mg, 0.026 mmol). The resulting mixture was evacuated and back filled with $N_2$ (3 times). Ethanol (6441 μL) was added. The resulting mixture was then evacuated and backfilled with $H_2$ (3 times), then stirred under 1 atm. $H_2$ at RT for 2 h. The reaction mixture was filtered through a Celite® pad, washed with ethanol. The filtrate was concentrated to provide the title compound, I-24, which was used without further purification. MS: 371 (M+1).

Scheme R: Synthesis of intermediate I-25

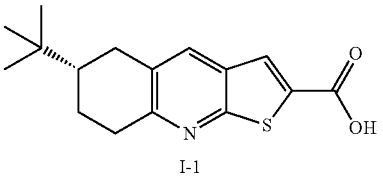

I-1

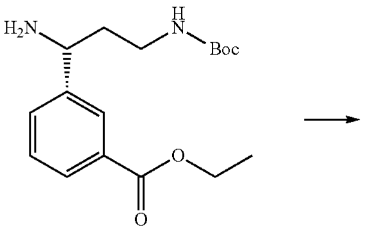

I-12

-continued

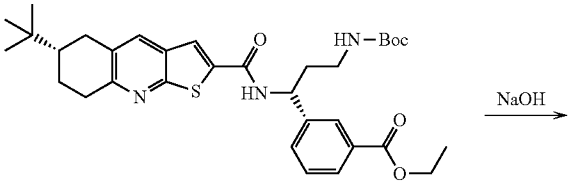

R-1

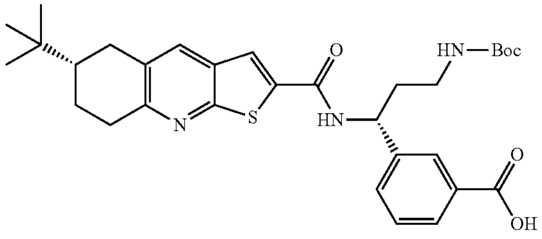

I-25

Step 1 ethyl 3-((R)-3-((tert-butoxycarbonyl)amino)-1-((S)-6-(tert-butyl)-5,6,7,8-tetrahydrothieno[2,3-b]quinoline-2-carboxamido) propyl)benzoate (R-1)

R-1

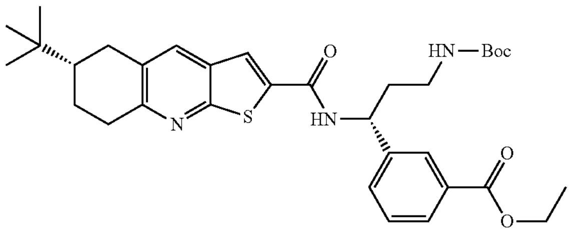

To a mixture of(S)-6-(tert-butyl)-5,6,7,8-tetrahydrothieno [2,3-b]quinoline-2-carboxylic acid (I-1) (1150 mg, 3.97 mmol), (R)-ethyl 3-(1-amino-3-((tert-butoxycarbonyl) amino) propyl)benzoate (I-12) (1409 mg, 4.37 mmol) and HATU (2720 mg, 7.15 mmol) in DMF (39 mL) was added DIPEA (1735 μL, 9.93 mmol). Then the reaction mixture was stirred at RT overnight. The mixture was taken up into EtOAc (100 mL) and washed with sat. aq. $NH_4Cl$ (100 mL), sat. aq. $NaHCO_3$ (100 mL), and brine (100 mL). The organic layers were dried over $Na_2SO_4$, and filtered. The filtrate was concentrated under reduced pressure to afford the title compound, R-1, which was used in the next step without further purification. MS: 594 (M+1).

Step 2 3-((R)-3-((tert-butoxycarbonyl)amino)-1-((S)-6-(tert-butyl)-5,6,7,8-tetrahydrothieno[2,3-b]quinoline-2-carboxamido) propyl)benzoic acid (I-25)

I-25

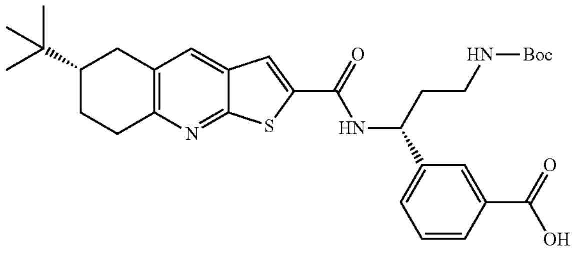

NaOH (600 mg, 15.00 mmol) was added to a solution of methyl 3-((R)-3-((tert-butoxycarbonyl)amino)-1-((S)-6-(tert-butyl)-5,6,7,8-tetrahydrothieno[2,3-b]quinoline-2-carboxamido) propyl)benzoate (R-1) (1.85 g, 3.19 mmol) in MeOH. To it was added 6 mL of water and the reaction mixture was stirred at RT for 1 h. MeOH was removed under reduced pressure. The remaining aq. layer was quenched with 1N HCl (30 mL) and extracted with EtOAc (3×200 mL). The organic layers were collected, dried over $Na_2SO_4$, filtered, and concentrated to afford title compound, which was used in the next step without further purification (I-25). MS: 566 (M+1).

I-26

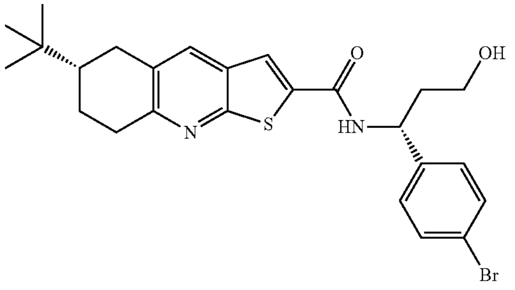

(S)-N-((R)-1-(4-bromophenyl)-3-hydroxypropyl)-6-(tert-butyl)-5,6,7,8-tetrahydrothieno[2,3-b]quinoline-2-carboxamide (I-26)

Scheme S: Synthesis of intermediate I-26

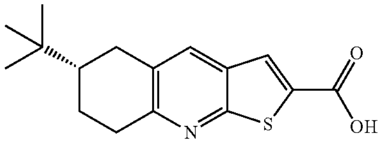

+

I-1

-continued

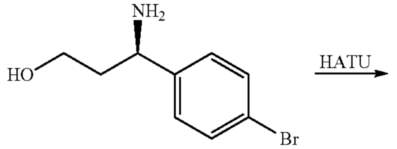

S-1

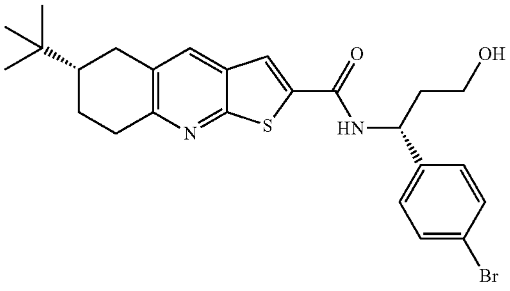

I-26

To a flask with(S)-6-(tert-butyl)-5,6,7,8-tetrahydrothieno[2,3-b]quinoline-2-carboxylic acid (I-1) (4.0 g, 13.82 mmol), (R)-3-amino-3-(4-bromophenyl)propan-1-ol (S-1) (3.18 g, 13.82 mmol), HOAt (2.446 g, 17.97 mmol) and HATU (6.83 g, 17.97 mmol) was added DMF (69.1 mL) followed by DIEA (7.24 mL, 41.5 mmol). The reaction was stirred at RT overnight. The reaction mixture was added dropwise to a stirring sat. aq $NaHCO_3$ solution (800 mL). The mixture was stirred for 20 min, then filtered. The filter cake was dried to afford the title compound, I-26, which was used in the next step without further purification. MS: 502 (M+1)

Scheme T: Synthesis of intermediate I-27

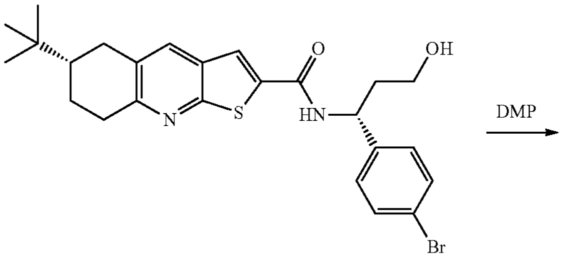

I-26

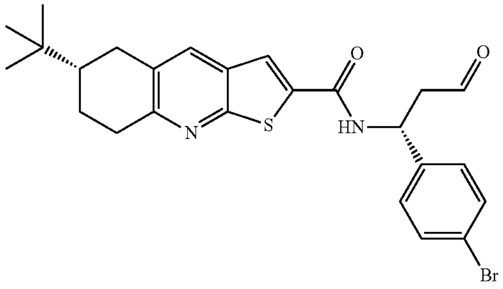

I-27

(S)-N-((R)-1-(4-bromophenyl)-3-oxopropyl)-6-(tert-butyl)-5,6,7,8-tetrahydrothieno[2,3-b]quinoline-2-carboxamide (I-27)

I-27

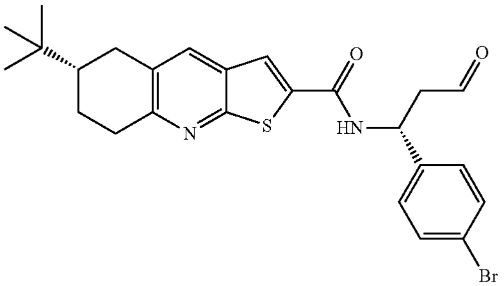

To a solution of(S)-N-((R)-1-(4-bromophenyl)-3-hydroxypropyl)-6-(tert-butyl)-5,6,7,8-tetrahydrothieno[2,3-b]quinoline-2-carboxamide (I-26) (3.5 g, 6.98 mmol) in DCM (200 mL) at 0° C. was added Dess-Martin Periodinane (3.40 g, 8.03 mmol). The reaction was stirred at rt for 3.5 h.

Upon reaction completion, the reaction was diluted with DCM (100 mL), quenched with sat. $NaHCO_3$ (aq., 100 mL) and sat. $Na_2S_2O_3$ (aq., 20 mL). The mixture was stirred for 30 mins. Two layers were separated. The organic layer was washed with brine, dried with anhydrous sodium sulfate, concentrated under reduced pressure to provide the title compound, I-27. MS: 500 (M+1).

Scheme U: Synthesis of intermediate I-28

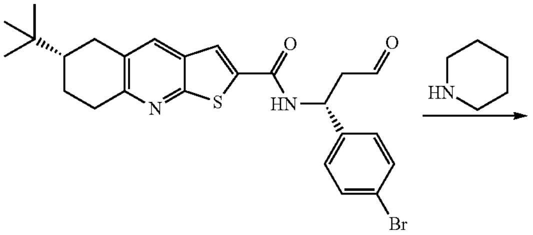

I-27

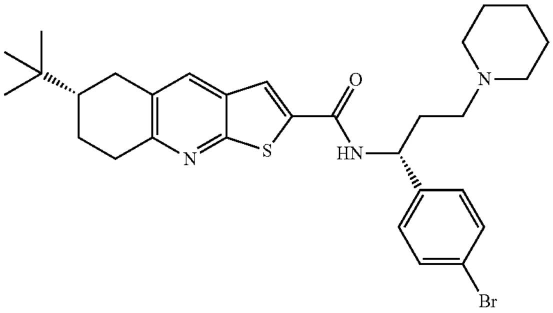

I-28

(S)-N-((R)-1-(4-bromophenyl)-3-(piperidin-1-yl)propyl)-6-(tert-butyl)-5,6,7,8-tetrahydrothieno[2,3-b]quinoline-2-carboxamide (1-28)

(S)-N-((R)-1-(4-bromophenyl)-3-oxopropyl)-6-(tert-butyl)-5,6,7,8-tetrahydrothieno[2,3-b]quinoline-2-carboxamide (2.0 g, 4.00 mmol) and piperidine (0.595 ml, 6.01 mmol) in DCE (40 mL) was stirred at RT for 5 min. Sodium triacetoxyborohydride (2.55 g, 12.01 mmol) was added, and the reaction mixture was stirred overnight. The reaction was quenched with sat. $NaHCO_3$ (aq.). The mixture was saturated with NaCl, extracted with DCM (50 mL×3). The combined organic layers were dried over $Na_2SO_4$ and filtered. The filtrate was concentrated and purified by silica chromatography (0 to 100% EtOAc in hexane) to provide the title compound. MS: 569 (M+1).

(S)-N-((R)-1-(3-bromophenyl)-3-hydroxypropyl)-6-(tert-butyl)-5,6,7,8-tetrahydrothieno[2,3-b]quinoline-2-carboxamide (I-29)

I-29

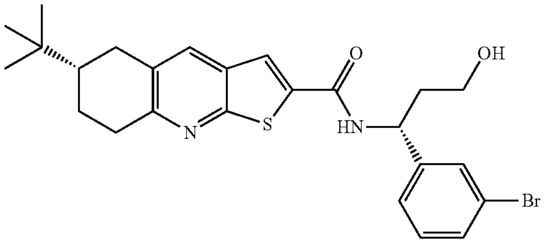

Following analogous methodology to that outlined for intermediate I-26 above, intermediate I-29 was prepared. MS: 502 (M+1)

Scheme V: Synthesis of intermediate I-30

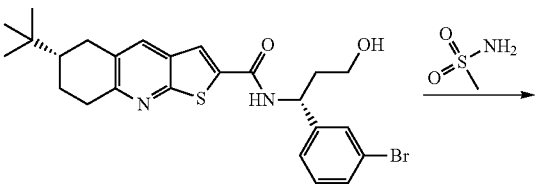

I-29

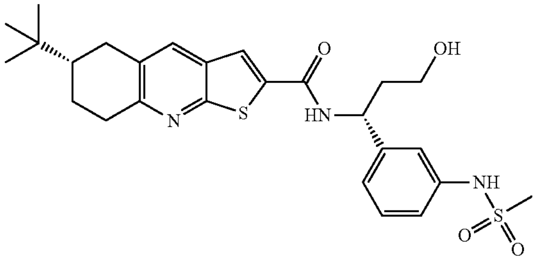

V-1

-continued

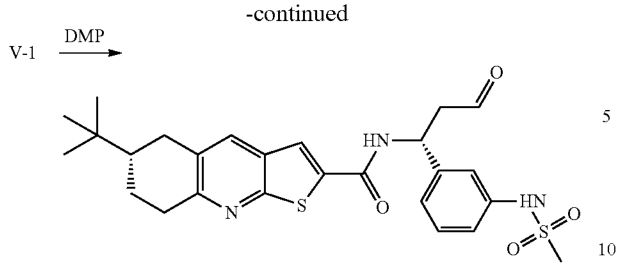

I-30

Step 1 (S)-6-(tert-butyl)-N-((R)-3-hydroxy-1-(3-(methylsulfonamido)phenyl)propyl)-5,6,7,8-tetrahydrothieno[2,3-b]quinoline-2-carboxamide (V-1)

A mixture of(S)-N-((R)-1-(3-bromophenyl)-3-hydroxypropyl)-6-(tert-butyl)-5,6,7,8-tetrahydrothieno[2,3-b]quinoline-2-carboxamide (I-29) (2000 mg, 3.99 mmol), copper (I) iodide (760 mg, 3.99 mmol), methanesulfonamide (1.5 g, 15.95 mmol), and potassium phosphate tribasic (2.5 g, 11.96 mmol) was evacuated and backfilled with $N_2$ three times. To the mixture was added dioxane (50 mL) and trans-N,N'-dimethylcyclohexane-1,2-diamine (1.1 g, 7.98 mmol). The reaction was stirred at 85° C. overnight. The reaction was treated with sat. $NH_4Cl$ solution (aq., 100 mL) and 300 ml ethyl acetate. The mixture was stirred for 10 min. The layers were separated. The organic layer was dried over $Na_2SO_4$, filtered and concentrated under reduced pressure. The residue was purified by silica chromatography (0 to 100% acetone in hexane) to provide the title compound. MS: 516 (M+1).

Step 2 (S)-6-(tert-butyl)-N-((R)-1-(3-(methylsulfonamido)phenyl)-3-oxopropyl)-5,6,7,8-tetrahydrothieno[2,3-b]quinoline-2-carboxamide (I-30)

I-30

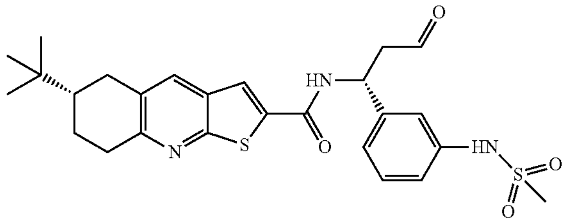

Following analogous methodology to that outlined for intermediate I-27 above, intermediate I-30 was prepared. MS: 514 (M+1).

Scheme W: Synthesis of intermediate I-31

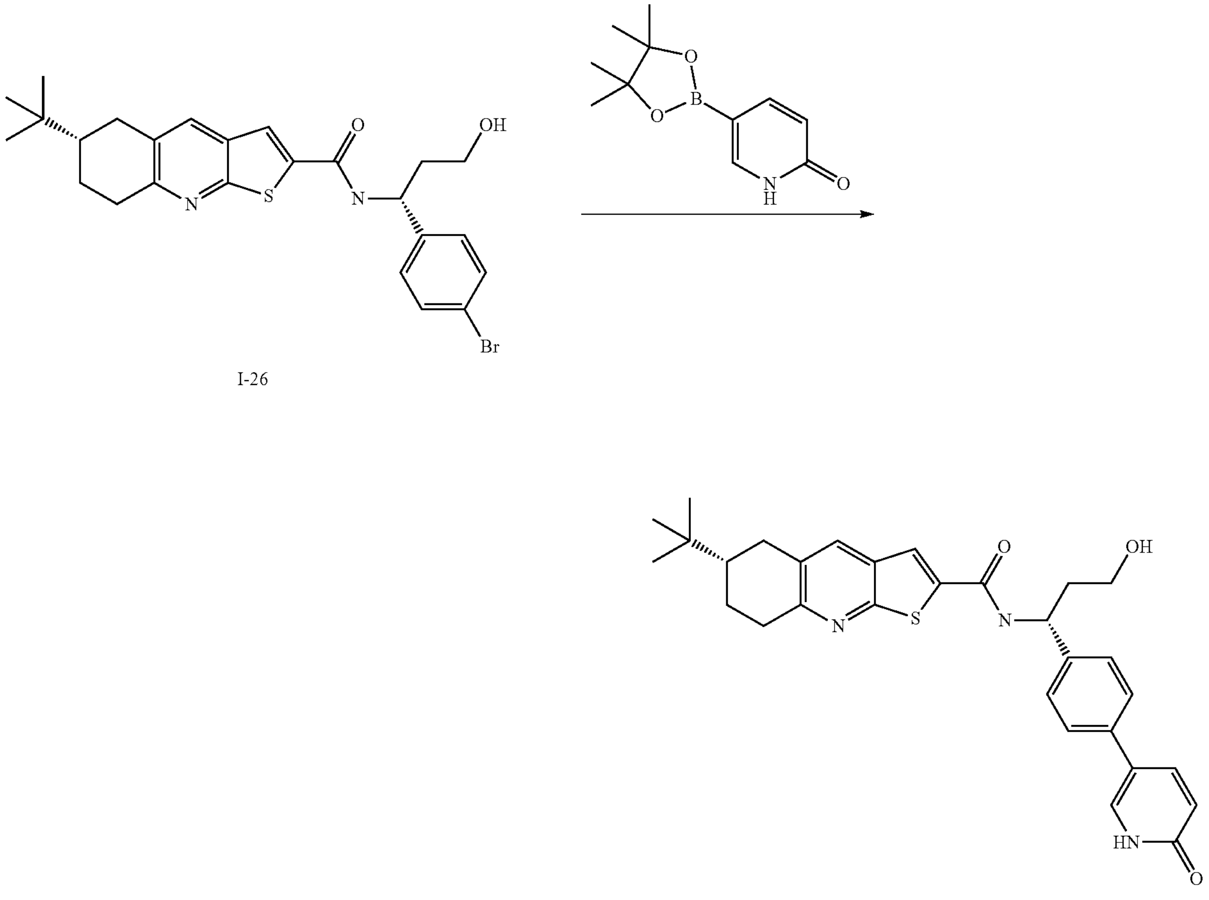

I-26

W-1

-continued

W-1

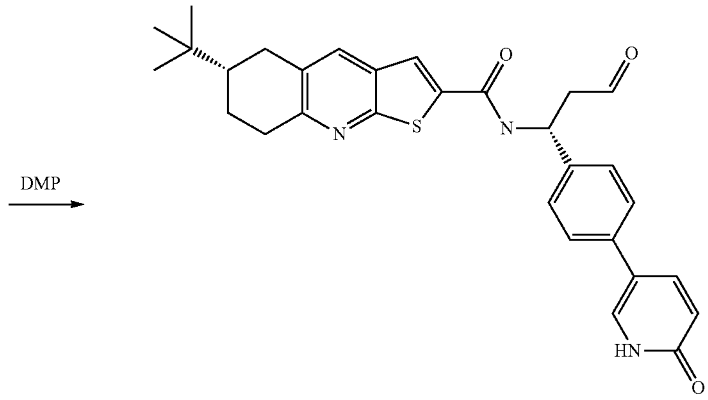

I-31

Step 1 (S)-6-(tert-butyl)-N-((R)-3-hydroxy-1-(4-(6-oxo-1,6-dihydropyridin-3-yl)phenyl)propyl)-5,6,7,8-tetrahydrothieno[2,3-b]quinoline-2-carboxamide (W-1)

To a 40 mL reaction vial was added Pd(dppf)$Cl_2$· $CH_2Cl_2$ (0.489 g, 0.598 mmol), potassium phosphate (2.54 g, 11.96 mmol), (S)-N-((R)-1-(4-bromophenyl)-3-hydroxypropyl)-6-(tert-butyl)-5,6,7,8-tetrahydrothieno[2,3-b]quinoline-2-carboxamide (I-26) (3 g, 5.98 mmol) and 5-(4,4,5,5-tetramethyl-1,3,2-dioxaborolan-2-yl)pyridin-2 (1H)-one (1.587 g, 7.18 mmol). The vial was capped, evacuated under vacuum and backfilled with nitrogen three times. Then dioxane (26.9 mL) and water (2.99 mL) was added. The reaction mixture was stirred at 85° C. overnight. Upon completion, the reaction was cooled to RT and poured into a mixture of $Na_2SO_4$ in MeOH. The mixture was stirred for 10 min, filtered and concentrated under reduced pressure to afford the title compound, W-1, which was used in the next step without further purification. MS: 516 (M+1).

Step 2 (S)-6-(tert-butyl)-N-((R)-3-oxo-1-(4-(6-oxo-1,6-dihydropyridin-3-yl)phenyl)propyl)-5,6,7,8-tetrahydrothieno[2,3-b]quinoline-2-carboxamide (I-31)

Following analogous methodology to that outlined for intermediate I-27 above, intermediate I-31 was prepared. MS: 514 (M+1).

Scheme X: Synthesis of intermediate I-32

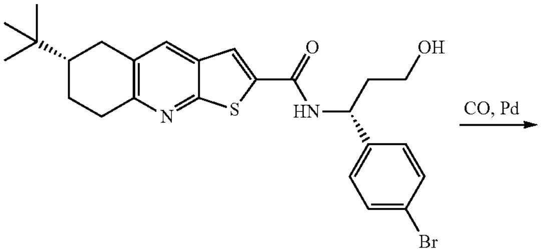

I-26

-continued

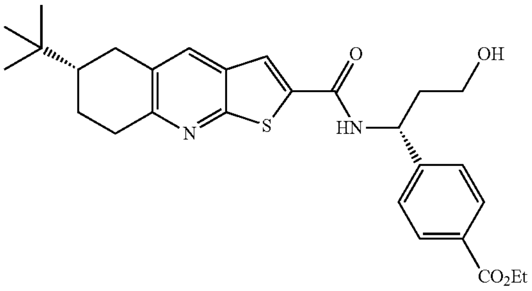

X-1

X-1

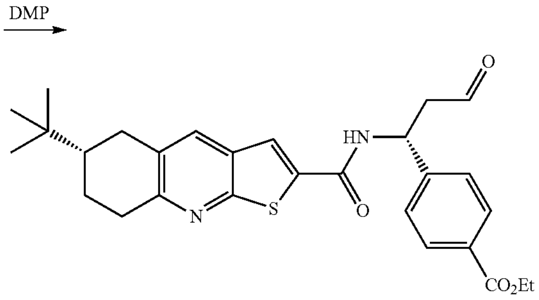

X-2

X-2

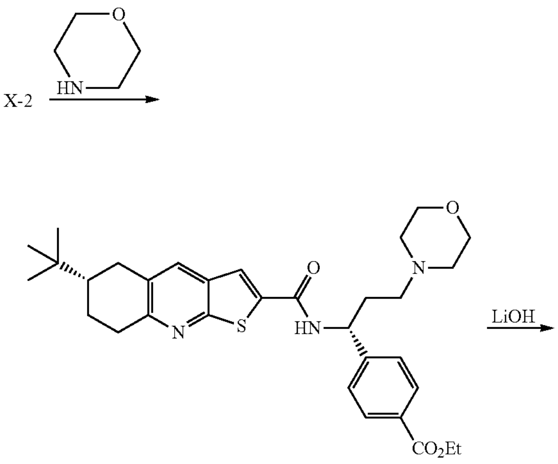

X-3

-continued

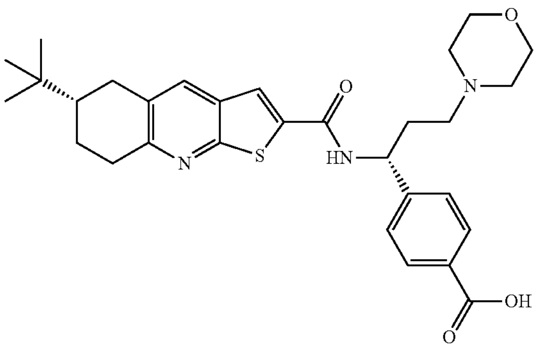

I-32

Step 1 ethyl 4-((R)-1-((S)-6-(tert-butyl)-5,6,7,8-tetrahydrothieno[2,3-b]quinoline-2-carboxamido)-3-hydroxypropyl)benzoate (X-1)

Following analogous methodology to that outlined for compound F-7 above, compound X-1 was prepared. MS: 495 (M+1).

Step 2 ethyl 4-((R)-1-((S)-6-(tert-butyl)-5,6,7,8-tetrahydrothieno[2,3-b]quinoline-2-carboxamido)-3-oxopropyl)benzoate (X-2)

Following analogous methodology to that outlined for intermediate I-27 above, compound X-2 was prepared. MS: 493 (M+1).

Step 3 ethyl 4-((R)-1-((S)-6-(tert-butyl)-5,6,7,8-tetrahydrothieno[2,3-b]quinoline-2-carboxamido)-3-morpholinopropyl)benzoate (X-3)

Following analogous methodology to that outlined for intermediate I-28 above, compound X-3 was prepared. MS: 564 (M+1).

Step 4: 4-((R)-1-((S)-6-(tert-butyl)-5,6,7,8-tetrahydrothieno[2,3-b]quinoline-2-carboxamido)-3-morpholinopropyl)benzoic acid (I-32)

To a solution of ethyl 4-((R)-1-((S)-6-(tert-butyl)-5,6,7,8-tetrahydrothieno[2,3-b]quinoline-2-carboxamido)-3-morpholinopropyl)benzoate (X-3) (75 mg, 0.133 mmol) in THF (2 mL) and MeOH (2 mL) was added aq. LiOH (1.0 M, 0.4 ml, 0.4 mmol). The mixture was stirred at RT overnight. The organic solvent was evaporated, the residue was neutralized with aq. HCl (1N) to about pH 6. A precipitate was formed. The mixture was stirred for 5 min, filtered. The filter cake was dried to afford the title compound, I-28, which was used without further purification. MS: 536 (M+1).

Intermediate I-33

(S)-7-(tert-butyl)-N-((R)-3-oxo-1-(4-(6-oxo-1,6-dihydropyridin-3-yl)phenyl)propyl)-5,6,7,8-tetrahydrothiazolo[5,4-b]quinoline-2-carboxamide

I-33

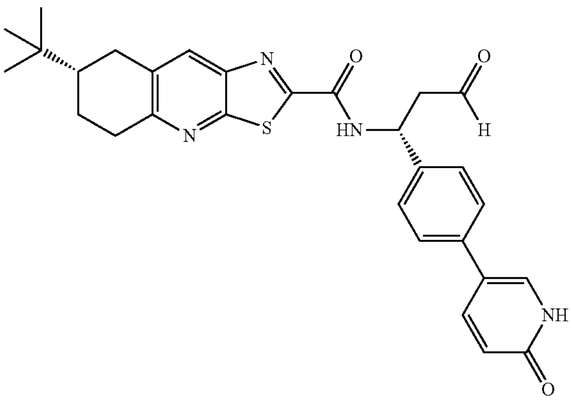

Following analogous methodology to that outlined for intermediate I-31 above, intermediate I-33 was prepared.

Scheme Y: Synthesis of intermediate I-34

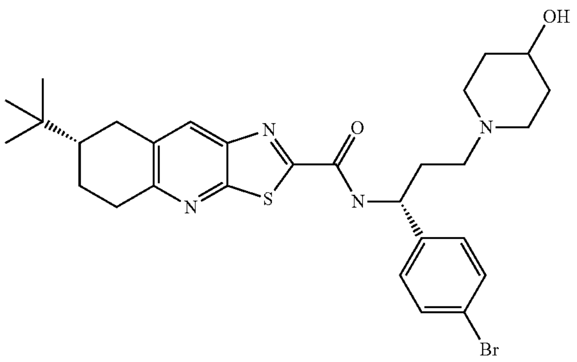

I-34

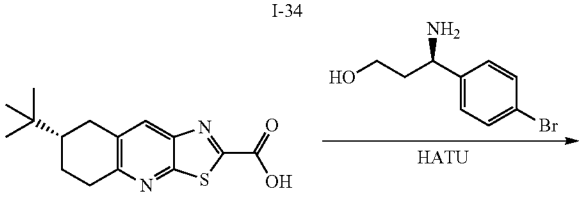

I-5

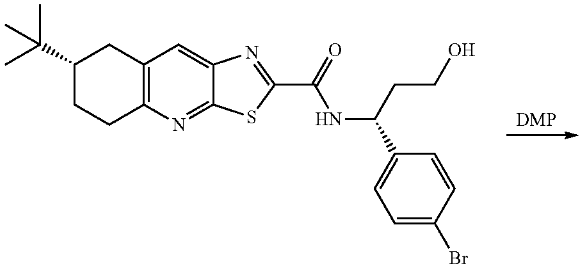

Y-1

-continued

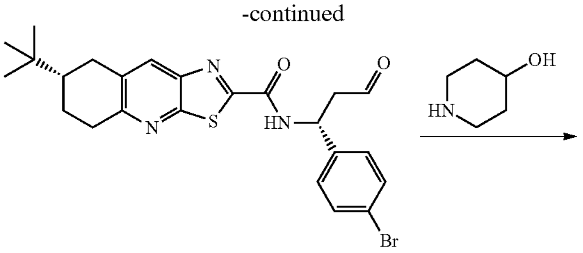

Y-2

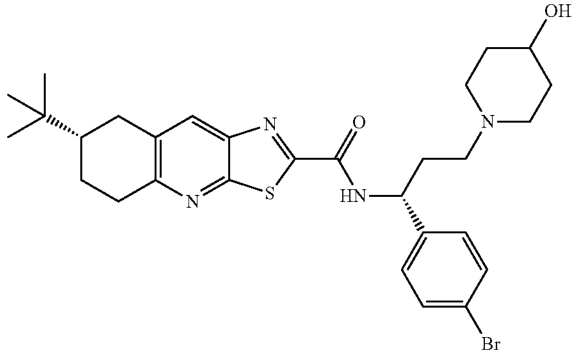

I-34

Step 1 (S)-N-((R)-1-(4-bromophenyl)-3-hydroxypropyl)-7-(tert-butyl)-5,6,7,8-tetrahydrothiazolo[5,4-b]quinoline-2-carboxamide (Y-1)

To a flask with(S)-7-(tert-butyl)-5,6,7,8-tetrahydrothiazolo[5,4-b]quinoline-2-carboxylic acid (I-5) (5 g, 17.22 mmol), (R)-3-amino-3-(4-bromophenyl)propan-1-ol (4.08 g, 17.74 mmol), HOAt (3.05 g, 22.38 mmol) and HATU (8.51 g, 22.38 mmol) was added DMF (86 mL) followed by DIEA (9.02 mL, 51.7 mmol). The reaction stirred at RT over two days. Sat. $NaHCO_3$ aq. solution was added and the resulting mixture was stirred for 20 min. The reaction mixture was extracted with EtOAc. The organics were washed with brine, dried over $Na_2SO_4$, filtered and concentrated under reduced pressure to give the title compound, Y-1, which was used in the next step without further purification. MS: 504 (M+1).

Step 2 (S)-N-((R)-1-(4-bromophenyl)-3-oxopropyl)-7-(tert-butyl)-5,6,7,8-tetrahydrothiazolo[5,4-b]quinoline-2-carboxamide (Y-2)

To a mixture of(S)-N-((R)-1-(4-bromophenyl)-3-hydroxypropyl)-7-(tert-butyl)-5,6,7,8-tetrahydrothiazolo[5,4-b]quinoline-2-carboxamide (Y-1) (5.1 g, 10.15 mmol) in DCM (300 mL) was added DMP (6.46 g, 15.22 mmol) at 0° C. The reaction was slowly warmed to RT and stirred at RT for 4 h. The reaction was quenched with saturated $NaHCO_3$ aqueous solution and saturated $Na_2SO_3$ aqueous solution. The mixture was stirred for 30 mins. The layers were separated. The aqueous layer was extracted with DCM. The combined organic layers were dried over $Na_2SO_4$, filtered and concentrated under reduced pressure. The residue was directly used in the next step without further purification. MS: 502 (M+1).

Step 3 (S)-N-((R)-1-(4-bromophenyl)-3-(4-hydroxypiperidin-1-yl)propyl)-7-(tert-butyl)-5,6,7,8-tetrahydrothiazolo[5,4-b]quinoline-2-carboxamide (I-34)

A solution of(S)-N-((R)-1-(4-bromophenyl)-3-oxopropyl)-7-(tert-butyl)-5,6,7,8-tetrahydrothiazolo[5,4-b]quinoline-2-carboxamide (Y-2) (4.8 g, 9.59 mmol) and piperidin-4-ol (1.940 g, 19.18 mmol) in DCE (99 mL) was stirred at RT for 5 minutes. Sodium triacetoxy borohydride (6.10 g, 28.8 mmol) was added. The reaction was stirred at RT overnight. The reaction was quenched with saturated $NaHCO_3$ aqueous solution and extracted with DCM. The combined organics were washed with brine, dried over $Na_2SO_4$, filtered and concentrated under reduced pressure. The residue was purified by silica gel flash chromatography (MeOH/DCM (1% $NH_4OH$)) to give the title compound, I-34. MS: 587 (M+1).

Scheme Z: Synthesis of intermediate I-35

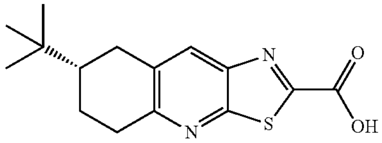

I-5

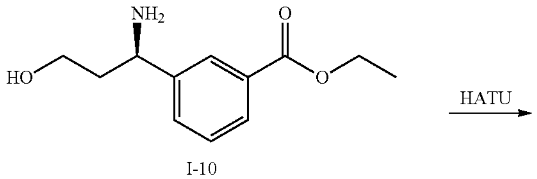

I-10

-continued
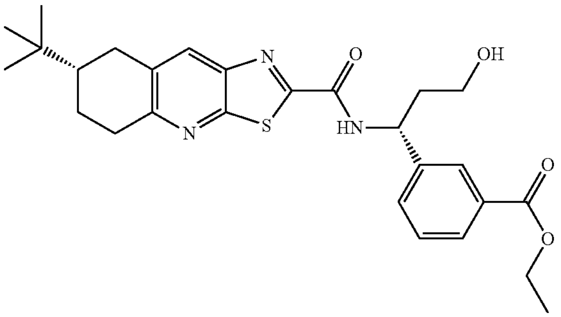
Z-1
Z-1
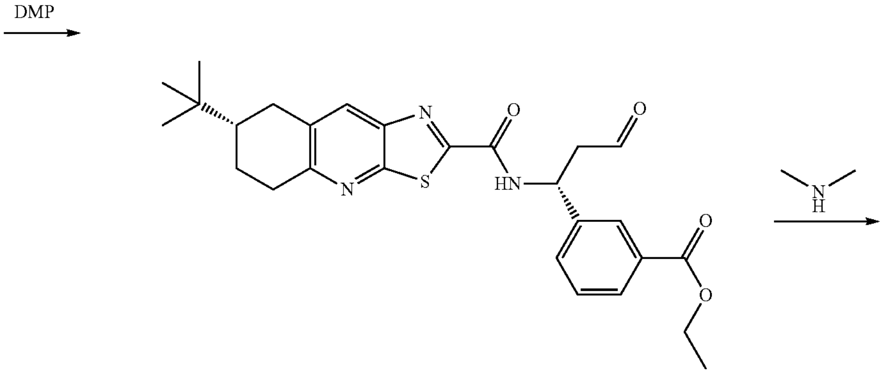
Z-2
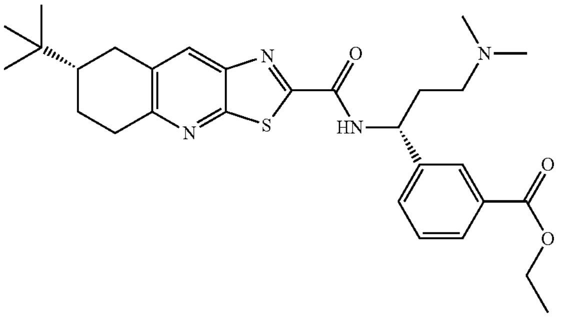
Z-3
Z-3
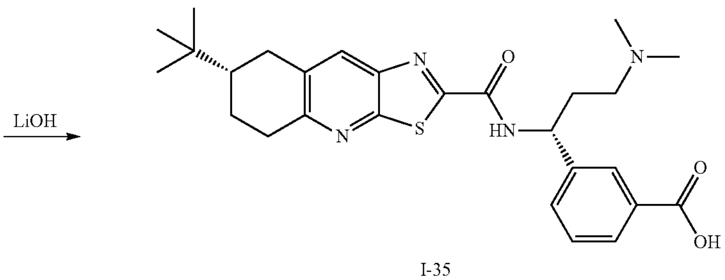
I-35

Step 1 ethyl 3-((R)-1-((S)-7-(tert-butyl)-5,6,7,8-tetrahydrothiazolo[5,4-b]quinoline-2-carboxamido)-3-hydroxypropyl)benzoate (Z-1)

A mixture of(S)-7-(tert-butyl)-5,6,7,8-tetrahydrothiazolo [5,4-b]quinoline-2-carboxylic acid (I-5) (2 g, 6.89 mmol), (R)-ethyl 3-(1-amino-3-hydroxypropyl)benzoate (I-10) HCl salt (1.843 g, 7.09 mmol), HOAt (1.219 g, 8.95 mmol) and HATU (3.40 g, 8.95 mmol) was added DMF (34.4 mL) followed by DIEA (3.61 mL, 20.66 mmol). The reaction stirred at RT overnight. The mixture was quenched with aqueous $NaHCO_3$ solution (200 mL), extracted with ethyl acetate (400 mL). The organic layer was washed with water, brine, dried over $Na_2SO_4$, filtered and evaporated under reduced pressure. The residue was purified by silica gel chromatography (acetone/hexane) to give the title compound, Z-1. MS: 496 (M+1). Following analogous methodology to that outlined for intermediate I-34 above, compound Z-3 was prepared. MS: 523 (M+1).

Step 2 3-((R)-1-((S)-7-(tert-butyl)-5,6,7,8-tetrahydrothiazolo[5,4-b]quinoline-2-carboxamido)-3-(dimethylamino) propyl)benzoic acid (I-35)

To a solution of ethyl 3-((R)-1-((S)-7-(tert-butyl)-5,6,7,8-tetrahydrothiazolo[5,4-b]quinoline-2-carboxamido)-3-(dimethylamino) propyl)benzoate (Z-3, 1.2 g, 2.29 mmol) in THF (15.3 mL) and MeOH (7.7 mL) was added aqueous LiOH (1.0 M, 4.6 mL, 4.6 mmol). The mixture was stirred at RT overnight. The organic solvent was evaporated. The residue was treated with 1N aqueous HCl to PH~6. The mixture was stirred for 5 min and filtered. The filter cake was rinsed with water and dried to give the title compound, I-35, which was used in the next step without further purification. MS: 495 (M+1).

Scheme AA: Synthesis of intermediate I-36

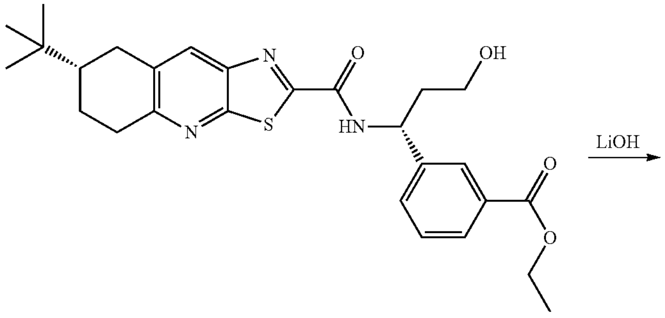

Z-1

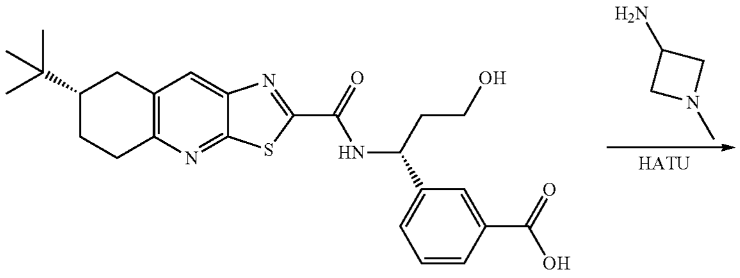

AA-1

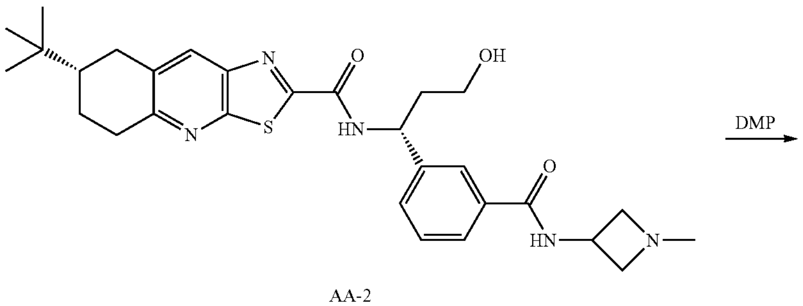

AA-2

-continued

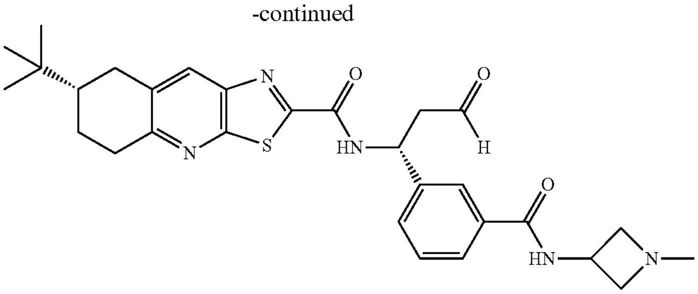

I-36

Step 1 3-((R)-1-((S)-7-(tert-butyl)-5,6,7,8-tetrahydrothiazolo[5,4-b]quinoline-2-carboxamido)-3-hydroxypropyl)benzoic acid (AA-1)

To a solution of ethyl 4-((R)-3-(4-hydroxypiperidin-1-yl)-1-((S)-7-(1-methylcyclopropyl)-5,6,7,8-tetrahydroacridine-2-carboxamido) propyl)benzoate (Z-1) (500 mg, 0.878 mmol) in THF (7.3 mL) and MeOH (3.6 mL) was added aqueous LiOH (1.0 M, 1931 μL, 1.931 mmol). The mixture was stirred at RT overnight. The organic solvent was evaporated. The residue was treated with 1N aqueous HCl to pH~6. The mixture was stirred for 5 min and filtered. The filter cake was rinsed with water and dried to give the title compound, AA-1, which was used in the next step without further purification. MS: 468 (M+1).

Step 2 (S)-7-(tert-butyl)-N-((R)-3-hydroxy-1-(3-((1-methylazetidin-3-yl) carbamoyl)phenyl)propyl)-5,6,7,8-tetrahydrothiazolo[5,4-b]quinoline-2-carboxamide (AA-2)

3-((R)-1-((S)-7-(tert-butyl)-5,6,7,8-tetrahydrothiazolo[5,4-b]quinoline-2-carboxamido)-3-hydroxypropyl)benzoic acid (AA-1) (600 mg, 1.283 mmol), 1-methylazetidin-3-amine oxalic acid salt (339 mg, 1.925 mmol), HOAt (227 mg, 1.668 mmol) and HATU (634 mg, 1.668 mmol) was added DMF (6.4 mL) followed by DIEA (672 μL, 3.85 mmol). The reaction was stirred at RT overnight. The mixture was quenched with aqueous $NaHCO_3$ solution (100 mL), extracted with ethyl acetate (200 mL). The organic layer was washed with water, brine, dried over $Na_2SO_4$, filtered and evaporated under reduced pressure. The residue was directly used in the next step without further purification. MS: 536 (M+1).

Step 3 (S)-7-(tert-butyl)-N-((R)-1-(3-((1-methylazetidin-3-yl) carbamoyl)phenyl)-3-oxopropyl)-5,6,7,8-tetrahydrothiazolo[5,4-b]quinoline-2-carboxamide (1-36)

Following analogous methodology to that outlined for compound Y-2 above, intermediate I-36 was prepared. MS: 534 (M+1).

Intermediate I-37

(S)-N-((R)-1-(3-bromophenyl)-3-(4-hydroxypiperidin-1-yl)propyl)-7-(tert-butyl)-5,6,7,8-tetrahydrothiazolo[5,4-b]quinoline-2-carboxamide (1-37)

I-37

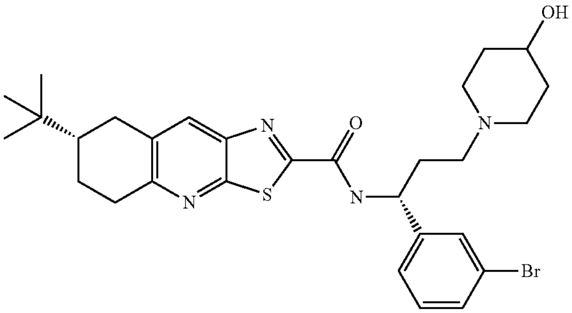

Following analogous methodology to that outlined for intermediate I-34 above, intermediate I-37 was prepared. MS: 585 (M+1).

Intermediate I-38

3-((R)-3-(4-(tert-butoxycarbonyl)piperidin-1-yl)-1-((S)-7-(tert-butyl)-5,6,7,8-tetrahydrothiazolo[5,4-b]quinoline-2-carboxamido) propyl)benzoic acid (1-38)

I-38

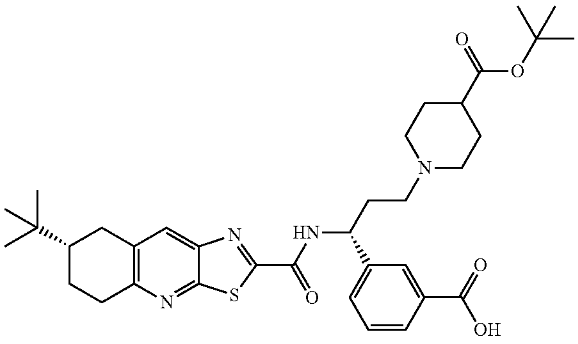

Following analogous methodology to that outlined for intermediate I-35 above, intermediate I-38 was prepared. MS: 635 (M+1).

Intermediate I-39

3-((R)-1-((S)-7-(tert-butyl)-5,6,7,8-tetrahydrothiazolo[5,4-b]quinoline-2-carboxamido)-3-(4-hydroxypiperidin-1-yl)propyl)benzoic acid (1-39)

I-39

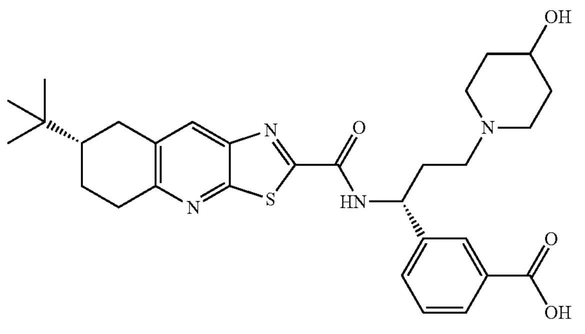

Following analogous methodology to that outlined for intermediate I-35 above, intermediate I-39 was prepared. MS: 551 (M+1).

Scheme AB: Synthesis of intermediate I-40

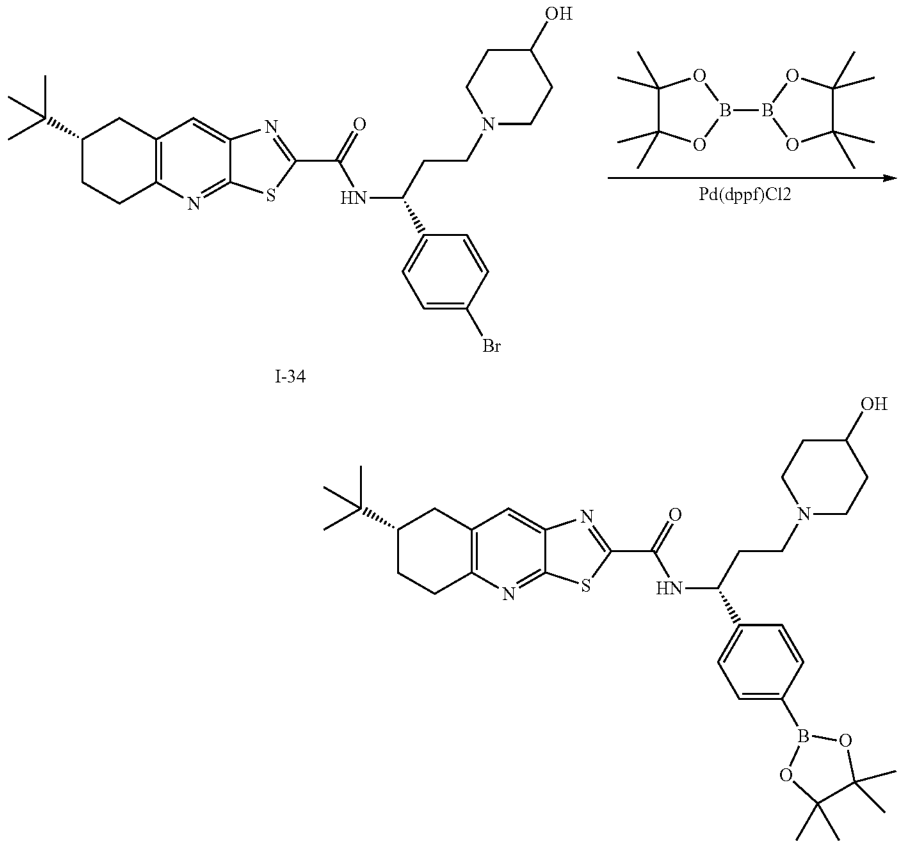

I-34

I-40

(S)-7-(tert-butyl)-N-((R)-3-(4-hydroxypiperidin-1-yl)-1-(4-(4,4,5,5-tetramethyl-1,3,2-dioxaborolan-2-yl)phenyl)propyl)-5,6,7,8-tetrahydrothiazolo[5,4-b]quinoline-2-carboxamide (I-40)

A mixture of(S)-N-((R)-1-(4-bromophenyl)-3-(4-hydroxypiperidin-1-yl)propyl)-7-(tert-butyl)-5,6,7,8-tetrahydrothiazolo[5,4-b]quinoline-2-carboxamide (I-34) (900 mg, 1.537 mmol), Pd (dppf) $C_{12}$ (178 mg, 0.154 mmol) and KOAc (377 mg, 3.84 mmol), and 4,4,4',4',5,5,5',5'-octamethyl-2,2'-bi (1,3,2-dioxaborolane) (468 mg, 1.844 mmol) was evacuated and back filled with $N_2$ three times. Then DMF (15 mL) was added and the mixture was evacuated and back filled with $N_2$ three times again. The mixture was stirred at 90° C. for 3 hr. The reaction was then cooled to RT, diluted with ethyl acetate (200 mL) and water. The mixture was filtered through Celite®. The layers were separated. The organic layer was washed with water (3×30 mL) and brine (50 mL). The organic layer was dried over anhydrous $Na_2SO_4$, filtered, and concentrated under reduced pressure. The residue was suspended in 50% EtOAc/n-Hexane (10 mL) and the mixture was filtered. The filtrate was further washed with 50% EtOAc/n-Hexane (5 mL). The filtrate was dried and directly used without further purification. MS: 633 (M+1).

Scheme AC: Synthesis of intermediate I-41

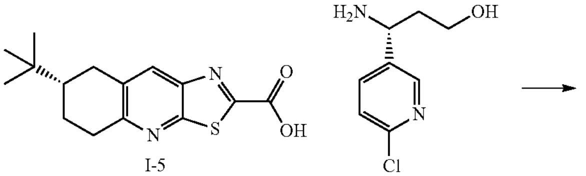

I-5

AC-1

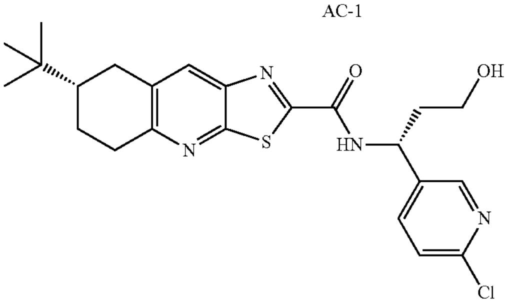

I-41

(S)-7-(tert-butyl)-N-((R)-1-(6-chloropyridin-3-yl)-3-hydroxypropyl)-5,6,7,8-tetrahydrothiazolo[5,4-b]quinoline-2-carboxamide (I-41)

A mixture of(S)-7-(tert-butyl)-5,6,7,8-tetrahydrothiazolo[5,4-b]quinoline-2-carboxylic acid (1-5) (6 g, 20.66 mmol), HATU (9.43 g, 24.80 mmol), HOAT (3.37 g, 24.80 mmol) was added DMF (60 mL). The mixture was stirred for 10 min, then (R)-3-amino-3-(6-chloropyridin-3-yl)propan-1-ol hydrochloride (4.98 g, 22.32 mmol) and DIPEA (14.44 mL, 83 mmol) was added. The mixture was stirred at RT for 4 h. The reaction mixture was added dropwise to saturated $NaHCO_3$ aqueous solution (800 mL). The mixture was stirred for 10 min, then filtered. The filter cake was dried to afford the title compound, I-41, which was directly used without further purification. MS: 459 (M+1).

Scheme AD: Synthesis of intermediate I-42

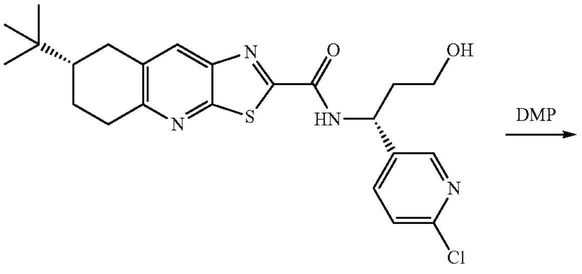

I-41

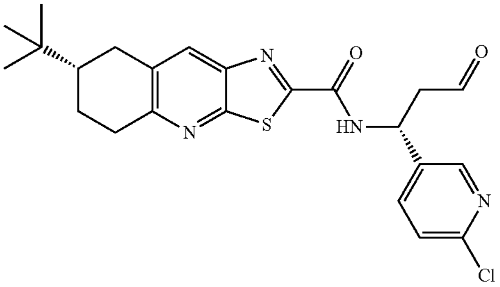

I-42

(S)-7-(tert-butyl)-N-((R)-1-(6-chloropyridin-3-yl)-3-oxopropyl)-5,6,7,8-tetrahydrothiazolo[5,4-b]quinoline-2-carboxamide (I-42)

To a solution of(S)-7-(tert-butyl)-N-((R)-1-(6-chloropyridin-3-yl)-3-hydroxypropyl)-5,6,7,8-tetrahydrothiazolo[5,4-b]quinoline-2-carboxamide (I-41) (6000 mg, 13.07 mmol) in DCM (300 mL) was added Dess-Martin Periodinane (8871 mg, 20.91 mmol). The reaction was stirred at RT for 1 h. Upon completion, the reaction mixture was quenched with saturated $NaHCO_3$ and $Na_2S_2O_3$ aqueous solution. The mixture was stirred for 30 min, and the layers were separated. The organic layer was dried over $MgSO_4$, filtered, and concentrated under reduced pressure to afford title compound, I-42, which was directly used without further purification. MS: 457 (M+1).

Scheme AE: Synthesis of intermediate I-43

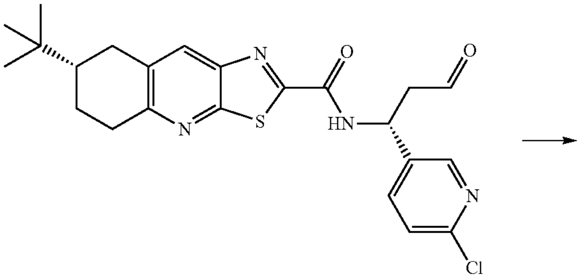

I-42

-continued

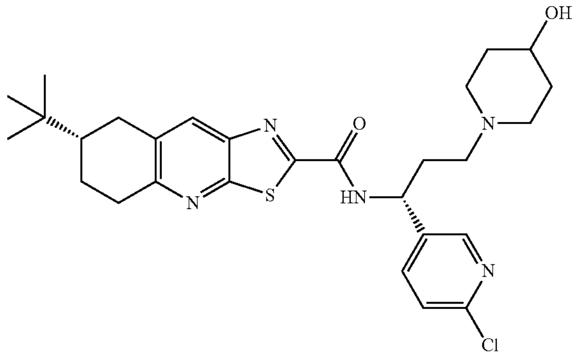

I-43

(S)-7-(tert-butyl)-N-((R)-1-(6-chloropyridin-3-yl)-3-(4-hydroxypiperidin-1-yl)propyl)-5,6,7,8-tetrahydrothiazolo[5,4-b]quinoline-2-carboxamide (I-43)

Following analogous methodology to that outlined for intermediate I-34 above, intermediate I-43 was prepared. MS: 542 (M+1).

Intermediate I-44

(S)-7-(tert-butyl)-N-((R)-1-(4-(5-fluoro-6-hydroxypyridin-3-yl)phenyl)-3-oxopropyl)-5,6,7,8-tetrahydrothiazolo[5,4-b]quinoline-2-carboxamide (I-44)

I-44

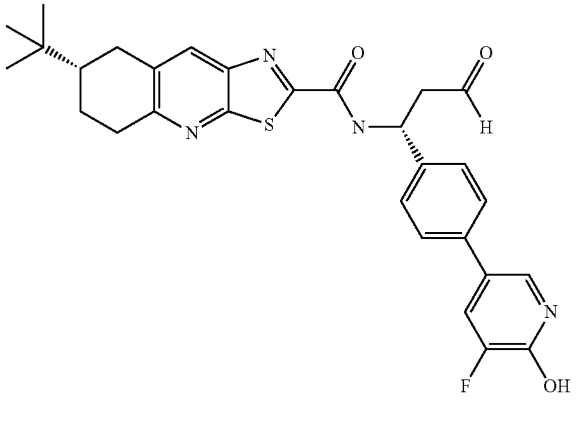

Following analogous methodology to that outlined for intermediate I-33 above, intermediate I-44 was prepared. MS: 533 (M+1).

Scheme AF: Synthesis of intermediate I-45

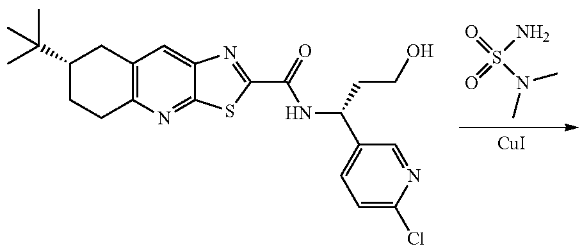

I-41

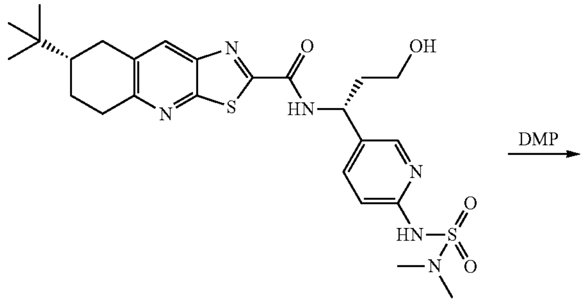

AF-1

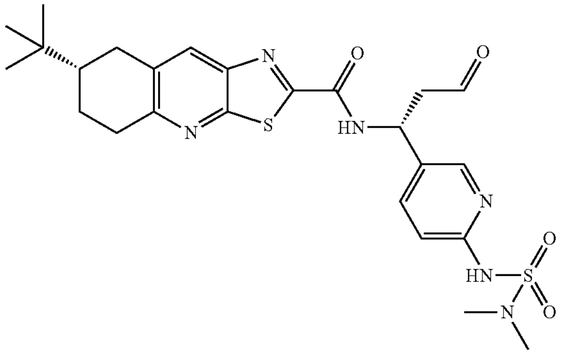

I-45

Step 1 (S)-7-(tert-butyl)-N-((R)-1-(6-((N,N-dimethylsulfamoyl)amino)pyridin-3-yl)-3-hydroxypropyl)-5,6,7,8-tetrahydrothiazolo[5,4-b]quinoline-2-carboxamide (AF-1)

Following analogous methodology to that outlined for intermediate I-23 above, compound AF-1 was prepared. MS: 547 (M+1).

Step 2 (S)-7-(tert-butyl)-N-((R)-1-(6-((N,N-dimethylsulfamoyl)amino)pyridin-3-yl)-3-oxopropyl)-5,6,7,8-tetrahydrothiazolo[5,4-b]quinoline-2-carboxamide (I-45)

Following analogous methodology to that outlined for intermediate I-42 above, compound I-45 was prepared. MS: 545 (M+1).

Intermediate I-46 methyl 1-((R)-3-((S)-7-(tert-butyl)-5,6,7,8-tetrahydrothiazolo[5,4-b]quinoline-2-carboxamido)-3-(6-chloropyridin-3-yl)propyl)piperidine-4-carboxylate (I-46)

I-46

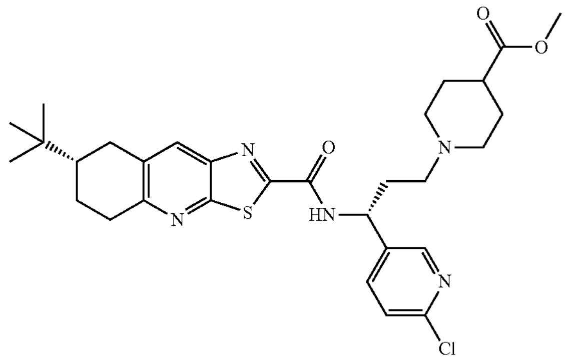

Following analogous methodology to that outlined for intermediate I-43 above, intermediate I-46 was prepared. MS: 584 (M+1).

Scheme AG: Synthesis of intermediate I-47

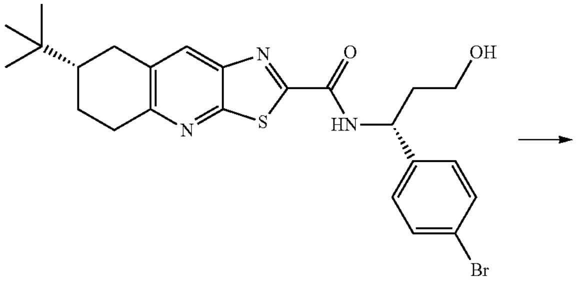

I-26

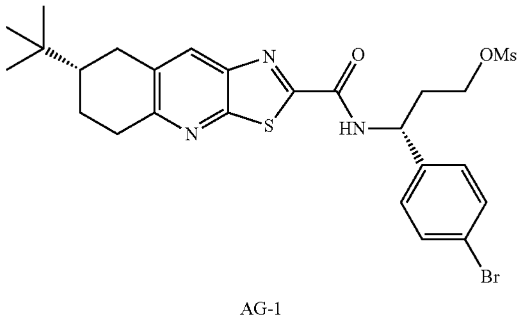

AG-1

-continued

AG-1

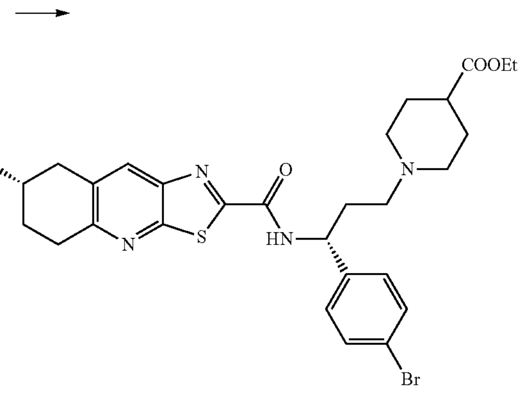

I-47

Step 1 (R)-3-(4-bromophenyl)-3-((S)-7-(tert-butyl)-5,6,7,8-tetrahydrothiazolo[5,4-b]quinoline-2-carboxamido) propyl methanesulfonate (AG-1)

To a stirred solution of(S)-N-((R)-1-(4-bromophenyl)-3-hydroxypropyl)-7-(tert-butyl)-5,6,7,8-tetrahydrothiazolo[5,4-b]quinoline-2-carboxamide (I-26) (1.2 g, 2.39 mmol) in DCM (24 mL) were added triethylamine (724 mg, 7.17 mmol) and methanesulfonyl chloride (408 mg, 3.58 mmol) at 0° C. The reaction mixture was stirred at 0° C. for 30 min and then stirred at RT for 2 hours. The reaction mixture was diluted with dichloromethane (20 mL) and $H_2O$ (10 mL). The layers were separated. The organic layer was washed with saturated $NH_4Cl$ aqueous solution (10 mL), saturated $NaHCO_3$ aqueous solution (10 mL), and brine (10 mL). The organic layer was dried over $Na_2SO_4$, filtered and concentrated under reduced pressure. The crude product was directly used in the next step without further purification. MS: 580 (M+1).

Step 2 ethyl 1-((R)-3-(4-bromophenyl)-3-((S)-7-(tert-butyl)-5,6,7,8-tetrahydrothiazolo[5,4-b]quinoline-2-carboxamido) propyl)piperidine-4-carboxylate (I-47)

To a stirred solution of (R)-3-(4-bromophenyl)-3-((S)-7-(tert-butyl)-5,6,7,8-tetrahydrothiazolo[5,4-b]quinoline-2-carboxamido) propyl methanesulfonate (AG-1) (1.20 g, 2.06 mmol) in $CH_3CN$ (20 mL) was added ethyl piperidine-4-carboxylate (3.25 g, 20.6 mmol). The mixture was stirred at 90° C. for 1.5 h. The reaction mixture was then concentrated under reduced pressure. To this residue, dichloromethane (50 mL) and $H_2O$ (20 mL), were added and the layers were separated. The organic layer was washed with brine (10 mL), dried over $Na_2SO_4$, filtered and concentrated under reduced pressure. The residue was purified by silica gel chromatography (EtOAc/hexane) to give the title compound, I-47. MS: 641 (M+1).

Intermediate I-48

(S)-6-(tert-butyl)-N-((R)-3-oxo-1-phenylpropyl)-5,6,7,8-tetrahydrothieno[2,3-b]quinoline-2-carboxamide

I-48

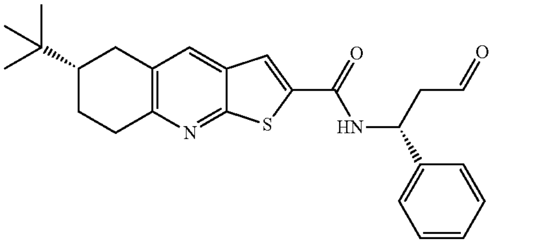

Following analogous methodology to that outlined for intermediate I-27 above, intermediate I-48 was prepared. MS: 421 (M+1).

Examples 1-7

Examples 1 to 7 were synthesized by a similar procedure as below:

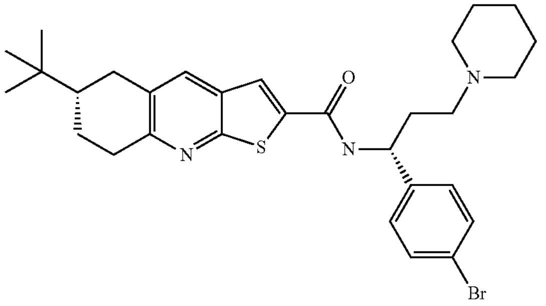

I-28

+

-continued

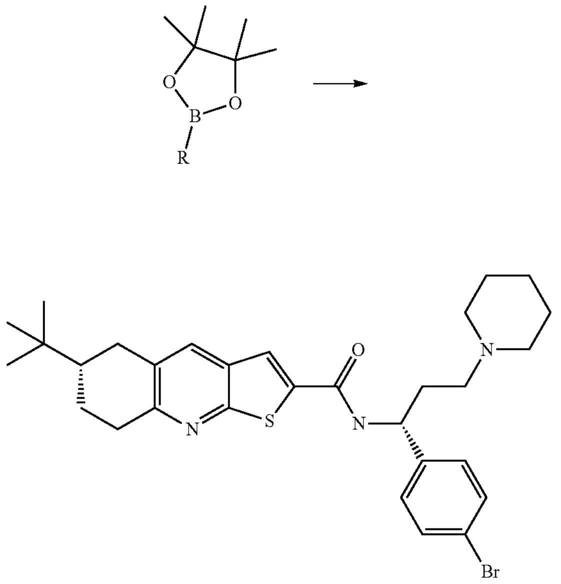

To a solution of(S)-N-(I-1-(4-bromophenyl)-3-(piperidin-1-yl)propyl)-6-(tert-butyl)-5,6,7,8-tetrahydrothieno[2,3-b]quinoline-2-carboxamide (I-28, 30 mg, 0.053 mmol) and boronic acid substrate (0.053 mmol) in dioxane (1 mL), was added Pd(dppf)$Cl_2$ (3.05 mg, 2.64 μmol) and 2.5 N $Na_2CO_3$ (0.063 mL, 0.158 mmol) at ambient temperature. The resulting reaction mixture was purged with $N_2$ for 5 mins and then stirred at 100° C. for 16 hrs.

The reaction was cooled to ambient temperature and partitioned between EtOAc (6 mL) and water (2 mL). The organic phase was washed with brine and evaporated in vacuum. The crude product was purified by reverse-phase HPLC (MeCN/water with 0.1% ammonium hydroxide modifier) to afford the desired product.

| Ex. No. | Structure | Chemical Name | Mass [M + H]+ | hNPRA EC50 (nM) |
|---|---|---|---|---|
| 1 | 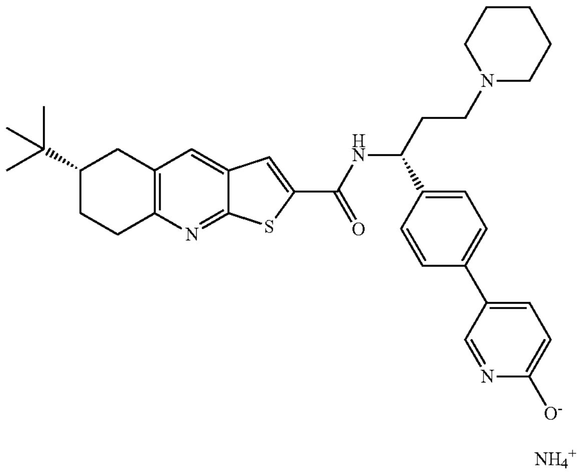 [SMILES: CC(C)(C)[C@H]1CCc2nc3sc(C(=O)N[C@H](CCN4CCCCC4)c4ccc(-c5ccc([O-])nc5)cc4)cc3cc2C1 ; [NH4+]] | ammonium;5-[4-[rac-(1R)-3-(1-piperidyl)-1-[[rac-(6S)-6-tert-butyl-5,6,7,8-tetrahydrothieno[2,3-b]quinoline-2-carbonyl]amino]propyl]phenyl]yridine-2-olate | 583.4 | 232.9 |

-continued

| Ex. No. | Structure | Chemical Name | Mass [M + H]+ | hNPRA EC50 (nM) |
|---|---|---|---|---|
| 2 | 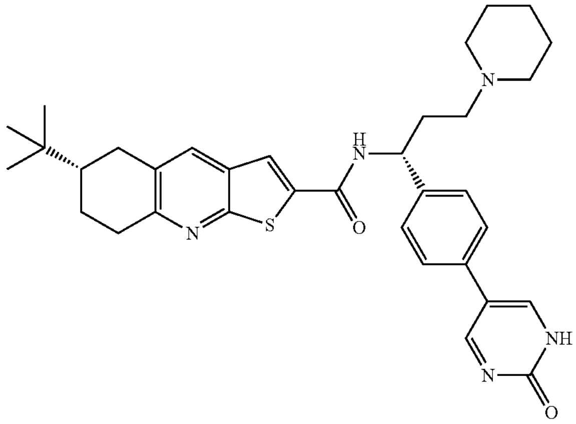 [SMILES: CC(C)(C)[C@H]1CCc2nc3sc(C(=O)N[C@H](CCN4CCCCC4)c4ccc(-c5cnc(=O)[nH]c5)cc4)cc3cc2C1] | rac-(6S)-6-tert-butyl-N-[rac-(1R)-1-[4-(2-oxo-1H-pyrimidin-5-yl)phenyl]-3-(1-piperidyl)propyl]-5,6,7,8-tetrahydrothieno[2,3-b]quinoline-2-carboxamide | 584.3 | 518.1 |
| 3 | 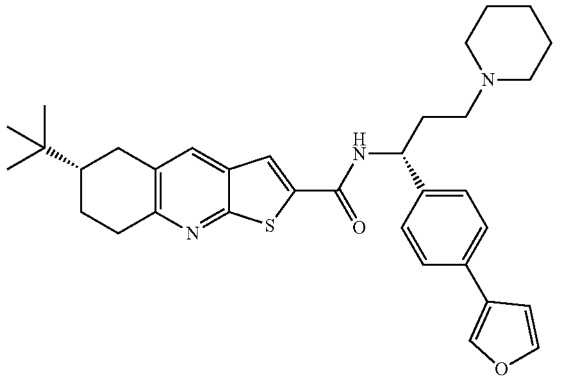 [SMILES: CC(C)(C)[C@H]1CCc2nc3sc(C(=O)N[C@H](CCN4CCCCC4)c4ccc(-c5ccoc5)cc4)cc3cc2C1] | rac-(6S)-6-tert-butyl-N-[rac-(1R)-1-[4-(3-furyl)phenyl]-3-(1-piperidyl)propyl]-5,6,7,8-tetrahydrothieno[2,3-b]quinoline-2-carboxamide | 556.29 | 675.3 |
| 4 | 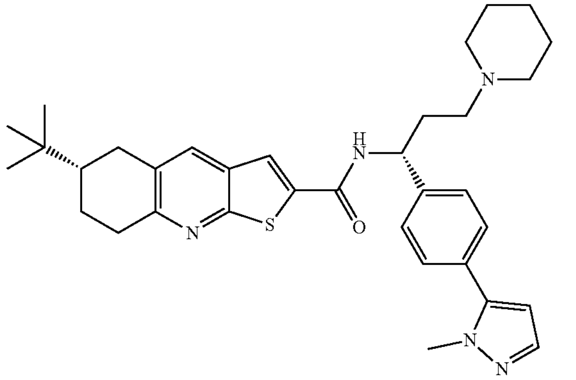 [SMILES: Cn1nccc1-c1ccc([C@@H](CCN2CCCCC2)NC(=O)c2cc3cc4c(nc3s2)CC[C@H](C(C)(C)C)C4)cc1] | rac-(6S)-6-tert-butyl-N-[rac-(1R)-1-[4-(2-methylpyrazol-3-yl)phenyl]-3-(1-piperidyl)propyl]-5,6,7,8-tetrahydrothieno[2,3-b]quinoline-2-carboxamide | 570.32 | 753.4 |
| 5 | 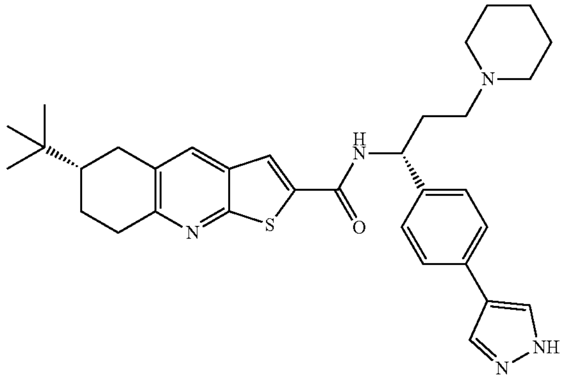 [SMILES: CC(C)(C)[C@H]1CCc2nc3sc(C(=O)N[C@H](CCN4CCCCC4)c4ccc(-c5cn[nH]c5)cc4)cc3cc2C1] | rac-(6S)-6-tert-butyl-N-[rac-(1R)-3-(1-piperidy])-1-[4-(1H-pyrazol-4-yl)phenyl]propyl]-5,6,7,8-tetrahydrothieno[2,3-b]quinoline-2-carboxamide | 556.3 | 777.3 |

-continued

| Ex. No. | Structure | Chemical Name | Mass [M + H]+ | hNPRA EC50 (nM) |
|---|---|---|---|---|
| 6 | 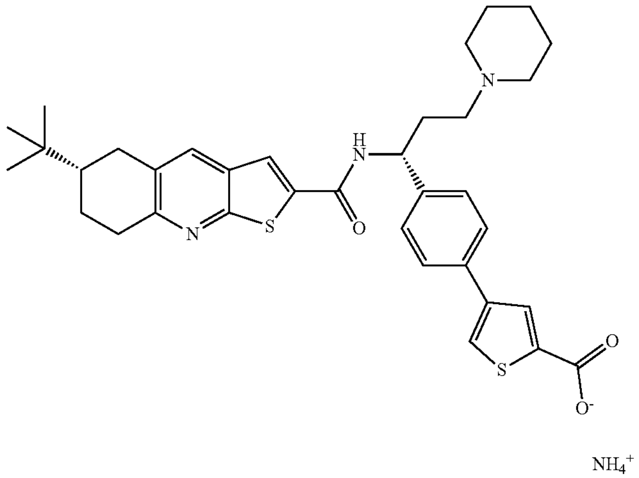 [SMILES: CC(C)(C)[C@H]1CCc2nc3sc(C(=O)N[C@H](CCN4CCCCC4)c4ccc(-c5csc(C(=O)[O-])c5)cc4)cc3cc2C1 ; [NH4+]] | ammonium;4-[4-[rac-(1R)-3-(1-piperidyl)-1-[rac-(6S)-6-tert-butyl-5,6,7,8-tetrahydrothieno[2,3-b]quinoline-2-carbonyl]amino]propyl]phenyl]thiophene-2-carboxylate | 616.3 | 877.1 |
| 7 | 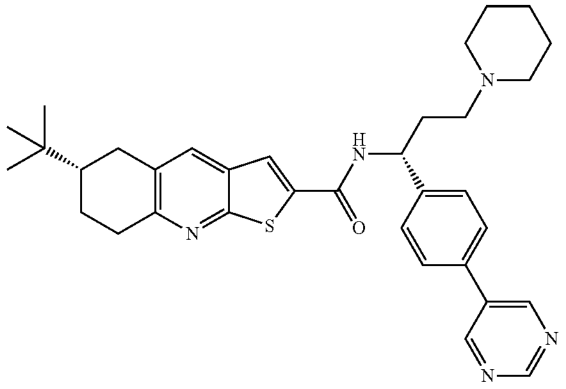 [SMILES: CC(C)(C)[C@H]1CCc2nc3sc(C(=O)N[C@H](CCN4CCCCC4)c4ccc(-c5cncnc5)cc4)cc3cc2C1] | rac-(6S)-6-tert-butyl-N-[rac-(1R)-3-(1-piperidyl)-1-(4-pyrimidin-5-ylphenyl)propyl]-5,6,7,8-tetrahydrothieno[2,3-b]quinoline-2-carboxamide | 568.3 | 2000 |

Examples 8-24

Examples 8-24 were synthesized by a similar procedure as below:

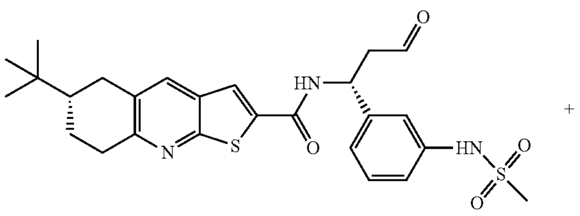

I-30

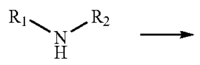

-continued

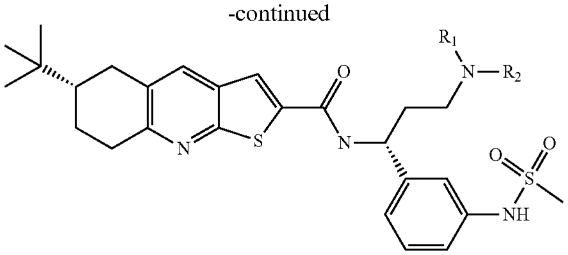

To a solution of(S)-6-(tert-butyl)-N-((R)-1-(3-(methylsulfonamido)phenyl)-3-oxopropyl)-5,6,7,8-tetrahydrothieno[2,3-b]quinoline-2-carboxamide (1-30, 30 mg, 0.057 mmol) in anhydrous 5% HOAc/MeOH (1.5 ml) was added amino substrate (0.114 mmol) and polystyrene supported $BH_3CN$ (65.7 mg, 2.45 mmol/g) at ambient temperature. The resulting reaction mixture was shaken at ambient temperature for 6 hrs.

The solution was filtered, and the solvent was evaporated under vacuum. The crude product was purified by reverse-phase HPLC (MeCN/water with 0.1% ammonium hydroxide modifier) to afford the desired product as an ammonium salt.

| Ex. No. | Structure | Chemical Name | Mass [M + H]+ | hNPRA EC50 (nM) |
|---|---|---|---|---|
| 8 | 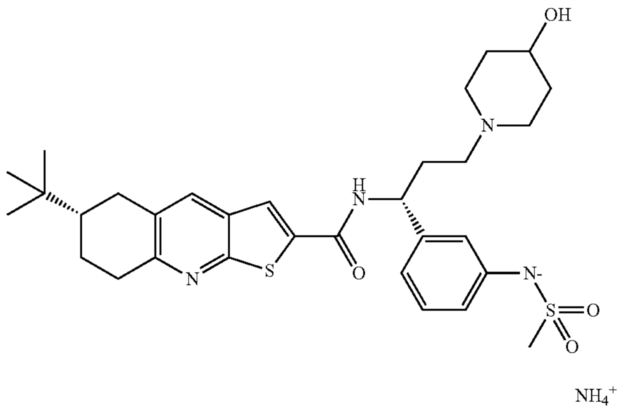 [SMILES: CC(C)(C)[C@H]1CCc2nc3sc(C(=O)N[C@H](CCN4CCC(O)CC4)c4cccc([N-]S(C)(=O)=O)c4)cc3cc2C1 ; [NH4+]] | ammonium; methylsulfonyl-[3-[rac-(1R)-3-(4-hydroxy-1-piperidyl)-1-[rac-(6S)-6-tert-butyl-5,6,7,8-tetrahydrothieno[2,3-b]quinoline-2-carbonyl]amino]propyl]phenyl]azanide | 599.3 | 452.8 |
| 9 | 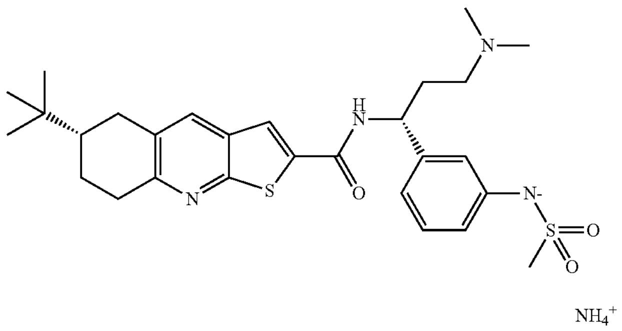 [SMILES: CN(C)CC[C@@H](NC(=O)c1cc2cc3c(nc2s1)CC[C@H](C(C)(C)C)C3)c1cccc([N-]S(C)(=O)=O)c1 ; [NH4+]] | ammonium; methylsulfonyl-[3-[rac-(1R)-3-(dimethylamino)-1-[rac-(6S)-6-tert-butyl-5,6,7,8-tetrahydrothieno[2,3-b]quinoline-2-carbonyl]amino]propyl]phenyl]azanide | 543.3 | 708.5 |
| 10 | 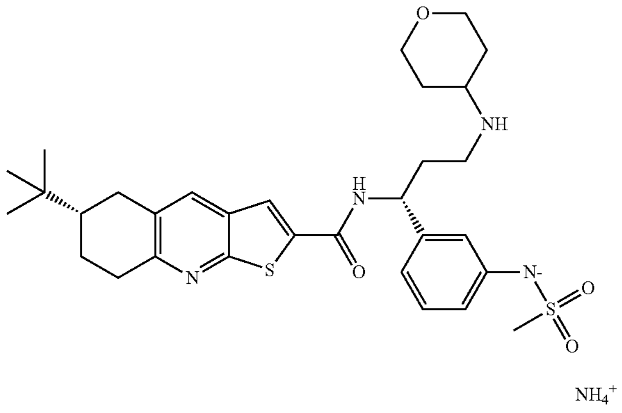 [SMILES: CC(C)(C)[C@H]1CCc2nc3sc(C(=O)N[C@H](CCNC4CCOCC4)c4cccc([N-]S(C)(=O)=O)c4)cc3cc2C1 ; [NH4+]] | ammonium; methylsulfonyl-[3-[rac-(1R)-1-[[rac-(6S)-6-tert-butyl-5,6,7,8-tetrahydrothieno[2,3-b]quinoline-2-carbonyl]amino]-3-(tetrahydro-pyran-4-ylamino)propyl]phenyl]azanide | 599.3 | 710.4 |

-continued

| Ex. No. | Structure | Chemical Name | Mass [M + H]+ | hNPRA EC50 (nM) |
|---|---|---|---|---|
| 11 | 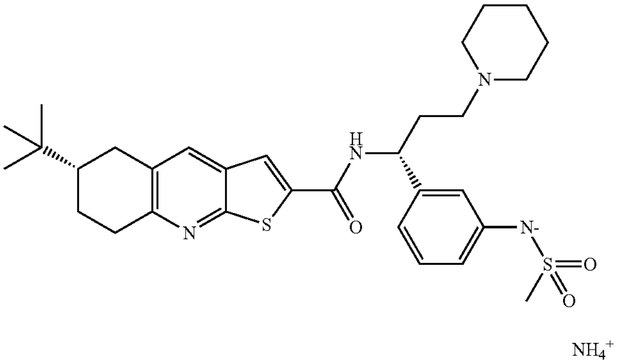 [SMILES: CC(C)(C)[C@H]1CCc2nc3sc(C(=O)N[C@H](CCN4CCCCC4)c4cccc([N-]S(C)(=O)=O)c4)cc3cc2C1 ; [NH4+]] | ammonium; methylsulfonyl-[3-[rac-(1R)-3-(1-piperidyl)-1-[rac-(6S)-6-tert-butyl-5,6,7,8-tetrahydrothieno[2,3-b]quinoline-2-carbonyl]amino]propyl]phenyl]azanide | 583.3 | 718.2 |
| 12 | 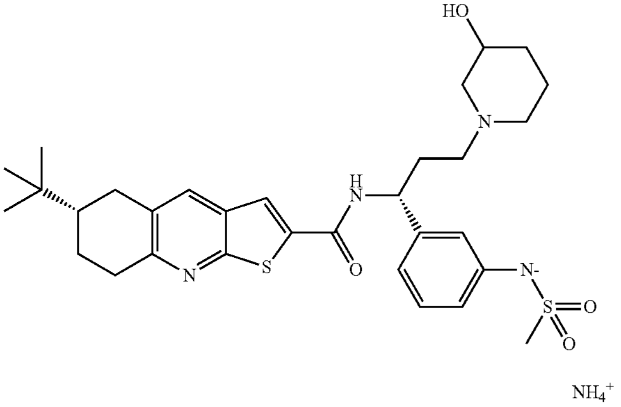 [SMILES: CC(C)(C)[C@H]1CCc2nc3sc(C(=O)N[C@H](CCN4CCCC(O)C4)c4cccc([N-]S(C)(=O)=O)c4)cc3cc2C1 ; [NH4+]] | ammonium; methylsulfonyl-[3-[rac-(1R)-3-(3-hydroxy-1-piperidyl)-1-[[rac-(6S)-6-tert-butyl-5,6,7,8-tetrahydrothieno[2,3-b]quinoline-2-carbonyl]amino]propyl]phenyl]azanide | 599.3 | 790.1 |
| 13 | 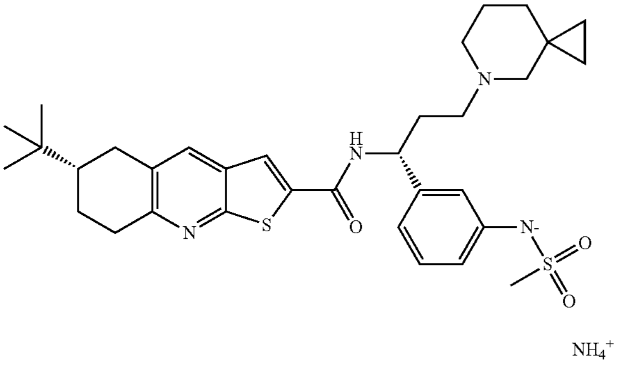 [SMILES: CC(C)(C)[C@H]1CCc2nc3sc(C(=O)N[C@H](CCN4CCCC5(CC5)C4)c4cccc([N-]S(C)(=O)=O)c4)cc3cc2C1 ; [NH4+]] | ammonium; methylsulfonyl-[3-[rac-(1R)-3-(5-azaspiro[2.5]octan-5-yl)-1-[[rac-(6S)-6-tert-butyl-5,6,7,8-tetrahydrothieno[2,3-b]quinoline-2-carbonyl]amino]propyl]phenyl]azanide | 609.4 | 809 |
| 14 | 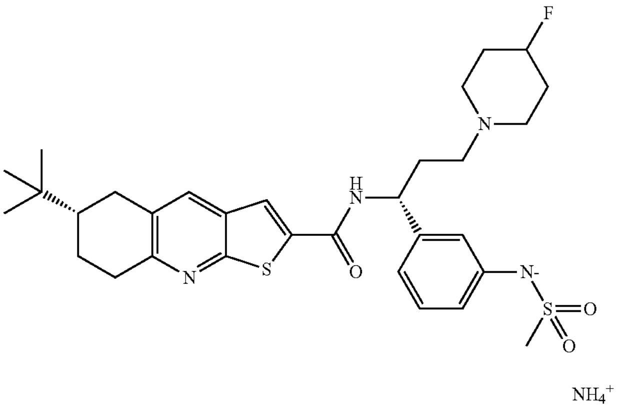 [SMILES: CC(C)(C)[C@H]1CCc2nc3sc(C(=O)N[C@H](CCN4CCC(F)CC4)c4cccc([N-]S(C)(=O)=O)c4)cc3cc2C1 ; [NH4+]] | ammonium; methylsulfonyl-[3-[rac-(1R)-3-(4-fluoro-1-piperidyl)-1-[[rac-(6S)-6-tert-butyl-5,6,7,8-tetrahydrothieno[2,3-b]quinoline-2-carbonyl]amino]propyl]phenyl]azanide | 601.4 | 834.3 |

-continued

| Ex. No. | Structure | Chemical Name | Mass [M + H]+ | hNPRA EC50 (nM) |
|---|---|---|---|---|
| 15 | 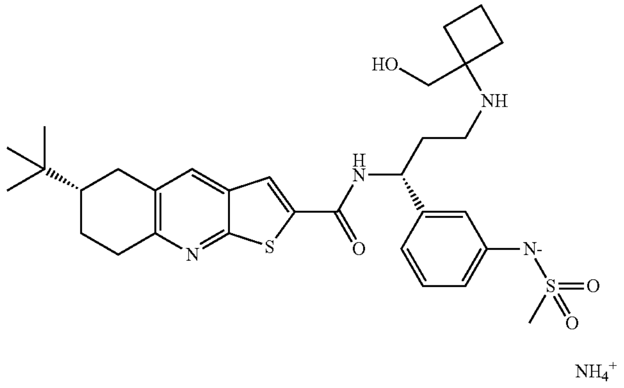 [SMILES: CC(C)(C)[C@H]1CCc2nc3sc(C(=O)N[C@H](CCNC4(CO)CCC4)c4cccc([N-]S(C)(=O)=O)c4)cc3cc2C1 ; [NH4+]] | ammonium; methylsulfonyl-1-[3-[rac-(1R)-3-[[1-(hydroxymethyl)cyclobutyl] amino]-1-[[rac-(6S)-6-tert-butyl-5,6,7,8-tetrahydrothieno[2,3-b] quinoline-2-carbonyl] amino]propyl]phenyl] azanide | 599.3 | 941.6 |
| 16 | 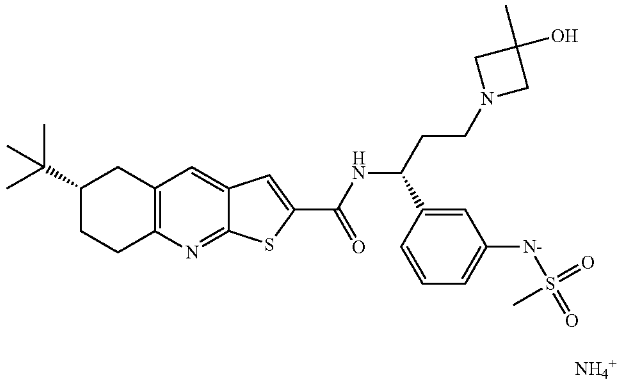 [SMILES: CC1(O)CN(CC[C@@H](NC(=O)c2cc3cc4c(nc3s2)CC[C@H](C(C)(C)C)C4)c2cccc([N-]S(C)(=O)=O)c2)C1 ; [NH4+]] | ammonium; methylsulfonyl-[3-[rac-(1R)-3-(3-hydroxy-3-methyl-azetidin-1-yl)-1-[[rac-(6S)-6-tert-butyl-5,6,7,8-tetrahydrothieno[2,3-b] quinoline-2-carbonyl] amino]propyl]phenyl] azanide | 585.3 | 1122 |
| 17 | 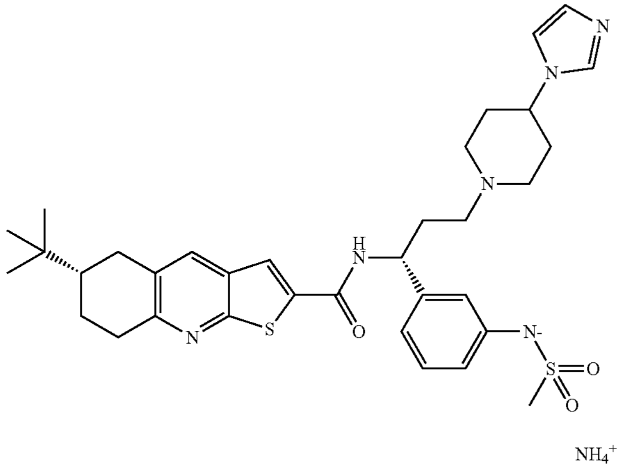 [SMILES: CC(C)(C)[C@H]1CCc2nc3sc(C(=O)N[C@H](CCN4CCC(n5ccnc5)CC4)c4cccc([N-]S(C)(=O)=O)c4)cc3cc2C1 ; [NH4+]] | ammonium; methylsulfonyl-[3-[rac-(1R)-3-(4-imidazol-1-yl-1-piperidyl)-1-[[rac-(6S)-6-tert-butyl-5,6,7,8-tetrahydrothieno[2,3-b] quinoline-2-carbonyl]amino] propyl]phenyl]azanide | 649.4 | 1257 |

-continued

| Ex. No. | Structure | Chemical Name | Mass [M + H]+ | hNPRA EC50 (nM) |
|---|---|---|---|---|
| 18 | 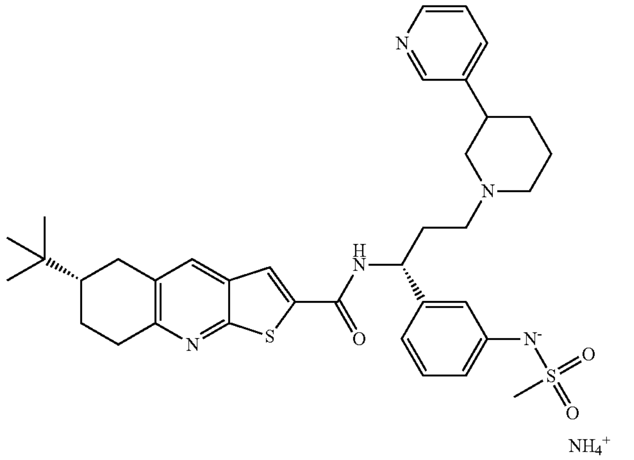 [SMILES: CC(C)(C)[C@H]1CCc2nc3sc(C(=O)N[C@H](CCN4CCCC(c5cccnc5)C4)c4cccc([N-]S(C)(=O)=O)c4)cc3cc2C1 ; [NH4+]] | ammonium; methylsulfonyl-[3-[rac-(1R)-3-[3-(3-pyridyl)-1-piperidyl]-1-[rac-(6S)-6-tert-butyl-5,6,7,8-tetrahydrothieno[2,3-b]quinoline-2-carbonyl]amino]propyl]phenyl]azanide | 660.4 | 1277 |
| 19 | 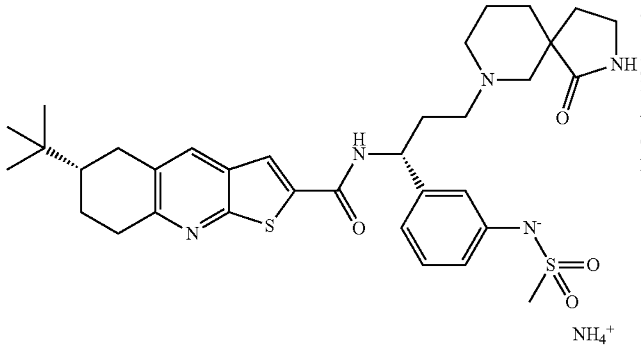 [SMILES: CC(C)(C)[C@H]1CCc2nc3sc(C(=O)N[C@H](CCN4CCCC5(CCNC5=O)C4)c4cccc([N-]S(C)(=O)=O)c4)cc3cc2C1 ; [NH4+]] | ammonium; methylsulfonyl-[3-[rac-(1R)-3-(1-oxo-2,9-diazaspiro[4.5]decan-9-yl)-1-[[rac-(6S)-6-tert-butyl-5,6,7,8-tetrahydrothieno[2,3-b]quinoline-2-carbonyl]amino]propyl]phenyl]azanide | 652.4 | 1577 |
| 20 | 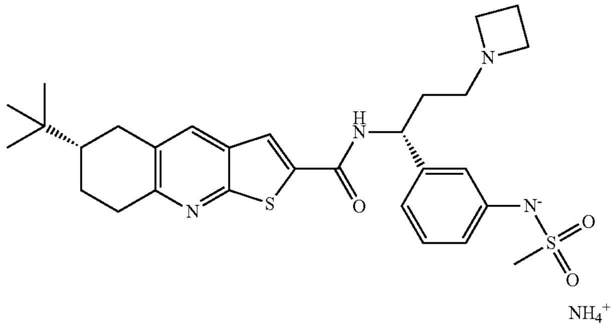 [SMILES: CC(C)(C)[C@H]1CCc2nc3sc(C(=O)N[C@H](CCN4CCC4)c4cccc([N-]S(C)(=O)=O)c4)cc3cc2C1 ; [NH4+]] | ammonium; methylsulfonyl-[3-[rac-(1R)-3-(azetidin-1-yl)-1-[[rac-(6S)-6-tert-butyl-5,6,7,8-tetrahydrothieno[2,3-b]quinoline-2-carbonyl]amino]propyl]phenyl]azanide | 555.3 | 1652 |
| 21 | 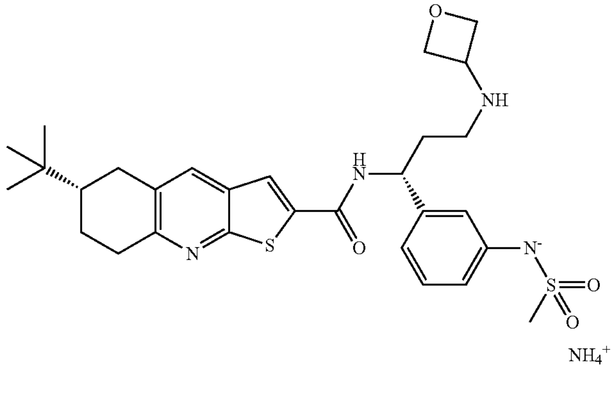 [SMILES: CC(C)(C)[C@H]1CCc2nc3sc(C(=O)N[C@H](CCNC4COC4)c4cccc([N-]S(C)(=O)=O)c4)cc3cc2C1 ; [NH4+]] | ammonium; methylsulfonyl-[3-[rac-(1R)-3-(oxetan-3-ylamino)-1-[[rac-(6S)-6-tert-butyl-5,6,7,8-tetrahydrothieno[2,3-b]quinoline-2-carbonyl]amino]propyl]phenyl]azanide | 571.3 | 1766 |

-continued

| Ex. No. | Structure | Chemical Name | Mass [M + H]+ | hNPRA EC50 (nM) |
|---|---|---|---|---|
| 22 | 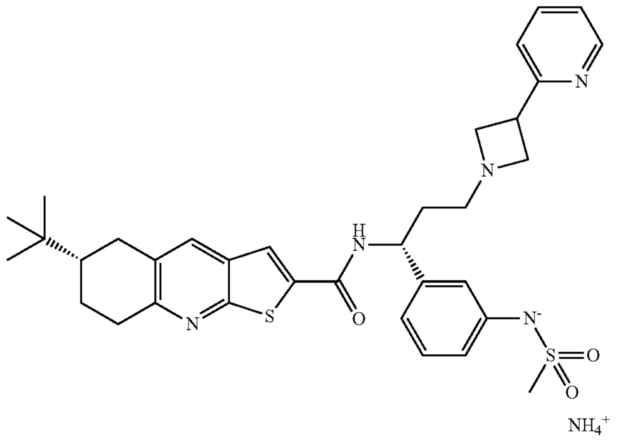 [SMILES: CC(C)(C)[C@H]1CCc2nc3sc(C(=O)N[C@H](CCN4CC(c5ccccn5)C4)c4cccc([N-]S(C)(=O)=O)c4)cc3cc2C1 ; [NH4+]] | ammonium; methylsulfonyl-[3-[rac-(1R)-3-[3-(2-pyridyl)azetidin-1-y1]-1-[[rac-(6S)-6-tert-butyl-5,6,7,8-tetrahydrothieno[2,3-b]quinoline-2-carbonyl]amino]propyl]phenyl]azanide | 632.3 | 1790 |
| 23 | 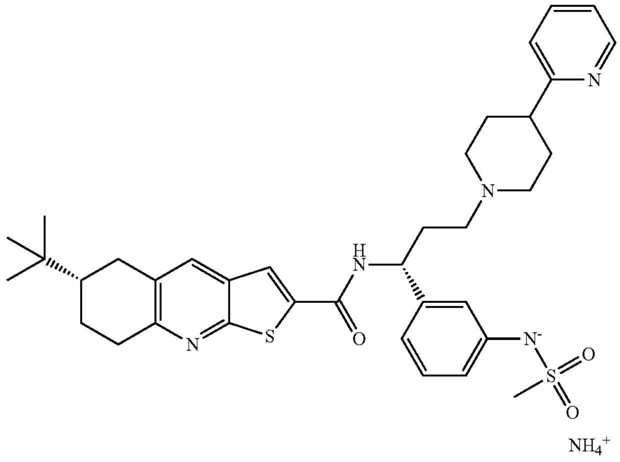 [SMILES: CC(C)(C)[C@H]1CCc2nc3sc(C(=O)N[C@H](CCN4CCC(c5ccccn5)CC4)c4cccc([N-]S(C)(=O)=O)c4)cc3cc2C1 ; [NH4+]] | ammonium;methylsulfonyl-[3-[rac-(1R)-3-[4-(2-pyridyl)-1-piperidyl]-1-[[rac-(6S)-6-tert-butyl-5,6,7,8-tetrahydrothieno[2,3-b]quinoline-2carbonyl]amino]propyl]phenyl]azanide | 660.4 | 1794 |
| 24 | 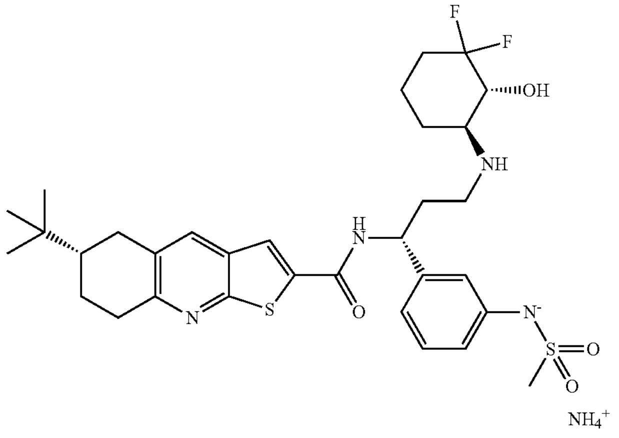 [SMILES: CC(C)(C)[C@H]1CCc2nc3sc(C(=O)N[C@H](CCN[C@H]4CCCC(F)(F)[C@@H]4O)c4cccc([N-]S(C)(=O)=O)c4)cc3cc2C1 ; [NH4+]] | ammonium; methylsulfony1-[3-[rac-(1R)-1-[[rac-(6S)-6-tert-buty1-5,6,7,8-tetrahydrothieno[2,3-b]quinoline-2-carbonyl]amino]-3-[[rac-(1S,2R)-3,3-difluoro-2-hydroxy-cyclohexyl]amino]propyl]phenyl]azanide | 649.4 | 1975 |

Examples 25-71

Examples 25-71 were synthesized by a similar procedure as below:

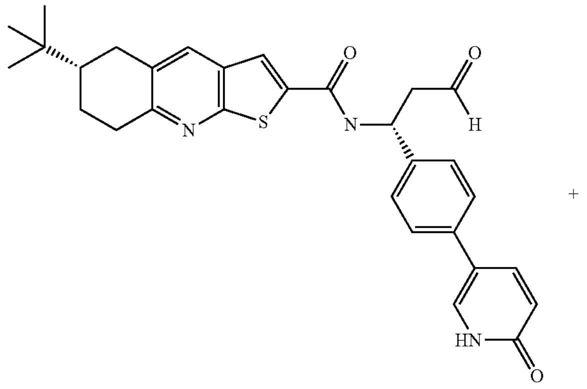

I-31

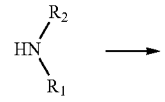

-continued

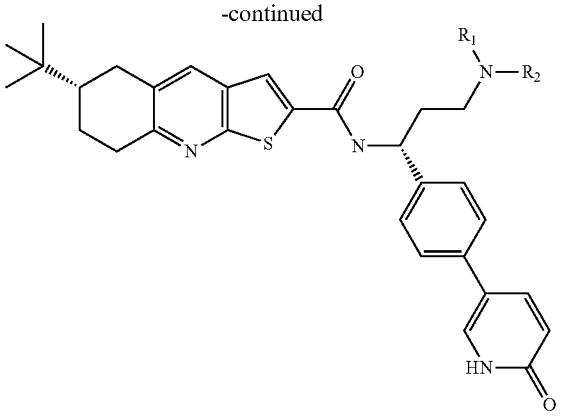

To a solution of(S)-6-(tert-butyl)-N-((R)-3-oxo-1-(4-(6-oxo-1,6-dihydropyridin-3-yl)phenyl)propyl)-5,6,7,8-tetra-hydrothieno[2,3-b]quinoline-2-carboxamide (I-31, 25 mg, 0.049 mmol) and amino substrate (0.098 mmol) in anhydrous 5% HOAc/MeOH (1.5 ml) was added polystyrene supported $BH_3CN$ at ambient temperature. The resulting reaction mixture was shaken at ambient temperature for 6 hrs.

The solution was filtered, and the solvent was evaporated in vacuum. The crude product was purified by reverse-phase HPLC (MeCN/water with 0.1% formic acid modifier) to afford the desired product as a formic acid salt.

| Ex. No. | Structure | Chemical Name | Mass [M + H]+ | hNPRA EC50 (nM) |
|---|---|---|---|---|
| 25 | 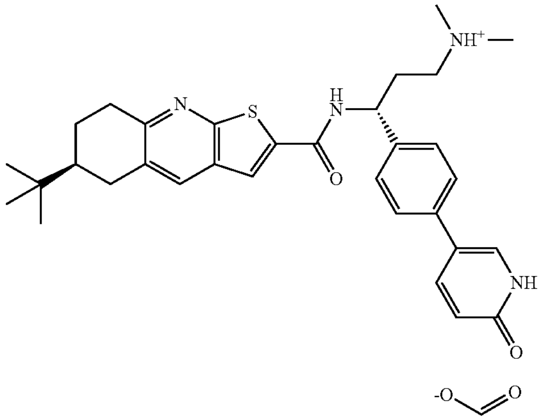 | dimethyl-[rac-(3R)-3-[4-(6-oxo-1H-pyridin-3-yl)phenyl]-3-[{rac-(6S)-6-tert-butyl-5,6,7,8-tetrahydrothieno[2,3-b]quinoline-2-carbonyl]amino]propyl] ammonium;formate | 543.4 | 218.2 |

-continued

| Ex. No. | Structure | Chemical Name | Mass [M + H]+ | hNPRA EC50 (nM) |
| --- | --- | --- | --- | --- |
| 26 | 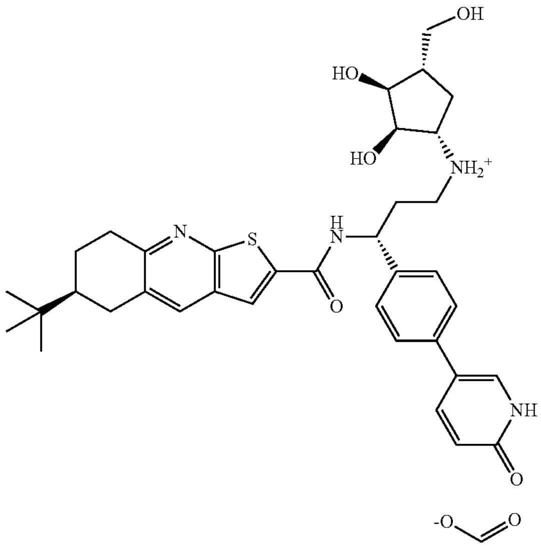 | [rac-(1S,2R,3S,4S)-2,3-dihydroxy-4-(hydroxymethyl)cyclopentyl]-[rac-(3R)-3-[4-(6-oxo-1H-pyridin-3-yl)phenyl]-3-[rac-(6S)-6-tert-butyl-5,6,7,8-tetrahydrothieno[2,3-b]quinoline-2-carbonyl]amino]propyl] ammonium;formate | 645.6 | 386.2 |
| 27 | 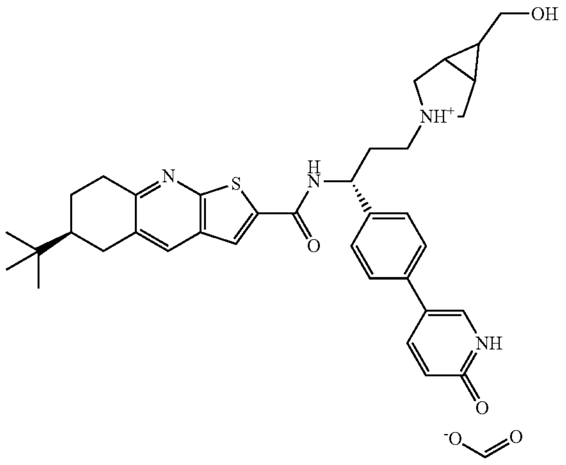 | rac-(6S)-6-tert-butyl-N-[rac-(1R)-3-[6-(hydroxymethyl)-3-azoniabicyclo[3.1.0]hexan-3-yl]-1-[4-(6-oxo-1H-pyridin-3-yl)phenyl]propyl]-5,6,7,8-tetrahydrothieno[2,3-b]quinoline-2-carboxamide;formate | 611.5 | 408.3 |
| 28 | 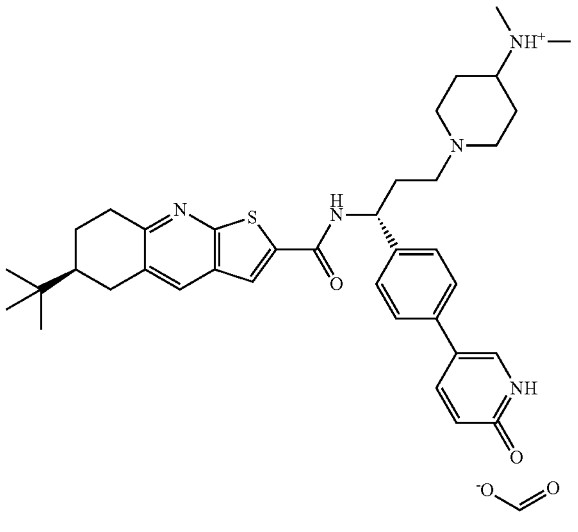 | dimethyl-[1-[rac-(3R)-3-[4-(6-oxo-1H-pyridin-3-yl)phenyl]-3-[[rac-(6S)-6-tert-butyl-5,6,7,8-tetrahydrothieno[2,3-b]quinoline-2-carbonyl]amino]propyl]-4-piperidyl]ammonium;formate | 626.6 | 446.4 |

-continued

| Ex. No. | Structure | Chemical Name | Mass [M + H]+ | hNPRA EC50 (nM) |
|---|---|---|---|---|
| 29 | 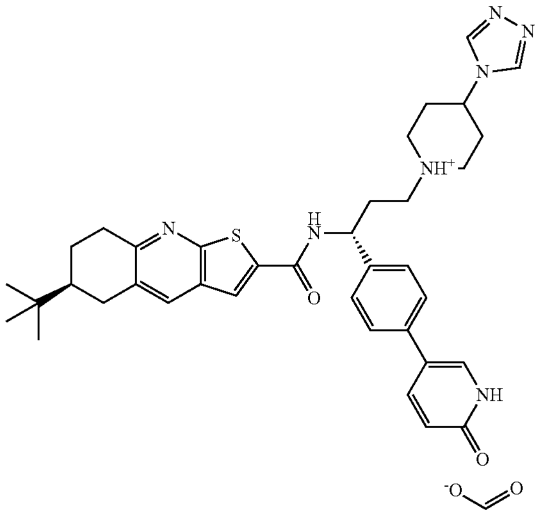 | rac-(6S)-6-tert-butyl-N-[rac-(1R)-1-[4-(6-oxo-1H-pyridin-3-yl)phenyl]-3-[4-(1,2,4-triazol-4-yl)piperidin-1-ium-1-yl]propyl]-5,6,7,8-tetrahydrothieno[2,3-b]quinoline-2-carboxamide;formate | 650.5 | 448.1 |
| 30 | 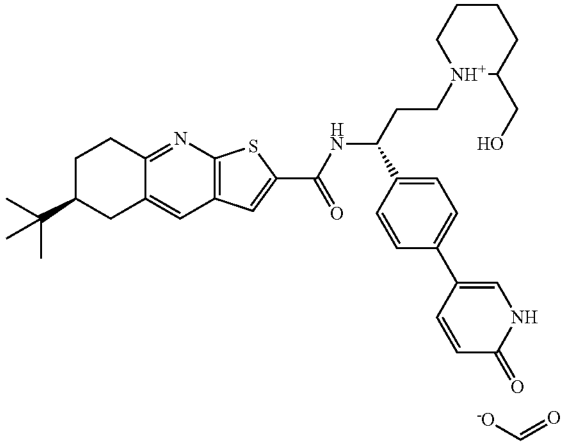 | rac-(6S)-6-tert-butyl-N-[rac-(1R)-3-[2-(hydroxymethyl)piperidin-1-ium-1-yl]-1-[4-(6-oxo-1H-pyridin-3-yl)phenyl]propyl]-5,6,7,8-tetrahydrothieno[2,3-b]quinoline-2-carboxamide;formate | 613.5 | 454.8 |
| 31 | 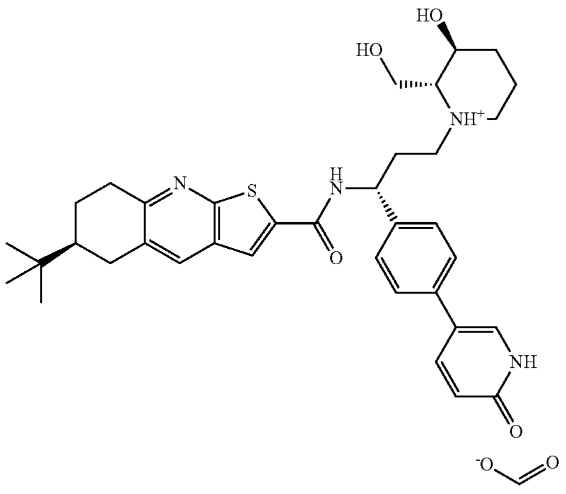 | rac-(6S)-6-tert-butyl-N-[rac-(1R)-1-[4-(6-oxo-1H-pyridin-3-yl)phenyl]-3-[rac-(2R,3S)-3-hydroxy-2-(hydroxymethyl)piperidin-1-ium-1-yl]propyl]-5,6,7,8-tetrahydrothieno[2,3-b]quinoline-2-carboxamide; formate | 629.5 | 472.5 |

-continued

| Ex. No. | Structure | Chemical Name | Mass [M + H]+ | hNPRA EC50 (nM) |
|---|---|---|---|---|
| 32 | 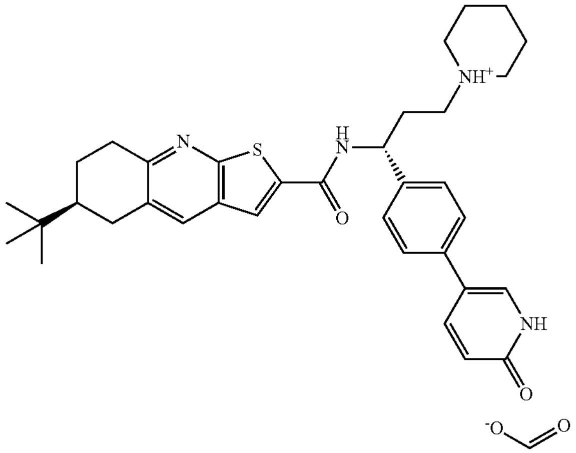 | rac-(6S)-6-tert-butyl-N-[rac-(1R)-1-[4-(6-oxo-1H-pyridin-3-yl)phenyl]-3-piperidin-1-ium-1-yl-propyl]-5,6,7,8-tetrahydrothieno[2,3-b]quinoline-2-carboxamide;formate | 583.5 | 477.6 |
| 33 | 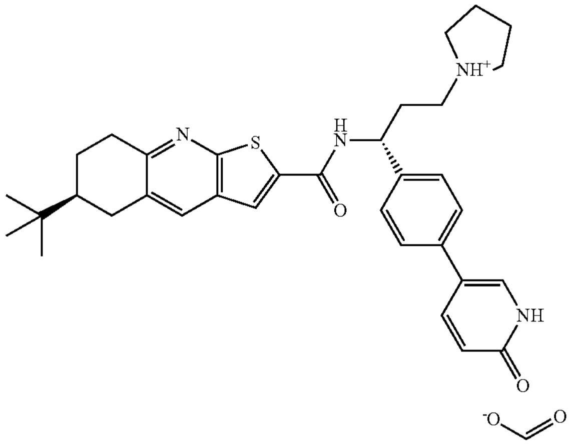 | rac-(6S)-6-tert-butyl-N-[rac-(1R)-1-[4-(6-oxo-1H-pyridin-3-yl)phenyl]-3-pyrrolidin-1-ium-1-yl-propyl]-5,6,7,8-tetrahydrothieno[2,3-b]quinoline-2-carboxamide;formate | 569.5 | 510.6 |
| 34 | 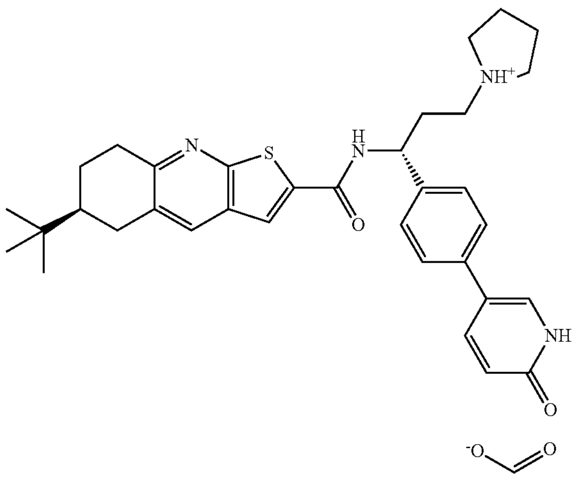 | rac-(6S)-6-tert-butyl-N-[rac-(1R)-3-[bis(2-hydroxyethyl)amino]-1-[4-(6-oxo-1H-pyridin-3-yl)phenyl]propyl]-5,6,7,8-tetrahydrothieno[2,3-b]quinoline-2-carboxamide | 603.43 | 530.4 |

-continued

| Ex. No. | Structure | Chemical Name | Mass [M + H]+ | hNPRA EC50 (nM) |
|---|---|---|---|---|
| 35 | 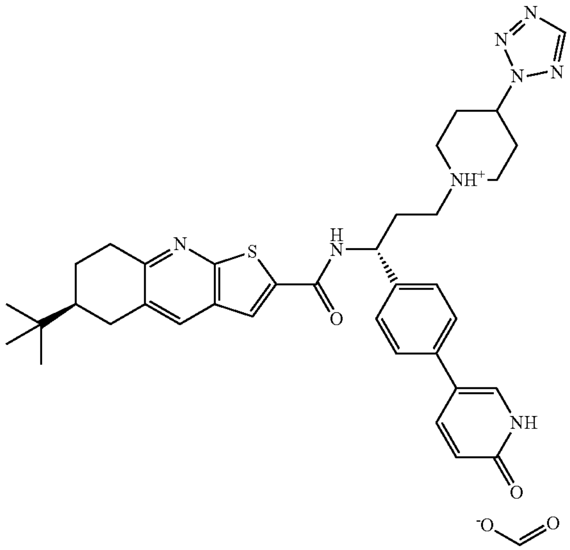 | rac-(6S)-6-tert-butyl-N-[rac-(1R)-1-[4-(6-oxo-1H-pyridin-3-yl)phenyl]-3-[4-(tetrazol-2-yl)piperidin-1-ium-1-yl]propyl]-5,6,7,8-tetrahydrothieno[2,3-b]quinoline-2-carboxamide;formate | 651.6 | 535.4 |
| 36 | 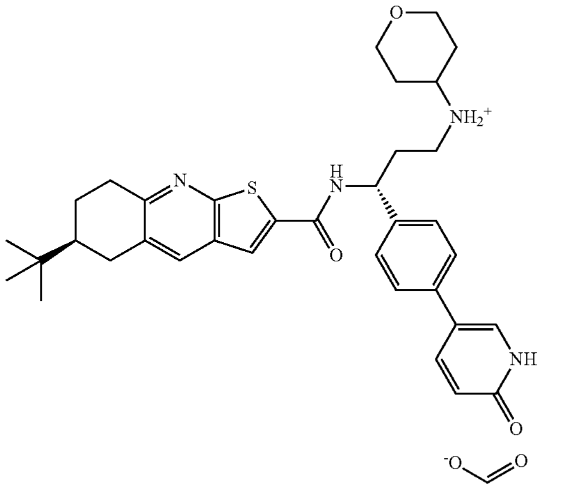 | [rac-(3R)-3-[4-(6-oxo-1H-pyridin-3-yl)phenyl]-3-[rac-(6S)-6-tert-butyl-5,6,7,8-tetrahydrothieno[2,3-b]quinoline-2-carbonyl]amino]propyl]-tetrahydropyran-4-yl-ammonium;formate | 599.4 | 557 |
| 37 | 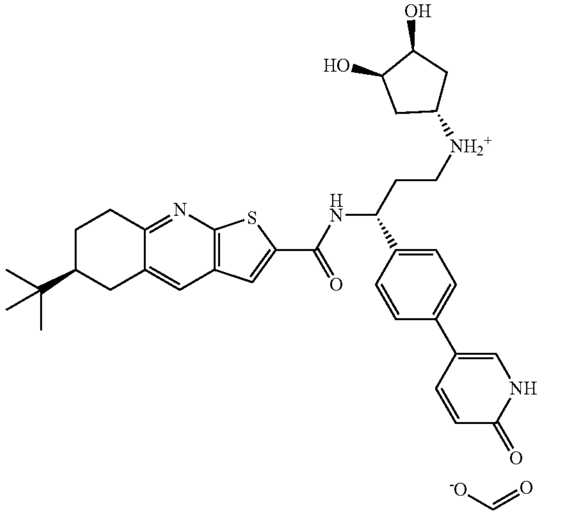 | [rac-(3R,4S)-3,4-dihydroxycyclopentyl]-[rac-(3R)-3-[4-(6-oxo-1H-pyridin-3-yl)phenyl]-3-[[rac-(6S)-6-tert-butyl-5,6,7,8-tetrahydrothieno[2,3-b]quinoline-2-carbonyl]amino]propyl]ammonium;formate | 615.5 | 575.1 |

-continued
| Ex. No. | Structure | Chemical Name | Mass [M + H]+ | hNPRA EC50 (nM) |
|---|---|---|---|---|
| 38 | 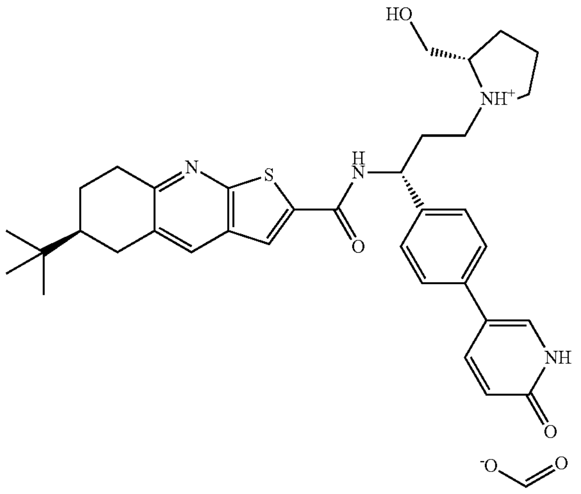 | rac-(6S)-6-tert-butyl-N-[rac-(1R)-1-[4-(6-oxo-1H-pyridin-3-yl)phenyl]-3-[rac-(2S)-2-(hydroxymethyl)pyrrolidin-1-ium-1-yl]propyl]-5,6,7,8-tetrahydrothieno[2,3-b]quinoline-2-carboxamide;formate | 599.4 | 581.7 |
| 39 | 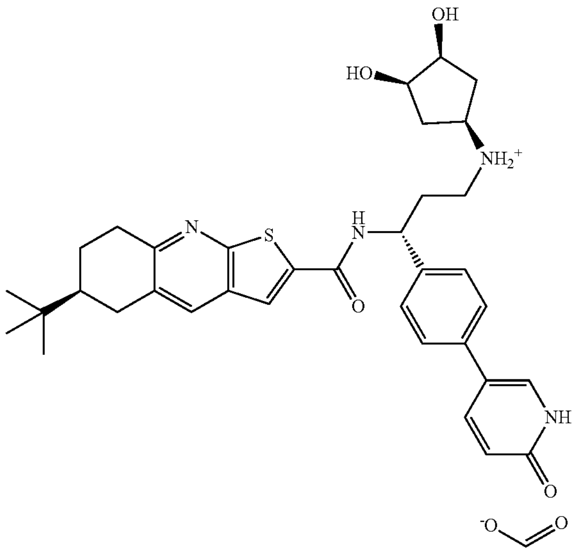 | [rac-(3R,4S)-3,4-dihydroxycyclopentyl]-[rac-(3R)-3-[4-(6-oxo-1H-pyridin-3-yl)phenyl]-3-[[rac-(6S)-6-tert-butyl-5,6,7,8-tetrahydrothieno[2,3-b]quinoline-2-carbonyl]amino]propyl]ammonium;formate | 615.5 | 654.5 |

-continued

| Ex. No. | Structure | Chemical Name | Mass [M + H]+ | hNPRA EC50 (nM) |
|---|---|---|---|---|
| 40 | 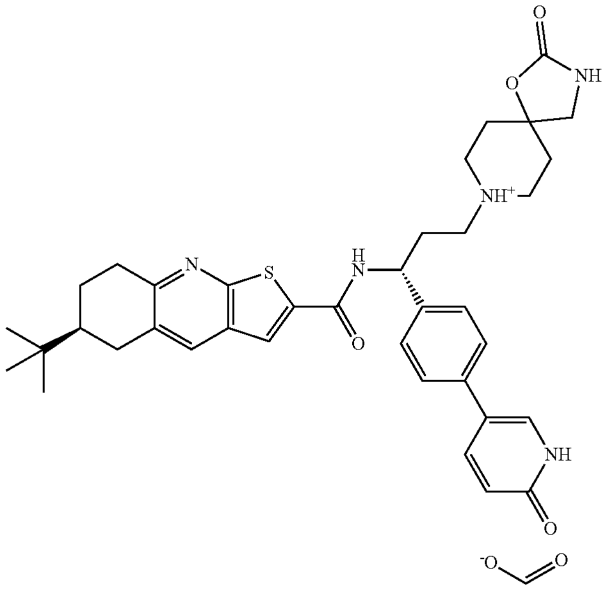 | rac-(6S)-6-tert-butyl-N-[rac-(1R)-3-(2-oxo-1-oxa-3-aza-8-azoniaspiro[4.5]decan-8-yl)-1-[4-(6-oxo-1H-pyridin-3-yl)phenyl]propyl]-5,6,7,8-tetrahydrothieno[2,3-b]quinoline-2-carboxamide;formate | 654.5 | 654.9 |
| 41 | 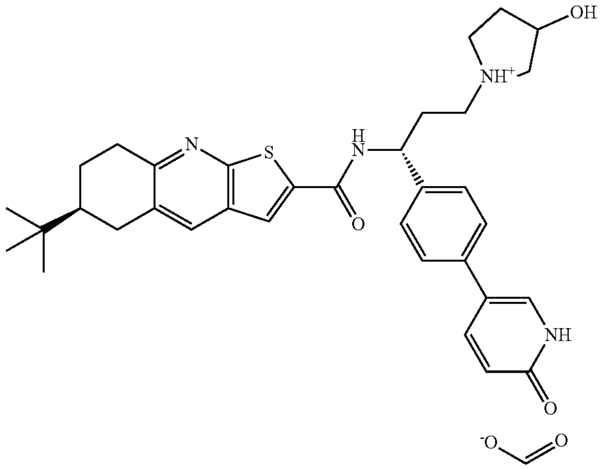 | rac-(6S)-6-tert-butyl-N-[rac-(1R)-3-(3-hydroxypyrrolidin-1-ium-1-yl)-1-[4-(6-oxo-1H-pyridin-3-yl)phenyl]propyl]-5,6,7,8-tetrahydrothieno[2,3-b]quinoline-2-carboxamide;formate | 585.5 | 656.1 |
| 42 | 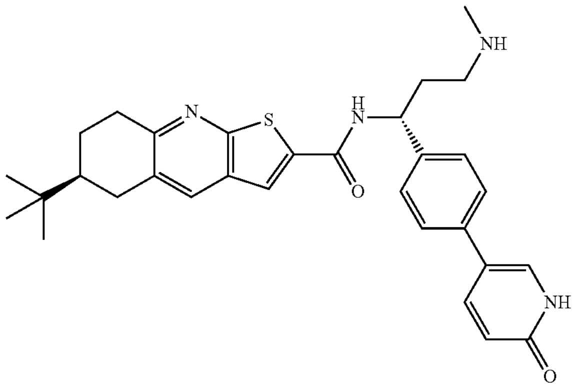 [SMILES: CNCC[C@@H](NC(=O)c1cc2cc3c(nc2s1)CC[C@H](C(C)(C)C)C3)c1ccc(-c2ccc(=O)[nH]c2)cc1] | rac-(6S)-6-tert-butyl-N-[rac-(1R)-3-(methylamino)-1-[4-(6-oxo-1H-pyridin-3-yl)phenyl]propyl]-5,6,7,8-tetrahydrothieno[2,3-b]quinoline-2-carboxamide | 529.4 | 658.4 |

-continued

| Ex. No. | Structure | Chemical Name | Mass [M + H]+ | hNPRA EC50 (nM) |
|---|---|---|---|---|
| 43 | 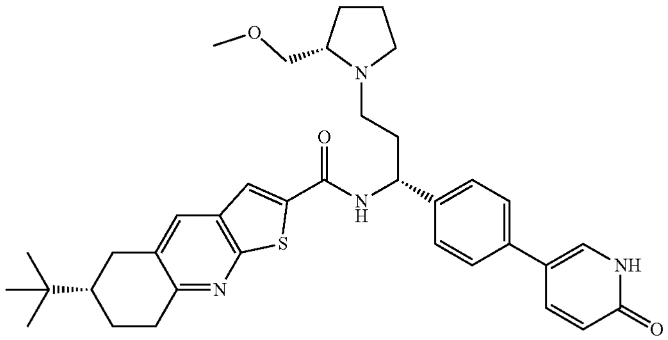 [SMILES: COC[C@@H]1CCCN1CC[C@@H](NC(=O)c1cc2cc3c(nc2s1)CC[C@H](C(C)(C)C)C3)c1ccc(-c2ccc(=O)[nH]c2)cc1] | rac-(6S)-6-tert-butyl-N-[rac-(1R)-1-[4-(6-oxo-1H-pyridin-3-yl)phenyl]-3-[rac-(2S)-2-(methoxymethyl)pyrrolidin-1-yl]propyl]-5,6,7,8-tetrahydrothieno[2,3-b]quinoline-2-carboxamide | 613.46 | 663.4 |
| 44 | 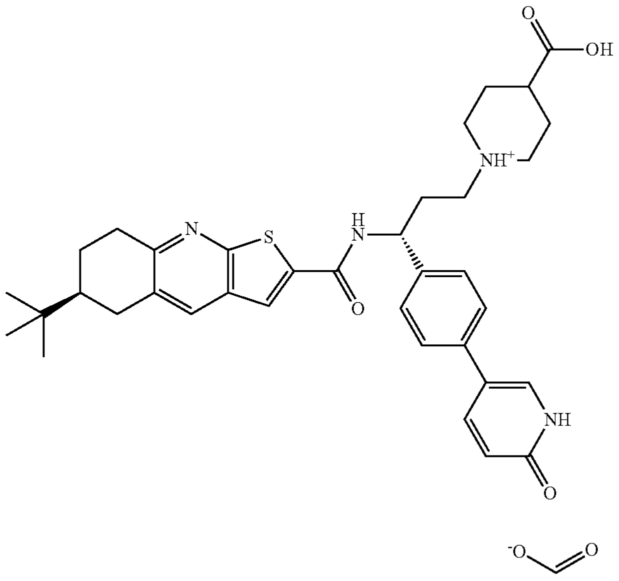 | 1-[rac-(3R)-3-[4-(6-oxo-1H-pyridin-3-yl)phenyl]-3-[rac-(6S)-6-tert-butyl-5,6,7,8-tetrahydrothieno[2,3-b]quinoline-2-carbonyl]amino]propyl]piperidin-1-ium-4-carboxylic acid;formate | 627.5 | 664.7 |
| 45 | 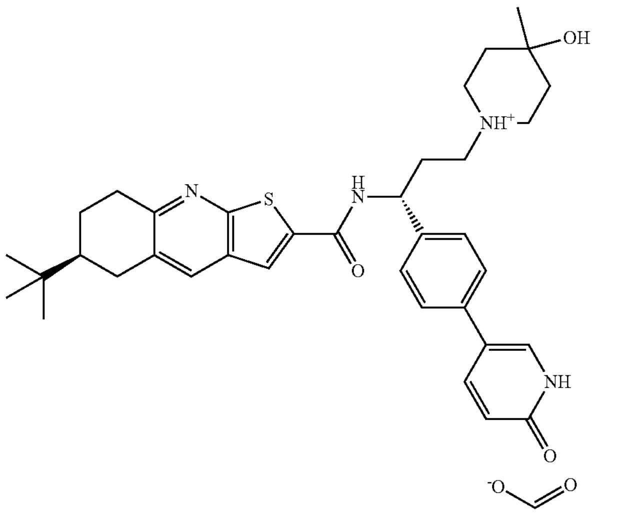 | rac-(6S)-6-tert-butyl-N-[rac-(1R)-3-(4-hydroxy-4-methyl-piperidin-1-ium-1-yl)-1-[4-(6-oxo-1H-pyridin-3-yl)phenyl]propyl]-5,6,7,8-tetrahydrothieno[2,3-b]quinoline-2-carboxamide;formate | 613.3 | 672.6 |

-continued

| Ex. No. | Structure | Chemical Name | Mass [M + H]+ | hNPRA EC50 (nM) |
|---|---|---|---|---|
| 46 | 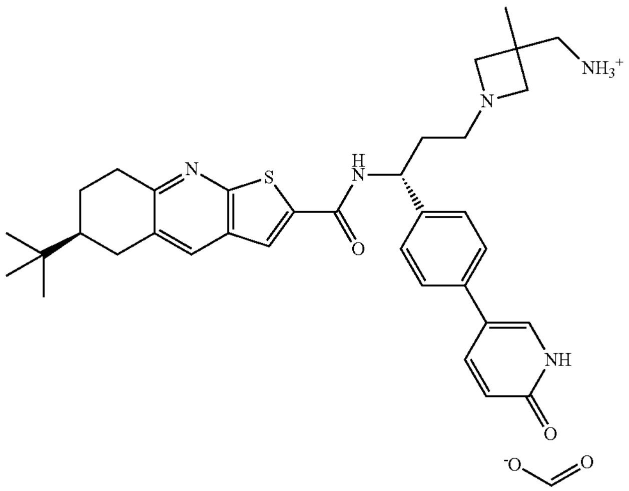 | [3-methyl-1-[rac-(3R)-3-[4-(6-oxo-1H-pyridin-3-yl)phenyl]-3-[[rac-(6S)-6-tert-butyl-5,6,7,8-tetrahydrothieno[2,3-b]quinoline-2-carbonyl]amino]propyl]azetidin-3-yl]methylammonium;formate | 598.5 | 673 |
| 47 | 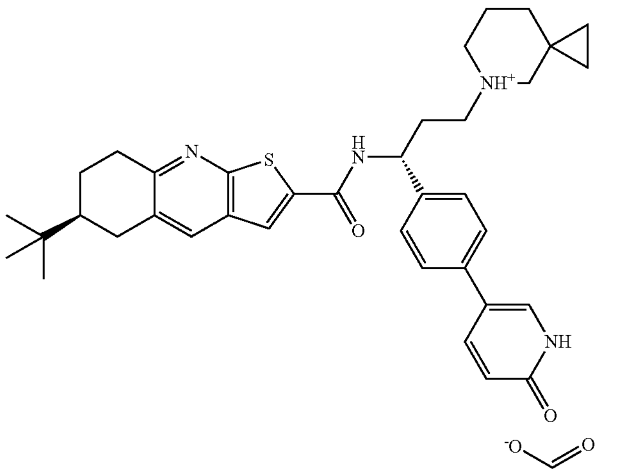 | rac-(6S)-6-tert-butyl-N-[rac-(1R)-3-(5-azoniaspiro[2.5]octan-5-yl)-1-[4-(6-oxo-1H-pyridin-3-yl)phenyl]propyl]-5,6,7,8-tetrahydrothieno[2,3-b]quinoline-2-carboxamide;formate | 609.4 | 674.4 |
| 48 | 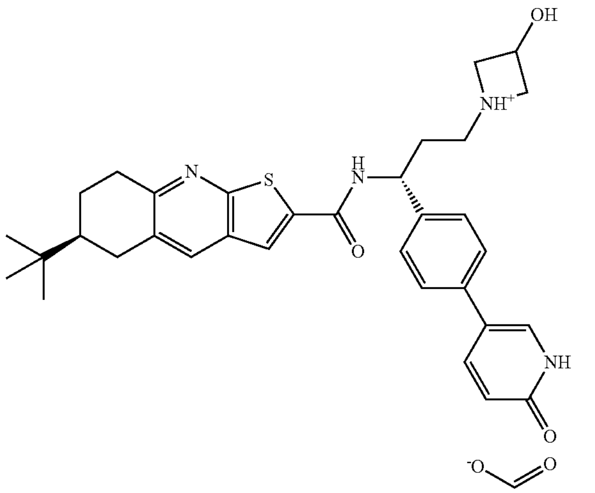 | rac-(6S)-6-tert-butyl-N-[rac-(1R)-3-(3-hydroxyazetidin-1-ium-1-yl)-1-[4-(6-oxo-1H-pyridin-3-yl)phenyl]propyl]-5,6,7,8-tetrahydrothieno[2,3-b]quinoline-2-carboxamide;formate | 571.4 | 679 |

-continued

| Ex. No. | Structure | Chemical Name | Mass [M + H]+ | hNPRA EC50 (nM) |
|---|---|---|---|---|
| 49 | 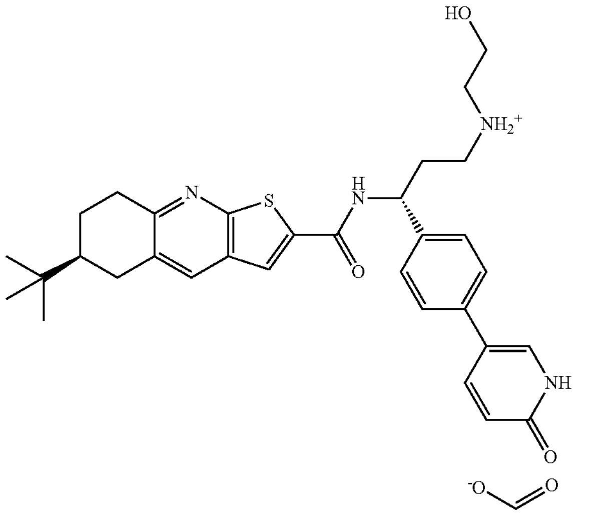 | 2-hydroxyethyl-[rac-(3R)-3-[4-(6-oxo-1H-pyridin-3-yl)phenyl]-3-[[rac-(6S)-6-tert-butyl-5,6,7,8-tetrahydrothieno[2,3-b]quinoline-2-carbonyl]amino}propyl] ammonium;formate | 559.4 | 682.3 |
| 50 | 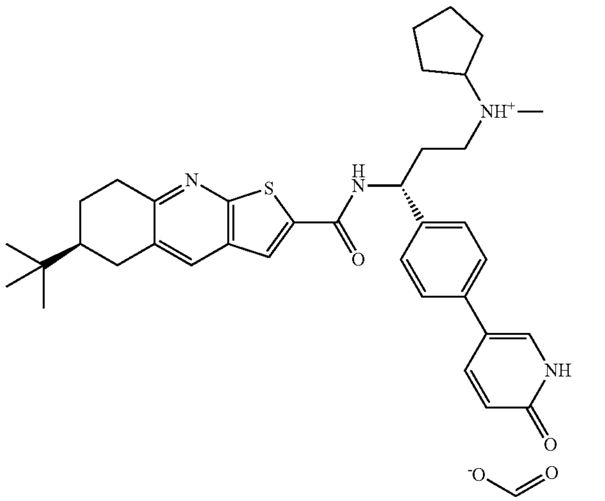 | cyclopentyl-methyl-[rac-(3R)-3-[4-(6-oxo-1H-pyridin-3-yl)phenyl]-3-[rac-(6S)-6-tert-butyl-5,6,7,8-tetrahydrothieno[2,3-b]quinoline-2-carbonyl]amino]propyl] ammonium;formate | 597.5 | 696 |
| 51 | 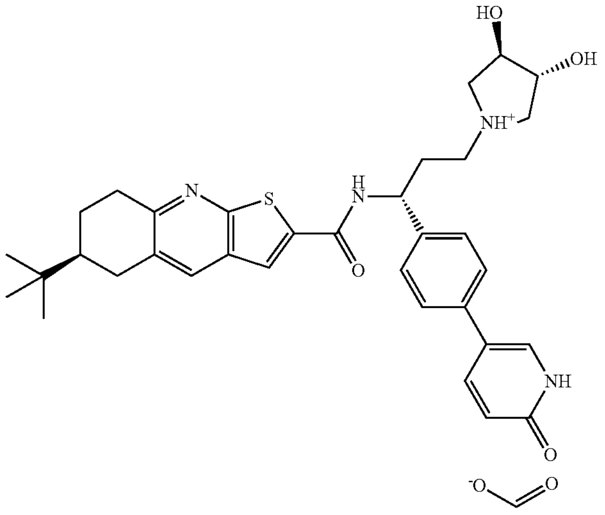 | rac-(6S)-6-tert-butyl-N-[rac-(1R)-1-[4-(6-oxo-1H-pyridin-3-yl)phenyl]-3-[rac-(3R,4R)-3,4-dihydroxypyrrolidin-1-ium-1-yl]propyl]-5,6,7,8-tetrahydrothieno[2,3-b]quinoline-2-carboxamide;formate | 601.5 | 705 |

-continued

| Ex. No. | Structure | Chemical Name | Mass [M + H]+ | hNPRA EC50 (nM) |
|---|---|---|---|---|
| 52 | 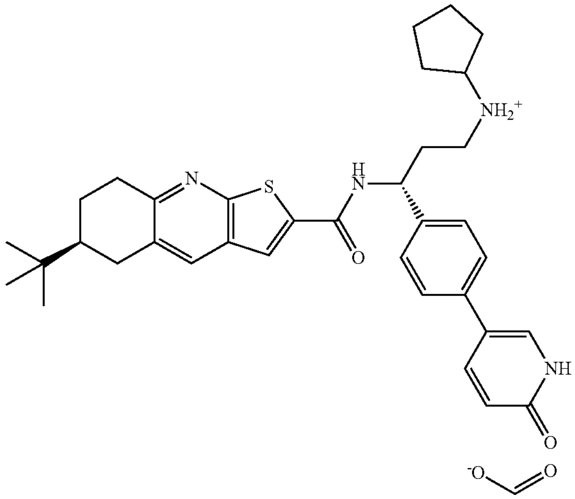 | cyclopentyl-[rac-(3R)-3-[4-(6-oxo-1H-pyridin-3-yl)phenyl]-3-[[rac-(6S)-6-tert-butyl-5,6,7,8-tetrahydrothieno[2,3-b]quinoline-2-carbonyl]amino]propyl] ammonium;formate | 583.5 | 728.8 |
| 53 | 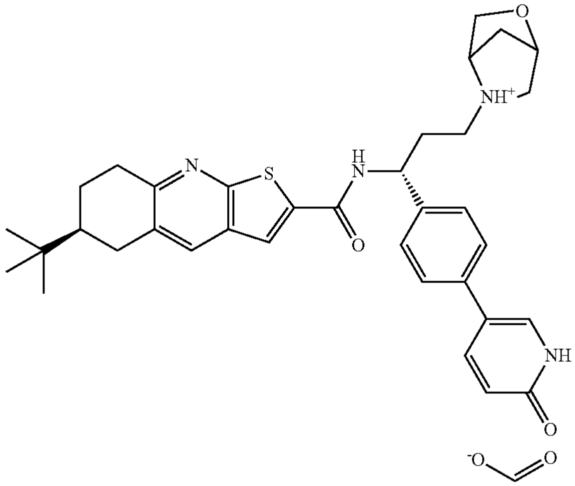 | rac-(6S)-6-tert-butyl-N-[rac-(1R)-3-(2-oxa-5-azoniabicyclo[2.2. 1 ]heptan-5-yl)-1-[4-(6-oxo-1H-pyridin-3-yl)phenyl]propyl]-5,6,7,8-tetrahydrothieno[2,3-b]quinoline-2-carboxamide;formate | 597.5 | 754.5 |
| 54 | 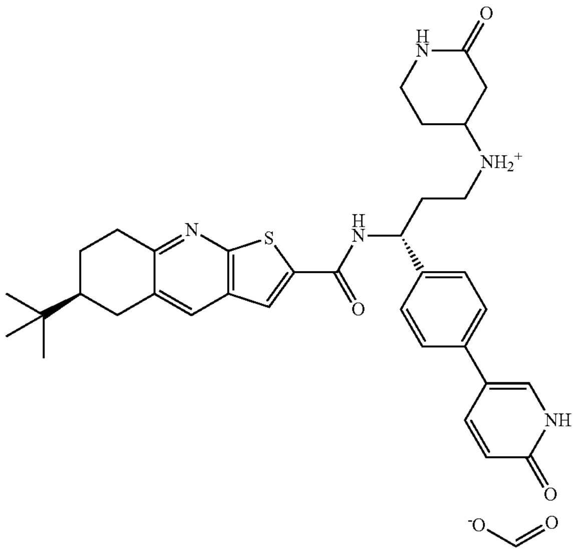 | (2-oxo-4-piperidyl)-[rac-(3R)-3-[4-(6-oxo-1H-pyridin-3-yl)phenyl]-3-[rac-(6S)-6-tert-butyl-5,6,7,8-tetrahydrothieno[2,3-b]quinoline-2-carbonyl]amino]propyl] ammonium;formate | 612.5 | 758.5 |

-continued
| Ex. No. | Structure | Chemical Name | Mass [M + H]+ | hNPRA EC50 (nM) |
|---|---|---|---|---|
| 55 | 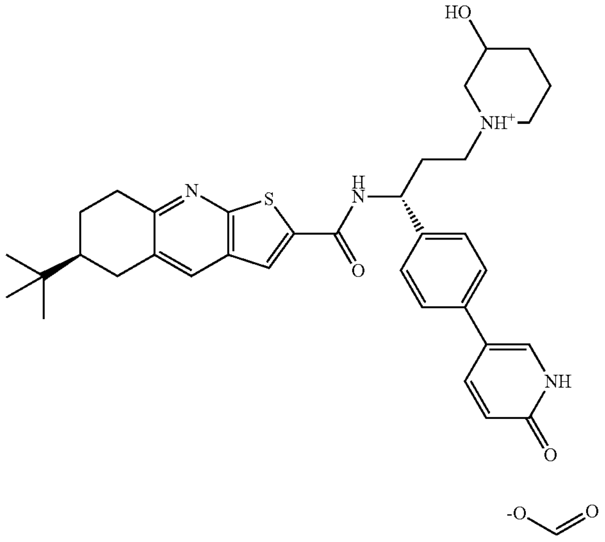 | rac-(6S)-6-tert-butyl-N-[rac-(1R)-3-(3-hydroxypiperidin-1-ium-1-yl)-1-[4-(6-oxo-1H-pyridin-3-yl)phenyl]propyl]-5,6,7,8-tetrahydrothieno[2,3-b]quinoline-2-carboxamide;formate | 599.5 | 791.6 |
| 56 | 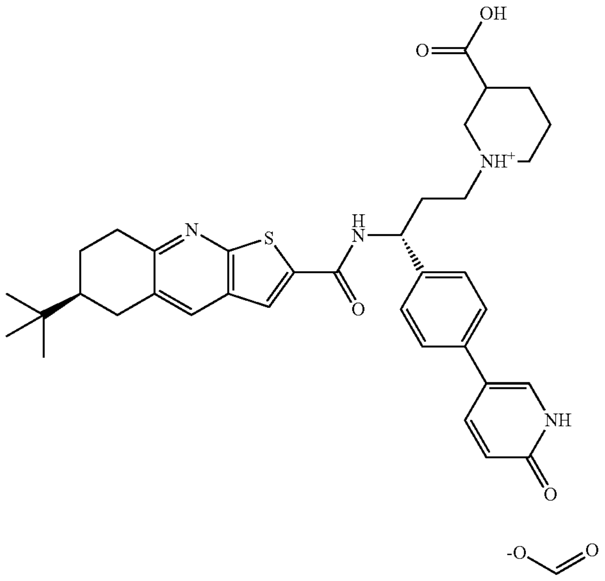 | 1-[rac-(3R)-3-[4-(6-oxo-1H-pyridin-3-yl)phenyl]-3-[[rac-(6S)-6-tert-butyl-5,6,7,8-tetrahydrothieno[2,3-b]quinoline-2-carbonyl]amino]propyl]piperidin-1-ium-3-carboxylic acid;formate | 627.4 | 810.9 |

-continued
| Ex. No. | Structure | Chemical Name | Mass [M + H]+ | hNPRA EC50 (nM) |
|---|---|---|---|---|
| 57 | 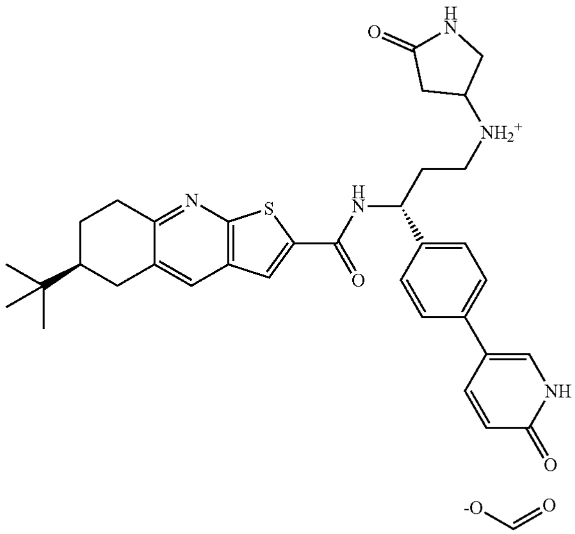 | (5-oxopyrrolidin-3-yl)-[rac-(3R)-3-[4-(6-oxo-1H-pyridin-3-yl)phenyl]-3-[[rac-(6S)-6-tert-butyl-5,6,7,8-tetrahydrothieno[2,3-b]quinoline-2-carbonyl]amino]propyl] ammonium;formate | 598.5 | 888.7 |
| 58 | 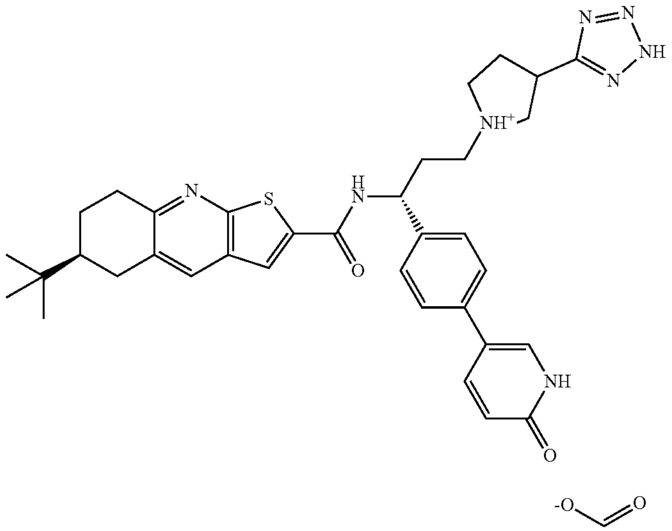 | rac-(6S)-6-tert-butyl-N-[rac-(1R)-1-[4-(6-oxo-1H-pyridin-3-yl)phenyl]-3-[3-(2H-tetrazol-5-yl)pyrrolidin-1-ium-1-yl]propyl]-5,6,7,8-tetrahydrothieno[2,3-b]quinoline-2-carboxamide;formate | 637.5 | 915.3 |

-continued
| Ex. No. | Structure | Chemical Name | Mass [M + H]+ | hNPRA EC50 (nM) |
|---|---|---|---|---|
| 59 | 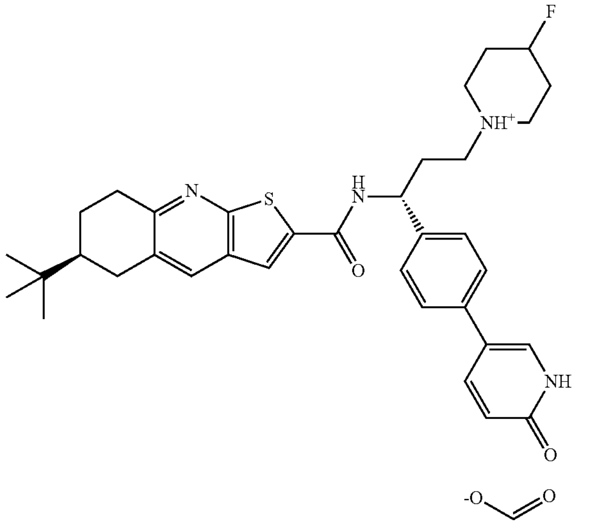 | rac-(6S)-6-tert-butyl-N-[rac-(1R)-3-(4-fluoropiperidin-1-ium-1-yl)-1-[4-(6-oxo-1H-pyridin-3-yl)phenyl]propyl]-5,6,7,8-tetrahydrothieno[2,3-b]quinoline-2-carboxamide;formate | 601.4 | 1008 |
| 60 | 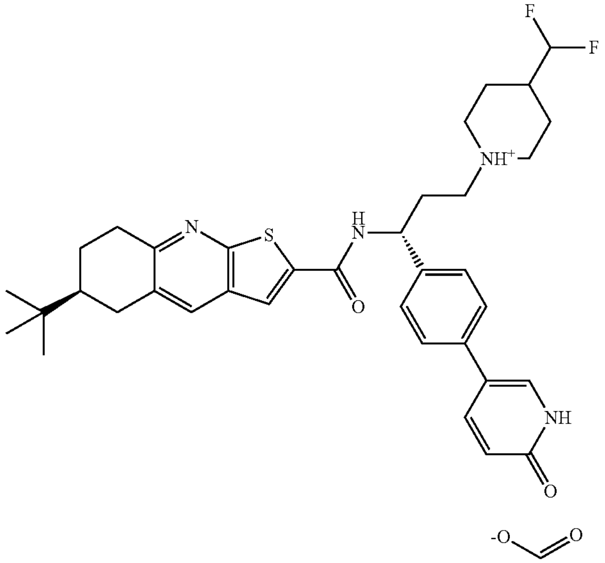 | rac-(6S)-6-tert-butyl-N-[rac-(1R)-3-[4-(difluoromethyl)piperidin-1-ium-1-yl]-1-[4-(6-oxo-1H-pyridin-3-yl)phenyl]propyl]-5,6,7,8-tetrahydrothieno[2,3-b]quinoline-2-carboxamide;formate | 633.4 | 1010 |

-continued

| Ex. No. | Structure | Chemical Name | Mass [M + H]+ | hNPRA EC50 (nM) |
|---|---|---|---|---|
| 61 | 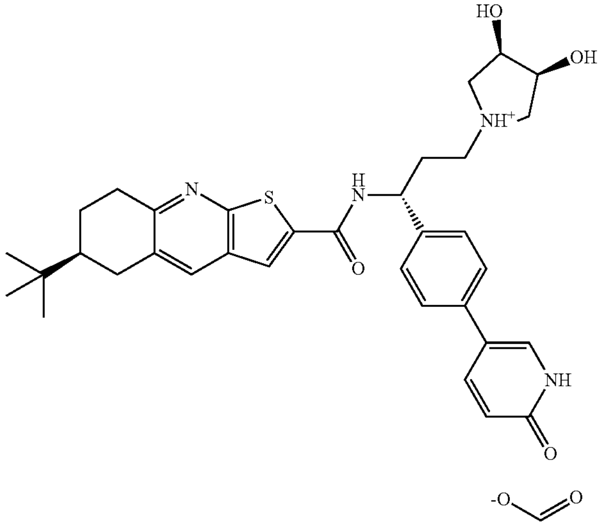 | rac-(6S)-6-tert-butyl-N-[rac-(1R)-1-[4-(6-oxo-1H-pyridin-3-yl)phenyl]-3-[rac-(3S,4R)-3,4-dihydroxypyrrolidin-1-ium-1-yl]propyl]-5,6,7,8-tetrahydrothieno[2,3-b]quinoline-2-carboxamide;formate | 601.5 | 1041 |
| 62 | 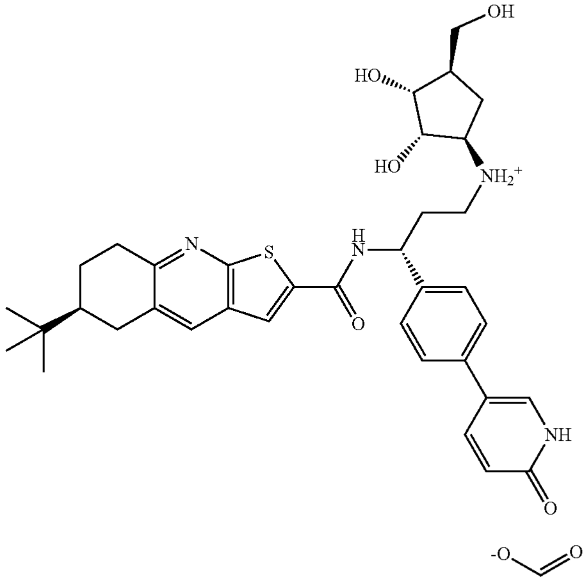 | [rac-(1R,2S,3R,4R)-2,3-dihydroxy-4-(hydroxymethyl)cyclopentyl]-[rac-(3R)-3-[4-(6-oxo-1H-pyridin-3-yl)phenyl]-3-[rac-(6S)-6-tert-butyl-5,6,7,8-tetrahydrothieno[2,3-b]quinoline-2-carbonyl]amino]propyl] ammonium;formate | 645.6 | 1125 |

-continued
| Ex. No. | Structure | Chemical Name | Mass [M + H]+ | hNPRA EC50 (nM) |
|---|---|---|---|---|
| 63 | 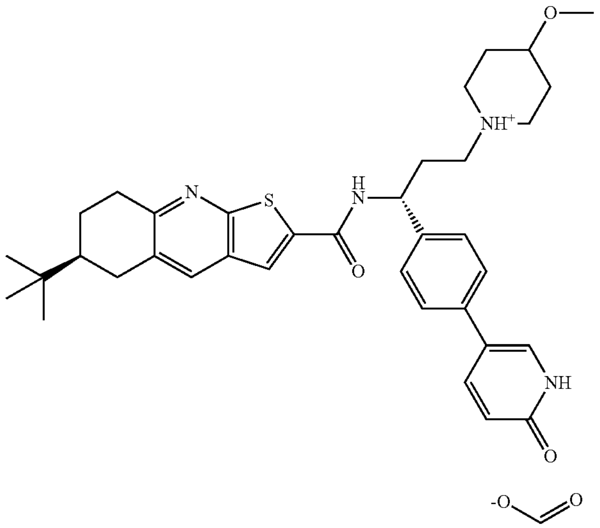 | rac-(6S)-6-tert-butyl-N-[rac-(1R)-3-(4-methoxypiperidin-1-ium-1-yl)-1-[4-(6-oxo-1H-pyridin-3-yl)phenyl]propyl]-5,6,7,8-tetrahydrothieno[2,3-b]quinoline-2-carboxamide;formate | 613.5 | 1192 |
| 64 | 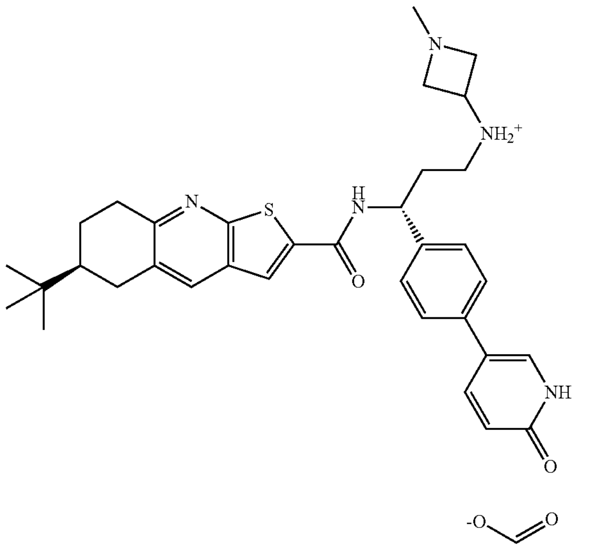 | (1-methylazetidin-3-yl)-[rac-(3R)-3-[4-(6-oxo-1H-pyridin-3-yl)phenyl]-3-[[rac-(6S)-6-tert-butyl-5,6,7,8-tetrahydrothieno[2,3-b]quinoline-2-carbonyl]amino]propyl]ammonium;formate | 584.5 | 1229 |

-continued

| Ex. No. | Structure | Chemical Name | Mass [M + H]+ | hNPRA EC50 (nM) |
|---|---|---|---|---|
| 65 | 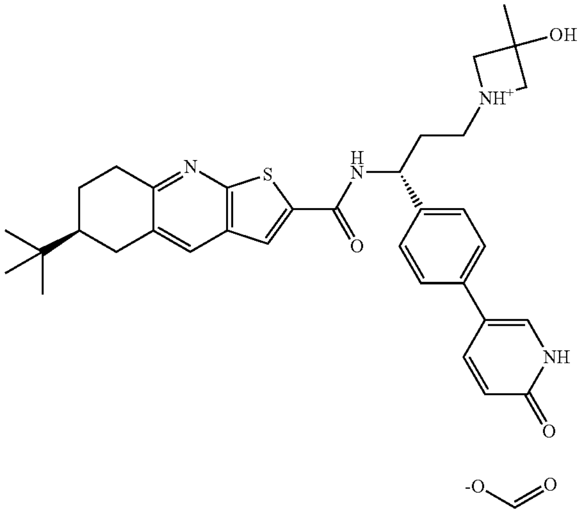 | rac-(6S)-6-tert-butyl-N-[rac-(1R)-3-(3-hydroxy-3-methyl-azetidin-1-ium-1-yl)-1-[4-(6-oxo-1H-pyridin-3-yl)phenyl]propyl]-5,6,7,8-tetrahydrothieno[2,3-b]quinoline-2-carboxamide;formate | 585.4 | 1303 |
| 66 | 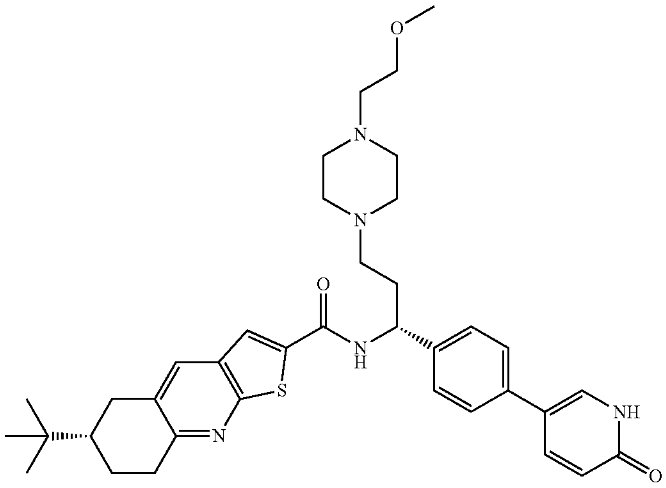 [SMILES: COCCN1CCN(CC[C@@H](NC(=O)c2cc3cc4c(nc3s2)CC[C@H](C(C)(C)C)C4)c2ccc(-c3ccc(=O)[nH]c3)cc2)CC1] | rac-(6S)-6-tert-butyl-N-[rac-(1R)-3-[4-(2-methoxyethyl)piperazin-1-yl]-1-[4-(6-oxo-1H-pyridin-3-yl)phenyl]propyl]-5,6,7,8-tetrahydrothieno[2,3-b]quinoline-2-carboxamide | 642.56 | 1326 |
| 67 | 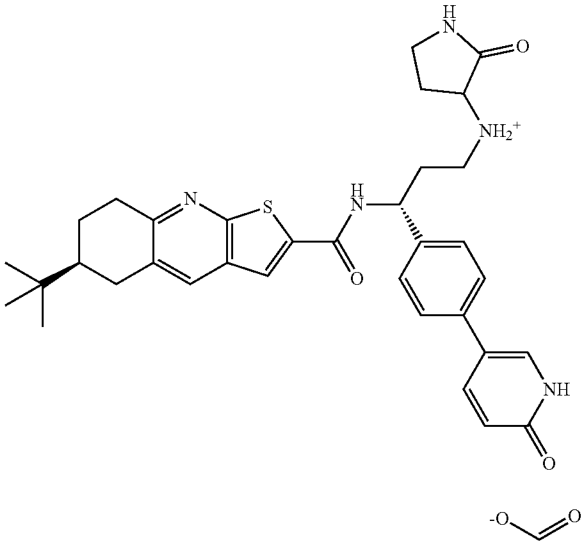 | (2-oxopyrrolidin-3-yl)-[rac-(3R)-3-[4-(6-oxo-1H-pyridin-3-yl)phenyl]-3-[rac-(6S)-6-tert-butyl-5,6,7,8-tetrahydrothieno[2,3-b]quinoline-2-carbonyl]amino]propyl]ammonium;formate | 598.4 | 1797 |

-continued
| Ex. No. | Structure | Chemical Name | Mass [M + H]+ | hNPRA EC50 (nM) |
|---|---|---|---|---|
| 68 | 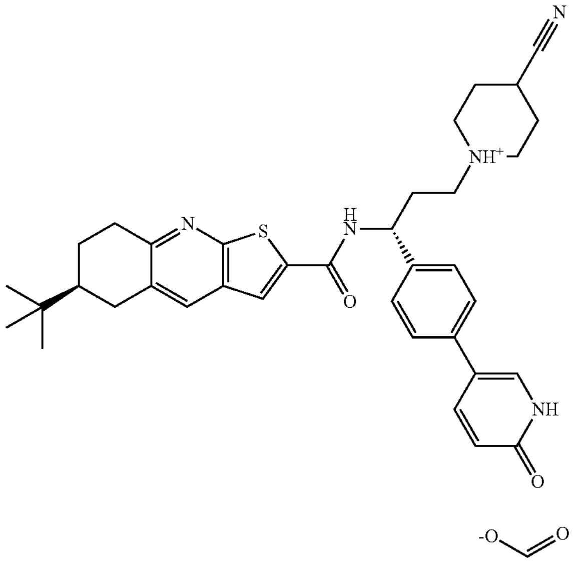 | rac-(6S)-6-tert-butyl-N-[rac-(1R)-3-(4-cyanopiperidin-1-ium-1-yl)-1-[4-(6-oxo-1H-pyridin-3-yl)phenyl]propyl]-5,6,7,8-tetrahydrothieno[2,3-b]quinoline-2-carboxamide;formate | 608.5 | 1815 |
| 69 | 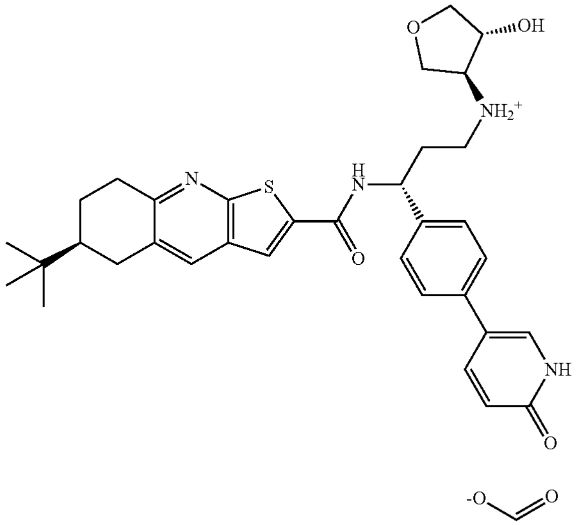 | [rac-(3S,4R)-4-hydroxytetrahydrofuran-3-yl]-[rac-(3R)-3-[4-(6-oxo-1H-pyridin-3-yl)phenyl]-3-[[rac-(6S)-6-tert-butyl-5,6,7,8-tetrahydrothieno[2,3-b]quinoline-2-carbonyl]amino]propyl]ammonium;formate | 601.5 | 1834 |

-continued

| Ex. No. | Structure | Chemical Name | Mass [M + H]+ | hNPRA EC50 (nM) |
|---|---|---|---|---|
| 70 | 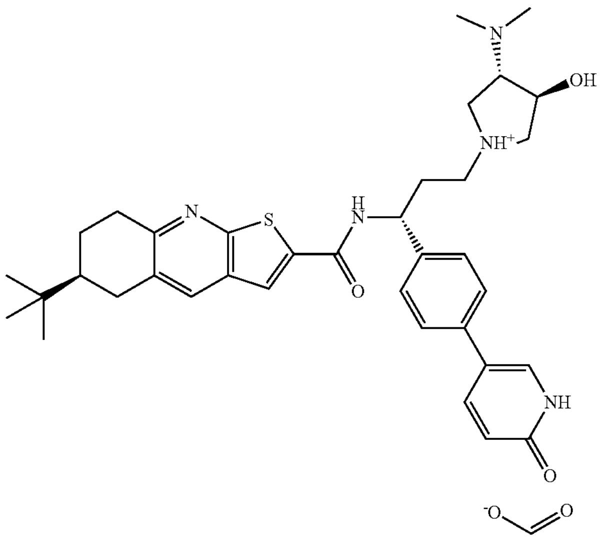 | rac-(6S)-6-tert-butyl-N-[rac-(1R)-1-[4-(6-oxo-1H-pyridin-3-yl)phenyl]-3-[rac-(3S,4S)-3-(dimethylamino)-4-hydroxy-pyrrolidin-1-ium-1-yl]propyl]-5,6,7,8-tetrahydrothieno[2,3-b]quinoline-2-carboxamide;formate | 628.5 | 1970 |
| 71 | 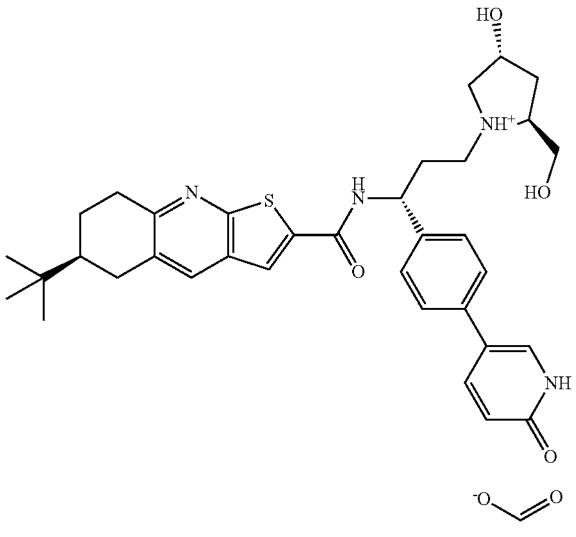 | rac-(6S)-6-tert-butyl-N-[rac-(1R)-1-[4-(6-oxo-1H-pyridin-3-yl)phenyl]-3-[rac-(2S,4R)-4-hydroxy-2-(hydroxymethyl)pyrrolidin-1-ium-1-yl]propyl]-5,6,7,8-tetrahydrothieno[2,3-b]quinoline-2-carboxamide;formate | 615.4 | 1986 |

Example 72

Example 72 was synthesized by a procedure as below:

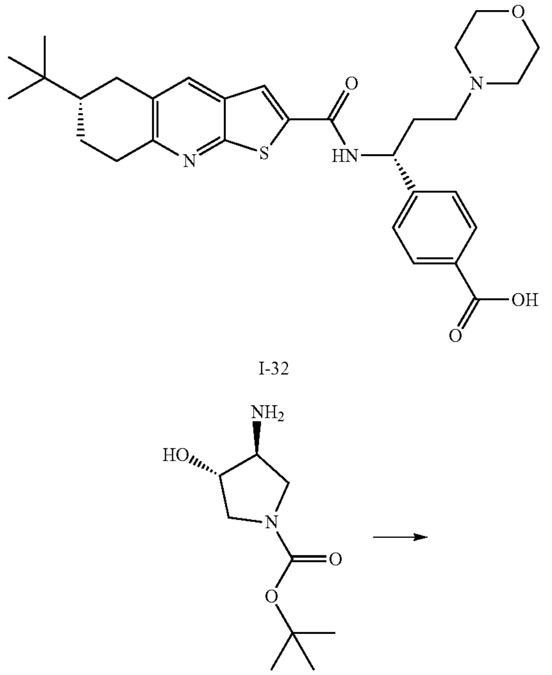

I-32

-continued

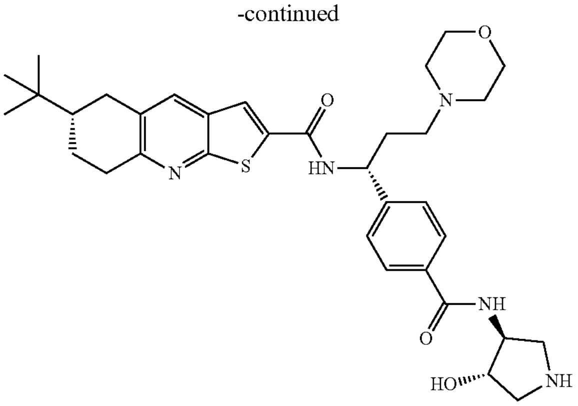

To a solution of 4-((R)-1-((S)-6-(tert-butyl)-5,6,7,8-tetrahydrothieno[2,3-b]quinoline-2-carboxamido)-3-morpholinopropyl)benzoic acid (I-32, 25 mg, 0.047 mmol) in anhydrous DMF (1.5 mL) was added tert-butyl (3S,4S)-3-amino-4-hydroxypyrrolidine-1-carboxylate (9.5 mg, 0.047 mmol), TBTU (14.98 mg, 0.047 mmol) and DIEA (8.14 µl, 0.047 mmol). The resulting reaction was stirred at ambient temperature for 6 hrs.

The reaction mixture was partitioned between EtOAc (6 mL) and water (2 mL). The organic phase was washed with brine and concentrated in vacuum. The crude product was dissolved in DCM (0.5 ml) and treated with TFA (0.5 mL) at ambient temperature for 1 hr. The reaction mixture was concentrated in vacuum. The crude product was purified by reverse-phase HPLC (MeCN/water with 0.1% ammonium hydroxide modifier) to afford the desired product

| Ex. No. | Structure | Chemical Name | Mass [M + H]+ | hNPRA EC50 (nM) |
|---|---|---|---|---|
| 72 | 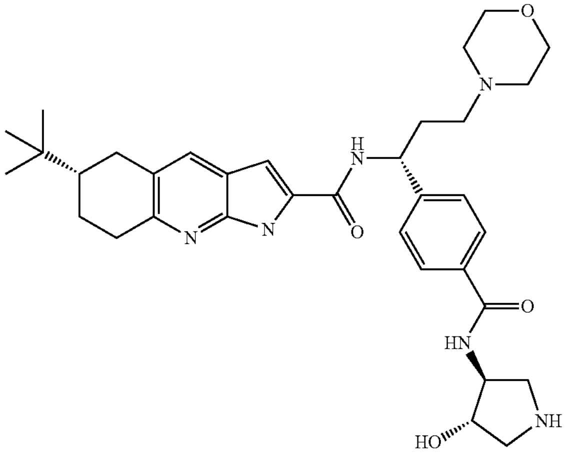 [SMILES: CC(C)(C)[C@H]1CCc2nc3[nH]c(C(=O)N[C@H](CCN4CCOCC4)c4ccc(C(=O)N[C@H]5CNC[C@@H]5O)cc4)cc3cc2C1] | rac-(6S)-6-tert-butyl-N-[rac-(1R)-3-morpholino-1-[4-[[rac-(3S,4S)-4-hydroxypyrrolidin-3-yl]carbamoyl]phenyl]propyl]-5,6,7,8-tetrahydrothieno[2,3-b]quinoline-2-carboxamide | 620.4 | 986.8 |

Examples 73-78

Examples 73-78 were synthesized by a similar procedure as below:

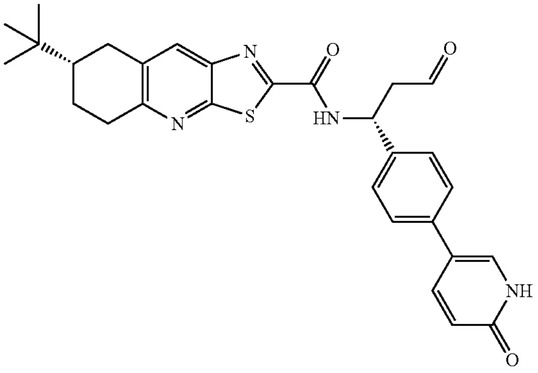

I-33

+

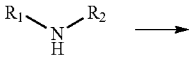

-continued

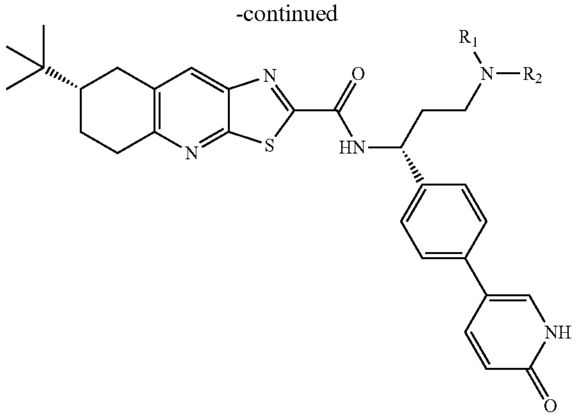

To a solution of(S)-7-(tert-butyl)-N-((R)-3-oxo-1-(4-(6-oxo-1,6-dihydropyridin-3-yl)phenyl)propyl)-5,6,7,8-tetrahydrothiazolo[5,4-b]quinoline-2-carboxamide (1-33, 30 mg, 0.057 mmol) and amino substrate (0.114 mmol) in anhydrous 5% HOAc/MeOH (1.5 ml) was added polystyrene supported $BH_3CN$ (70 mg, 2.45 mmol/g) at ambient temperature. The resulting reaction mixture was shaken at ambient temperature for 12 hrs.

The solution was filtered, and the solvent was evaporated in vacuum. The crude product was purified by reverse-phase HPLC (MeCN/water with 0.1% ammonium hydroxide modifier) to afford the desired product.

| Ex. No. | Structure | Chemical Name | Mass [M + H]+ | hNPRA EC50 (nM) |
|---|---|---|---|---|
| 73 | 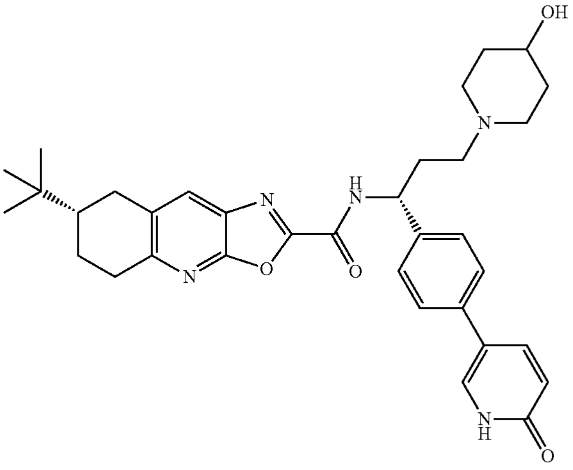 [SMILES: CC(C)(C)[C@H]1CCc2nc3oc(C(=O)N[C@H](CCN4CCC(O)CC4)c4ccc(-c5ccc(=O)[nH]c5)cc4)nc3cc2C1] | rac-(7S)-7-tert-butyl-N-[rac-(1R)-3-(4-hydroxy-1-piperidyl)-1-[4-(6-oxo-1H-pyridin-3-yl)phenyl]propyl]-5,6,7,8-tetrahydrothiazolo[5,4-b]quinoline-2-carboxamide | 600.5 | 269 |

-continued

| Ex. No. | Structure | Chemical Name | Mass [M + H]+ | hNPRA EC50 (nM) |
|---|---|---|---|---|
| 74 | 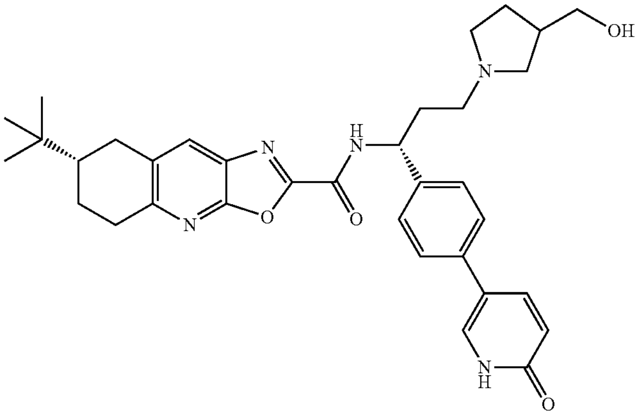 [SMILES: CC(C)(C)[C@H]1CCc2nc3oc(C(=O)N[C@H](CCN4CCC(CO)C4)c4ccc(-c5ccc(=O)[nH]c5)cc4)nc3cc2C1] | rac-(7S)-7-tert-butyl-N-[rac-(1R)-3-[3-(hydroxymethyl)pyrrolidin-1-yl]-1-[4-(6-oxo-1H-pyridin-3-yl)phenyl]propyl]-5,6,7,8-tetrahydrothiazolo[5,4-b]quinoline-2-carboxamide | 600.5 | 327.6 |
| 75 | 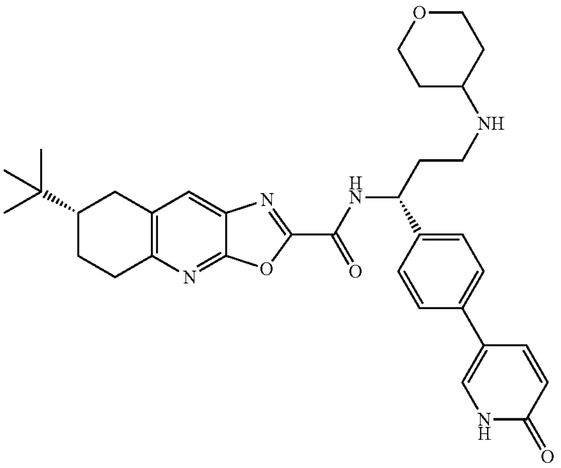 [SMILES: CC(C)(C)[C@H]1CCc2nc3oc(C(=O)N[C@H](CCNC4CCOCC4)c4ccc(-c5ccc(=O)[nH]c5)cc4)nc3cc2C1] | rac-(7S)-7-tert-butyl-N-[rac-(1R)-1-[4-(6-oxo-1H-pyridin-3-yl)phenyl]-3-(tetrahydropyran-4-ylamino)propyl]-5,6,7,8-tetrahydrothiazolo[5,4-b]quinoline-2-carboxamide | 600.4 | 633.7 |
| 76 | 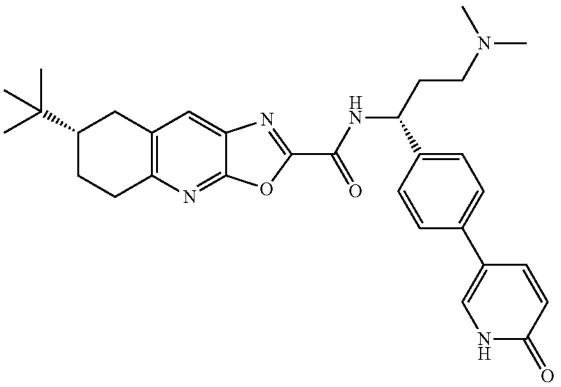 [SMILES: CN(C)CC[C@@H](NC(=O)c1nc2cc3c(nc2o1)CC[C@H](C(C)(C)C)C3)c1ccc(-c2ccc(=O)[nH]c2)cc1] | rac-(7S)-7-tert-butyl-N-[rac-(1R)-3-(dimethylamino)-1-[4-(6-oxo-1H-pyridin-3-yl)phenyl]propyl]-5,6,7,8-tetrahydrothiazolo[5,4-b]quinoline-2-carboxamide | 544.4 | 665 |

-continued

| Ex. No. | Structure | Chemical Name | Mass [M + H]+ | hNPRA EC50 (nM) |
|---|---|---|---|---|
| 77 | 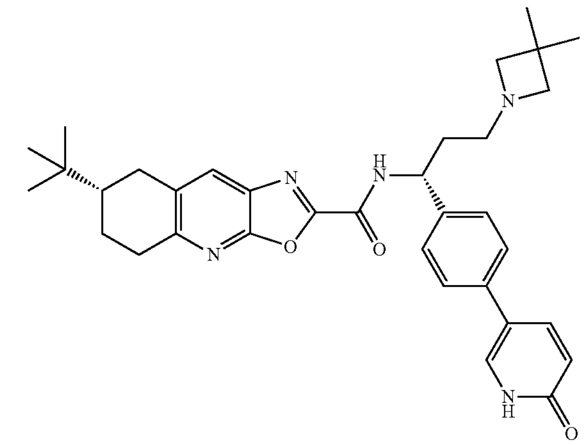 [SMILES: CC1(C)CN(CC[C@@H](NC(=O)c2nc3cc4c(nc3o2)CC[C@H](C(C)(C)C)C4)c2ccc(-c3ccc(=O)[nH]c3)cc2)C1] | rac-(7S)-7-tert-butyl-N-[rac-(1R)-3-(3,3-dimethylazetidin-1-yl)-1-[4-(6-oxo-1H-pyridin-3-yl)phenyl]propyl]-5,6,7,8-tetrahydrothiazolo[5,4-b]quinoline-2-carboxamide | 584.5 | 681 |
| 78 | 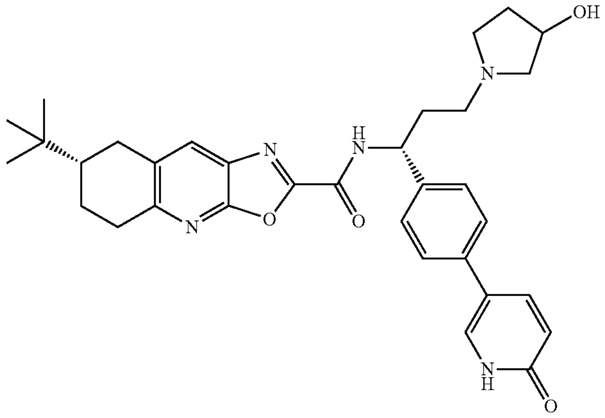 [SMILES: CC(C)(C)[C@H]1CCc2nc3oc(C(=O)N[C@H](CCN4CCC(O)C4)c4ccc(-c5ccc(=O)[nH]c5)cc4)nc3cc2C1] | rac-(7S)-7-tert-butyl-N-[rac-(1R)-3-(3-hydroxypyrrolidin-1-yl)-1-[4-(6-oxo-1H-pyridin-3-yl)phenyl]propyl]-5,6,7,8-tetrahydrothiazolo[5,4-b]quinoline-2-carboxamide | 586.5 | 692.1 |

Examples 79-82

Examples 79-82 were synthesized by a similar procedure as below:

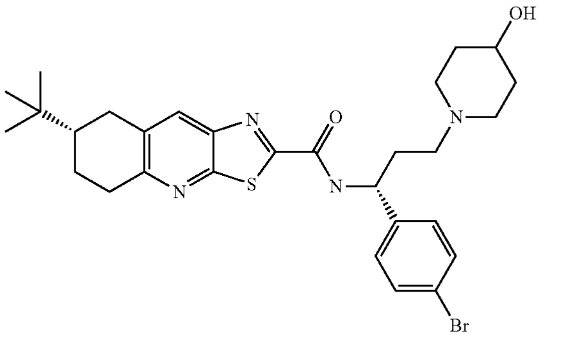

I-34

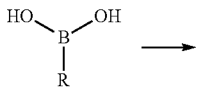

+

-continued

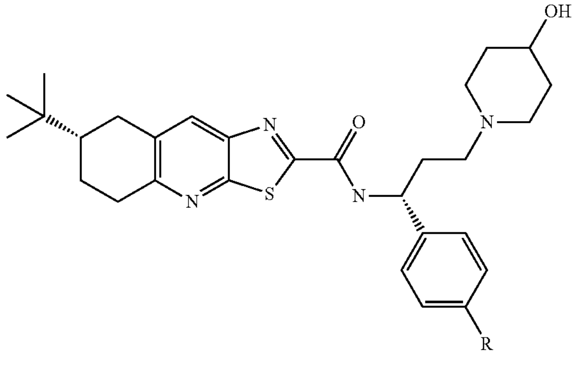

To a solution of(S)-N-((R)-1-(4-bromophenyl)-3-(4-hydroxypiperidin-1-yl)propyl)-7-(tert-butyl)-5,6,7,8-tetrahydrothiazolo[5,4-b]quinoline-2-carboxamide (I-34, 30 mg, 0.051 mmol), $Pd(dppf)Cl_2$ (59.2 mg, 0.051 mmol) and boronic acid substrate (0.102 mmol) in dioxane (1 ml) was added $Na_2CO_3$ (2.5 N, 0.061 ml, 0.154 mmol) at ambient temperature. The resulting reaction mixture was purged with $N_2$ for 5 mins and then stirred at 100° C. for 16 hr.

The reaction was cooled to ambient temperature and partitioned between EtOAc (6 mL) and water (2 mL). The organic phase was washed with brine and evaporated in vacuum. The crude product was purified by reverse-phase HPLC (MeCN/water with 0.1% formic acid modifier) to afford the desired product as a formic acid salt.

| Ex. No. | Structure | Chemical Name | Mass [M + H]+ | hNPRA EC50 (nM) |
| --- | --- | --- | --- | --- |
| 79 | 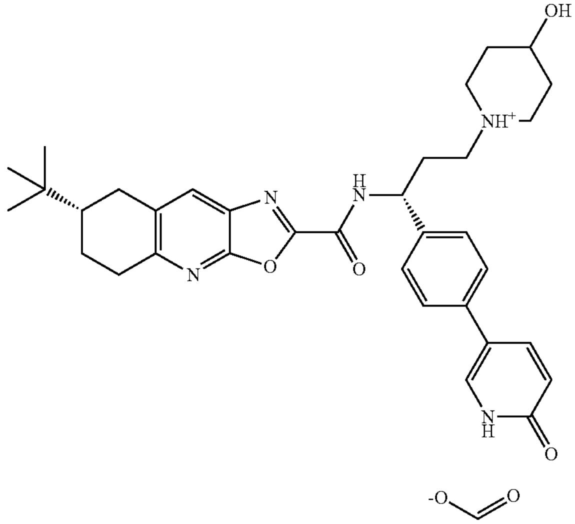 | rac-(7S)-7-tert-butyl-N-[rac-(1R)-3-(4-hydroxypiperidin-1-ium-1-yl)-1-[4-(6-oxo-1H-pyridin-3-yl)phenyl]propyl]-5,6,7,8-tetrahydrothiazolo[5,4-b]quinoline-2-carboxamide; formate | 600.5 | 270.1 |
| 80 | 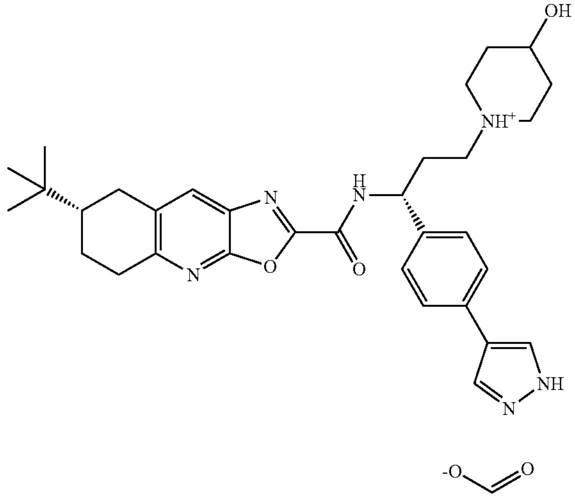 | rac-(7S)-7-tert-butyl-N-[rac-(1R)-3-(4-hydroxypiperidin-1-ium-1-yl)-1-[4-(1H-pyrazol-4-yl)phenyl]propyl]-5,6,7,8-tetrahydrothiazolo[5,4-b]quinoline-2-carboxamide; formate | 573.6 | 753.3 |
| 81 | 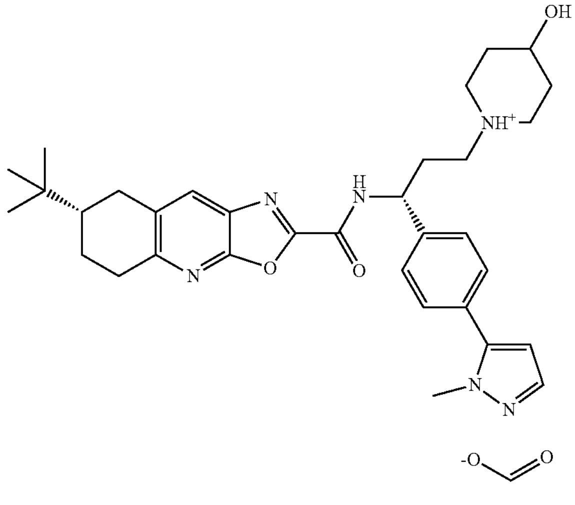 | rac-(7S)-7-tert-butyl-N-[rac-(1R)-3-(4-hydroxypiperidin-1-ium-1-yl)-1-[4-(2-methylpyrazol-3-yl)phenyl]propyl]-5,6,7,8-tetrahydrothiazolo[5,4-b]quinoline-2-carboxamide; formate | 587.5 | 913.6 |

-continued

| Ex. No. | Structure | Chemical Name | Mass [M + H]+ | hNPRA EC50 (nM) |
|---|---|---|---|---|
| 82 | 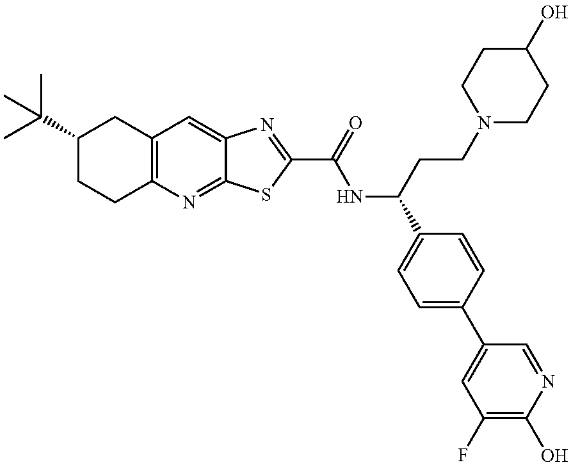 [SMILES: CC(C)(C)[C@H]1CCc2nc3sc(C(=O)N[C@H](CCN4CCC(O)CC4)c4ccc(-c5cnc(O)c(F)c5)cc4)nc3cc2C1] | (7S)-7-tert-butyl-N-[(1R)-1-[4-(5-fluoro-6-hydroxy-3-pyridyl)phenyl]-3-(4-hydroxy-1-piperidyl)propyl]-5,6,7,8-tetrahydrothiazolo[5,4-b]quinoline-2-carboxamide | 618 | 196 |

Examples 83-84

Examples 83-84 were synthesized by a similar procedure as below:

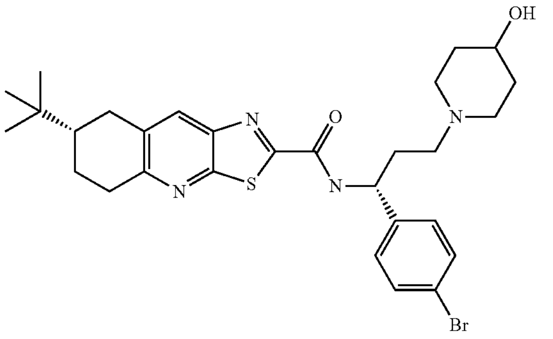

I-34

+

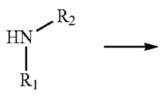

-continued

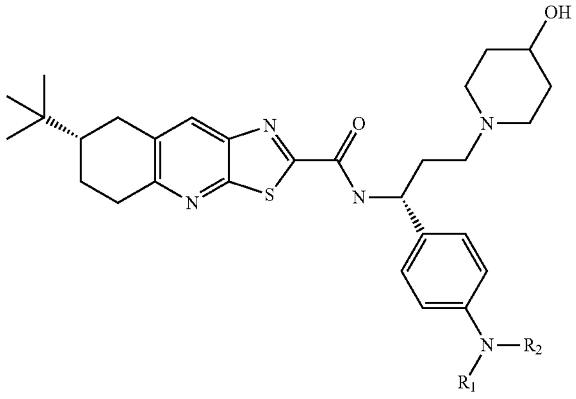

To a solution of(S)-N-((R)-1-(4-bromophenyl)-3-(4-hydroxypiperidin-1-yl)propyl)-7-(tert-butyl)-5,6,7,8-tetrahydrothiazolo[5,4-b]quinoline-2-carboxamide (I-34, 25 mg, 0.043 mmol), CuI (0.811 mg, 4.27 μmol), (1R,2S)-$N_1$,$N_2$-dimethylcyclohexane-1,2-diamine (2 mg, 0.009 mmol) and amino substrate (0.086 mmol) in DMSO (1 mL) was added $K_2CO_3$ (17.67 mg, 0.128 mmol) at ambient temperature. The resulting reaction mixture was purged with $N_2$ for 5 mins and then stirred at 110° C. for 16 hrs.

The reaction was cooled to ambient temperature and then partitioned between EtOAc (6 mL) and ammonium hydroxide (2 N, 2 mL). The organic phase was washed with brine and evaporated in vacuum. The crude product was purified by reverse-phase HPLC (MeCN/water with 0.1% TFA modifier) to afford the desired product as a TFA salt.

| Ex. No. | Structure | Chemical Name | Mass [M + H]+ | hNPRA EC50 (nM) |
|---|---|---|---|---|
| 83 | 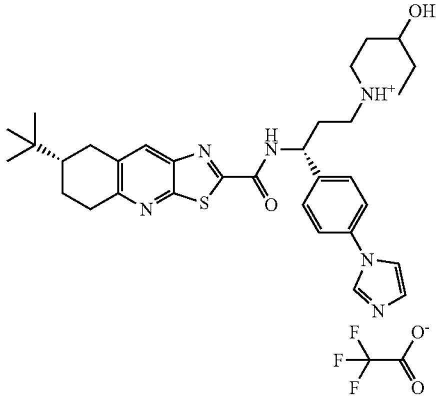 [SMILES: CC(C)(C)[C@H]1CCc2nc3sc(C(=O)N[C@H](CC[NH+]4CCC(O)CC4)c4ccc(-n5ccnc5)cc4)nc3cc2C1 ; O=C([O-])C(F)(F)F] | rac-(7S)-7-tert-butyl-N-[rac-(1R)-3-(4-hydroxy-piperidin-1-ium-1-yl)-1-(4-imidazol-1-ylphenyl) propyl]-5,6,7,8-tetrahydro-thiazolo[5,4-b] quinoline-2-carboxamide; 2,2,2-trifluoroacetate | 573.5 | 681 |
| 84 | Chiral 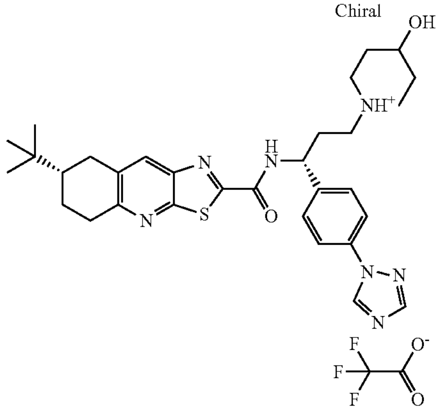 [SMILES: CC(C)(C)[C@H]1CCc2nc3sc(C(=O)N[C@H](CC[NH+]4CCC(O)CC4)c4ccc(-n5cncn5)cc4)nc3cc2C1 ; O=C([O-])C(F)(F)F] | (7S)-7-tert-butyl-N-[(1R)-3-(4-hydroxy-piperidin-1-ium-1-yl)-1-[4-(1,2,4-triazol-1-yl)phenyl]propyl]-5,6,7,8-tetra-hydrothiazolo[5,4-b] quinoline-2-carboxamide; 2,2,2-trifluoro-acetate | 574.5 | 802.4 |

Example 85

Example 85 was synthesized by a procedure as below:

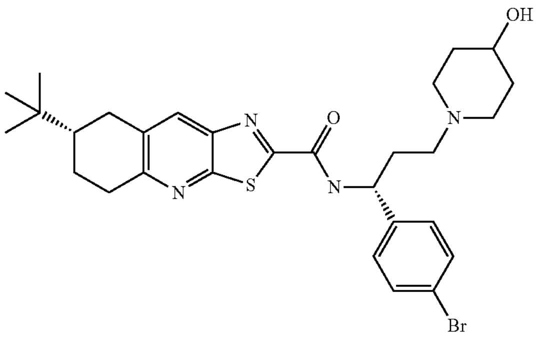

I-34

+

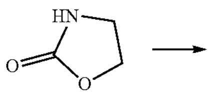

-continued

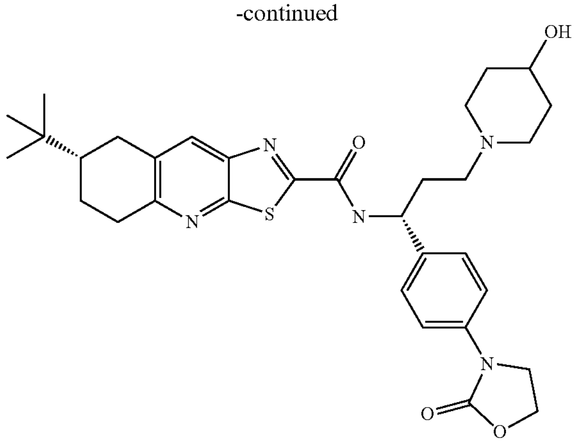

In a glove box, to a solution of(S)-N-((R)-1-(4-bromophenyl)-3-(4-hydroxypiperidin-1-yl)propyl)-7-(tert-butyl)-5,6,7,8-tetrahydrothiazolo[5,4-b]quinoline-2-carboxamide (I-34, 25 mg, 0.043 mmol) and oxazolidin-2-one (8 mg, 0.086 mmol) in dioxane (1 mL) was added $Pd_2(dba)_3$ (3.91 mg, 4.27 µmol), Xantphos (4.94 mg, 8.54 µmol) and $Cs_2CO_3$ (41.8 mg, 0.128 mmol). The reaction was sealed and heated to 85° C. for 24 hrs.

The reaction was cooled to ambient temperature and quenched with water (0.2 mL). The reaction mixture was partitioned between EtOAc (6 mL) and water (2 mL). The organic phase was washed with brine and then evaporated under reduced pressure. The crude product was purified by reverse-phase HPLC (MeCN/water with 0.1% ammonium hydroxide modifier) to afford the desired product.

| Ex. No. | Structure | Chemical Name | Mass [M + H]+ | hNPRA EC50 (nM) |
|---|---|---|---|---|
| 85 | 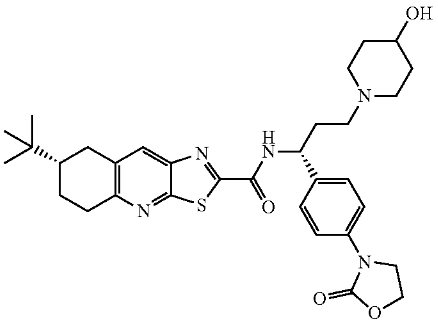 [SMILES: CC(C)(C)[C@H]1CCc2nc3sc(C(=O)N[C@H](CCN4CCC(O)CC4)c4ccc(N5CCOC5=O)cc4)nc3cc2C1] | [rac-(1R)-3-(4-hydroxy-1-piperidyl)-1-[4-(2-oxooxazolidin-3-yl)phenyl]propyl]-5,6,7,8-tetrahydrothiazolo[5,4-b]quinoline-2-carboxamide | 592.5 | 1025 |

Examples 86-100

Examples 86-100 were synthesized by a similar procedure as below:

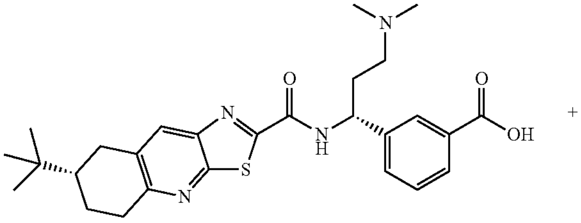

I-35

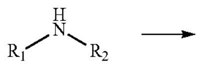

-continued

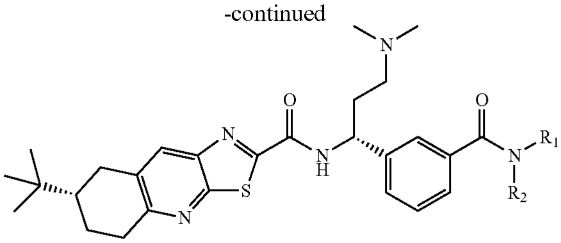

To a mixture of TBTU (26.0 mg, 0.081 mmol) and amino substrate (0.080 mmol) was added 3-((R)-1-((S)-7-(tert-butyl)-5,6,7,8-tetrahydrothiazolo[5,4-b]quinoline-2-carboxamido)-3-(dimethylamino) propyl)benzoic acid (1-35, 20 mg, 0.040 mmol) solution in anhydrous DMF (1.5 mL) and DIEA (0.042 mL, 0.242 mmol). The resulting reaction was stirred at ambient temperature for 6 hrs.

The reaction was quenched with water (0.2 mL) and partitioned between EtOAc (6 mL) and water (2 mL). The organic phase was washed with brine and evaporated in vacuum. The product with Boc protecting group was dissolved in DCM (0.5 mL) and treated with TFA (0.5 mL) at ambient temperature for 1 hrs and then the reaction mixture was concentrated in vacuum. The crude product was purified by reverse-phase HPLC (MeCN/water with 0.1% ammonium hydroxide modifier) to afford the desired product.

| Ex. No. | Structure | Chemical Name | Mass [M + H]+ | hNPRA EC50 (nM) |
|---|---|---|---|---|
| 86 | 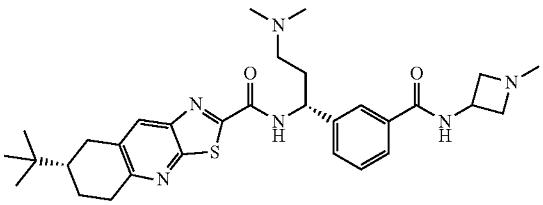 [SMILES: CN(C)CC[C@@H](NC(=O)c1nc2cc3c(nc2s1)CC[C@H](C(C)(C)C)C3)c1cccc(C(=O)NC2CN(C)C2)c1] | rac-(7S)-7-tert-butyl-N-[rac-(1R)-3-(dimethylamino)-1-[3-[(1-methylazetidin-3-yl)carbamoyl]phenyl]propyl]-5,6,7,8-tetrahydrothiazolo[5,4-b]quinoline-2-carboxamide | 563.44 | 183.5 |

-continued

| Ex. No. | Structure | Chemical Name | Mass [M + H]+ | hNPRA EC50 (nM) |
|---|---|---|---|---|
| 87 | 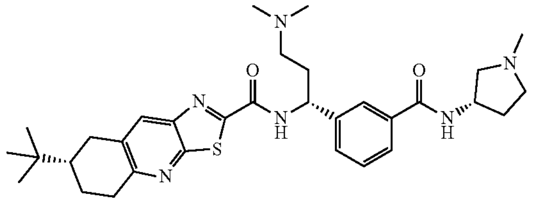 [SMILES: CN(C)CC[C@@H](NC(=O)c1nc2cc3c(nc2s1)CC[C@H](C(C)(C)C)C3)c1cccc(C(=O)N[C@H]2CCN(C)C2)c1] | rac-(7S)-7-tert-butyl-N-[rac-(1R)-3-(dimethyl-amino)-1-[3-[rac-(3S)-1-methylpyrrolidin-3-yl]carbamoyl]phenyl]propyl]-5,6,7,8-tetrahydrothiazolo[5,4-b]quinoline-2-carboxamide | 577.56 | 206.6 |
| 88 | 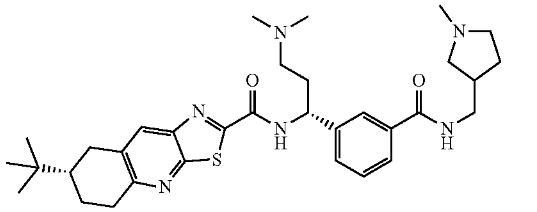 [SMILES: CN(C)CC[C@@H](NC(=O)c1nc2cc3c(nc2s1)CC[C@H](C(C)(C)C)C3)c1cccc(C(=O)NCC2CCN(C)C2)c1] | rac-(7S)-7-tert-butyl-N-[rac-(1R)-3-(dimethylamino)-1-[3-[(1-methylpyrrolidin-3-yl)methylcarbamoyl]phenyl]propyl]-5,6,7,8-tetrahydrothiazolo[5,4-b]quinoline-2-carboxamide | 591.48 | 229.9 |
| 89 | 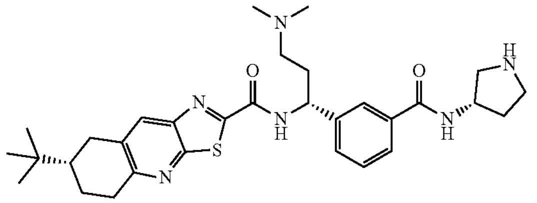 [SMILES: CN(C)CC[C@@H](NC(=O)c1nc2cc3c(nc2s1)CC[C@H](C(C)(C)C)C3)c1cccc(C(=O)N[C@H]2CCNC2)c1] | rac-(7S)-7-tert-butyl-N-[rac-(1R)-3-(dimethylamino)-1-[3-[rac-(3S)-pyrrolidin-3-yl]carbamoyl]phenyl]propyl]-5,6,7,8-tetrahydrothiazolo[5,4-b]quinoline-2-carboxamide | 563.43 | 230.2 |
| 90 | 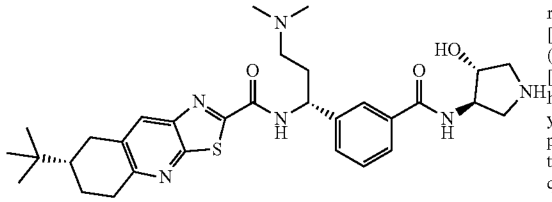 | rac-(7S)-7-tert-butyl-N-[rac-(1R)-3-(dimethylamino)-1-[3-[[rac-(3R,4R)-4-hydroxypyrrolidin-3-yl]carbamoyl]phenyl]propyl]-5,6,7,8-tetrahydrothiazolo[5,4-b]quinoline-2-carboxamide | 579.42 | 270.5 |
| 91 | 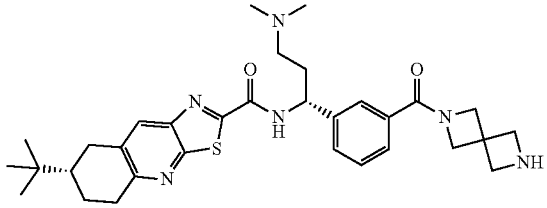 [SMILES: CN(C)CC[C@@H](NC(=O)c1nc2cc3c(nc2s1)CC[C@H](C(C)(C)C)C3)c1cccc(C(=O)N2CC3(CNC3)C2)c1] | rac-(7S)-7-tert-butyl-N-[rac-(1R)-1-[3-(2,6-diazaspiro[3.3]heptane-2-carbonyl)phenyl]-3-(dimethylamino)propyl]-5,6,7,8-tetrahydrothiazolo[5,4-b]quinoline-2-carboxamide | 575.46 | 291.9 |
| 92 | 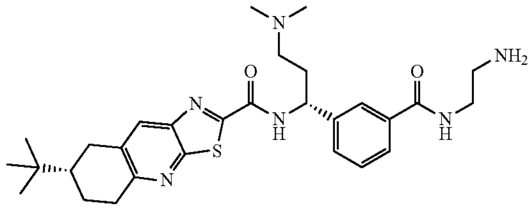 [SMILES: CN(C)CC[C@@H](NC(=O)c1nc2cc3c(nc2s1)CC[C@H](C(C)(C)C)C3)c1cccc(C(=O)NCCN)c1] | rac-(7S)-7-tert-butyl-N-[rac-(1R)-1-[3-(2-aminoethylcarbamoyl)phenyl]-3-(dimethyl-amino)propyl]-5,6,7,8-tetrahydrothiazolo[5,4-b]quinoline-2-carboxamide | 537.43 | 347.7 |
| 93 | 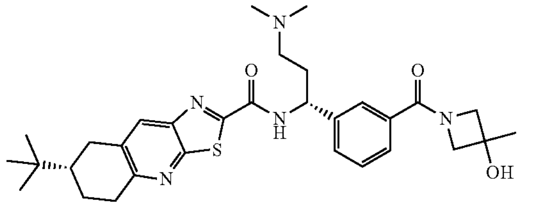 [SMILES: CN(C)CC[C@@H](NC(=O)c1nc2cc3c(nc2s1)CC[C@H](C(C)(C)C)C3)c1cccc(C(=O)N2CC(C)(O)C2)c1] | rac-(7S)-7-tert-butyl-N-[rac-(1R)-3-(dimethylamino)-1-[3-(3-hydroxy-3-methyl-azetidine-1-carbonyl)phenyl]propyl]-5,6,7,8-tetrahydrothiazolo[5,4-b]quinoline-2-carboxamide | 564.43 | 527.2 |

-continued

| Ex. No. | Structure | Chemical Name | Mass [M + H]+ | hNPRA EC50 (nM) |
|---|---|---|---|---|
| 94 | 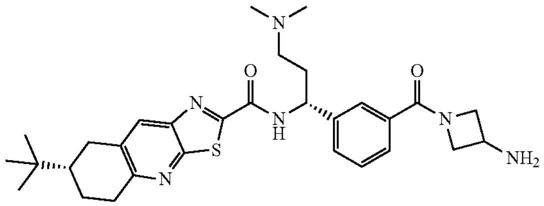 [SMILES: CN(C)CC[C@@H](NC(=O)c1nc2cc3c(nc2s1)CC[C@H](C(C)(C)C)C3)c1cccc(C(=O)N2CC(N)C2)c1] | rac-(7S)-7-tert-butyl-N-[rac-(1R)-1-[3-(3-aminoazetidine-1-carbonyl)phenyl]-3-(dimethylamino)propyl]-5,6,7,8-tetrahydrothiazolo[5,4-b]quinoline-2-carboxamide | 549.44 | 566.2 |
| 95 | 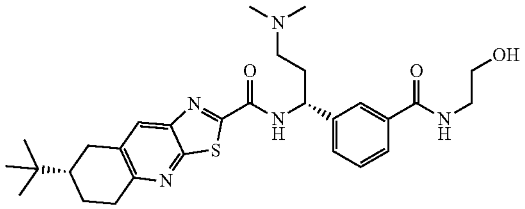 [SMILES: CN(C)CC[C@@H](NC(=O)c1nc2cc3c(nc2s1)CC[C@H](C(C)(C)C)C3)c1cccc(C(=O)NCCO)c1] | rac-(7S)-7-tert-butyl-N-[rac-(1R)-3-(dimethylamino)-1-[3-(2-hydroxyethylcarbamoyl)phenyl]propyl]-5,6,7,8-tetrahydrothiazolo[5,4-b]quinoline-2-carboxamide | 538.42 | 690.1 |
| 96 | 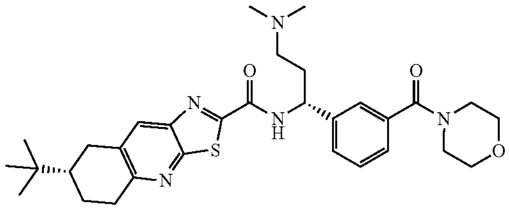 [SMILES: CN(C)CC[C@@H](NC(=O)c1nc2cc3c(nc2s1)CC[C@H](C(C)(C)C)C3)c1cccc(C(=O)N2CCOCC2)c1] | rac-(7S)-7-tert-butyl-N-[rac-(1R)-3-(dimethylamino)-1-[3-(morpholine-4-carbonyl)phenyl]propyl]-5,6,7,8-tetrahydrothiazolo[5,4-b]quinoline-2-carboxamide | 564.43 | 1022 |
| 97 | 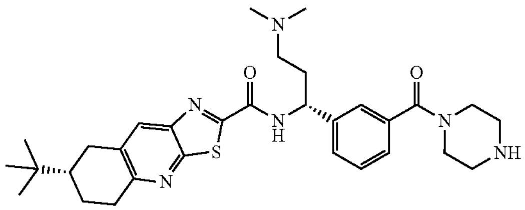 [SMILES: CN(C)CC[C@@H](NC(=O)c1nc2cc3c(nc2s1)CC[C@H](C(C)(C)C)C3)c1cccc(C(=O)N2CCNCC2)c1] | rac-(7S)-7-tert-butyl-N-[rac-(1R)-3-(dimethyl-amino)-1-[3-(piperazine-1-carbonyl)phenyl]propyl]-5,6,7,8-tetrahydrothiazolo[5,4-b]quinoline-2-carboxamide | 563.44 | 1385 |
| 98 | 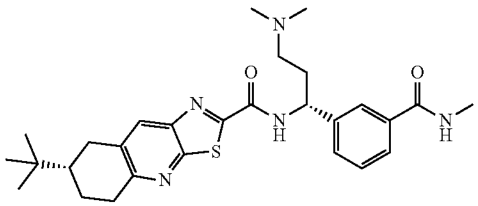 [SMILES: CNC(=O)c1cccc([C@@H](CCN(C)C)NC(=O)c2nc3cc4c(nc3s2)CC[C@H](C(C)(C)C)C4)c1] | rac-(7S)-7-tert-butyl-N-[rac-(1R)-3-(dimethyl-amino)-1-[3-(methylcarbamoyl)phenyl]propyl]-5,6,7,8-tetrahydrothiazolo[5,4-b]quinoline-2-carboxamide | 508.42 | 1453 |
| 99 | 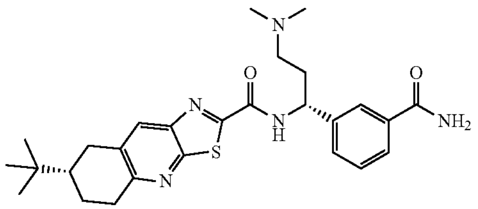 [SMILES: CN(C)CC[C@@H](NC(=O)c1nc2cc3c(nc2s1)CC[C@H](C(C)(C)C)C3)c1cccc(C(N)=O)c1] | rac-(7S)-7-tert-butyl-N-[rac-(1R)-1-(3-carbamoylphenyl)-3-(dimethylamino)propyl]-5,6,7,8-tetrahydrothiazolo[5,4-b]quinoline-2-carboxamide | 494.42 | 1832 |

-continued

| Ex. No. | Structure | Chemical Name | Mass [M + H]+ | hNPRA EC50 (nM) |
|---|---|---|---|---|
| 100 | 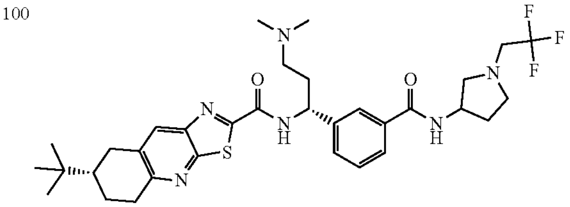 | rac-(7S)-7-tert-butyl-N-[rac-(1R)-3-(dimethyl-amino)-1-[3-[[1-(2,2,2-trifluoroethyl)pyrrolidin-3-yl]carbamoyl]phenyl]propyl]-5,6,7,8-tetrahydrothiazolo[5,4-b]quinoline-2-carboxamide | 645.43 | 1998 |

Examples 101-115

Examples 101-115 were synthesized by a similar procedure as below:

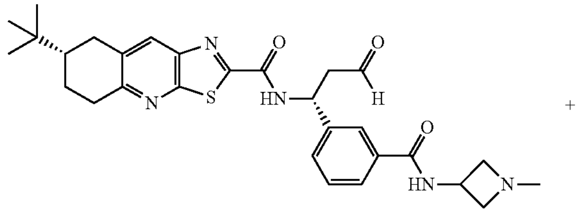

I-36

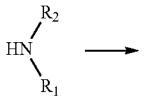

-continued

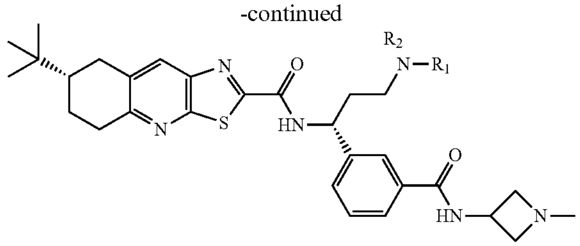

To a solution of(S)-7-(tert-butyl)-N-((R)-1-(3-((1-methyl-azetidin-3-yl) carbamoyl)phenyl)-3-oxopropyl)-5,6,7,8-tetrahydrothiazolo[5,4-b]quinoline-2-carboxamide (1-36, 25 mg, 0.047 mmol) in anhydrous 5% HOAc/MeOH (1.5 ml) was added amino substrate (0.094 mmol) and polystyrene supported $BH_3CN$ (70 mg, 2.45 mmol/g) at ambient temperature. The resulting reaction mixture was shaken at ambient temperature for 6 hrs.

The reaction was filtered, and the solvent was evaporated in vacuum. The crude product was purified by reverse-phase HPLC (MeCN/water with 0.1% TFA modifier) to afford the desired product as a TFA salt.

| Ex. No. | Structure | Chemical Name | Mass [M + H]+ | hNPRA EC50 (nM) |
|---|---|---|---|---|
| 101 | 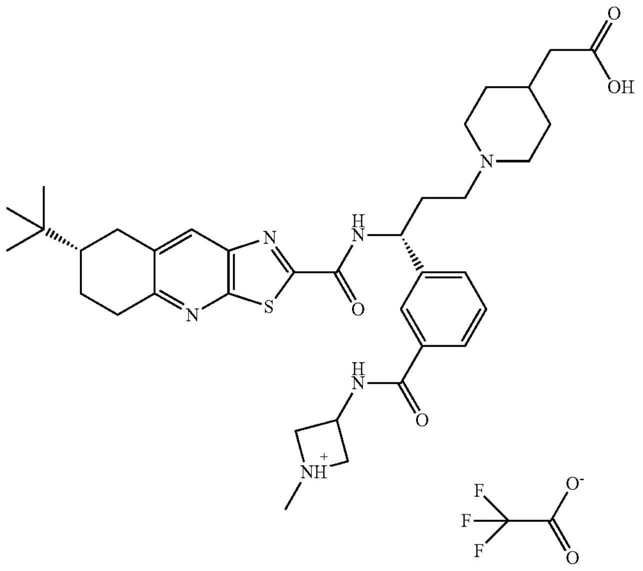 [SMILES: CN1CC(NC(=O)c2cccc([C@@H](CCN3CCC(CC(=O)O)CC3)NC(=O)c3nc4cc5c(nc4s3)CC[C@H](C(C)(C)C)C5)c2)C1 ; O=C([O-])C(F)(F)F] | 2-[1-[rac-(3R)-3-[3-[(1-methylazetidin-1-ium-3-yl)carbamoyl]phenyl]-3-[[rac-(7S)-7-tert-butyl-5,6,7,8-tetrahydrothiazolo[5,4-b]quinoline-2-carbonyl]amino]propyl]-4-piperidyl]acetic acid; 2,2,2-trifluoroacetate | 661.35 | 145.9 |

-continued

| Ex. No. | Structure | Chemical Name | Mass [M + H]+ | hNPRA EC50 (nM) |
|---|---|---|---|---|
| 102 | 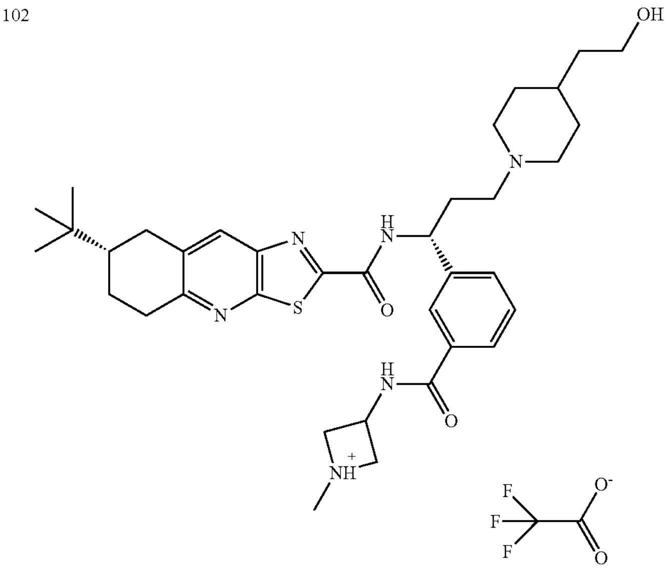 | rac-(7S)-7-tert-butyl-N-[rac-(1R)-3-[4-(2-hydroxyethyl)-1-piperidyl]-1-[3-[(1-methylazetidin-1-ium-3-yl)carbamoyl]phenyl]propyl]-5,6,7,8-tetrahydrothiazolo[5,4-b]quinoline-2-carboxamide; 2,2,2-trifluoroacetate | 647.37 | 158.3 |
| 103 | 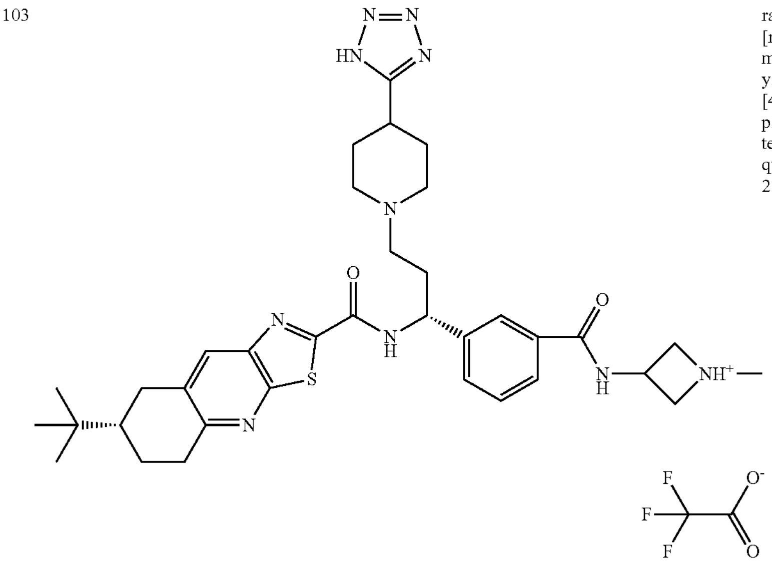 | rac-(7S)-7-tert-butyl-N-[rac-(1R)-1-[3-[(1-methylazetidin-1-ium-3-yl)carbamoyl]phenyl]-3-[4-(1H-tetrazol-5-yl)-1-piperidyl]propyl]-5,6,7,8-tetrahydrothiazolo[5,4-b]quinoline-2-carboxamide; 2,2,2-trifluoroacetate | 671.52 | 160.2 |

-continued

| Ex. No. | Structure | Chemical Name | Mass [M + H]+ | hNPRA EC50 (nM) |
|---|---|---|---|---|
| 104 | 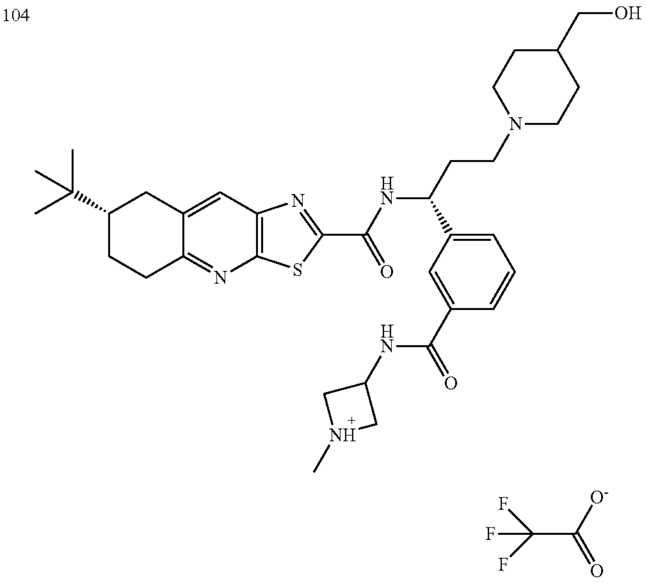 | rac-(7S)-7-tert-butyl-N-[rac-(1R)-3-[4-(hydroxymethyl)-1-piperidyl]-1-[3-[(1-methylazetidin-1-ium-3-yl)carbamoyl]phenyl]propyl]-5,6,7,8-tetrahydrothiazolo[5,4-b]quinoline-2-carboxamide; 2,2,2-trifluoroacetate | 633.35 | 186.3 |
| 105 | 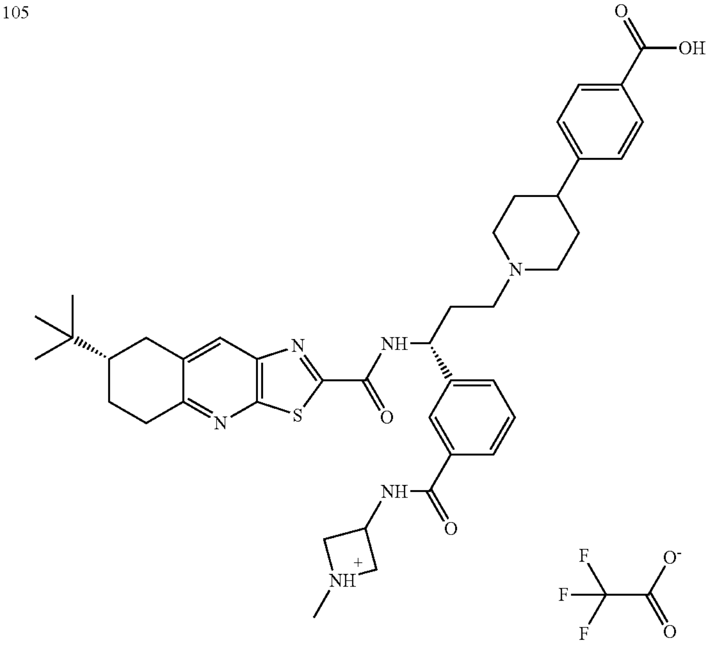 | 4-[1-[rac-(3R)-3-[3-[(1-methylazetidin-1-ium-3-yl)carbamoyl]phenyl]-3-[rac-(7S)-7-tert-butyl-5,6,7,8-tetrahydrothiazolo[5,4-b]quinoline-2-carbonyl]amino]propyl]-4-piperidyl]benzoic acid; 2,2,2-trifluoroacetate | 723.36 | 315.2 |

-continued

| Ex. No. | Structure | Chemical Name | Mass [M + H]+ | hNPRA EC50 (nM) |
| --- | --- | --- | --- | --- |
| 106 | 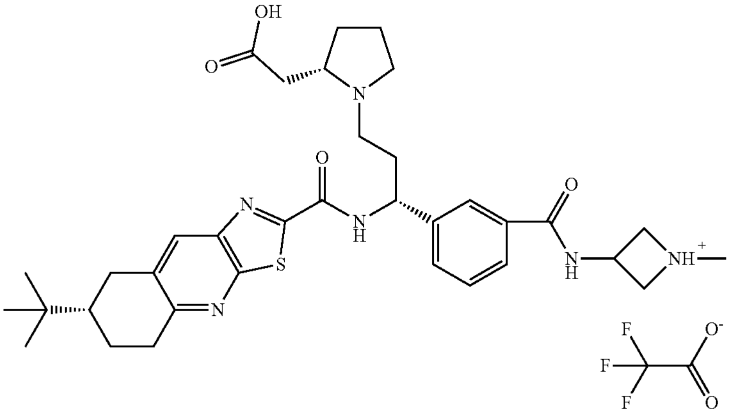 [SMILES: CN1CC(NC(=O)c2cccc([C@@H](CCN3CCC[C@H]3CC(=O)O)NC(=O)c3nc4cc5c(nc4s3)CC[C@H](C(C)(C)C)C5)c2)C1 ; O=C([O-])C(F)(F)F] | 2-[rac-(2S)-1-[rac-(3R)-3-[3-[(1-methylazetidin-1-ium-3-yl)carbamoyl]phenyl]-3-[rac-(7S)-7-tert-butyl-5,6,7,8-tetrahydrothiazolo[5,4-b]quinoline-2-carbonyl]amino]propyl]pyrrolidin-2-yl]acetic acid; 2,2,2-trifluoroacetate | 647.49 | 520.8 |
| 107 | 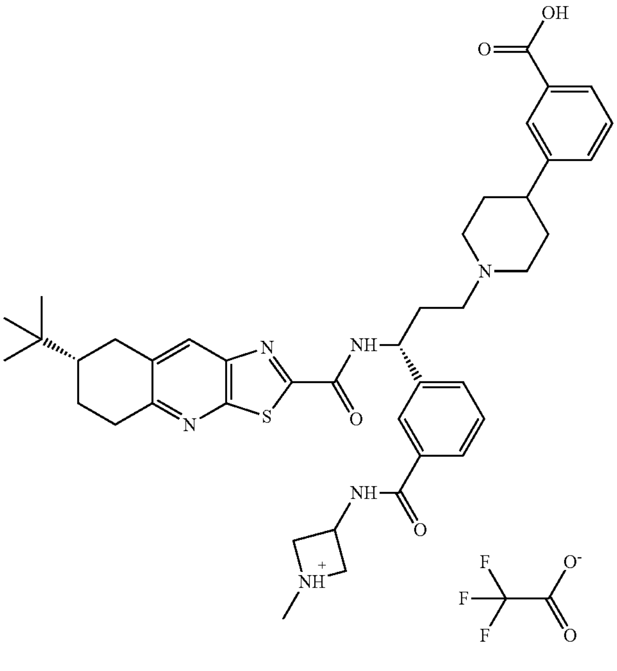 [SMILES: CN1CC(NC(=O)c2cccc([C@@H](CCN3CCC(c4cccc(C(=O)O)c4)CC3)NC(=O)c3nc4cc5c(nc4s3)CC[C@H](C(C)(C)C)C5)c2)C1 ; O=C([O-])C(F)(F)F] | 3-[1-[rac-(3R)-3-[3-[(1-methylazetidin-1-ium-3-yl)carbamoyl]phenyl]-3-[rac-(7S)-7-tert-butyl-5,6,7,8-tetrahydrothiazolo[5,4-b]quinoline-2-carbonyl]amino]propyl]-4-piperidyl]benzoic acid; 2,2,2-trifluoroacetate | 723.36 | 526.4 |

-continued

| Ex. No. | Structure | Chemical Name | Mass [M + H]+ | hNPRA EC50 (nM) |
|---|---|---|---|---|
| 108 | 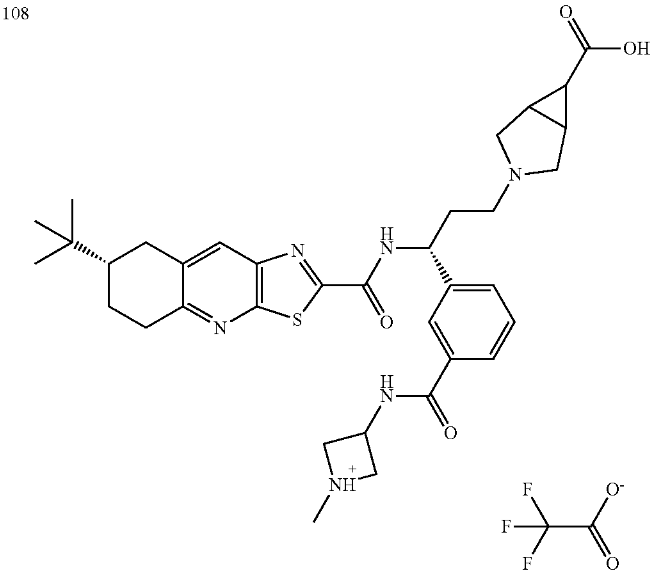 | 3-[rac-(3R)-3-[3-[(1-methylazetidin-1-ium-3-yl)carbamoyl]phenyl]-3-[[rac-(7S)-7-tert-butyl-5,6,7,8-tetrahydrothiazolo[5,4-b]quinoline-2-carbonyl]amino]propyl]-3-azabicyclo[3.1.0]hexane-6-carboxylic acid; 2,2,2-trifluoroacetate | 645.31 | 620.6 |
| 109 | 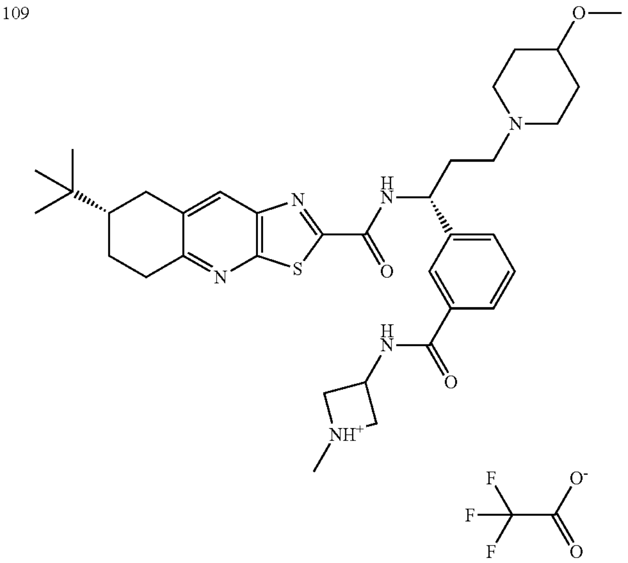 | rac-(7S)-7-tert-butyl-N-[rac-(1R)-3-(4-methoxy-1-piperidyl)-1-[3-[(1-methylazetidin-1-ium-3-yl)carbamoyl]phenyl]propyl]-5,6,7,8-tetrahydrothiazolo[5,4-b]quinoline-2-carboxamide; 2,2,2-trifluoroacetate | 633.35 | 629.4 |

-continued

| Ex. No. | Structure | Chemical Name | Mass [M + H]+ | hNPRA EC50 (nM) |
|---|---|---|---|---|
| 110 | 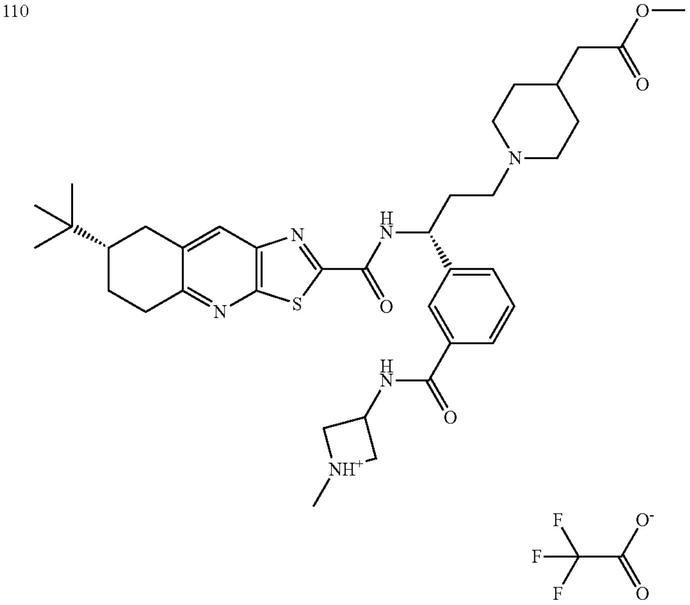 | methyl 2-[1-[rac-(3R)-3-[3-{(1-methylazetidin-1-ium-3-yl)carbamoyl] phenyl]-3-[rac-(7S)-7-tert-butyl-5,6,7,8-tetrahydrothiazolo[5,4-b] quinoline-2-carbonyl] amino]propyl]-4-piperidyl]acetate; 2,2,2-trifluoroacetate | 675.36 | 632 |
| 111 | 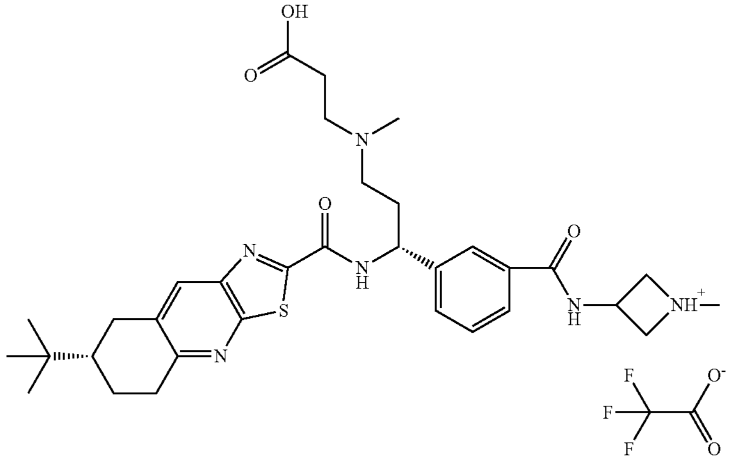 [SMILES: CN(CCC(=O)O)CC[C@@H](NC(=O)c1nc2cc3c(nc2s1)CC[C@H](C(C)(C)C)C3)c1cccc(C(=O)NC2CN(C)C2)c1 ; O=C([O-])C(F)(F)F] | 3-[methyl-[rac-(3R)-3-[3-[(1-methylazetidin-1-ium-3-yl)carbamoyl]phenyl]-3-[[rac-(7S)-7-tert-butyl-5,6,7,8-tetrahydrothiazolo[5,4-b] quinoline-2-carbonyl] amino]propyl]amino] propanoic acid; 2,2,2-trifluoroacetate | 621.3 | 645.2 |
| 112 | 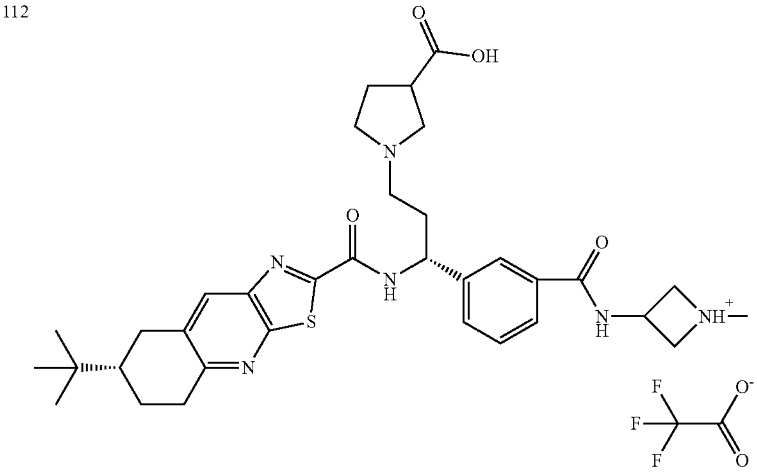 | rac-(3R)-1-[rac-(3R)-3-[3-[(1-methylazetidin-1-ium-3-yl)carbamoyl]phenyl]-3-[rac-(7S)-7-tert-butyl-5,6,7,8-tetrahydrothiazolo[5,4-b] quinoline-2-carbonyl] amino]propyl]pyrrolidine-3-carboxylic acid; 2,2,2-trifluoroacetate | 633.45 | 753.6 |

-continued

| Ex. No. | Structure | Chemical Name | Mass [M + H]+ | hNPRA EC50 (nM) |
|---|---|---|---|---|
| 113 | 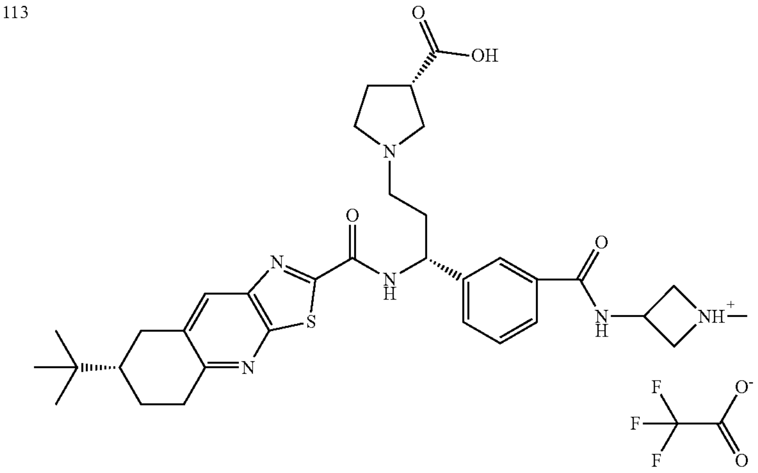 | rac-(3S)-1-[rac-(3R)-3-[3-[(1-methylazetidin-1-ium-3-yl)carbamoyl]phenyl]-3-[[rac-(7S)-7-tert-butyl-5,6,7,8-tetrahydrothiazolo[5,4-b]quinoline-2-carbonyl]amino]propyl]pyrrolidine-3-carboxylic acid; 2,2,2-trifluoroacetate | 633.4 | 938.7 |
| 114 | 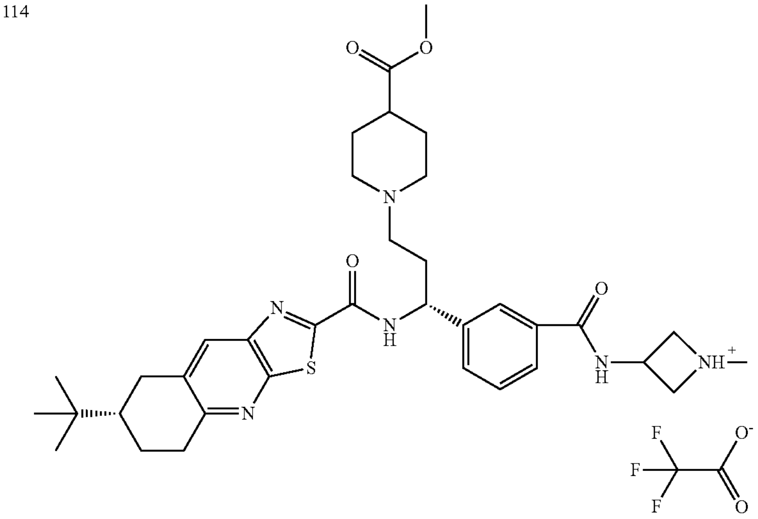 | methyl 1-[rac-(3R)-3-[3-[(1-methylazetidin-1-ium-3-yl)carbamoyl]phenyl]-3-[[rac-(7S)-7-tert-butyl-5,6,7,8-tetrahydrothiazolo[5,4-b]quinoline-2-carbonyl]amino]propyl]piperidine-4-carboxylate; 2,2,2-trifluoroacetate | 661.47 | 671 |
| 115 | 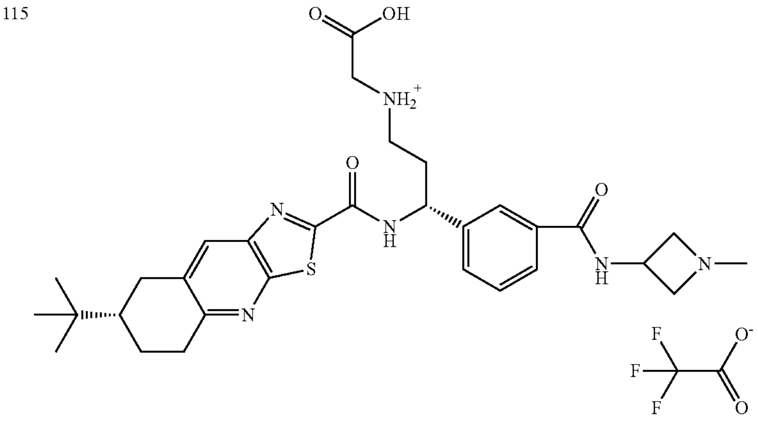 | carboxymethyl-[rac-(3R)-3-[3-[(1-methylazetidin-3-yl)carbamoyl]phenyl]-3-[rac-(7S)-7-tert-butyl-5,6,7,8-tetrahydrothiazolo[5,4-b]quinoline-2-carbonyl]amino]propyl]ammonium; 2,2,2-trifluoroacetate | 593.42 | 1414 |

Examples 116-120

Examples 116-120 were synthesized by a similar procedure as below:

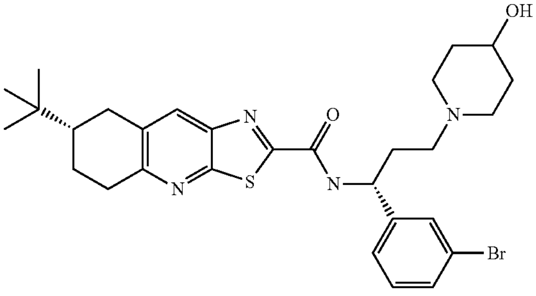

I-37

+

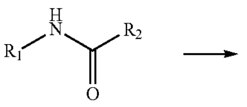

-continued

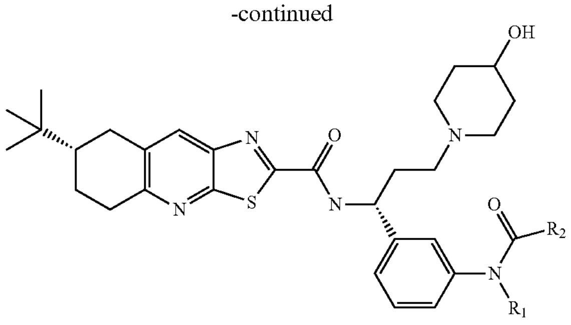

In a glove box, to a solution of(S)-N-((R)-1-(4-bromophenyl)-3-(4-hydroxypiperidin-1-yl)propyl)-7-(tert-butyl)-5,6,7,8-tetrahydrothiazolo[5,4-b]quinoline-2-carboxamide (I-37, 25 mg, 0.043 mmol) and amide/carbamate/urea substrate (0.086 mmol) in dioxane (1 mL) was added $Pd_2(dba)_3$ (3.91 mg, 4.27 μmol), Xantphos (4.94 mg, 8.54 μmol) and $Cs_2CO_3$ (41.8 mg, 0.128 mmol). The reaction was then sealed and heated to 85° C. for 24 hrs.

The reaction was cooled to ambient temperature and quenched with water (0.2 mL). The reaction mixture was partitioned between EtOAc (6 mL) and water (2 mL). The organic phase was washed with brine and then evaporated under reduced pressure. The product with Boc protecting group was treated with HCl in dioxane (2 N, 2 mL) at ambient temperature for 1 hr. The reaction mixture was concentrated in vacuum. The crude product was purified by reverse-phase HPLC (MeCN/water with 0.1% TFA modifier) to afford the desired product as a TFA salt.

| Ex. No. | Structure | Chemical Name | Mass [M + H]+ | hNPRA EC50 (nM) |
|---|---|---|---|---|
| 116 | 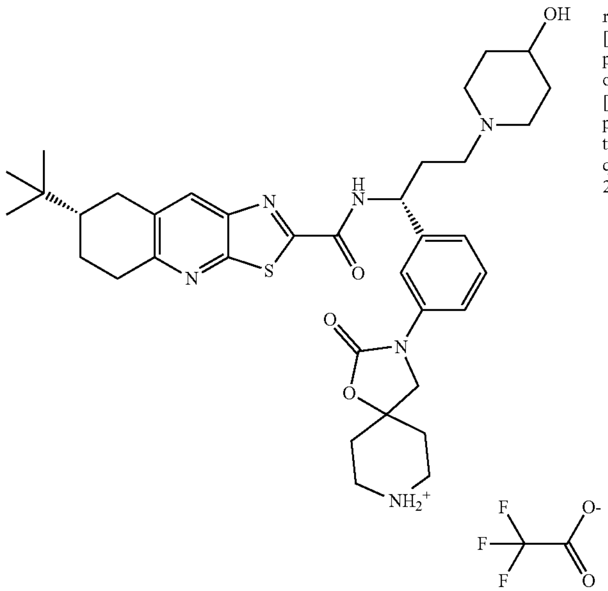 | rac-(7S)-7-tert-butyl-N-[rac-(1R)-3-(4-hydroxy-1-piperidyl)-1-[3-(2-oxo-1-oxa-3-aza-8-azoniaspiro[4.5]decan-3-yl)phenyl]propyl]-5,6,7,8-tetrahydrothiazolo[5,4-b]quinoline-2-carboxamide; 2,2,2-trifluoroacetate | 661.2 | 622.4 |

-continued

| Ex. No. | Structure | Chemical Name | Mass [M + H]+ | hNPRA EC50 (nM) |
| --- | --- | --- | --- | --- |
| 117 | 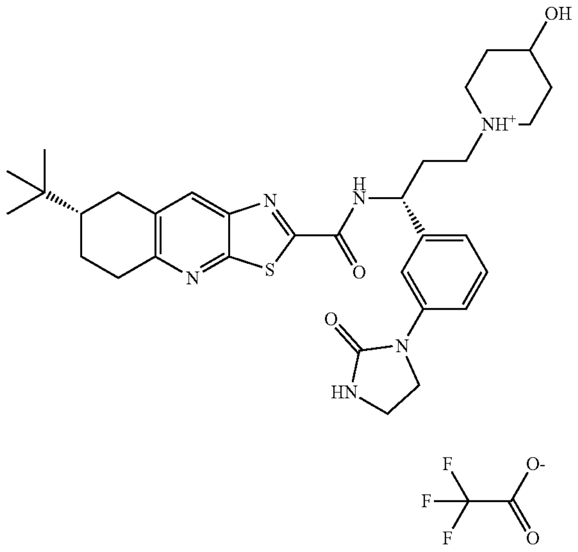 [SMILES: CC(C)(C)[C@H]1CCc2nc3sc(C(=O)N[C@H](CC[NH+]4CCC(O)CC4)c4cccc(N5CCNC5=O)c4)nc3cc2C1 ; O=C([O-])C(F)(F)F] | rac-(7S)-7-tert-butyl-N-[rac-(1R)-3-(4-hydroxypiperidin-1-ium-1-yl)-1-[3-(2-oxoimidazolidin-1-yl)phenyl]propyl]-5,6,7,8-tetrahydrothiazolo[5,4-b] quinoline-2-carboxamide; 2,2,2-trifluoroacetate | 591.21 | 795.4 |
| 118 | 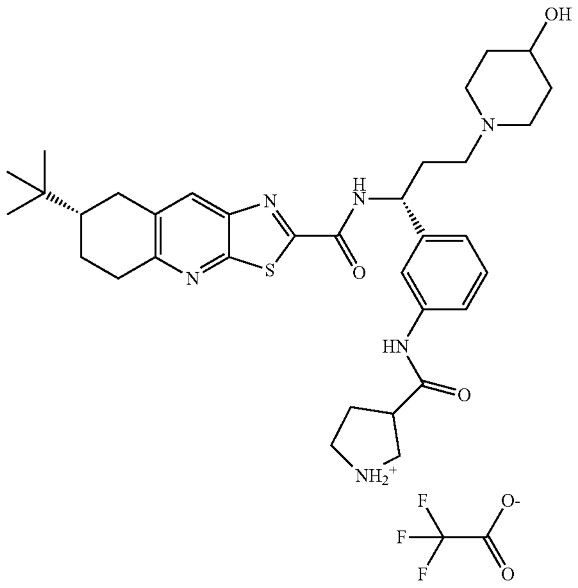 [SMILES: CC(C)(C)[C@H]1CCc2nc3sc(C(=O)N[C@H](CCN4CCC(O)CC4)c4cccc(NC(=O)C5CC[NH2+]C5)c4)nc3cc2C1 ; O=C([O-])C(F)(F)F] | rac-(7S)-7-tert-butyl-N-[rac-(1R)-3-(4-hydroxy-1-piperidyl)-1-[3-(pyrrolidin-1-ium-3-carbonylamino) phenyl]propyl]-5,6,7,8-tetrahydrothiazolo[5,4-b] quinoline-2-carboxamide; 2,2,2 trifluoroacetate | 619.36 | 984.9 |

-continued
| Ex. No. | Structure | Chemical Name | Mass [M + H]+ | hNPRA EC50 (nM) |
|---|---|---|---|---|
| 119 | 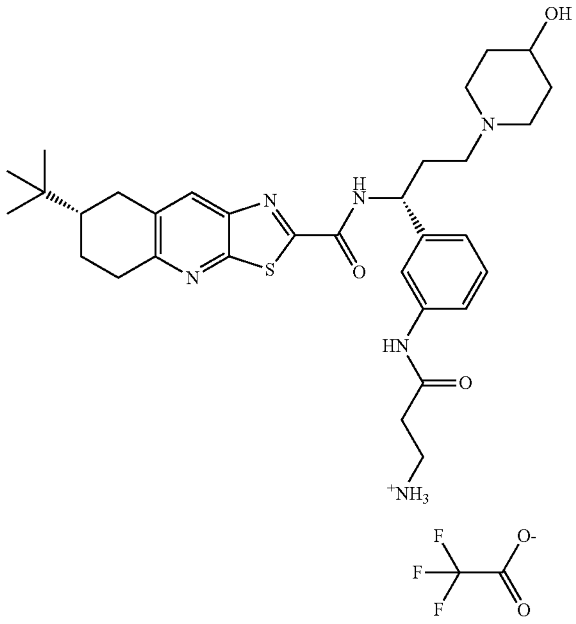 [SMILES: CC(C)(C)[C@H]1CCc2nc3sc(C(=O)N[C@H](CCN4CCC(O)CC4)c4cccc(NC(=O)CC[NH3+])c4)nc3cc2C1 ; O=C([O-])C(F)(F)F] | [3-oxo-3-[3-[rac-(1R)-3-(4-hydroxy-1-piperidyl)-1-[[rac-(7S)-7-tert-butyl-5,6,7,8-tetrahydrothiazolo[5,4-b]quinoline-2-carbonyl]amino]propyl]anilino]propyl]ammonium; 2,2,2-trifluoroacetate | 593.21 | 1209 |
| 120 | 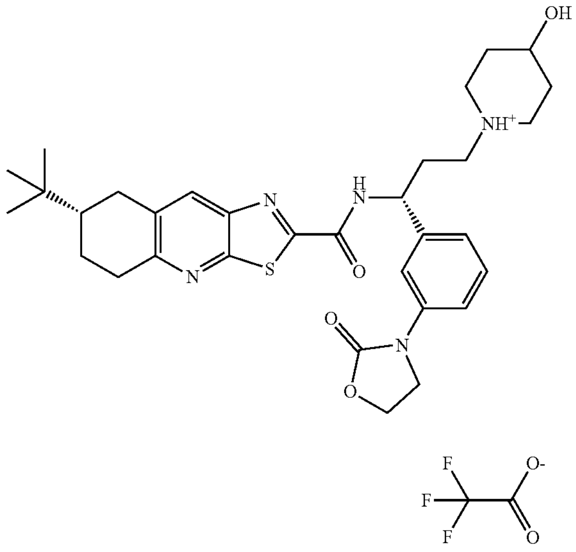 [SMILES: CC(C)(C)[C@H]1CCc2nc3sc(C(=O)N[C@H](CC[NH+]4CCC(O)CC4)c4cccc(N5CCOC5=O)c4)nc3cc2C1 ; O=C([O-])C(F)(F)F] | rac-(7S)-7-tert-butyl-N-[rac-(1R)-3-(4-hydroxypiperidin-1-ium-1-yl)-1-[3-(2-oxooxazolidin-3-yl)phenyl]propyl]-5,6,7,8-tetrahydrothiazolo[5,4-b]quinoline-2-carboxamide; 2,2,2-trifluoroacetate | 592.26 | 1669 |

Examples 121-125

Examples 121-125 were synthesized by a similar procedure as below:

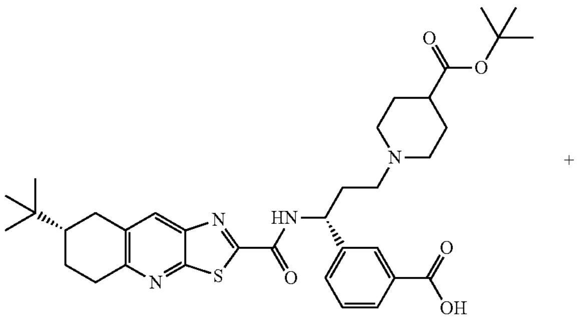

I-38

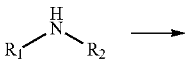

-continued

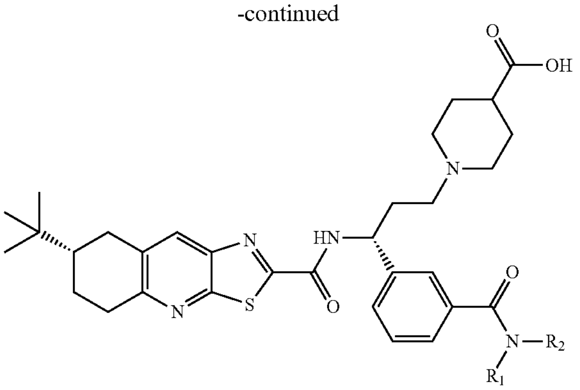

To a mixture of TBTU (25.3 mg, 0.079 mmol) and amino substrate (0.078 mmol) was added 3-((R)-3-(4-(tert-butoxycarbonyl)piperidin-1-yl)-1-((S)-7-(tert-butyl)-5,6,7,8-tetrahydrothiazolo[5,4-b]quinoline-2-carboxamido) propyl)benzoic acid (1-38, 25 mg, 0.039 mmol) solution in anhydrous DMF (1.5 mL) and DIEA (0.021 ml, 0.118 mmol). The resulting reaction mixture was stirred at ambient temperature for 6 hrs.

The reaction was partitioned between EtOAc (6 mL) and water (2 mL). The organic phase was washed with brine and then evaporated in vacuum. The residue was dissolved 10% $H_2O$/TFA (1 mL) and stirred at ambient temperature for 16 hrs and then the reaction mixture was concentrated in vacuum. The crude product was purified by reverse-phase HPLC (MeCN/water with 0.1% TFA modifier) to afford the desired product as a TFA salt.

| Ex. No. | Structure | Chemical Name | Mass [M + H]+ | hNPRA EC50 (nM) |
|---|---|---|---|---|
| 121 | 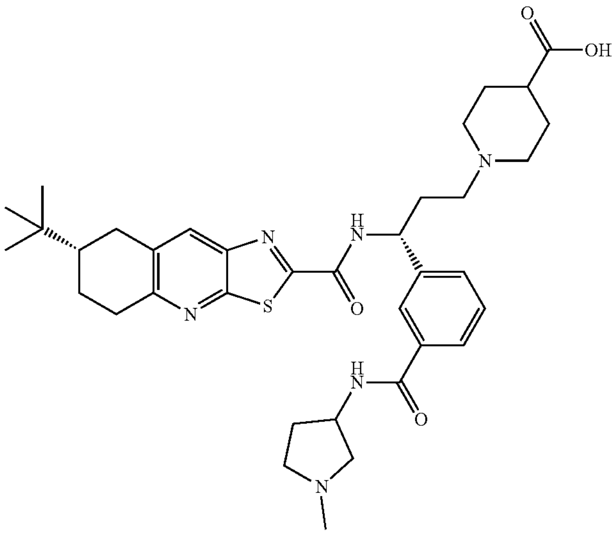 [SMILES: CN1CCC(NC(=O)c2cccc([C@@H](CCN3CCC(C(=O)O)CC3)NC(=O)c3nc4cc5c(nc4s3)CC[C@H](C(C)(C)C)C5)c2)C1] | 1-[rac-(3R)-3-[3-[(1-methylpyrrolidin-3-yl)carbamoyl]phenyl]-3-[[rac-(7S)-7-tert-butyl-5,6,7,8-tetrahydrothiazolo [5,4-b]quinoline-2-carbonyl] amino]propyl]piperidine-4-carboxylic acid | 661.35 | 224.2 |

-continued

| Ex. No. | Structure | Chemical Name | Mass [M + H]+ | hNPRA EC50 (nM) |
|---|---|---|---|---|
| 122 | 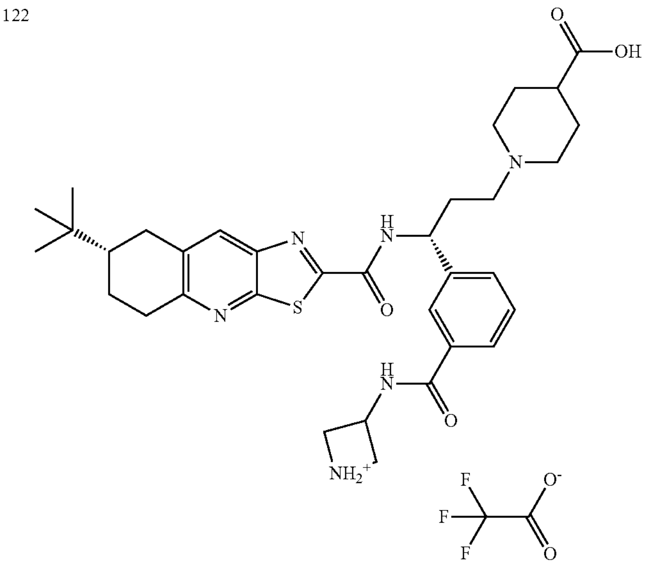 | 1-[rac-(3R)-3-[3-(azetidin-1-ium-3-ylcarbamoyl)phenyl]-3-[rac-(7S)-7-tert-butyl-5,6,7,8-tetrahydrothiazolo[5,4-b]quinoline-2-carbonyl]amino]propyl]piperidine-4-carboxylic acid; 2,2,2-trifluoroacetate | 633.31 | 636.6 |
| 123 | 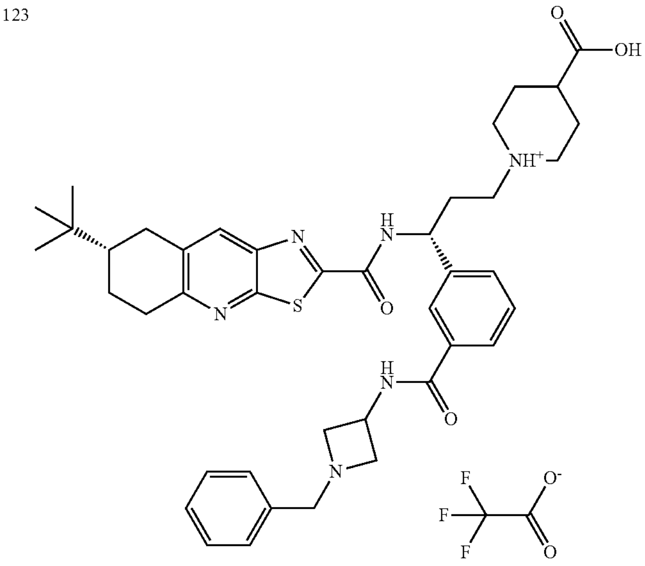 | 1-[rac-(3R)-3-[3-{(1-benzylazetidin-3-yl)carbamoyl]phenyl]-3-[[rac-(7S)-7-tert-butyl-5,6,7,8-tetrahydrothiazolo[5,4-b]quinoline-2-carbonyl]amino]propyl]piperidin-1-ium-4-carboxylic acid; 2,2,2-trifluoroacetate | 723.36 | 657.3 |

-continued

| Ex. No. | Structure | Chemical Name | Mass [M + H]+ | hNPRA EC50 (nM) |
| --- | --- | --- | --- | --- |
| 124 | 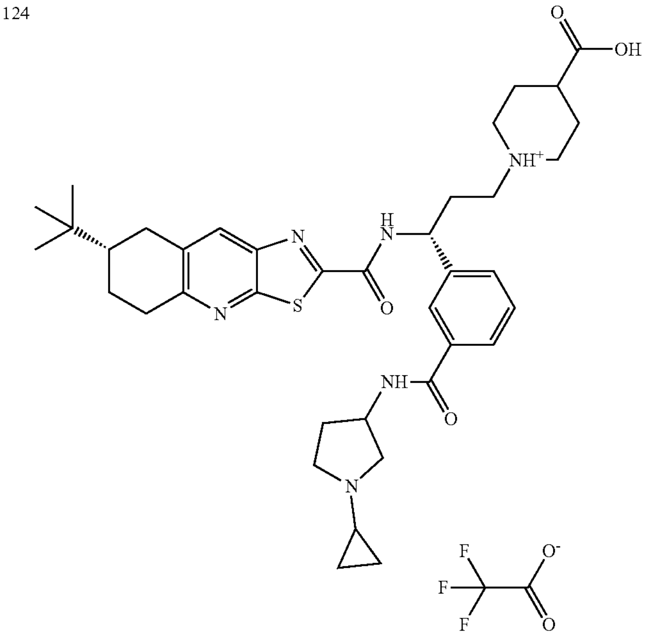 | 1-[rac-(3R)-3-[3-[(1-cyclopropylpyrrolidin-3-yl)carbamoyl]phenyl]-3-[[rac-(7S)-7-tert-butyl-5,6,7,8-tetrahydrothiazolo[5,4-b]quinoline-2-carbonyl]amino]propyl]piperidin-1-ium-4-carboxylic acid; 2,2,2-trifluoroacetate | 687.36 | 929.4 |
| 125 | 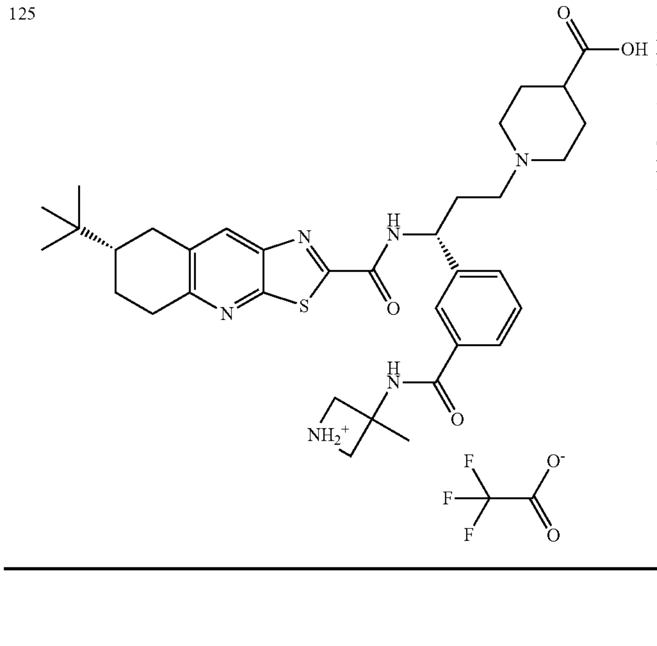 | 1-[rac-(3R)-3-[3-[(3-methylazetidin-1-ium-3-yl)carbamoyl]phenyl]-3-[[rac-(7S)-7-tert-butyl-5,6,7,8-tetrahydrothiazolo[5,4-b]quinoline-2-carbonyl]amino]propyl]piperidine-4-carboxylic acid; 2,2,2-trifluoroacetate | 647.35 | 1997 |

Examples 126-129

Examples 126-129 were synthesized by a similar procedure as below:

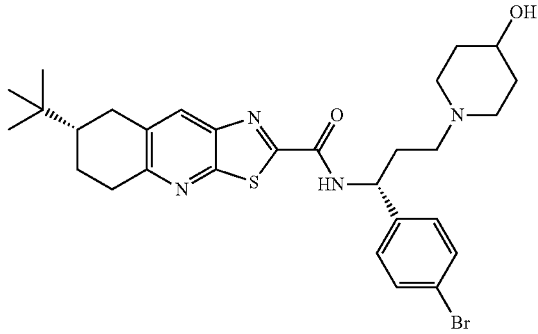

+

I-34

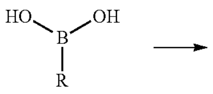

-continued

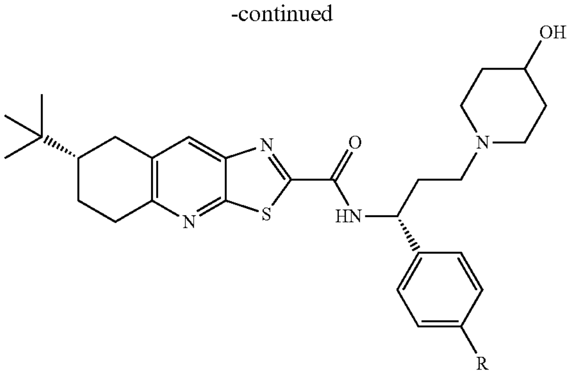

To a solution of(S)-N-((R)-1-(4-bromophenyl)-3-(4-hydroxypiperidin-1-yl)propyl)-7-(tert-butyl)-5,6,7,8-tetrahydrothiazolo[5,4-b]quinoline-2-carboxamide (1-34, 30 mg, 0.051 mmol) in dioxane (1 ml) was added Pd(dppf)$Cl_2$ (6 mg, 0.0051 mmol), boronic acid substrate (0.102 mmol) and $Na_2CO_3$ solution (2.5 N, 0.061 ml, 0.154 mmol) at ambient temperature. The resulting reaction mixture was purged with $N_2$ for 5 mins and then heated to 120° C. for 30 min in microwave.

The reaction was cooled to ambient temperature and partitioned between EtOAc (6 mL) and water (2 mL). The organic phase was washed with brine and then evaporated in vacuum. The crude product was purified by reverse-phase HPLC (MeCN/water with 0.1% TFA modifier) to afford the desired product as a TFA salt.

| Ex. No. | Structure | Chemical Name | Mass [M + H]+ | hNPRA EC50 (nM) |
|---|---|---|---|---|
| 126 | 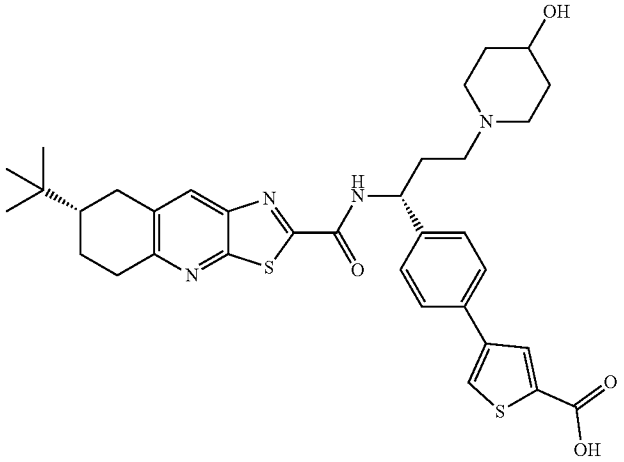 [SMILES: CC(C)(C)[C@H]1CCc2nc3sc(C(=O)N[C@H](CCN4CCC(O)CC4)c4ccc(-c5csc(C(=O)O)c5)cc4)nc3cc2C1] | 4-[4-[rac-(1R)-3-(4-hydroxy-1-piperidyl)-1-[[rac-(7S)-7-tert-butyl-5,6,7,8-tetrahydrothiazolo[5,4-b]quinoline-2-carbonyl]amino]propyl]phenylthiophene-2-carboxylic acid | 633.25 | 373.7 |

-continued
| Ex. No. | Structure | Chemical Name | Mass [M + H]+ | hNPRA EC50 (nM) |
|---|---|---|---|---|
| 127 | 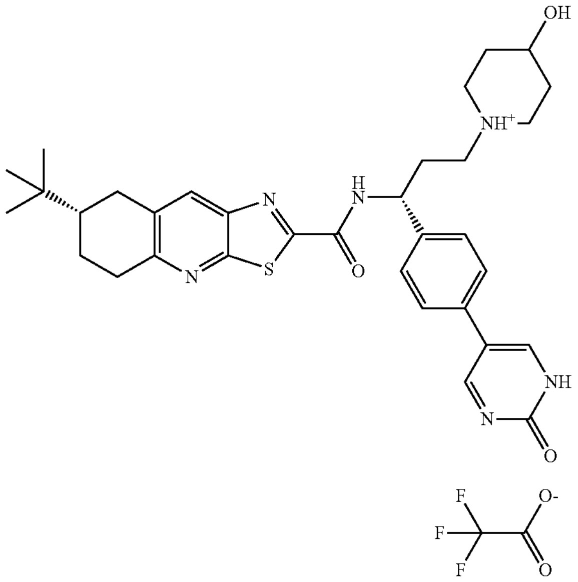 [SMILES: CC(C)(C)[C@H]1CCc2nc3sc(C(=O)N[C@H](CC[NH+]4CCC(O)CC4)c4ccc(-c5cnc(=O)[nH]c5)cc4)nc3cc2C1 ; O=C([O-])C(F)(F)F] | rac-(7S)-7-tert-butyl-N-[rac-(1R)-3-(4-hydroxypiperidin-1-ium-1-yl)-1-[4-(2-oxo-1H-pyrimidin-5-yl)phenyl]propyl]-5,6,7,8-tetrahydrothiazolo[5,4-b]quinoline-2-carboxamide; 2,2,2-trifluoroacetate | 601.29 | 452.2 |
| 128 | 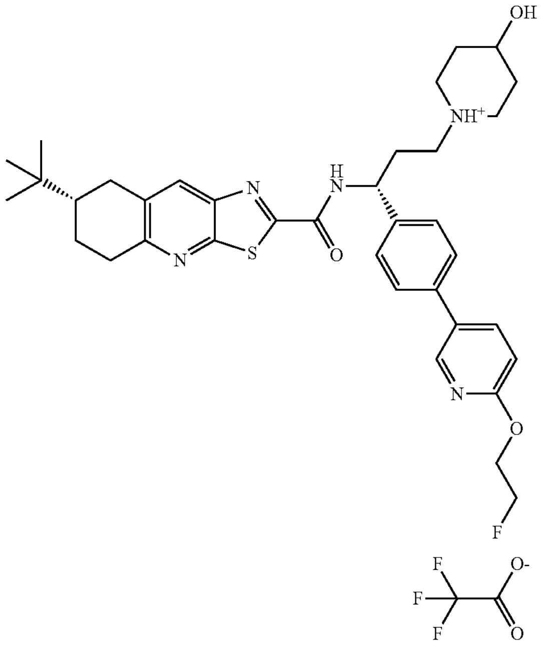 [SMILES: CC(C)(C)[C@H]1CCc2nc3sc(C(=O)N[C@H](CC[NH+]4CCC(O)CC4)c4ccc(-c5ccc(OCCF)nc5)cc4)nc3cc2C1 ; O=C([O-])C(F)(F)F] | rac-(7S)-7-tert-butyl-N-[rac-(1R)-1-[4-[6-(2-fluoroethoxy)-3-pyridyl]phenyl]-3-(4-hydroxypiperidin-1-ium-1-yl)propyl]-5,6,7,8-tetrahydrothiazolo[5,4-b]quinoline-2-carboxamide; 2,2,2-trifluoroacetate | 646.32 | 1181 |

-continued

| Ex. No. | Structure | Chemical Name | Mass [M + H]+ | hNPRA EC50 (nM) |
| --- | --- | --- | --- | --- |
| 129 | 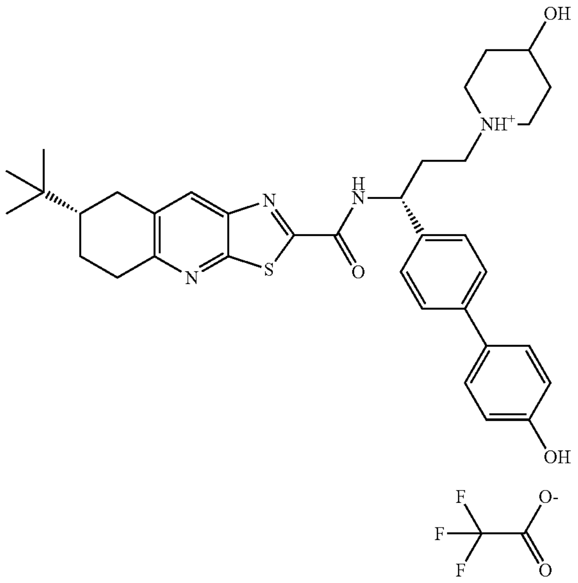 [SMILES: CC(C)(C)[C@H]1CCc2nc3sc(C(=O)N[C@H](CC[NH+]4CCC(O)CC4)c4ccc(-c5ccc(O)cc5)cc4)nc3cc2C1 ; O=C([O-])C(F)(F)F] | rac-(7S)-7-tert-butyl-N-[rac-(1R)-1-[4-(4-hydroxyphenyl)phenyl]-3-(4-hydroxypiperidin-1-ium-1-yl)propyl]-5,6,7,8-tetrahydrothiazolo[5,4-b]quinoline-2-carboxamide; 2,2,2-trifluoroacetate | 599.3 | 1438 |

Examples 130-161

Examples 130-161 were synthesized by a similar procedure as below:

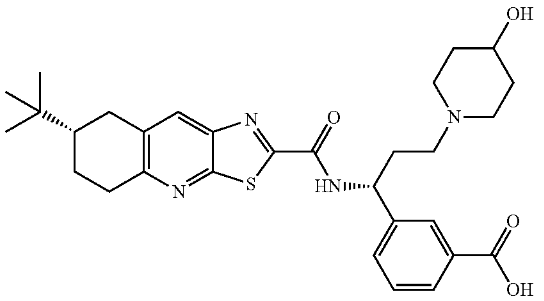

I-39

+

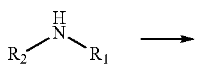

-continued

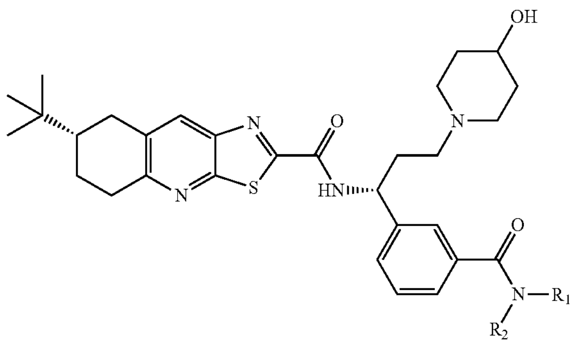

To a mixture of TBTU (29.1 mg, 0.091 mmol) and amino substrate (0.09 mmol) was added 3-((R)-1-((S)-7-(tert-butyl)-5,6,7,8-tetrahydrothiazolo[5,4-b]quinoline-2-carboxamido)-3-(4-hydroxypiperidin-1-yl)propyl)benzoic acid (1-39, 25 mg, 0.045 mmol) solution in anhydrous DMF (1.5 mL) and DIEA (0.048 mL, 0.272 mmol). The resulting reaction mixture was stirred at ambient temperature for 6 hrs.

The reaction was partitioned between EtOAc (6 mL) and water (2 mL). The organic phase was washed with brine and evaporated in vacuum. The product with Boc protecting group was treated with HCl in dioxane (2 N, 2 mL). The reaction was stirred for 4 hrs and then concentrated in vacuum. The crude product was purified by reverse-phase HPLC (MeCN/water with 0.1% ammonium hydroxide modifier) to afford the product.

| Ex. No. | Structure | Chemical Name | Mass [M + H]+ | hNPRA EC50 (nM) |
|---|---|---|---|---|
| 130 | 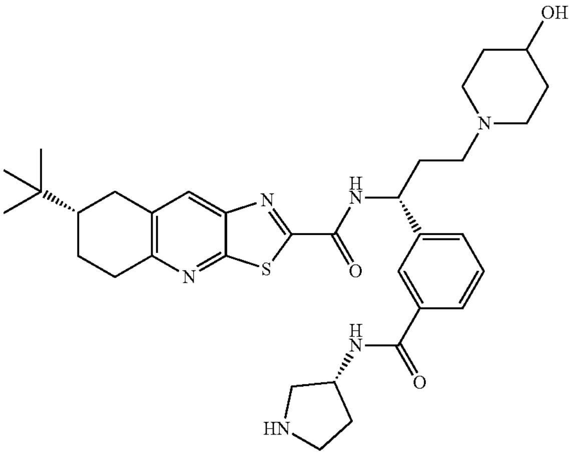 [SMILES: CC(C)(C)[C@H]1CCc2nc3sc(C(=O)N[C@H](CCN4CCC(O)CC4)c4cccc(C(=O)N[C@@H]5CCNC5)c4)nc3cc2C1] | rac-(7S)-7-tert-butyl-N-[rac-(1R)-3-(4-hydroxy-1-piperidyl)-1-[3-[[rac-(3R)-pyrrolidin-3-yl]carbamoyl]phenyl]propyl]-5,6,7,8-tetrahydrothiazolo[5,4-b]quinoline-2-carboxamide | 619.28 | 96.55 |
| 131 | 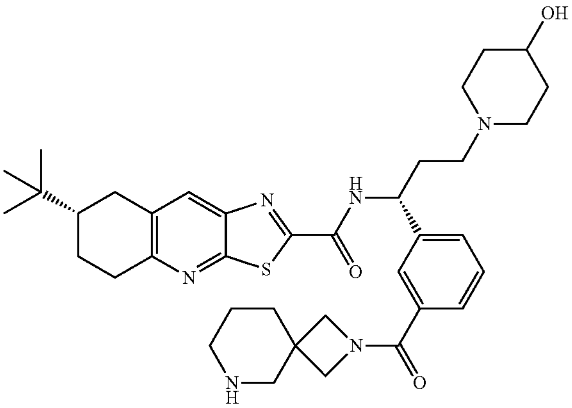 [SMILES: CC(C)(C)[C@H]1CCc2nc3sc(C(=O)N[C@H](CCN4CCC(O)CC4)c4cccc(C(=O)N5CC6(CCCNC6)C5)c4)nc3cc2C1] | rac-(7S)-7-tert-butyl-N-[rac-(1R)-1-[3-(2,8-diazaspiro[3.5]nonane-2-carbonyl)phenyl]-3-(4-hydroxy-1-piperidyl)propyl]-5,6,7,8-tetrahydrothiazolo[5,4-b]quinoline-2-carboxamide | 659.29 | 96.66 |
| 132 | 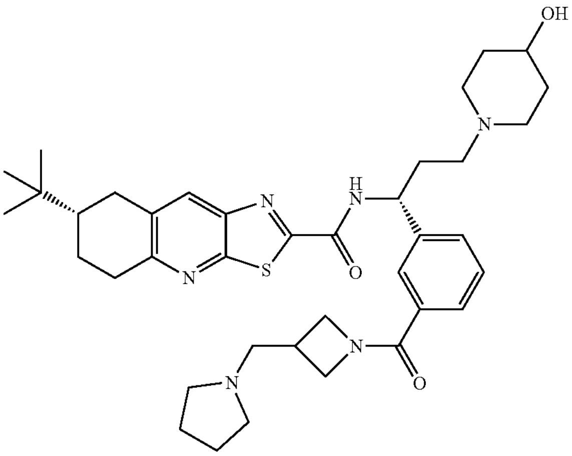 [SMILES: CC(C)(C)[C@H]1CCc2nc3sc(C(=O)N[C@H](CCN4CCC(O)CC4)c4cccc(C(=O)N5CC(CN6CCCC6)C5)c4)nc3cc2C1] | rac-(7S)-7-tert-butyl-N-[rac-(1R)-3-(4-hydroxy-1-piperidyl)-1-[3-[3-(pyrrolidin-1-ylmethyl)azetidine-1-carbonyl]phenyl]propyl]-5,6,7,8-tetrahydrothiazolo[5,4-b]quinoline-2-carboxamide | 673.27 | 101.7 |

-continued

| Ex. No. | Structure | Chemical Name | Mass [M + H]+ | hNPRA EC50 (nM) |
|---|---|---|---|---|
| 133 | 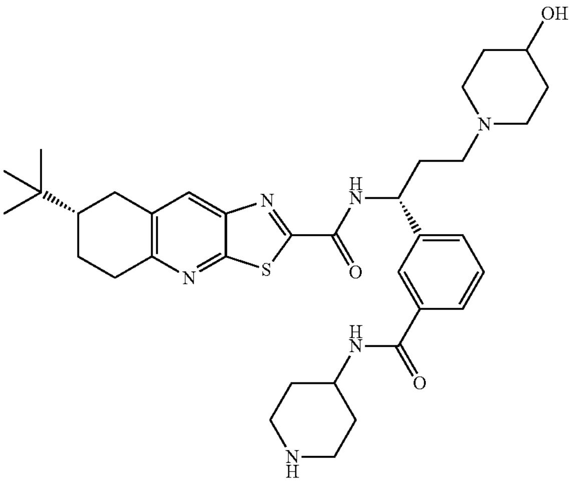 [SMILES: CC(C)(C)[C@H]1CCc2nc3sc(C(=O)N[C@H](CCN4CCC(O)CC4)c4cccc(C(=O)NC5CCNCC5)c4)nc3cc2C1] | rac-(7S)-7-tert-butyl-N-[rac-(1R)-3-(4-hydroxy-1-piperidyl)-1-[3-(4-piperidylcarbamoyl)phenyl]propyl]-5,6,7,8-tetrahydrothiazolo[5,4-b]quinoline-2-carboxamide | 633.22 | 116.7 |
| 134 | 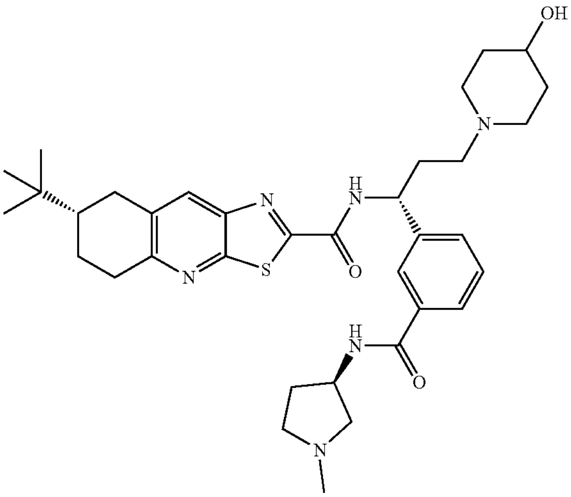 [SMILES: CN1CC[C@@H](NC(=O)c2cccc([C@@H](CCN3CCC(O)CC3)NC(=O)c3nc4cc5c(nc4s3)CC[C@H](C(C)(C)C)C5)c2)C1] | rac-(7S)-7-tert-butyl-N-[rac-(1R)-3-(4-hydroxy-1-piperidyl)-1-[3-[[rac-(3R)-1-methylpyrrolidin-3-yl]carbamoyl]phenyl]propyl]-5,6,7,8-tetrahydrothiazolo[5,4-b]quinoline-2-carboxamide | 633.27 | 126.1 |
| 135 | 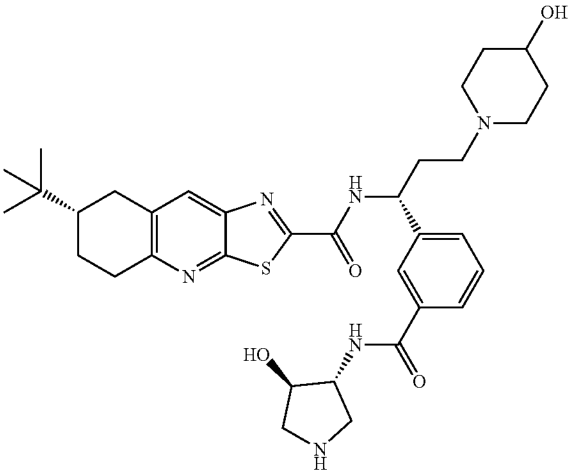 [SMILES: CC(C)(C)[C@H]1CCc2nc3sc(C(=O)N[C@H](CCN4CCC(O)CC4)c4cccc(C(=O)N[C@@H]5CNC[C@H]5O)c4)nc3cc2C1] | rac-(7S)-7-tert-butyl-N-[rac-(1R)-3-(4-hydroxy-1-piperidyl)-1-[3-[[rac-(3R,4R)-4-hydroxypyrrolidin-3-yl]carbamoyl]phenyl]propyl]-5,6,7,8-tetrahydrothiazolo[5,4-b]quinoline-2-carboxamide | 635.24 | 132.3 |

-continued

| Ex. No. | Structure | Chemical Name | Mass [M + H]+ | hNPRA EC50 (nM) |
|---|---|---|---|---|
| 136 | 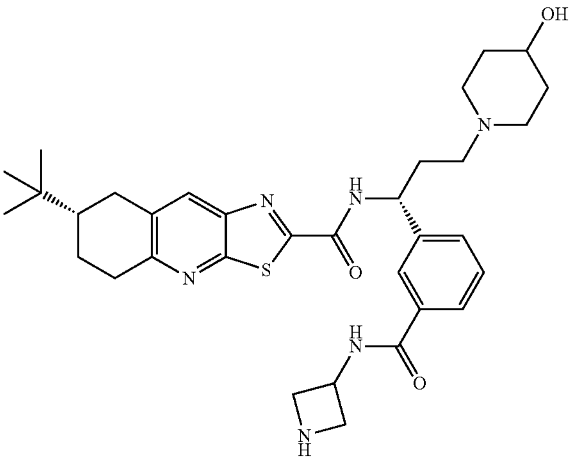 [SMILES: CC(C)(C)[C@H]1CCc2nc3sc(C(=O)N[C@H](CCN4CCC(O)CC4)c4cccc(C(=O)NC5CNC5)c4)nc3cc2C1] | rac-(7S)-7-tert-butyl-N-[rac-(1R)-1-[3-(azetidin-3-ylcarbamoyl)phenyl]-3-(4-hydroxy-1-piperidyl)propyl]-5,6,7,8-tetrahydrothiazolo[5,4-b]quinoline-2-carboxamide | 605.23 | 137.6 |
| 137 | 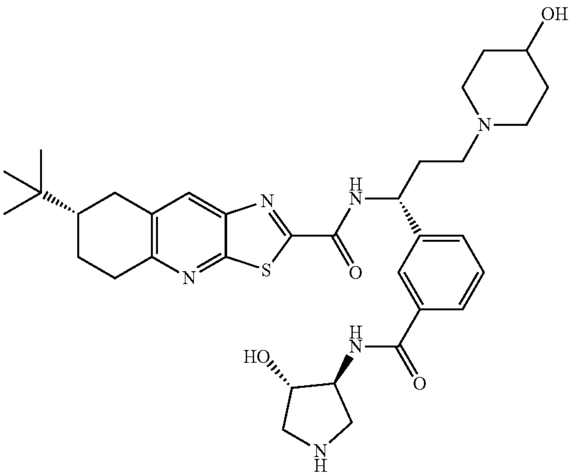 [SMILES: CC(C)(C)[C@H]1CCc2nc3sc(C(=O)N[C@H](CCN4CCC(O)CC4)c4cccc(C(=O)N[C@H]5CNC[C@@H]5O)c4)nc3cc2C1] | rac-(7S)-7-tert-butyl-N-[rac-(1R)-3-(4-hydroxy-1-piperidyl)-1-[3-[[rac-(3S,4S)-4-hydroxypyrrolidin-3-yl]carbamoyl]phenyl]propyl]-5,6,7,8-tetrahydrothiazolo[5,4-b]quinoline-2-carboxamide | 635.32 | 175.8 |
| 138 | 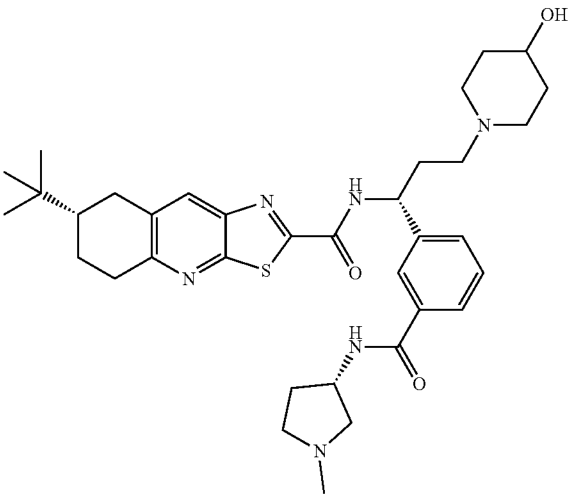 [SMILES: CN1CC[C@H](NC(=O)c2cccc([C@@H](CCN3CCC(O)CC3)NC(=O)c3nc4cc5c(nc4s3)CC[C@H](C(C)(C)C)C5)c2)C1] | rac-(7S)-7-tert-butyl-N-[rac-(1R)-3-(4-hydroxy-1-piperidyl)-1-[3-[[rac-(3S)-1-methylpyrrolidin-3-yl]carbamoyl]phenyl]propyl]-5,6,7,8-tetrahydrothiazolo[5,4-b]quinoline-2-carboxamide | 633.3 | 210 |

-continued

| Ex. No. | Structure | Chemical Name | Mass [M + H]+ | hNPRA EC50 (nM) |
|---|---|---|---|---|
| 139 | 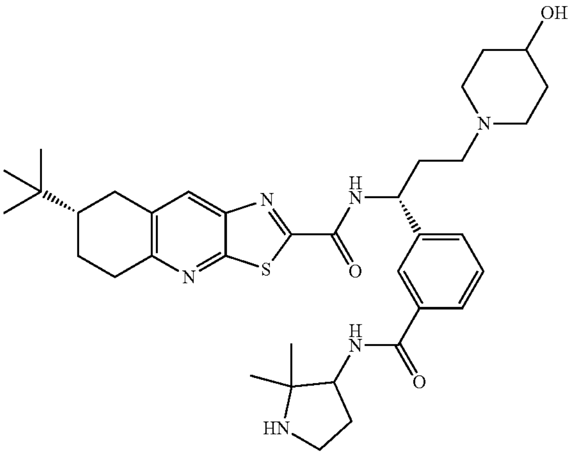 [SMILES: CC1(C)NCCC1NC(=O)c1cccc([C@@H](CCN2CCC(O)CC2)NC(=O)c2nc3cc4c(nc3s2)CC[C@H](C(C)(C)C)C4)c1] | rac-(7S)-7-tert-butyl-N-[rac-(1R)-1-[3-[(2,2-dimethylpyrrolidin-3-yl)carbamoyl]phenyl]-3-(4-hydroxy-1-piperidyl)propyl]-5,6,7,8-tetrahydrothiazolo[5,4-b]quinoline-2-carboxamide | 647.29 | 219.5 |
| 140 | 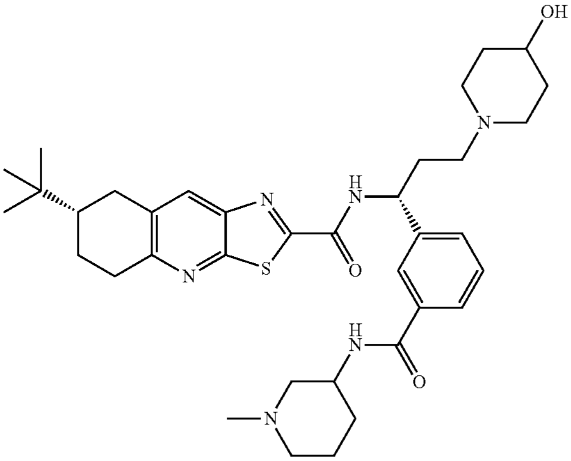 [SMILES: CN1CCCC(NC(=O)c2cccc([C@@H](CCN3CCC(O)CC3)NC(=O)c3nc4cc5c(nc4s3)CC[C@H](C(C)(C)C)C5)c2)C1] | rac-(7S)-7-tert-butyl-N-[rac-(1R)-3-(4-hydroxy-1-piperidyl)-1-[3-[(1-methyl-3-piperidyl)carbamoyl]phenyl]propyl]-5,6,7,8-tetrahydrothiazolo[5,4-b]quinoline-2-carboxamide | 647.3 | 224.5 |
| 141 | 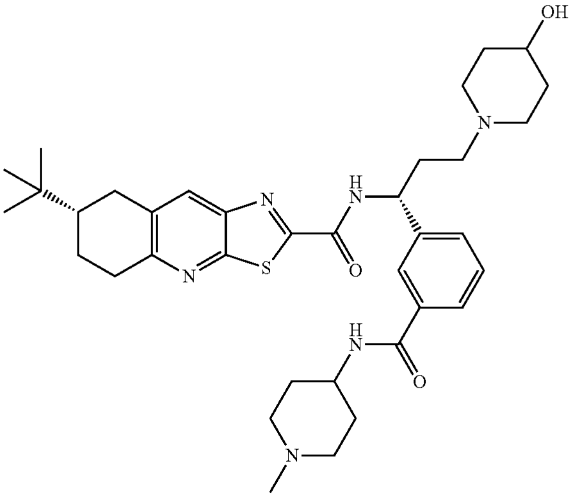 [SMILES: CN1CCC(NC(=O)c2cccc([C@@H](CCN3CCC(O)CC3)NC(=O)c3nc4cc5c(nc4s3)CC[C@H](C(C)(C)C)C5)c2)CC1] | rac-(7S)-7-tert-butyl-N-[rac-(1R)-3-(4-hydroxy-1-piperidyl)-1-[3-[(1-methyl-4-piperidyl)carbamoyl]phenyl]propyl]-5,6,7,8-tetrahydrothiazolo[5,4-b]quinoline-2-carboxamide | 647.15 | 257.6 |

-continued

| Ex. No. | Structure | Chemical Name | Mass [M + H]+ | hNPRA EC50 (nM) |
|---|---|---|---|---|
| 142 | 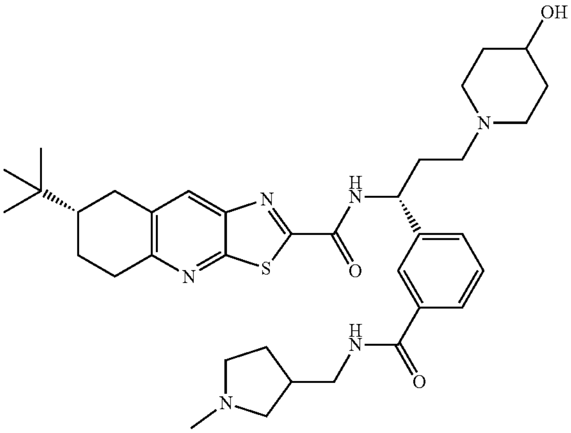 [SMILES: CN1CCC(CNC(=O)c2cccc([C@@H](CCN3CCC(O)CC3)NC(=O)c3nc4cc5c(nc4s3)CC[C@H](C(C)(C)C)C5)c2)C1] | rac-(7S)-7-tert-butyl-N-[rac-(1R)-3-(4-hydroxy-1-piperidyl)-1-[3-[(1-methylpyrrolidin-3-yl)methylcarbamoyl]phenyl]propyl]-5,6,7,8-tetrahydrothiazolo[5,4-b]quinoline-2-carboxamide | 647.22 | 258.5 |
| 143 | 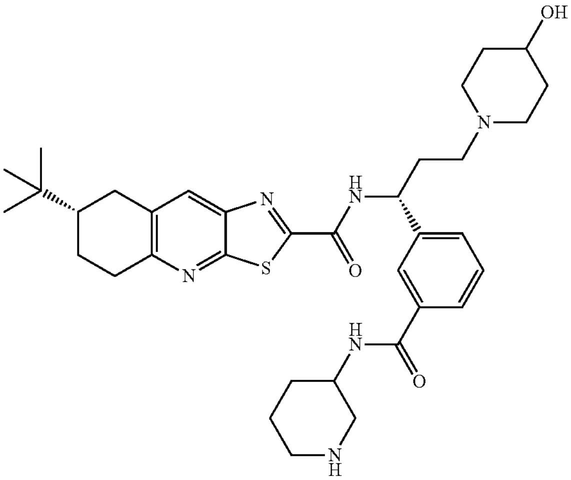 [SMILES: CC(C)(C)[C@H]1CCc2nc3sc(C(=O)N[C@H](CCN4CCC(O)CC4)c4cccc(C(=O)NC5CCCNC5)c4)nc3cc2C1] | rac-(7S)-7-tert-butyl-N-[rac-(1R)-3-(4-hydroxy-1-piperidyl)-1-[3-(3-piperidylcarbamoyl)phenyl]propyl]-5,6,7,8-tetrahydrothiazolo[5,4-b]quinoline-2-carboxamide | 633.27 | 276 |
| 144 | 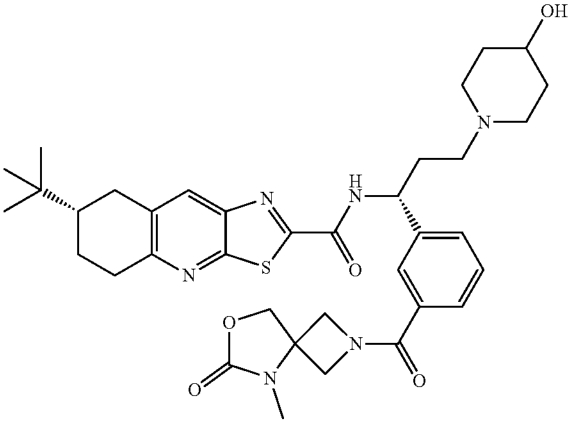 [SMILES: CN1C(=O)OCC12CN(C(=O)c1cccc([C@@H](CCN3CCC(O)CC3)NC(=O)c3nc4cc5c(nc4s3)CC[C@H](C(C)(C)C)C5)c1)C2] | rac-(7S)-7-tert-butyl-N-[rac-(1R)-3-(4-hydroxy-1-piperidyl)-1-[3-(5-methyl-6-oxo-7-oxa-2,5-diazaspiro[3.4]octane-2-carbonyl)phenyl]propyl]-5,6,7,8-tetrahydrothiazolo[5,4-b]quinoline-2-carboxamide | 675.25 | 461.8 |

-continued

| Ex. No. | Structure | Chemical Name | Mass [M + H]+ | hNPRA EC50 (nM) |
|---|---|---|---|---|
| 145 | 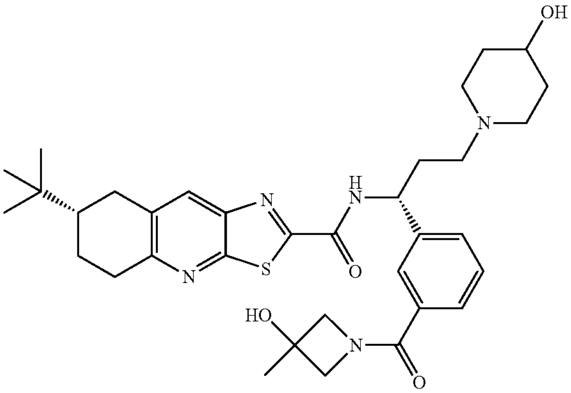 [SMILES: CC1(O)CN(C(=O)c2cccc([C@@H](CCN3CCC(O)CC3)NC(=O)c3nc4cc5c(nc4s3)CC[C@H](C(C)(C)C)C5)c2)C1] | rac-(7S)-7-tert-butyl-N-[rac-(1R)-1-[3-(3-hydroxy-3-methyl-azetidine-1-carbonyl)phenyl]-3-(4-hydroxy-1-piperidyl)propyl]-5,6,7,8-tetrahydrothiazolo[5,4-b]quinoline-2-carboxamide | 620.22 | 553.5 |
| 146 | 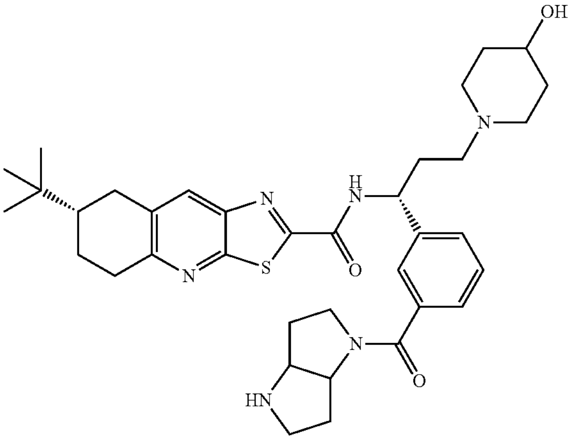 [SMILES: CC(C)(C)[C@H]1CCc2nc3sc(C(=O)N[C@H](CCN4CCC(O)CC4)c4cccc(C(=O)N5CCC6NCCC65)c4)nc3cc2C1] | rac-(7S)-7-tert-butyl-N-[rac-(1R)-1-[3-(2,3,3a,5,6,6a-hexahydro-1H-pyrrolo[3,2-b]pyrrole-4-carbonyl)phenyl]-3-(4-hydroxy-1-piperidyl)propyl]-5,6,7,8-tetrahydrothiazolo[5,4-b]quinoline-2-carboxamide | 645.27 | 606.5 |
| 147 | 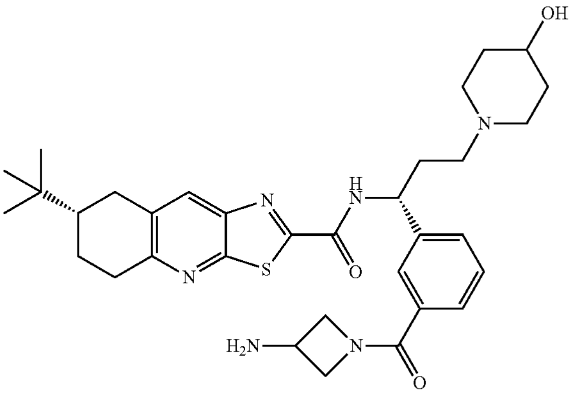 [SMILES: CC(C)(C)[C@H]1CCc2nc3sc(C(=O)N[C@H](CCN4CCC(O)CC4)c4cccc(C(=O)N5CC(N)C5)c4)nc3cc2C1] | rac-(7S)-7-tert-butyl-N-[rac-(1R)-1-[3-(3-aminoazetidine-1-carbonyl)phenyl]-3-(4-hydroxy-1-piperidyl)propyl]-5,6,7,8-tetrahydrothiazolo[5,4-b]quinoline-2-carboxamide | 605.29 | 639.7 |

-continued

| Ex. No. | Structure | Chemical Name | Mass [M + H]+ | hNPRA EC50 (nM) |
|---|---|---|---|---|
| 148 | 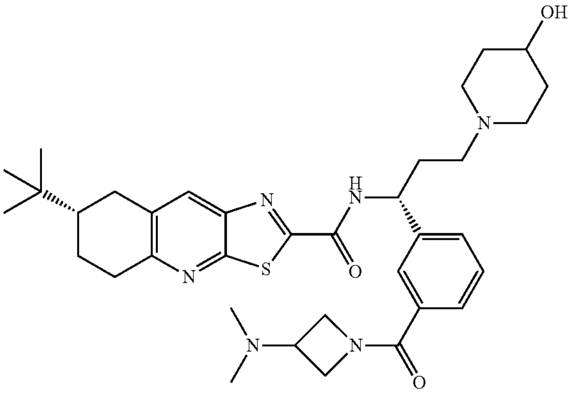 [SMILES: CN(C)C1CN(C(=O)c2cccc([C@@H](CCN3CCC(O)CC3)NC(=O)c3nc4cc5c(nc4s3)CC[C@H](C(C)(C)C)C5)c2)C1] | rac-(7S)-7-tert-butyl-N-[rac-(1R)-1-[3-[3-(dimethylamino)azetidine-1-carbonyl]phenyl]-3-(4-hydroxy-1-piperidyl)propyl]-5,6,7,8-tetrahydrothiazolo[5,4-b]quinoline-2-carboxamide | 633.27 | 655.6 |
| 149 | 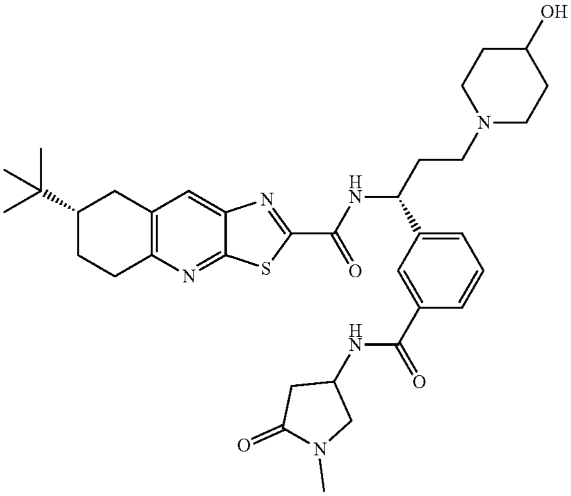 [SMILES: CN1CC(NC(=O)c2cccc([C@@H](CCN3CCC(O)CC3)NC(=O)c3nc4cc5c(nc4s3)CC[C@H](C(C)(C)C)C5)c2)CC1=O] | rac-(7S)-7-tert-butyl-N-[rac-(1R)-3-(4-hydroxy-1-piperidyl)-1-[3-[(1-methyl-5-oxo-pyrrolidin-3-yl)carbamoyl]phenyl]propyl]-5,6,7,8-tetrahydrothiazolo[5,4-b]quinoline-2-carboxamide | 647.26 | 656.4 |
| 150 | 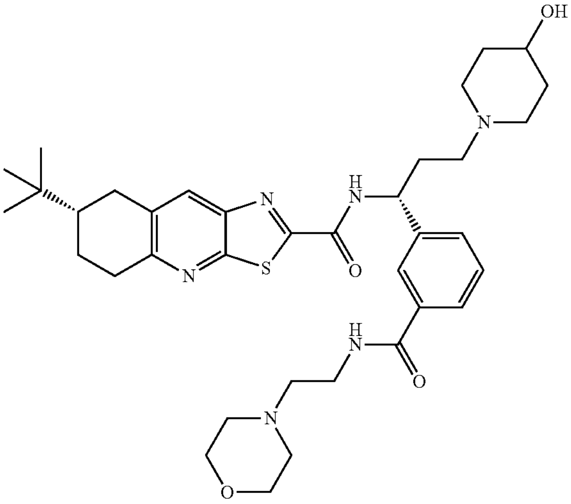 [SMILES: CC(C)(C)[C@H]1CCc2nc3sc(C(=O)N[C@H](CCN4CCC(O)CC4)c4cccc(C(=O)NCCN5CCOCC5)c4)nc3cc2C1] | rac-(7S)-7-tert-butyl-N-[rac-(1R)-3-(4-hydroxy-1-piperidyl)-1-[3-(2-morpholinoethylcarbamoyl)phenyl]propyl]-5,6,7,8-tetrahydrothiazolo[5,4-b]quinoline-2-carboxamide | 663.17 | 681.8 |

-continued

| Ex. No. | Structure | Chemical Name | Mass [M + H]+ | hNPRA EC50 (nM) |
|---|---|---|---|---|
| 151 | 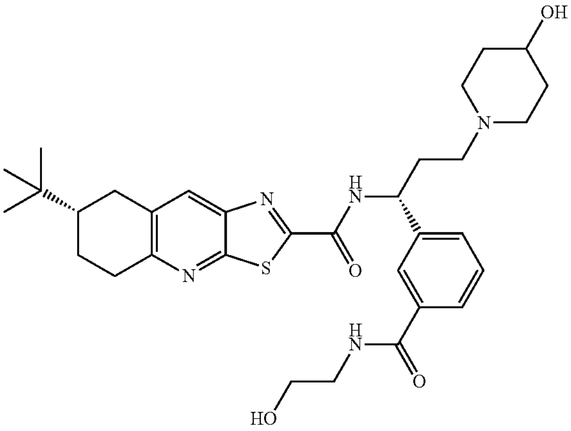 [SMILES: CC(C)(C)[C@H]1CCc2nc3sc(C(=O)N[C@H](CCN4CCC(O)CC4)c4cccc(C(=O)NCCO)c4)nc3cc2C1] | rac-(7S)-7-tert-butyl-N-[rac-(1R)-1-[3-(2-hydroxyethylcarbamoyl)phenyl]-3-(4-hydroxy-1-piperidyl)propyl]-5,6,7,8-tetrahydrothiazolo[5,4-b]quinoline-2-carboxamide | 594.14 | 681.9 |
| 152 | 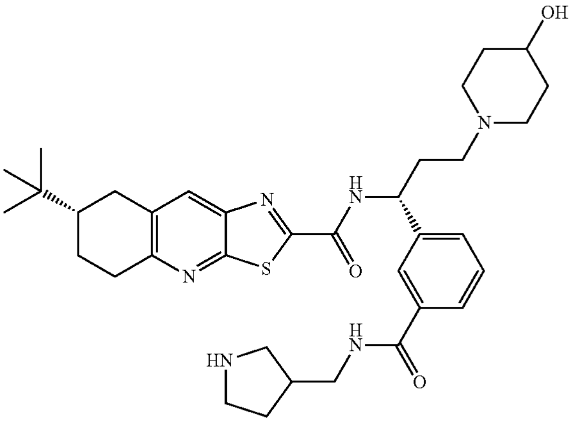 [SMILES: CC(C)(C)[C@H]1CCc2nc3sc(C(=O)N[C@H](CCN4CCC(O)CC4)c4cccc(C(=O)NCC5CCNC5)c4)nc3cc2C1] | rac-(7S)-7-tert-butyl-N-[rac-(1R)-3-(4-hydroxy-1-piperidyl)-1-[3-(pyrrolidin-3-ylmethylcarbamoyl)phenyl]propyl]-5,6,7,8-tetrahydrothiazolo[5,4-b]quinoline-2-carboxamide | 633.3 | 685.9 |
| 153 | 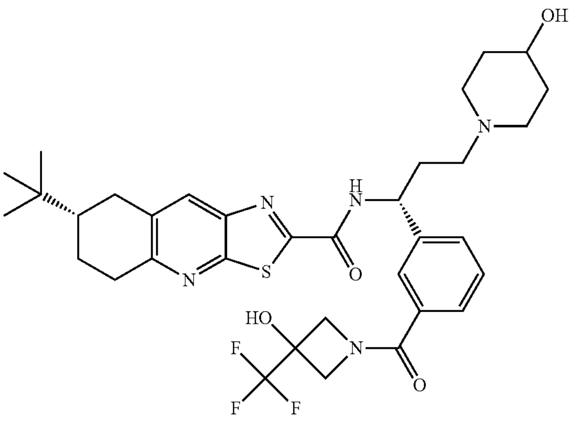 [SMILES: CC(C)(C)[C@H]1CCc2nc3sc(C(=O)N[C@H](CCN4CCC(O)CC4)c4cccc(C(=O)N5CC(O)(C(F)(F)F)C5)c4)nc3cc2C1] | rac-(7S)-7-tert-butyl-N-[rac-(1R)-3-(4-hydroxy-1-piperidyl)-1-[3-[3-hydroxy-3-(trifluoromethyl)azetidine-1-carbonyl]phenyl]propyl]-5,6,7,8-tetrahydrothiazolo[5,4-b]quinoline-2-carboxamide | 674.2 | 716.5 |

-continued

| Ex. No. | Structure | Chemical Name | Mass [M + H]+ | hNPRA EC50 (nM) |
|---|---|---|---|---|
| 154 | 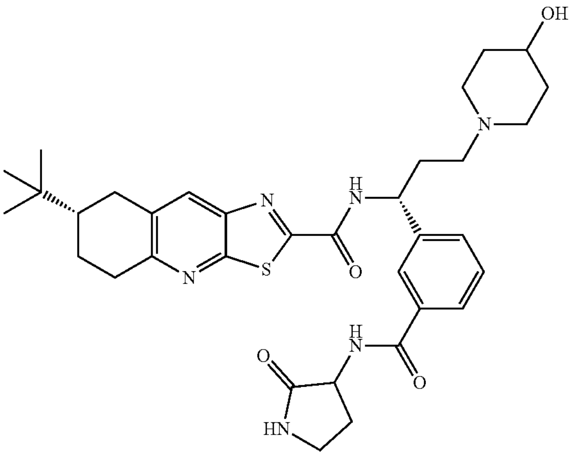 [SMILES: CC(C)(C)[C@H]1CCc2nc3sc(C(=O)N[C@H](CCN4CCC(O)CC4)c4cccc(C(=O)NC5CCNC5=O)c4)nc3cc2C1] | rac-(7S)-7-tert-butyl-N-[rac-(1R)-3-(4-hydroxy-1-piperidyl)-1-[3-[(2-oxopyrrolidin-3-yl)carbamoyl]phenyl]propyl]-5,6,7,8-tetrahydrothiazolo[5,4-b]quinoline-2-carboxamide | 633.35 | 721.2 |
| 155 | 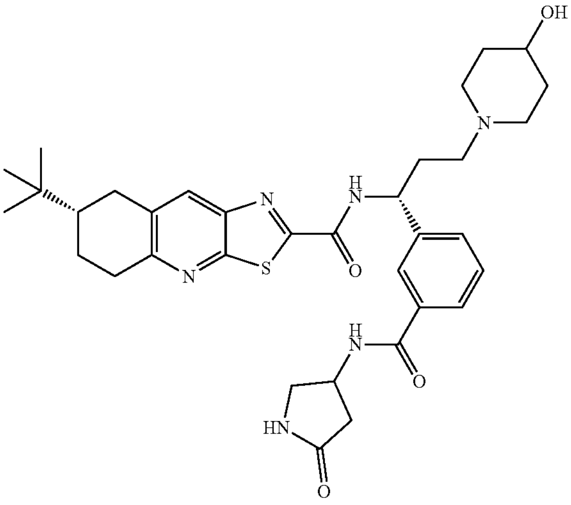 [SMILES: CC(C)(C)[C@H]1CCc2nc3sc(C(=O)N[C@H](CCN4CCC(O)CC4)c4cccc(C(=O)NC5CNC(=O)C5)c4)nc3cc2C1] | rac-(7S)-7-tert-butyl-N-[rac-(1R)-3-(4-hydroxy-1-piperidyl)-1-[3-[(5-oxopyrrolidin-3-yl)carbamoyl]phenyl]propyl]-5,6,7,8-tetrahydrothiazolo[5,4-b]quinoline-2-carboxamide | 633.31 | 765.8 |
| 156 | 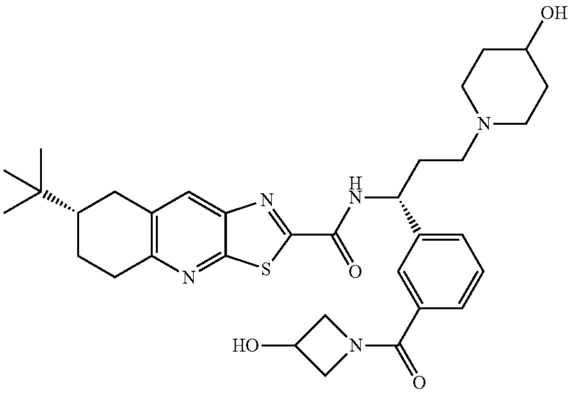 | rac-(7S)-7-tert-butyl-N-[rac-(1R)-1-[3-(3-hydroxyazetidine-1-carbonyl)phenyl]-3-(4-hydroxy-1-piperidyl)propyl]-5,6,7,8-tetrahydrothiazolo[5,4-b]quinoline-2-carboxamide | 606.19 | 829.8 |

-continued

| Ex. No. | Structure | Chemical Name | Mass [M + H]+ | hNPRA EC50 (nM) |
|---|---|---|---|---|
| 157 | 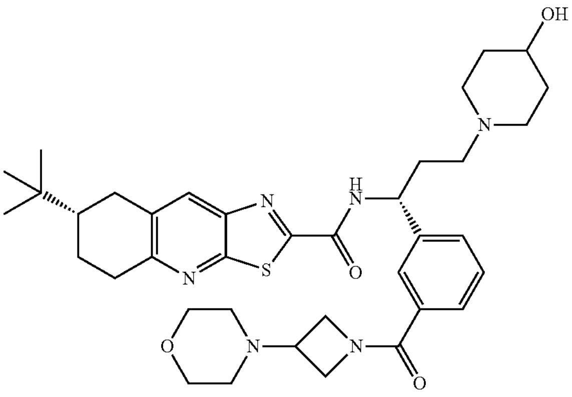 [SMILES: CC(C)(C)[C@H]1CCc2nc3sc(C(=O)N[C@H](CCN4CCC(O)CC4)c4cccc(C(=O)N5CC(N6CCOCC6)C5)c4)nc3cc2C1] | rac-(7S)-7-tert-butyl-N-[rac-(1R)-3-(4-hydroxy-1-piperidyl)-1-[3-(3-morpholinoazetidine-1-carbonyl)phenyl]propyl]-5,6,7,8-tetrahydrothiazolo[5,4-b]quinoline-2-carboxamide | 675.22 | 876.1 |
| 158 | 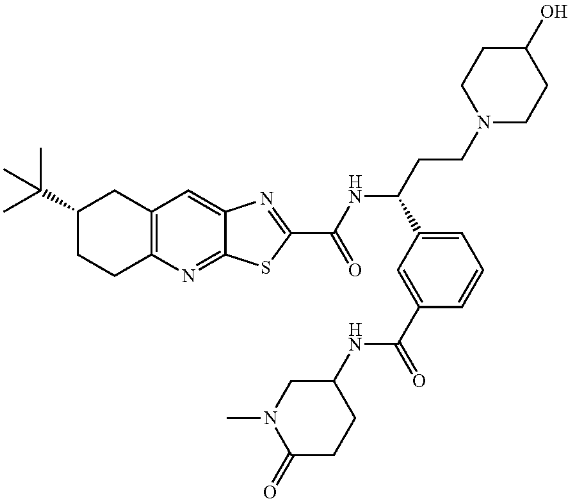 [SMILES: CN1CC(NC(=O)c2cccc([C@@H](CCN3CCC(O)CC3)NC(=O)c3nc4cc5c(nc4s3)CC[C@H](C(C)(C)C)C5)c2)CCC1=O] | rac-(7S)-7-tert-butyl-N-[rac-(1R)-3-(4-hydroxy-1-piperidyl)-1-[3-[(1-methyl-6-oxo-3-piperidyl)carbamoyl]phenyl] propyl]-5,6,7,8-tetrahydrothiazolo[5,4-b]quinoline-2-carboxamide | 661.26 | 890.2 |
| 159 | 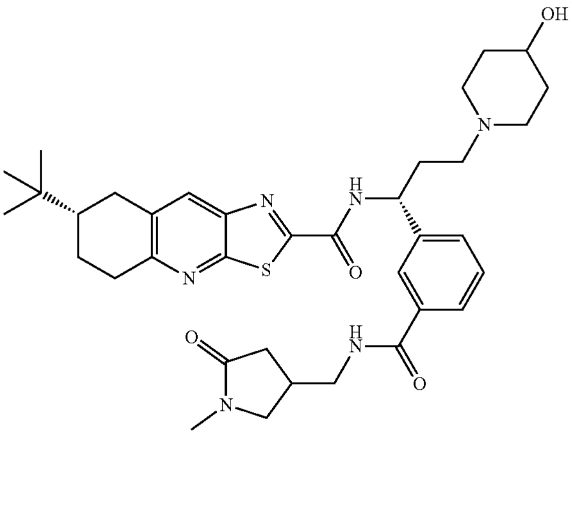 [SMILES: CN1CC(CNC(=O)c2cccc([C@@H](CCN3CCC(O)CC3)NC(=O)c3nc4cc5c(nc4s3)CC[C@H](C(C)(C)C)C5)c2)CC1=O] | rac-(7S)-7-tert-butyl-N-[rac-(1R)-3-(4-hydroxy-1-piperidyl)-1-[3-[(1-methyl-5-oxo-pyrrolidin-3-yl)methylcarbamoyl]phenyl] propyl]-5,6,7,8-tetrahydrothiazolo[5,4-b]quinoline-2-carboxamide | 661.31 | 901.2 |

-continued

| Ex. No. | Structure | Chemical Name | Mass [M + H]+ | hNPRA EC50 (nM) |
|---|---|---|---|---|
| 160 | 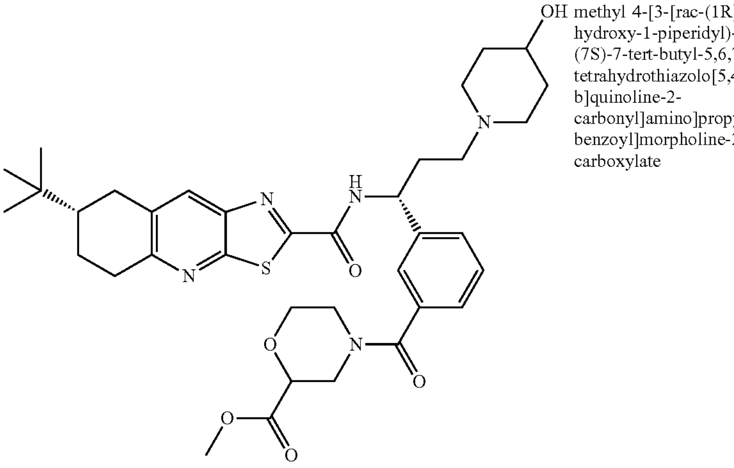 | methyl 4-[3-[rac-(1R)-3-(4-hydroxy-1-piperidyl)-1-[[rac-(7S)-7-tert-butyl-5,6,7,8-tetrahydrothiazolo[5,4-b]quinoline-2-carbonyl]amino]propyl] benzoyl]morpholine-2-carboxylate | 678.27 | 1212 |
| 161 | 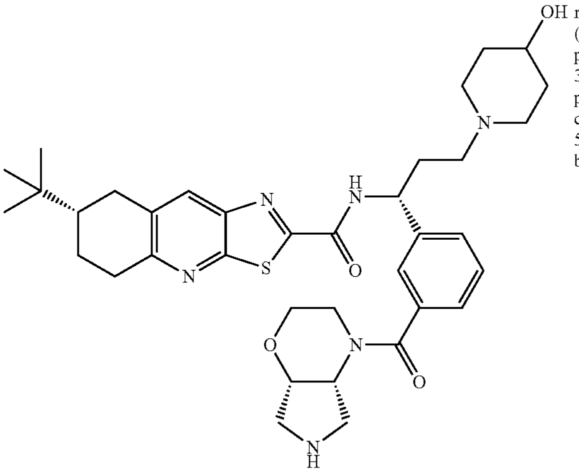 | rac-(7S)-7-tert-butyl-N-[rac-(1R)-3-(4-hydroxy-1-piperidyl)-1-[3-[rac-(4aR,7aS)-3,4a,5,6,7,7a-hexahydro-2H-pyrrolo[3,4-b][1,4]oxazine-4-carbonyl]phenyl]propyl]-5,6,7,8-tetrahydrothiazolo[5,4-b]quinoline-2-carboxamide | 661.2 | 1954 |

Examples 162-185

Examples 162-185 were synthesized by a similar procedure as below:

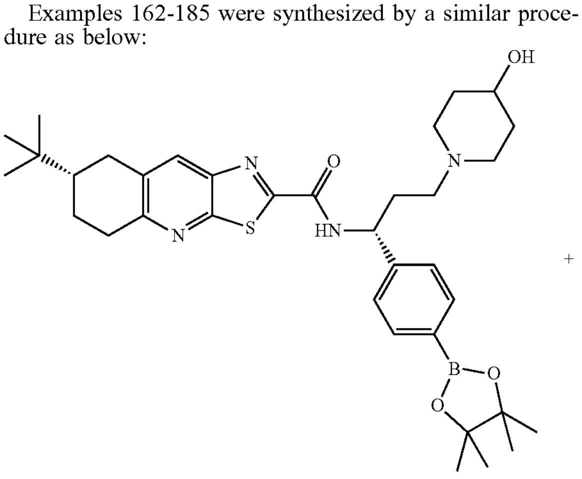

I-40

Br—R

-continued

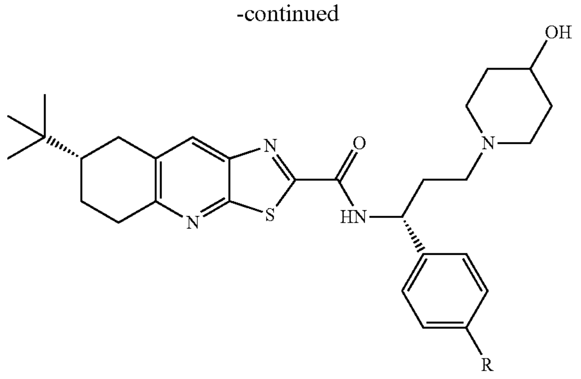

To a solution of(S)-7-(tert-butyl)-N-((R)-3-(4-hydroxypiperidin-1-yl)-1-(4-(4,4,5,5-tetramethyl-1,3,2-dioxaborolan-2-yl)phenyl)propyl)-5,6,7,8-tetrahydrothiazolo[5,4-b]quinoline-2-carboxamide (I-40, 25 mg, 0.040 mmol) in dioxane (1 mL) was added Pd(dppf)$Cl_2$ (4.57 mg, 3.95 μmol), bromo substrate (0.08 mmol) and $Na_2CO_3$ solution (2.5 N, 0.032 ml, 0.079 mmol) at ambient temperature. The resulting reaction mixture was purged with $N_2$ for 5 mins and then stirred at 100° C. for 16 hrs.

The reaction was cooled to ambient temperature and partitioned between EtOAc (6 mL) and water (2 mL). The organic phase was washed with brine and then concentrated in vacuum. The crude product was purified by reverse-phase HPLC (MeCN/water with 0.1% TFA modifier) to afford the product as a TFA salt.

| Ex. No. | Structure | Chemical Name | Mass [M + H]+ | hNPRA EC50 (nM) |
|---|---|---|---|---|
| 162 | 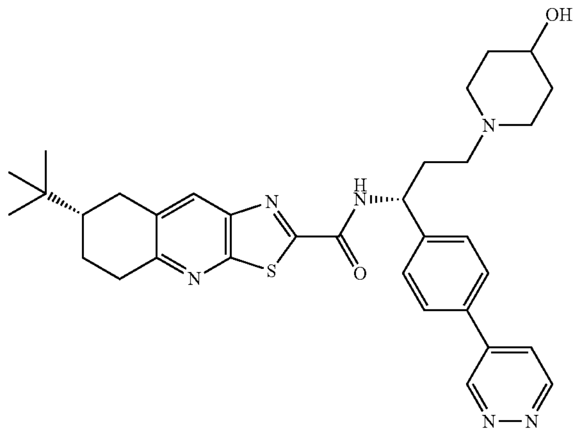 [SMILES: CC(C)(C)[C@H]1CCc2nc3sc(C(=O)N[C@H](CCN4CCC(O)CC4)c4ccc(-c5ccnnc5)cc4)nc3cc2C1] | rac-(7S)-7-tert-butyl-N-[rac-(1R)-3-(4-hydroxy-1-piperidyl)-1-(4-pyridazin-4-ylphenyl)propyl]-5,6,7,8-tetrahydrothiazolo[5,4-b]quinoline-2-carboxamide | 585.34 | 198.2 |
| 163 | 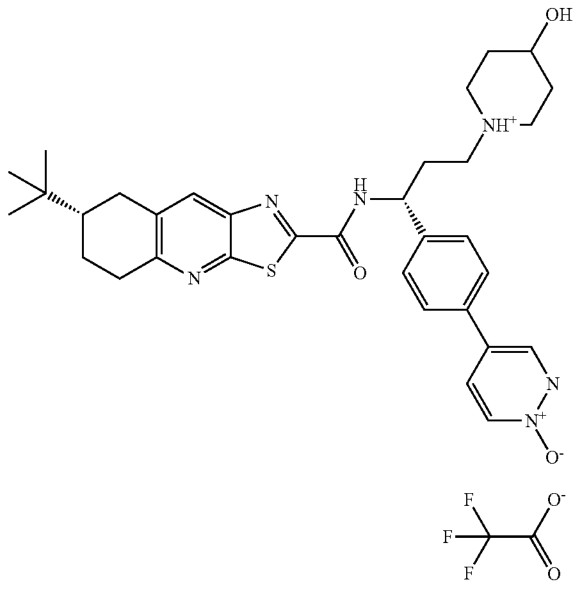 [SMILES: CC(C)(C)[C@H]1CCc2nc3sc(C(=O)N[C@H](CC[NH+]4CCC(O)CC4)c4ccc(C5=CN[NH+]([O-])C=C5)cc4)nc3cc2C1 ; O=C([O-])C(F)(F)F] | rac-(7S)-7-tert-butyl-N-[rac-(1R)-3-(4-hydroxypiperidin-1-ium-1-yl)-1-[4-(1-oxidopyridazin-1-ium-4-yl)phenyl]propyl]-5,6,7,8-tetrahydrothiazolo[5,4-b]quinoline-2-carboxamide; 2,2,2-trifluoroacetate | 601.25 | 356.6 |

-continued
| Ex. No. | Structure | Chemical Name | Mass [M + H]+ | hNPRA EC50 (nM) |
|---|---|---|---|---|
| 164 | 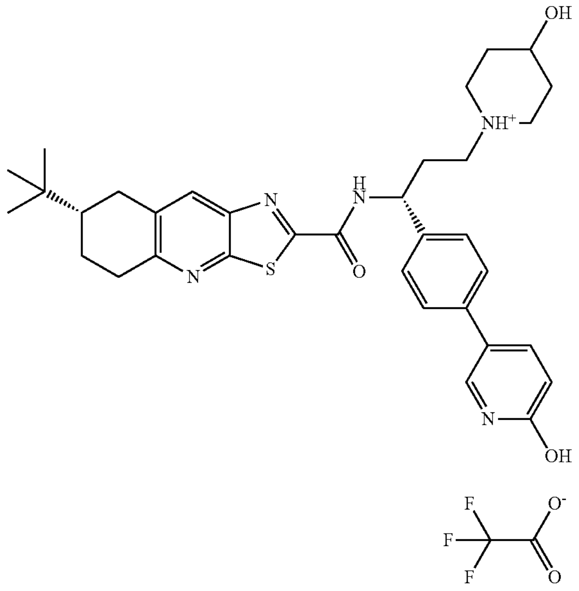 [SMILES: CC(C)(C)[C@H]1CCc2nc3sc(C(=O)N[C@H](CC[NH+]4CCC(O)CC4)c4ccc(-c5ccc(O)nc5)cc4)nc3cc2C1 ; O=C([O-])C(F)(F)F] | rac-(7S)-7-tert-butyl-N-[rac-(1R)-3-(4-hydroxypiperidin-1-ium-1-yl)-1-[4-(6-hydroxy-3-pyridyl)phenyl]propyl]-5,6,7,8-tetrahydrothiazolo[5,4-b]quinoline-2-carboxamide; 2,2,2-trifluoroacetate | 600.24 | 589.7 |
| 165 | 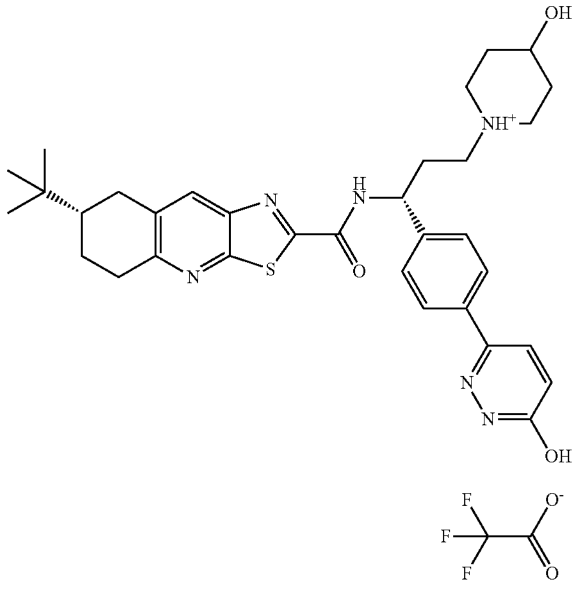 [SMILES: CC(C)(C)[C@H]1CCc2nc3sc(C(=O)N[C@H](CC[NH+]4CCC(O)CC4)c4ccc(-c5ccc(O)nn5)cc4)nc3cc2C1 ; O=C([O-])C(F)(F)F] | rac-(7S)-7-tert-butyl-N-[rac-(1R)-3-(4-hydroxypiperidin-1-ium-1-yl)-1-[4-(6-hydroxypyridazin-3-yl)phenyl]propyl]-5,6,7,8-tetrahydrothiazolo[5,4-b]quinoline-2-carboxamide; 2,2,2-trifluoroacetate | 601.23 | 611.2 |

-continued

| Ex. No. | Structure | Chemical Name | Mass [M + H]+ | hNPRA EC50 (nM) |
|---|---|---|---|---|
| 166 | 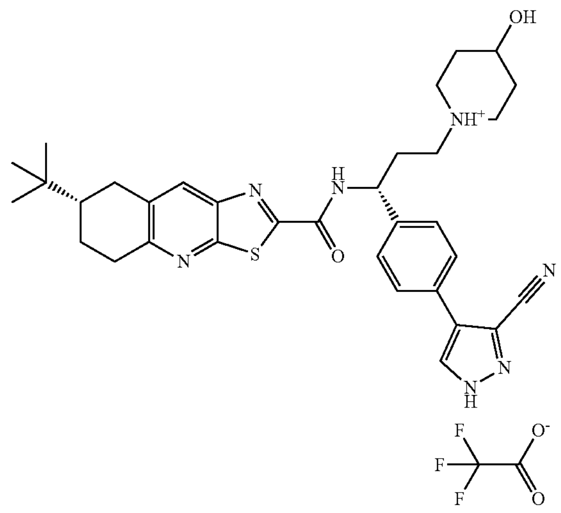 [SMILES: CC(C)(C)[C@H]1CCc2nc3sc(C(=O)N[C@H](CC[NH+]4CCC(O)CC4)c4ccc(-c5c[nH]nc5C#N)cc4)nc3cc2C1 ; O=C([O-])C(F)(F)F] | rac-(7S)-7-tert-butyl-N-[rac-(1R)-1-[4-(3-cyano-1H-pyrazol-4-yl)phenyl]-3-(4-hydroxypiperidin-1-ium-1-yl)propyl]-5,6,7,8-tetrahydrothiazolo[5,4-b]quinoline-2-carboxamide; 2,2,2-trifluoroacetate | 598.24 | 613.8 |
| 167 | 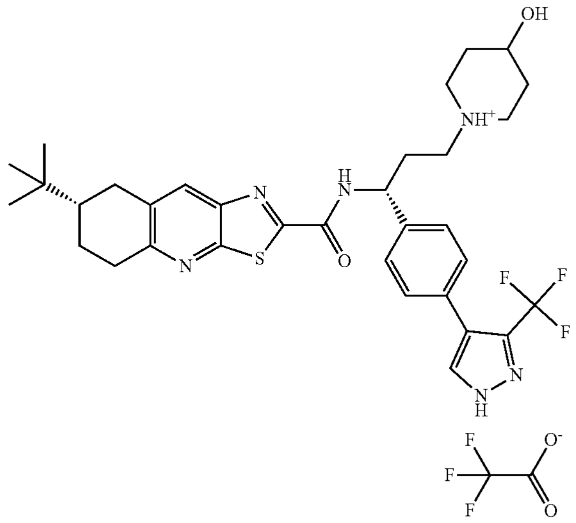 [SMILES: CC(C)(C)[C@H]1CCc2nc3sc(C(=O)N[C@H](CC[NH+]4CCC(O)CC4)c4ccc(-c5c[nH]nc5C(F)(F)F)cc4)nc3cc2C1 ; O=C([O-])C(F)(F)F] | rac-(7S)-7-tert-butyl-N-[rac-(1R)-3-(4-hydroxypiperidin-1-ium-1-yl)-1-[4-[3-(trifluoromethyl)-1H-pyrazol-4-yl]phenyl]propyl]-5,6,7,8-tetrahydrothiazolo[5,4-b]quinoline-2-carboxamide; 2,2,2-trifluoroacetate | 641.26 | 665.7 |
| 168 | 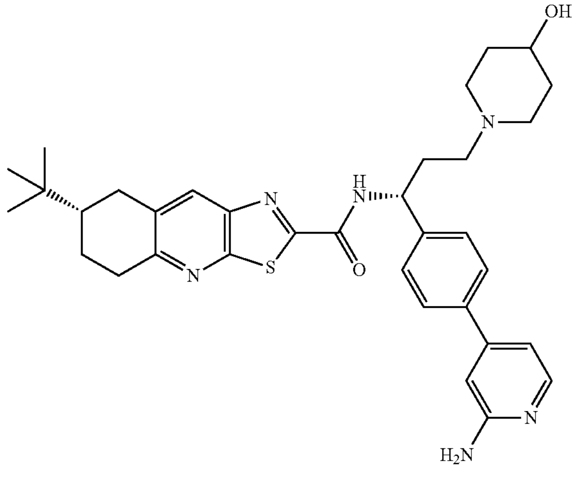 [SMILES: CC(C)(C)[C@H]1CCc2nc3sc(C(=O)N[C@H](CCN4CCC(O)CC4)c4ccc(-c5ccnc(N)c5)cc4)nc3cc2C1] | rac-(7S)-7-tert-butyl-N-[rac-(1R)-1-[4-(2-amino-4-pyridyl)phenyl]-3-(4-hydroxy-1-piperidyl)propyl]-5,6,7,8-tetrahydrothiazolo[5,4-b]quinoline-2-carboxamide | 599.33 | 772.7 |

-continued

| Ex. No. | Structure | Chemical Name | Mass [M + H]+ | hNPRA EC50 (nM) |
|---|---|---|---|---|
| 169 | 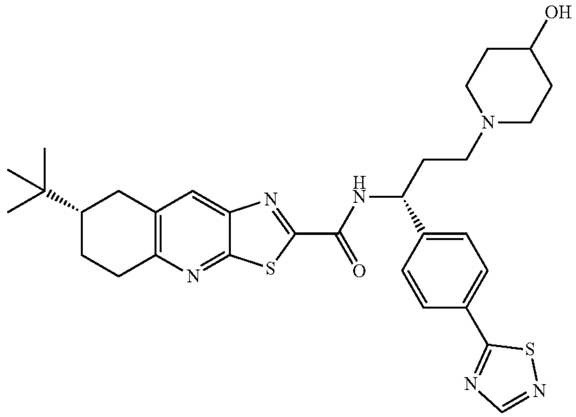 [SMILES: CC(C)(C)[C@H]1CCc2nc3sc(C(=O)N[C@H](CCN4CCC(O)CC4)c4ccc(-c5ncns5)cc4)nc3cc2C1] | rac-(7S)-7-tert-butyl-N-[rac-(1R)-3-(4-hydroxy-1-piperidyl)-1-[4-(1,2,4-thiadiazol-5-yl)phenyl]propyl]-5,6,7,8-tetrahydrothiazolo[5,4-b]quinoline-2-carboxamide | 591.14 | 792.7 |
| 170 | 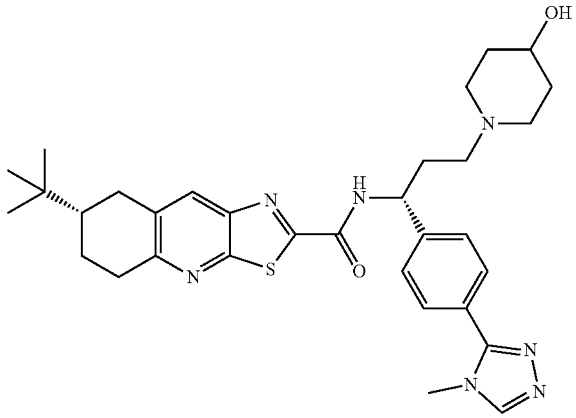 [SMILES: Cn1cnnc1-c1ccc([C@@H](CCN2CCC(O)CC2)NC(=O)c2nc3cc4c(nc3s2)CC[C@H](C(C)(C)C)C4)cc1] | rac-(7S)-7-tert-butyl-N-[rac-(1R)-3-(4-hydroxy-1-piperidyl)-1-[4-(4-methyl-1,2,4-triazol-3-yl)phenyl]propyl]-5,6,7,8-tetrahydrothiazolo[5,4-b]quinoline-2-carboxamide | 588.15 | 863.3 |
| 171 | 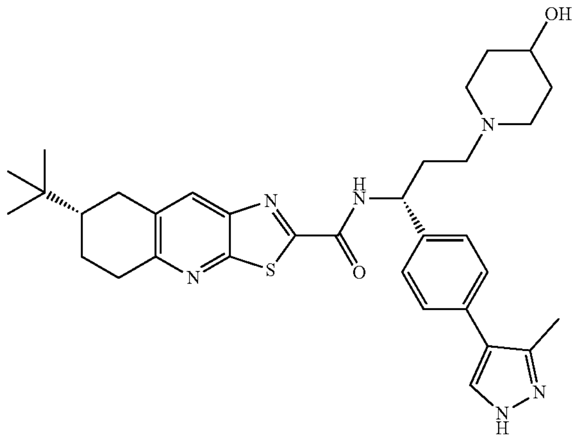 [SMILES: Cc1n[nH]cc1-c1ccc([C@@H](CCN2CCC(O)CC2)NC(=O)c2nc3cc4c(nc3s2)CC[C@H](C(C)(C)C)C4)cc1] | rac-(7S)-7-tert-butyl-N-[rac-(1R)-3-(4-hydroxy-1-piperidyl)-1-[4-(3-methyl-1H-pyrazol-4-yl)phenyl]propyl]-5,6,7,8-tetrahydrothiazolo[5,4-b]quinoline-2-carboxamide | 587.15 | 912.9 |

-continued

| Ex. No. | Structure | Chemical Name | Mass [M + H]+ | hNPRA EC50 (nM) |
|---|---|---|---|---|
| 172 | 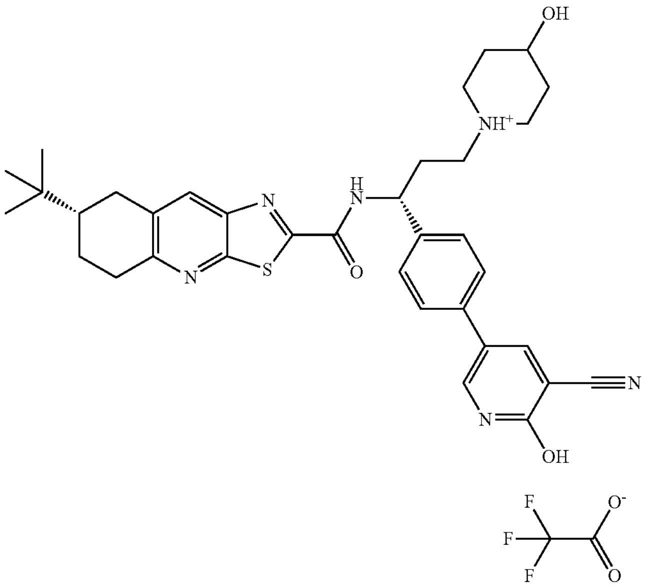 [SMILES: CC(C)(C)[C@H]1CCc2nc3sc(C(=O)N[C@H](CC[NH+]4CCC(O)CC4)c4ccc(-c5cnc(O)c(C#N)c5)cc4)nc3cc2C1 ; O=C([O-])C(F)(F)F] | rac-(7S)-7-tert-butyl-N-[rac-(1R)-1-[4-(5-cyano-6-hydroxy-3-pyridyl)phenyl]-3-(4-hydroxypiperidin-1-ium-1-yl)propyl]-5,6,7,8-tetrahydrothiazolo[5,4-b]quinoline-2-carboxamide; 2,2,2-trifluoroacetate | 625.21 | 924.8 |
| 173 | 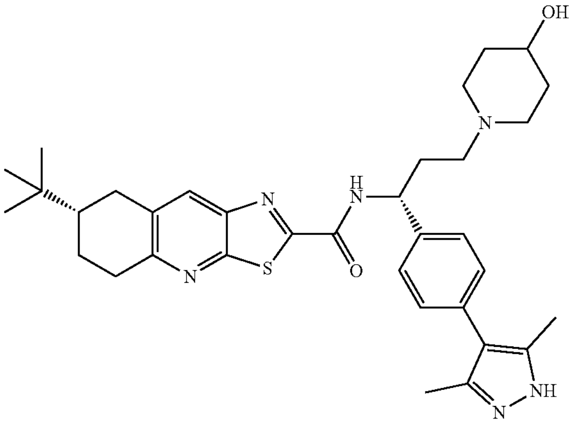 [SMILES: Cc1n[nH]c(C)c1-c1ccc([C@@H](CCN2CCC(O)CC2)NC(=O)c2nc3cc4c(nc3s2)CC[C@H](C(C)(C)C)C4)cc1] | rac-(7S)-7-tert-butyl-N-[rac-(1R)-1-[4-(3,5-dimethyl-1H-pyrazol-4-yl)phenyl]-3-(4-hydroxy-1-piperidyl)propyl]-5,6,7,8-tetrahydrothiazolo[5,4-b]quinoline-2-carboxamide | 601.07 | 959.4 |
| 174 | 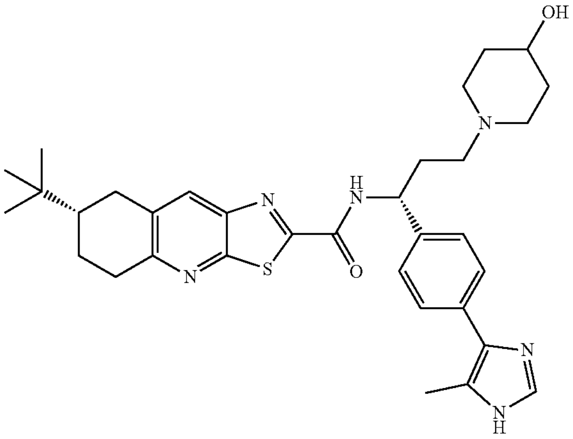 [SMILES: Cc1[nH]cnc1-c1ccc([C@@H](CCN2CCC(O)CC2)NC(=O)c2nc3cc4c(nc3s2)CC[C@H](C(C)(C)C)C4)cc1] | rac-(7S)-7-tert-butyl-N-[rac-(1R)-3-(4-hydroxy-1-piperidyl)-1-[4-(5-methyl-1H-imidazol-4-yl)phenyl]propyl]-5,6,7,8-tetrahydrothiazolo[5,4-b]quinoline-2-carboxamide | 587.19 | 990.8 |

-continued

| Ex. No. | Structure | Chemical Name | Mass [M + H]+ | hNPRA EC50 (nM) |
|---|---|---|---|---|
| 175 | 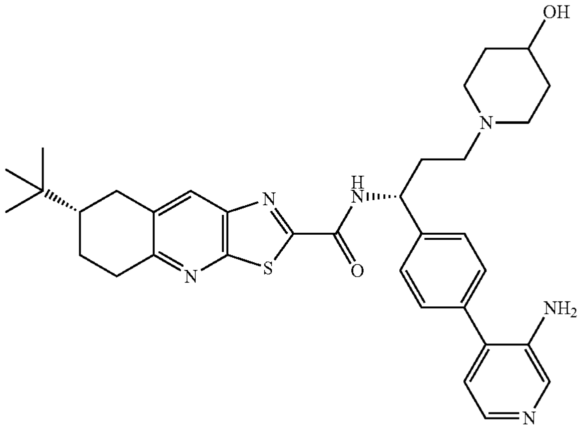 [SMILES: CC(C)(C)[C@H]1CCc2nc3sc(C(=O)N[C@H](CCN4CCC(O)CC4)c4ccc(-c5ccncc5N)cc4)nc3cc2C1] | rac-(7S)-7-tert-butyl-N-[rac-(1R)-1-[4-(3-amino-4-pyridyl)phenyl]-3-(4-hydroxy-1-piperidyl)propyl]-5,6,7,8-tetrahydrothiazolo[5,4-b]quinoline-2-carboxamide | 599.37 | 1017 |
| 176 | 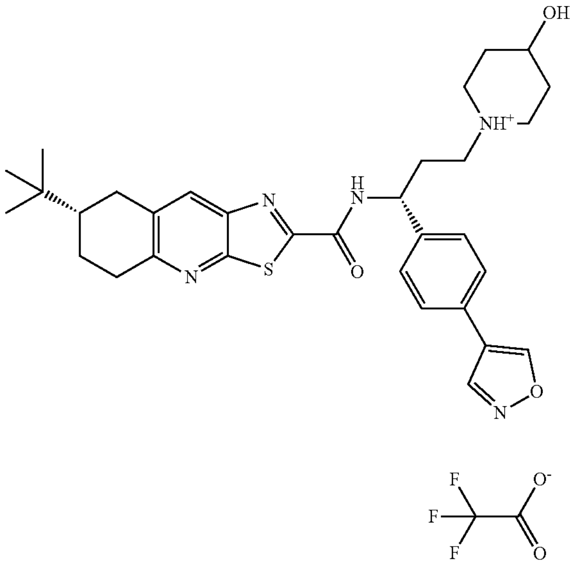 [SMILES: CC(C)(C)[C@H]1CCc2nc3sc(C(=O)N[C@H](CC[NH+]4CCC(O)CC4)c4ccc(-c5cnoc5)cc4)nc3cc2C1 ; O=C([O-])C(F)(F)F] | rac-(7S)-7-tert-butyl-N-[rac-(1R)-3-(4-hydroxypiperidin-1-ium-1-yl)-1-(4-isoxazol-4-ylphenyl)propyl]-5,6,7,8-tetrahydrothiazolo[5,4-b]quinoline-2-carboxamide; 2,2,2-trifluoroacetate | 574.21 | 1030 |
| 177 | 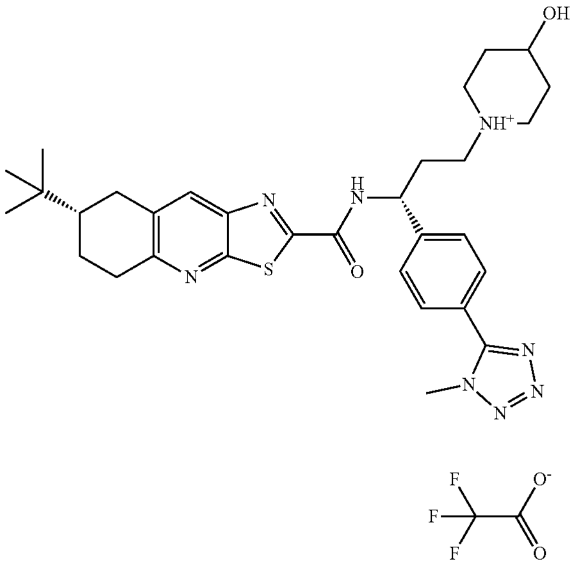 [SMILES: Cn1nnnc1-c1ccc([C@@H](CC[NH+]2CCC(O)CC2)NC(=O)c2nc3cc4c(nc3s2)CC[C@H](C(C)(C)C)C4)cc1 ; O=C([O-])C(F)(F)F] | rac-(7S)-7-tert-butyl-N-[rac-(1R)-3-(4-hydroxypiperidin-1-ium-1-yl)-1-[4-(1-methyltetrazol-5-yl)phenyl]propyl]-5,6,7,8-tetrahydrothiazolo[5,4-b]quinoline-2-carboxamide; 2,2,2-trifluoroacetate | 589.25 | 1154 |

-continued

| Ex. No. | Structure | Chemical Name | Mass [M + H]+ | hNPRA EC50 (nM) |
|---|---|---|---|---|
| 178 | 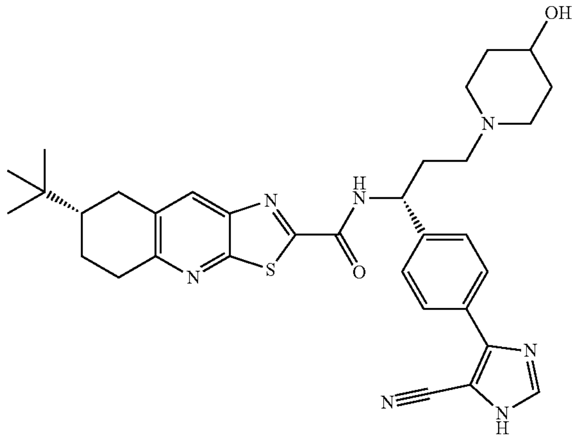 [SMILES: CC(C)(C)[C@H]1CCc2nc3sc(C(=O)N[C@H](CCN4CCC(O)CC4)c4ccc(-c5nc[nH]c5C#N)cc4)nc3cc2C1] | rac-(7S)-7-tert-butyl-N-[rac-(1R)-1-[4-(5-cyano-1H-imidazol-4-yl)phenyl]-3-(4-hydroxy-1-piperidyl)propyl]-5,6,7,8-tetrahydrothiazolo[5,4-b]quinoline-2-carboxamide | 598.21 | 1253 |
| 179 | 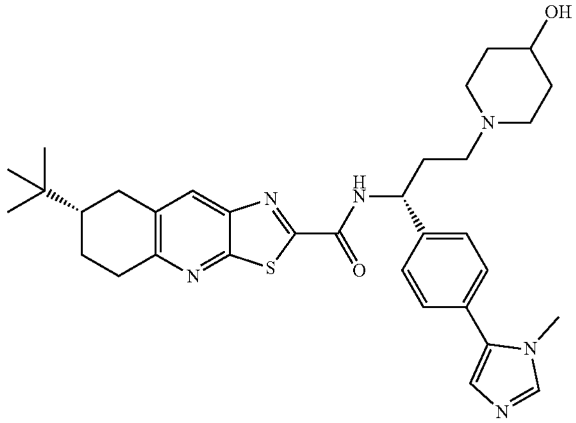 [SMILES: Cn1cncc1-c1ccc([C@@H](CCN2CCC(O)CC2)NC(=O)c2nc3cc4c(nc3s2)CC[C@H](C(C)(C)C)C4)cc1] | rac-(7S)-7-tert-butyl-N-[rac-(1R)-3-(4-hydroxy-1-piperidyl)-1-[4-(3-methylimidazol-4-yl)phenyl]propyl]-5,6,7,8-tetrahydrothiazolo[5,4-b]quinoline-2-carboxamide | 587.11 | 1419 |
| 180 | 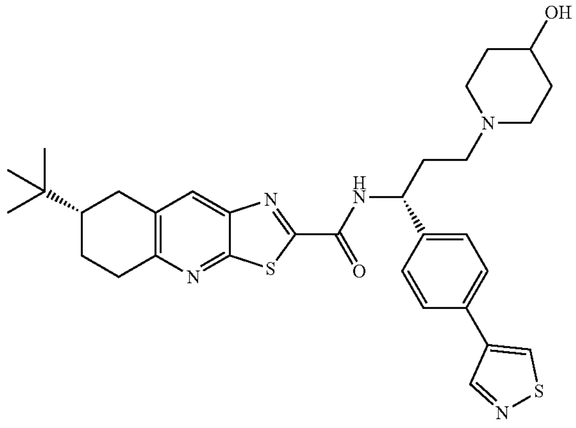 [SMILES: CC(C)(C)[C@H]1CCc2nc3sc(C(=O)N[C@H](CCN4CCC(O)CC4)c4ccc(-c5cnsc5)cc4)nc3cc2C1] | rac-(7S)-7-tert-butyl-N-[rac-(1R)-3-(4-hydroxy-1-piperidyl)-1-(4-isothiazol-4-ylphenyl)propyl]-5,6,7,8-tetrahydrothiazolo[5,4-b]quinoline-2-carboxamide | 590.13 | 1437 |

-continued

| Ex. No. | Structure | Chemical Name | Mass [M + H]+ | hNPRA EC50 (nM) |
|---|---|---|---|---|
| 181 | 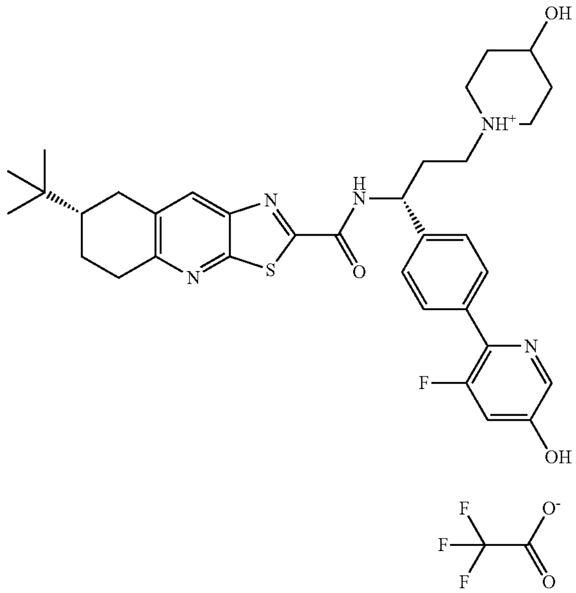 [SMILES: CC(C)(C)[C@H]1CCc2nc3sc(C(=O)N[C@H](CC[NH+]4CCC(O)CC4)c4ccc(-c5ncc(O)cc5F)cc4)nc3cc2C1 ; O=C([O-])C(F)(F)F] | rac-(7S)-7-tert-butyl-N-[rac-(1R)-1-[4-(3-fluoro-5-hydroxy-2-pyridyl)phenyl]-3-(4-hydroxypiperidin-1-ium-1-yl)propyl]-5,6,7,8-tetrahydrothiazolo[5,4-b]quinoline-2-carboxamide; 2,2,2-trifluoroacetate | 618.2 | 1445 |
| 182 | 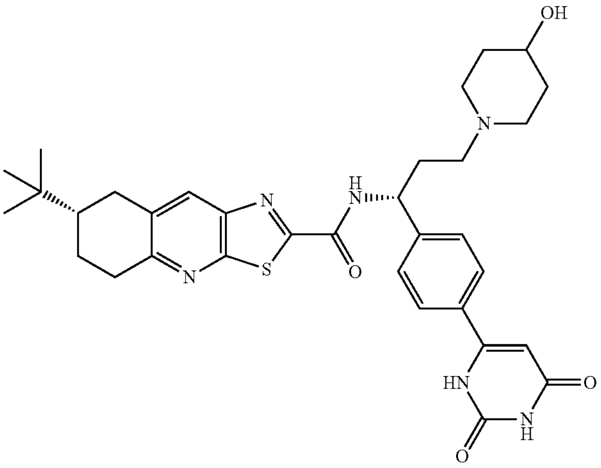 [SMILES: CC(C)(C)[C@H]1CCc2nc3sc(C(=O)N[C@H](CCN4CCC(O)CC4)c4ccc(-c5cc(=O)[nH]c(=O)[nH]5)cc4)nc3cc2C1] | rac-(7S)-7-tert-butyl-N-[rac-(1R)-1-[4-(2,4-dioxo-1H-pyrimidin-6-yl)phenyl]-3-(4-hydroxy-1-piperidyl)propyl]-5,6,7,8-tetrahydrothiazolo[5,4-b]quinoline-2-carboxamide | 617.28 | 1609 |
| 183 | 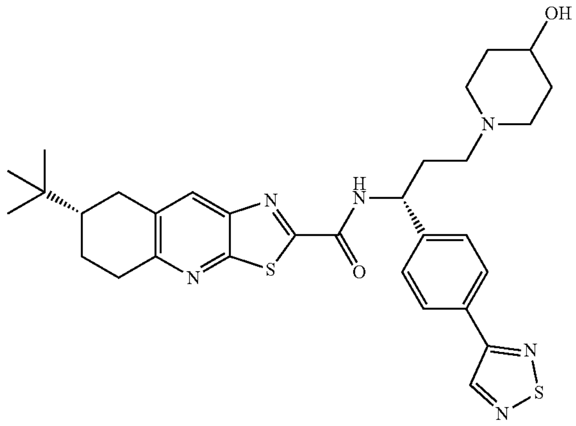 [SMILES: CC(C)(C)[C@H]1CCc2nc3sc(C(=O)N[C@H](CCN4CCC(O)CC4)c4ccc(-c5cnsn5)cc4)nc3cc2C1] | rac-(7S)-7-tert-butyl-N-[rac-(1R)-3-(4-hydroxy-1-piperidyl)-1-[4-(1,2,5-thiadiazol-3-yl)phenyl]propyl]-5,6,7,8-tetrahydrothiazolo[5,4-b]quinoline-2-carboxamide | 591.15 | 1656 |

-continued

| Ex. No. | Structure | Chemical Name | Mass [M + H]+ | hNPRA EC50 (nM) |
|---|---|---|---|---|
| 184 | 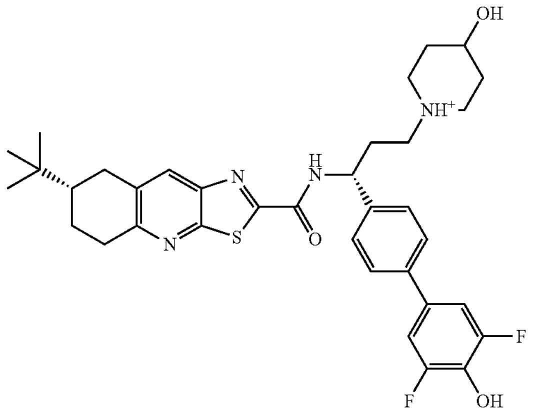 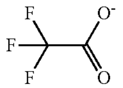 | rac-(7S)-7-tert-butyl-N-[rac-(1R)-1-[4-(3,5-difluoro-4-hydroxy-phenyl)phenyl]-3-(4-hydroxypiperidin-1-ium-1-yl)propyl]-5,6,7,8-tetrahydrothiazolo[5,4-b]quinoline-2-carboxamide; 2,2,2-trifluoroacetate | 635.23 | 1703 |
| 185 | 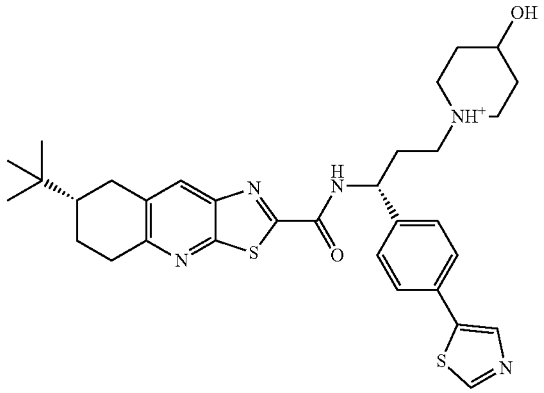 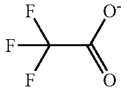 | rac-(7S)-7-tert-butyl-N-[rac-(1R)-3-(4-hydroxypiperidin-1-ium-1-yl)-1-(4-thiazol-5-ylphenyl)propyl]-5,6,7,8-tetrahydrothiazolo[5,4-b]quinoline-2-carboxamide; 2,2,2-trifluoroacetate | 590.22 | 1915 |

Examples 186-190

Examples 186-190 were synthesized by a similar procedure as below:

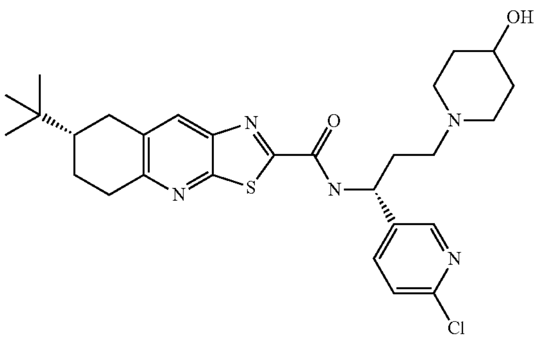

I-43

+

-continued

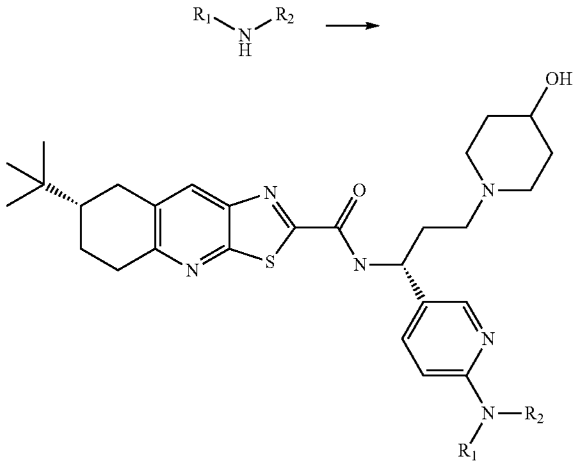

In a glove box, to a solution of ((S)-7-(tert-butyl)-N-((R)-1-(6-chloropyridin-3-yl)-3-(4-hydroxypiperidin-1-yl)propyl)-5,6,7,8-tetrahydrothiazolo[5,4-b]quinoline-2-carboxamide (1-43, 25 mg, 0.046 mmol) in dioxane (1 mL) was added amino substrate (0.092 mmol), $Pd_2(dba)_3$ (4.22 mg, 4.61 μmol), Xantphos (5.34 mg, 9.22 μmol) and $Cs_2CO_3$ (45.1 mg, 0.138 mmol). The resulting reaction mixture was sealed and heated to 95° C. for 24 hrs.

The reaction was cooled to ambient temperature and was partitioned between EtOAc (6 mL) and water (2 mL). The organic phase was washed with brine and then concentrated in vacuum. The crude product was purified by reverse-phase HPLC (MeCN/water with 0.1% ammonium hydroxide modifier) to afford the desired product.

| Ex. No. | Structure | Chemical Name | Mass [M + H]+ | hNPRA EC50 (nM) |
|---|---|---|---|---|
| 186 | 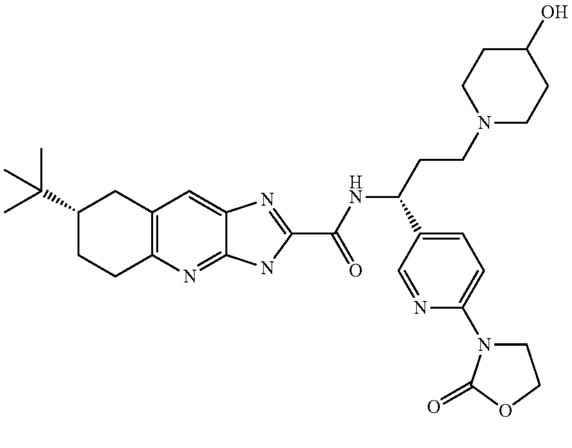 [SMILES: CC(C)(C)[C@H]1CCc2nc3[nH]c(C(=O)N[C@H](CCN4CCC(O)CC4)c4ccc(N5CCOC5=O)nc4)nc3cc2C1] | rac-(7S)-7-tert-butyl-N-[rac-(1R)-3-(4-hydroxy-1-piperidyl)-1-[6-(2-oxooxazolidin-3-yl)-3-pyridyl]propyl]-5,6,7,8-tetrahydrothiazolo[5,4-b]quinoline-2-carboxamide | 593.2 | 350.4 |
| 187 | 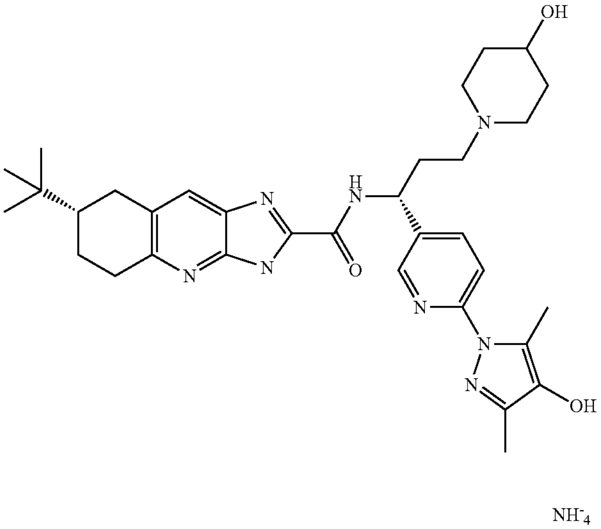 | ammonium; 3,5-dimethyl-1-[5-[rac-(1R)-3-(4-hydroxy-1-piperidyl)-1-[[rac-(7S)-7-tert-butyl-5,6,7,8-tetrahydrothiazolo[5,4-b]quinoline-2-carbonyl]amino]propyl]-2-pyridyl]pyrazol-4-olate | 618.39 | 641 |

-continued

| Ex. No. | Structure | Chemical Name | Mass [M + H]+ | hNPRA EC50 (nM) |
|---|---|---|---|---|
| 188 | 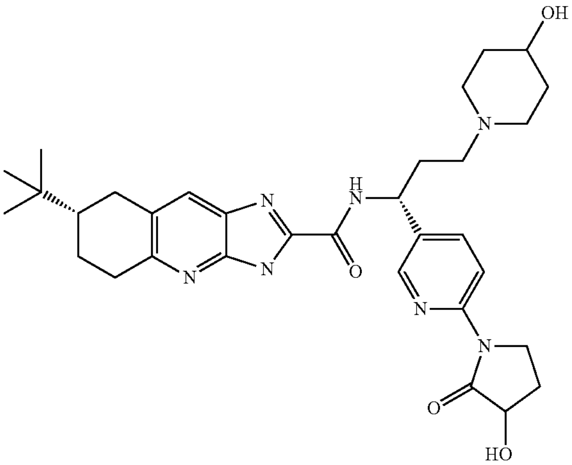 [SMILES: CC(C)(C)[C@H]1CCc2nc3[nH]c(C(=O)N[C@H](CCN4CCC(O)CC4)c4ccc(N5CCC(O)C5=O)nc4)nc3cc2C1] | rac-(7S)-7-tert-butyl-N-[rac-(1R)-1-[6-(3-hdyroxy-2-oxo-pyrrolidin-1-yl)-3-pyridyl]-3-(4-hydroxy-1-piperidyl)propyl]-5,6,7,8-tetrahydrothiazolo[5,4-b]quinoline-2-carboxamide | 607.14 | 938.3 |
| 189 | 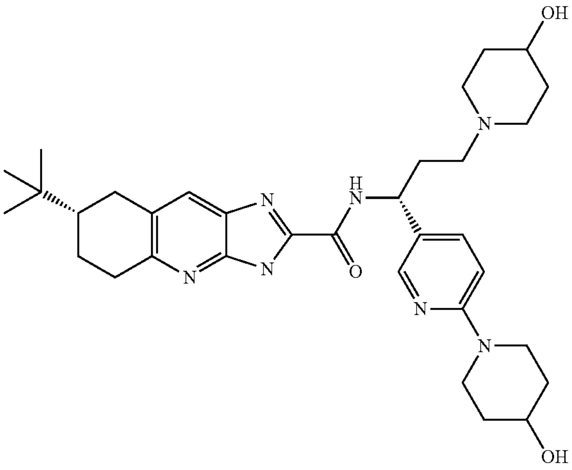 [SMILES: CC(C)(C)[C@H]1CCc2nc3[nH]c(C(=O)N[C@H](CCN4CCC(O)CC4)c4ccc(N5CCC(O)CC5)nc4)nc3cc2C1] | rac-(7S)-7-tert-butyl-N-[rac-(1R)-3-(4-hydroxy-1-piperidyl)-1-[6-(4-hydroxy-1-piperidyl)-3-pyridyl]propyl]-5,6,7,8-tetrahydrothiazolo[5,4-b]quinoline-2-carboxamide | 607.33 | 1375 |
| 190 | 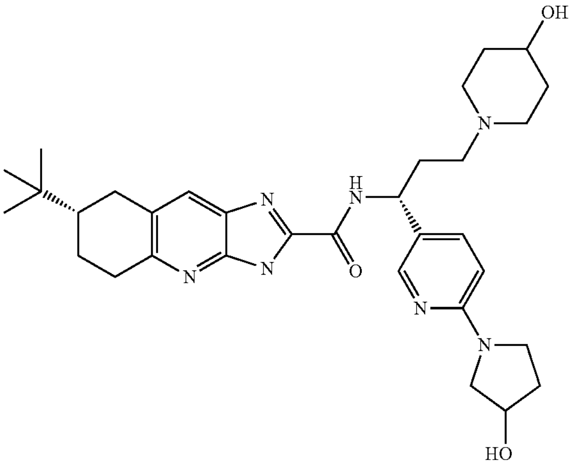 [SMILES: CC(C)(C)[C@H]1CCc2nc3[nH]c(C(=O)N[C@H](CCN4CCC(O)CC4)c4ccc(N5CCC(O)C5)nc4)nc3cc2C1] | rac-(7S)-7-tert-butyl-N-[rac-(1R)-3-(4-hydroxy-1-piperidyl)-1-[6-(3-hydroxypyrrolidin-1-yl)-3-pyridyl]propyl]-5,6,7,8-tetrahydrothiazolo[5,4-b]quinoline-2-carboxamide | 593.17 | 1907 |

Examples 191-194

Examples 191-194 were synthesized by a similar procedure as below:

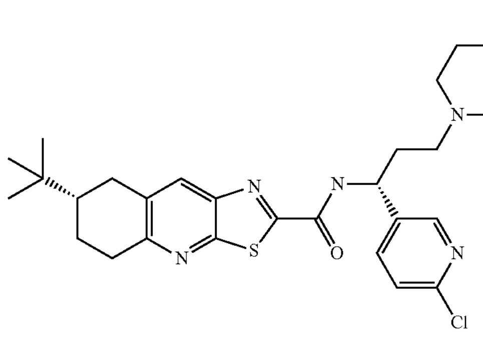

I-43

+

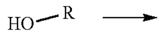

-continued

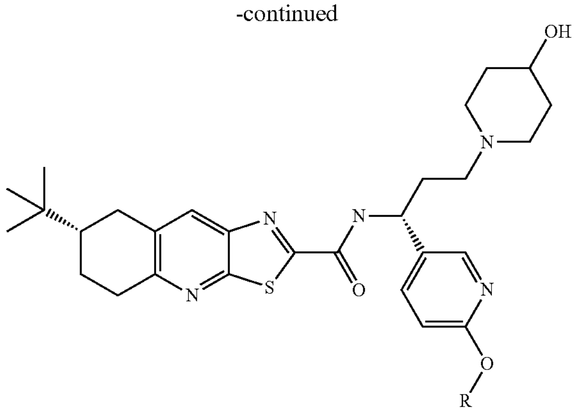

In a glove box, to a solution of(S)-7-(tert-butyl)-N-((R)-1-(6-chloropyridin-3-yl)-3-(4-hydroxypiperidin-1-yl)propyl)-5,6,7,8-tetrahydrothiazolo[5,4-b]quinoline-2-carboxamide (I-43, 25 mg, 0.046 mmol) in dioxane (1 mL) was added alcohol/phenol substrate (0.092 mmol), BrettPhos precatalyst (3.64 mg, 4.61 μmol) and $Cs_2CO_3$ (45.0 mg, 0.138 mmol) at ambient temperature. The resulting reaction mixture was stirred at 100° C. for 20 hrs.

The reaction was cooled to ambient temperature and partitioned between EtOAc (6 mL) and water (2 mL). The organic phase was washed with brine and concentrated in vacuum. The crude product was purified by reverse-phase HPLC (MeCN/water with 0.1% ammonium hydroxide modifier) to afford the desired product.

| Ex. No. | Structure | Chemical Name | Mass [M + H]+ | hNPRA EC50 (nM) |
|---|---|---|---|---|
| 191 | 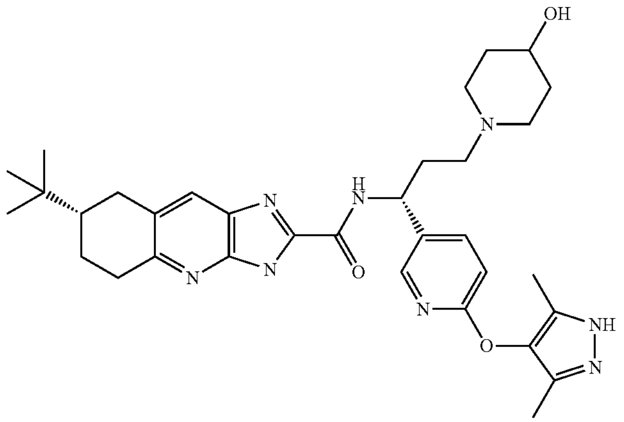 [SMILES: Cc1n[nH]c(C)c1Oc1ccc([C@@H](CCN2CCC(O)CC2)NC(=O)c2nc3cc4c(nc3[nH]2)CC[C@H](C(C)(C)C)C4)cn1] | rac-(7S)-7-tert-butyl-N-[rac-(1R)-1-[6-[(3,5-dimethyl-1H-pyrazol-4-yl)oxy]-3-pyridyl]-3-(4-hydroxy-1-piperidyl)propyl]-5,6,7,8-tetrahydrothiazolo[5,4-b]quinoline-2-carboxamide | 618.05 | 632 |

-continued

| Ex. No. | Structure | Chemical Name | Mass [M + H]+ | hNPRA EC50 (nM) |
|---|---|---|---|---|
| 192 | 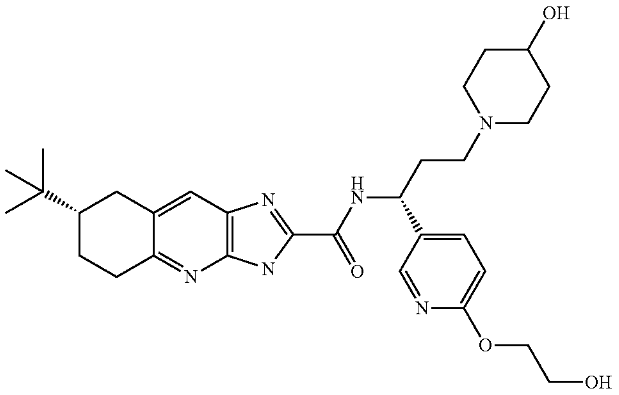 [SMILES: CC(C)(C)[C@H]1CCc2nc3[nH]c(C(=O)N[C@H](CCN4CCC(O)CC4)c4ccc(OCCO)nc4)nc3cc2C1] | rac-(7S)-7-tert-butyl-N-[rac-(1R)-1-[6-(2-hydroxyethoxy)-3-pyridyl]-3-(4-hydroxy-1-piperidyl)propyl]-5,6,7,8-tetrahydrothiazolo[5,4-b]quinoline-2-carboxamide | 568.19 | 664.7 |
| 193 | 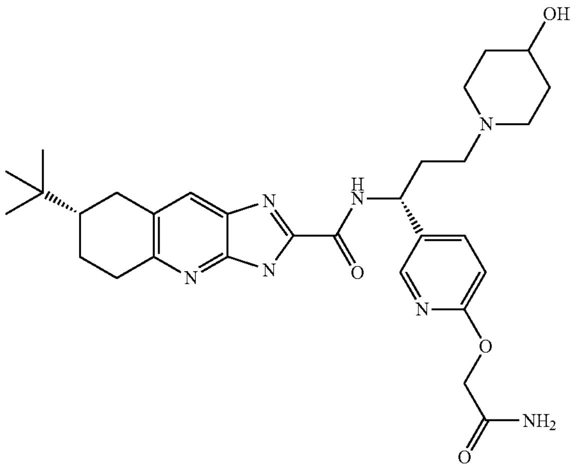 [SMILES: CC(C)(C)[C@H]1CCc2nc3[nH]c(C(=O)N[C@H](CCN4CCC(O)CC4)c4ccc(OCC(N)=O)nc4)nc3cc2C1] | rac-(7S)-7-tert-butyl-N-[rac-(1R)-1-[6-(2-amino-2-oxo-ethoxy)-3-pyridyl]-3-(4-hydroxy-1-piperidyl)propyl]-5,6,7,8-tetrahydrothiazolo[5,4-b]quinoline-2-carboxamide | 581.28 | 787.4 |
| 194 | 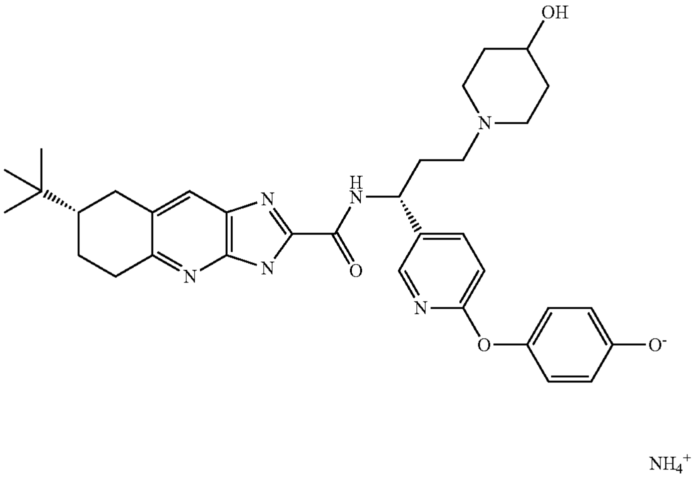 [SMILES: CC(C)(C)[C@H]1CCc2nc3[nH]c(C(=O)N[C@H](CCN4CCC(O)CC4)c4ccc(Oc5ccc([O-])cc5)nc4)nc3cc2C1 ; [NH4+]] | ammonium; 4-[[5-[rac-(1R)-3-(4-hydroxy-1-piperidyl)-1-[[rac-(7S)-7-tert-butyl-5,6,7,8-tetrahydrothiazolo[5,4-b]quinoline-2-carbonyl]amino]propyl]-2-pyridyl]oxy]phenolate | 616.15 | 1502 |

Examples 195-197

Examples 195-197 were synthesized by a similar procedure as below:

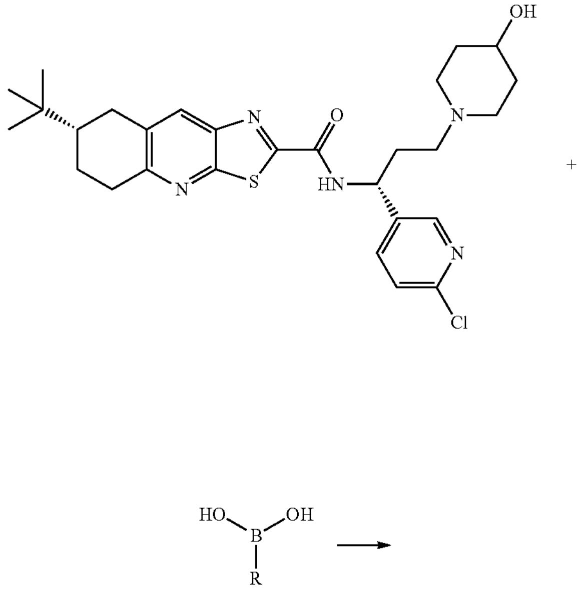

-continued

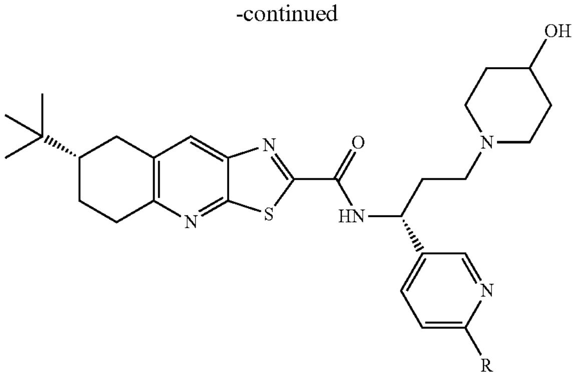

To a mixture of(S)-7-(tert-butyl)-N-((R)-1-(6-chloropyridin-3-yl)-3-(4-hydroxypiperidin-1-yl)propyl)-5,6,7,8-tetrahydrothiazolo[5,4-b]quinoline-2-carboxamide (I-43, 25 mg, 0.046 mmol), Pd(dppf)$Cl_2$ (53.3 mg, 0.046 mmol) and boronic acid substrate (0.092 mmol) was added dioxane (1 mL) and $Na_2CO_3$ solution (2.5 N, 0.018 ml, 0.046 mmol) at ambient temperature. The resulting reaction mixture was purged with $N_2$ for 5 mins and then heated to 90° C. for 16 hrs.

The reaction was cooled to ambient temperature and partitioned between EtOAc (6 mL) and water (2 mL). The organic phase was washed with brine and evaporated in vacuum. The crude product was purified by reverse-phase HPLC (MeCN/water with 0.1% ammonium hydroxide modifier) to afford product as a white solid.

| Ex. No. | Structure | Chemical Name | Mass [M + H]+ | hNPRA EC50 (nM) |
| --- | --- | --- | --- | --- |
| 195 | 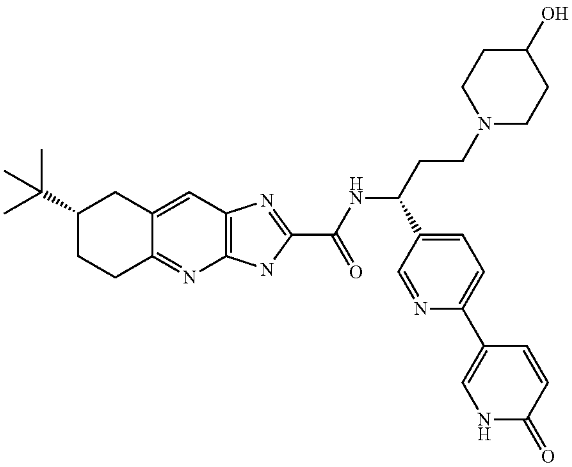 [SMILES: CC(C)(C)[C@H]1CCc2nc3[nH]c(C(=O)N[C@H](CCN4CCC(O)CC4)c4ccc(-c5ccc(=O)[nH]c5)nc4)nc3cc2C1] | rac-(7S)-7-tert-butyl-N-[rac-(1R)-3-(4-hydroxy-1-piperidyl)-1-[6-(6-oxo-1H-pyridin-3-yl)-3-pyridyl]propyl]-5,6,7,8-tetrahydrothiazolo[5,4-b]quinoline-2-carboxamide | 601.15 | 125.9 |

-continued
| Ex. No. | Structure | Chemical Name | Mass [M + H]+ | hNPRA EC50 (nM) |
|---|---|---|---|---|
| 196 | 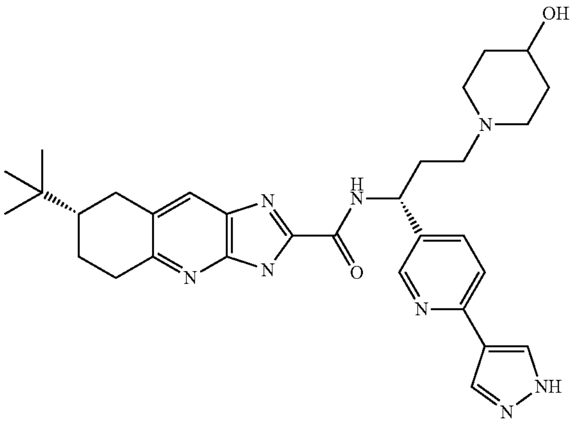 [SMILES: CC(C)(C)[C@H]1CCc2nc3[nH]c(C(=O)N[C@H](CCN4CCC(O)CC4)c4ccc(-c5cn[nH]c5)nc4)nc3cc2C1] | rac-(7S)-7-tert-butyl-N-[rac-(1R)-3-(4-hydroxy-1-piperidyl)-1-[6-(1H-pyrazol-4-yl)-3-pyridyl]propyl]-5,6,7,8-tetrahydrothiazolo[5,4-b]quinoline-2-carboxamide | 574.11 | 303.5 |
| 197 | 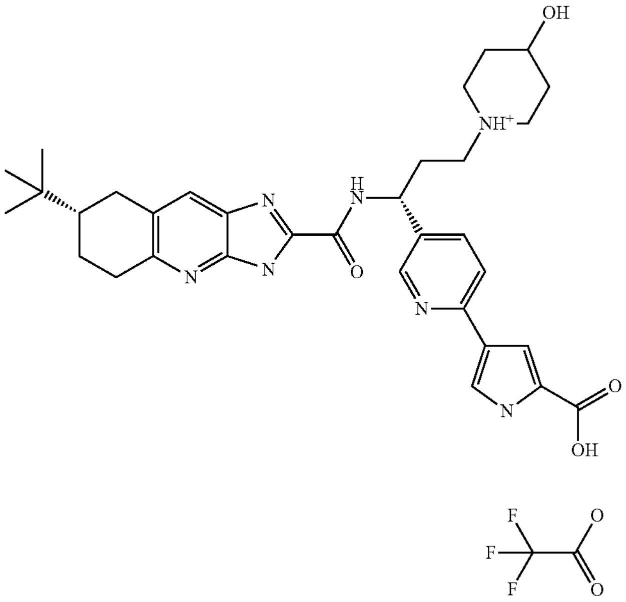 [SMILES: CC(C)(C)[C@H]1CCc2nc3[nH]c(C(=O)N[C@H](CC[NH+]4CCC(O)CC4)c4ccc(-c5c[nH]c(C(=O)O)c5)nc4)nc3cc2C1 ; O=C(O)C(F)(F)F] | 4-[5-[rac-(1R)-3-(4-hydroxypiperidin-1-ium-1-yl)-1-[[rac-(7S)-7-tert-butyl-5,6,7,8-tetrahydrothiazolo[5,4-b]quinoline-2-carbonyl]amino]propyl]-2-pyridyl]thiophene-2-carboxylic acid; 2,2,2-trifluoroacetate | 634.32 | 559.6 |

Examples 198-204

Examples 198-204 were synthesized by a similar procedure as below:

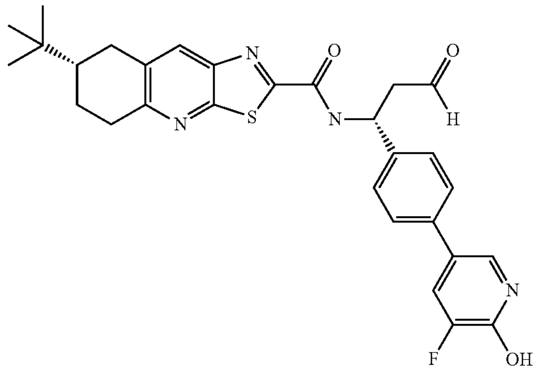

I-44

+

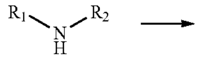

-continued

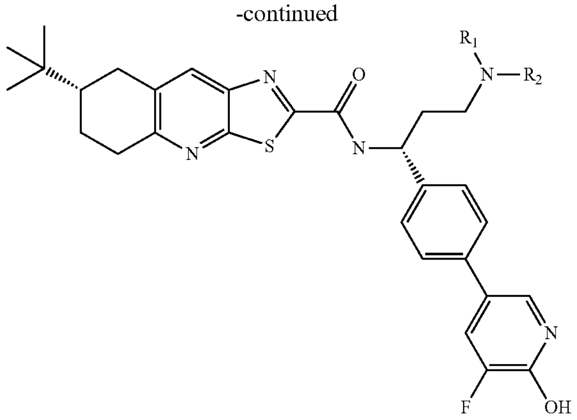

To a solution of(S)-7-(tert-butyl)-N-((R)-1-(4-(5-fluoro-6-hydroxypyridin-3-yl)phenyl)-3-oxopropyl)-5,6,7,8-tetrahydrothiazolo[5,4-b]quinoline-2-carboxamide (I-44, 25 mg, 0.047 mmol) in 5% HOAc/MeOH (1 mL) was added amino substrate (0.094 mmol), polystyrene supported $BH_3CN$ (70 mg, 2.45 mmol/g). The reaction was shaken at ambient temperature for 16 hrs.

The reaction mixture was filtered, and the solvent was evaporated in vacuum. The product with Boc protecting group was treated with HCl (2 N, 2 mL) at ambient temperature for 1 hr and then concentrated in vacuum. The crude product was purified by reverse-phase HPLC (MeCN/water with 0.1% formic acid modifier) to afford the product as a formic acid salt.

| Ex. No. | Structure | Chemical Name | Mass [M + H]+ | hNPRA EC50 (nM) |
|---|---|---|---|---|
| 198 | 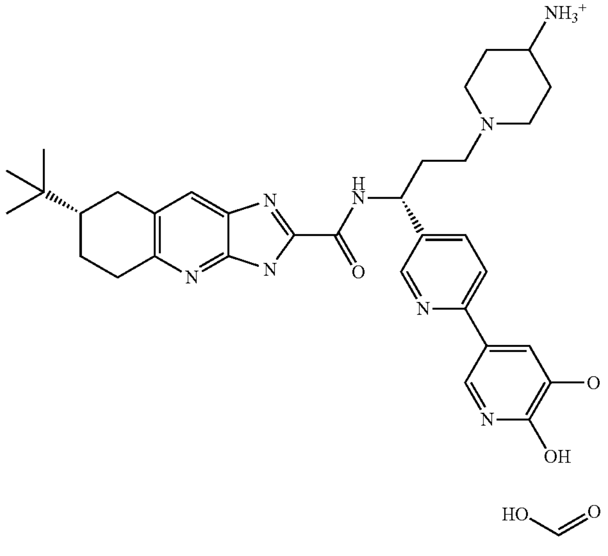 [SMILES: CC(C)(C)[C@H]1CCc2nc3[nH]c(C(=O)N[C@H](CCN4CCC([NH3+])CC4)c4ccc(-c5cnc(O)c(O)c5)nc4)nc3cc2C1 ; O=CO] | [1-[rac-(3R)-3-[4-(5-fluoro-6-hydroxy-3-pyridyl)phenyl]-3-[[rac-(7S)-7-tert-butyl-5,6,7,8-tetrahydrothiazolo[5,4-b]quinoline-2-carbonyl]amino]propyl]-4-piperidyl]ammonium; formate | 617.37 | 220 |

-continued

| Ex. No. | Structure | Chemical Name | Mass [M + H]+ | hNPRA EC50 (nM) |
|---|---|---|---|---|
| 199 | 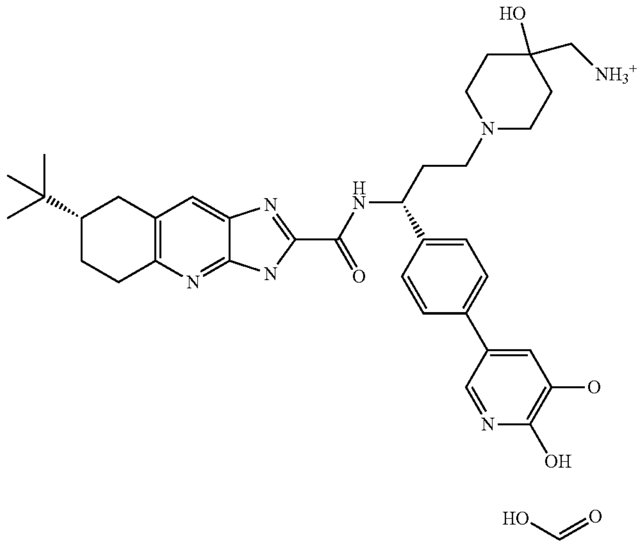 [SMILES: CC(C)(C)[C@H]1CCc2nc3[nH]c(C(=O)N[C@H](CCN4CCC(O)(C[NH3+])CC4)c4ccc(-c5cnc(O)c(O)c5)cc4)nc3cc2C1 ; O=CO] | [4-hydroxy-1-[rac-(3R)-3-[4-(5-fluoro-6-hydroxy-3-pyridyl)phenyl]-3-[[rac-(7S)-7-tert-butyl-5,6,7,8-tetrahydrothiazolo[5,4-b]quinoline-2-carbonyl]amino]propyl]-4-piperidyl]methylammonium; formate | 647.38 | 222 |
| 200 | 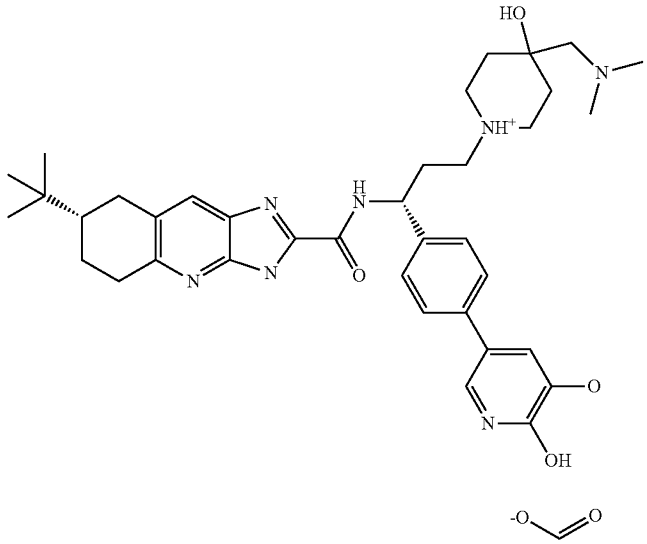 | rac-(7S)-7-tert-butyl-N-[rac-(1R)-3-[4-[(dimethylamino)methyl]-4-hydroxy-piperidin-1-ium-1-yl]-1-[4-(5-fluoro-6-hydroxy-3-pyridyl)phenyl]propyl]-5,6,7,8-tetrahydrothiazolo[5,4-b]quinoline-2-carboxamide; formate | 675.47 | 243.1 |

-continued
| Ex. No. | Structure | Chemical Name | Mass [M + H]+ | hNPRA EC50 (nM) |
|---|---|---|---|---|
| 201 | 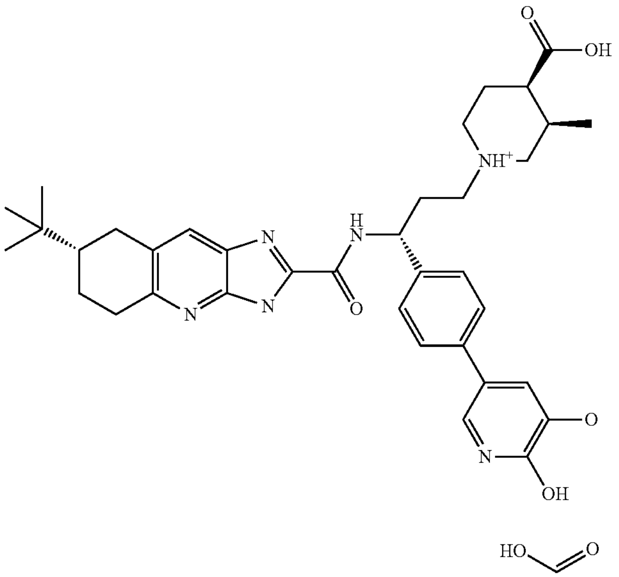 [SMILES: C[C@H]1C[NH+](CC[C@@H](NC(=O)c2nc3cc4c(nc3[nH]2)CC[C@H](C(C)(C)C)C4)c2ccc(-c3cnc(O)c(O)c3)cc2)CC[C@H]1C(=O)O ; O=CO] | rac-(3R,4S)-3-fluoro-1-[rac-(3R)-3-[4-(5-fluoro-6-hydroxy-3-pyridyl)phenyl]-3-[[rac-(7S)-7-tert-butyl-5,6,7,8-tetrahydrothiazolo[5,4-b]quinoline-2-carbonyl]amino]propyl]piperidin-1-ium-4-carboxylic acid; formate | 664.39 | 447 |
| 202 | 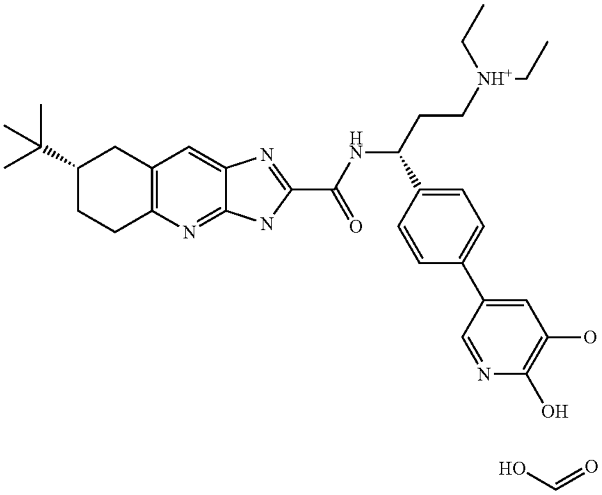 [SMILES: CC[NH+](CC)CC[C@@H](NC(=O)c1nc2cc3c(nc2[nH]1)CC[C@H](C(C)(C)C)C3)c1ccc(-c2cnc(O)c(O)c2)cc1 ; O=CO] | diethyl-[rac-(3R)-3-[4-(5-fluoro-6-hydroxy-3-pyridyl)phenyl]-3-[[rac-(7S)-7-tert-butyl-5,6,7,8-tetrahydrothiazolo[5,4-b]quinoline-2-carbonyl]amino]propyl]ammonium; formate | 590.32 | 513.8 |

-continued

| Ex. No. | Structure | Chemical Name | Mass [M + H]+ | hNPRA EC50 (nM) |
|---|---|---|---|---|
| 203 | 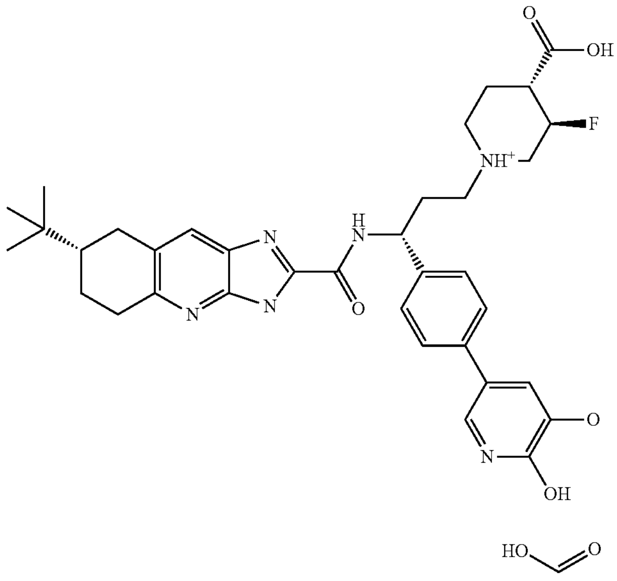 [SMILES: CC(C)(C)[C@H]1CCc2nc3[nH]c(C(=O)N[C@H](CC[NH+]4CC[C@H](C(=O)O)[C@@H](F)C4)c4ccc(-c5cnc(O)c(O)c5)cc4)nc3cc2C1 ; O=CO] | rac-(3R,4R)-3-fluoro-1-[rac-(3R)-3-[4-(5-fluoro-6-hydroxy-3-pyridyl)phenyl]-3-[[rac-(7S)-7-tert-butyl-5,6,7,8-tetrahydrothiazolo[5,4-b]quinoline-2-carbonyl]amino]propyl]piperidin-1-ium-4-carboxylic acid; formate | 664.36 | 1188 |
| 204 | 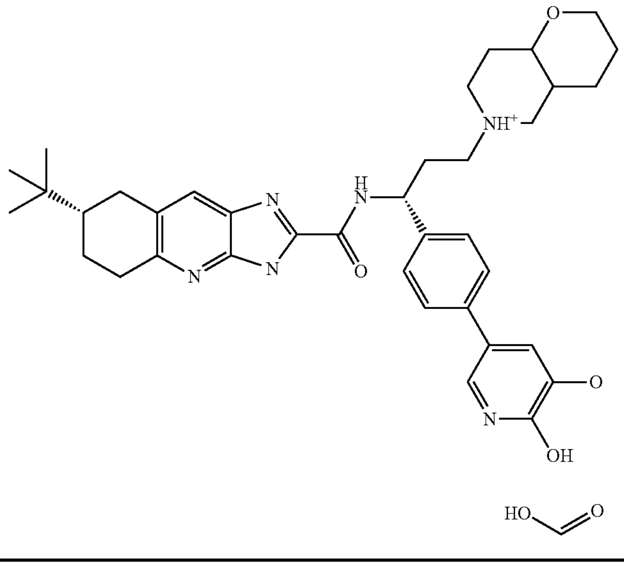 | rac-(7S)-7-tert-butyl-N-[rac-(1R)-3-(3,4,4a,5,6,7,8,8a-octahydro-2H-pyrano[3,2-c]pyridin-6-ium-6-yl)-1-[4-(5-fluoro-6-hydroxy-3-pyridyl)phenyl]propyl]-5,6,7,8-tetrahydrothiazolo[5,4-b]quinoline-2-carboxamide; formate | 658.43 | 1289 |

Examples 205-215

Examples 205-215 were synthesized by a similar procedure as below:

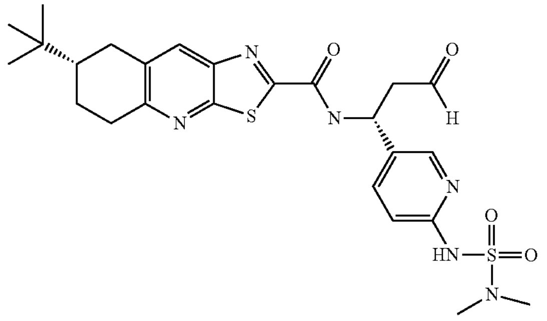

I-45

+

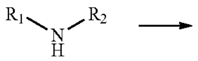

-continued

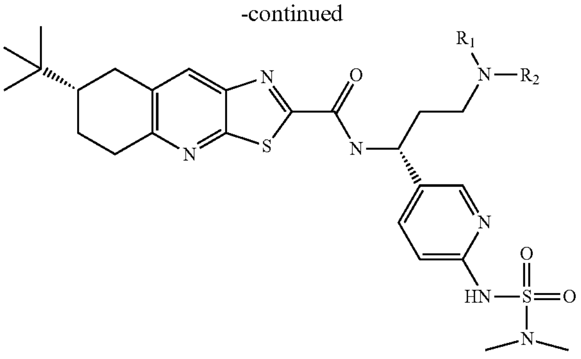

To a solution of(S)-7-(tert-butyl)-N-((R)-1-(4-(5-fluoro-6-hydroxypyridin-3-yl)phenyl)-3-oxopropyl)-5,6,7,8-tetrahydrothiazolo[5,4-b]quinoline-2-carboxamide (1-45, 25 mg, 0.047 mmol) in 5% HOAc/MeOH (1 mL) as added amino substrate (0.094 mmol) and polystyrene supported $BH_3CN$ (70 mg, 2.45 mmol/g). The reaction was shaken at ambient temperature for 16 hrs.

The reaction mixture was filtered, and the solvent was evaporated in vacuum. The crude product was purified by reverse-phase HPLC (MeCN/water with 0.1% TFA modifier) to afford the product as a TFA salt.

| Ex. No. | Structure | Chemical Name | Mass [M + H]+ | hNPRA EC50 (nM) |
|---|---|---|---|---|
| 205 | 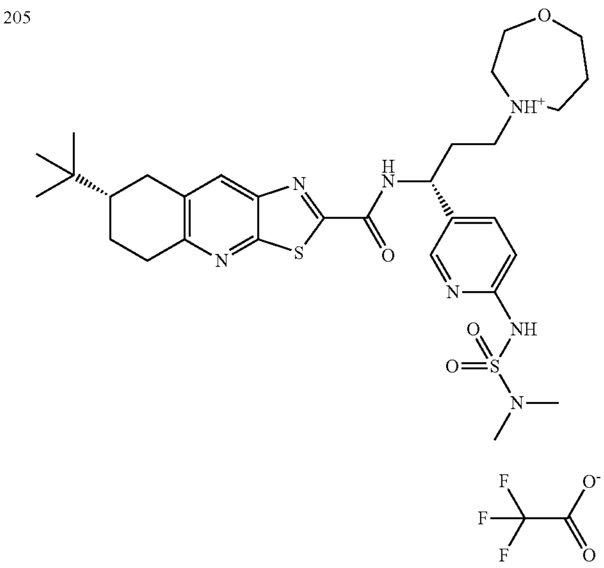 | rac-(7S)-7-tert-butyl-N-[rac-(1R)-1-[6-(dimethylsulfamoylamino)-3-pyridyl]-3-(1,4-oxazepan-4-ium-4-yl)propyl]-5,6,7,8-tetrahydrothiazolo[5,4-b]quinoline-2-carboxamide; 2,2,2-trifluoroacetate | 630.28 | 563.2 |

-continued

| Ex. No. | Structure | Chemical Name | Mass [M + H]+ | hNPRA EC50 (nM) |
|---|---|---|---|---|
| 206 | 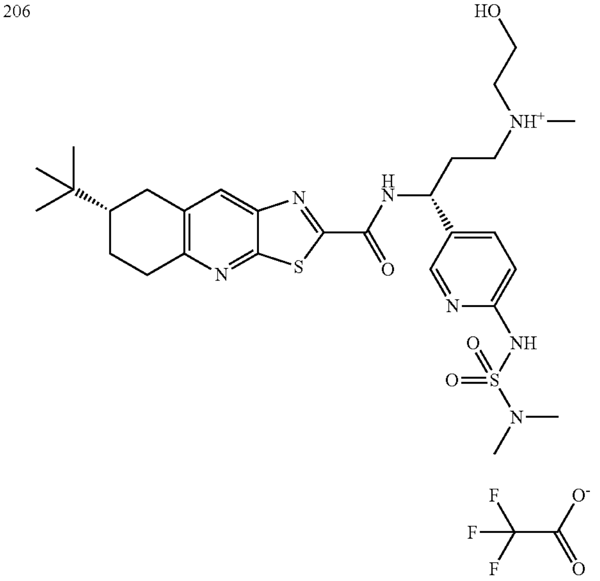 | 2-hydroxyethyl-methyl-[rac-(3R)-3-[6-(dimethylsulfamoylamino)-3-pyridyl]-3-[[rac-(7S)-7-tert-butyl-5,6,7,8-tetrahydrothiazolo[5,4-b]quinoline-2-carbonyl]amino]propyl]ammonium; 2,2,2-trifluoroacetate | 604.23 | 673.5 |
| 207 | 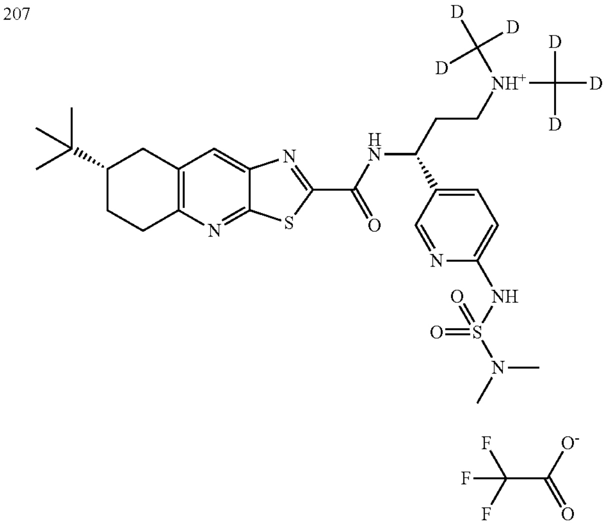 | [rac-(3R)-3-[6-(dimethylsulfamoylamino)-3-pyridyl]-3-[[rac-(7S)-7-tert-butyl-5,6,7,8-tetrahydrothiazolo[5,4-b]quinoline-2-carbonyl]amino]propyl]-bis(trideuteriomethyl)ammonium; 2,2,2-trifluoroacetate | 580.26 | 678.8 |

-continued

| Ex. No. | Structure | Chemical Name | Mass [M + H]+ | hNPRA EC50 (nM) |
|---|---|---|---|---|
| 208 | 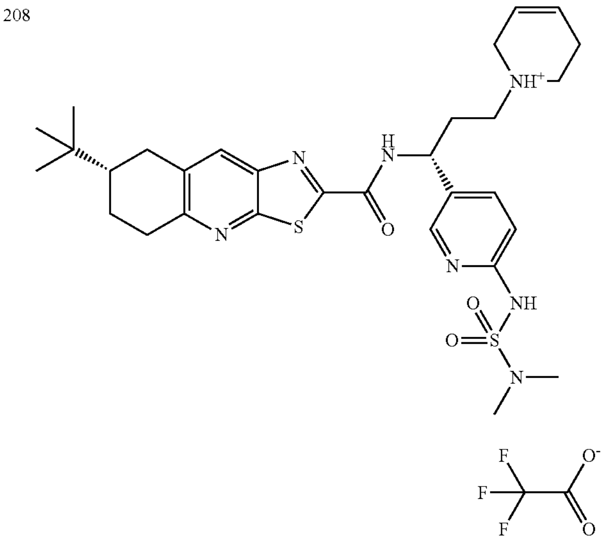 | rac-(7S)-7-tert-butyl-N-[rac-(1R)-1-[6-(dimethylsulfamoylamino)-3-pyridyl]-3-(1,2,3,6-tetrahydropyridin-1-ium-1-yl)propyl]-5,6,7,8-tetrahydrothiazolo[5,4-b]quinoline-2-carboxamide; 2,2,2-trifluoroacetate | 612.3 | 712 |
| 209 | 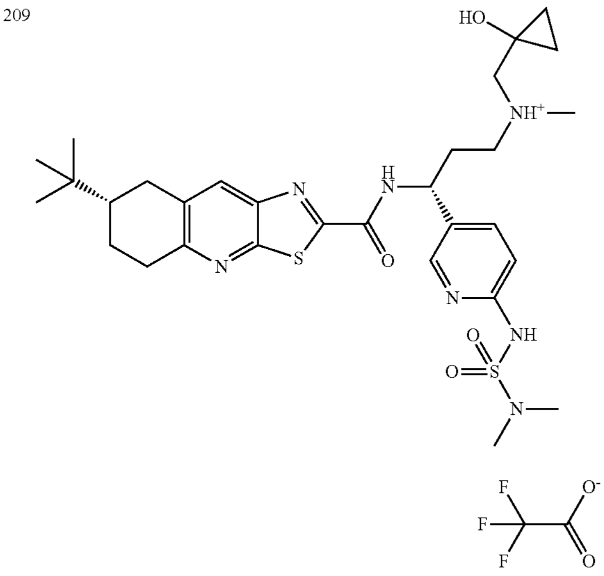 | (1-hydroxycyclopropyl)methyl-methyl-[rac-(3R)-3-[6-(dimethylsulfamoylamino)-3-pyridyl]-3-[[rac-(7S)-7-tert-butyl-5,6,7,8-tetrahydrothiazolo[5,4-b]quinoline-2-carbonyl]amino]propyl]ammonium; 2,2,2-trifluoroacetate | 630.28 | 734.8 |

-continued

| Ex. No. | Structure | Chemical Name | Mass [M + H]+ | hNPRA EC50 (nM) |
|---|---|---|---|---|
| 210 | 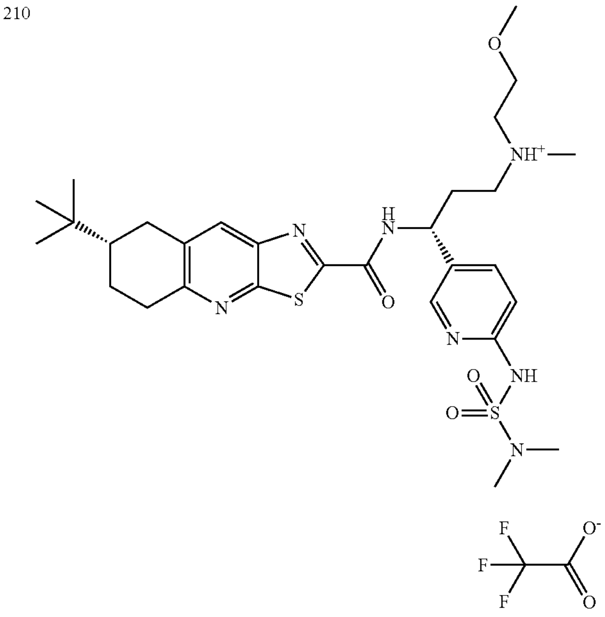 | 2-methoxyethyl-methyl-[rac-(3R)-3-[6-(dimethylsulfamoylamino)-3-pyridyl]-3-[rac-(7S)-7-tert-butyl-5,6,7,8-tetrahydrothiazolo[5,4-b]quinoline-2-carbonyl]amino]propyl]ammonium; 2,2,2-trifluoroacetate | 618.29 | 764 |
| 211 | 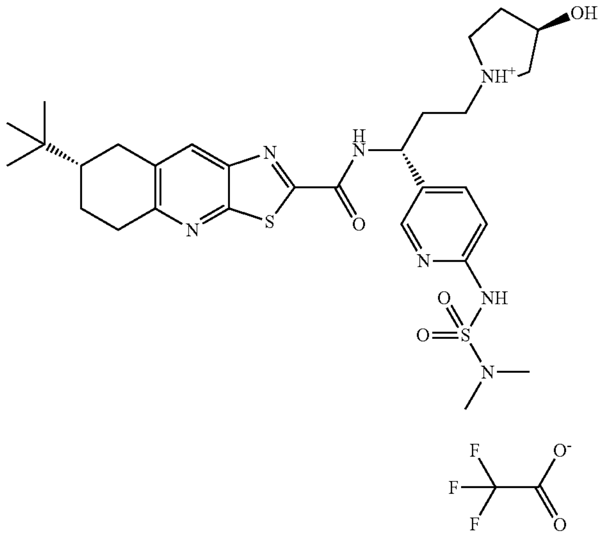 [SMILES: CN(C)S(=O)(=O)Nc1ccc([C@@H](CC[NH+]2CC[C@@H](O)C2)NC(=O)c2nc3cc4c(nc3s2)CC[C@H](C(C)(C)C)C4)cn1 ; O=C([O-])C(F)(F)F] | rac-(7S)-7-tert-butyl-N-[rac-(1R)-1-[6-(dimethylsulfamoylamino)-3-pyridyl]-3-[rac-(3R)-3-hydroxypyrrolidin-1-ium-1-yl]propyl]-5,6,7,8-tetrahydrothiazolo[5,4-b]quinoline-2-carboxamide; 2,2,2-trifluoroacetate | 616.26 | 764.4 |

-continued

| Ex. No. | Structure | Chemical Name | Mass [M + H]+ | hNPRA EC50 (nM) |
|---|---|---|---|---|
| 212 | 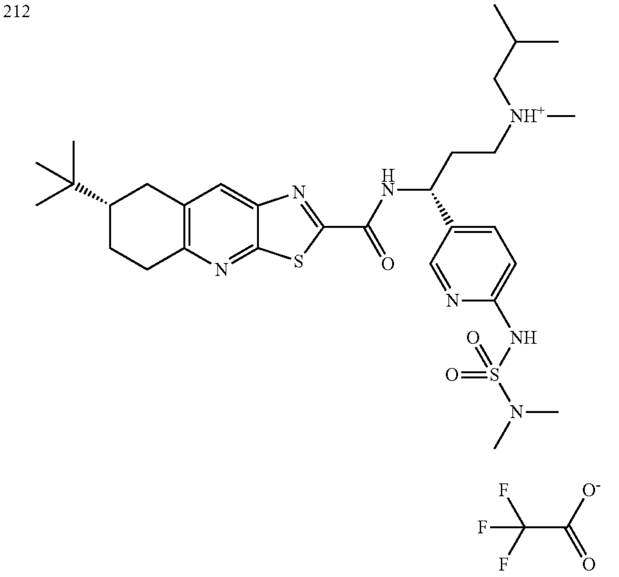 | isobutyl-methyl-[rac-(3R)-3-[6-(dimethylsulfamoylamino)-3-pyridyl]-3-[rac-(7S)-7-tert-butyl-5,6,7,8-tetrahydrothiazolo[5,4-b] quinoline-2-carbonyl] amino]propyl]ammonium; 2,2,2-trifluoroacetate | 616.32 | 985.7 |
| 213 | 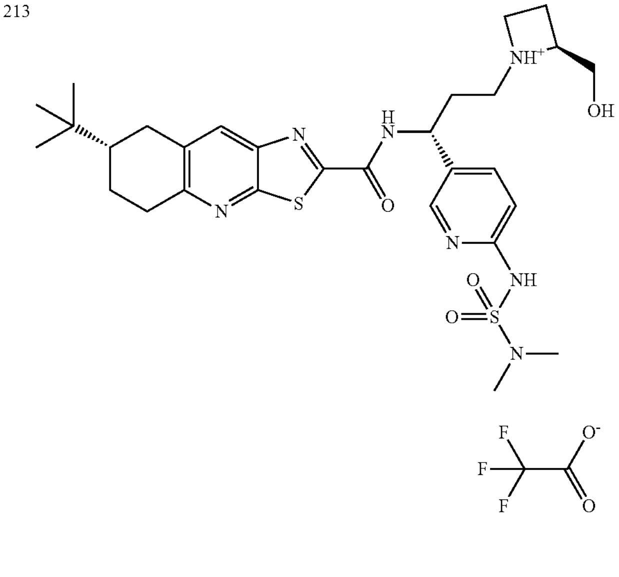 | rac-(7S)-7-tert-butyl-N-[rac-(1R)-1-[6-(dimethylsulfamoylamino)-3-pyridyl]-3-[rac-(2S)-2-(hydroxymethyl)azetidin-1-ium-1-yl]propyl]-5,6,7,8-tetrahydrothiazolo[5,4-b] quinoline-2-carboxamide; 2,2,2-trifluoroacetate | 616.22 | 1013 |

-continued

| Ex. No. | Structure | Chemical Name | Mass [M + H]+ | hNPRA EC50 (nM) |
|---|---|---|---|---|
| 214 | 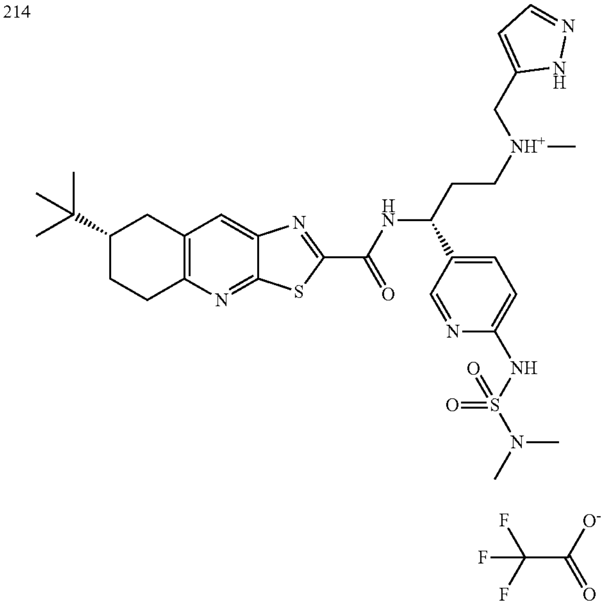 | methyl-(1H-pyrazol-5-ylmethyl)-[rac-(3R)-3-[6-(dimethylsulfamoylamino)-3-pyridyl]-3-[rac-(7S)-7-tert-butyl-5,6,7,8-tetrahydrothiazolo[5,4-b]quinoline-2-carbonyl]amino]propyl]ammonium; 2,2,2-trifluoroacetate | 640.27 | 1244 |
| 215 | 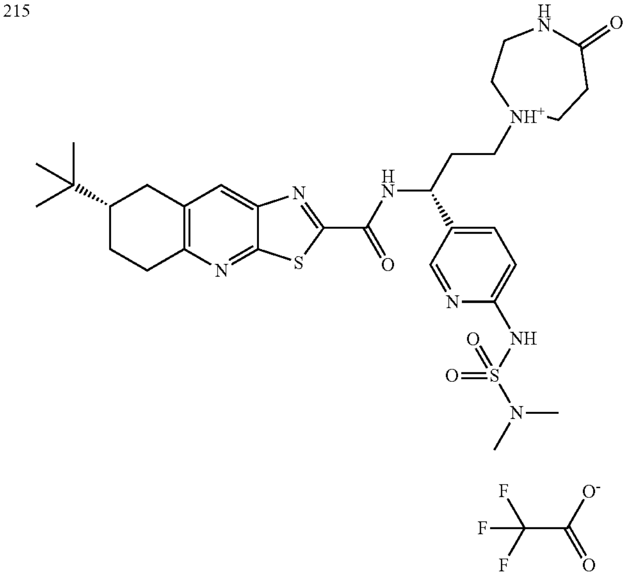 | rac-(7S)-7-tert-butyl-N-[rac-(1R)-1-[6-(dimethylsulfamoylamino)-3-pyridyl]-3-(5-oxo-1,4-diazepan-1-ium-1-yl)propyl]-5,6,7,8-tetrahydrothiazolo[5,4-b]quinoline-2-carboxamide; 2,2,2-trifluoroacetate | 643.33 | 1605 |

Example 216

Example 216 was synthesized by a procedure as below:

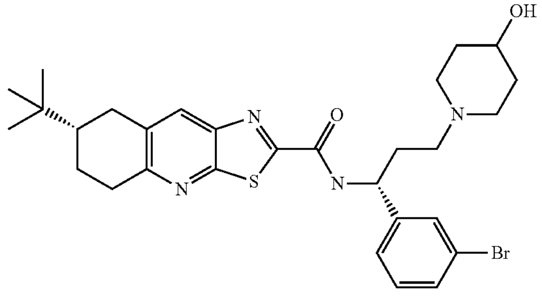

I-37

+

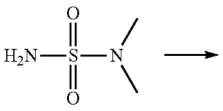

-continued

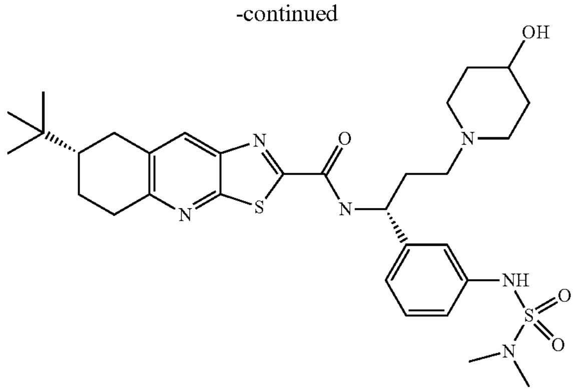

To a solution of(S)-N-((R)-1-(3-bromophenyl)-3-(4-hydroxypiperidin-1-yl)propyl)-7-(tert-butyl)-5,6,7,8-tetrahydrothiazolo[5,4-b]quinoline-2-carboxamide (I-37, 25 mg, 0.043 mmol) solution in DMSO (1 mL) was added N,N-dimethylsulfamide (6 mg, 0.043 mmol), CuI (9.73 mg, 0.051 mmol), (1S,2S)-$N_1$,$N_2$-dimethylcyclohexane-1,2-diamine (7.29 mg, 0.051 mmol) and $K_2CO_3$ (69.4 mg, 0.213 mmol). The reaction was purged with $N_2$ for 5 min. The vial was sealed and the reaction was stirred at 120° C. for 16 hrs.

The reaction was cooled to ambient temperature and then partitioned between EtOAc (6 mL) and ammonium hydroxide (2 N, 2 mL). The organic phase was washed with brine and concentrated in vacuum. The crude product was purified by reverse-phase HPLC (MeCN/water with 0.1% formic acid modifier) to afford the product as a formic acid salt.

| Ex. No. | Structure | Chemical Name | Mass [M + H]+ | hNPRA EC50 (nM) |
|---|---|---|---|---|
| 216 | 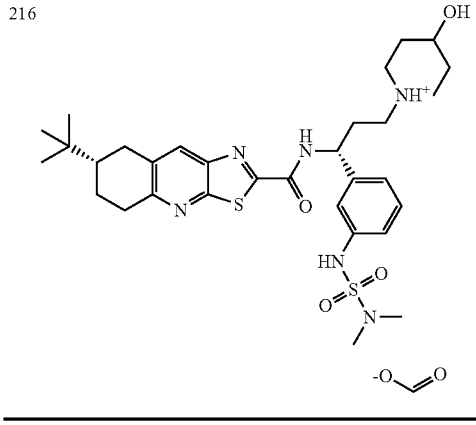 | (7S)-7-tert-butyl-N-[rac-(1R)-1-[3-(dimethylsulfamoylamino)phenyl]-3-(4-hydroxypiperidin-1-ium-1-yl)propyl]-5,6,7,8-tetrahydrothiazolo[5,4-b]quinoline-2-carboxamide; formate | 629.11 | 1980 |

Example 217

(S)-N-((R)-1-(6-(3,3-dioxido-1,3,4-oxathiazinan-4-yl)pyridin-3-yl)-3-(4-hydroxypiperidin-1-yl)propyl)-7-fluoro-7-isopropyl-5,6,7,8-tetrahydrothiazolo[5,4-b]quinoline-2-carboxamide (Ex 217)

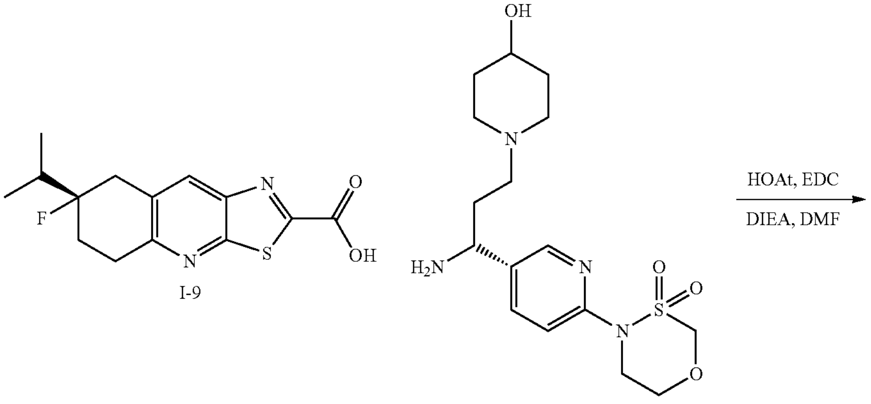

I-9

I-24

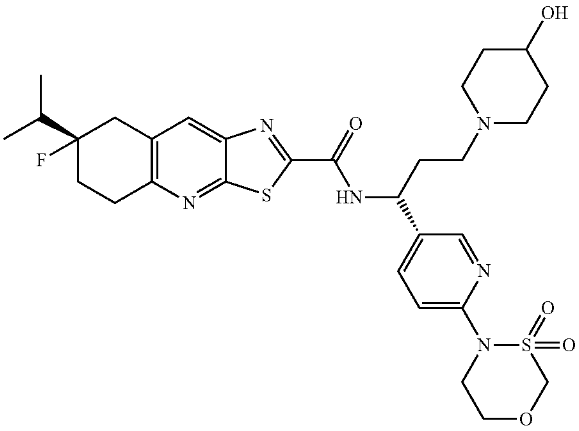

Ex. 217

To a solution of 7-fluoro-7-isopropyl-5,6,7,8-tetrahydrothiazolo[5,4-b]quinoline-2-carboxylic acid (1-9, 15 mg, 0.051 mmol) in anhydrous DMF (1 ml) was added HOAt (9.02 mg, 0.066 mmol) and EDC (12.70 mg, 0.066 mmol). The mixture was stirred at RT for 10 min, then (R)-4-(5-(1-amino-3-(4-hydroxypiperidin-1-yl)propyl)pyridin-2-yl)-1,3,4-oxathiazinane 3,3-dioxide (I-24, 28.3 mg, 0.076 mmol) and DIEA (0.053 mL, 0.306 mmol) was added. The reaction was stirred at RT for 5 h. The reaction was filtered and purified by column chromatography on C-18 column (ACN/water with 0.05% TFA modifier) to afford the product as the TFA salt.

| Ex. No. | Structure | Chemical Name | Mass [M + H]+ | hNPRA EC50 (nM) |
|---|---|---|---|---|
| 217 | 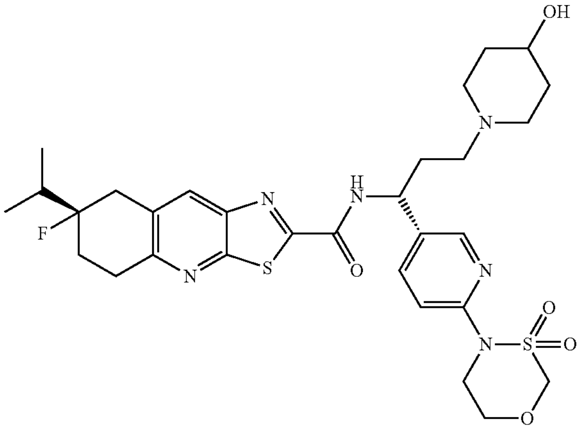 | (S)-N-((R)-1-(6-(3,3-dioxido-1,3,4-oxathiazinan-4-yl)pyridin-3-yl)-3-(4-hydroxypiperidin-1-yl)propyl)-7-fluoro-7-isopropyl-5,6,7,8-tetrahydrothiazolo[5,4-b]quinoline-2-carboxamide | 647 | 71 |

Examples 218-221

Examples 218-221 were prepared by following an analogous procedure to that described in Example 217.

| Ex. No. | Structure | Chemical Name | Mass [M + H]+ | hNPRA EC50 (nM) |
|---|---|---|---|---|
| 218 | 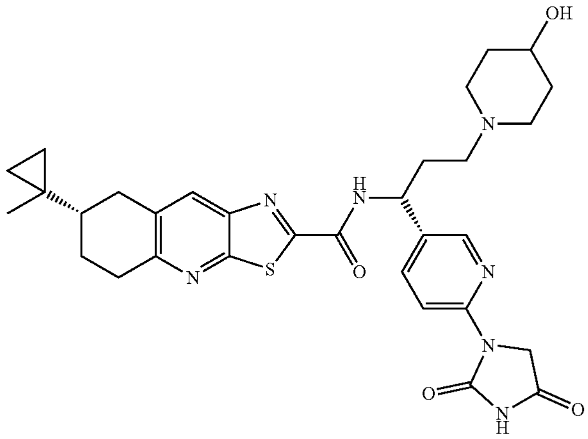 | (S)-N-((R)-1-(6-(2,4-dioxoimidazolidin-1-yl)pyridin-3-yl)-3-(4-hydroxypiperidin-1-yl)propyl)-7-(1-methylcyclopropyl)-5,6,7,8-tetrahydrothiazolo[5,4-b]quinoline-2-carboxamide | 604 | 242 |
| 219 | 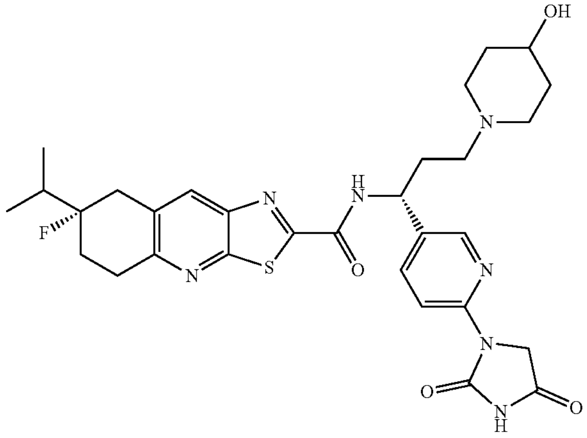 [SMILES: CC(C)[C@]1(F)CCc2nc3sc(C(=O)N[C@H](CCN4CCC(O)CC4)c4ccc(N5CC(=O)NC5=O)nc4)nc3cc2C1] | (S)-N-((R)-1-(6-(2,4-dioxoimidazolidin-1-yl)pyridin-3-yl)-3-(4-hydroxypiperidin-1-yl)propyl)-7-fluoro-7-isopropyl-5,6,7,8-tetrahydrothiazolo[5,4-b]quinoline-2-carboxamide | 610 | 384 |

-continued

| Ex. No. | Structure | Chemical Name | Mass [M + H]+ | hNPRA EC50 (nM) |
|---|---|---|---|---|
| 220 | 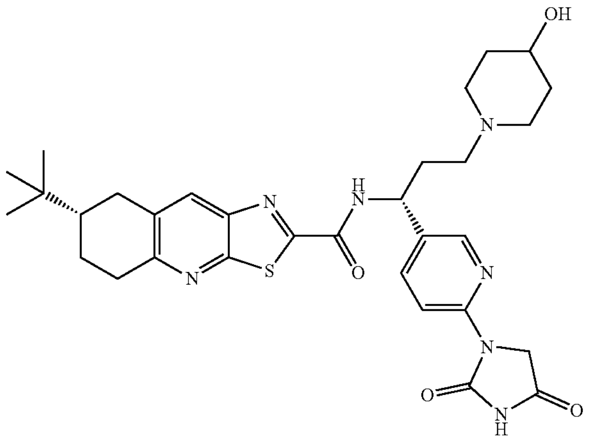 [SMILES: CC(C)(C)[C@H]1CCc2nc3sc(C(=O)N[C@H](CCN4CCC(O)CC4)c4ccc(N5CC(=O)NC5=O)nc4)nc3cc2C1] | (S)-7-(tert-butyl)-N-((R)-1-(6-(2,4-dioxoimidazolidin-1-yl)pyridin-3-yl)-3-(4-hydroxypiperidin-1-yl)propyl)-5,6,7,8-tetrahydrothiazolo[5,4-b]quinoline-2-carboxamide | 606 | 277 |
| 221 | 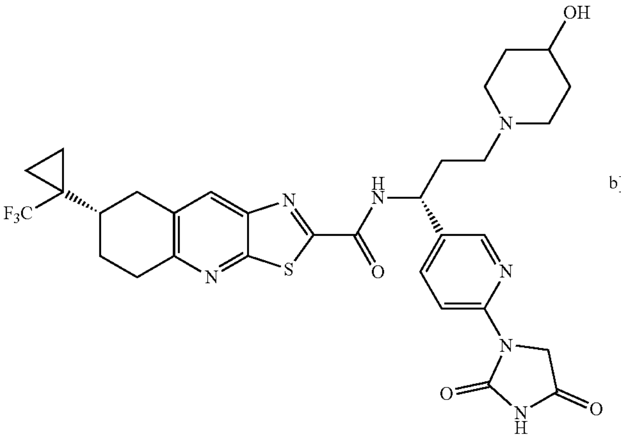 | (S)-N-((R)-1-(6-(2,4-dioxoimidazolidin-1-yl)pyridin-3-yl)-3-(4-hydroxypiperidin-1-yl)propyl)-7-(1-(trifluoromethyl)cyclopropyl)-5,6,7,8-tetrahydrothiazolo[5,4-b]quinoline-2-carboxamide | 658 | 1140 |

Example 222

1-((R)-3-((S)-7-(tert-butyl)-5,6,7,8-tetrahydrothiazolo[5,4-b]quinoline-2-carboxamido)-3-(6-(2,4-dioxoimidazolidin-1-yl)pyridin-3-yl)propyl)piperidine-4-carboxylic acid (Ex. 222)

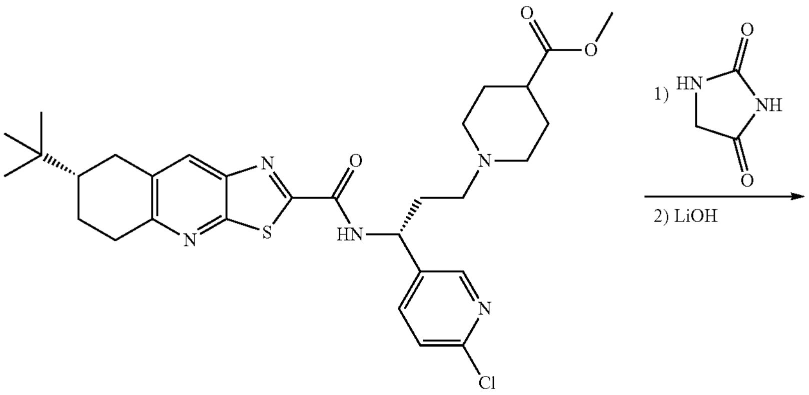

I-46

-continued

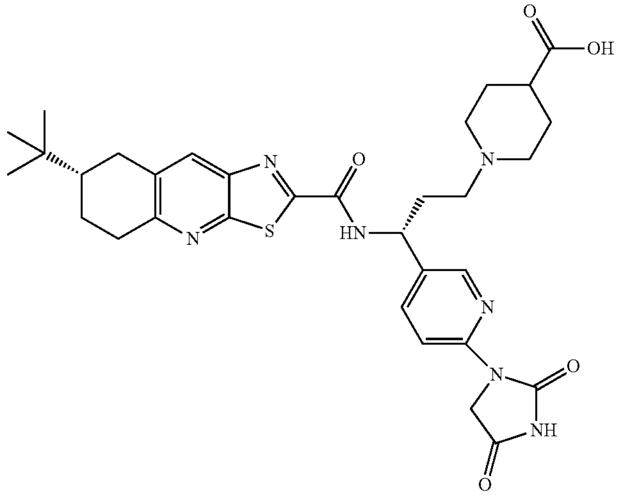

Ex. 222

A mixture of $Cs_2CO_3$ (600 mg, 1.842 mmol), $Pd(Oac)_2$ (41.3 mg, 0.184 mmol), Xantphos (213 mg, 0.368 mmol), methyl 1-((R)-3-((S)-7-(tert-butyl)-5,6,7,8-tetrahydrothiazolo[5,4-b]quinoline-2-carboxamido)-3-(6-chloropyridin-3-yl)propyl)piperidine-4-carboxylate (I-46, 538 mg, 0.921 mmol), imidazolidine-2,4-dione (276 mg, 2.76 mmol) was evacuated and back filled with $N_2$ three times. Then dioxane (11 mL) was added. The mixture was evacuated and back filled with $N_2$ three times. The mixture was stirred at 100° C. for 3 h. The reaction mixture was then cooled to rt, MeOH and THE was added, followed by aq. LiOH solution (1.0 M, 8.5 mL). The mixture was stirred at rt for 3 h. Upon completion, the reaction was quenched with acetic acid, diluted with DMSO, filtered and purified by reverse phase HPLC (ACN/water with 0.05% TFA modifier) to afford the title compound. MS: 634 (M+1).

| Ex. No. | Structure | Chemical Name | Mass [M + H]+ | hNPRA EC50 (nM) |
|---|---|---|---|---|
| 222 | 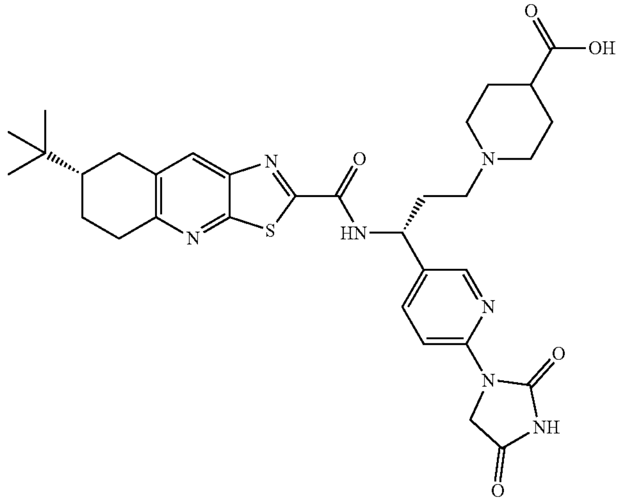 [SMILES: CC(C)(C)[C@H]1CCc2nc3sc(C(=O)N[C@H](CCN4CCC(C(=O)O)CC4)c4ccc(N5CC(=O)NC5=O)nc4)nc3cc2C1] | 1-((R)-3-((S)-7-(tert-butyl)-5,6,7,8-tetrahydrothiazolo[5,4-b]quinoline-2-carboxamido)-3-(6-(2,4-dioxoimidazolidin-1-yl)pyridin-3-yl)propyl)piperidine-4-carboxylic acid | 634 | 626 |

Examples 223-224
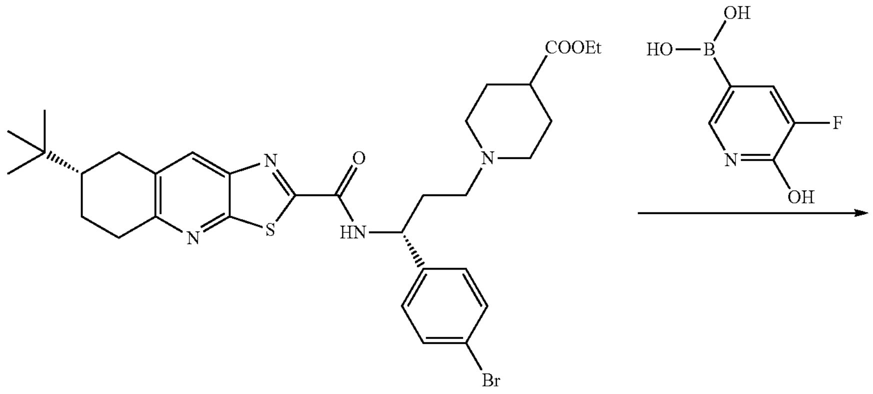
I-47
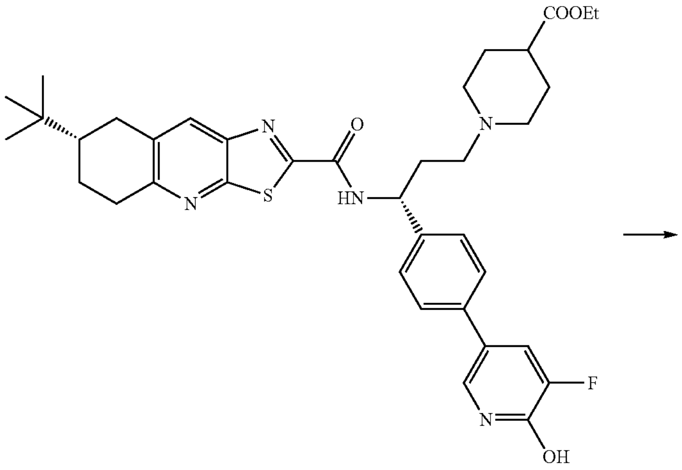
IAW-1
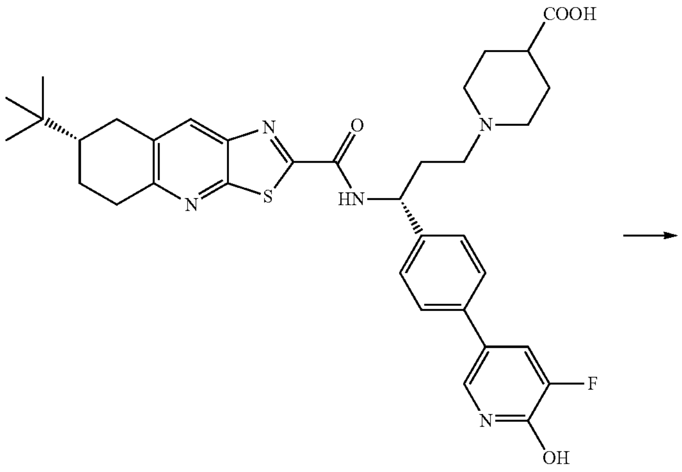
Example 223

-continued

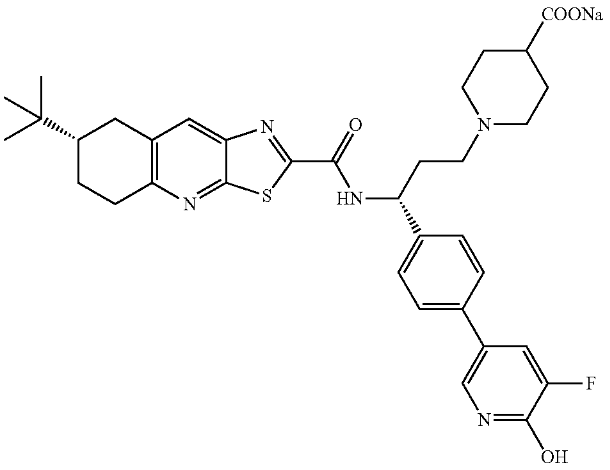

Example 224 ethyl 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylate (IAW-1)

To a solution of ethyl 1-((R)-3-(4-bromophenyl)-3-((S)-7-(tert-butyl)-5,6,7,8-tetrahydrothiazolo[5,4-b]quinoline-2-carboxamido) propyl)piperidine-4-carboxylate (I-47, 300 mg, 0.468 mmol) in dioxane/water (9 ml/1 ml) was added (5-fluoro-6-hydroxypyridin-3-yl) boronic acid (110 mg, 0.701 mmol), $Na_2CO_3$ (0.468 ml, 1.169 mmol). The mixture was degassed with $N_2$ for 10 min. [1,1'bis(diphenylphosphino) ferrocene]dichloropalladium (II) (51.3 mg, 0.070 mmol) was added and degassed for another 2 min. The vial was sealed and was heated at 100° C. for 2 hours. Reaction mixture was concentrated to dryness. The residue was purified on a RediSep® Rr 12 g column (Teledyne ISCO, Inc, Lincoln, NE, USA) using DCM/MeOH (0-6%) to afford impure product mixture. This was further purified on a RediSep® Rf 12 g using DCM/ethyl acetate (0-100%) afforded ethyl 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylate (270 mg, 86%). MS: 674 (M+1). $^1$H NMR (300 MHz, $CDCl_3$) δ 10.5 (d, J=7.0 Hz, 1H), 8.24 (s, 1H), 7.52 (dd, J=11.0, 1.9 Hz, 1H), 7.26-7.41 (m, 5H), 5.38 (br s, 1H), 4.21 (q, J=7.1 Hz, 2H), 2.95-3.24 (m, 5H), 2.76 (m, 1H), 2.57 (m, 1H), 2.24-2.49 (m, 4H), 2.11-2.18 (m, 4H), 1.84-2.07 (m, 3H), 1.52-1.59 (m, 2H), 1.25 (t, J=7.1 Hz, 3H), 1.00 (s, 9H).

Example 223

1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylic acid (Example 223)

To the solution of compound ethyl 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylate (IAW-1) (270 mg, 0.401 mmol) in MeOH (5 mL) was added NaOH (1.0 ml, 10% aq. Solution) and the reaction was stirred at room temperature for 4 h. After completion, MeOH was evaporated, and the pH of the aqueous residue was adjusted to 4 using 2 N HCl. The mixture was then extracted with 20% MeOH in DCM (5×3 mL). The combined organic layers were dried on $Na_2SO_4$, filtered and concentrated to give 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylic acid, Example 223. MS: 646 (M+1). $^1$H NMR (400 MHZ, $CD_3OD$) δ 8.23 (s, 1H), 7.78 (dd, J=11.4, 2.0 Hz, 1H), 7.53-7.59 (m, 5H), 5.27 (t, J=6.6 Hz, 1H), 3.41-3.48 (m, 2H), 2.97-3.29 (m, 7H), 2.77 (m, 1H), 2.57 (m, 1H), 2.35-2.45 (m, 2H), 1.96-2.16 (m, 5H), 1.54-1.59 (m, 2H), 1.02 (s, 9H).

Example 224 sodium 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylate Example 224

To solution of 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylic acid (Example 223) (154 mg, 0.238 mmol) in water (10 mL) and acetonitrile (50 mL), 1N NaOH (aq) (0.23 ml, 0.23 mmol) was added. The mixture was stirred for 20 minutes, and then lyophilized to give sodium 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylate (Example 224). MS: 644 (M−1).

| Ex. No. | Structure | Chemical Name | Mass [M + H]+ | hNPRA EC50 (nM) |
|---|---|---|---|---|
| 223 | 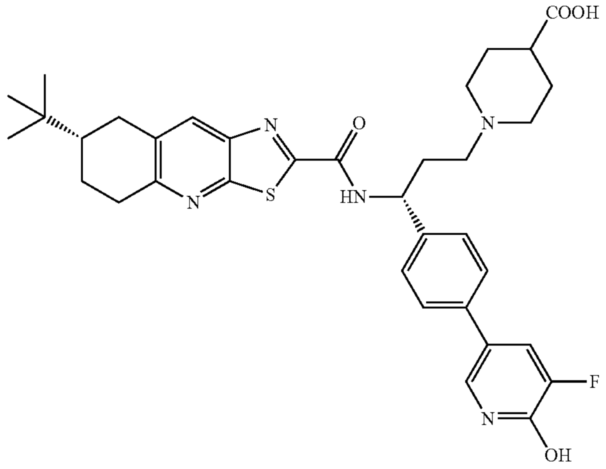 [SMILES: CC(C)(C)[C@H]1CCc2nc3sc(C(=O)N[C@H](CCN4CCC(C(=O)O)CC4)c4ccc(-c5cnc(O)c(F)c5)cc4)nc3cc2C1] | 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylic acid | 646 | 200 |
| 224 | 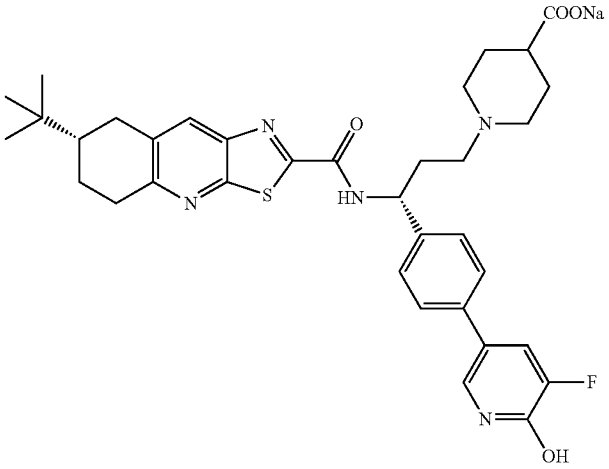 | sodium 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylate | 644 [M − H]+ | 198 |

Example 225

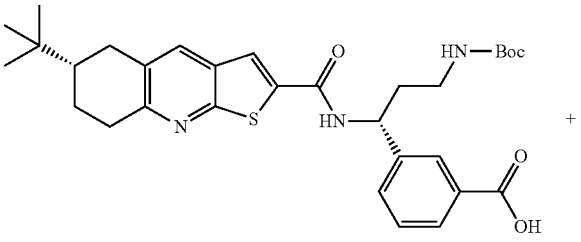

I-25

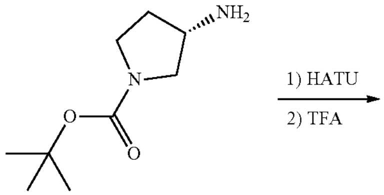

-continued

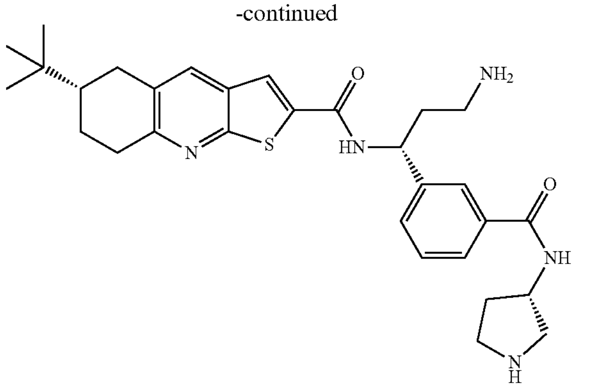

A mixture of 3-((R)-3-((tert-butoxycarbonyl)amino)-1-((S)-6-(tert-butyl)-5,6,7,8-tetrahydrothieno[2,3-b]quinoline-2-carboxamido) propyl)benzoic acid (I-25, 100 mg, 0.18 mmol), tert-butyl(S)-3-aminopyrrolidine-1-carboxylate (HCl salt, 59 mg, 0.27 mmol), HATU (121 mg, 0.32 mmol), and DIEA (93 μL, 0.53 mmol) in DMF (1768 μL) was stirred at RT for 2 h. The reaction was diluted with EtOAc (10 mL)

and sat. aq. $NH_4Cl$ (10 mL). The organic layer was separated and washed with sat. aq. $NaHCO_3$ (10 mL) and brine (10 mL), dried over $Na_2SO_4$, filtered, and concentrated under reduced pressure. The residue was dissolved in DCM (600 μL), TFA (600 μL, 7.79 mmol) was added. The reaction was stirred for at RT for 30 min. The reaction mixture was evaporated under reduced pressure, and the residue was purified by preparative HPLC Reverse phase (C-18), eluting with Acetonitrile/Water+0.1% TFA (ACN 10% to 70%), to give the title compound as TFA salt.

| Ex. No. | Structure | Chemical Name | Mass [M + H]+ | hNPRA EC50 (nM) |
|---|---|---|---|---|
| 225 | 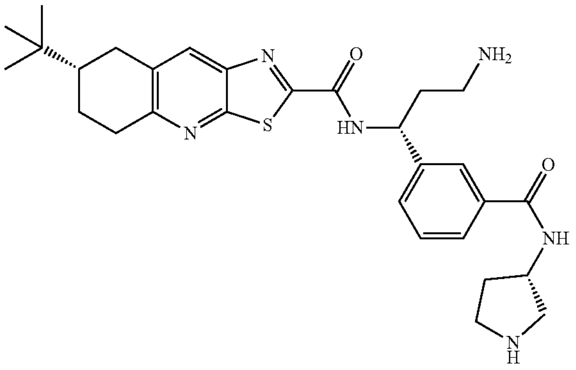 [SMILES: CC(C)(C)[C@H]1CCc2nc3sc(C(=O)N[C@H](CCN)c4cccc(C(=O)N[C@H]5CCNC5)c4)nc3cc2C1] | (S)-N-((R)-3-amino-1-(3-(((S)-pyrrolidin-3-yl)carbamoyl)phenyl)propyl)-6-(tert-butyl-5,6,7,8-tetrahydrothieno[2,3-b]quinoline-2-carboxamide | 534 | 292 |

Example 226

(S)-N-((R)-1-(4-bromo-3-fluorophenyl)-3-hydroxy-propyl)-7-(tert-butyl)-5,6,7,8-tetrahydrothiazolo[5,4-b]quinoline-2-carboxamide

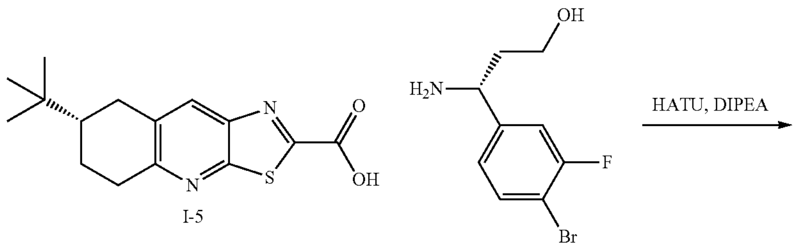

I-5

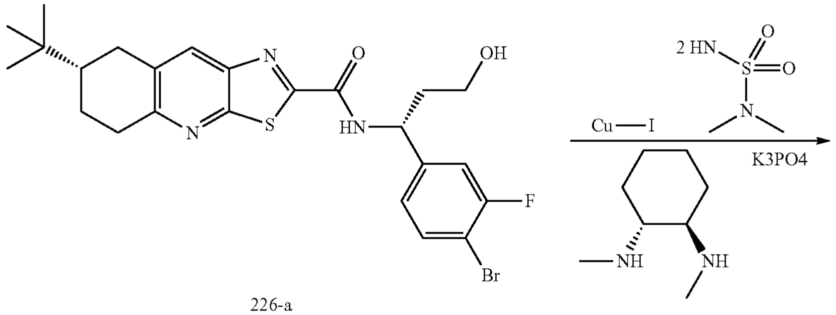

226-a

-continued
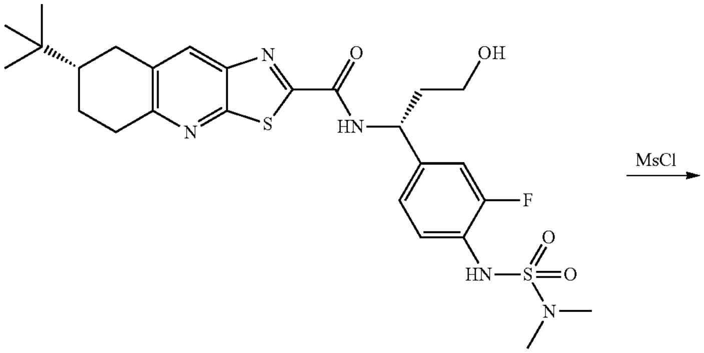
226-b
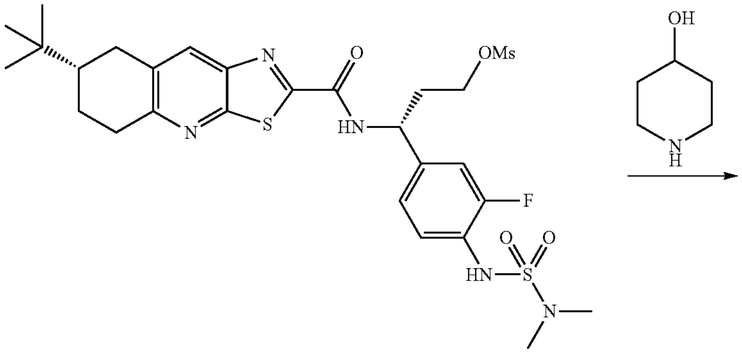
226-c
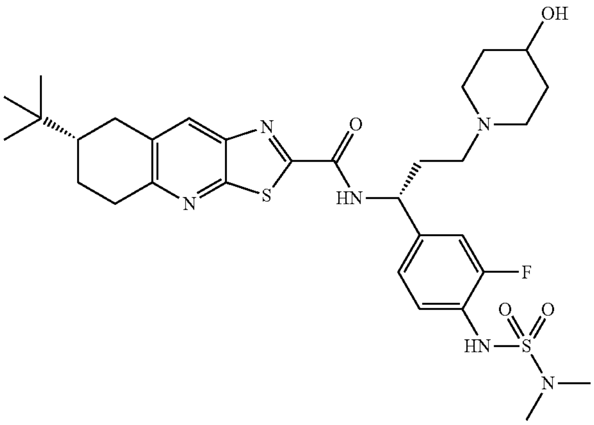
Example 226

Step 1 (S)-N-((R)-1-(4-bromo-3-fluorophenyl)-3-hydroxypropyl)-7-(tert-butyl)-5,6,7,8-tetrahydrothiazolo[5,4-b]quinoline-2-carboxamide (226-a)

(S)-7-(tert-butyl)-5,6,7,8-tetrahydrothiazolo[5,4-b]quinoline-2-carboxylic acid (I-5, 500 mg, 1.722 mmol), (R)-3-amino-3-(4-bromo-3-fluorophenyl)propan-1-ol hydrochloride (500 mg, 1.757 mmol), HATU (982 mg, 2.58 mmol), and DIPEA (902 μL, 5.17 mmol) were mixed together in DMF (8609 μl). The mixture was stirred at rt for 16 h. The mixture was diluted with EtOAc (20 mL). The organic layer was washed with sat. $NH_4Cl$ (20 mL), sat. $NaHCO_3$ (20 mL), water (20 mL), brine (20 mL), dried over $Na_2SO_4$, filtered, and concentrated to dryness. The residue was purified by column chromatography on silica gel, eluting with 10% to 100% EtOAc/hexane to afford(S)-N-((R)-1-(4-bromo-3-fluorophenyl)-3-hydroxypropyl)-7-(tert-butyl)-5,6,7,8-tetrahydrothiazolo[5,4-b]quinoline-2-carboxamide (226-a). MS: 520 (M+1).

Step 2 (S)-7-(tert-butyl)-N-((R)-1-(4-((N,N-dimethylsulfamoyl)amino)-3-fluorophenyl)-3-hydroxypropyl)-5,6,7,8-tetrahydrothiazolo[5,4-b]quinoline-2-carboxamide (226-b)

(S)-N-((R)-1-(4-bromo-3-fluorophenyl)-3-hydroxypropyl)-7-(tert-butyl)-5,6,7,8-tetrahydrothiazolo[5,4-b]quinoline-2-carboxamide (226-a) (60 mg, 0.115 mmol), N,N-dimethylsulfamide (57.3 mg, 0.461 mmol), CuI (21.96, 0.115 mmol), trans-N,N'-dimethylcyclohexane-1,2-diamine (36.4 μL, 0.231 mmol), and potassium phosphate tribasic (98 mg, 0.461 mmol) were mixed together in dioxane (1153 μl). The mixture was stirred for 1.5 days at 100° C. The reaction mixture was cooled down to rt, filtered through a Celite® pad washing with MeOH. The filtrate was concentrated. The crude was purified by preparative HPLC with C-18 column, eluting with Acetonitrile/Water+0.1% TFA, to afford the title compound 226-b. MS: 564 (M+1).

Step 3 (R)-3-((S)-7-(tert-butyl)-5,6,7,8-tetrahydrothiazolo[5,4-b]quinoline-2-carboxamido)-3-(4-((N,N-dimethylsulfamoyl)amino)-3-fluorophenyl) propyl methanesulfonate (226-c)

To a solution of(S)-7-(tert-butyl)-N-((R)-1-(4-((N,N-dimethylsulfamoyl)amino)-3-fluorophenyl)-3-hydroxypropyl)-5,6,7,8-tetrahydrothiazolo[5,4-b]quinoline-2-carboxamide (226-b) (33 mg, 0.059 mmol) in $CH_2Cl_2$ (390 μl) was added TEA (16.32 μl, 0.117 mmol) followed by addition of methanesulfonyl chloride (5.93 μl, 0.076 mmol). The reaction mixture was stirred at rt for 1 h. 2 mL of EtOAc was added and the organic layer was washed with sat. $NaHCO_3$ (2 mL). The organic layer was collected, dried over $Na_2SO_4$, filtered, and concentrated to afford the title compound, 226-c. MS: 642 (M+1).

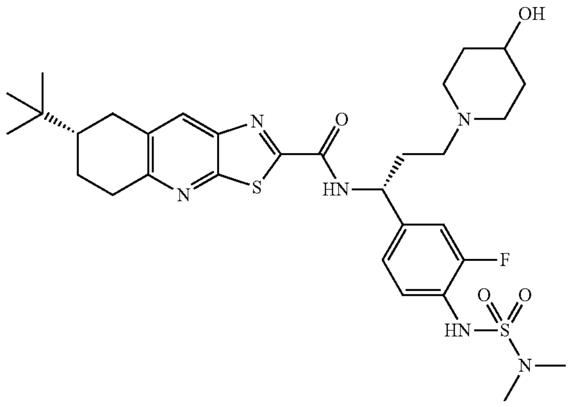 [SMILES: CN(C)S(=O)(=O)Nc1ccc([C@@H](CCN2CCC(O)CC2)NC(=O)c2nc3cc4c(nc3s2)CC[C@H](C(C)(C)C)C4)cc1F]

Step 4 (S)-7-(tert-butyl)-N-((R)-1-(4-((N,N-dimethylsulfamoyl)amino)-3-fluorophenyl)-3-(4-hydroxypiperidin-1-yl)propyl)-5,6,7,8-tetrahydrothiazolo[5,4-b]quinoline-2-carboxamide (Example 226)

(R)-3-((S)-7-(tert-butyl)-5,6,7,8-tetrahydrothiazolo[5,4-b]quinoline-2-carboxamido)-3-(4-((N,N-dimethylsulfamoyl)amino)-3-fluorophenyl)propyl methanesulfonate (226-c) (37 mg, 0.058 mmol) and 4-hydroxypiperidine (20 mg, 0.198 mmol) were mixed together in acetonitrile (577 μl). The mixture was heated at 90° C. for 2 h. The reaction was cooled down to RT and diluted with ACN to 4 mL. This solution was purified by preparative HPLC eluting with 18% to 78% Acetonitrile/Water+0.1% TFA, to afford the title compound, Example 226. MS: 647 (m+1).

| Ex. No. | Structure | Chemical Name | Mass [M + H]+ | hNPRA EC50 (nM) |
|---|---|---|---|---|
| 226 | 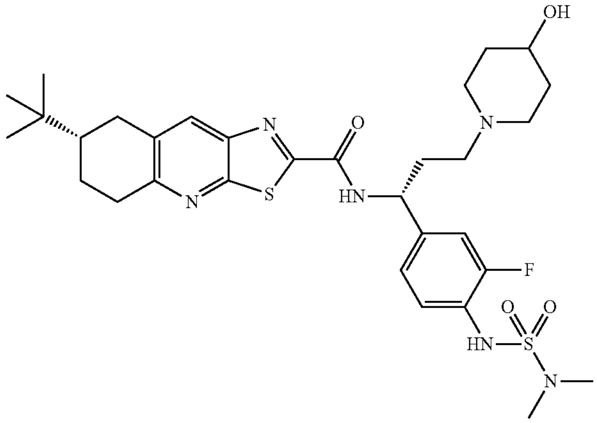 [SMILES: CN(C)S(=O)(=O)Nc1ccc([C@@H](CCN2CCC(O)CC2)NC(=O)c2nc3cc4c(nc3s2)CC[C@H](C(C)(C)C)C4)cc1F] | (S)-7-(tert-butyl)-N-((R)-1-(4-((N,N-dimethylsulfamoyl)amino)-3-fluorophenyl)-3-(4-hydroxypiperidin-1-yl)propyl)-5,6,7,8-tetrahydrothiazolo[5,4-b]quinoline-2-carboxamide | 647 | 677 |

Example 227

(S)-7-(tert-butyl)-N-((R)-1-(6-(ethylsulfonyl)pyridin-3-yl)-3-(4-hydroxypiperidin-1-yl)propyl)-5,6,7,8-tetrahydrothiazolo[5,4-b]quinoline-2-carboxamide (Example 227)

Step 1 (S)-7-(tert-butyl)-N-((R)-1-(6-(ethylsulfonyl)pyridin-3-yl)-3-hydroxypropyl)-5,6,7,8-tetrahydrothiazolo[5,4-b]quinoline-2-carboxamide (227-a)

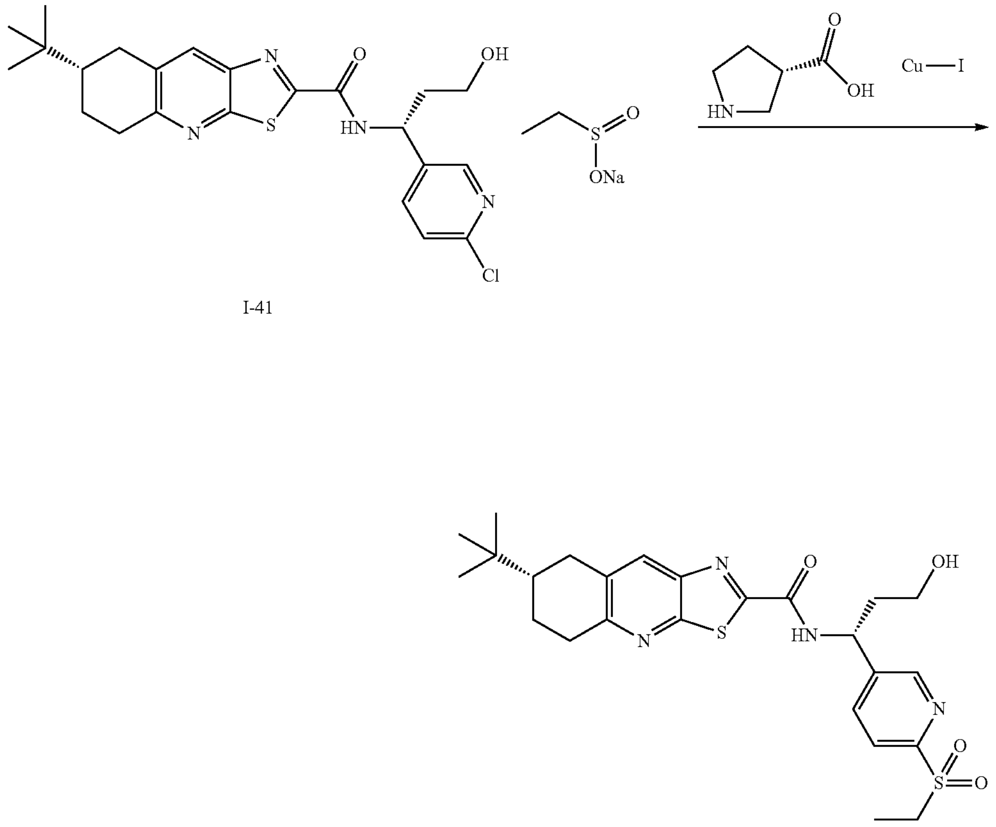

I-41

227-a (S)-7-(tert-butyl)-N-((R)-1-(6-chloropyridin-3-yl)-3-hydroxypropyl)-5,6,7,8-tetrahydrothiazolo[5,4-b]quinoline-2-carboxamide (I-41) (200 mg, 0.436 mmol), sodium ethanesulfinate (304 mg, 2.61 mmol), (S)-pyrrolidine-3-carboxylic acid (66 mg, 0.573 mmol), and CuI (45 mg, 0.236 mmol) were mixed together in DMSO (4357 μl). After flushing with $N_2$, the reaction was stirred at 120° C. for 24 h. The reaction was cooled down to RT then filtered through a Celite®, washing the Celite® pad with 5 mL EtOAc and 5 mL MeOH. The solvent was removed and the residue was purified by column chromatography on a C18 reverse-phase column eluting with 0% to 100% ACN/water+0.1% TFA to afford the title compound, 227-a. LCMS m/z 517 $[M+H]^+$.

Step 2 (S)-7-(tert-butyl)-N-((R)-1-(6-(ethylsulfonyl)pyridin-3-yl)-3-oxopropyl)-5,6,7,8-tetrahydrothiazolo[5,4-b]quinoline-2-carboxamide (227-b)

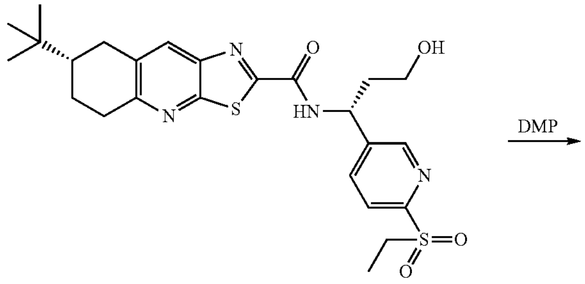

227-a

-continued

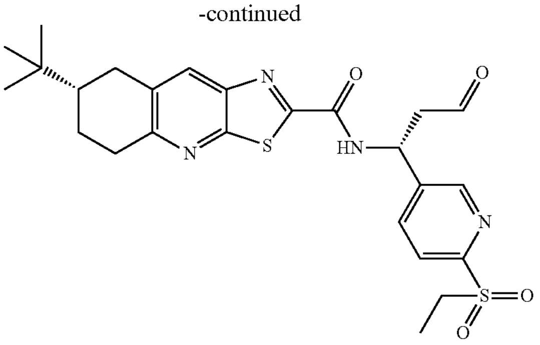

227-b (S)-7-(tert-butyl)-N-((R)-1-(6-(ethylsulfonyl)pyridin-3-yl)-3-hydroxypropyl)-5,6,7,8-tetrahydrothiazolo[5,4-b]quinoline-2-carboxamide (227-a) (60 mg, 0.116 mmol) in $CH_2Cl_2$ (1161 µl) at 0° C. was added DMP (73.9 mg, 0.174 mmol) and the resulting mixture was stirred for 2 h at RT. 3 mL of EtOAc was added to the RN followed by 2 mL of aq. sat. $NaHCO_3$. The layers were separated, the organic layer was collected and dried over $Na_2SO_4$ and filtered. The filtrate was concentrated to dryness to afford the title compound, 227-b. LCMS m/z 513 [M−H].

Step 3 (S)-7-(tert-butyl)-N-((R)-1-(6-(ethylsulfonyl)pyridin-3-yl)-3-(4-hydroxypiperidin-1-yl)propyl)-5,6,7,8-tetrahydrothiazolo[5,4-b]quinoline-2-carboxamide (Example 227)

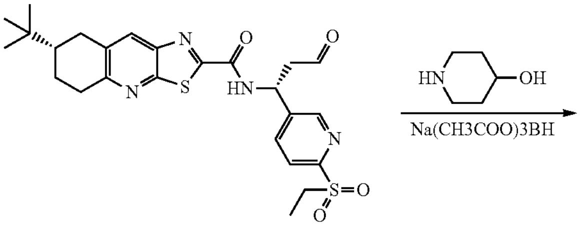

227-b

-continued

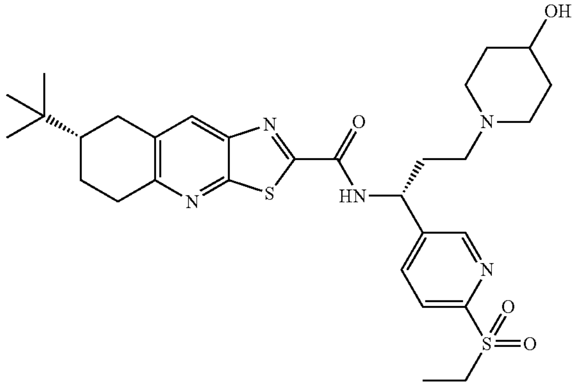

Ex 227

To (S)-7-(tert-butyl)-N-((R)-1-(6-(ethylsulfonyl)pyridin-3-yl)-3-oxopropyl)-5,6,7,8-tetrahydrothiazolo[5,4-b]quinoline-2-carboxamide (227-b) (60 mg, 0.117 mmol) and piperidin-4-ol (23.58 mg, 0.233 mmol) in $CH_2Cl_2$ (1422 µl) was added a drop of Acetic Acid (35.5 µl). After 20 min of stirring at RT, sodium triacetoxyborohydride (49.4 mg, 0.233 mmol) was added, and the RN was continued to stir for 1 h. The reaction was diluted in EtOAc (5 mL) and quenched with sat. $NaHCO_3$ (5 mL). The layers were separated. The aq. layer was extracted with EtOAc (5 mL). The organic layers were combined, dried over $Na_2SO_4$, filtered, and concentrated to dryness. The residue was purified by preparative HPLC eluting with 14% to 60% Acetonitrile/Water+0.1% TFA to afford the tittle compound, Example 227.

| Ex. No. | Structure | Chemical Name | Mass [M + H]+ | hNPRA EC50 (nM) |
|---|---|---|---|---|
| 227 | 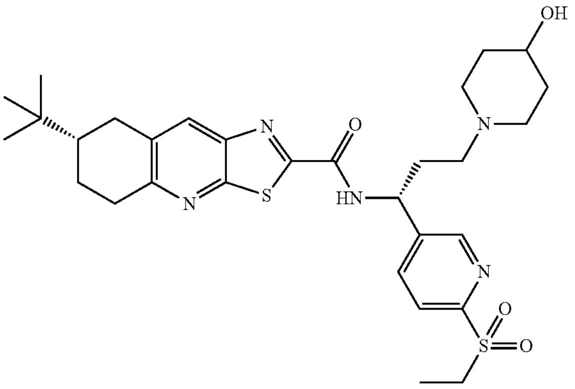 [SMILES: CCS(=O)(=O)c1ccc([C@@H](CCN2CCC(O)CC2)NC(=O)c2nc3cc4c(nc3s2)CC[C@H](C(C)(C)C)C4)cn1] | (S)-7-(tert-butyl)-N-((R)-1-(6-(ethylsulfonyl)pyridin-3-yl)-3-(4-hydroxypiperidin-1-yl)propyl)-5,6,7,8-tetrahydrothiazolo[5,4-b]quinoline-2-carboxamide | 600 | 696 |

Example 228

(S)-7-(tert-butyl)-N-((R)-1-(4-(4-fluoro-5-hydroxy-pyridin-2-yl)phenyl)-3-(4-hydroxypiperidin-1-yl) propyl)-5,6,7,8-tetrahydrothiazolo[5,4-b]quinoline-2-carboxamide Step 1 (S)-7-(tert-butyl)-N-((R)-1-(4-(4-fluoro-5-(methoxymethoxy)pyridin-2-yl)phenyl)-3-(4-hydroxypiperidin-1-yl)propyl)-5,6,7,8-tetrahydrothiazolo[5,4-b]quinoline-2-carboxamide (228-a)

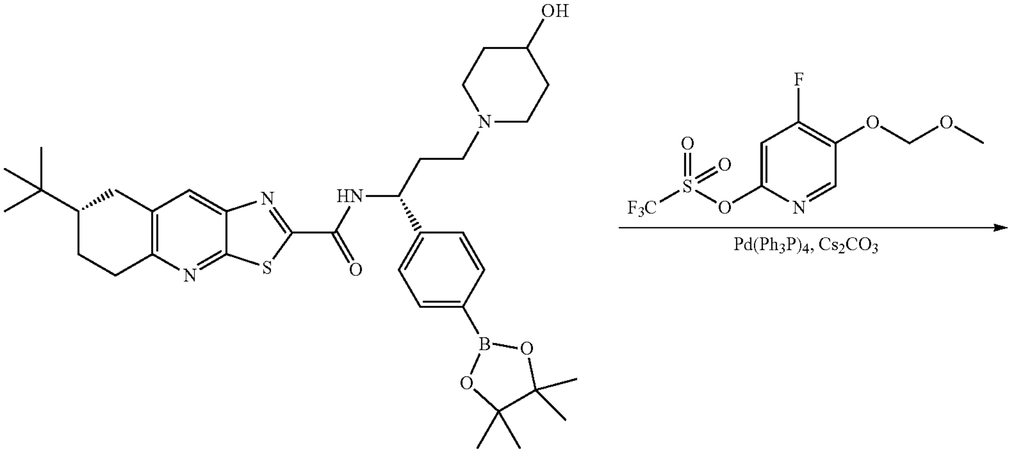

I-40

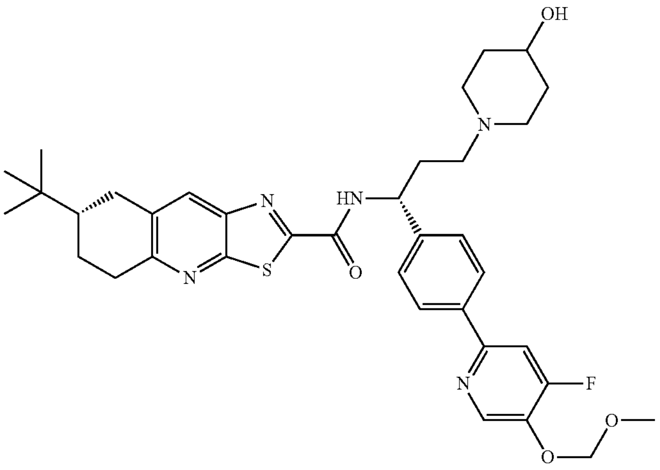

228-a

To a degassed solution of(S)-7-(tert-butyl)-N-((R)-3-(4-hydroxypiperidin-1-yl)-1-(4-(4,4,5,5-tetramethyl-1,3,2-dioxaborolan-2-yl)phenyl)propyl)-5,6,7,8-tetrahydrothiazolo [5,4-b]quinoline-2-carboxamide (I-40) (250 mg, 0.395 mmol) in 1,4-dioxane (1.2 mL) was added 4-fluoro-5-(methoxymethoxy)pyridin-2-yl trifluoromethanesulfonate (241 mg, 0.790 mmol), $Cs_2CO_3$ (386 mg, 1.185 mmol) and $Pd(Ph_3P)_4$ (91 mg, 0.079 mmol) under Argon in a sealed tube. The vessel was sealed, and the reaction was stirred for 16 h at 90° C. The reaction was then cooled to room temperature. Water was added to reaction mixture. The mixture was extracted with EtOAc. The organic layer was dried with anhydrous sodium sulfate, filtered and concentrated. The residue was purified by silica chromatography (MeOH in DCM) to provide the title compound, 228-a. LCMS 662 [M+H].

Step 2: (S)-7-(tert-butyl)-N-((R)-1-(4-(4-fluoro-5-hydroxypyridin-2-yl)phenyl)-3-(4-hydroxypiperidin-1-yl)propyl)-5,6,7,8-tetrahydrothiazolo[5,4-b]quinoline-2-carboxamide (Example 228)

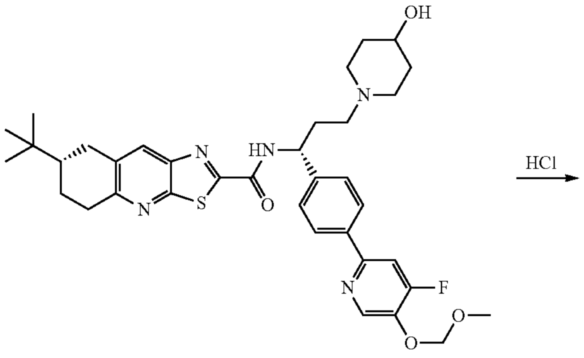

228-a

-continued

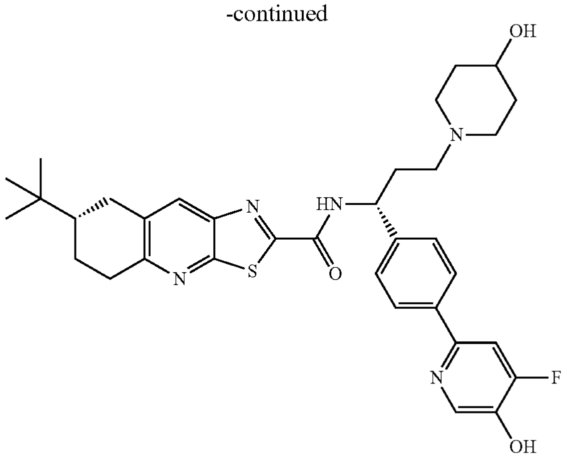

Ex. 228

To a solution of methyl(S)-7-(tert-butyl)-N-((R)-1-(4-(4-fluoro-5-(methoxymethoxy)pyridin-2-yl)phenyl)-3-(4-hydroxypiperidin-1-yl)propyl)-5,6,7,8-tetrahydrothiazolo[5,4-b]quinoline-2-carboxamide (228-a) (70 mg, 0.106 mmol) in MeOH was added 6 N aq. HCl (1 mL). The reaction mixture was stirred at RT for 3 h. The reaction mixture was evaporated under reduced pressure. The residue was purified by reverse phase C18 column chromatography (Acetonitrile/Water+0.1% TFA) to give the title compound, Example 228.

| Ex. No. | Structure | Chemical Name | Mass [M + H]+ | hNPRA EC50 (nM) |
|---|---|---|---|---|
| 228 | 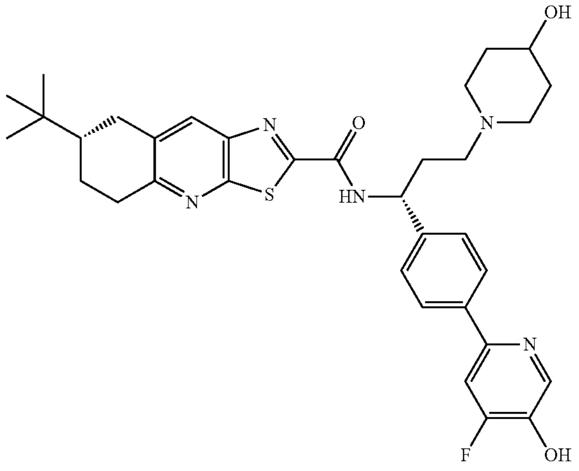 [SMILES: CC(C)(C)[C@H]1CCc2nc3sc(C(=O)N[C@H](CCN4CCC(O)CC4)c4ccc(-c5cc(F)c(O)cn5)cc4)nc3cc2C1] | (S)-7-(tert-butyl)-N-((R)-1-(4-(4-fluoro-5-hydroxypyridin-2-yl)phenyl)-3-(4-hydroxypiperidin-1-yl)propyl)-5,6,7,8-tetrahydrothiazolo[5,4-b]quinoline-2-carboxamide | 618 | 305 |

Example 229

(S)-N-((R)-3-amino-1-phenylpropyl)-6-(tert-butyl)-5,6,7,8-tetrahydrothieno[2,3-b]quinoline-2-carboxamide (Ex. 229)

Step 1 6-(tert-butyl)-N-((R)-2-cyano-1-phenylethyl)-5,6,7,8-tetrahydrothieno[2,3-b]quinoline-2-carboxamide (229-a)

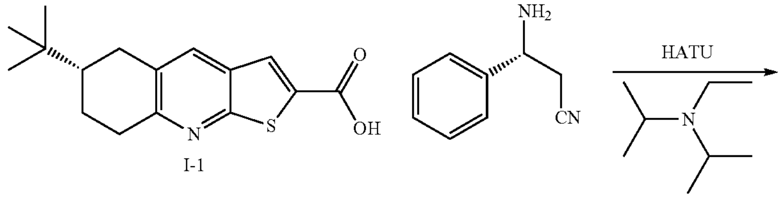

I-1

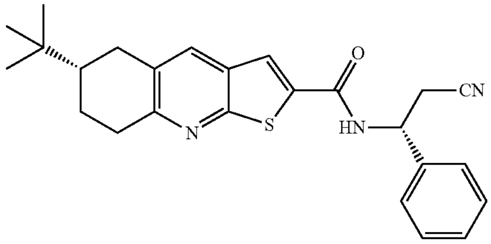

229-a (R)-3-amino-3-phenylpropanenitrile (35 mg, 0.239 mmol), (S)-6-(tert-butyl)-5,6,7,8-tetrahydrothieno[2,3-b]quinoline-2-carboxylic acid (1-1) (45.3 mg, 0.157 mmol) and HATU (91.1 mg, 0.240 mmol) was added DMF (2 ml) followed by DIPEA (0.082 ml, 0.470 mmol). The reaction stirred at RT overnight. The reaction was diluted with aqueous HCl (0.5 M, 30 mL) and then extracted with 40 mL of ethyl acetate. The organic layer was dried over sodium sulfate, filtered and concentrated. The residue was purified by RP-HPLC (Reversed Phase High-Performance Liquid Chromatography) [C18 column, water (0.1% TFA)-$CH_3CN$] to give the title compound, 299-a. LCMS 418 [M+H].

Step 2 (S)-N-((R)-3-amino-1-phenylpropyl)-6-(tert-butyl)-5,6,7,8-tetrahydrothieno[2,3-b]quinoline-2-carboxamide (Example 229)

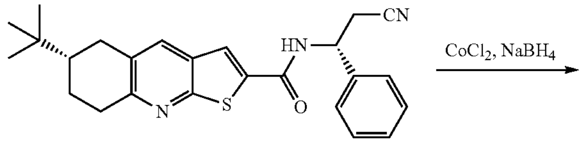

229-a

-continued

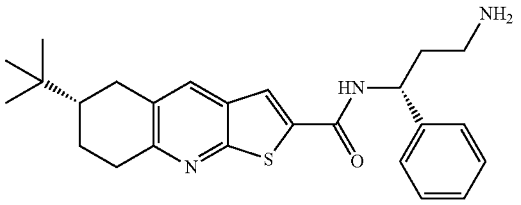

Example 229

A solution of 6-(tert-butyl)-N-((R)-2-cyano-1-phenylethyl)-5,6,7,8-tetrahydrothieno[2,3-b]quinoline-2-carboxamide (229-b) (20 mg, 0.048 mmol) and cobalt (II) chloride hexahydrate (22.22 mg, 0.093 mmol) in THF (300 μL) and methanol (900 μL) was cooled to −5° C. $NaBH_4$ (9.06 mg, 0.239 mmol) was added. The reaction was stirred at RT overnight. The reaction was quenched with 2 mL 4N aq. HCl and then it stirred at room temperature for 1 h. The reaction mixture was filtered, and the filtrate was evaporated under reduced pressure. The residue was purified by RP-HPLC [C18 column, water (0.1% TFA)-$CH_3CN$] to give the product, Example 229.

| Ex. No. | Structure | Chemical Name | Mass [M + H]+ | hNPRA EC50 (nM) |
|---|---|---|---|---|
| 229 | 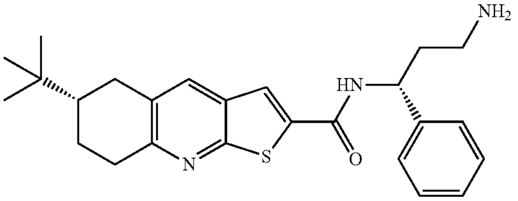 [SMILES: CC(C)(C)[C@H]1CCc2nc3sc(C(=O)N[C@H](CCN)c4ccccc4)cc3cc2C1] | (S)-N-((R)-3-amino-1-phenylpropyl)-6-(tert-butyl)-5,6,7,8-tetrahydrothieno[2,3-b]quinoline-2-carboxamide | 422 | >2000 |

Example 230

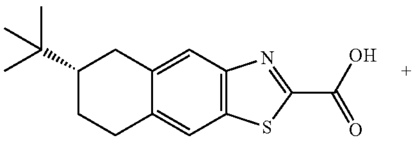

I-5

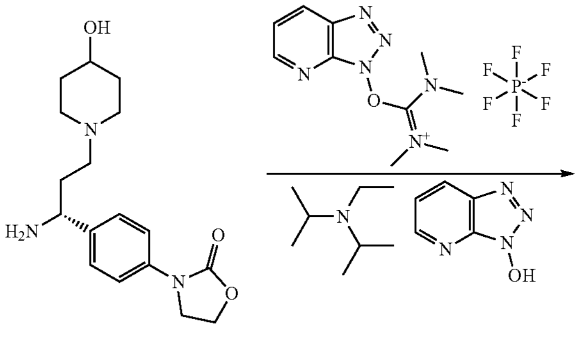

-continued

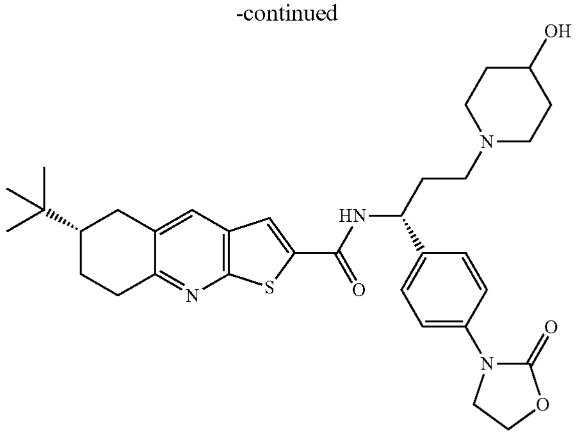

Ex. 230

To (S)-7-(tert-butyl)-5,6,7,8-tetrahydrothiazolo[5,4-b]quinoline-2-carboxylic acid (I-5) (20.19 mg, 0.070 mmol), (R)-3-(4-(1-amino-3-(4-hydroxypiperidin-1-yl)propyl)phenyl) oxazolidin-2-one (1-17) (HCl salt, 30 mg, 0.076 mmol), 3H-[1,2,3]triazolo[4,5-b]pyridin-3-ol (13.25 mg, 0.097 mmol) and HATU (37.0 mg, 0.097 mmol) was added DMF (1 mL) followed by DIEA (0.061 ml, 0.348 mmol). The reaction mixture was stirred at RT for 1 h. The reaction mixture was filtered and purified by RP-HPLC [C18 column, water (0.1% TFA)-$CH_3CN$] to give the product, Example 230.

| Ex. No. | Structure | Chemical Name | Mass [M + H]+ | hNPRA EC50 (nM) |
|---|---|---|---|---|
| 230 | 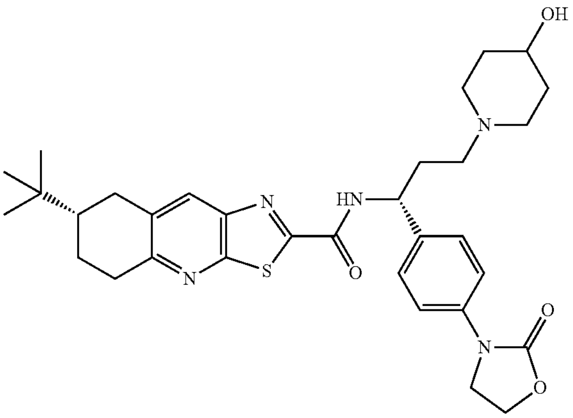 [SMILES: CC(C)(C)[C@H]1CCc2nc3sc(C(=O)N[C@H](CCN4CCC(O)CC4)c4ccc(N5CCOC5=O)cc4)nc3cc2C1] | (S)-7-(tert-butyl)-N-((R)-3-(4-hydroxypiperidin-1-yl)-1-(4-(2-oxooxazolidin-3-yl)phenyl)propyl)-5,6,7,8-tetrahydrothiazolo[5,4-b]quinoline-2-carboxamide | 592 | 1025 |

Examples 231-235

Examples 231-235 were prepared by following a similar procedure to that disclosed for Example 230.

| Ex. No. | Structure | Chemical Name | Mass [M + H]+ | hNPRA EC50 (nM) |
| --- | --- | --- | --- | --- |
| 231 | 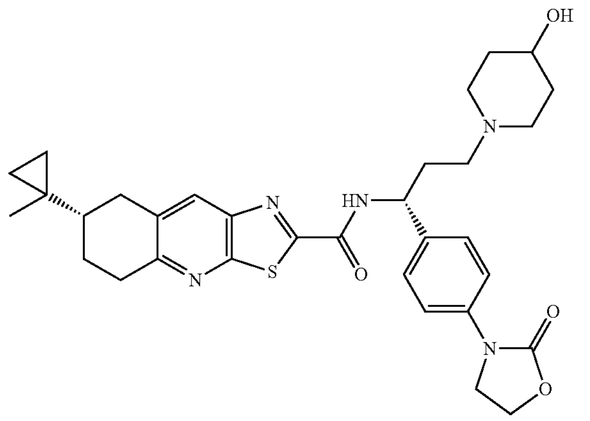 [SMILES: CC1([C@H]2CCc3nc4sc(C(=O)N[C@H](CCN5CCC(O)CC5)c5ccc(N6CCOC6=O)cc5)nc4cc3C2)CC1] | (S)-N-((R)-3-(4-hydroxypiperidin-1-yl)-1-(4-(2-oxooxazolidin-3-yl)phenyl)propyl)-7-(1-methylcyclopropyl)-5,6,7,8-tetrahydrothiazolo[5,4-b]quinoline-2-carboxamide | 590 | 725 |
| 232 | 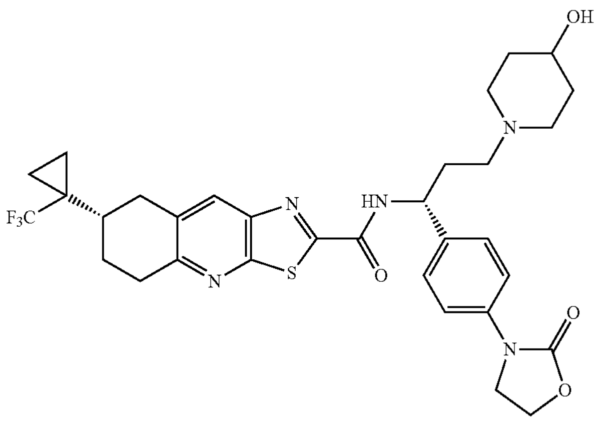 [SMILES: O=C(N[C@H](CCN1CCC(O)CC1)c1ccc(N2CCOC2=O)cc1)c1nc2cc3c(nc2s1)CC[C@H](C1(C(F)(F)F)CC1)C3] | (S)-N-((R)-3-(4-hydroxypiperidin-1-yl)-1-(4-(2-oxooxazolidin-3-yl)phenyl)propyl)-7-(1-(trifluoromethyl) cyclopropyl)-5,6,7,8-tetrahydrothiazolo[5,4-b]quinoline-2-carboxamide | 644 | 2197 |
| 233 | 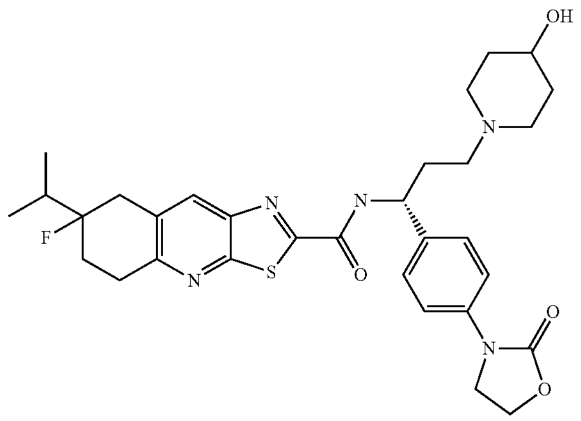 [SMILES: CC(C)C1(F)CCc2nc3sc(C(=O)N[C@H](CCN4CCC(O)CC4)c4ccc(N5CCOC5=O)cc4)nc3cc2C1] | 7-fluoro-N-((R)-3-(4-hydroxypiperidin-1-yl)-1-(4-(2-oxooxazolidin-3-yl)phenyl)propyl)-7-isopropyl-5,6,7,8-tetrahydrothiazolo[5,4-b]quinoline-2-carboxamide | 596 | 2044 |

-continued
| Ex. No. | Structure | Chemical Name | Mass [M + H]+ | hNPRA EC50 (nM) |
|---|---|---|---|---|
| 234 | 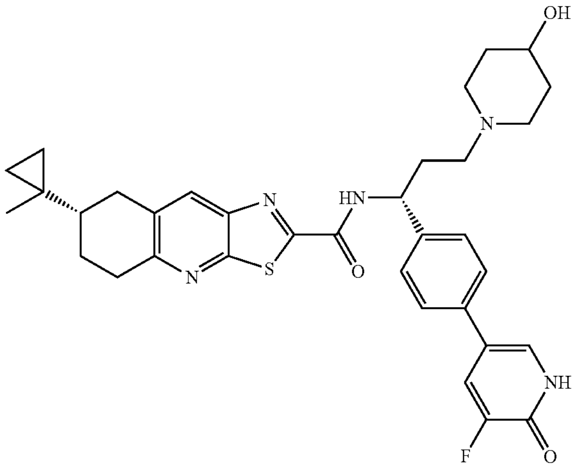 [SMILES: CC1([C@H]2CCc3nc4sc(C(=O)N[C@H](CCN5CCC(O)CC5)c5ccc(-c6c[nH]c(=O)c(F)c6)cc5)nc4cc3C2)CC1] | (S)-N-((R)-1-(4-(5-fluoro-6-oxo-1,6-dihydropyridin-3-yl)phenyl)-3-(4-hydroxypiperidin-1-yl)propyl)-7-(1-methylcyclopropyl)-5,6,7,8-tetrahydrothiazolo[5,4-b]quinoline-2-carboxamide | 616 | 120 |
| 235 | 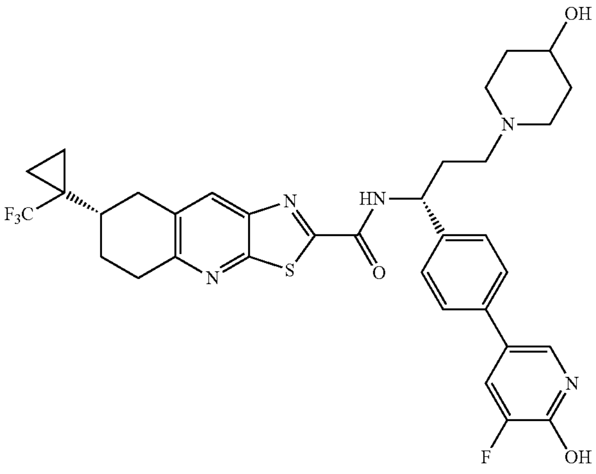 [SMILES: O=C(N[C@H](CCN1CCC(O)CC1)c1ccc(-c2cnc(O)c(F)c2)cc1)c1nc2cc3c(nc2s1)CC[C@H](C1(C(F)(F)F)CC1)C3] | (S)-N-((R)-1-(4-(5-fluoro-6-oxo-1,6-dihydropyridin-3-yl)phenyl)-3-(4-hydroxypiperidin-1-yl)propyl)-7-(1-(trifluoromethyl) cyclopropyl)-5,6,7,8-tetrahydrothiazolo[5,4-b]quinoline-2-carboxamide | 670 | 560 |

Example 236

Example 236 was prepared by following a similar procedure to that disclosed for Example 126.

| Ex. No. | Structure | Chemical Name | Mass [M + H]+ | hNPRA EC50 (nM) |
|---|---|---|---|---|
| 236 | 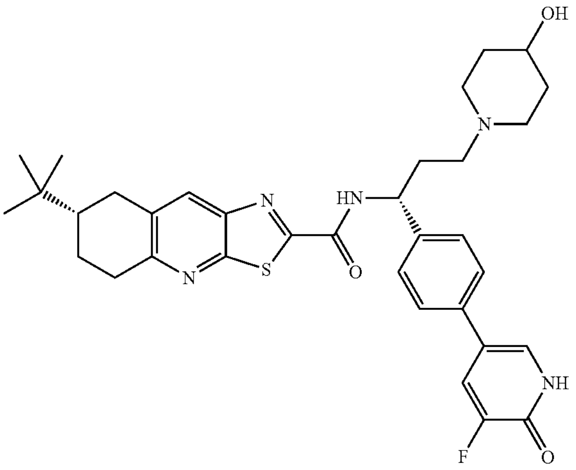 [SMILES: CC(C)(C)[C@H]1CCc2nc3sc(C(=O)N[C@H](CCN4CCC(O)CC4)c4ccc(-c5c[nH]c(=O)c(F)c5)cc4)nc3cc2C1] | (S)-7-(tert-butyl)-N-((R)-1-(4-(5-fluoro-6-oxo-1,6-dihydropyridin-3-yl)phenyl)-3-(4-hydroxypiperidin-1-yl)propyl)-5,6,7,8-tetrahydrothiazolo[5,4-b]quinoline-2-carboxamide | 618 | 140 |

Examples 237-241

Examples 237-241 were prepared by following a similar procedure to that disclosed for Example 1.

| Ex. No. | Structure | Chemical Name | Mass [M + H]+ | hNPRA EC50 (nM) |
|---|---|---|---|---|
| 237 | 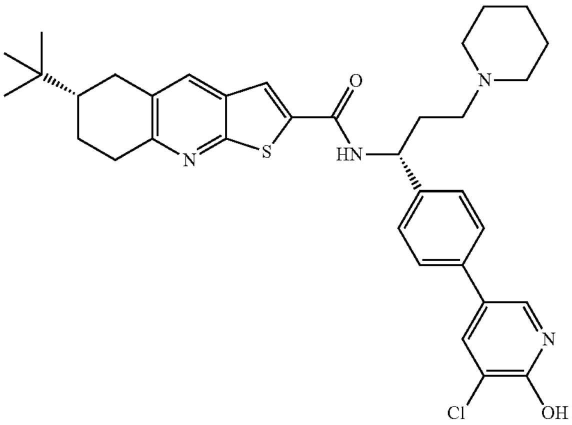 [SMILES: CC(C)(C)[C@H]1CCc2nc3sc(C(=O)N[C@H](CCN4CCCCC4)c4ccc(-c5cnc(O)c(Cl)c5)cc4)cc3cc2C1] | (6S)-6-tert-butyl-N-{(1R)-1-[4-(5-chloro-6-hydroxypyridin-3-yl)phenyl]-3-piperidin-1-ylpropyl}-5,6,7,8-tetrahydrothieno[2,3-b]quinoline-2-carboxamide | 618 | 20000 |

-continued

| Ex. No. | Structure | Chemical Name | Mass [M + H]+ | hNPRA EC50 (nM) |
|---|---|---|---|---|
| 238 | 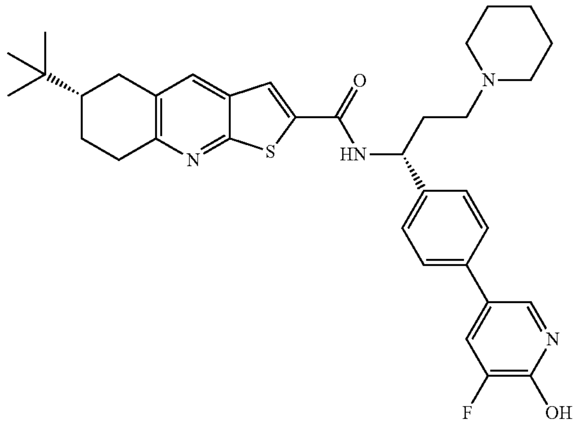 [SMILES: CC(C)(C)[C@H]1CCc2nc3sc(C(=O)N[C@H](CCN4CCCCC4)c4ccc(-c5cnc(O)c(F)c5)cc4)cc3cc2C1] | (S)-6-(tert-butyl)-N-((R)-1-(4-(5-fluoro-6-hydroxypyridin-3-yl)phenyl)-3-(piperidin-1-yl)propyl)-5,6,7,8-tetrahydrothieno[2,3-b]quinoline-2-carboxamide | 601 | 235 |
| 239 | 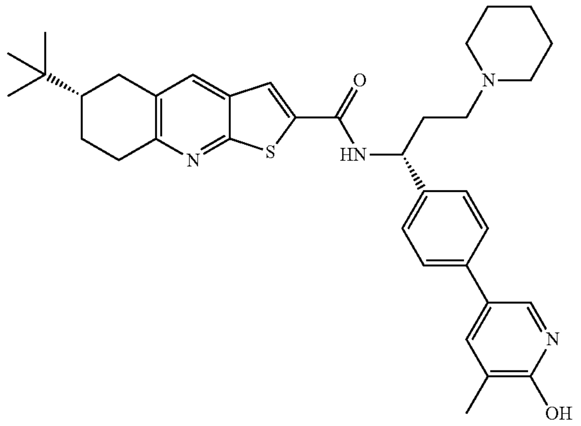 [SMILES: Cc1cc(-c2ccc([C@@H](CCN3CCCCC3)NC(=O)c3cc4cc5c(nc4s3)CC[C@H](C(C)(C)C)C5)cc2)cnc1O] | (6S)-6-tert-butyl-N-{(1R)-1-[4-(6-hydroxy-5-methylpyridin-3-yl)phenyl]-3-piperidin-1-ylpropyl}-5,6,7,8-tetrahydrothieno[2,3-b]quinoline-2-carboxamide | 597 | 1399 |
| 240 | 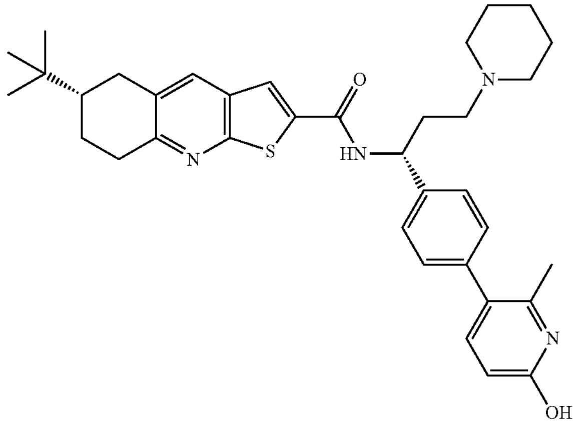 [SMILES: Cc1nc(O)ccc1-c1ccc([C@@H](CCN2CCCCC2)NC(=O)c2cc3cc4c(nc3s2)CC[C@H](C(C)(C)C)C4)cc1] | (6S)-6-tert-butyl-N-{(1R)-1-[4-(6-hydroxy-2-methylpyridin-3-yl)phenyl]-3-piperidin-1-ylpropyl}-5,6,7,8-tetrahydrothieno[2,3-b]quinoline-2-carboxamide | 597 | 1661 |

-continued

| Ex. No. | Structure | Chemical Name | Mass [M + H]+ | hNPRA EC50 (nM) |
|---|---|---|---|---|
| 241 | 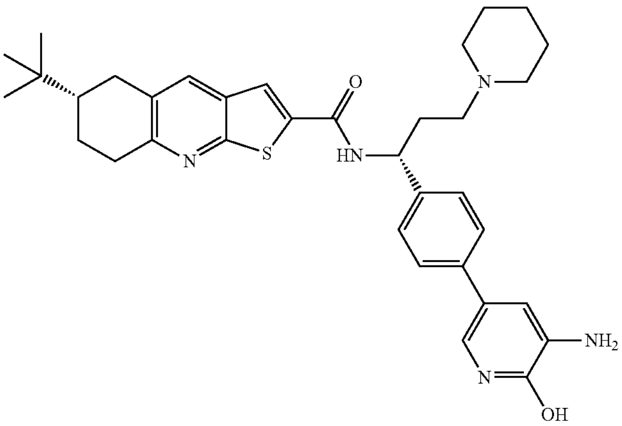 [SMILES: CC(C)(C)[C@H]1CCc2nc3sc(C(=O)N[C@H](CCN4CCCCC4)c4ccc(-c5cnc(O)c(N)c5)cc4)cc3cc2C1] | (6S)-N-{(1R)-1-[4-(5-amino-6-hydroxypyridin-3-yl)phenyl]-3-piperidin-1-ylpropyl}-6-tert-butyl-5,6,7,8-tetrahydrothieno[2,3-b]quinoline-2-carboxamide | 598 | 1734 |

Examples 242-262

Examples 242-262 were synthesized by utilizing the following general procedure:

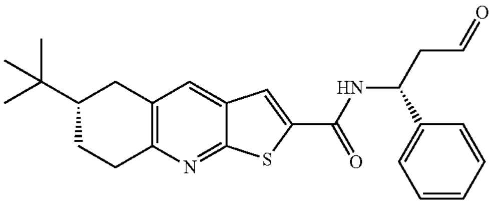

I-48

+

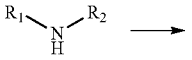

-continued

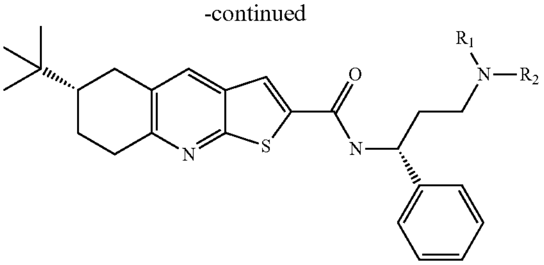

To a solution of(S)-6-(tert-butyl)-N-((R)-1-(3-(methylsulfonamido)phenyl)-3-oxopropyl)-5,6,7,8-tetrahydrothieno[2,3-b]quinoline-2-carboxamide (I-48, 30 mg, 0.057 mmol) in anhydrous 5% HOAc/MeOH (1.5 ml) was added amino substrate (0.114 mmol) and polystyrene supported $BH_3CN$ (65.7 mg, 2.45 mmol/g) at ambient temperature. The resulting reaction mixture was shaken at ambient temperature for 6 hrs.

The solution was filtered, and the solvent was evaporated under vacuum. The crude product was purified by reverse-phase HPLC (C18 column, MeCN/water with 0.1% TFA) to afford the desired product Examples 242-262.

| Ex. No. | Structure | Chemical Name | Exact Mass [M + H]+ | hNPRA EC50 (nM) |
|---|---|---|---|---|
| 242 | 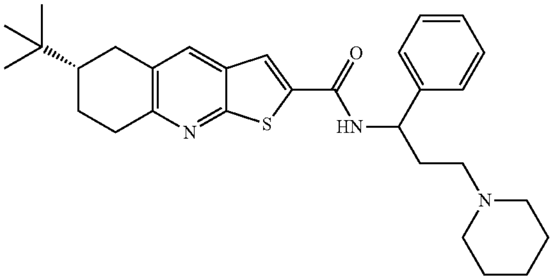 [SMILES: CC(C)(C)[C@H]1CCc2nc3sc(C(=O)NC(CCN4CCCCC4)c4ccccc4)cc3cc2C1] | (6S)-6-tert-butyl-N-(1-phenyl-3-piperidin-1-ylpropyl)-5,6,7,8-tetrahydrothieno[2,3-b]quinoline-2-carboxamide | 490 | 1875 |

-continued

| Ex. No. | Structure | Chemical Name | Exact Mass [M + H]+ | hNPRA EC50 (nM) |
|---|---|---|---|---|
| 243 | 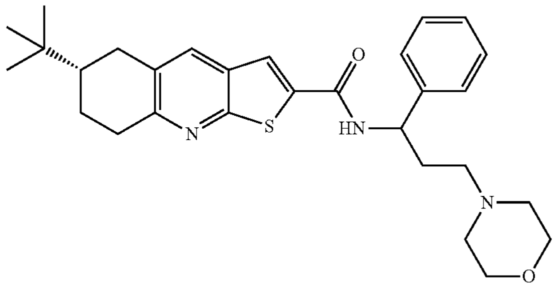 | (6S)-6-tert-butyl-N-(3-morpholin-4-yl-1-phenylpropyl)-5,6,7,8-tetrahydrothieno[2,3-b]quinoline-2-carboxamide | 492 | 6325 |
| 244 | 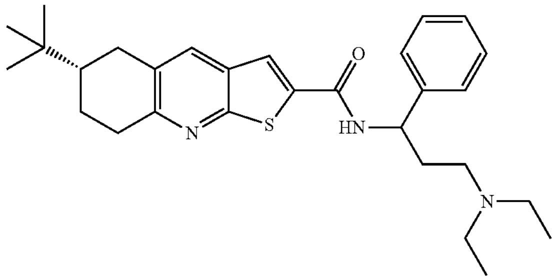 [SMILES: CCN(CC)CCC(NC(=O)c1cc2cc3c(nc2s1)CC[C@H](C(C)(C)C)C3)c1ccccc1] | (6S)-6-tert-butyl-N-[3-(diethylamino)-1-phenylpropyl]-5,6,7,8-tetrahydrothieno[2,3-b]quinoline-2-carboxamide | 478 | 2199 |
| 245 | 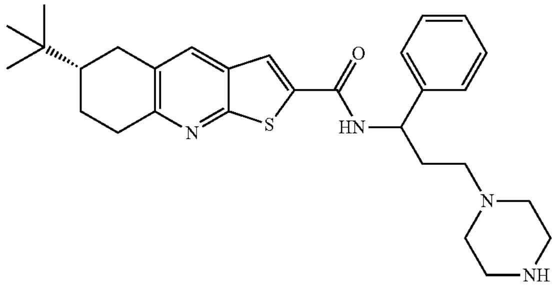 [SMILES: CC(C)(C)[C@H]1CCc2nc3sc(C(=O)NC(CCN4CCNCC4)c4ccccc4)cc3cc2C1] | (6S)-6-tert-butyl-N-(1-phenyl-3-piperazin-1-ylpropyl)-5,6,7,8-tetrahydrothieno[2,3-b]quinoline-2-carboxamide | 491 | 6325 |
| 246 | 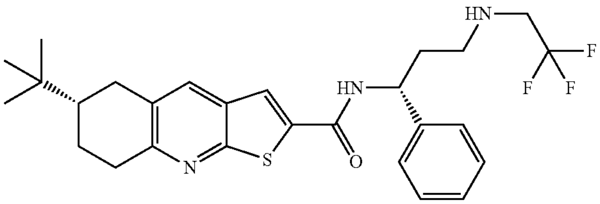 [SMILES: CC(C)(C)[C@H]1CCc2nc3sc(C(=O)N[C@H](CCNCC(F)(F)F)c4ccccc4)cc3cc2C1] | (6S)-6-tert-butyl-N-{(1R)-1-phenyl-3-[(2,2,2-trifluoroethyl)amino]propyl}-5,6,7,8-tetrahydrothieno[2,3-b]quinoline-2-carboxamide | 504 | 20000 |
| 247 | 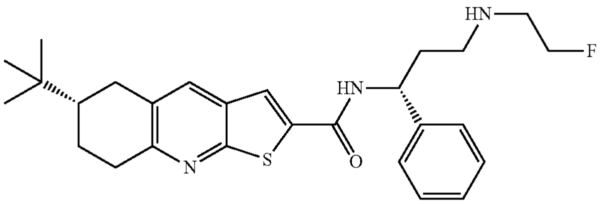 [SMILES: CC(C)(C)[C@H]1CCc2nc3sc(C(=O)N[C@H](CCNCCF)c4ccccc4)cc3cc2C1] | (6S)-6-tert-butyl-N-{(1R)-3-[(2-fluoroethyl)amino]-1-phenylpropyl}-5,6,7,8-tetrahydrothieno[2,3-b]quinoline-2-carboxamide | 468 | 20000 |

-continued

| Ex. No. | Structure | Chemical Name | Exact Mass [M + H]+ | hNPRA EC50 (nM) |
|---|---|---|---|---|
| 248 | 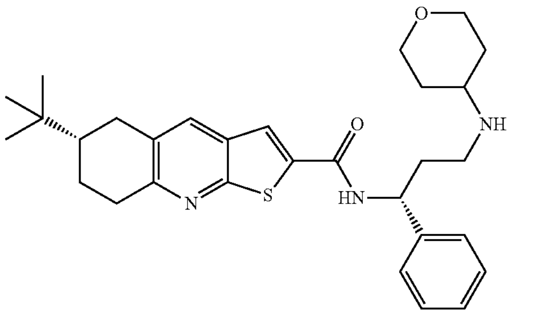 [SMILES: CC(C)(C)[C@H]1CCc2nc3sc(C(=O)N[C@H](CCNC4CCOCC4)c4ccccc4)cc3cc2C1] | (6S)-6-tert-butyl-N-[(1R)-1-phenyl-3-(tetrahydro-2H-pyran-4-ylamino)propyl]-5,6,7,8-tetrahydrothieno[2,3-b]quinoline-2-carboxamide | 506 | 6320 |
| 249 | 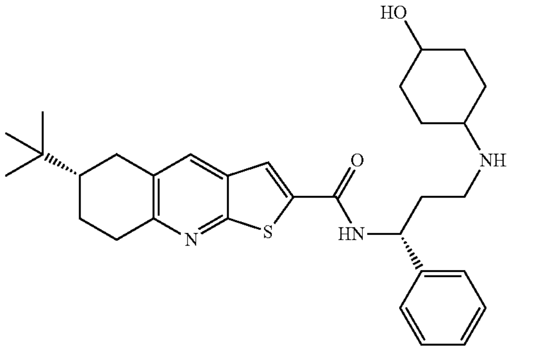 [SMILES: CC(C)(C)[C@H]1CCc2nc3sc(C(=O)N[C@H](CCNC4CCC(O)CC4)c4ccccc4)cc3cc2C1] | (6S)-6-tert-butyl-N-{(1R)-3-[(4-hydroxy-cyclohexyl)amino]-1-phenylpropyl}-5,6,7,8-tetrahydrothieno[2,3-b]quinoline-2-carboxamide | 520 | 20000 |
| 250 | 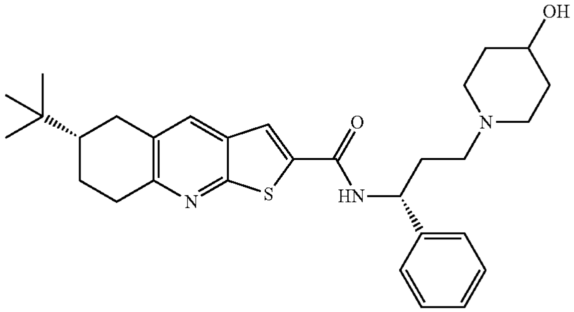 [SMILES: CC(C)(C)[C@H]1CCc2nc3sc(C(=O)N[C@H](CCN4CCC(O)CC4)c4ccccc4)cc3cc2C1] | (6S)-6-tert-butyl-N-[(1R)-3-(4-hydroxypiperidin-1-yl)-1-phenylpropyl]-5,6,7,8-tetrahydrothieno[2,3-b]quinoline-2-carboxamide | 506 | 632 |
| 251 | 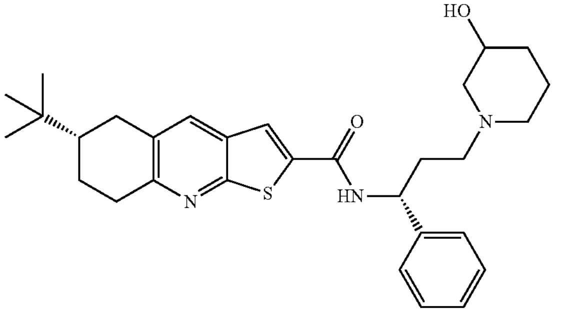 [SMILES: CC(C)(C)[C@H]1CCc2nc3sc(C(=O)N[C@H](CCN4CCCC(O)C4)c4ccccc4)cc3cc2C1] | (6S)-6-tert-butyl-N-[(1R)-3-(3-hydroxypiperidin-1-yl)-1-phenylpropyl]-5,6,7,8-tetrahydrothieno[2,3-b]quinoline-2-carboxamide | 506 | 632 |

-continued

| Ex. No. | Structure | Chemical Name | Exact Mass [M + H]+ | hNPRA EC50 (nM) |
|---|---|---|---|---|
| 252 | 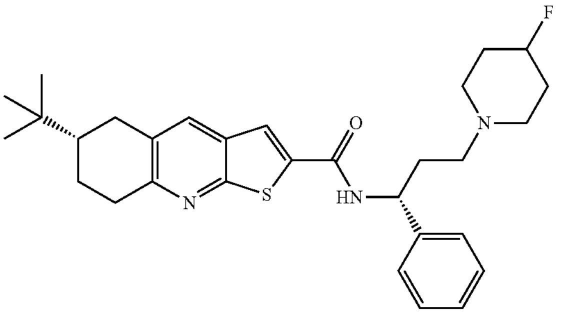 [SMILES: CC(C)(C)[C@H]1CCc2nc3sc(C(=O)N[C@H](CCN4CCC(F)CC4)c4ccccc4)cc3cc2C1] | (6S)-6-tert-butyl-N-[(1R)-3-(4-fluoropiperidin-1-yl)-1-phenylpropyl]-5,6,7,8-tetrahydrothieno[2,3-b]quinoline-2-carboxamide | 508 | 6300 |
| 253 | 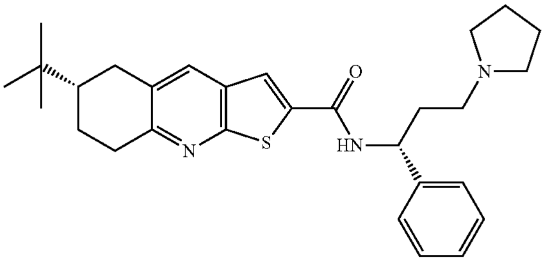 [SMILES: CC(C)(C)[C@H]1CCc2nc3sc(C(=O)N[C@H](CCN4CCCC4)c4ccccc4)cc3cc2C1] | (6S)-6-tert-butyl-N-[(1R)-1-phenyl-3-pyrrolidin-1-ylpropyl]-5,6,7,8-tetrahydrothieno[2,3-b]quinoline-2-carboxamide | 476 | 3220 |
| 254 | 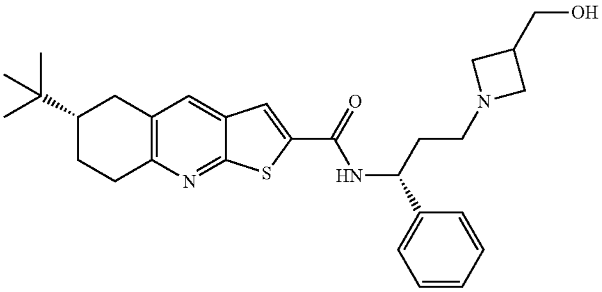 [SMILES: CC(C)(C)[C@H]1CCc2nc3sc(C(=O)N[C@H](CCN4CC(CO)C4)c4ccccc4)cc3cc2C1] | (6S)-6-tert-butyl-N-{(1R)-3-[3-(hydroxymethyl)azetidin-1-yl]-1-phenylpropyl}-5,6,7,8-tetrahydrothieno[2,3-b]quinoline-2-carboxamide | 492 | 20000 |
| 255 | 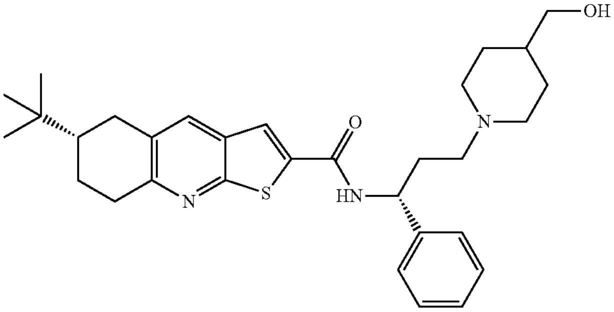 [SMILES: CC(C)(C)[C@H]1CCc2nc3sc(C(=O)N[C@H](CCN4CCC(CO)CC4)c4ccccc4)cc3cc2C1] | (6S)-6-tert-butyl-N-{(1R)-3-[4-(hydroxymethyl)piperidin-1-yl]-1-phenylpropyl}-5,6,7,8-tetrahydrothieno[2,3-b]quinoline-2-carboxamide | 520 | 2931 |
| 256 | 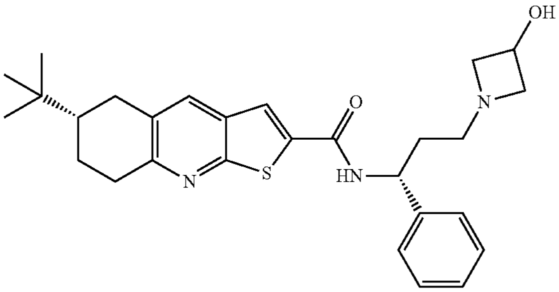 [SMILES: CC(C)(C)[C@H]1CCc2nc3sc(C(=O)N[C@H](CCN4CC(O)C4)c4ccccc4)cc3cc2C1] | (6S)-6-tert-butyl-N-[(1R)-3-(3-hydroxyazetidin-1-yl)-1-phenylpropyl]-5,6,7,8-tetrahydrothieno[2,3-b]quinoline-2-carboxamide | 478 | 3100 |

-continued

| Ex. No. | Structure | Chemical Name | Exact Mass [M + H]+ | hNPRA EC50 (nM) |
|---|---|---|---|---|
| 257 | 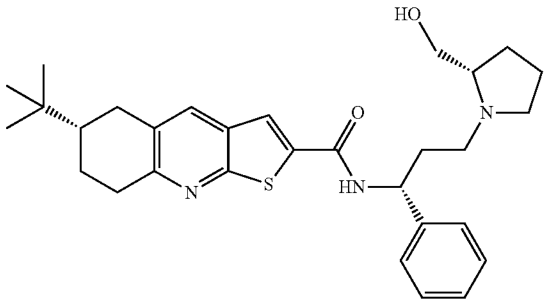 [SMILES: CC(C)(C)[C@H]1CCc2nc3sc(C(=O)N[C@H](CCN4CCC[C@H]4CO)c4ccccc4)cc3cc2C1] | (6S)-6-tert-butyl-N-{(1R)-3-[(2S)-2-(hydroxymethyl)pyrrolidin-1-yl]-1-phenylpropyl}-5,6,7,8-tetrahydrothieno[2,3-b]quinoline-2-carboxamide | 506 | 886 |
| 258 | 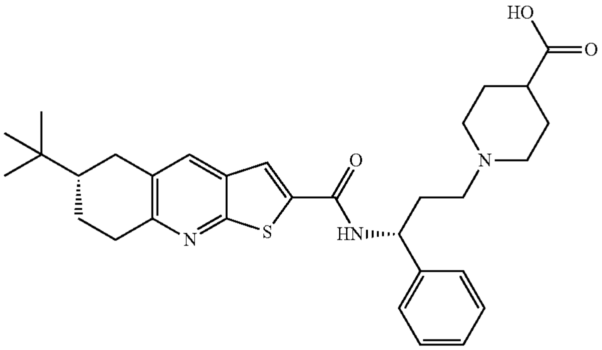 [SMILES: CC(C)(C)[C@H]1CCc2nc3sc(C(=O)N[C@H](CCN4CCC(C(=O)O)CC4)c4ccccc4)cc3cc2C1] | 1-[(3R)-3-({[(6S)-6-tert-butyl-5,6,7,8-tetrahydrothieno[2,3-b]quinolin-2-yl]carbonyl}amino)-3-phenylpropyl]piperidine-4-carboxylic acid | 534 | 2082 |
| 259 | 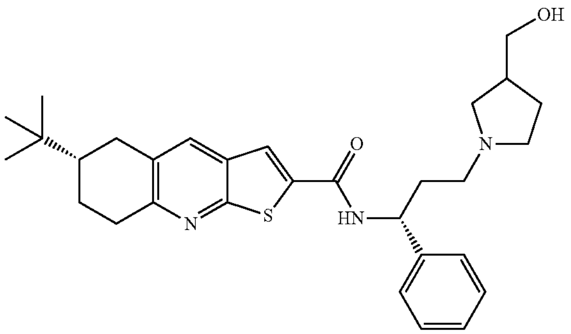 [SMILES: CC(C)(C)[C@H]1CCc2nc3sc(C(=O)N[C@H](CCN4CCC(CO)C4)c4ccccc4)cc3cc2C1] | (6S)-6-tert-butyl-N-{(1R)-3-[3-(hydroxymethyl)pyrrolidin-1-yl]-1-phenylpropyl}-5,6,7,8-tetrahydrothieno[2,3-b]quinoline-2-carboxamide | 506 | 1821 |

-continued

| Ex. No. | Structure | Chemical Name | Exact Mass [M + H]+ | hNPRA EC50 (nM) |
| --- | --- | --- | --- | --- |
| 260 | 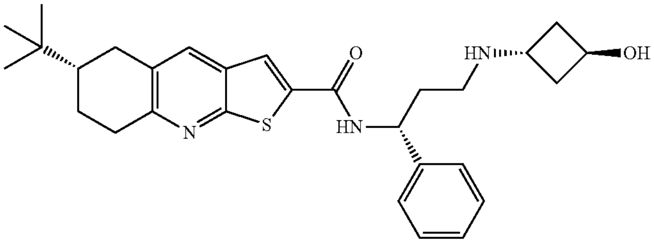 [SMILES: CC(C)(C)[C@H]1CCc2nc3sc(C(=O)N[C@H](CCN[C@H]4C[C@H](O)C4)c4ccccc4)cc3cc2C1] | (6S)-6-tert-butyl-N-{(1R)-3-[(trans-3-hydroxycyclobutyl)amino]-1-phenylpropyl}-5,6,7,8-tetrahydrothieno[2,3-b]quinoline-2-carboxamide | 492 | 2000 |
| 261 | 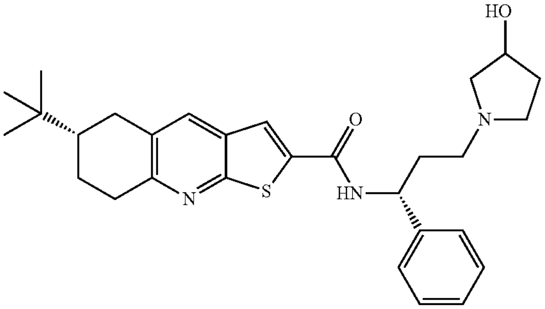 [SMILES: CC(C)(C)[C@H]1CCc2nc3sc(C(=O)N[C@H](CCN4CCC(O)C4)c4ccccc4)cc3cc2C1] | (6S)-6-tert-butyl-N-[(1R)-3-(3-hydroxypyrrolidin-1-yl)-1-phenylpropyl]-5,6,7,8-tetrahydrothieno[2,3-b]quinoline-2-carboxamide | 492 | 6325 |
| 262 | 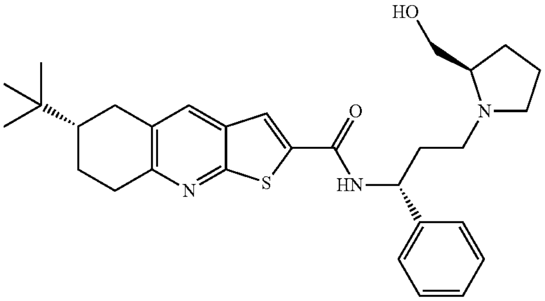 [SMILES: CC(C)(C)[C@H]1CCc2nc3sc(C(=O)N[C@H](CCN4CCC[C@@H]4CO)c4ccccc4)cc3cc2C1] | (6S)-6-tert-butyl-N-{(1R)-3-[(2R)-2-(hydroxymethyl)pyrrolidin-1-yl]-1-phenylpropyl}-5,6,7,8-tetrahydrothieno[2,3-b]quinoline-2-carboxamide | 506 | 6320 |

Example 263

Example 263 is prepared by following a similar procedure to that disclosed for Example 195.

| Ex. No. | Structure | Chemical Name | Mass [M + H]+ | hNPRA EC50 (nM) |
|---|---|---|---|---|
| 263 | 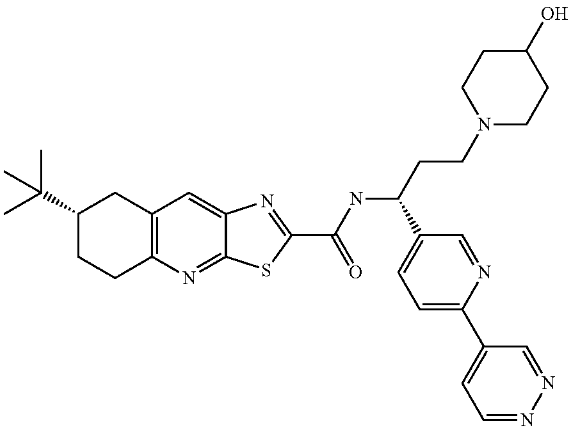 [SMILES: CC(C)(C)[C@H]1CCc2nc3sc(C(=O)N[C@H](CCN4CCC(O)CC4)c4ccc(-c5ccnnc5)nc4)nc3cc2C1] | (S)-7-(tert-butyl)-N-((R)-3-(4-hydroxypiperidin-1-yl)-1-(6-(pyridazin-4-yl)pyridin-3-yl)propyl)-5,6,7,8-tetrahydrothiazolo[5,4-b]quinoline-2-carboxamide | 586 | 129 |

Examples 264-266

Examples 264-266 are prepared by following a similar procedure to that disclosed for Example 230.

| Ex. No. | Structure | Chemical Name | Mass [M + H]+ | hNPRA EC50 (nM) |
|---|---|---|---|---|
| 264 | 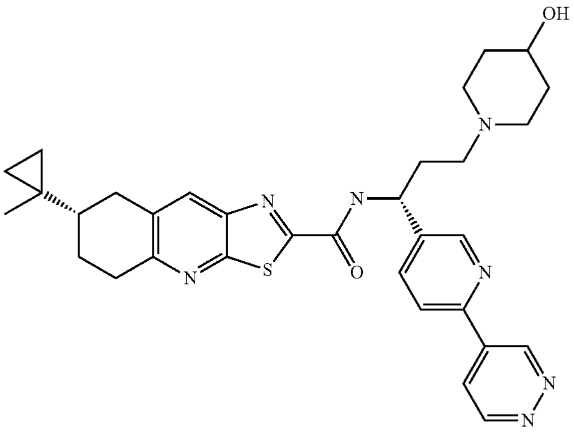 [SMILES: CC1([C@H]2CCc3nc4sc(C(=O)N[C@H](CCN5CCC(O)CC5)c5ccc(-c6ccnnc6)nc5)nc4cc3C2)CC1] | (S)-N-((R)-3-(4-hydroxypiperidin-1-yl)-1-(6-(pyridazin-4-yl)pyridin-3-yl)propyl)-7-(1-methylcyclopropyl)-5,6,7,8-tetrahydrothiazolo[5,4-b]quinoline-2-carboxamide | 584 | 113 |

-continued

| Ex. No. | Structure | Chemical Name | Mass [M + H]+ | hNPRA EC50 (nM) |
|---|---|---|---|---|
| 265 | 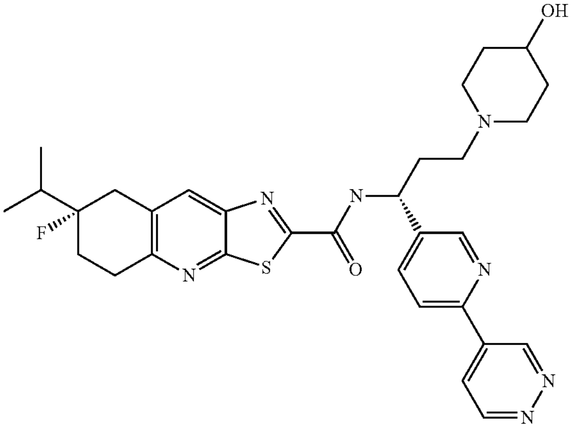 [SMILES: CC(C)[C@]1(F)CCc2nc3sc(C(=O)N[C@H](CCN4CCC(O)CC4)c4ccc(-c5ccnnc5)nc4)nc3cc2C1] | (S)-7-fluoro-N-((R)-3-(4-hydroxypiperidin-1-yl)-1-(6-(pyridazin-4-yl)pyridin-3-yl)propyl)-7-isopropyl-5,6,7,8-tetrahydrothiazolo[5,4-b]quinoline-2-carboxamide | 590 | 248 |
| 266 | 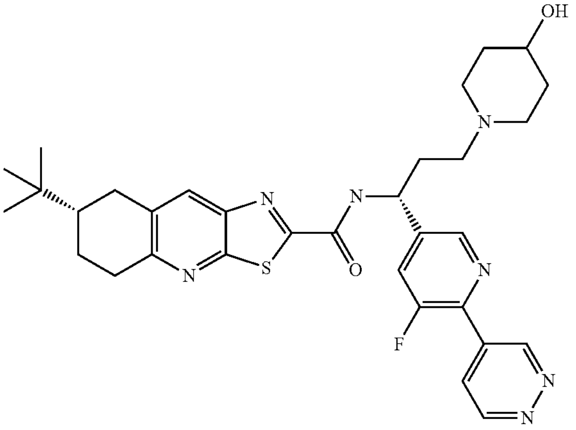 [SMILES: CC(C)(C)[C@H]1CCc2nc3sc(C(=O)N[C@H](CCN4CCC(O)CC4)c4cnc(-c5ccnnc5)c(F)c4)nc3cc2C1] | (S)-7-(tert-butyl)-N-((R)-1-(5-fluoro-6-(pyridazin-4-yl)pyridin-3-yl)-3-(4-hydroxypiperidin-1-yl)propyl)-5,6,7,8-tetrahydrothiazolo[5,4-b]quinoline-2-carboxamide | 604 | 142 |

Examples 267-268

Examples 267-268 are prepared by following a similar procedure to that disclosed for Example 230.

| Ex. No. | Structure | Chemical Name | Mass [M + H]+ | hNPRA EC50 (nM) |
|---|---|---|---|---|
| 267 | 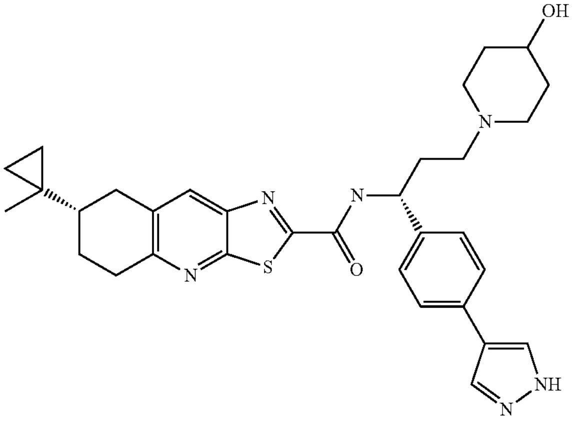 [SMILES: CC1([C@H]2CCc3nc4sc(C(=O)N[C@H](CCN5CCC(O)CC5)c5ccc(-c6cn[nH]c6)cc5)nc4cc3C2)CC1] | (S)-N-((R)-1-(4-(1H-pyrazol-4-yl)phenyl)-3-(4-hydroxypiperidin-1-yl)propyl)-7-(1-methylcyclopropyl)-5,6,7,8-tetrahydrothiazolo[5,4-b]quinoline-2-carboxamide | 571 | 655 |

-continued

| Ex. No. | Structure | Chemical Name | Mass [M + H]+ | hNPRA EC50 (nM) |
|---|---|---|---|---|
| 268 | 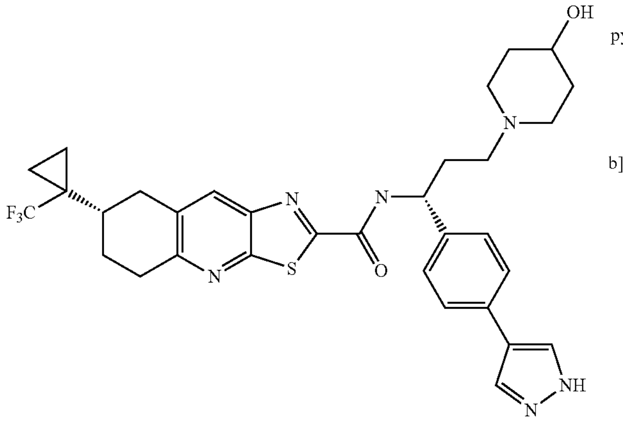 | (S)-N-((R)-1-(4-(1H-pyrazol-4-yl)phenyl)-3-(4-hydroxypiperidin-1-yl)propyl)-7-(1-(trifluoromethyl)cyclopropyl)-5,6,7,8-tetrahydrothiazolo[5,4-b]quinoline-2-carboxamide | 625 | 2032 |

Example 269 methyl 1-((R)-3-((S)-7-fluoro-7-isopropyl-5,6,7,8-tetrahydrothiazolo[5,4-b]quinoline-2-carboxamido)-3-(6-(pyridazin-4-yl)pyridin-3-yl)propyl)piperidine-4-carboxylate Example 269

Example 269 was prepared by following a similar procedure to that disclosed for Example 230.

| Ex. No. | Structure | Chemical Name | Mass [M + H]+ | hNPRA EC50 (nM) |
|---|---|---|---|---|
| 269 | 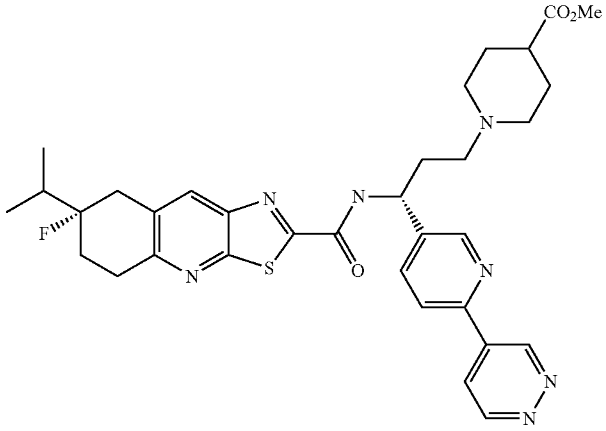 [SMILES: COC(=O)C1CCN(CC[C@@H](NC(=O)c2nc3cc4c(nc3s2)CC[C@@](F)(C(C)C)C4)c2ccc(-c3ccnnc3)nc2)CC1] | methyl 1-((R)-3-((S)-7-fluoro-7-isopropyl-5,6,7,8-tetrahydrothiazolo[5,4-b]quinoline-2-carboxamido)-3-(6-(pyridazin-4-yl)pyridin-3-yl)propyl)piperidine-4-carboxylate | 632 | 1854 |

Example 270

1-((R)-3-((S)-7-fluoro-7-isopropyl-5,6,7,8-tetrahydrothiazolo[5,4-b]quinoline-2-carboxamido)-3-(6-(pyridazin-4-yl)pyridin-3-yl)propyl)piperidine-4-carboxylic acid Example 270

Examples 270 was prepared by following a similar procedure to that disclosed for Example 230 but utilizing Example 269 as starting material.

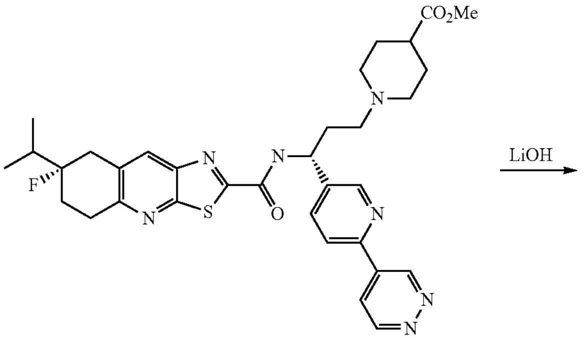

example 269

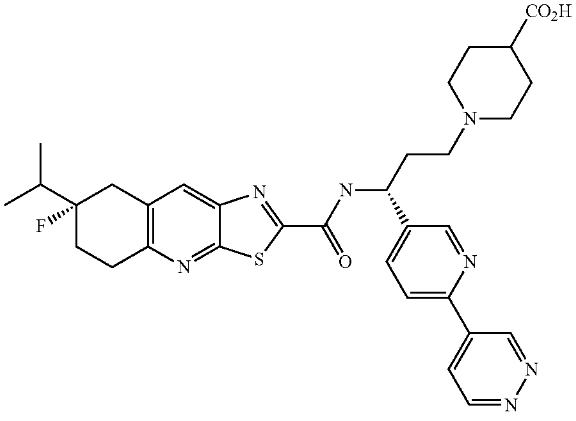

example 270

| Ex. No. | Structure | Chemical Name | Mass [M + H]+ | hNPRA EC50 (nM) |
|---|---|---|---|---|
| 270 | 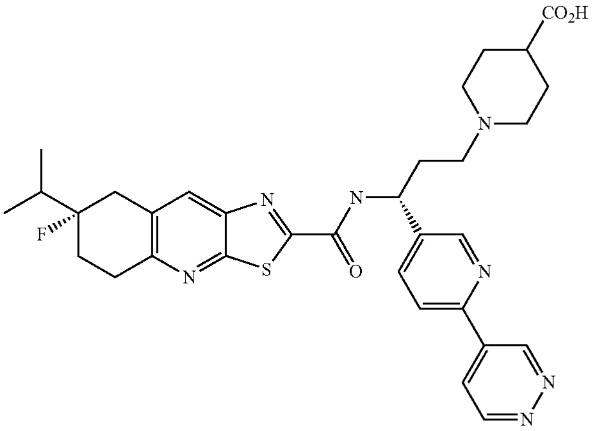 [SMILES: CC(C)[C@]1(F)CCc2nc3sc(C(=O)N[C@H](CCN4CCC(C(=O)O)CC4)c4ccc(-c5ccnnc5)nc4)nc3cc2C1] | 1-((R)-3-((S)-7-fluoro-7-isopropyl-5,6,7,8-tetrahydrothiazolo[5,4-b]quinoline-2-carboxamido)-3-(6-(pyridazin-4-yl)pyridin-3-yl)propyl)piperidine-4-carboxylic acid | 618 | 1207 |

Example 271

(R)-N-((R)-3-(4-(2H-tetrazol-5-yl)piperidin-1-yl)-1-(4-(5-fluoro-6-hydroxypyridin-3-yl)phenyl)propyl)-7-(tert-butyl)-5,6,7,8-tetrahydrothiazolo[5,4-b]quinoline-2-carboxamide Example 271

Example 271 was prepared by following a similar procedure to that disclosed for Example 198.

| Ex. No. | Structure | Chemical Name | Mass [M + H]+ | hNPRA EC50 (nM) |
|---|---|---|---|---|
| 271 | 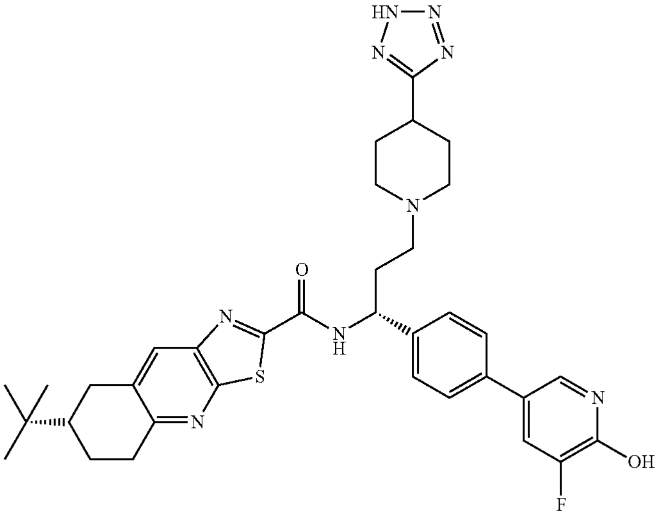 | (R)-N-((R)-3-(4-(2H-tetrazol-5-yl)piperidin-1-yl)-1-(4-(5-fluoro-6-hydroxypyridin-3-yl)phenyl)propyl)-1-(tert-butyl)-5,6,7,8-tetrahydrothiazolo[5,4-b]quinoline-2-carboxamide | 670 | 1098 |

Example 272

(7S)-7-(tert-butyl)-N-(1-(pyridin-4-yl)-3-(pyrrolidin-1-yl)propyl)-5,6,7,8-tetrahydrothiazolo[5,4-b]quinoline-2-carboxamide (Example 272)

Example 272 was prepared by following a similar procedure to that disclosed for Example 230.

| Ex. No. | Structure | Chemical Name | Mass [M + H]+ | hNPRA EC50 (nM) |
|---|---|---|---|---|
| 272 | 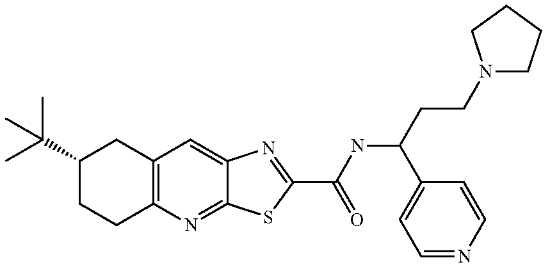 [SMILES: CC(C)(C)[C@H]1CCc2nc3sc(C(=O)NC(CCN4CCCC4)c4ccncc4)nc3cc2C1] | (7S)-7-(tert-butyl)-N-(1-(pyridin-4-yl)-3-(pyrrolidin-1-yl)propyl)-5,6,7,8-tetrahydrothiazolo[5,4-b]quinoline-2-carboxamide | 478 | 940 |

Example 273

(S)-7-(tert-butyl)-N-((R)-1-(6-(3,3-dioxido-1,3,4-oxathiazinan-4-yl)pyridin-3-yl)-3-(4-hydroxypiperidin-1-yl)propyl)-5,6,7,8-tetrahydrothiazolo[5,4-b]quinoline-2-carboxamide (Ex. 273)

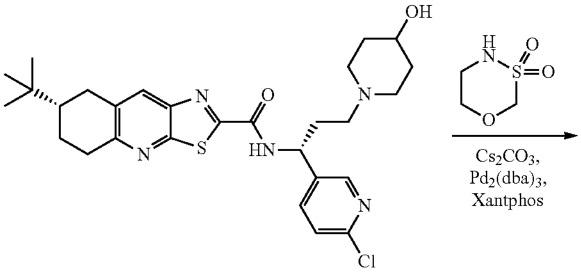

I-43

-continued

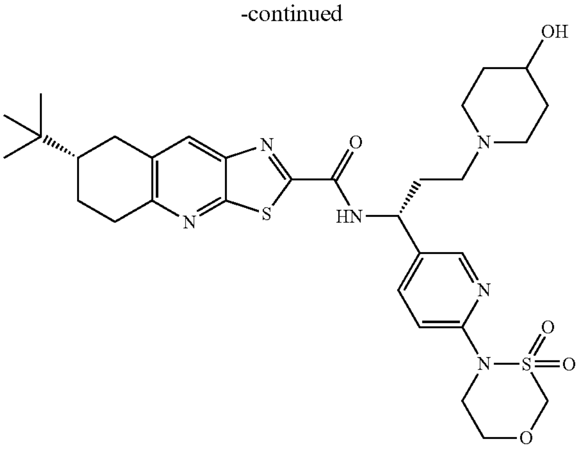

Example 273

A mixture of(S)-7-(tert-butyl)-N-((R)-1-(6-chloropyridin-3-yl)-3-(4-hydroxypiperidin-1-yl)propyl)-5,6,7,8-tetrahydrothiazolo[5,4-b]quinoline-2-carboxamide (I-43) (40 mg, 0.074 mmol), 1,3,4-oxathiazinane 3,3-dioxide (10 mg, 0.074 mmol), $Cs_2CO_3$ (120 mg, 0.37 mmol), $Pd_2(dba)_3$ (6.8 mg, 7.4 μmmol), Xantphos (8.5 mg, 0.015 mmol) was added dioxane (738 μL). The mixture was flushed with $N_2$ for 2 min, and then stirred at 100° C. for 3 h. The reaction was cooled down to RT then partitioned between EtOAc (3 mL) and water (3 mL). The organic layer was collected, dried over $Na_2SO_4$, filtered, and concentrated. The residue was purified by reverse-phase HPLC (C18 column, MeCN/water with 0.1% TFA) to afford the product.

| Ex. No. | Structure | Chemical Name | Mass [M + H]+ | hNPRA EC50 (nM) |
|---|---|---|---|---|
| 273 | 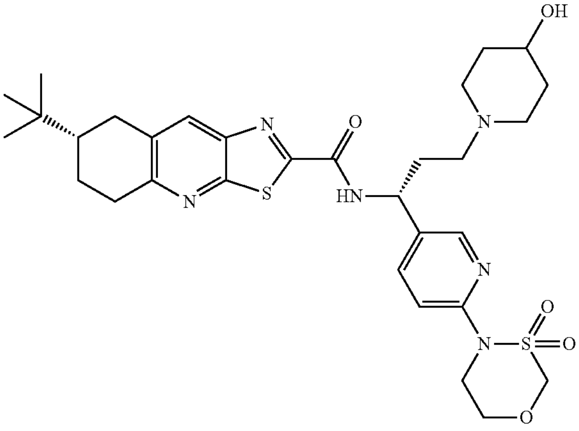 [SMILES: CC(C)(C)[C@H]1CCc2nc3sc(C(=O)N[C@H](CCN4CCC(O)CC4)c4ccc(N5CCOCS5(=O)=O)nc4)nc3cc2C1] | (S)-7-(tert-butyl)-N-((R)-1-(6-(3,3-dioxido-1,3,4-oxathiazinan-4-yl)pyridin-3-yl)-3-(4-hydroxypiperidin-1-yl)propyl)-5,6,7,8-tetrahydrothiazolo[5,4-b]quinoline-2-carboxamide | 643 | 182 |

What is claimed is:

1. A compound of the formula I, or a pharmaceutically acceptable salt thereof:

I

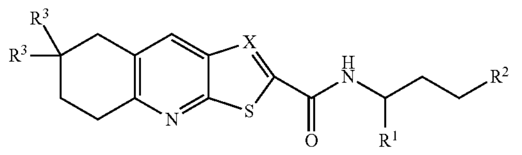

wherein

X is N or CH;

$R^1$ is selected from phenyl, pyridyl, thiazolyl, imidazolyl, pyrazinyl, and oxadiazolyl, wherein $R^1$ is substituted by 0, 1, 2, or 3, $R^5$;

$R^2$ is independently selected from:

arylC$_{0-10}$ alkyl,
C$_{3-12}$ cycloalkylC$_{0-10}$ alkyl,
heteroarylC$_{0-10}$ alkyl,
heterocyclylC$_{0-10}$ alkyl,
C$_{1-10}$alkylaminoC$_{0-10}$ alkyl,
heteroarylC$_{0-10}$alkylaminoC$_{0-10}$ alkyl,
heterocyclylC$_{0-10}$alkylaminoC$_{0-10}$ alkyl,
C$_{1-10}$ heteroalkyl aminoC$_{0-10}$ alkyl,
C$_{3-12}$ cycloalkyl C$_{0-10}$ alkylaminoC$_{0-10}$ alkyl,
aryl C$_{0-10}$ alkylaminoC$_{0-10}$ alkyl,
amino, and
(C$_{1-10}$ alkyl)$_{1-2}$ amino;

wherein $R^2$ is each substituted with 0, 1, 2, 3, or 4 $R^4$ substituents;

each $R^3$ is independently selected from hydrogen, halogen, C$_{1-6}$alkyl, and C$_{3-12}$ cycloalkyl C$_{0-10}$ alkyl, and heterocyclylC$_{0-10}$ alkyl, wherein $R^3$ is substituted by 0, 1, 2 or 3 groups independently selected from C$_{1-6}$ alkyl, C$_{1-6}$ haloalkyl, and halogen;

each $R^4$ is independently selected from:

halogen,
C$_{1-10}$ alkyl,
C$_{1-10}$ heteroalkyl,
aryl C$_{0-10}$ alkyl,
C$_{3-12}$ cycloalkyl C$_{0-10}$ alkyl,
heteroaryl C$_{0-10}$ alkyl,
heterocyclylC$_{0-10}$ alkyl,
amino C$_{0-10}$ alkyl,
((C$_{1-10}$)alkyl)$_{1-2}$amino,
—CO$_2$ (C$_{1-10}$ alkyl),
—(C$_{0-10}$ alkyl) CO$_2$H,
OXO,
hydroxy,
—(C$_{1-10}$ alkyl)OH,
C$_{1-10}$ alkoxy,
cyano, and
C$_{1-6}$haloalkyl;

wherein $R^4$ is each substituted with 0, 1, 2, 3, or 4 $R^8$ substituents and each $R^8$ is independently selected from: C$_{1-10}$ alkyl, —CO$_2$ (C$_{1-10}$ alkyl), —(C$_{0-10}$ alkyl) CO$_2$H, C$_{1-10}$ alkoxy, halogen, C$_{1-6}$haloalkyl, cyano, oxo, hydroxy, and amino;

$R^5$ is independently selected from:

halogen,
C$_{1-10}$ alkyl,
aryl C$_{0-10}$ alkyl,
C$_{3-12}$ cycloalkylC$_{0-10}$ alkyl,
heteroaryl C$_{0-10}$ alkyl,
heterocyclyl C$_{0-10}$ alkyl,
C$_{1-10}$ alkylcarbonylC$_{0-10}$ alkyl,
C$_{1-10}$ heteroalkylcarbonylC$_{0-10}$ alkyl,
arylcarbonylC$_{0-10}$ alkyl,
(C$_{3-12}$)cycloalkyl carbonylC$_{0-10}$ alkyl,
heteroarylcarbonylC$_{0-10}$ alkyl,
heterocyclylcarbonylC$_{0-10}$ alkyl,
((C$_{0-10}$)alkyl)$_{1-2}$aminocarbonyl,
C$_{1-10}$ alkoxy,
aryl C$_{0-10}$ alkyloxy,
C$_{3-12}$ cycloalkyloxy,
heteroaryl C$_{0-10}$ alkyloxy,
heterocyclyl C$_{0-10}$ alkyloxy,
(C$_{0-10}$)alkylaminocarbonyl,
(C$_{1-10}$)heteroalkylaminocarbonyl,
aryl(C$_{0-10}$)alkylaminocarbonyl,
(C$_{3-12}$)cycloalkyl(C$_{0-10}$)alkylaminocarbonyl,
heteroaryl(C$_{0-10}$)alkylaminocarbonyl,
heterocyclyl(C$_{0-10}$)alkylaminocarbonyl,
C$_{0-10}$ alkylcarbonylaminoC$_{0-10}$ alkyl,
C$_{1-10}$ heteroalkylcarbonylaminoC$_{0-10}$ alkyl,
C$_{3-12}$ cycloalkyl C$_{0-10}$ alkylcarbonylaminoC$_{0-10}$ alkyl,
aryl C$_{0-10}$ alkylcarbonylaminoC$_{0-10}$ alkyl,
heteroaryl C$_{0-10}$ alkylcarbonylaminoC$_{0-10}$ alkyl,
heterocyclyl C$_{0-10}$ alkylcarbonylamino,
—SO$_2$N(C$_{1-6}$ alkyl)$_{0-2}$,
C$_{0-6}$ alkylS(O)$_{1-2}$amino,
—SO$_2$CF$_3$,
—SO$_2$CF$_2$H,
amino,
(C$_{0-10}$ alkyl)$_{1-2}$ amino,
hydroxy,
(C$_{1-10}$ alkyl)OH,
cyano,
C$_{1-6}$haloalkyl,
—CO$_2$ (C$_{1-10}$ alkyl),
(C$_{0-10}$ alkyl) CO$_2$H,
OXO,
C$_{1-10}$ alkylS(O)$_{1-2}$,
C$_{1-10}$ heteroalkyl S(O)$_{1-2}$,
(C$_{3-12}$)cycloalkylS(O)$_{1-2}$,
heterocyclyl S(O)$_{1-2}$,
heteroarylS(O)$_{1-2}$, and
arylS(O)$_{1-2}$;

wherein $R^5$ is each substituted with 0, 1, 2, 3, or 4 $R^6$;

each $R^6$ is independently selected from:

halogen,
C$_{1-10}$ alkyl,
C$_{1-6}$ haloalkyl,
C$_{1-10}$ heteroalkyl,
aryl C$_{0-10}$ alkyl,
C$_{3-12}$ cycloalkyl C$_{0-10}$ alkyl,
heteroaryl C$_{0-10}$ alkyl,
heterocyclyl C$_{0-10}$ alkyl,
amino C$_{0-10}$ alkyl,
((C$_{1-10}$)alkyl)$_{1-2}$amino,
—CO$_2$ (C$_{1-10}$ alkyl),
—(C$_{0-10}$ alkyl) CO$_2$H,
OXO,
hydroxy,
—(C$_{1-10}$ alkyl)OH,
C$_{1-10}$ alkoxy,
cyano, and
aminocarbonyl; and wherein $R^6$ is each substituted with 0, 1, 2, or 3, $R^7$ substituents and each $R^7$ is independently selected from: $C_{1-4}$ alkyl, hydroxy, —$CO_2$ ($C_{1-6}$ alkyl), —($C_{0-6}$ alkyl) $CO_2H$, $C_{1-6}$ alkoxy, halogen, $C_{1-6}$haloalkyl, cyano, and amino.

2. The compound of claim 1 or a pharmaceutically acceptable salt thereof, wherein X is N.

3. The compound of claim 1 or a pharmaceutically acceptable salt thereof, wherein X is CH.

4. The compound of claim 3 or a pharmaceutically acceptable salt thereof, wherein $R^1$ is phenyl or pyridyl, wherein $R^1$ is substituted by 0, 1, 2 or 3 $R^5$.

5. The compound of claim 4 or a pharmaceutically acceptable salt thereof, wherein $R^5$ is independently selected from: halogen, $C_{1-10}$ alkyl, aryl $C_{0-10}$ alkyl, $C_{3-12}$ cycloalkyl$C_0$-10 alkyl, heteroaryl $C_{0-10}$ alkyl, heterocyclyl $C_{0-10}$ alkyl, $C_{1-10}$ alkylcarbonyl$C_{0-10}$ alkyl, $C_{1-10}$ heteroalkylcarbonyl$C_{0-10}$ alkyl, arylcarbonyl$C_{0-10}$ alkyl, ($C_{3-12}$)cycloalkyl carbonyl$C_{0-10}$ alkyl, heteroarylcarbonyl$C_{0-10}$ alkyl, heterocyclylcarbonyl$C_{0-10}$ alkyl, (($C_{0-10}$)alkyl)$_{1-2}$aminocarbonyl, $C_{1-10}$ alkoxy, aryl $C_{0-10}$ alkyloxy, $C_{3-12}$ cycloalkyloxy, heteroaryl $C_{0-10}$ alkyloxy, heterocyclyl $C_{0-10}$ alkyloxy, ($C_{0-10}$) alkylaminocarbonyl, ($C_{1-10}$)heteroalkylaminocarbonyl, aryl ($C_{0-10}$)alkylaminocarbonyl, ($C_3$-12)cycloalkyl($C_{0-10}$) alkylaminocarbonyl, heteroaryl($C_{0-10}$)alkylaminocarbonyl, heterocyclyl($C_{0-10}$)alkylaminocarbonyl, $C_{0-10}$ alkylcarbonylamino$C_{0-10}$ alkyl, heterocyclyl $C_{0-10}$ alkylcarbonylamino, —$SO_2N$($C_{1-6}$ alkyl)$_{0-2}$, $C_{0-6}$ alkylS(O)$_{1-2}$amino, amino, ($C_{0-10}$ alkyl)$_{1-2}$ amino, hydroxy, —($C_{1-10}$ alkyl)OH, cyano, $C_{1-6}$haloalkyl, —($C_{0-10}$ alkyl) $CO_2H$, oxo, $C_{1-10}$ alkylS(O)$_{1-2}$, wherein $R^5$ is each substituted with 0, 1, 2, 3, or 4 $R^6$.

6. The compound of claim 5 or a pharmaceutically acceptable salt thereof, wherein $R^5$ is independently selected from: pyridyl, pyrimidinyl, furyl, pyrazolyl, thiophenyl, methylsulfonylamino, pyrrolidinylcarbamoyl, imidazolyl, triazoylyl, oxazolidinyl, azetidinylcarbamoyl, (pyrrolidinylmethyl) carbamoyl, diazaspiro[3.3]heptane-carbonyl, ethylcarbamoyl, azetidinylcarbonyl, aminocarbonyl, morpholinylcarbonyl, piperazinylcarbonyl, methylcarbamoyl, 1-oxa-3,8-diazaspiro[4.5]decanyl, imidazolidinyl, pyrrolidinylcarbonylamino, ethylcarbonylamino, thiophenyl, phenyl, 1-oxa-4,7-diazaspiro[4,4]nonane-carbonyl, 2,8-diazaspiro[3.5]nonane-carbonyl, piperidylcarbamoyl, octahydropyrrolo[2,3-b]pyrrole-carbonyl, (morpholinoethyl) carbamoyl, morpholinocarbonyl, octahydropyrrolo[3,4-b][1,4]oxazine-carbonyl, pyridazinyl, 1,2-dihydropyridazinyl, 1,2,4-thiadiazolyl, 1,2,4-triazolyl, isoxazolyl, tetrazolyl, 1,2,3,4-tetrahydropyrimidinyl, 1,2,4-thiadiazolyl, pyrrolidinyl, pyrazolyloxy, ethoxy, phenoxy, 1,2-dihydropyridinyl, —NHS(O)2H, 1,3,4-oxathiazinanyl, halogen, and pyridazinyl, wherein $R^5$ is each substituted with 0, 1, 2, 3, or 4 $R^6$.

7. The compound of claim 6 or a pharmaceutically acceptable salt thereof, wherein each $R^6$ is independently selected from hydroxy, oxo, methyl, carboxy, fluoro, chloro, amino, hydroxyethyl, pyrrolidinylmethyl, 2,2,2-trifluoroethyl, benzyl, cyclopropyl, ethoxy, morpholinyl, cyano, trifluoromethyl, methylcarboxy, aminocarbonyl (carbamoyl), dimethylamino, dimethylsulfamoyl, ethylsulfonyl, and methoxy, wherein $R^6$ is each substituted with 0,1, or 2, $R^7$ substituents, and the other groups are provided in the general formula above, or as in the first through sixth embodiments.

8. The compound of claim 7 or a pharmaceutically acceptable salt thereof, wherein each $R^2$ is independently selected from: piperidinyl, dimethylamino, tetrahydropyranylamino, 5-azaspiro[2.5]octanyl, cyclobutylamino, 2,7-diazaspiro[4.5]decanyl, azetidinyl, oxetanylamino, cyclohexylamino, cyclopentylamino, azabicyclo[3.1.0]hexanyl, pyrrolidinyl, diethylamino, tetrazolyl, 1-oxa-3-azaspiro[4.5]decanyl, methylamino, ethylamino, 2-oxa-5-azabicyclo[2.2.1]heptanyl, piperidylamino, pyrrolidinylamino, piperazinyl, (tetrahydrofuranyl)amino, morpholinyl, N-methylethylamino, octahydro-2H-pyrano[3,2-c]pyridine, oxazepanyl, 1,2,3,6-tetrahydropyridyl, cyclopropylamino, isobutylamino, (pyrazolylmethyl)amino, and diazepanyl; wherein $R^2$ is each substituted with 0, 1, 2, 3, or 4 $R^4$ substituents.

9. The compound of claim 8 or a pharmaceutically acceptable salt thereof, wherein $R^4$ is independently selected from: halogen, $C_{1-10}$ alkyl, aryl $C_{0-10}$ alkyl, $C_{3-12}$ cycloalkyl $C_{0-10}$ alkyl, heteroaryl $C_{0-10}$ alkyl, amino $C_{0-10}$ alkyl, (($C_{1-10}$)alkyl)$_{1-2}$amino, —$CO_2$ ($C_{1-10}$ alkyl), —($C_{0-10}$ alkyl) $CO_2H$, oxo, hydroxy, —($C_{1-10}$ alkyl)OH, $C_{1-10}$ alkoxy, cyano, and $C_{1-6}$haloalkyl; wherein $R^4$ is each substituted with 0, 1, 2, 3, or 4 $R^8$.

10. The compound of claim 9 or a pharmaceutically acceptable salt thereof, wherein each $R^8$ is independently selected from methyl, ethyl, propyl, methoxy, ethoxy, amino or carboxy.

11. The compound of claim 10 or a pharmaceutically acceptable salt thereof, wherein each $R^3$ is independently selected from hydrogen, halogen, $C_{1-6}$alkyl, and $C_{3-12}$ cycloalkyl $C_{0-10}$ alkyl, wherein $R^3$ is substituted by 0, 1, 2 or 3 groups independently selected from $C_{1-6}$ alkyl, $C_{1-6}$ haloalkyl, and halogen.

12. The compound of claim 1, or a pharmaceutically acceptable salt thereof, selected from ammonium;5-[4-[(1R)-3-(1-piperidyl)-1-[[(6S)-6-tert-butyl-5,6,7,8-tetrahydrothieno[2,3-b]quinoline-2-carbonyl]amino]propyl]phenyl]yridine-2-olate;

(6S)-6-tert-butyl-N-[(1R)-1-[4-(2-oxo-1H-pyrimidin-5-yl)phenyl]-3-(1-piperidyl)propyl]-5,6,7,8-tetrahydrothieno[2,3-b]quinoline-2-carboxamide;

(6S)-6-tert-butyl-N-[(1R)-1-[4-(3-furyl)phenyl]-3-(1-piperidyl)propyl]-5,6,7,8-tetrahydrothieno[2,3-b]quinoline-2-carboxamide;

(6S)-6-tert-butyl-N-[(1R)-1-[4-(3-furyl)phenyl]-3-(1-piperidyl)propyl]-5,6,7,8-tetrahydrothieno[2,3-b]quinoline-2-carboxamide;

(6S)-6-tert-butyl-N-[(1R)-1-[4-(2-methylpyrazol-3-yl) phenyl]-3-(1-piperidyl)propyl]-5,6,7,8-tetrahydrothieno[2,3-b]quinoline-2-carboxamide;

(6S)-6-tert-butyl-N-[(1R)-3-(1-piperidyl)-1-[4-(1H-pyrazol-4-yl)phenyl]propyl]-5,6,7,8-tetrahydrothieno[2,3-b]quinoline-2-carboxamide;

ammonium;4-[4-[(1R)-3-(1-piperidyl)-1-[[(6S)-6-tert-butyl-5,6,7,8-tetrahydrothieno[2,3-b]quinoline-2-carbonyl]amino]propyl]phenyl]thiophene-2-carboxylate;

(6S)-6-tert-butyl-N-[(1R)-3-(1-piperidyl)-1-(4-pyrimidin-5-ylphenyl)propyl]-5,6,7,8-tetrahydrothieno[2,3-b]quinoline-2-carboxamide;

ammonium; methylsulfonyl-[3-[(1R)-3-(4-hydroxy-1-piperidyl)-1-[[(6S)-6-tert-butyl-5,6,7,8-tetrahydrothieno[2,3-b]quinoline-2-carbonyl]amino]propyl]phenyl]azanide;

ammonium methylsulfonyl-[3-[(1R)-3-(dimethylamino)-1-[[(6S)-6-tert-butyl-5,6,7,8-tetrahydrothieno[2,3-b]quinoline-2-carbonyl]amino]propyl]phenyl]azanide;

ammonium methylsulfonyl-[3-[(1R)-1-[[(6S)-6-tert-butyl-5,6,7,8-tetrahydrothieno[2,3-b]quinoline-2-carbonyl]amino]-3-(tetrahydropyran-4-ylamino) propyl]phenyl]azanide;

ammonium; methylsulfonyl-[3-[(1R)-3-(1-piperidyl)-1-[[(6S)-6-tert-butyl-5,6,7,8-tetrahydrothieno[2,3-b]quinoline-2-carbonyl]amino]propyl]phenyl]azanide;

ammonium methylsulfonyl-[3-[(1R)-3-(3-hydroxy-1-piperidyl)-1-[[(6S)-6-tert-butyl-5,6,7,8-tetrahydrothieno[2,3-b]quinoline-2-carbonyl]amino]propyl]phenyl]azanide;

ammonium methylsulfonyl-[3-[(1R)-3-(5-azaspiro[2.5]octan-5-yl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(4-fluoro-1-piperidyl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[[(1R)-3-[1-(hydroxymethyl)cyclobutyl]amino]-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(3-hydroxy-3-methyl-azetidin-1-yl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(4-imidazol-1-yl-1-piperidyl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-[3-(3-pyridyl)-1-piperidyl]-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(1-oxo-2,9-diazaspiro[4.5]decan-9-yl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(azetidin-1-yl)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-(oxetan-3-ylamino)-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-[3-(2-pyridyl)azetidin-1-yl]-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-3-[4-(2-pyridyl)-1-piperidyl]-1-[[(6S)-6-tert-butyl-5,6,7,8-tetrahydrothieno[2,3-b]quinoline-2-carbonyl]amino]propyl]phenyl]azanide;

ammonium; methylsulfonyl-[3-[(1R)-1-[[(6S)-6-tert-butyl-5,6,7,8-tetrahydrothieno[2,3-b]quinoline-2-carbonyl]amino]-3-[[(1S,2R)-3,3-difluoro-2-hydroxy-cyclohexyl]amino]propyl]phenyl]azanide;

dimethyl-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

[(1S,2R,3S,4S)-2,3-dihydroxy-4-(hydroxymethyl)cyclopentyl]-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-[6-(hydroxymethyl)-3-azoniabicyclo[3.1.0]hexan-3-yl]-1-[4-(6-oxo-1H-pyridin-3-yl)phenyl]propyl]-5,6,7,8-tetrahydrothieno[2,3-b]quinoline-2-carboxamide;formate;

dimethyl-[1-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]-4-piperidyl]ammonium;formate;

(6S)-6-tert-butyl-N-[(1R)-1-[4-(6-oxo-1H-pyridin-3-yl)phenyl]-3-[4-(1,2,4-triazol-4-yl)piperidin-1-ium-1-yl]propyl]-5,6,7,8-tetrahydrothieno[2,3-b]quinoline-2-carboxamide;formate;

(6S)-6-tert-butyl-N-[(1R)-3-[2-(hydroxymethyl)piperidin-1-ium-1-yl]-1-[4-(6-oxo-1H-pyridin-3-yl)phenyl]propyl]-5,6,7,8-tetrahydrothieno[2,3-b]quinoline-2-carboxamide;formate;

(6S)-6-tert-butyl-N-[(1R)-1-[4-(6-oxo-1H-pyridin-3-yl)phenyl]-3-[(2R,3S)-3-hydroxy-2-(hydroxymethyl)piperidin-1-ium-1-yl]propyl]-5,6,7,8-tetrahydrothieno[2,3-b]quinoline-2-carboxamide;formate;

(6S)-6-tert-butyl-N-[(1R)-1-[4-(6-oxo-1H-pyridin-3-yl)phenyl]-3-piperidin-1-ium-1-yl-propyl]-5,6,7,8-tetrahydrothieno[2,3-b]quinoline-2-carboxamide;formate;

(6S)-6-tert-butyl-N-[(1R)-1-[4-(6-oxo-1H-pyridin-3-yl)phenyl]-3-pyrrolidin-1-ium-1-yl-propyl]-5,6,7,8-tetrahydrothieno[2,3-b]quinoline-2-carboxamide;formate;

(6S)-6-tert-butyl-N-[(1R)-3-[bis(2-hydroxyethyl)amino]-1-[4-(6-oxo-1H-pyridin-3-yl)phenyl]propyl]-5,6,7,8-tetrahydrothieno[2,3-b]quinoline-2-carboxamide;

(6S)-6-tert-butyl-N-[(1R)-1-[4-(6-oxo-1H-pyridin-3-yl)phenyl]-3-[4-(tetrazol-2-yl) piperidin-1-ium-1-yl]propyl]-5,6,7,8-tetrahydrothieno[2,3-b]quinoline-2-carboxamide;formate;

[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]-tetrahydropyran-4-yl-ammonium;formate;

[(3R,4S)-3,4-dihydroxycyclopentyl]-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-1-[4-(6-oxo-1H-pyridin-3-yl)phenyl]-3-[(2S)-2-(hydroxymethyl)pyrrolidin-1-ium-1-yl]propyl]-5,6,7,8-tetrahydrothieno[2,3-b]quinoline-2-carboxamide;formate;

[(3R,4S)-3,4-dihydroxycyclopentyl]-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-(2-oxo-1-oxa-3-aza-8-azoniaspiro[4.5]decan-8-yl)-1-[4-(6-oxo-1H-pyridin-3-yl)phenyl]propyl]-5,6,7,8-tetrahydrothieno[2,3-b]quinoline-2-carboxamide;formate;

(6S)-6-tert-butyl-N-[(1R)-3-(3-hydroxypyrrolidin-1-ium-1-yl)-1-[4-(6-oxo-1H-pyridin-3-yl)phenyl]propyl]-5,6,7,8-tetrahydrothieno[2,3-b]quinoline-2-carboxamide;formate;

(6S)-6-tert-butyl-N-[(1R)-3-(methylamino)-1-[4-(6-oxo-1H-pyridin-3-yl)phenyl]propyl]-5,6,7,8-tetrahydrothieno[2,3-b]quinoline-2-carboxamide;

(6S)-6-tert-butyl-N-[(1R)-1-[4-(6-oxo-1H-pyridin-3-yl)phenyl]-3-[(2S)-2-(methoxymethyl)pyrrolidin-1-yl]propyl]-5,6,7,8-tetrahydrothieno[2,3-b]quinoline-2-carboxamide;

1-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]piperidin-1-ium-4-carboxylic acid;formate;

(6S)-6-tert-butyl-N-[(1R)-3-(4-hydroxy-4-methyl-piperidin-1-ium-1-yl)-1-[4-(6-oxo-1H-pyridin-3-yl)phenyl]propyl]-5,6,7,8-tetrahydrothieno[2,3-b]quinoline-2-carboxamide;formate;

[3-methyl-1-[(3R)-3-[4-(6-oxo-1H-pyridin-3-yl)phenyl]-3-[[(6S)-6-tert-butyl-5,6,7,8-tetrahydrothieno[2,3-b]

quinoline-2-carbonyl]amino]propyl]azetidin-3-yl] methylammonium;formate;

(6S)-6-tert-butyl-N-[(1R)-3-(5-azoniaspiro[2.5]octan-5-yl)-1-[4-(6-oxo-1H-pyridin-3-yl)phenyl]propyl]-5,6,7,8-tetrahydrothieno[2,3-b]quinoline-2-carboxamide; formate;

(6S)-6-tert-butyl-N-[(1R)-3-(3-hydroxyazetidin-1-ium-1-yl)-1-[4-(6-oxo-1H-pyridin-3-yl)phenyl]propyl]-5,6,7,8-tetrahydrothieno[2,3-b]quinoline-2-carboxamide; formate;

2-hydroxyethyl-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

cyclopentyl-methyl-[(3R)-3-[4-(6-oxo-1H-pyridin-3-yl) phenyl]-3-[[(6S)-6-tert-butyl-5,6,7,8-tetrahydrothieno [2,3-b]quinoline-2-carbonyl]amino]propyl]ammonium;formate;

(6S)-6-tert-butyl-N-[(1R)-1-[4-(6-oxo-1H-pyridin-3-yl) phenyl]-3-[(3R,4R)-3,4-dihydroxypyrrolidin-1-ium-1-yl]propyl]-5,6,7,8-tetrahydrothieno[2,3-b]quinoline-2-carboxamide;formate;

cyclopentyl-[(3R)-3-[4-(6-oxo-1H-pyridin-3-yl)phenyl]-3-[[(6S)-6-tert-butyl-5,6,7,8-tetrahydrothieno[2,3-b] quinoline-2-carbonyl]amino]propyl]ammonium;formate;

(6S)-6-tert-butyl-N-[(1R)-3-(2-oxa-5-azoniabicyclo [2.2.1]heptan-5-yl)-1-[4-(6-oxo-1H-pyridin-3-yl)phenyl]propyl]-5,6,7,8-tetrahydrothieno[2,3-b]quinoline-2-carboxamide;formate;

(2-oxo-4-piperidyl)-[(3R)-3-[4-(6-oxo-1H-pyridin-3-yl) phenyl]-3-[[(6S)-6-tert-butyl-5,6,7,8-tetrahydrothieno [2,3-b]quinoline-2-carbonyl]amino]propyl]ammonium;formate;

(6S)-6-tert-butyl-N-[(1R)-3-(3-hydroxypiperidin-1-ium-1-yl)-1-[4-(6-oxo-1H-pyridin-3-yl)phenyl]propyl]-5,6,7,8-tetrahydrothieno[2,3-b]quinoline-2-carboxamide; formate;

1-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]piperidin-1-ium-3-carboxylic acid;formate;

(5-oxopyrrolidin-3-yl)-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-1-[4-(6-oxo-1H-pyridin-3-yl) phenyl]-3-[3-(2H-tetrazol-5-yl)pyrrolidin-1-ium-1-yl] propyl]-5,6,7,8-tetrahydrothieno[2,3-b]quinoline-2-carboxamide;formate;

(6S)-6-tert-butyl-N-[(1R)-3-(4-fluoropiperidin-1-ium-1-yl)-1-[4-(6-oxo-1H-pyridin-3-yl)phenyl]propyl]-5,6,7,8-tetrahydrothieno[2,3-b]quinoline-2-carboxamide; formate;

(6S)-6-tert-butyl-N-[(1R)-3-[4-(difluoromethyl)piperidin-1-ium-1-yl]-1-[4-(6-oxo-1H-pyridin-3-yl)phenyl] propyl]-5,6,7,8-tetrahydrothieno[2,3-b]quinoline-2-carboxamide;formate;

(6S)-6-tert-butyl-N-[(1R)-1-[4-(6-oxo-1H-pyridin-3-yl) phenyl]-3-[(3S,4R)-3,4-dihydroxypyrrolidin-1-ium-1-yl]propyl]-5,6,7,8-tetrahydrothieno[2,3-b]quinoline-2-carboxamide;formate;

[(1R,2S,3R,4R)-2,3-dihydroxy-4-(hydroxymethyl)cyclopentyl]-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-(4-methoxypiperidin-1-ium-1-yl)-1-[4-(6-oxo-1H-pyridin-3-yl)phenyl]propyl]-5,6,7,8-tetrahydrothieno[2,3-b]quinoline-2-carboxamide; formate;

(1-methylazetidin-3-yl)-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-(3-hydroxy-3-methyl-azetidin-1-ium-1-yl)-1-[4-(6-oxo-1H-pyridin-3-yl)phenyl] propyl]-5,6,7,8-tetrahydrothieno[2,3-b]quinoline-2-carboxamide;formate;

(6S)-6-tert-butyl-N-[(1R)-3-[4-(2-methoxyethyl)piperazin-1-yl]-1-[4-(6-oxo-1H-pyridin-3-yl)phenyl]propyl]-5,6,7,8-tetrahydrothieno[2,3-b]quinoline-2-carboxamide;

(2-oxopyrrolidin-3-yl)-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl]amino]propyl]ammonium;formate;

(6S)-6-tert-butyl-N-[(1R)-3-(4-cyanopiperidin-1-ium-1-yl)-1-[4-(6-oxo-1H-pyridin-3-yl)phenyl]propyl]-5,6,7,8-tetrahydrothieno[2,3-b]quinoline-2-carboxamide; formate;

[(3S,4R)-4-hydroxytetrahydrofuran-3-yl]-[(3R)-3-[4-(6-oxo-1H-pyridin-3-yl)phenyl]-3-[[(6S)-6-tert-butyl-5,6,7,8-tetrahydrothieno[2,3-b]quinoline-2-carbonyl] amino]propyl]ammonium;formate;

(6S)-6-tert-butyl-N-[(1R)-1-[4-(6-oxo-1H-pyridin-3-yl) phenyl]-3-[(3S,4S)-3-(dimethylamino)-4-hydroxy-pyrrolidin-1-ium-1-yl]propyl]-5,6,7,8-tetrahydrothieno[2,3-b]quinoline-2-carboxamide;formate;

(6S)-6-tert-butyl-N-[(1R)-1-[4-(6-oxo-1H-pyridin-3-yl) phenyl]-3-[(2S,4R)-4-hydroxy-2-(hydroxymethyl)pyrrolidin-1-ium-1-yl]propyl]-5,6,7,8-tetrahydrothieno[2,3-b]quinoline-2-carboxamide;formate;

(6S)-6-tert-butyl-N-[(1R)-3-morpholino-1-[4-[[(3S,4S)-4-hydroxypyrrolidin-3-yl]carbamoyl]phenyl]propyl]-5,6,7,8-tetrahydrothieno[2,3-b]quinoline-2-carboxamide;

(7S)-7-tert-butyl-N-[(1R)-3-(4-hydroxy-1-piperidyl)-1-[4-(6-oxo-1H-pyridin-3-yl)phenyl]propyl]-5,6,7,8-tetrahydrothiazolo[5,4-b]quinoline-2-carboxamide;

(7S)-7-tert-butyl-N-[(1R)-3-[3-(hydroxymethyl)pyrrolidin-1-yl]-1-[4-(6-oxo-1H-pyridin-3-yl)phenyl]propyl]-5,6,7,8-tetrahydrothiazolo[5,4-b]quinoline-2-carboxamide;

(7S)-7-tert-butyl-N-[(1R)-1-[4-(6-oxo-1H-pyridin-3-yl) phenyl]-3-(tetrahydropyran-4-ylamino) propyl]-5,6,7,8-tetrahydrothiazolo[5,4-b]quinoline-2-carboxamide;

(7S)-7-tert-butyl-N-[(1R)-3-(dimethylamino)-1-[4-(6-oxo-1H-pyridin-3-yl)phenyl]propyl]-5,6,7,8-tetrahydrothiazolo[5,4-b]quinoline-2-carboxamide;

(7S)-7-tert-butyl-N-[(1R)-3-(3,3-dimethylazetidin-1-yl)-1-[4-(6-oxo-1H-pyridin-3-yl)phenyl]propyl]-5,6,7,8-tetrahydrothiazolo[5,4-b]quinoline-2-carboxamide;

(7S)-7-tert-butyl-N-[(1R)-3-(3-hydroxypyrrolidin-1-yl)-1-[4-(6-oxo-1H-pyridin-3-yl)phenyl]propyl]-5,6,7,8-tetrahydrothiazolo[5,4-b]quinoline-2-carboxamide;

(7S)-7-tert-butyl-N-[(1R)-3-(4-hydroxypiperidin-1-ium-1-yl)-1-[4-(6-oxo-1H-pyridin-3-yl)phenyl]propyl]-5,6,7,8-tetrahydrothiazolo[5,4-b]quinoline-2-carboxamide;formate;

(7S)-7-tert-butyl-N-[(1R)-3-(4-hydroxypiperidin-1-ium-1-yl)-1-[4-(1H-pyrazol-4-yl)phenyl]propyl]-5,6,7,8-tetrahydrothiazolo[5,4-b]quinoline-2-carboxamide;formate;

(7S)-7-tert-butyl-N-[(1R)-3-(4-hydroxypiperidin-1-ium-1-yl)-1-[4-(2-methylpyrazol-3-yl)phenyl]propyl]-5,6,7,8-tetrahydrothiazolo[5,4-b]quinoline-2-carboxamide;formate;

(7S)-7-tert-butyl-N-[(1R)-1-[4-(5-fluoro-6-hydroxy-3-pyridyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxypiperidin-1-ium-1-yl)-1-(4-imidazol-1-ylphenyl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-[4-(1,2,4-triazol-1-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxy-1-piperidyl)-1-[4-(2-oxooxazolidin-3-yl)phenyl]propyl]-5,6,7,8-tetrahydrothiazolo[5,4-b]quinoline-2-carboxamide;

(7S)-7-tert-butyl-N-[(1R)-3-(dimethylamino)-1-[3-[(1-methylazetidin-3-yl) carbamoyl]phenyl]propyl]-5,6,7,8-tetrahydrothiazolo[5,4-b]quinoline-2-carboxamide;

(7S)-7-tert-butyl-N-[(1R)-3-(dimethylamino)-1-[3-[[(3S)-1-methylpyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-3-(dimethylamino)-1-[3-[(1-methylpyrrolidin-3-yl)methylcarbamoyl]phenyl]propyl]-5,6,7,8-tetrahydrothiazolo[5,4-b]quinoline-2-carboxamide;

(7S)-7-tert-butyl-N-[(1R)-3-(dimethylamino)-1-[3-[[(3S)-pyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-3-(dimethylamino)-1-[3-[[(3R,4R)-4-hydroxypyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-1-[3-(2,6-diazaspiro[3.3]heptane-2-carbonyl)phenyl]-3-(dimethylamino) propyl]-5,6,7,8-tetrahydrothiazolo[5,4-b]quinoline-2-carboxamide;

(7S)-7-tert-butyl-N-[(1R)-1-[3-(2-aminoethylcarbamoyl)phenyl]-3-(dimethylamino) propyl]-5,6,7,8-tetrahydrothiazolo[5,4-b]quinoline-2-carboxamide;

(7S)-7-tert-butyl-N-[(1R)-3-(dimethylamino)-1-[3-(3-hydroxy-3-methyl-azetidine-1-carbonyl)phenyl]propyl]-5,6,7,8-tetrahydrothiazolo[5,4-b]quinoline-2-carboxamide;

(7S)-7-tert-butyl-N-[(1R)-1-[3-(3-aminoazetidine-1-carbonyl)phenyl]-3-(dimethylamino) propyl]-5,6,7,8-tetrahydrothiazolo[5,4-b]quinoline-2-carboxamide;

(7S)-7-tert-butyl-N-[(1R)-3-(dimethylamino)-1-[3-(2-hydroxyethylcarbamoyl)phenyl]propyl]-5,6,7,8-tetrahydrothiazolo[5,4-b]quinoline-2-carboxamide;

(7S)-7-tert-butyl-N-[(1R)-3-(dimethylamino)-1-[3-(morpholine-4-carbonyl)phenyl]propyl]-5,6,7,8-tetrahydrothiazolo[5,4-b]quinoline-2-carboxamide;

(7S)-7-tert-butyl-N-[(1R)-3-(dimethylamino)-1-[3-(piperazine-1-carbonyl)phenyl]propyl]-5,6,7,8-tetrahydrothiazolo[5,4-b]quinoline-2-carboxamide;

(7S)-7-tert-butyl-N-[(1R)-3-(dimethylamino)-1-[3-(methylcarbamoyl)phenyl]propyl]-5,6,7,8-tetrahydrothiazolo[5,4-b]quinoline-2-carboxamide;

(7S)-7-tert-butyl-N-[(1R)-1-(3-carbamoylphenyl)-3-(dimethylamino) propyl]-5,6,7,8-tetrahydrothiazolo[5,4-b]quinoline-2-carboxamide;

(7S)-7-tert-butyl-N-[(1R)-3-(dimethylamino)-1-[3-[[1-(2,2,2-trifluoroethyl)pyrrolidin-3-yl]carbamoyl]phenyl]propyl]-5,6,7,8-tetrahydrothiazolo[5,4-b]quinoline-2-carboxamide;

2-[1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]-4-piperidyl]acetic acid;2,2,2-trifluoroacetate;

(7S)-7-tert-butyl-N-[(1R)-3-[4-(2-hydroxyethyl)-1-piperidyl]-1-[3-[(1-methylazetidin-1-ium-3-yl) carbamoyl]phenyl]propyl]-5,6,7,8-tetrahydrothiazolo[5,4-b]quinoline-2-carboxamide;2,2,2-trifluoroacetate;

(7S)-7-tert-butyl-N-[(1R)-1-[3-[(1-methylazetidin-1-ium-3-yl) carbamoyl]phenyl]-3-[4-(1H-tetrazol-5-yl)-1-piperidyl]propyl]-5,6,7,8-tetrahydrothiazolo[5,4-b]quinoline-2-carboxamide;2,2,2-trifluoroacetate;

(7S)-7-tert-butyl-N-[(1R)-3-[4-(hydroxymethyl)-1-piperidyl]-1-[3-[(1-methylazetidin-1-ium-3-yl) carbamoyl]phenyl]propyl]-5,6,7,8-tetrahydrothiazolo[5,4-b]quinoline-2-carboxamide;2,2,2-trifluoroacetate;

4-[1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]-4-piperidyl]benzoic acid;2,2,2-trifluoroacetate;

2-[(2S)-1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]pyrrolidin-2-yl]acetic acid;2,2,2-trifluoroacetate;

3-[1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]-4-piperidyl]benzoic acid;2,2,2-trifluoroacetate;

3-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]-3-azabicyclo[3.1.0]hexane-6-carboxylic acid;2,2,2-trifluoroacetate;

(7S)-7-tert-butyl-N-[(1R)-3-(4-methoxy-1-piperidyl)-1-[3-[(1-methylazetidin-1-ium-3-yl) carbamoyl]phenyl]propyl]-5,6,7,8-tetrahydrothiazolo[5,4-b]quinoline-2-carboxamide;2,2,2-trifluoroacetate;

methyl 2-[1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]-4-piperidyl]acetate;2,2,2-trifluoroacetate;

3-[methyl-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]amino]propanoic acid;2,2,2-trifluoroacetate;

(3R)-1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]pyrrolidine-3-carboxylic acid;2,2,2-trifluoroacetate;

(3S)-1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]pyrrolidine-3-carboxylic acid;2,2,2-trifluoroacetate;

methyl 1-[(3R)-3-[3-[(1-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]piperidine-4-carboxylate;2,2,2-trifluoroacetate;

carboxymethyl-[(3R)-3-[3-[(1-methylazetidin-3-yl) carbamoyl]phenyl]-3-[[(7S)-7-tert-butyl-5,6,7,8-tetrahydrothiazolo[5,4-b]quinoline-2-carbonyl]amino]propyl]ammonium;2,2,2-trifluoroacetate;

(7S)-7-tert-butyl-N-[(1R)-3-(4-hydroxy-1-piperidyl)-1-[3-(2-oxo-1-oxa-3-aza-8-azoniaspiro[4.5]decan-3-yl)

phenyl]propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-[3-(2-oxoimidazolidin-1-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxy-1-piperidyl)-1-[3-(pyrrolidin-1-ium-3-carbonylamino)phenyl]propyl]-5,6,7,8-tetrahydrothiazolo[5,4-b]quinoline-2-carboxamide;2,2,2 trifluoroacetate;

[3-oxo-3-[3-[(1R)-3-(4-hydroxy-1-piperidyl)-1-[[(7S)-7-tert-butyl-5,6,7,8-tetrahydrothiazolo[5,4-b]quinoline-2-carbonyl]amino]propyl]anilino]propyl]ammonium; 2,2,2-trifluoroacetate;

(7S)-7-tert-butyl-N-[(1R)-3-(4-hydroxypiperidin-1-ium-1-yl)-1-[3-(2-oxooxazolidin-3-yl)phenyl]propyl]-5,6,7,8-tetrahydrothiazolo[5,4-b]quinoline-2-carboxamide;2,2,2-trifluoroacetate;

1-[(3R)-3-[3-[(1-methylpyrrolidin-3-yl) carbamoyl]phenyl]-3-[[(7S)-7-tert-butyl-5,6,7,8-tetrahydrothiazolo[5,4-b]quinoline-2-carbonyl]amino]propyl]piperidine-4-carboxylic acid;

1-[(3R)-3-[3-(azetidin-1-ium-3-ylcarbamoyl)phenyl]-3-[[(7S)-7-tert-butyl-5,6,7,8-tetrahydrothiazolo[5,4-b]quinoline-2-carbonyl]amino]propyl]piperidine-4-carboxylic acid;2,2,2-trifluoroacetate;

1-[(3R)-3-[3-[(1-benzylazetidin-3-yl) carbamoyl]phenyl]-3-[[(7S)-7-tert-butyl-5,6,7,8-tetrahydrothiazolo[5,4-b]quinoline-2-carbonyl]amino]propyl]piperidin-1-ium-4-carboxylic acid;2,2,2-trifluoroacetate;

1-[(3R)-3-[3-[(1-cyclopropylpyrrolidin-3-yl) carbamoyl]phenyl]-3-[[(7S)-7-tert-butyl-5,6,7,8-tetrahydrothiazolo[5,4-b]quinoline-2-carbonyl]amino]propyl]piperidin-1-ium-4-carboxylic acid;2,2,2-trifluoroacetate;

1-[(3R)-3-[3-[(3-methylazetidin-1-ium-3-yl) carbamoyl]phenyl]-3-[[(7S)-7-tert-butyl-5,6,7,8-tetrahydrothiazolo[5,4-b]quinoline-2-carbonyl]amino]propyl]piperidine-4-carboxylic acid;2,2,2-trifluoroacetate;

4-[4-[(1R)-3-(4-hydroxy-1-piperidyl)-1-[[(7S)-7-tert-butyl-5,6,7,8-tetrahydrothiazolo[5,4-b]quinoline-2-carbonyl]amino]propyl]phenyl]thiophene-2-carboxylic acid;

(7S)-7-tert-butyl-N-[(1R)-3-(4-hydroxypiperidin-1-ium-1-yl)-1-[4-(2-oxo-1H-pyrimidin-5-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-1-[4-[6-(2-fluoroethoxy)-3-pyridyl]phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-1-[4-(4-hydroxyphenyl)phenyl]-3-(4-hydroxypiperidin-1-ium-1-yl)propyl]-5,6,7,8-tetrahydrothiazolo[5,4-b]quinoline-2-carboxamide; 2,2,2-trifluoroacetate;

(7S)-7-tert-butyl-N-[(1R)-3-(4-hydroxy-1-piperidyl)-1-[3-[[(3R)-pyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-1-[3-(2,8-diazaspiro[3.5]nonane-2-carbonyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[3-(pyrrolidin-1-ylmethyl) azetidine-1-carbonyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(4-piperidylcarbamoyl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[[(3R)-1-methylpyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[[(3R,4R)-4-hydroxypyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-1-[3-(azetidin-3-ylcarbamoyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[[(3S,4S)-4-hydroxypyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[[(3S)-1-methylpyrrolidin-3-yl]carbamoyl]phenyl]propyl]-5,6,7,8-tetrahydrothiazolo[5,4-b]quinoline-2-carboxamide;

(7S)-7-tert-butyl-N-[(1R)-1-[3-[(2,2-dimethylpyrrolidin-3-yl) carbamoyl]phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methyl-3-piperidyl) carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methyl-4-piperidyl) carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methylpyrrolidin-3-yl)methylcarbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(3-piperidylcarbamoyl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(5-methyl-6-oxo-7-oxa-2,5-diazaspiro[3.4]octane-2-carbonyl)phenyl]propyl]-5,6,7,8-tetrahydrothiazolo[5,4-b]quinoline-2-carboxamide;

(7S)-7-tert-butyl-N-[(1R)-1-[3-(3-hydroxy-3-methyl-azetidine-1-carbonyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-1-[3-(2,3,3a,5,6,6a-hexahydro-1H-pyrrolo[3,2-b]pyrrole-4-carbonyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-1-[3-(3-aminoazetidine-1-carbonyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-1-[3-[3-(dimethylamino) azetidine-1-carbonyl]phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methyl-5-oxo-pyrrolidin-3-yl) carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(2-morpholinoethylcarbamoyl)phenyl]propyl]-5,6,7,8-tetrahydrothiazolo[5,4-b]quinoline-2-carboxamide;

(7S)-7-tert-butyl-N-[(1R)-1-[3-(2-hydroxyethylcarbamoyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(pyrrolidin-3-ylmethylcarbamoyl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[3-hydroxy-3-(trifluoromethyl) azetidine-1-carbonyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(2-oxopyrrolidin-3-yl) carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(5-oxopyrrolidin-3-yl) carbamoyl]phenyl]propyl]-5,6,7,8-tetrahydrothiazolo[5,4-b]quinoline-2-carboxamide;

(7S)-7-tert-butyl-N-[(1R)-1-[3-(3-hydroxyazetidine-1-carbonyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-(3-morpholinoazetidine-1-carbonyl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methyl-6-oxo-3-piperidyl) carbamoyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[3-[(1-methyl-5-oxo-pyrrolidin-3-yl)methylcarbamoyl]phenyl]propyl]-5,6,7,8-tetrahydrothiazolo[5,4-b]quinoline-2-carboxamide;

methyl 4-[3-[(1R)-3-(4-hydroxy-1-piperidyl)-1-[[(7S)-7-tert-butyl-5,6,7,8-tetrahydrothiazolo[5,4-b]quinoline-2-carbonyl]amino]propyl]benzoyl]morpholine-2-carboxylate;

(7S)-7-tert-butyl-N-[(1R)-3-(4-hydroxy-1-piperidyl)-1-[3-[(4aR,7aS)-3,4a,5,6,7,7a-hexahydro-2H-pyrrolo[3,4-b][1,4]oxazine-4-carbonyl]phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-(4-pyridazin-4-ylphenyl)propyl]-5,6,7,8-tetrahydrothiazolo[5,4-b]quinoline-2-carboxamide;

(7S)-7-tert-butyl-N-[(1R)-3-(4-hydroxypiperidin-1-ium-1-yl)-1-[4-(1-oxidopyridazin-1-ium-4-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-[4-(6-hydroxy-3-pyridyl)phenyl]propyl]-5,6,7,8-tetrahydrothiazolo[5,4-b]quinoline-2-carboxamide; 2,2,2-trifluoroacetate;

(7S)-7-tert-butyl-N-[(1R)-3-(4-hydroxypiperidin-1-ium-1-yl)-1-[4-(6-hydroxypyridazin-3-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-1-[4-(3-cyano-1H-pyrazol-4-yl)phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-[4-[3-(trifluoromethyl)-1H-pyrazol-4-yl]phenyl]propyl]-5,6,7,8-tetrahydrothiazolo[5,4-b]quinoline-2-carboxamide;2,2,2-trifluoroacetate;

(7S)-7-tert-butyl-N-[(1R)-1-[4-(2-amino-4-pyridyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(1,2,4-thiadiazol-5-yl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(4-methyl-1,2,4-triazol-3-yl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(3-methyl-1H-pyrazol-4-yl)phenyl]propyl]-5,6,7,8-tetrahydrothiazolo[5,4-b]quinoline-2-carboxamide;

(7S)-7-tert-butyl-N-[(1R)-1-[4-(5-cyano-6-hydroxy-3-pyridyl)phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-1-[4-(3,5-dimethyl-1H-pyrazol-4-yl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(5-methyl-1H-imidazol-4-yl)phenyl]propyl]-5,6,7,8-tetrahydrothiazolo[5,4-b]quinoline-2-carboxamide;

(7S)-7-tert-butyl-N-[(1R)-1-[4-(3-amino-4-pyridyl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxypiperidin-1-ium-1-yl)-1-(4-isoxazol-4-ylphenyl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-[4-(1-methyltetrazol-5-yl)phenyl]propyl]-5,6,7,8-tetrahydrothiazolo[5,4-b]quinoline-2-carboxamide;2,2,2-trifluoroacetate;

(7S)-7-tert-butyl-N-[(1R)-1-[4-(5-cyano-1H-imidazol-4-yl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(3-methylimidazol-4-yl)phenyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-(4-isothiazol-4-ylphenyl)propyl]-5,6,7,8-tetrahydrothiazolo[5,4-b]quinoline-2-carboxamide;

(7S)-7-tert-butyl-N-[(1R)-1-[4-(3-fluoro-5-hydroxy-2-pyridyl)phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-1-[4-(2,4-dioxo-1H-pyrimidin-6-yl)phenyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[4-(1,2,5-thiadiazol-3-yl)phenyl]propyl]-5,6,7,8-tetrahydrothiazolo[5,4-b]quinoline-2-carboxamide;

(7S)-7-tert-butyl-N-[(1R)-1-[4-(3,5-difluoro-4-hydroxyphenyl)phenyl]-3-(4-hydroxypiperidin-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxypiperidin-1-ium-1-yl)-1-(4-thiazol-5-ylphenyl)propyl]-5,6,7,8-tetrahydrothiazolo[5,4-b]quinoline-2-carboxamide;2,2,2-trifluoroacetate;

(7S)-7-tert-butyl-N-[(1R)-3-(4-hydroxy-1-piperidyl)-1-[6-(2-oxooxazolidin-3-yl)-3-pyridyl]propyl]-5,6,7,8-tetrahydrothiazolo[5,4-b]quinoline-2-carboxamide;

ammonium;3,5-dimethyl-1-[5-[(1R)-3-(4-hydroxy-1-piperidyl)-1-[[(7S)-7-tert-butyl-5,6,7,8-tetrahydrothiazolo[5,4-b]quinoline-2-carbonyl]amino]propyl]-2-pyridyl]pyrazol-4-olate;

(7S)-7-tert-butyl-N-[(1R)-1-[6-(3-hydroxy-2-oxo-pyrrolidin-1-yl)-3-pyridyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[6-(4-hydroxy-1-piperidyl)-3-pyridyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[6-(3-hydroxypyrrolidin-1-yl)-3-pyridyl]propyl]-5,6,7,8-tetrahydrothiazolo[5,4-b]quinoline-2-carboxamide;

(7S)-7-tert-butyl-N-[(1R)-1-[6-[(3,5-dimethyl-1H-pyrazol-4-yl)oxy]-3-pyridyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-1-[6-(2-hydroxyethoxy)-3-pyridyl]-3-(4-hydroxy-1-piperidyl)propyl]-5,6,7,8-tetrahydrothiazolo[5,4-b]quinoline-2-carboxamide;

(7S)-7-tert-butyl-N-[(1R)-1-[6-(2-amino-2-oxo-ethoxy)-3-pyridyl]-3-(4-hydroxy-1-piperidyl)propyl]-5,6,7,8-tetrahydrothiazolo[5,4-b]quinoline-2-carboxamide;

ammonium;4-[5-[(1R)-3-(4-hydroxy-1-piperidyl)-1-[[(7S)-7-tert-butyl-5,6,7,8-tetrahydrothiazolo[5,4-b]quinoline-2-carbonyl]amino]propyl]-2-pyridyl]oxy]phenolate;

(7S)-7-tert-butyl-N-[(1R)-3-(4-hydroxy-1-piperidyl)-1-[6-(6-oxo-1H-pyridin-3-yl)-3-pyridyl]propyl]-5,6,7,8-tetrahydrothiazolo[5,4-b]quinoline-2-carboxamide;

(7S)-7-tert-butyl-N-[(1R)-3-(4-hydroxy-1-piperidyl)-1-[6-(1H-pyrazol-4-yl)-3-pyridyl]propyl]-5,6,7,8-tetrahydrothiazolo[5,4-b]quinoline-2-carboxamide;

4-[5-[(1R)-3-(4-hydroxypiperidin-1-ium-1-yl)-1-[[(7S)-7-tert-butyl-5,6,7,8-tetrahydrothiazolo[5,4-b]quinoline-2-carbonyl]amino]propyl]-2-pyridyl]thiophene-2-carboxylic acid;2,2,2-trifluoroacetate;

[1-[(3R)-3-[4-(5-fluoro-6-hydroxy-3-pyridyl)phenyl]-3-[[(7S)-7-tert-butyl-5,6,7,8-tetrahydrothiazolo[5,4-b]quinoline-2-carbonyl]amino]propyl]-4-piperidyl]ammonium;formate;

[4-hydroxy-1-[(3R)-3-[4-(5-fluoro-6-hydroxy-3-pyridyl)phenyl]-3-[[(7S)-7-tert-butyl-5,6,7,8-tetrahydrothiazolo[5,4-b]quinoline-2-carbonyl]amino]propyl]-4-piperidyl]methylammonium;formate;

(7S)-7-tert-butyl-N-[(1R)-3-[4-[(dimethylamino)methyl]-4-hydroxy-piperidin-1-ium-1-yl]-1-[4-(5-fluoro-6-hydroxy-3-pyridyl)phenyl]propyl]-5,6,7,8-tetrahydrothiazolo[5,4-b]quinoline-2-carboxamide;formate;

(3R,4S)-3-fluoro-1-[(3R)-3-[4-(5-fluoro-6-hydroxy-3-pyridyl)phenyl]-3-[[(7S)-7-tert-butyl-5,6,7,8-tetrahydrothiazolo[5,4-b]quinoline-2-carbonyl]amino]propyl]piperidin-1-ium-4-carboxylic acid;formate;

diethyl-[(3R)-3-[4-(5-fluoro-6-hydroxy-3-pyridyl)phenyl]-3-[[(7S)-7-tert-butyl-5,6,7,8-tetrahydrothiazolo[5,4-b]quinoline-2-carbonyl]amino]propyl]ammonium;formate;

(3R,4R)-3-fluoro-1-[(3R)-3-[4-(5-fluoro-6-hydroxy-3-pyridyl)phenyl]-3-[[(7S)-7-tert-butyl-5,6,7,8-tetrahydrothiazolo[5,4-b]quinoline-2-carbonyl]amino]propyl]piperidin-1-ium-4-carboxylic acid;formate;

(7S)-7-tert-butyl-N-[(1R)-3-(3,4,4a,5,6,7,8,8a-octahydro-2H-pyrano[3,2-c]pyridin-6-ium-6-yl)-1-[4-(5-fluoro-6-hydroxy-3-pyridyl)phenyl]propyl]-5,6,7,8-tetrahydrothiazolo[5,4-b]quinoline-2-carboxamide;formate;

(7S)-7-tert-butyl-N-[(1R)-1-[6-(dimethylsulfamoylamino)-3-pyridyl]-3-(1,4-oxazepan-4-ium-4-yl)propyl]-5,6,7,8-tetrahydrothiazolo[5,4-b]quinoline-2-carboxamide;2,2,2-trifluoroacetate;

2-hydroxyethyl-methyl-[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]ammonium;2,2,2-trifluoroacetate;

[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]-bis(trideuteriomethyl) ammonium;2,2,2-trifluoroacetate;

(7S)-7-tert-butyl-N-[(1R)-1-[6-(dimethylsulfamoylamino)-3-pyridyl]-3-(1,2,3,6-tetrahydropyridin-1-ium-1-yl)propyl]-5,6,7,8-tetrahydrothiazolo[5,4-b]quinoline-2-carboxamide;2,2,2-trifluoroacetate;

(1-hydroxycyclopropyl)methyl-methyl-[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]ammonium;2,2,2-trifluoroacetate;

2-methoxyethyl-methyl-[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]ammonium;2,2,2-trifluoroacetate;

(7S)-7-tert-butyl-N-[(1R)-1-[6-(dimethylsulfamoylamino)-3-pyridyl]-3-[(3R)-3-hydroxypyrrolidin-1-ium-1-yl]propyl]-5,6,7,8-tetrahydrothiazolo[5,4-b]quinoline-2-carboxamide;2,2,2-trifluoroacetate;

isobutyl-methyl-[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]ammonium;2,2,2-trifluoroacetate;

(7S)-7-tert-butyl-N-[(1R)-1-[6-(dimethylsulfamoylamino)-3-pyridyl]-3-[(2S)-2-(hydroxymethyl) azetidin-1-ium-1-yl]propyl]-5,6,7,8-tetrahydrothiazolo[5,4-b]quinoline-2-carboxamide;2,2,2-trifluoroacetate;

methyl-(1H-pyrazol-5-ylmethyl)-[(3R)-3-[6-(dimethylsulfamoylamino)-3-pyridyl]-3-[[(7S)-7-tert-butyl-5,6,7,8-tetrahydrothiazolo[5,4-b]quinoline-2-carbonyl]amino]propyl]ammonium;2,2,2-trifluoroacetate;

(7S)-7-tert-butyl-N-[(1R)-1-[6-(dimethylsulfamoylamino)-3-pyridyl]-3-(5-oxo-1,4-diazepan-1-ium-1-yl)propyl]-5,6,7,8-tetrahydrothiazolo[5,4-b]quinoline-2-carboxamide;2,2,2-trifluoroacetate;

(7S)-7-tert-butyl-N-[(1R)-1-[3-(dimethylsulfamoylamino)phenyl]-3-(4-hydroxypiperidin-1-ium-1-yl)propyl]-5,6,7,8-tetrahydrothiazolo[5,4-b]quinoline-2-carboxamide;

formate;

(S)-N-((R)-1-(6-(3,3-dioxido-1,3,4-oxathiazinan-4-yl)pyridin-3-yl)-3-(4-hydroxypiperidin-1-yl)propyl)-7-fluoro-7-isopropyl-5,6,7,8-tetrahydrothiazolo[5,4-b]quinoline-2-carboxamide;

(S)-N-((R)-1-(6-(2,4-dioxoimidazolidin-1-yl)pyridin-3-yl)-3-(4-hydroxypiperidin-1-yl)propyl)-7-(1-methylcyclopropyl)-5,6,7,8-tetrahydrothiazolo[5,4-b]quinoline-2-carboxamide;

(S)-N-((R)-1-(6-(2,4-dioxoimidazolidin-1-yl)pyridin-3-yl)-3-(4-hydroxypiperidin-1-yl)propyl)-7-fluoro-7-isopropyl-5,6,7,8-tetrahydrothiazolo[5,4-b]quinoline-2-carboxamide;

(S)-7-(tert-butyl)-N-((R)-1-(6-(2,4-dioxoimidazolidin-1-yl)pyridin-3-yl)-3-(4-hydroxypiperidin-1-yl)propyl)-5,6,7,8-tetrahydrothiazolo[5,4-b]quinoline-2-carboxamide;

(S)-N-((R)-1-(6-(2,4-dioxoimidazolidin-1-yl)pyridin-3-yl)-3-(4-hydroxypiperidin-1-yl)propyl)-7-(1-(trifluoromethyl)cyclopropyl)-5,6,7,8-tetrahydrothiazolo[5,4-b]quinoline-2-carboxamide;

1-((R)-3-((S)-7-(tert-butyl)-5,6,7,8-tetrahydrothiazolo[5,4-b]quinoline-2-carboxamido)-3-(6-(2,4-dioxoimidazolidin-1-yl)pyridin-3-yl)propyl)piperidine-4-carboxylic acid;

1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylic acid;

sodium 1-((R)-3-((S)-7-(tert-butyl)-5,6,7,8-tetrahydrothiazolo[5,4-b]quinoline-2-carboxamido)-3-(4-(5-fluoro-6-hydroxypyridin-3-yl)phenyl)propyl)piperidine-4-carboxylate;

(S)-N-((R)-3-amino-1-(3-(((S)-pyrrolidin-3-yl) carbamoyl)phenyl)propyl)-6-(tert-butyl)-5,6,7,8-tetrahydrothieno[2,3-b]quinoline-2-carboxamide;

(S)-7-(tert-butyl)-N-((R)-1-(4-((N,N-dimethylsulfamoyl) amino)-3-fluorophenyl)-3-(4-hydroxypiperidin-1-yl) propyl)-5,6,7,8-tetrahydrothiazolo[5,4-b]quinoline-2-carboxamide;

(S)-7-(tert-butyl)-N-((R)-1-(6-(ethylsulfonyl)pyridin-3-yl)-3-(4-hydroxypiperidin-1-yl)propyl)-5,6,7,8-tetrahydrothiazolo[5,4-b]quinoline-2-carboxamide;

(S)-7-(tert-butyl)-N-((R)-1-(4-(4-fluoro-5-hydroxypyridin-2-yl)phenyl)-3-(4-hydroxypiperidin-1-yl)propyl)-5,6,7,8-tetrahydrothiazolo[5,4-b]quinoline-2-carboxamide;

(S)-N-((R)-3-amino-1-phenylpropyl)-6-(tert-butyl)-5,6,7,8-tetrahydrothieno[2,3-b]quinoline-2-carboxamide;

(S)-7-(tert-butyl)-N-((R)-3-(4-hydroxypiperidin-1-yl)-1-(4-(2-oxooxazolidin-3-yl)phenyl)propyl)-5,6,7,8-tetrahydrothiazolo[5,4-b]quinoline-2-carboxamide;

(S)-N-((R)-3-(4-hydroxypiperidin-1-yl)-1-(4-(2-oxooxazolidin-3-yl)phenyl)propyl)-7-(1-methylcyclopropyl)-5,6,7,8-tetrahydrothiazolo[5,4-b]quinoline-2-carboxamide;

(S)-N-((R)-3-(4-hydroxypiperidin-1-yl)-1-(4-(2-oxooxazolidin-3-yl)phenyl)propyl)-7-(1-(trifluoromethyl)cyclopropyl)-5,6,7,8-tetrahydrothiazolo[5,4-b]quinoline-2-carboxamide;

7-fluoro-N-((R)-3-(4-hydroxypiperidin-1-yl)-1-(4-(2-oxooxazolidin-3-yl)phenyl)propyl)-7-isopropyl-5,6,7,8-tetrahydrothiazolo[5,4-b]quinoline-2-carboxamide;

(S)-N-((R)-1-(4-(5-fluoro-6-oxo-1,6-dihydropyridin-3-yl)phenyl)-3-(4-hydroxypiperidin-1-yl)propyl)-7-(1-methylcyclopropyl)-5,6,7,8-tetrahydrothiazolo[5,4-b]quinoline-2-carboxamide;

(S)-N-((R)-1-(4-(5-fluoro-6-oxo-1,6-dihydropyridin-3-yl)phenyl)-3-(4-hydroxypiperidin-1-yl)propyl)-7-(1-(trifluoromethyl)cyclopropyl)-5,6,7,8-tetrahydrothiazolo[5,4-b]quinoline-2-carboxamide;

(S)-7-(tert-butyl)-N-((R)-1-(4-(5-fluoro-6-oxo-1,6-dihydropyridin-3-yl)phenyl)-3-(4-hydroxypiperidin-1-yl) propyl)-5,6,7,8-tetrahydrothiazolo[5,4-b]quinoline-2-carboxamide;

(6S)-6-tert-butyl-N-{(1R)-1-[4-(5-chloro-6-hydroxypyridin-3-yl)phenyl]-3-piperidin-1-ylpropyl}-5,6,7,8-tetrahydrothieno[2,3-b]quinoline-2-carboxamide;

(S)-6-(tert-butyl)-N-((R)-1-(4-(5-fluoro-6-hydroxypyridin-3-yl)phenyl)-3-(piperidin-1-yl)propyl)-5,6,7,8-tetrahydrothieno[2,3-b]quinoline-2-carboxamide;

(6S)-6-tert-butyl-N-{(1R)-1-[4-(6-hydroxy-5-methylpyridin-3-yl)phenyl]-3-piperidin-1-ylpropyl}-5,6,7,8-tetrahydrothieno[2,3-b]quinoline-2-carboxamide;

(6S)-6-tert-butyl-N-{(1R)-1-[4-(6-hydroxy-2-methylpyridin-3-yl)phenyl]-3-piperidin-1-ylpropyl}-5,6,7,8-tetrahydrothieno[2,3-b]quinoline-2-carboxamide;

(6S)-N-{(1R)-1-[4-(5-amino-6-hydroxypyridin-3-yl)phenyl]-3-piperidin-1-ylpropyl}-6-tert-butyl-5,6,7,8-tetrahydrothieno[2,3-b]quinoline-2-carboxamide;

(6S)-6-tert-butyl-N-(1-phenyl-3-piperidin-1-ylpropyl)-5,6,7,8-tetrahydrothieno[2,3-b]quinoline-2-carboxamide;

(6S)-6-tert-butyl-N-(3-morpholin-4-yl-1-phenylpropyl)-5,6,7,8-tetrahydrothieno[2,3-b]quinoline-2-carboxamide;

(6S)-6-tert-butyl-N-[3-(diethylamino)-1-phenylpropyl]-5,6,7,8-tetrahydrothieno[2,3-b]quinoline-2-carboxamide;

(6S)-6-tert-butyl-N-(1-phenyl-3-piperazin-1-ylpropyl)-5,6,7,8-tetrahydrothieno[2,3-b]quinoline-2-carboxamide;

(6S)-6-tert-butyl-N-{(1R)-1-phenyl-3-[(2,2,2-trifluoroethyl)amino]propyl}-5,6,7,8-tetrahydrothieno[2,3-b] quinoline-2-carboxamide;

(6S)-6-tert-butyl-N-{(1R)-3-[(2-fluoroethyl)amino]-1-phenylpropyl}-5,6,7,8-tetrahydrothieno[2,3-b]quinoline-2-carboxamide;

(6S)-6-tert-butyl-N-[(1R)-1-phenyl-3-(tetrahydro-2H-pyran-4-ylamino) propyl]-5,6,7,8-tetrahydrothieno[2,3-b]quinoline-2-carboxamide;

(6S)-6-tert-butyl-N-{(1R)-3-[(4-hydroxycyclohexyl) amino]-1-phenylpropyl}-5,6,7,8-tetrahydrothieno[2,3-b]quinoline-2-carboxamide;

(6S)-6-tert-butyl-N-[(1R)-3-(4-hydroxypiperidin-1-yl)-1-phenylpropyl]-5,6,7,8-tetrahydrothieno[2,3-b]quinoline-2-carboxamide;

(6S)-6-tert-butyl-N-[(1R)-3-(3-hydroxypiperidin-1-yl)-1-phenylpropyl]-5,6,7,8-tetrahydrothieno[2,3-b]quinoline-2-carboxamide;

(6S)-6-tert-butyl-N-[(1R)-3-(4-fluoropiperidin-1-yl)-1-phenylpropyl]-5,6,7,8-tetrahydrothieno[2,3-b]quinoline-2-carboxamide;

(6S)-6-tert-butyl-N-[(1R)-1-phenyl-3-pyrrolidin-1-ylpropyl]-5,6,7,8-tetrahydrothieno[2,3-b]quinoline-2-carboxamide;

(6S)-6-tert-butyl-N-{(1R)-3-[3-(hydroxymethyl) azetidin-1-yl]-1-phenylpropyl}-5,6,7,8-tetrahydrothieno[2,3-b]quinoline-2-carboxamide;

(6S)-6-tert-butyl-N-{(1R)-3-[4-(hydroxymethyl)piperidin-1-yl]-1-phenylpropyl}-5,6,7,8-tetrahydrothieno[2,3-b]quinoline-2-carboxamide;

(6S)-6-tert-butyl-N-[(1R)-3-(3-hydroxyazetidin-1-yl)-1-phenylpropyl]-5,6,7,8-tetrahydrothieno[2,3-b]quinoline-2-carboxamide;

(6S)-6-tert-butyl-N-{(1R)-3-[(2S)-2-(hydroxymethyl) pyrrolidin-1-yl]-1-phenylpropyl}-5,6,7,8-tetrahydrothieno[2,3-b]quinoline-2-carboxamide;

1-[(3R)-3-({[(6S)-6-tert-butyl-5,6,7,8-tetrahydrothieno [2,3-b]quinolin-2-yl]carbonyl}amino)-3-phenylpropyl] piperidine-4-carboxylic acid;

(6S)-6-tert-butyl-N-{(1R)-3-[3-(hydroxymethyl)pyrrolidin-1-yl]-1-phenylpropyl}-5,6,7,8-tetrahydrothieno[2,3-b]quinoline-2-carboxamide;

(6S)-6-tert-butyl-N-{(1R)-3-[(trans-3-hydroxycyclobutyl)amino]-1-phenylpropyl}-5,6,7,8-tetrahydrothieno[2,3-b]quinoline-2-carboxamide;

(6S)-6-tert-butyl-N-[(1R)-3-(3-hydroxypyrrolidin-1-yl)-1-phenylpropyl]-5,6,7,8-tetrahydrothieno[2,3-b]quinoline-2-carboxamide;

(6S)-6-tert-butyl-N-{(1R)-3-[(2R)-2-(hydroxymethyl)pyrrolidin-1-yl]-1-phenylpropyl}-5,6,7,8-tetrahydrothieno[2,3-b]quinoline-2-carboxamide;

(S)-7-(tert-butyl)-N-((R)-3-(4-hydroxypiperidin-1-yl)-1-(6-(pyridazin-4-yl)pyridin-3-yl) propyl)-5,6,7,8-tetrahydrothiazolo[5,4-b]quinoline-2-carboxamide;

(S)-N-((R)-3-(4-hydroxypiperidin-1-yl)-1-(6-(pyridazin-4-yl)pyridin-3-yl)propyl)-7-(1-methylcyclopropyl)-5,6,7,8-tetrahydrothiazolo[5,4-b]quinoline-2-carboxamide;

(S)-7-fluoro-N-((R)-3-(4-hydroxypiperidin-1-yl)-1-(6-(pyridazin-4-yl)pyridin-3-yl) propyl)-7-isopropyl-5,6,7,8-tetrahydrothiazolo[5,4-b]quinoline-2-carboxamide;

(S)-7-(tert-butyl)-N-((R)-1-(5-fluoro-6-(pyridazin-4-yl)pyridin-3-yl)-3-(4-hydroxypiperidin-1-yl)propyl)-5,6,7,8-tetrahydrothiazolo[5,4-b]quinoline-2-carboxamide;

(S)-N-((R)-1-(4-(1H-pyrazol-4-yl)phenyl)-3-(4-hydroxypiperidin-1-yl)propyl)-7-(1-methylcyclopropyl)-5,6,7,8-tetrahydrothiazolo[5,4-b]quinoline-2-carboxamide;

(S)-N-((R)-1-(4-(1H-pyrazol-4-yl)phenyl)-3-(4-hydroxypiperidin-1-yl)propyl)-7-(1-(trifluoromethyl)cyclopropyl)-5,6,7,8-tetrahydrothiazolo[5,4-b]quinoline-2-carboxamide;

methyl 1-((R)-3-((S)-7-fluoro-7-isopropyl-5,6,7,8-tetrahydrothiazolo[5,4-b]quinoline-2-carboxamido)-3-(6-(pyridazin-4-yl)pyridin-3-yl)propyl)piperidine-4-carboxylate;

1-((R)-3-((S)-7-fluoro-7-isopropyl-5,6,7,8-tetrahydrothiazolo[5,4-b]quinoline-2-carboxamido)-3-(6-(pyridazin-4-yl)pyridin-3-yl)propyl)piperidine-4-carboxylic acid;

(R)-N-((R)-3-(4-(2H-tetrazol-5-yl)piperidin-1-yl)-1-(4-(5-fluoro-6-hydroxypyridin-3-yl)phenyl)propyl)-7-(tert-butyl)-5,6,7,8-tetrahydrothiazolo[5,4-b]quinoline-2-carboxamide;

(7S)-7-(tert-butyl)-N-(1-(pyridin-4-yl)-3-(pyrrolidin-1-yl)propyl)-5,6,7,8-tetrahydrothiazolo[5,4-b]quinoline-2-carboxamide; and (S)-7-(tert-butyl)-N-((R)-1-(6-(3,3-dioxido-1,3,4-oxathiazinan-4-yl)pyridin-3-yl)-3-(4-hydroxypiperidin-1-yl)propyl)-5,6,7,8-tetrahydrothiazolo[5,4-b]quinoline-2-carboxamide.

13. A pharmaceutical composition comprising an effective amount of a compound of claim 12, or a pharmaceutically acceptable salt thereof, and a pharmaceutically acceptable carrier.

14. The pharmaceutical composition of claim 13, further comprising one or more additional therapeutic agents.

15. A method for treatment of cardiometabolic diseases, kidney disease, or diabetes which comprises administering to a subject in need of such treatment a therapeutically effective amount of a compound or a pharmaceutically acceptable salt thereof, according to claim 1.

* * * * *